United States Patent
Mori et al.

[11] Patent Number: 6,140,330
[45] Date of Patent: Oct. 31, 2000

[54] THIAZOLE DERIVATIVE

[75] Inventors: Toyoki Mori, Naruto; Michiaki Tominaga, Tokushima; Fujio Tabusa, Tokushima; Kazuyoshi Nagami, Tokushima; Kaoru Abe, Tokushima; Kenji Nakaya, Tokushima; Isao Takemura, Tokyo; Tomoichi Shinohara; Yoshihisa Tanada, both of Naruto; Takahito Yamauchi, Tokushima, all of Japan

[73] Assignee: Otsuka Pharmaceutical Company, Limited, Tokyo, Japan

[21] Appl. No.: 09/043,642

[22] PCT Filed: Jul. 29, 1997

[86] PCT No.: PCT/JP97/02609

§ 371 Date: Mar. 24, 1998

§ 102(e) Date: Mar. 24, 1998

[87] PCT Pub. No.: WO98/04536

PCT Pub. Date: Feb. 5, 1998

[30] Foreign Application Priority Data

Jul. 31, 1996  [JP]  Japan ..................................... 8-200898

[51] Int. Cl.$^7$ ...................... A61K 31/495; A61K 31/445; C07D 413/02

[52] U.S. Cl. ................. 514/254.03; 514/318; 514/235.8; 514/365; 514/370; 544/121; 544/364; 544/368; 548/192; 548/195; 548/204; 548/205

[58] Field of Search ..................................... 548/192, 204, 548/205, 195; 514/365, 370, 254.03, 235.8, 318; 544/364, 121, 368

[56] References Cited

FOREIGN PATENT DOCUMENTS

| | | |
|---|---|---|
| 0 318 084 | 5/1989 | European Pat. Off. . |
| 0 343 893 | 11/1989 | European Pat. Off. . |
| 0 412 404 | 2/1991 | European Pat. Off. . |
| 0 638 564 | 2/1995 | European Pat. Off. . |
| 2306916 | 12/1990 | Japan . |
| 93/21168 | 10/1993 | WIPO . |
| 93/21169 | 10/1993 | WIPO . |

*Primary Examiner*—Joseph K. McKane
*Assistant Examiner*—Ebenezer Sackey
*Attorney, Agent, or Firm*—Finnegan, Henderson, Farabow, Garrett & Dunner, L.L.P.

[57] ABSTRACT

A thiazole compound of the formula:

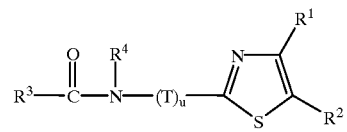

wherein T is lower alkylene; u is 0 or 1; $R^1$ and $R^2$ are the same or different and are each H, or lower alkyl, etc.; $R^3$ is

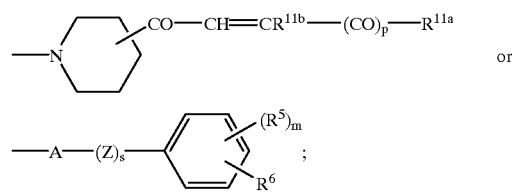

$R^4$ is H or lower alkanoyloxy-lower alkyl, which shows inhibitory activity on protein kinase C (PKC, $Ca^{2+}$/phospholipid-depending serine/threonine protein phosphatase), and are useful as a protein kinase C inhibitor.

29 Claims, No Drawings

THIAZOLE DERIVATIVE

This application is a 371 of PCT/JP97/02609 filed Jul. 29, 1997.

TECHNICAL FIELD

The present invention relates to a novel thiazole derivative.

BACKGROUND ART

There have hitherto been known various thiazole derivatives, among which some compounds having a somewhat similar substituents to those of the present invention are disclosed in the following literatures.

JP-A-2-306916 discloses inhibitors for platelet adhesion comprising a benzazole compound of the following formula:

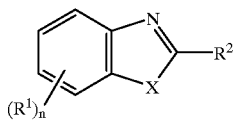

wherein X is S or >N—$R^3$ ($R^3$ is H, lower alkyl, etc.); $R^1$ is halogen, cyano, cyano-substituted lower alkoxy, phenylalkyl having a substituent on benzene ring, substituted furyl-alkoxy, substituted pyrrolidinyl-alkyl, substituted amino, substituted amino-alkyl or -alkoxy, etc.; $R^2$ is pyrrolyl having optionally alkyl substituent, thienyl, pyridylthio-lower alkyl, phenyl group which has optionally 1 to 3 substituents selected from lower alkoxy, lower alkyl, OH, halogen, or —O—Y—$NR^8R^9$ (Y is lower alkylene, $R^8$ and $R^9$ are each H, lower alkyl, cycloalkyl, or both combine to form a nitrogen-containing 5- or 6-membered saturated hetero-cyclic group, or —$NR^{10}R^{11}$ ($R^{10}$ and $R^{11}$ are each H, lower alkyl, substituted phenyl, or both combine to form a heterocyclic group). However, the benzazole compounds of this literature are significantly different from the thiazole compounds of the present invention in the substituents at 2-position of the thiazole nucleus. Besides, this literature does not disclose any compounds having protein kinase C inhibitory activities as in the present invention.

European Patent 318 084 (=U.S. Pat. Nos. 4,957,932 and 5,037,840) discloses that the benzoheterazoles of the following formula are leukotriene antagonists and inhibitors of leukotriene biosynthesis and are useful as antiasthmetic, antiallergic, anti-inflammatory and cytoprotective agents.

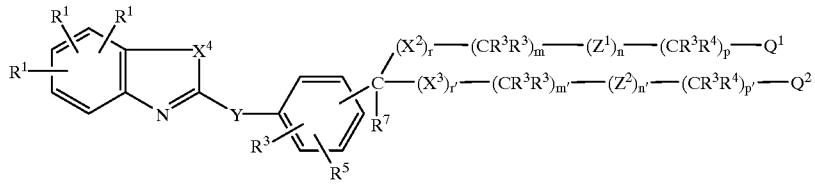

wherein $R^1$ is H, halogen, alkyl, etc.; $R^2$ is alkyl, alkenyl, etc.; $R^3$ is H or $R^2$; $R^4$ is H, halogen, —$NO_2$, etc.; $R^5$ is H, halogen, —$NO_2$, etc.; $R^7$ is H or alkyl; $X^2$ and $X^3$ are O, S, S(O), etc.; $X^4$ is $NR^3$, O or S; $Z^1$ and $Z^2$ are —$CONR^3$— or —HET(—$R^3$,—$R^5$)—; and $Q^1$ and $Q^2$ are —$COOR^3$, —$CONHS(O)_2R^{13}$, —CN, etc. However, these benzoheterazoles of this literature are essentially different from the thiazole compounds of the present invention in the substituent at 2-position of the azole nucleus. Besides, this literature does not disclose any compounds having protein kinase C inhibitory activity.

Some thiazole or benzothiazole compounds having similar chemical structure to the benzoheterazoles of the above European Patent 318084 are also disclosed in PCT publications WO 93/21168 and WO 93/21169 and therein it is mentioned that those compounds are useful as leukotriene antagonist, but these thiazole or benzothiazole compounds of these literatures are clearly different from the thiazole compounds of the present invention in the substituent at 2-position likewise, and further these literatures do not disclose any compound having protein kinase C inhibitory activity, either.

DISCLOSURE OF INVENTION

The thiazole derivatives of the present invention are novel compounds, and have not been disclosed in any literature, and have the following formula (1).

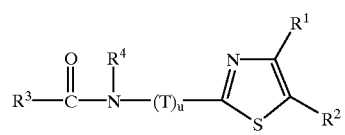

(1)

wherein T is a lower alkylene;

u is 0 or 1;

$R^1$ and $R^2$ are the same or different and are each a hydrogen atom or a lower alkyl, or both combine to form a group: —$(CH_2)_n$— (n is 4 or 5) or to form a benzene ring which may optionally be substituted by a member selected from a lower alkyl, a lower alkoxy, a nitro, an amino having optionally a lower alkyl substituent, or a halogen atom;

$R^3$ is a group of the formula:

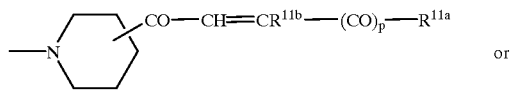

or

-continued

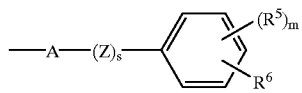

wherein $R^{11b}$, p, $R^{11a}$ are defined hereinafter; A is a lower alkylene; Z is O or S; s is 0 or 1; m is 1 or 2;

$R^4$ is a hydrogen atom or a lower alkanoyloxy-lower alkyl;

$R^5$s are the same or different and are each a member selected from (a) a hydrogen atom, (b) an alkyl having optionally a hydroxy substituent, (c) a halogen atom, (d) a group of the formula: —(O)$_t$—A—(CO)$_l$—NR$^7$R$^8$ (wherein t is 0 or 1, A is a lower alkylene, l is 0 or 1, and $R^7$ and $R^8$ are the same or different and are each a hydrogen atom or a lower alkyl, or both combine together with the nitrogen atom to which they bond to form a 5- to 7-membered saturated heterocyclic group which may be intervened with a nitrogen or oxygen atom, said heterocyclic group being optionally substituted by a member selected from a group of the formula: —(A)$_l$—NR$^9$R$^{10}$ (wherein A and 1 are as defined above, and $R^9$ and $R^{10}$ are the same or different and are each a hydrogen atom or a lower alkyl, or both combine together with the nitrogen atom to which they bond to form a 5- to 7-membered saturated heterocyclic group which may be intervened with a nitrogen or oxygen atom, said heterocyclic group having optionally a lower alkyl substituent), a lower alkyl having optionally a hydroxy substituent, a hydroxy group, and a lower alkanoyl), (e) a lower alkoxycarbonyl-lower alkyl, (f) a lower alkanoyloxy-lower alkyl, (g) a lower alkoxy having optionally a halogen substituent, (h) a halogen-substituted lower alkyl, (i) a carboxyl-substituted lower alkyl, (j) a lower alkoxycarbonyl, (k) a lower alkenyloxy, (l) a phenyl-lower alkoxy, (m) a cycloalkyloxy, (n) a phenyl, (o) a phenyloxy, (p) a hydroxy, (q) a lower alkylthio, (r) a lower alkenyl, or (s) an amino having optionally a lower alkyl substituent;

$R^6$ is a group of the formula:

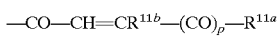  (1)

or

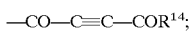  (2)

p is 0 or 1;

$R^{11b}$ is a hydrogen atom or a lower alkyl;

$R^{11a}$ is a hydroxy, a lower alkoxy, or a 5- to 10-membered, monocyclic or dicyclic, saturated or unsaturated heterocyclic group which contains 1 to 4 hetero atoms selected from a nitrogen, oxygen or sulfur atom as a ring member, said heterocyclic group having optionally 1 to 3 substituents selected from the group consisting of (i) a lower alkyl, (ii) a group of the formula: —(B)$_l$—NR$^{12}$R$^{13}$ (wherein 1 is as defined above, B is —CO—A— (A is as defined above), a carbonyl, or a lower alkylene, and $R^{12}$ and $R^{13}$ are the same or different and are each a hydrogen atom, a lower alkyl, or a lower alkyl substituted by an amino having optionally a lower alkyl substituent, or both combine together with the nitrogen atom to which they bond to form a 5- to 12-membered saturated, monocyclic, dicyclic or spirocyclic heterocyclic group which may be intervened with a nitrogen or oxygen atom, said heterocyclic group having optionally a substituent selected from a lower alkyl, a lower alkoxycarbonyl, a lower alkoxy-substituted lower alkyl, an amino having optionally a lower alkyl substituent, and a hydroxy-substituted lower alkyl), (iii) a lower alkoxycarbonyl, (iv) a hydroxy-substituted lower alkyl, (v) a pyridyl being optionally substituted by a lower alkyl having optionally a halogen substituent on the pyridine ring, (vi) a halogen-substituted lower alkyl, (vii) a lower alkoxy, (viii) a cycloalkyl, (ix) a hydroxy, (x) a tetrahydropyranyloxy-substituted lower alkyl, (xi) a pyrimidyl, (xii) a lower alkoxy-substituted lower alkyl, (xiii) a carboxyl, (xiv) a phenyl-lower alkoxy, (xv) a phenyl-lower alkyl having optionally a lower alkylenedioxy on the phenyl ring, (xvi) a lower alkanoyloxy, and (xvii) a piperidinyl having optionally a lower alkyl substituent on the piperidine ring;

$R^{14}$ is a hydroxy or a lower alkoxy; and when m is 1, the groups A and $R^5$ may combine to form a group of the formula:

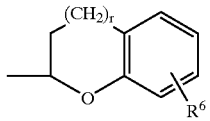

(wherein $R^6$ is as defined above, and r is 0, 1 or 2), or when m is 2, two $R^5$ groups may combine to form a lower alkylenedioxy, a lower alkylene, or a group of the formula: —(CH$_2$)$_2$—CONH—, or the groups $R^5$ and $R^6$ may combine to form a group of the formula: —CO—CH(R$^{28}$)—CH(R$^{28'}$)—W— (wherein $R^{28}$ and $R^{28'}$ are a hydrogen atom or a carboxyl group, provided that both $R^{28}$ and $R^{28'}$ are not simultaneously a carboxyl group, and W is —N(R$^{29a}$)— or

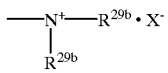

(wherein $R^{29a}$ is a hydrogen atom or a lower alkyl, $R^{29b}$ is a lower alkyl, and X is a halogen atom)), or a salt thereof.

The thiazole derivatives of the formula (1) show inhibitory activity on protein kinase C (PKC, Ca$^{2+}$/phospholipid-depending serine/threonine protein phosphatase), and are useful as a protein kinase C inhibitor.

It has been proved that PKC plays an important role in the regulation of various biological functions such as the metabolism regulation, the cell proliferation, the cell differentiation, the release reaction of neurotransmitter,etc. Therefore, it is indicated that a PKC inhibitor may be useful in the prophylaxis or treatment of various diseases caused by the hyperaction of the above-mentioned biological functions being participated by PKC.

More particularly, the protein kinase C inhibitors containing as an active ingredient the present thiazole derivative are useful as an agent for treatment of autoimmune diseases such as rheumatoid arthritis, systemic lupus erythematosus, multiple sclerosis, psoriasis, etc., various allergic diseases such as Crohn's disease, colitis ulcerosa, asthma, atopic dermatitis; an agent for protection of rejection in organ transplant, GVHD reaction, etc.; an agent for prophylaxis or treatment of various ischemic diseases in the organs such as heart, liver, kidney, brain, etc., acute pancreatitis, sepsis, multiple organs failure introduced by burn, ARDS, by inhibiting the production of cytokinin derived from T-cell such as IL-2, or inflammatory cytokinin such as TNF-α.

Further, by other biological functions such as cell proliferation, hormone secretion, regulation of metabolism, etc. which are concerned with PKC, the protein kinase C inhibitors of the present invention are useful in the prophylaxis or treatment of cancer, diabetes, Alzheimer disease, arteriosclerosis, HIV infection, nephritis, angiitis, etc.

Each group in the above formula (1) specially means the following groups.

The lower alkyl group includes a straight chain or branched chain $C_1$–$C_6$ alkyl group such as methyl, ethyl, propyl, isopropyl, butyl, isobutyl, tert-butyl, pentyl, hexyl, etc.

The lower alkoxy group includes a straight chain or branched chain $C_1$–$C_6$ alkoxy group, for example, methoxy, ethoxy, propoxy, isopropoxy, butoxy, tert-butoxy, pentyloxy, hexyloxy, etc.

The halogen atom is fluorine atom, chlorine atom, bromine atom or iodine atom.

The lower alkanoyloxy-substituted lower alkyl group includes a straight chain or branched chain $C_1$–$C_6$ alkyl group which is substituted by 1 or 2 straight chain or branched chain $C_2$–$C_6$ alkanoyloxy groups, for example, acetyloxymethyl, 2-propionyloxyethyl, 1-butyryloxyethyl, 3-acetyloxypropyl, 4-acetyloxybutyl, 4-isobutyryloxybutyl, 5-pentanoyloxypentyl, 6-acetyloxyhexyl, 6-tert-butylcarbonyloxyhexyl, 1,1-dimethyl-2-hexanoyloxyethyl, 2-methyl-3-acetyloxypropyl, diacetyloxymethyl, 1,3-diacetyloxypropyl, etc.

The alkyl group having optionally a hydroxy substituent includes a straight chain or branched chain $C_1$–$C_8$ alkyl group which may optionally have 1 to 3 hydroxy substituents, for example, methyl, ethyl, propyl, isopropyl, butyl, isobutyl, tert-butyl, pentyl, hexyl, heptyl, octyl, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 1,3-dihydroxypropyl, 5,5,4-trihydroxypentyl, 5-hydroxypentyl, 6-hydroxyhexyl, 1-hydroxyisopropyl, 2-methyl-3-hydroxypropyl, 7-hydroxyheptyl, 8-hydroxyoctyl, etc.

The lower alkylene group includes a straight chain or branched chain $C_1$–$C_6$ alkylene group, for example, methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene, etc.

The 5- to 7-membered saturated heterocyclic group which is formed by combining $R^7$ and $R^8$, or $R^9$ and $R^{10}$ together with the adjacent nitrogen atom with or without being intervening with another nitrogen atom or an oxygen atom, for example, pyrrolidinyl, piperidinyl, piperazinyl, morpholino, homopiperazinyl, homomorpholino, etc.

The lower alkyl group having optionally a hydroxy substituent includes, in addition to the above lower alkyl groups, a straight chain or branched chain $C_1$–$C_6$ alkyl group which may optionally have 1 to 3 hydroxy substituents, for example, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, etc.

The lower alkanoyl group includes a straight chain or branched chain $C_1$–$C_6$ alkanoyl group, for example, formyl, acetyl, propionyl, butyryl, isobutyryl, pentanoyl, t-butylcarbonyl, hexanoyl, etc.

The above heterocyclic group which is substituted by a group of the formula: —(A)$_l$—NR$^9$N$^{10}$ (A is a lower alkylene group, l is 0 or 1, R$^9$ an R$^{10}$ are the same or different and each are a hydrogen atom or a lower alkyl group, or R$^9$ and R$^{10}$ combine together with the nitrogen atom to which they bond to form a 5- or 7-membered saturated heterocyclic group with or without being intervened with another nitrogen atom or an oxygen atom, and said heterocyclic group having optionally a lower alkyl substituent), a lower alkyl group having optionally a hydroxy substituent, a hydroxy group and a lower alkanoyl group includes the above mentioned heterocyclic groups having 1 to 3 sustituents selected from a group of the formula: —(A)$_l$—NR$^9$N$^{10}$ (A is a straight chain or branched chain $C_1$–$C_6$ alkylene group, l is 0 or 1, R$^9$ an R$^{10}$ are the same or different and each are a hydrogen atom or a straight chain or branched chain $C_1$–$C_6$ alkyl group, or R$^9$ and R$^{10}$ combine together with the nitrogen atom to which they bond to form a 5- or 7-membered saturated heterocyclic group with or without being intervened with another nitrogen atom or an oxygen atom, and said heterocyclic group having optionally 1 to 3 straight chain or branched chain $C_1$–$C_6$ alkyl substituents), a straight chain or branched chain alkyl group having optionally 1 to 3 hydroxy substituents, a hydroxy group and a straight chain or branched chain $C_1$–$C_6$ alkanoyl group, for example, 4-methylpiperazinyl, 2-(4-methyl-1-piperazinyl) methylmorpholino, 4-(4-methyl-1-piperazinyl)piperidinyl, 4-methylhomopiperazinyl, 4-(2-hydroxyethyl)piperazinyl, 4-morpholinopiperidinyl, 2-[(1-pyrrolidinyl)methyl] morpholino, 4-hydroxypiperidinyl, 4-acetylpiperazinyl, 4-dimethylaminopiperidinyl, 4-(4-methyl-1-homopiperazinyl)piperidinyl, 4-(4,5-dimethyl-1-homopiperazinyl)piperidinyl, 4-(3-methyl-4-ethyl-1-piperazinyl)piperidnyl, 4-(3-methyl-4-n-propyl-1-piperazinyl)piperidinyl, 4-(3,4-dimethyl-1-piperazinyl) piperidinyl, 4-(4-isopropyl-3-methylpiperazinyl) piperidinyl, 4-(4-methyl-3-isopropylpiperazinyl) piperidinyl, 2-methylpyrrolidinyl, 3-ethylpyrrolidinyl, 2,3-dimethylpyrrolidinyl, 2,3,4-trimethylpyrrolidinyl, 2-propylmorpholino, 3-(1-pyrrolidinyl)pyrrolidinyl, 3-isopropylmorpholino, 2,3-dimethylmorpholino, 4-n-butylpiperidinyl, 3,4,5-trimethylpiperidinyl, 3-pentylpiperidinyl, 4-methylhomopiperazinyl, 4,5-dimethylhomopiperazinyl, 4-hexylhomopiperazinyl, 3-methyl-4-ethylpiperazinyl, 3-methyl-4-n-propyl-1-piperazinyl, 3,4-dimethylpiperazinyl, 4-isopropyl-3-methylpiperazinyl, 4-methyl-3-isopropylpiperazinyl, 4-methylhomomorpholino, 3-propionylpyrrolidinyl, 4-butyrylpiperidinyl, 4-pentanoylpiperazinyl, 3-hexanoylmorpholino, 4-acetylhomopiperazinyl, 3-hydroxymorpholino, 4-hydroxyhomopiperazinyl, 4-hydroxypiperazinyl, 3-hydroxypyrrolidinyl, 3-hydroxymethylpyrrolidinyl, 3-(3-hydroxypropyl) morpholino, 2-hydroxymethylhomomorpholino, 2-(4-methyl-1-piperazinyl)methylhomomorpholino, 4-(1,3-dihydroxy-2-propyl)piperazinyl, 4-ethylhomopiperazinyl, 3-(4-methyl-1-homopiperazinyl)pyrrolidinyl, 4-methyl-3-(1-piperidinyl)methylpiperazinyl, 4-methyl-3-(4-methyl-1-homopiperazinyl)methylpiperazinyl, 4-methyl-3-(4-methyl-1-piperazinyl)methylpiperazinyl, etc.

The above heterocyclic group substituted by a lower alkyl group includes the above heterocyclic groups substituted by 1 to 3 straight chain or branched chain $C_1$–$C_6$ alkyl groups, for example, 4-methylpiperazinyl, 3,4-dimethylpiperazinyl, 3-ethylpyrrolidinyl, 2-propylpyrrolidinyl, 1-methylpyrrolidinyl, 3,4,5-trimethylpiperidinyl, 4-butylpiperidinyl, 3-pentylmorpholino, 4-ethylhomopiperazinyl, 4-methylhomopiperazinyl, 4-hexylpiperazinyl, 4-methylhomopiperazinyl, 4,5-dimethylhomopiperazinyl, 3-methyl-4-ethylpiperazinyl, 3-methyl-4-n-propylpiperazinyl, 4-isopropyl-3-methylpiperazinyl, 4-methyl-3-isopropylpiperazinyl, 4-methylhomomorpholino, etc.

The lower alkoxycarbonyl-substituted lower alkyl group includes a straight chain or branched chain $C_1$–$C_6$ alkyl group which is substituted by a straight chain or branched chain alkoxycarbonyl group having 1 to 6 carbon atoms, for example, methoxycarbonylmethyl, 3-methoxycarbonylpropyl, ethoxycarbonylmethyl, 3-ethoxycarbonylpropyl, 4-ethoxycarbonylbutyl, 5-isopropoxycarbonylpentyl, 6-propoxycarbonylhexyl, 1,1-dimethyl-2-butoxycarbonylethyl, 2-methyl-3-tert-butoxycarbonylpropyl, 2-pentyloxycarbonylethyl, hexyloxycarbonylmethyl, etc.

The lower alkanoyloxy-substituted lower alkyl group includes a straight chain or branched chain $C_1$–$C_6$ alkyl group which is substituted by a straight chain or branched chain $C_2$–$C_6$ alkanoyloxy group, for example, acetyloxymethyl, 2-propionyloxyethyl, 1-butyryloxyethyl, 3-acetyloxypropyl, 4-acetyloxybutyl, 4-isobutyryloxybutyl, 5-pentanoyloxypentyl, 6-acetyloxyhexyl, 6-tert-butylcarbonyloxyhexyl, 1,1-dimethyl-2-hexanoyloxyethyl, 2-methyl-3-acetyloxypropyl, etc.

The lower alkoxy group having optionally a halogen substituent includes a straight chain or branched chain $C_1$–$C_6$ alkoxy group which optionally has 1 to 3 halogen substituents, for example, in addition to the above lower alkoxy groups, trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-chloropropoxy, 2,3-dichloropropoxy, 4,4,4-trichlorobutoxy, 4-fluorobutoxy, 5-chloropentyloxy, 3-chloro-2-methylpropoxy, 6-bromohexyloxy, 5,6-dichlorohexyloxy, etc.

The halogen-substituted lower alkyl group includes a straight chain or branched chain $C_{1-6}$ alkyl group, which has 1 to 3 halogen substituents, for example, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 6-bromohexyl, 5,6-dichlorohexyl, etc.

The carboxy-substituted lower alkyl group includes a carboxyalkyl group wherein the alkyl moiety is a straight chain or branched chain $C_1$–$C_6$ alkyl group, for example, carboxymethyl, 2-carboxyethyl, 1-carboxyethyl, 3-carboxypropyl, 4-carboxybutyl, 5-carboxypentyl, 6-carboxyhexyl, 1,1-dimethyl-2-carboxyethyl, 2-methyl-3-carboxypropyl, etc.

The lower alkoxycarbonyl group includes a straight chain or branched chain alkoxycarbonyl group having 1 to 6 carbon atoms in the alkoxy moiety, for example, methoxycarbonyl, ethoxycarbonyl, propoxycarbonyl, isopropoxycarbonyl, butoxycarbonyl, tert-butoxycarbonyl, pentyloxycarbonyl, hexyloxycarbonyl, etc.

The aminocarbonyl-substituted lower alkoxy group having optionally a lower alkyl group includes a straight chain or branched chain $C_1$–$C_6$ alkoxy group, which has an aminocarbonyl group having optionally 1 to 2 straight chain or branched chain $C_1$–$C_6$ alkyl group, for example, aminocarbonylmethoxy, 2-aminocarbonylethoxy, 1-aminocarbonylethoxy, 3-aminocarbonylpropoxy, 4-aminocarbonylbutoxy, 5-aminocarbonylpentyloxy, 6-aminocarbonylhexyloxy, 1,1-dimethyl-2-aminocarbonylethoxy, 2-methyl-3-aminocarbonylpropoxy, methylaminocarbonylmethoxy, 1-ethylaminocarbonylethoxy, 2-propylaminocarbonylethoxy, 1-ethylaminocarbonylethoxy, 2-propylaminocarbonylethoxy, 3-isopropylaminocarbonylpropoxy, 4-butylaminocarbonylbutoxy, 5-pentylaminocarbonylpentyloxy, 6-hexylaminocarbonylhexyloxy, dimethylaminocarbonylmethoxy, 2-diethylaminocarbonylethoxy, 2-dimethylaminocarbonylethoxy, (N-ethyl-N-propylamino)carbonylmethoxy, 2-(N-methyl-N-hexylamino)carbonylethoxy, etc.

The amino-substituted lower alkyl group having optionally a lower alkyl substituent includes a straight chain or branched chain $C_1$–$C_6$ alkyl group which is substituted by an amino group having optionally 1 to 2 $C_1$–$C_6$ alkyl substituents, for example, aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, 1-ethylaminoethyl, 2-propylaminoethyl, 3-isopropylaminopropyl, 4-butylaminobutyl 5-pentylaminopentyl, 6-hexylaminohexyl, dimethylaminomethyl, (N-ethyl-N-propylamino)methyl, 2-(N-methyl-N-hexylamino)ethyl, etc.

The 5- to 12-membered saturated heteromonocyclic, heterobicyclic or heterospirocyclic group which is formed by combining $R^{12}$ and $R^{13}$ together with the adjacent nitrogen atom to which they bond with or without being intervened with another nitrogen atom or an oxygen atom includes, for example, pyrrolidinyl, piperidinyl, piperazinyl, morpholino, homopiperazinyl, homomorpholino, 1,4-diazabicyclo[4.3.0]nonyl, 1,4-diazabicyclo[4.4.0]decyl, 1,4-diazaspiro[5.5]undecyl, etc.

The lower alkoxy-substituted lower alkyl group includes a straight chain or branched chain $C_1$–$C_6$ alkyl group which has 1 to 3 straight chain or branched chain $C_1$–$C_6$ alkoxy groups, for example, methoxymethyl 3-methoxypropyl, ethoxymethyl, 2-methoxyethyl, 3-ethoxypropyl, 4-ethoxybutyl, 5-isopropoxypentyl, 6-propoxyhexyl, 1,1-dimethyl-2-butoxyethyl, 2-methyl- 3-tert-butoxypropyl, 2-pentyloxyethyl, hexyloxymethyl, etc.

The amino group having optionally a lower alkyl substituent includes an amino group having optionally 1 to 2 straight chain or branched chain $C_1$–$C_6$ alkyl groups, for example, amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, etc.

The above heterocyclic group having a substituent selected from a lower alkyl group, a lower alkoxy-substituted lower alkyl group, a lower alkoxycarbonyl group, an amino group having optionally a lower alkyl substituent and a hydroxy-substituted lower alkyl group includes the above mentioned heterocyclic groups having 1 to 3 substituents selected from a straight chain or branched chain $C_1$–$C_6$ alkyl group, a straight chain or branched chain $C_1$–$C_6$ alkyl group which has 1 to 3 straight chain or branched chain $C_1$–$C_6$ alkoxy group, a straight chain or branched chain alkoxycarbonyl group having 1 to 6 carbon atoms in the alkoxy moiety, an amino group having optionally 1 to 2 straight chain or branched chain $C_1$–$C_6$ alkyl groups and a straight chain or branched chain $C_1$–$C_6$ alkyl group which has 1 to 3 hydroxy substituents, for example, 4-methylpiperazinyl, 3,4-dimethylpiperazinyl, 4-ethylpiperazinyl, 4-methylhomopiperazinyl, 4-dimethylaminopiperidinyl, 4-tert-butoxycarbonylhomopiperazinyl, 4-n-butylhomopiperazinyl, 4-(2-hydroxyethyl)piperazinyl, 3-methylpiperazinyl, 4-(1,3-dihydroxy-2-propyl) piperazinyl, 4-(1,3-dihydroxy-2-propyl)homopiperazinyl, 3,4,5-trimethylpiperazinyl, 4-isopropylpiperazinyl, 3,3,4-trimethylpiperazinyl, 4,5-dimethylhomopiperazinyl, 3-methyl-4-ethylpiperazinyl, 3-methyl-4-n-propylpiperazinyl, 3-n-propyl-4-methylpiperazinyl, 3-methyl-4-isopropylpiperazinyl, 3-ethyl-4-methylpiperazinyl, 3-methyl-4-(2-methoxyethyl) piperazinyl, 3-methyl-4-(2-hydroxyethyl)piperazinyl, 3-isopropyl-4-methylpiperazinyl, 4-methyl-1,4-diazasprio [5.5]undecyl, 3-amino-1,4-diazabicyclo[4.4.0]decyl, 5-hydroxymethyl-1,4-diazabicyclo[4.3.0]nonyl, 3-ethoxycarbonylhomomorpholino, 3-diethylaminomorpholino, 3-methoxymethylpyrrolidinyl, etc.

The lower alkyl group having optionally a halogen substituent includes, for example, in addition to the above lower alkyl groups and halogen-substituted lower alkyl groups.

The pyridyl group having optionally a lower alkyl substituent which may optionally have a halogen substituent on the pyridine ring includes a pyridyl group having 1 to 3 straight chain or branched chain $C_1$–$C_6$ alkyl groups which may optionally 1 to 3 halogen substituents on the pyridine ring, for example, pyridyl, 3-methylpyridyl, 4-ethylpyridyl, 2-propylpyridyl, 3-butylpyridyl, 4-pentylpyridyl, 4-hexylpyridyl, 3,4-dimethylpyridyl, 3,4,5-trimethylpyridyl, 3-trifluoromethylpyridyl, 2-chloromethylpyridyl, 4-(5-bromohexyl)pyridyl, 3-iodomethylpyridyl, 4-(2,2,2,-trifluoroethyl)pyridyl, 4-(5, 6-dichlorohexyl)pyridyl, etc.

The cycloalkyl group includes a $C_3$–$C_8$ cycloalkyl group, for example, cyclopropyl, cyclobutyl, cyclopentyl, cyclohexyl, cycloheptyl, cyclooctyl, etc.

The tetrahydropyranyloxy-substituted lower alkyl group includes a tetrahydropyranyloxy-substituted alkyl group wherein the alkyl moiety is a straight chain or branched chain $C_1$–$C_6$ alkyl group, for example, (2-tetrahydropyranyl)oxymethyl, 2-(3-tetrahydropyranyl) oxyethyl, 1-(4-tetrahydropyranyl)oxyethyl, 3-(2-tetrahydropyranyl)oxypropyl, 4-(3-tetrahydropyranyl) oxybutyl, 5-(4-tetrahydropyranyl)oxypentyl, 6-(2-tetrahydropyranyl)oxyhexyl, 1,1-dimethyl-2-(3-tetrahydropyranyl)oxyethyl, 2-methyl-3-(4-tetrahydropyranyl)oxypropyl, etc.

The phenyl-lower alkyl group includes a phenylalkyl group wherein the alkyl moiety is a straight chain or branched chain $C_1$–$C_6$ alkyl group, for example, benzyl, 2-phenylethyl, 1-phenylethyl, 3-phenylpropyl, 4-phenylbutyl, 5-phenylpentyl, 6-phenylhexyl, 1,1-dimethyl-2-phenylethyl, 2-methyl-3-phenylpropyl, etc.

The phenyl-lower alkoxy group includes a phenylalkoxy group wherein the alkoxy moiety is a straight chain or branched chain $C_1$–$C_6$ alkoxy group, for example, benzyloxy, 2-phenylethoxy, 1-phenylethoxy, 3-phenylpropoxy, 4-phenylbutoxy, 5-phenylpentyloxy, 6-phenylhexyloxy, 1,1-dimethyl-2-phenylethoxy, 2-methyl-3-phenylpropoxy, etc.

The lower alkanoyloxy group includes a straight chain or branched chain $C_1$–$C_6$ alkanoyloxy group, for example, formyloxy, acetyloxy, propionyloxy, butyryloxy, isobutyryloxy, pentanoyloxy, tert-butylcarbonyloxy, hexanoyloxy, etc.

The piperidinyl group having optionally a lower alkyl substituent on the piperidine ring includes a piperidinyl group having optionally a straight chain or branched chain $C_1$–$C_6$ alkyl group, for example, piperidinyl, 1-methyl-4-piperidinyl, 1-ethyl-3-piperidinyl, 1-ethyl-2-piperidinyl, 1-propyl-4-piperidinyl, 1-butyl-4-piperidinyl, 1-pentyl-4-piperidinyl, 1-hexyl-4-piperidinyl, 1-isobutyl-3-piperidinyl, 1-tert-butyl-2-piperidinyl, etc.

The phenyl-lower alkyl group having optionally a lower alkylenedioxy substituent on the phenyl ring includes a phenylalkyl group having optionally a straight chain or branched chain $C_1$–$C_4$ alkylenedioxy group on the phenyl ring wherein the alkyl moiety is a straight chain or branched chain $C_1$–$C_6$ alkyl. group, in addition to the above phenyl-lower alkyl groups, for example, 3,4-methylenedioxybenzyl, 2-(3,4-ethylenedioxyphenyl)ethyl, 1-(3,4-ethylenedioxyphenyl)ethyl, 3-(2,3-trimethylenedioxyphenyl)propyl, 4-(3,4-tetramethylenedioxyphenyl)butyl, 5-(3,4-methylenedioxyphenyl)pentyl, 6-(2,3-trimethylenedioxyphenyl)hexyl, etc.

The lower alkylenedioxy group includes a straight chain or branched chain $C_1$–$C_4$ alkylenedioxy group, for example, methylenedioxy, ethylenedioxy, trimethylenedioxy, tetramethylenedioxy, etc.

The 5- to 10-membered, saturated or unsaturated heteromonocyclic or heterobicyclic residue having 1 to 4 heteroatoms selected from a nitrogen atom, an oxygen atom and a sulfur atom includes, for example, pyrrolidinyl, piperidinyl, piperazinyl, morpholino, 1-azabicyclooctyl, homopiperazinyl, homomorpholino, 1,4-diazabicyclo[4.3.0] nonyl, 1,4-diazabicyclo[4.4.0]decyl, pyridyl, 1,2,5,6-tetrahydropyridyl, thienyl, 1,2,4-triazolyl, 1,2,3,4-tetrazolyl, 1,3,4-triazoly, quinolyl, 1,4-dihydroquinolyl, benzothiazolyl, pyrazyl, pyrimidyl, pyridazinyl, pyrrolyl, pyrrolinyl, carbostyril, 1,3-dioxolanyl, thiomorpholino, 3,4-dihydrocarbostyril, 1,2,3,4-tetrahydroquinolyl, 2,3,4,5-tetrahydrofuryl, indolyl, isoindolyl, 3H-indolyl, indolinyl, indolidinyl, indazolyl, benzimidazolyl, benzoxazolyl, imidazolinyl, imidazolidinyl, isoquinolyl, naphthylidinyl, quinazolidinyl, quinoxalinyl, cinnolinyl, phthalazinyl, chromanyl, isoindolinyl, isochromanyl, pyrazolyl, 1,3,4-oxadiazolyl, 1,3,4-thiadiazolyl, thienyl, imidazolyl, pyrazolidinyl, benzofuryl, 2,3-dihydrobenzo[b]furyl, benzothienyl, tetrahydropyranyl, 4H-chromenyl, 1H-indazolyl, 2-imidazolinyl, 2-pyrrolinyl, furyl, oxazolyl, isoxazolyl, thiazolyl, thiazolinyl, isothiazolyl, pyranyl, pyrazolidinyl, 2-pyrazolinyl, quinuclidinyl, 1,4-benzoxazinyl, 3,4-dihydro-2H-1,4-benzoxazinyl, 3,4-dihydro-2H-1,4-benzothiazinyl, 1,4-benzothiazinyl, 1,2,3,4-tetrahydroisoquinolyl, 1,2,3,4-tetrahydroquinoxalinyl, 1,3-dithia-2,4-dihydronaphthalenyl, 1,4-dithianaphthalenyl, 2,5-dihydrofurano[3.4-c]pyridyl, 2,3,4,5,6,7-hexahydro-1H-azepinyl, 1,2,3,4,5,6,7,8-octahydroazocinyl, 1,2,3,4,5,6, -tetrahydrooxepinyl, 1,3-dioxolanyl, 3,4,5,6-tetrahydro-2H-pyranyl, 5,6-dihydro-2H-pyranyl, etc.

The above heterocyclic groups having 1 to 3 substituents selected from (i) a lower alkyl group; (ii) a group: —(B)$_l$— NR$^{12}$R$^{13}$ (l is the same as defined above, B is a group: —CO—A— (A is the same as defined above), a carbonyl group or a lower alkylene group, R$^{12}$ and R$^{13}$ are the same or different, and each are a hydrogen atom, a lower alkyl group, an amino-substituted lower alkyl group having optionally a lower alkyl substituent, or combine together with the adjacent nitrogen atom to which they bond to form a 5- to 12-membered saturated heteromonocyclic, heterobicyclic or spiro-cyclic hetero ring with or without being intervened with another nitrogen atom or an oxygen atom, said heterocyclic group may optionally have a substituent selected from a lower alkyl group, a lower alkoxycarbonyl group, a lower alkoxy-substituted lower alkyl group, an amino group having optionally a lower alkyl substituent and a hydroxy-substituted lower alkyl group); (iii) a lower alkoxycarbonyl group; (iv) a hydroxy-substituted lower alkyl group; (v) a pyridyl group being optionally substituted by a lower alkyl group having optionally a halogen substituent on the pyridine ring; (vi) a halogen-substituted lower alkyl group; (vii) a lower alkoxy group; (viii) a cycloalkyl group; (ix) a hydroxy group; (x) a tetrahydropyranyloxy-substituted lower alkyl group; (xi) a pyrimidyl group; (xii) a lower alkoxy-substituted lower alkyl group; (xiii) a carboxyl group; (xiv) a phenyl-lower alkoxy group; (xv) a phenyl-lower alkyl group having optionally a lower alkylenedioxy substituent on the phenyl ring; (xvi) a lower alkanoyloxy group; and (xvii) a piperidinyl group having optionally a lower alkyl substituent on the piperidine ring includes the above heterocyclic groups having 1 to 3 substituents selected from (i) a straight chain or branched chain $C_1$–$C_6$ alkyl group; (ii) a group: —(B)$_l$—NR$^{12}$R$^{13}$ (l is the same as defined above, B is a group: —CO—A— (A is the same as defined above), a carbonyl group or a straight chain or branched chain $C_1$–$C_6$ alkylene group, R$^{12}$ and R$^{13}$ are the same or different, and each are a hydrogen atom, a straight chain or branched chain $C_1$–$C_6$ alkyl group, or a straight chain or branched chain $C_1$–$C_6$ alkyl group which has an amino group having optionally 1 to 2 straight chain or branched chain alkyl substituents, or both combine together with the adjacent nitrogen atom to which they bond to form a 5- to 12-membered saturated heteromonocyclic, heterobicyclic or sprio-cyclic hetero ring with or without being intervened with another nitrogen atom or an oxygen atom, said heterocyclic group may optionally have 1 to 3 substituents selected from a straight chain or branched chain $C_1$–$C_6$ alkyl group, a straight chain or branched chain $C_1$–$C_6$ alkyl group which has 1 to 3 straight chain or branched chain $C_1$–$C_6$ alkoxy substituents, a straight chain or branched chain alkoxycarbonyl group having 1 to 6 carbon atoms in the alkoxy moiety, an amino group having optionally 1 to 2 straight chain or branched chain $C_1$–$C_6$ alkyl substituent and a straight chain or branched chain $C_1$–$C_6$ alkyl group having 1 to 3 hydroxy substituents); (iii) an alkoxycarbonyl group having 1 to 6 carbon atoms in the alkoxy moiety; (iv) a straight chain or branched chain $C_1$–$C_6$ alkyl group having 1 to 3 hydroxy substituents; (v) a pyridyl group having optionally 1 to 3 straight chain or branched chain $C_1$–$C_6$ alkyl groups which have optionally 1 to 3 halogen substituents on the pyridine ring; (vi) a straight chain or branched chain $C_1$–$C_6$ alkyl group having 1 to 3 halogen substituents; (vii) a straight chain or branched chain $C_1$–$C_6$ alkoxy group; (viii) a $C_3$–$C_8$ cycloalkyl group; (ix) a hydroxy group; (x) a tetrahydropyranyloxy-substituted alkyl group wherein the alkyl moiety is a straight chain or branched chain $C_1$–$C_6$ alkyl group; (xi) a pyrimidyl group; (xii) a straight chain or branched chain $C_1$–$C_6$ alkyl group having 1 to 3 straight chain or branched chain $C_1$–$C_6$ alkoxy substituents; (xiii) a carboxyl group; (xiv) a phenyl alkoxy group wherein the alkoxy moiety is a straight chain or branched chain $C_1$–$C_6$ alkoxy group; (xv) a phenylalkyl group having optionally a straight chain or branched chain $C_1$–$C_4$ alkylenedioxy substituent on the phenyl ring, wherein the alkyl moiety is a straight chain or branched chain $C_1$–$C_6$ alkyl group; (xvi) a straight chain or branched chain $C_1$–$C_6$ alkanoyloxy group; and (xvii) a piperidinyl group having optionally 1 to 3 straight chain or branched chain $C_1$–$C_6$ alkyl substituents on the piperidine ring, for example, 4-methylpiperazinyl, 4-(4-methyl-1-piperazinyl)piperidinyl, 2-(4-methyl-1-piperazinylmethyl)morpholino, 2-(4-methyl-1-piperazinylmethyl)pyrrolidinyl, 3-(4-methyl-1-piperazinyl)pyrrolidinyl, 1-ethyl-1,2,3,4-tetrazolyl, 1-tert-butoxycarbonylpiperidinyl, 1-methylpiperidinyl, 2,2-dimethyl-1,3-dioxolanyl, 4-(3,4-dimethyl-1-piperazinyl)piperidinyl, 4-(4-ethyl-1-piperazinyl)piperidinyl, 4-[N-(2-diethylaminoethyl)-N-methylamino]piperidinyl, 4-(4-methyl-1-homopiperazinyl)piperidinyl, 2-(4-ethyl-1-piperazinylmethyl)morpholino, 4-dimethylaminopiperidinyl, 2-morpholinomethylpyrrolidinyl, 4-(1-pyrrolidinyl)piperdinyl, 4-isopentylpiperazinyl, 4-(2-hydroxyethyl)piperazinyl, 2-(1-pyrrolidinylmethyl)morpholino, 4-morpholinopiperidinyl, 2-aminomethylmorphlino, 1-dimethylaminomethylcarbonylpiperidinyl, 1-methylimidazolyl, 4-(2-pyridyl)piperazinyl, 4-(3,4-methylenedioxybenzyl)piperazinyl, 1-(4-chlorobutyl)-1,2,3,4-tetrazolyl, 2-methoxycarbonylpyridyl, 2-carboxypyridyl, 4-isopropylpyridyl, 4-hydroxypiperidinyl, 2-methyl-3-hydroxy-2,5-dihydrofuran[3,4-c]pyridyl, 1-cyclohexyl-1,2,34-tetrazolyl, 3-(4-methyl-1-piperazinyl)pyrrolidinyl, 1-[(3-3,4,5,6-tetrahydro-2H-pyranyl)methyl]-1,2,3,4-tetrazolyl, 1-(3-chloropropyl)-1,2,3,4-tetrazolyl, 2-carbamoylpyrrolidinyl, 4-(3-trifluoromethyl-2-pyridyl)piperazinyl, 4-benzylpiperidinyl, 4-n-butyl-1,2,3,4-tetrazolyl, 4-carbamoylpiperidinyl, 2-(4-methyl-1-piperazinyl)homomorpholino, 2-methylmorpholino, 2-methoxymethylmorpholino, 2-chloromethylmorpholino, 2-hydroxymethylmorpholino, 2-n-butoxymethylmorpholino, 2-(4-methyl-1-homopiperazinylmethyl)morpholino, 6,7-dimethoxy-1,2,3,4-tetrahydroisoquinolyl, 2-(4-methyl-1-homopiperazinylmethyl)homomorpholino, 2-chloromethylhomomorpholino, 2-hydroxymethylhomomorpholino, 4-hydroxypiperazinyl, 2-methoxymethyl-1,2,3,4,5,6-hexahydrooxepinyl, 4-(2-phenylethoxy)piperidinyl, 4-benzyloxypiperidinyl, 4-hydroxy-3-methylpiperazinyl, 4-methylhomopiperazinyl, 4-acetyloxypiperazinyl, 4-methoxypiperazinyl, 4-(4-tert-butoxycarbonyl-1-homopiperazinyl)piperidnyl, 4-(4-n-butyl-1-homopiperazinyl)piperidinyl, 4-(1-methyl-4-piperidinyl)homopiperazinyl, 3-(4-methyl-1-homopiperazinyl)piperidinyl, 2-(4-dimethylamino-1-piperidinylmethyl)morpholino, 2-(4-methyl-1-piperazinylmethyl)homomorpholino, 2-[4-(2-hydroxyethyl)-1-piperazinylmethyl]morpholino, 4-(3-methyl-1-piperazinyl)piperidinyl, 4-(4-ethyl-1-homopiperazinyl)piperidinyl, 3-(4-methyl-1-homopiperazinyl)pyrrolidinyl, 4-[4-(1,3-dihydroxy-2-propyl)-1-piperazinyl]piperidinyl, 4-[4-(1,3-dihydoxy-2-propyl)-1-homopiperazinyl]piperidnyl, 4-methyl-3-(1-piperidinylmethyl)piperazinyl, 4-methyl-3-(4-methyl-1-piperazinylmethyl)piperazinyl, 4-methyl-3-(4-methyl-1-homopiperazinylmethyl)piperazinyl, 3,4,5-trimethoxypiperazinyl, 4-isopropylpiperazinyl, 4-(1,4-diazabicyclo[4.3.0]nonyl)piperidinyl, (3,3,4-trimethyl-1-piperazinyl)piperidinyl, 4-(1,4-diazabicyclo[4.4.0]decyl)piperidinyl, 4-(3-methyl-4-ethyl-1-piperazinyl)piperidinyl, 4-(3-methyl-4-propyl-1-piperazinyl)piperidinyl, 4-(3-propyl-4-methyl-1-piperazinyl)piperidinyl, 4-(3-methyl-4-isopropyl-1-piperazinyl)piperidinyl, 4-(3-ethyl-4-methyl-1-piperazinyl)piperidinyl, 4-[3-methyl-4-(2-methoxyethyl)-1-piperazinyl]piperidinyl, 4-[3-methyl-4-(2-hydroxyethyl)-1-piperazinyl]piperidinyl, 4-(4-methyl-1-1,4-diazaspiro[5.5]undecyl)piperidinyl, 4-(4-methyl-3-isopropyl-1-piperazinyl)piperidinyl, 4-(2-pyrimidyl)piperazinyl, etc.

The lower alkenyloxy group includes a $C_2$–$C_6$ straight chain or branched chain alkenyloxy group, for example, vinyloxy, 1-methylvinyloxy, 2,2-dimethylvinyloxy, 1,2-dimethylvinyloxy, 1-propylvinyloxy, allyloxy, 2-butenyloxy, 3-butenyloxy, 1-ethylvinyloxy, 1-methylallyloxyl, 1-pentenyloxy, 2-pentenyloxy, 2-hexenyloxy, 3-methyl-1-butenyloxy, 1-butenyloxy, etc.

The cycloalkyloxy group includes a $C_3$–$C_8$ cycloalkyloxy group, for example, cyclopropyloxy, cyclobutyloxy, cyclopentyloxy, cyclohexyloxy, cycloheptyloxy, cyclooctyloxy, etc.

The lower alkylthio group includes a $C_1$–$C_6$ straight chain or branched chain alkylthio group, for example, methylthio, ethylthio, propylthio, isopropylthio, butylthio, isobutylthio, tert-butylthio, pentylthio, hexylthio, etc.

The lower alkenyl group includes a $C_2$–$C_6$ straight chain or branched chain alkenyl group, for example, vinyl, 1-methylvintyl, 2,2-dimethylvinyl, 1,2-dimethylvinyl, 1-propenylvinyl, allyl, 2-butenyl, 3-butenyl, 1-ethylvinyl, 1-methylallyl, 1-pentenyl, 2-pentenyl, 2-hexenyl, 3-methyl-1-butenyl, 1-butenyl, etc.

The present invention specifically includes the following compounds.

(1) A thiazole derivative of the formula (1) wherein $R^1$ and $R^2$ are the same or different and each are a hydrogen atom or a lower alkyl group, $R^3$ is a group of the formula:

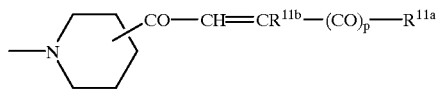

($R^{11b}$, p and $R^{11a}$ are the same as defined in the formula (1)), $R^4$ is a hydrogen atom, and u is 0, or a salt thereof.

(2) A thiazole derivative of the formula (1) wherein $R^1$ and $R^2$ are the same or different and each are a hydrogen atom or a lower alkyl group, $R^3$ is a group of the formula:

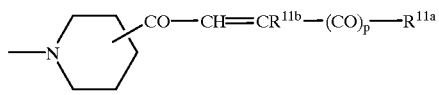

($R^{11b}$, p and $R^{11a}$ are the same as defined in the formula (1)), $R^4$ is a lower alkanoyloxy-lower alkyl group, and u is 0, or a salt thereof.

(3) A thiazole derivative of the formula (1) wherein $R^1$ and $R^2$ are the same or different and each are a hydrogen atom or a lower alkyl group, $R^3$ is a group of the formula:

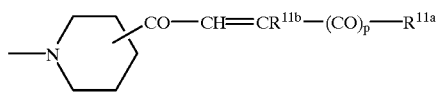

($R^{11b}$, p and $R^{11a}$ are the same as defined in the formula (1)), $R^4$ is a hydrogen atom, and u is 1, or a salt thereof.

(4) A thiazole derivative of the formula (1) wherein $R^1$ and $R^2$ are the same or different and each are a hydrogen atom or a lower alkyl group, $R^3$ is a group of the formula:

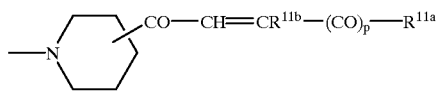

($R^{11b}$, p and $R^{11a}$ are the same as defined in the formula (1)), $R^4$ is a lower alkanoyloxy-lower alkyl group, and u is 1, or a salt thereof.

(5) A thiazole derivative of the formula (1) wherein $R^1$ and $R^2$ combine to form a group: —$(CH_2)_n$— (n is 4), $R^3$ is a group of the formula:

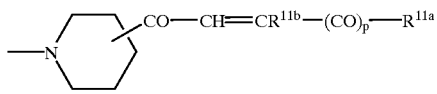

($R^{11b}$, p and $R^{11a}$ are the same as defined in the formula (1)), $R^4$ is a hydrogen atom, and u is 0, or a salt thereof.

(6) A thiazole derivative of the formula (1) wherein $R^1$ and $R^2$ combine to form a group: —$(CH_2)_n$— (n is 4), $R^3$ is a group of the formula:

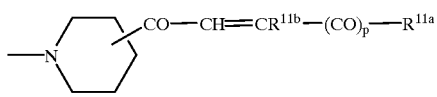

($R^{11b}$, p and $R^{11a}$ are the same as defined in the formula (1)), $R^4$ is a lower alkanoyloxy-lower alkyl group and u is 0, or a salt thereof.

(7) A thiazole derivative of the formula (1) wherein $R^1$ and $R^2$ combine to form a group: —$(CH_2)_n$— (n is 4), $R^3$ is a group of the formula:

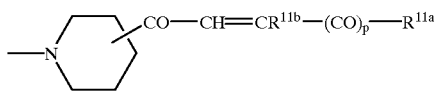

($R^{11b}$, p and $R^{11a}$ are the same as defined in the formula (1)), $R^4$ is a hydrogen atom, and u is 1, or a salt thereof.

(8) A thiazole derivative of the formula (1) wherein $R^1$ and $R^2$ combine to form a group: —$(CH_2)_n$— (n is 4), $R^3$ is a group of the formula:

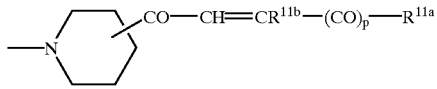

($R^{11b}$, p and $R^{11a}$ are the same as defined in the formula (1)), $R^4$ is a lower alkanoyloxy-lower alkyl group and u is 1, or a salt thereof.

(9) A thiazole derivative of the formula (1) wherein $R^1$ and $R^2$ combine to form a group: —$(CH_2)_n$— (n is 5), $R^3$ is a group of the formula:

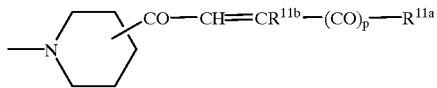

($R^{11b}$, p and $R^{11a}$ are the same as defined in the formula (1)), $R^4$ is a hydrogen atom, and u is 0, or a salt thereof.

(10) A thiazole derivative of the formula (1) wherein $R^1$ and $R^2$ combine to form a group: —$(CH_2)_n$— (n is 5), $R^3$ is a group of the formula:

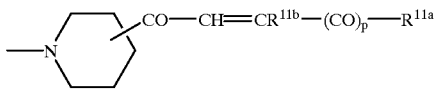

($R^{11b}$, p and $R^{11a}$ are the same as defined in the formula (1)), $R^4$ is a lower alkanoyloxy-lower alkyl group and u is 0, or a salt thereof.

(11) A thiazole derivative of the formula (1) wherein $R^1$ and $R^2$ combine to form a group: —$(CH_2)_n$— (n is 5), $R^3$ is a group of the formula:

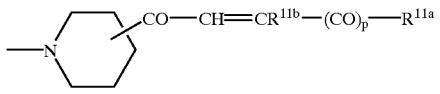

($R^{11b}$, p and $R^{11a}$ are the same as defined in the formula (1)), $R^4$ is a hydrogen atom, and u is 1, or a salt thereof.

(12) A thiazole derivative of the formula (1) wherein $R^1$ and $R^2$ combine to form a group: —$(CH_2)_n$— (n is 5), $R^3$ is a group of the formula:

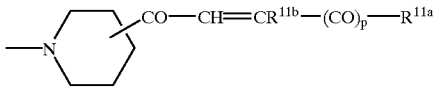

($R^{11b}$, p and $R^{11a}$ are the same as defined in the formula (1)), $R^4$ is a lower alkanoyloxy-lower alkyl group and u is 1, or a salt thereof.

(13) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

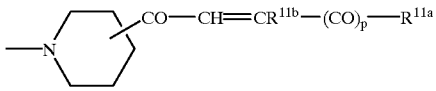

($R^{11b}$, p and $R^{11a}$ are the same as defined in the formula (1)), $R^4$ is a hydrogen atom, and u is 0, or a salt thereof.

(14) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

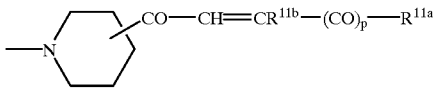

($R^{11b}$, p and $R^{11a}$ are the same as defined in the formula (1)), $R^4$ is a lower alkanoyloxy-lower alkyl group and u is 0, or a salt thereof.

(15) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

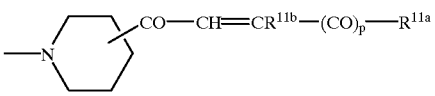

($R^{11b}$, p and $R^{11a}$ are the same as defined in the formula (1)), $R^4$ is a hydrogen atom, and u is 1, or a salt thereof.

(16) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

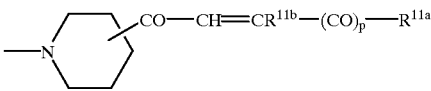

($R^{11b}$, p and $R^{11a}$ are the same as defined in the formula (1)), $R^4$ is a lower alkanoyloxy-lower alkyl group and u is 1, or a salt thereof.

(17) A thiazole derivative of the formula (1) wherein $R^1$ and $R^2$ are the same or different and each are a hydrogen atom or a lower alkyl group, $R^3$ is a group of the formula:

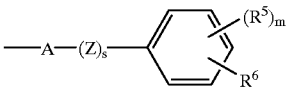

(s is 0, $R^6$ is a group: —CO—CH=$CR^{11b}$—$(CO)_p$—$R^{11a}$ ($R^{11b}$, p and $R^{11a}$ are the same as defined in the formula (1)), $R^5$, m, A and Z are the same as defined in the formula (1)), $R^4$ is a hydrogen atom, and u is 0, or a salt thereof.

(18) A thiazole derivative of the formula (1) wherein $R^1$ and $R^2$ are the same or different and each are a hydrogen atom or a lower alkyl group, $R^3$ is a group of the formula:

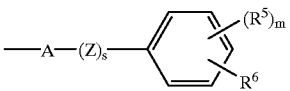

(s is 0, $R^6$ is a group: —CO—CH=$CR^{11b}$—$(CO)_p$—$R^{11a}$ ($R^{11b}$, p and $R^{11a}$ are the same as defined in the formula (1)), $R^5$, m, A and Z are the same as defined in the formula (1)), $R^4$ is a lower alkanoyloxy-lower alkyl group and u is 0, or a salt thereof.

(19) A thiazole derivative of the formula (1) wherein $R^1$ and $R^2$ are the same or different and each are a hydrogen atom or a lower alkyl group, $R^3$ is a group of the formula:

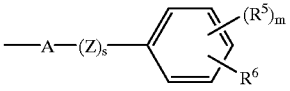

(s is 0, $R^6$ is a group: —CO—CH=$CR^{11b}$—$(CO)_p$—$R^{11a}$ ($R^{11b}$, p and $R^{11a}$ are the same as defined in the formula (1)), $R^5$, m, A and Z are the same as defined in the formula (1)), $R^4$ is a hydrogen atom, and u is 1, or a salt thereof.

(20) A thiazole derivative of the formula (1) wherein $R^1$ and $R^2$ are the same or different and each are a hydrogen atom or a lower alkyl group, $R^3$ is a group of the formula:

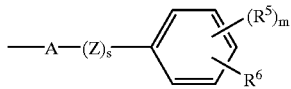

(s is 0, $R^6$ is a group: —CO—CH=$CR^{11b}$—$(CO)_p$—$R^{11a}$ ($R^{11b}$, p and $R^{11a}$ are the same as defined in the formula (1)), $R^5$, m, A and Z are the same as defined in the formula (1)), $R^4$ is a lower alkanoyloxy-lower alkyl group and u is 1, or a salt thereof.

(21) A thiazole derivative of the formula (1) wherein $R^1$ and $R^2$ combine to form a group: —$(CH_2)_n$— (n is 4), $R^3$ is a group of the formula:

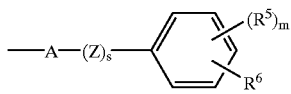

(s is 0, $R^6$ is a group: —CO—CH=$CR^{11b}$—$(CO)_p$—$R^{11a}$ ($R^{11b}$, p and $R^{11a}$ are the same as defined in the formula (1)), $R^5$, m, A and Z are the same as defined in the formula (1)), $R^4$ is a hydrogen atom, and u is 0, or a salt thereof.

(22) A thiazole derivative of the formula (1) wherein $R^1$ and $R^2$ combine to form a group: —$(CH_2)_n$— (n is 4), $R^3$ is a group of the formula:

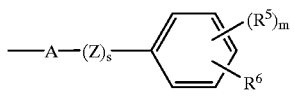

(s is 0, $R^6$ is a group: —CO—CH=$CR^{11b}$—$(CO)_p$—$R^{11a}$ ($R^{11b}$, p and $R^{11a}$ are the same as defined in the formula (1)), $R^5$, m, A and Z are the same as defined in the formula (1)), $R^4$ is a lower alkanoyloxy-lower alkyl group and u is 0, or a salt thereof.

(23) A thiazole derivative of the formula (1) wherein $R^1$ and $R^2$ combine to form a group: —$(CH_2)_n$— (n is 4), $R^3$ is a group of the formula:

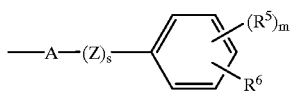

(s is 0, $R^6$ is a group: —CO—CH=$CR^{11b}$—$(CO)_p$—$R^{11a}$ ($R^{11b}$, p and $R^{11a}$ are the same as defined in the formula (1)), $R^5$, m, A and Z are the same as defined in the formula (1)), $R^4$ is a hydrogen atom, and u is 1, or a salt thereof.

(24) A thiazole derivative of the formula (1) wherein $R^1$ and $R^2$ combine to form a group: —$(CH_2)_n$— (n is 4), $R^3$ is a group of the formula:

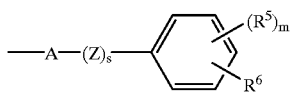

(s is 0, $R^6$ is a group: —CO—CH=$CR^{11b}$—$(CO)_p$—$R^{11a}$ ($R^{11b}$, p and $R^{11a}$ are same as defined in the formula (1)), $R^5$, m, A and Z are the same as defined in the formula (1)), $R^4$ is a lower alkanoyloxy-lower alkyl group and u is 1, or a salt thereof.

(25) A thiazole derivative of the formula (1) wherein $R^1$ and $R^2$ combine to form a group: —$(CH_2)_n$— (n is 5), $R^3$ is a group of the formula:

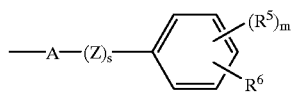

(s is 0, $R^6$ is a group: —CO—CH=$CR^{11b}$—$(CO)_p$—$R^{11a}$ ($R^{11b}$, p and $R^{11a}$ are the same as defined in the formula (1)), $R^5$, m, A and Z are the same as defined in the formula (1)), $R^4$ is a hydrogen atom, and u is 0, or a salt thereof.

(26) A thiazole derivative of the formula (1) wherein $R^1$ and $R^2$ combine to form a group: —$(CH_2)_n$— (n is 5), $R^3$ is a group of the formula:

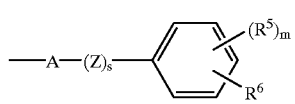

(s is 0, $R^6$ is a group: —CO—CH=$CR^{11b}$—$(CO)_p$—$R^{11a}$ ($R^{11b}$, p and $R^{11a}$ are the same as defined in the formula (1)), $R^5$, m, A and Z are the same as defined in the formula (1)), $R^4$ is a lower alkanoyloxy-lower alkyl group and u is 0, or a salt thereof.

(27) A thiazole derivative of the formula (1) wherein $R^1$ and $R^2$ combine to form a group: —$(CH_2)_n$— (n is 5), $R^3$ is a group of the formula:

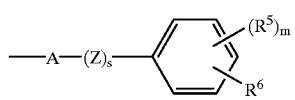

(s is 0, $R^6$ is a group: —CO—CH=$CR^{11b}$—$(CO)_p$—$R^{11a}$ ($R^{11b}$, p and $R^{11a}$ are the same as defined in the formula (1)), $R^5$, m, A and Z are the same as defined in the formula (1)), $R^4$ is a hydrogen atom, and u is 1, or a salt thereof.

(28) A thiazole derivative of the formula (1) wherein $R^1$ and $R^2$ combine to form a group: —$(CH_2)_n$— (n is 5), $R^3$ is a group of the formula:

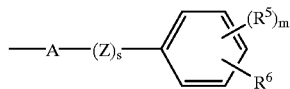

(s is 0, $R^6$ is a group: —CO—CH=$CR^{11b}$—$(CO)_p$—$R^{11a}$ ($R^{11b}$, p and $R^{11a}$ are the same as defined in the formula (1)), $R^5$, m, A and Z are the same as defined in the formula (1)), $R^4$ is a lower alkanoyloxy-lower alkyl group and u is 1, or a salt thereof.

(29) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

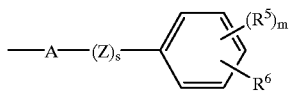

(s is 0, $R^6$ is a group: —CO—CH=$CR^{11b}$—$(CO)_p$—$R^{11a}$ ($R^{11b}$, p and $R^{11a}$ are the same as defined in the formula (1)), $R^5$, m, A and Z are the same as defined in the formula (1)), $R^4$ is a hydrogen atom, and u is 0, or a salt thereof.

(30) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

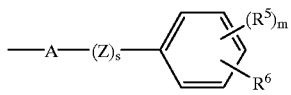

(s is 0, $R^6$ is a group: —CO—CH=$CR^{11b}$—$(CO)_p$—$R^{11a}$ ($R^{11b}$, p and $R^{11a}$ are the same as defined in the formula (1)), $R^5$, m, A and Z are the same as defined in the formula (1)), $R^4$ is a lower alkanoyloxy-lower alkyl group and u is 0, or a salt thereof.

(31) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

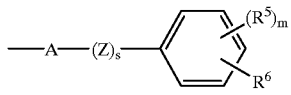

(s is 0, $R^6$ is a group: —CO—CH=$CR^{11b}$—$(CO)_p$—$R^{11a}$ ($R^{11b}$, p and $R^{11a}$ are the same as defined in the formula (1)), $R^5$, m, A and Z are the same as defined in the formula (1)), $R^4$ is a hydrogen atom, and u is 1, or a salt thereof.

(32) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

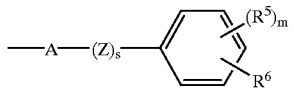

(s is 0, $R^6$ is a group: —CO—CH=$CR^{11b}$—$(CO)_p$—$R^{11a}$ ($R^{11b}$, p and $R^{11a}$ are the same as defined in the formula (1)), $R^5$, m, A and Z are the same as defined in the formula (1)), $R^4$ is a lower alkanoyloxy-lower alkyl group and u is 1, or a salt thereof.

(33) A thiazole derivative of the formula (1) wherein $R^1$ and $R^2$ are the same or different, and each are a hydrogen atom or a lower alkyl group, $R^3$ is a group of the formula:

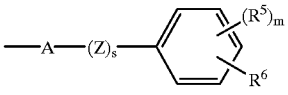

(s is 1, Z is an oxygen atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a hydrogen atom, and u is 0, or a salt thereof.

(34) A thiazole derivative of the formula (1) wherein $R^1$ and $R^2$ are the same or different, and each are a hydrogen atom or a lower alkyl group, $R^3$ is a group of the formula:

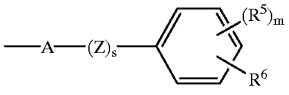

(s is 1, Z is an oxygen atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a lower alkanoyloxy-lower alkyl group and u is 0, or a salt thereof.

(35) A thiazole derivative of the formula (1) wherein $R^1$ and $R^2$ are the same or different, and each are a hydrogen atom or a lower alkyl group, $R^3$ is a group of the formula:

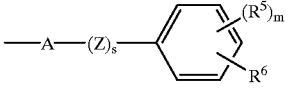

(s is 1, Z is an oxygen atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a hydrogen atom, and u is 1, or a salt thereof.

(36) A thiazole derivative of the formula (1) wherein $R^1$ and $R^2$ are the same or different, and each are a hydrogen atom or a lower alkyl group, $R^3$ is a group of the formula:

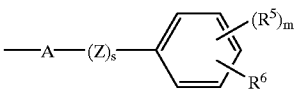

(s is 1, Z is an oxygen atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a lower alkanoyloxy-lower alkyl group and u is 1, or a salt thereof.

(37) A thiazole derivative of the formula (1) wherein $R^1$ and $R^2$ combine to form a group: —$(CH_2)_n$— (n is 4), $R^3$ is a group of the formula:

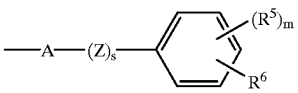

(s is 1, Z is an oxygen atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a hydrogen atom, and u is 0, or a salt thereof.

(38) A thiazole derivative of the formula (1) wherein $R^1$ and $R^2$ combine to form a group: —$(CH_2)_n$— (n is 4), $R^3$ is a group of the formula:

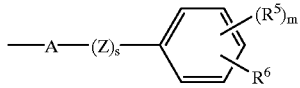

(s is 1, Z is an oxygen atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a lower alkanoyloxy-lower alkyl group and u is 0, or a salt thereof.

(39) A thiazole derivative of the formula (1) wherein $R^1$ and $R^2$ combine to form a group: —$(CH_2)_n$— (n is 4), $R^3$ is a group of the formula:

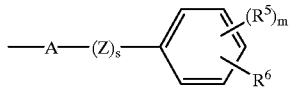

(s is 1, Z is an oxygen atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a hydrogen atom, and u is 1, or a salt thereof.

(40) A thiazole derivative of the formula (1) wherein $R^1$ and $R^2$ combine to form a group: —$(CH_2)_n$— (n is 4), $R^3$ is a group of the formula:

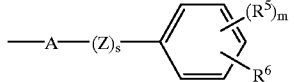

(s is 1, Z is an oxygen atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a lower alkanoyloxy-lower alkyl group and u is 1, or a salt thereof.

(41) A thiazole derivative of the formula (1) wherein $R^1$ and $R^2$ combine to form a group: —$(CH_2)_n$— (n is 5), $R^3$ is a group of the formula:

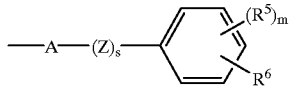

(s is 1, Z is an oxygen atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a hydrogen atom, and u is 0, or a salt thereof.

(42) A thiazole derivative of the formula (1) wherein $R^1$ and $R^2$ combine to form a group: —$(CH_2)_n$— (n is 5), $R^3$ is a group of the formula:

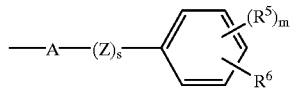

(s is 1, Z is an oxygen atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a lower alkanoyloxy-lower alkyl group and u is 0, or a salt thereof.

(43) A thiazole derivative of the formula (1) wherein $R^1$ and $R^2$ combine to form a group: —$(CH_2)_n$— (n is 5), $R^3$ is a group of the formula:

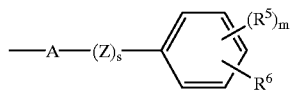

(s is 1, Z is an oxygen atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a hydrogen atom, and u is 1, or a salt thereof.

(44) A thiazole derivative of the formula (1) wherein $R^1$ and $R^2$ combine to form a group: —$(CH_2)_n$— (n is 5), $R^3$ is a group of the formula:

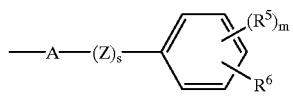

(s is 1, Z is an oxygen atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a lower alkanoyloxy-lower alkyl group and u is 1, or a salt thereof.

(45) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

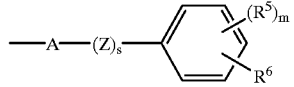

(s is 1, Z is an oxygen atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a hydrogen atom, and u is 0, or a salt thereof.

(46) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

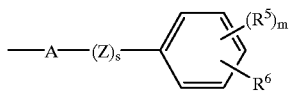

(s is 1, Z is an oxygen atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a lower alkanoyloxy-lower alkyl group and u is 0, or a salt thereof.

(47) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

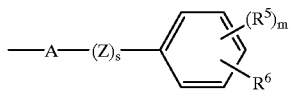

(s is 1, Z is an oxygen atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a hydrogen atom, and u is 1, or a salt thereof.

(48) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

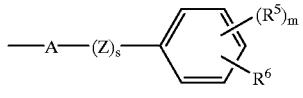

(s is 1, Z is an oxygen atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a lower alkanoyloxy-lower alkyl group and u is 1, or a salt thereof.

(49) A thiazole derivative of the formula (1) wherein $R^1$ and $R^2$ are the same or different and each are a hydrogen atom or a lower alkyl group, $R^3$ is a group of the formula:

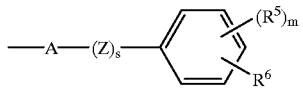

(s is 1, Z is a sulfur atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a hydrogen atom, and u is 0, or a salt thereof.

(50) A thiazole derivative of the formula (1) wherein $R^1$ and $R^2$ are the same or different and each are a hydrogen atom or a lower alkyl group, $R^3$ is a group of the formula:

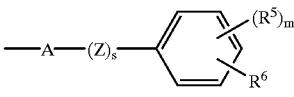

(s is 1, Z is a sulfur atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a lower alkanoyloxy-lower alkyl group and u is 0, or a salt thereof.

(51) A thiazole derivative of the formula (1) wherein $R^1$ and $R^2$ are the same or different and each are a hydrogen atom or a lower alkyl group, $R^3$ is a group of the formula:

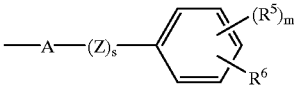

(s is 1, Z is a sulfur atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a hydrogen atom, and u is 1, or a salt thereof.

(52) A thiazole derivative of the formula (1) wherein $R^1$ and $R^2$ are the same or different and each are a hydrogen atom or a lower alkyl group, $R^3$ is a group of the formula:

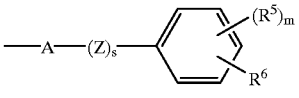

(s is 1, Z is a sulfur atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a lower alkanoyloxy-lower alkyl group and u is 1, or a salt thereof.

(53) A thiazole derivative of the formula (1) wherein $R^1$ and $R^2$ combine to form a group: —$(CH_2)_n$— (n is 4), $R^3$ is a group of the formula:

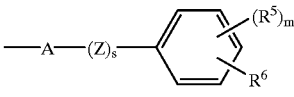

(s is 1, Z is a sulfur atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a hydrogen atom, and u is 0, or a salt thereof.

(54) A thiazole derivative of the formula (1) wherein $R^1$ and $R^2$ combine to form a group: —$(CH_2)_n$— (n is 4), $R^3$ is a group of the formula:

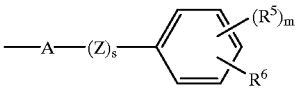

(s is 1, Z is a sulfur atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a lower alkanoyloxy-lower alkyl group and u is 0, or a salt thereof.

(55) A thiazole derivative of the formula (1) wherein $R^1$ and $R^2$ combine to form a group: —$(CH_2)_n$— (n is 4), $R^3$ is a group of the formula:

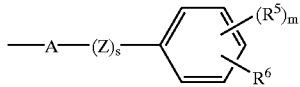

(s is 1, Z is a sulfur atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a hydrogen atom, and u is 1, or a salt thereof.

(56) A thiazole derivative of the formula (1) wherein $R^1$ and $R^2$ combine to form a group: —$(CH_2)_n$— (n is 4), $R^3$ is a group of the formula:

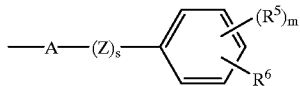

(s is 1, Z is a sulfur atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a lower alkanoyloxy-lower alkyl group and u is 1, or a salt thereof.

(57) A thiazole derivative of the formula (1) wherein $R^1$ and $R^2$ combine to form a group: —$(CH_2)_n$— (n is 5), $R^3$ is a group of the formula:

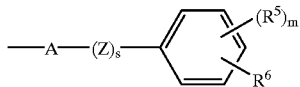

(s is 1, Z is a sulfur atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a hydrogen atom, and u is 0, or a salt thereof.

(58) A thiazole derivative of the formula (1) wherein $R^1$ and $R^2$ combine to form a group: —$(CH_2)_n$— (n is 5), $R^3$ is a group of the formula:

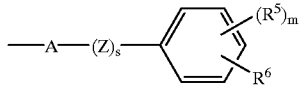

(s is 1, Z is a sulfur atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a lower alkanoyloxy-lower alkyl group and u is 0, or a salt thereof.

(59) A thiazole derivative of the formula (1) wherein $R^1$ and $R^2$ combine to form a group: —$(CH_2)_n$— (n is 5), $R^3$ is a group of the formula:

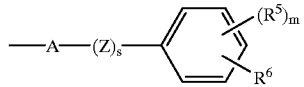

(s is 1, Z is a sulfur atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a hydrogen atom, and u is 1, or a salt thereof.

(60) A thiazole derivative of the formula (1) wherein $R^1$ and $R^2$ combine to form a group: —$(CH_2)_n$— (n is 5), $R^3$ is a group of the formula:

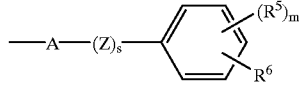

(s is 1, Z is a sulfur atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a lower alkanoyloxy-lower alkyl group and u is 1, or a salt thereof.

(61) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

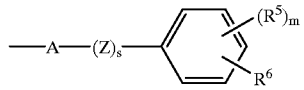

(s is 1, Z is a sulfur atom, $R^6$ is a group: —CO—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a hydrogen atom, and u is 0, or a salt thereof.

(62) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

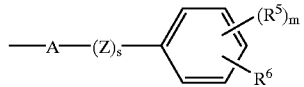

(s is 1, Z is a sulfur atom, $R^6$ is a group: —O—CH=$CR^{11b}$—$(CO)_p$—$R^{11a}$ ($R^{11b}$, p and $R^{11a}$ are the same as defined in the formula (1)), $R^5$, m and A are the same as defined in the formula (1)), $R^4$ is a lower alkanoyloxy-lower alkyl group and u is 0, or a salt thereof.

(63) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

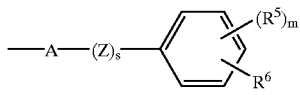

(s is 1, Z is a sulfur atom, $R^6$ is a group: —CO—CH=$CR^{11b}$—(CO)$_p$—$R^{11a}$ ($R^{11b}$, p and $R^{11a}$ are the same as defined in the formula (1)), $R^5$, m and A are the same as defined in the formula (1)), $R^4$ is a hydrogen atom, and u is 1, or a salt thereof.

(64) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

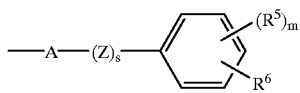

(s is 1, Z is a sulfur atom, $R^6$ is a group: —CO—CH=$CR^{11b}$—(CO)$_p$—$R^{11a}$ ($R^{11b}$, p and $R^{11a}$ are the same as defined in the formula (1)), $R^5$, m and A are the same as defined in the formula (1)), $R^4$ is a lower alkanoyloxy-lower alkyl group and u is 1, or a salt thereof.

(65) A thiazole derivative of the formula (1) wherein $R^1$ and $R^2$ are the same or different and each are a hydrogen atom or a lower alkyl group, $R^3$ is a group of the formula:

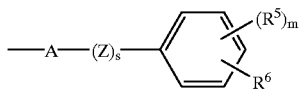

(s is 0, $R^6$ is a group: —CO—C≡C—$COR^{14}$ ($R^{14}$ is the same as defined in the formula (1)), $R^5$, Z, m and A are the same as defined in the formula (1)), $R^4$ is a hydrogen atom, and u is 0, or a salt thereof.

(66) A thiazole derivative of the formula (1) wherein $R^1$ and $R^2$ are the same or different and each are a hydrogen atom or a lower alkyl group, $R^3$ is a group of the formula:

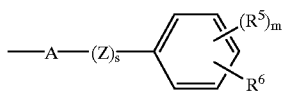

(s is 0, $R^6$ is a group: —CO—C≡C—$COR^{14}$ ($R^{14}$ is the same as in the formula (1)), $R^5$, Z, m and A are the same as defined in the formula (1)), $R^4$ is a lower alkanoyloxy-lower alkyl group and u is 0, or a salt thereof.

(67) A thiazole derivative of the formula (1) wherein $R^1$ and $R^2$ are the same or different and each are a hydrogen atom or a lower alkyl group, $R^3$ is a group of the formula:

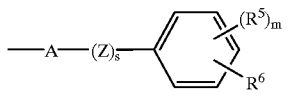

s is 0, $R^6$ is a group: —CO—C≡C—$COR^{14}$ ($R^{14}$ is the same as n the formula (1)), $R^5$, Z, m and A are the same as defined in the formula (1)), $R^4$ is a hydrogen atom, and u is 1, or a salt thereof.

(68) A thiazole derivative of the formula (1) wherein $R^1$ and $R^2$ are the same or different and each are a hydrogen atom or a lower alkyl group, $R^3$ is a group of the formula:

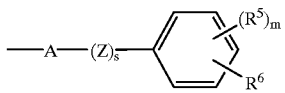

(s is 0, $R^6$ is a group: —CO—C≡C—$COR^{14}$ ($R^{14}$ is the same as defined in the formula (1)), $R^5$, Z, m and A are the same as defined in the formula (1)), $R^4$ is a lower alkanoyloxy-lower alkyl group and u is 1, or a salt thereof.

(69) A thiazole derivative of the formula (1) wherein $R^1$ and $R^2$ combine to form a group: —(CH$_2$)$_n$— (n is 4), $R^3$ is a group of the fornula:

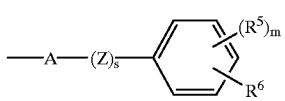

(s is 0, $R^6$ is a group: —CO—C≡C—$COR^{14}$ ($R^{14}$ is the same as defined in the formula (1)), $R^5$, Z, m and A are the same as defined in the formula (1)), $R^4$ is a hydrogen atom, and u is 0, or a salt thereof.

(70) A thiazole derivative of the formula (1) wherein $R^1$ and $R^2$ combine to form a group: —(CH$_2$)$_n$— (n is 4), $R^3$ is a group of the formula:

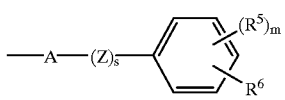

(s is 0, $R^6$ is a group: —CO—C≡C—$COR^{14}$ ($R^{14}$ is the same as defined in the formula (1)), $R^5$, Z, m and A are the same as defined in the formula (1)), $R^4$ is a lower alkanoyloxy-lower alkyl group and u is 0, or a salt thereof.

(71) A thiazole derivative of the formula (1) wherein $R^1$ and $R^2$ combine to form a group: —(CH$_2$)$_n$— (n is 4), $R^3$ is a group of the fornula:

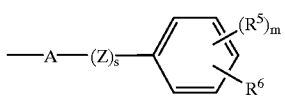

(s is 0, $R^6$ is a group: —CO—C≡C—$COR^{14}$ ($R^{14}$ is the same as defined in the formula (1)), $R^5$, Z, m and A are the same as defined in the formula (1)), $R^4$ is a hydrogen atom, and u is 1, or a salt thereof.

(72) A thiazole derivative of the formula (1) wherein $R^1$ and $R^2$ combine to form a group: —(CH$_2$)$_n$— (n is 4), $R^3$ is a group of the formula:

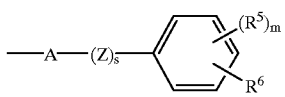

(s is 0, $R^6$ is a group: —CO—C≡C—$COR^{14}$ ($R^{14}$ is the same as defined in the formula (1)), $R^5$, Z, m and A are the same as defined in the formula (1)), $R^4$ is a lower alkanoyloxy-lower alkyl group and u is 1, or a salt thereof.

(73) A thiazole derivative of the formula (1) wherein $R^1$ and $R^2$ combine to form a group: —$(CH_2)_n$— (n is 5), $R^3$ is a group of the formula:

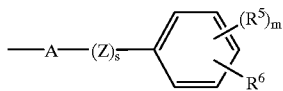

(s is 0, $R^6$ is a group: —CO—C≡C—$COR^{14}$ ($R^{14}$ is the same as defined in the formula (1)), $R^5$, Z, m and A are the same as defined in the formula (1)), $R^4$ is a hydrogen atom, and u is 0, or a salt thereof.

(74) A thiazole derivative of the formula (1) wherein $R^1$ and $R^2$ combine to form a group: —$(CH_2)_n$— (n is 5), $R^3$ is a group of the formula:

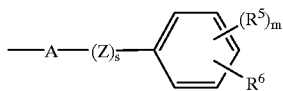

(s is 0, $R^6$ is a group: —CO—C≡C—$COR^{14}$ ($R^{14}$ is the same as defined in the formula (1)), $R^5$, Z, m and A are the same as defined in the formula (1)), $R^4$ is a lower alkanoyloxy-lower alkyl group and u is 0, or a salt thereof.

(75) A thiazole derivative of the formula (1) wherein $R^1$ and $R^2$ combine to form a group: —$(CH_2)_n$— (n is 5), $R^3$ is a group of the formula:

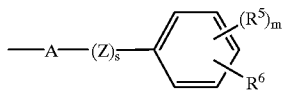

(s is 0, $R^6$ is a group: —CO—C≡C—$COR^{14}$ ($R^{14}$ is the same as defined in the formula (1)), $R^5$, Z, m and A are the same as defined in the formula (1)), $R^4$ is a hydrogen atom, and u is 1, or a salt thereof.

(76) A thiazole derivative of the formula (1) wherein $R^1$ and $R^2$ combine to form a group: —$(CH_2)_n$— (n is 5), $R^3$ is a group of the formula:

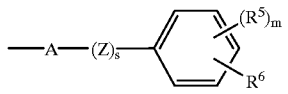

(s is 0, $R^6$ is a group: —CO—C≡C—$COR^{14}$ ($R^{14}$ is the same as defined in the formula (1)), $R^5$, Z, m and A are the same as defined in the formula (1)), $R^4$ is a lower alkanoyloxy-lower alkyl group and u is 1, or a salt thereof.

(77) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

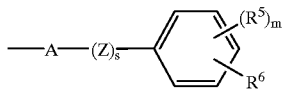

(s is 0, $R^6$ is a group: —CO—C≡C—$COR^{14}$ ($R^{14}$ is the same as defined in the formula (1)), $R^5$, Z, m and A are the same as defined in the formula (1)), $R^4$ is a hydrogen atom, and u is 0, or a salt thereof.

(78) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

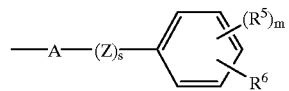

(s is 0, $R^6$ is a group: —CO—C≡C—$COR^{14}$ ($R^{14}$ is the same as defined in the formula (1)), $R^5$, Z, m and A are the same as defined in the formula (1)), $R^4$ is a lower alkanoyloxy-lower alkyl group and u is 0, or a salt thereof.

(79) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

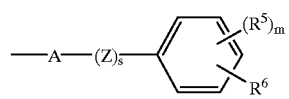

(s is 0, $R^6$ is a group: —CO—C≡C—$COR^{14}$ ($R^{14}$ is the same as defined in the formula (1)), $R^5$, Z, m and A are the same as defined in the formula (1)), $R^4$ is a hydrogen atom, and u is 1, or a salt thereof.

(80) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

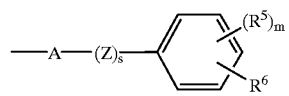

(s is 0, $R^6$ is a group: —CO—C≡C—$COR^{14}$ ($R^{14}$ is the same as defined in the formula (1)), $R^5$, Z, m and A are the same as defined in the formula (1)), $R^4$ is a lower alkanoyloxy-lower alkyl group and u is 1, or a salt thereof.

(81) A thiazole derivative of the formula (1) wherein $R^1$ and $R^2$ are the same or different and each are a hydrogen atom or a lower alkyl group, $R^3$ is a group of the formula:

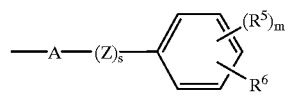

(s is 1, Z is an oxygen atom, $R^6$ is a group: —CO—C≡C—$COR^{14}$ ($R^{14}$ is the same as defined in the formula (1)), $R^5$, m and A are the same as defined in the formula (1)), $R^4$ is a hydrogen atom, and u is 0, or a salt thereof.

(82) A thiazole derivative of the formula (1) wherein $R^1$ and $R^2$ are the same or different and each are a hydrogen atom or a lower alkyl group, $R^3$ is a group of the formula:

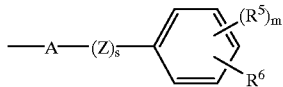

(s is 1, Z is an oxygen atom, $R^6$ is a group: —CO—C≡C—$COR^{14}$ ($R^{14}$ is the same as defined in the formula (1)), $R^5$, m and A are the same as defined in the formula (1)), $R^4$ is a lower alkanoyloxy-lower alkyl group and u is 0, or a salt thereof.

(83) A thiazole derivative of the formula (1) wherein $R^1$ and $R^2$ are the same or different and each are a hydrogen atom or a lower alkyl group, $R^3$ is a group of the formula:

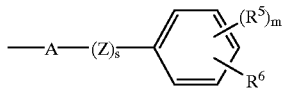

(s is 1, Z is an oxygen atom, $R^6$ is a group: —CO—C≡C—$COR^{14}$ ($R^{14}$ is the same as defined in the formula (1)), $R^5$, m and A are the same as defined in the formula (1)), $R^4$ is a hydrogen atom, and u is 1, or a salt thereof.

(84) A thiazole derivative of the formula (1) wherein $R^1$ and $R^2$ are the same or different and each are a hydrogen atom or a lower alkyl group, $R^3$ is a group of the formula:

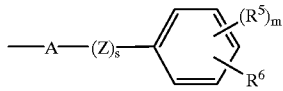

(s is 1, Z is an oxygen atom, $R^6$ is a group: —CO—C≡C—$COR^{14}$ ($R^{14}$ is the same as defined in the formula (1)), $R^5$, m and A are the same as defined in the formula (1)), $R^4$ is a lower alkanoyloxy-lower alkyl group and u is 1, or a salt thereof.

(85) A thiazole derivative of the formula (1) wherein $R^1$ and $R^2$ combine to form a group: —$(CH_2)_n$— (n is 4), $R^3$ is a group of the formula:

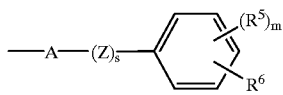

(s is 1, Z is an oxygen atom, $R^6$ is a group: —CO—C≡C—$COR^{14}$ ($R^{14}$ is the same as defined in the formula (1)), $R^5$, m and A are the same as defined in the formula (1)), $R^4$ is a hydrogen atom, and u is 0, or a salt thereof.

(86) A thiazole derivative of the formula (1) wherein $R^1$ and $R^2$ combine to form a group: —$(CH_2)_n$— (n is 4), $R^3$ is a group of the formula:

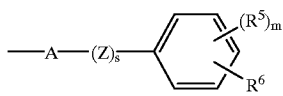

(s is 1, Z is an oxygen atom, $R^6$ is a group: —CO—C≡C—$COR^{14}$ ($R^{14}$ is the same as defined in the formula (1)), $R^5$, m and A are the same as defined in the formula (1)), $R^4$ is a lower alkanoyloxy-lower alkyl group and u is 0, or a salt thereof.

(87) A thiazole derivative of the formula (1) wherein $R^1$ and $R^2$ combine to form a group: —$(CH_2)_n$— (n is 4), $R^3$ is a group of the formula:

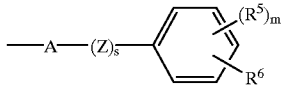

(s is 1, Z is an oxygen atom, $R^6$ is a group: —CO—C≡C—$COR^{14}$ ($R^{14}$ is the same as defined in the formula (1)), $R^5$, m and A are the same as defined in the formula (1)), $R^4$ is a hydrogen atom, and u is 1, or a salt thereof.

(88) A thiazole derivative of the formula (1) wherein $R^1$ and $R^2$ combine to form a group: —$(CH_2)_n$— (n is 4), $R^3$ is a group of the formula:

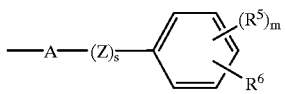

(s is 1, Z is an oxygen atom, $R^6$ is a group: —CO—C≡C—$COR^{14}$ ($R^{14}$ is the same as defined in the formula (1)), $R^5$, m and A are the same as defined in the formula (1)), $R^4$ is a lower alkanoyloxy-lower alkyl group and u is 1, or a salt thereof.

(89) A thiazole derivative of the formula (1) wherein $R^1$ and $R^2$ combine to form a group: —$(CH_2)_n$— (n is 5), $R^3$ is a group of the formula:

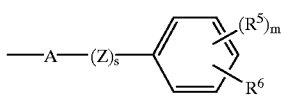

(s is 1, Z is an oxygen atom, $R^6$ is a group: —CO—C≡C—$COR^{14}$ ($R^{14}$ is the same as defined in the formula (1)), $R^5$, m and A are the same as defined in the formula (1)), $R^4$ is a hydrogen atom, and u is 0, or a salt thereof.

(90) A thiazole derivative of the formula (1) wherein $R^1$ and $R^2$ combine to form a group: —$(CH_2)_n$— (n is 5), $R^3$ is a group of the formula:

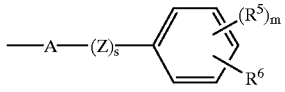

(s is 1, Z is an oxygen atom, $R^6$ is a group: —CO—C≡C—$COR^{14}$ ($R^{14}$ is the same as defined in the formula (1)), $R^5$, m and A are the same as defined in the formula (1)), $R^4$ is a lower alkanoyloxy-lower alkyl group and u is 0, or a salt thereof.

(91) A thiazole derivative of the formula (1) wherein $R^1$ and $R^2$ combine to form a group: —$(CH_2)_n$— (n is 5), $R^3$ is a group of the formula:

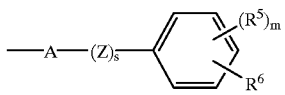

(s is 1, Z is an oxygen atom, $R^6$ is a group: —CO—C≡C—$COR^{14}$ ($R^{14}$ is the same as defined in the formula (1)), $R^5$, m and A are the same as defined in the formula (1)), $R^4$ is a hydrogen atom, and u is 1, or a salt thereof.

(92) A thiazole derivative of the formula (1) wherein $R^1$ and $R^2$ combine to form a group: —$(CH_2)_n$— (n is 5), $R^3$ is a group of the formula:

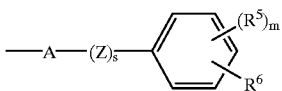

(s is 1, Z is an oxygen atom, $R^6$ is a group: —CO—C≡C—$COR^{14}$ ($R^{14}$ is the same as defined in the formula (1)), $R^5$, m and A are the same as defined in the formula (1)), $R^4$ is a lower alkanoyloxy-lower alkyl group and u is 1, or a salt thereof.

(93) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

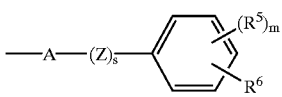

(s is 1, Z is an oxygen atom, $R^6$ is a group: —CO—C≡C—$COR^{14}$ ($R^{14}$ is the same as defined in the formula (1)), $R^5$, m and A are the same as defined in the formula (1)), $R^4$ is a hydrogen atom, and u is 0, or a salt thereof.

(94) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

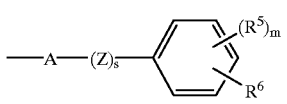

(s is 1, Z is an oxygen atom, $R^6$ is a group: —CO—C≡C—$COR^{14}$ ($R^{14}$ is the same as defined in the formula (1)), $R^5$, m and A are the same as defined in the formula (1)), $R^4$ is a lower alkanoyloxy-lower alkyl group and u is 0, or a salt thereof.

(95) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

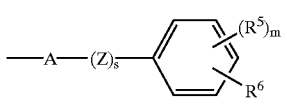

(s is 1, Z is an oxygen atom, $R^6$ is a group: —CO—C≡C—$COR^{14}$ ($R^{14}$ is the same as defined in the formula (1)), $R^5$, m and A are the same as defined in the formula (1)), $R^4$ is a hydrogen atom, and u is 1, or a salt thereof.

(96) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

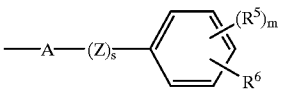

(s is 1, Z is an oxygen atom, $R^6$ is a group: —CO—C≡C—$COR^{14}$ ($R^{14}$ is the same as defined in the formula (1)), $R^5$, m and A are the same as defined in the formula (1)), $R^4$ is a lower alkanoyloxy-lower alkyl group and u is 1, or a salt thereof.

(97) A thiazole derivative of the formula (1) wherein $R^1$ and $R^2$ are the same or different and each are a hydrogen atom or a lower alkyl group, $R^3$ is a group of the formula:

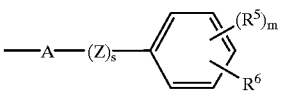

(s is 1, Z is a sulfur atom, $R^6$ is a group: —CO—C≡C—$COR^{14}$ ($R^{14}$ is the same as defined in the formula (1)), $R^5$, m and A are the same as defined in the formula (1)), $R^4$ is a hydrogen atom, and u is 0, or a salt thereof.

(98) A thiazole derivative of the formula (1) wherein $R^1$ and $R^2$ are the same or different and each are a hydrogen atom or a lower alkyl group, $R^3$ is a group of the formula:

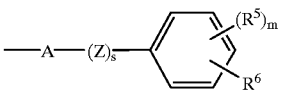

(s is 1, Z is a sulfur atom, $R^6$ is a group: —CO—C≡C—$COR^{14}$ ($R^{14}$ is the same as defined in the formula (1)), $R^5$, m and A are the same as defined in the formula (1)), $R^4$ is a lower alkanoyloxy-lower alkyl group and u is 0, or a salt thereof.

(99) A thiazole derivative of the formula (1) wherein $R^1$ and $R^2$ are the same or different and each are a hydrogen atom or a lower alkyl group, $R^3$ is a group of the formula:

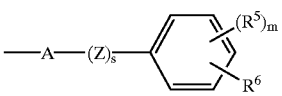

(s is 1, Z is a sulfur atom, $R^6$ is a group: —CO—C≡C—$COR^{14}$ ($R^{14}$ is the same as defined in the formula (1)), $R^5$, m and A are the same as defined in the formula (1)), $R^4$ is a hydrogen atom, and u is 1, or a salt thereof.

(100) A thiazole derivative of the formula (1) wherein $R^1$ and $R^2$ are the same or different and each are a hydrogen atom or a lower alkyl group, $R^3$ is a group of the formula:

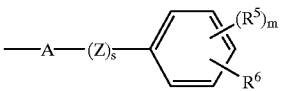

(s is 1, Z is a sulfur atom, $R^6$ is a group: —CO—C≡C—$COR^{14}$ ($R^{14}$ is the same as defined in the formula (1)), $R^5$, m and A are the same as defined in the formula (1)), $R^4$ is a lower alkanoyloxy-lower alkyl group and u is 1, or a salt thereof.

(101) A thiazole derivative of the formula (1) wherein $R^1$ and $R^2$ combine to form a group: —$(CH_2)_n$— (n is 4), $R^3$ is a group of the formula:

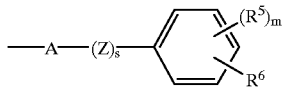

(s is 1, Z is a sulfur atom, $R^6$ is a group: —CO—C≡C—$COR^{14}$ ($R^{14}$ is the same as defined in the formula (1)), $R^5$, m and A are the same as defined in the formula (1)), $R^4$ is a hydrogen atom, and u is 0, or a salt thereof.

(102) A thiazole derivative of the formula (1) wherein $R^1$ and $R^2$ combine to form a group: —$(CH_2)_n$— (n is 4), $R^3$ is a group of the formula:

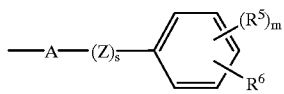

(s is 1, Z is a sulfur atom, $R^6$ is a group: —CO—C≡C—$COR^{14}$ ($R^{14}$ is the same as defined in the formula (1)), $R^5$, m and A are the same as defined in the formula (1)), $R^4$ is a lower alkanoyloxy-lower alkyl group and u is 0, or a salt thereof.

(103) A thiazole derivative of the formula (1) wherein $R^1$ and $R^2$ combine to form a group: —$(CH_2)_n$— (n is 4), $R^3$ is a group of the formula:

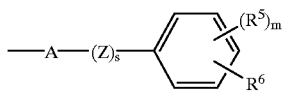

(s is 1, Z is a sulfur atom, $R^6$ is a group: —CO—C≡C—$COR^{14}$ ($R^{14}$ is the same as defined in the formula (1)), $R^5$, m and A are the same as defined in the formula (1)), $R^4$ is a hydrogen atom, and u is 1, or a salt thereof.

(104) A thiazole derivative of the formula (1) wherein $R^1$ and $R^2$ combine to form a group: —$(CH_2)_n$— (n is 4), $R^3$ is a group of the formula:

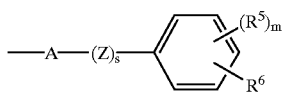

(s is 1, Z is a sulfur atom, $R^6$ is a group: —CO—C≡C—$COR^{14}$ ($R^{14}$ is the same as defined in the formula (1)), $R^5$, m and A are the same as defined in the formula (1)), $R^4$ is a lower alkanoyloxy-lower alkyl group and u is 1, or a salt thereof.

(105) A thiazole derivative of the formula (1) wherein $R^1$ and $R^2$ combine to form a group: —$(CH_2)_n$— (n is 5), $R^3$ is a group of the formula:

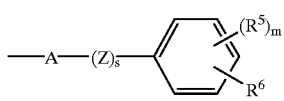

(s is 1, Z is a sulfur atom, $R^6$ is a group: —CO—C≡C—$COR^{14}$ is the same as defined in the formula (1)), $R^5$, m and A are the same as defined in the formula (1)), $R^4$ is a hydrogen atom, and u is 0, or a salt thereof.

(106) A thiazole derivative of the formula (1) wherein $R^1$ and $R^2$ combine to form a group: —$(CH_2)_n$— (n is 5), $R^3$ is a group of the formula:

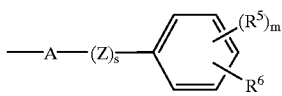

(s is 1, Z is a sulfur atom, $R^6$ is a group: —CO—C≡C—$COR^{14}$ ($R^{14}$ is the same as defined in the formula (1)), $R^5$, m and A are the same as defined in the formula (1)), $R^4$ is a lower alkanoyloxy-lower alkyl group and u is 0, or a salt thereof.

(107) A thiazole derivative of the formula (1) wherein $R^1$ and $R^2$ combine to form a group: —$(CH_2)_n$— (n is 5), $R^3$ is a group of the formula:

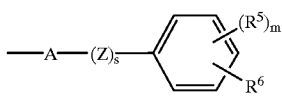

(s is 1, Z is a sulfur atom, $R^6$ is a group: —CO—C≡C—$COR^{14}$ ($R^{14}$ is the same as defined in the formula (1)), $R^5$, m and A are the same as defined in the formula (1)), $R^4$ is a hydrogen atom, and u is 1, or a salt thereof.

(108) A thiazole derivative of the formula (1) wherein $R^1$ and $R^2$ combine to form a group: —$(CH_2)_n$— (n is 5), $R^3$ is a group of the formula:

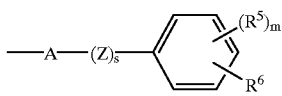

(s is 1, Z is a sulfur atom, $R^6$ is a group: —CO—C≡C—$COR^{14}$ ($R^{14}$ is the same as defined in the formula (1)), $R^5$, m and A are the same as defined in the formula (1)), $R^4$ is a lower alkanoyloxy-lower alkyl group and u is 1, or a salt thereof.

(109) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

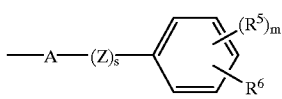

(s is 1, Z is a sulfur atom, $R^6$ is a group: —CO—C≡C—$COR^{14}$ ($R^{14}$ is the same as defined in the formula (1)), $R^5$, m and A are the same as defined in the formula (1)), $R^4$ is a hydrogen atom, and u is 0, or a salt thereof.

(110) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

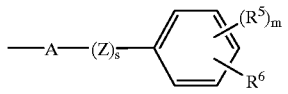

(s is 1, Z is a sulfur atom, $R^6$ is a group: —CO—C≡C—$COR^{14}$ ($R^{14}$ is the same as defined in the formula (1)), $R^5$, m and A are the same as defined in the formula (1)), $R^4$ is a lower alkanoyloxy-lower alkyl group and u is 0, or a salt thereof.

(111) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

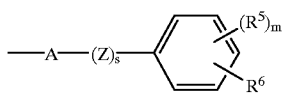

(s is 1, Z is a sulfur atom, $R^6$ is a group: —CO—C≡C—$COR^{14}$ ($R^{14}$ is the same as defined in the formula (1)), $R^5$, m and A are the same as defined in the formula (1)), $R^4$ is a hydrogen atom, and u is 1, or a salt thereof.

(112) A thiazole derivative of the formula (1) wherein $R^1$ and $R^2$ combine to form a benzene ring which may optionally have a substituent selected from a lower alkyl group, a lower alkoxy group, a nitro group, an amino group having optionally a lower alkyl substituent and a halogen atom, $R^3$ is a group of the formula:

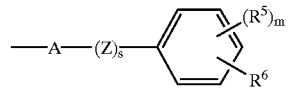

(s is 1, Z is a sulfur atom, $R^6$ is a group: —CO—C≡C—$COR^{14}$ ($R^{14}$ is the same as defined in the formula (1)), $R^5$, m and A are the same as defined in the formula (1)), $R^4$ is a lower alkanoyloxy-lower alkyl group and u is 1, or a salt thereof.

The compounds of the present invention of the formula (1) may be prepared by various processes, but preferably prepared by the following processes.

Reaction Scheme-1

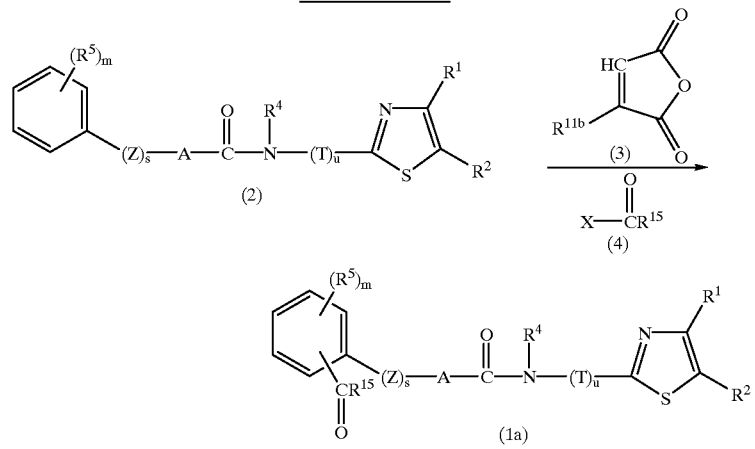

wherein $R^1$, $R^2$, $R^4$, $R^5$, Z, m, s, T, u and A are the same as defined above, $R^{15}$ is a group: —CH=C($R^{11b}$)($COR^{16}$) ($R^{11b}$ is the same as defined above, and $R^{16}$ is a hydroxy group or a lower alkoxy group), or a group: —C≡C—$COR^{14}$ ($R^{14}$ is the same as defined above), and X is a halogen atom.

The reaction between the compound (2) and the compound (3) or the compound (4) is called Friedel-Crafts Reaction, and carried out in the presence of a Lewis acid in a suitable solvent. The Lewis acid may be any conventional Lewis acids which are used in this kind of Friedel-Crafts Reaction, and is, for example, aluminum chloride, zinc chloride, iron chloride, stannous chloride, boron tribromide, boron trifluoride, conc. sulfuric acid, etc. The solvent may be, for example, carbon disulfide, aromatic hydrocarbons such as nitrobenzene, chlorobenzene, halogenated hydrocarbons such as dichloromethane, dichloroethane, carbon tetrachloride, tetrachloroethane, aliphatic nitro compounds such as nitroethane, nitromethane, or a mixture of these solvents. The compound (3) and the compound (4) are used each at least in an equimolar amount, preferably in an amount of 1 to 5 moles, to 1 mole of the compound (2). The Lewis acid is usually used in an a mount of 1 to 6 moles, to 1 mole of the compound (2). The reaction is usually carried out at 0 to 120° C., preferably at 0 to 70° C., for about 0.5 to 24 hours.

The compound wherein $R^{15}$ is a group: —CH=C($R^{11b}$)(COR$^{16}$), and the double bond thereof shows a cis-configuration can be isomerized into the compound wherein the double bond shows a trans-configuration by heating it at about 50° C. to 100° C. in dimethylformamide.

The compound (1a) wherein $R^{15}$ is a group: —CH=C($R^{11b}$)(COR$^{16}$) or a group: —C≡C—COR$^{14}$, and $R^{16}$ and $R^{14}$ are both a lower alkoxy group may be converted into a compound (1a) wherein a corresponding $R^{16}$ and $R^{14}$ are a hydroxy group, by treating it under the same conditions as in the reaction of converting the compound (1d) into the compound (1e) in Reaction Scheme 4, described hereinbelow.

Reaction Scheme-2

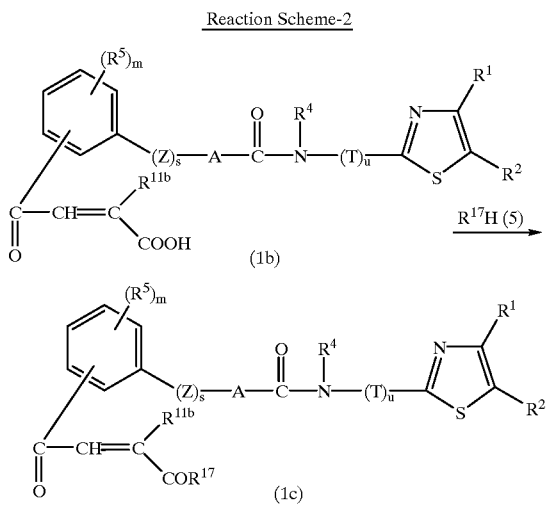

wherein $R^1$, $R^2$, $R^4$, $R^5$, $R^{11b}$, Z, m, s, T, u and A are the same as defined above, $R^{17}$ is the heterocyclic residues as defined for $R^{11a}$ but having at least one

in the heterocyclic nucleus.

The process of Reaction Scheme-2 is a conventional amido bond producing reaction, and is carried out by reacting the thiazole compound (1b) and the amine compound (5). The amido bond producing reaction can be carried out under the same conditions as those of the conventional amino bond producing reaction, for example, (a) a mixed acid anhydride process, i.e. a process of reacting the carboxylic acid compound (1b) with an alkyl halocarbonate to form a mixed acid anhydride and reacting the resultant with the amine compound (5);

(b) an activated ester process, i.e. a process of converting the carboxylic acid compound (1b) into an activated ester such as p-nitrophenyl ester, N-hydroxysuccinimide ester, 1-hydroxybenzotriazole ester, etc., and reacting the resultant with the amine compound (5);

(c) a carbodiimide process, i.e. a process of condensing the carboxylic acid compound (1b) and the amine compound (5) in the presence of an activating agent such as dicyclohexylcarbodiimide, carbonyldiimidazole, etc.;

(d) other processes, i.e. a process of converting the carboxylic acid compound (1b) into a carboxylic anhydride by treating it with a dehydrating agent such as acetic anhydride, and reacting the resultant with the amine compound (5); a process of reacting an ester of the carboxylic acid compound (1b) with a lower alcohol and the amine compound (5) at high temperature under high pressure; a process of reacting an acid halide compound of the carboxylic acid compound (1b), i.e. a carboxylic acid halide, with the amine compound (5).

The mixed acid anhydride used in the above mixed acid anhydride process (a) is obtained by the known Schötten-Baumann reaction, and the reaction product is used without isolating from the reaction mixture for the reaction with the amine compound (5) to give the desired compound (1) of the present invention. The Schötten-Baumann reaction is usually carried out in the presence of a basic compound. The basic compound is any conventional compounds used for the Schotten-Baumann reaction and includes, for example, organic basic compounds such as triethylamine, trimethylamine, pyridine, dimethylaniline, N-methylmorpholine, 4-dimethylaminopyridine, 1,5-diazabicyclo[4.3.0]nonene-5 (DBN), 1,8-diazabicyclo[5.4.0]undecene-7 (DBU), 1,4-diazabicyclo[2.2.2]octane (DABCO), etc., and inorganic basic compounds such as potassium carbonate, sodium carbonate, potassium hydrogen carbonate, sodium hydrogen carbonate, etc. The reaction is usually carried out at a temperature from about −20° C. to about 100° C., preferably at a temperature of −20° C. to about 50° C., for about 5 minutes to about 10 hours, preferably for 5 minutes to about 2 hours.

The reaction between the mixed acid anhydride thus obtained and the amine compound (5) is usually carried out at a temperature of −20° C. to about 150° C., preferably at a temperature of −20° C. to about 50° C., for about 5 minutes to about 35 hours, preferably for about 5 minutes to 30 hours. The mixed acid anhydride process is usually carried out in a solvent in the presence of a basic compound. The basic compounds may be any basic compounds used in the above Schötten-Baumann reaction. The solvent may be any conventional solvents which are usually used in the mixed acid anhydride process and includes, for example, halogenated hydrocarbons (e.g. chloroform, dichloromethane, dichloroethane, etc.), aromatic hydrocarbons (e.g. benzene, p-chlorobenzene, toluene, xylene, etc.), ethers (e.g. diethyl ether, diisopropyl ether, tetrahydrofuran, dimethoxyethane, etc.), esters (e.g. methyl acetate, ethyl acetate, etc.), aprotic polar solvents (e.g. N,N-dimethylformamide, dimethylsulfoxide, acetonitrile, hexamethylphosphoric triamide, 1-methyl-2-pyrrolidinone (NMP), etc.), or a mixture of these solvents. The alkyl halocarbonate used in the mixed acid anhydride process includes, for example, methyl chloroformate, methyl bromoformate, ethyl chloroformate, ethyl bromoformate, isobutyl chloroformate, and the like. In said process, the carboxylic acid compound (1b), the alkyl halocarbonate ester and the amine compound (5) are usually used in equimolar amount each, but preferably the alkyl halocarbonate ester and the amine compound (5) are used in an amount of about 1 to 1.5 mole, to 1 mole of the carboxylic acid (1b).

Among the above other processes (d), in case of the process of reacting the carboxylic acid halide with the amine compound (5), the reaction is usually carried out in the presence of a basic compound in a suitable solvent. The basic compound is any conventional basic compounds and includes, for example, in addition to the basic compounds used in the above mentioned Schötten-Baumann reaction, sodium hydroxide, potassium hydroxide, sodium hydride, potassium hydride, and the like. The solvent includes, for example, in addition to the solvents used in the mixed acid anhydride process, alcohols (e.g. methanol, ethanol, propanol, butanol, 3-methoxy-1-butanol, ethylcellosolve, methylcellosolve, etc.), pyridine, acetone, water, or a mixture of two or more these solvents, and the like. The amount of the amine compound (5) and the carboxylic acid halide is not critical, but the amine compound (5) is usually used at least in equimolar amount, preferably in an amount of about 1 to 5 moles, to 1 mole of the carboxylic acid halide. The reaction is usually carried out at a temperature of about −70° C. to about 180° C., preferably at a temperature of about −50° C. to about 150° C., for about 5 minutes to about 30 hours.

Besides, the amido bond producing reaction of Reaction Scheme-2 may also be carried out by reacting the carboxylic acid compound (1b) and the amine compound (5) in the presence of a condensing agent such as phosphorus compounds (e.g. phenylphosphine-2,2'-dithiopyridine, diphenylphosphinyl chloride, phenyl-N-phenylphosphoramide chloridate, diethyl cyanophosphate, diethyl cyanophosphate, diphenylphosphoryl azide, N,N'-bis(2-oxo-3-oxazolidinyl) phosphinic chloride, etc.).

The reaction is usually carried out in the presence of the same solvent and the same basic compound which can be used in the above reaction of the carboxylic acid halide compound and the amine compound (5). The reaction is usually carried out at a temperature of −20° C. to about 150° C., preferably at a temperature of 0° C. to about 100° C., for about 5 minutes to about 30 hours. The condensing agent and the amine compound (5) are used at least in equimolar amount, preferably in an amount of about 1 to 2 moles, to 1 mole of the carboxylic acid compound (1b).

Reaction Scheme-3

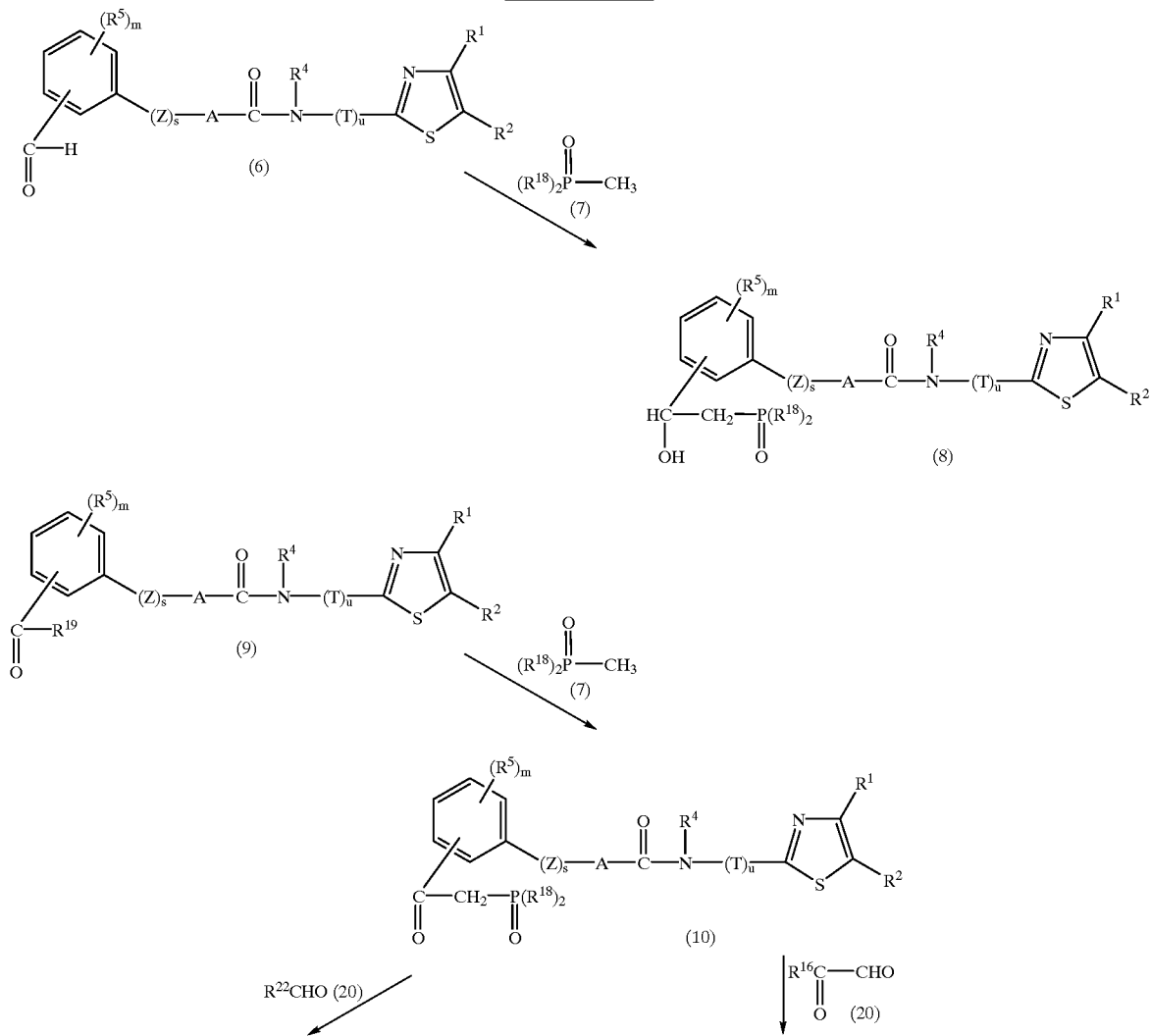

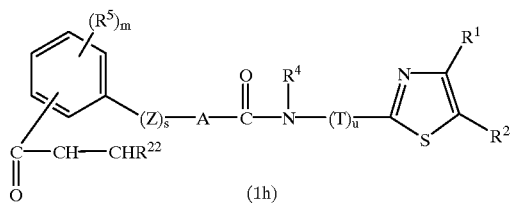

(1h)

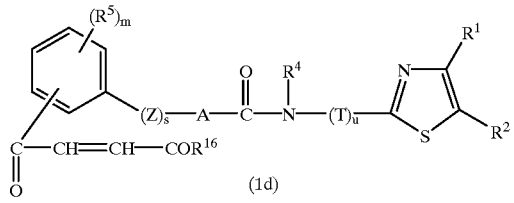

(1d)

wherein $R^1$, $R^2$, $R^3$, $R^4$, $R^5$, Z, m, s, T, u, $R^{16}$ and A are the same as defined above, $R^{18}$ and $R^{19}$ are a lower alkoxy group, and $R^{22}$ is the same as defined below.

The reaction of the compound (6) and the compound (7) is carried out in the presence of a basic compound in a suitable solvent. The basic compound includes inorganic basic compounds such as metal sodium, metal potassium, sodium hydride, sodium amide, sodium hydroxide, potassium hydroxide, sodium carbonate, potassium carbonate, sodium hydrogen carbonate, etc., organic basic compounds such as alkali metal alkoxide (e.g., sodium methylate, sodium ethylate, potassium t-butoxide), an alkyl lithium, aryl lithium or lithium amide (e.g., methyl lithium, n-butyl lithium, phenyl lithium, lithium diisopropylamide), pyridine, piperidine, quinoline, triethylamine, N,N-dimethylaniline, etc. The solvent may be any one which does not disturb the reaction, for example, water, ethers (e.g., diethyl ether, dioxane, tetrahydrofuran, monoglyme, diglyme, etc.), aromatic hydrocarbons (e.g., benzene, toluene, xylene, etc.), aliphatic hydrocarbons (e.g., n-hexane, heptane, cyclohexane, etc.), amines (e.g., pyridine, N,N-dimethylaniline, etc), aprotic polar solvents (e.g., N,N-dimethylformamide, dimethylsulfoxide, hexamethylphosphoric triamide, etc.), halogenated hydrocarbons (e.g., dichloromethane, chloroform, carbon tetrachloride, etc.), alcohols (e.g., methanol, ethanol, isopropyl alcohol, etc.), ureas (e.g., N,N'-dimethylpropylene urea (DMPU), etc.), 1,3-dimethyl-3,4,5,6-tetrahydro-2(1H)-pyrimidinone, or a mixture of these solvents. The reaction is usually carried out at −80° C. to 150° C., preferably at about −80° to 120° C., for 0.5 to about 15 hours.

The compound (7) is usually used at least in an equimolar amount, preferably in an amount of 1 to 5 moles, to 1 mole of the compound (6).

The reaction of converting the compound (8) into the compound (10) is carried out in the presence of an oxidizing agent in a suitable solvent. The oxidizing agent includes, for example, benzoquinones (e.g., 2,3-dichloro-5,6-dicyano-1,4-benzoquinone (DDQ)), pyridinium chromates (e.g., pyridinium chlorochromate, pyridium dichrorochromate, etc.), dimethylsulfoxide-oxazolyl chloride, dichromic acid, dichromates (e.g. sodium dichromate, potassium dichromate, etc.), permanganic acid, permanganates (e.g. potassium permanganate, sodium permanganate, etc.), manganese dioxide, etc. The solvent includes, for example, water, organic acids (e.g. formic acid, acetic acid, trifluoroacetic acid, etc.), alcohols (e.g. methanol, ethanol, .etc.), halogenated hydrocarbons (e.g. chloroform, dichloromethane, etc.), ethers (e.g., tetrahydrofuran, diethyl ether, dioxane, etc.), dimethylsulfoxide, dimethylformamide, or a mixture of these solvents. The oxidizing agent is preferably used in an excess amount to the amount of the starting compound. The above reaction is usually carried out at 0° C. to 200° C., preferably at 0° C. to about 150° C., for 1 hour to about 10 hours.

The reaction of the compound (9) and the compound (7) is carried out under the same conditions as those in the reaction of the compound (6) and the compound (7).

The reaction of the compound (10) and the compound (12) is carried out under the same conditions as those in the reaction of the compound (6) and the compound (7).

The reaction of the compound (10) and the compound (20) is carried out under the same conditions as those in the reaction of the compound (6) and the compound (7).

Reaction Scheme-4

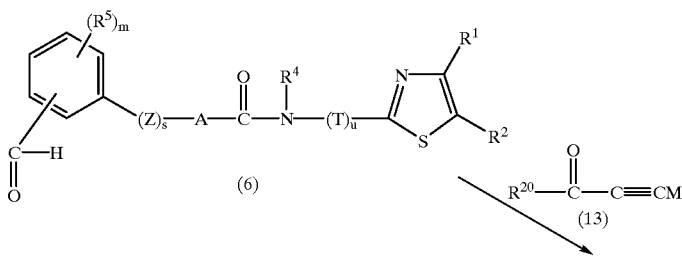

-continued

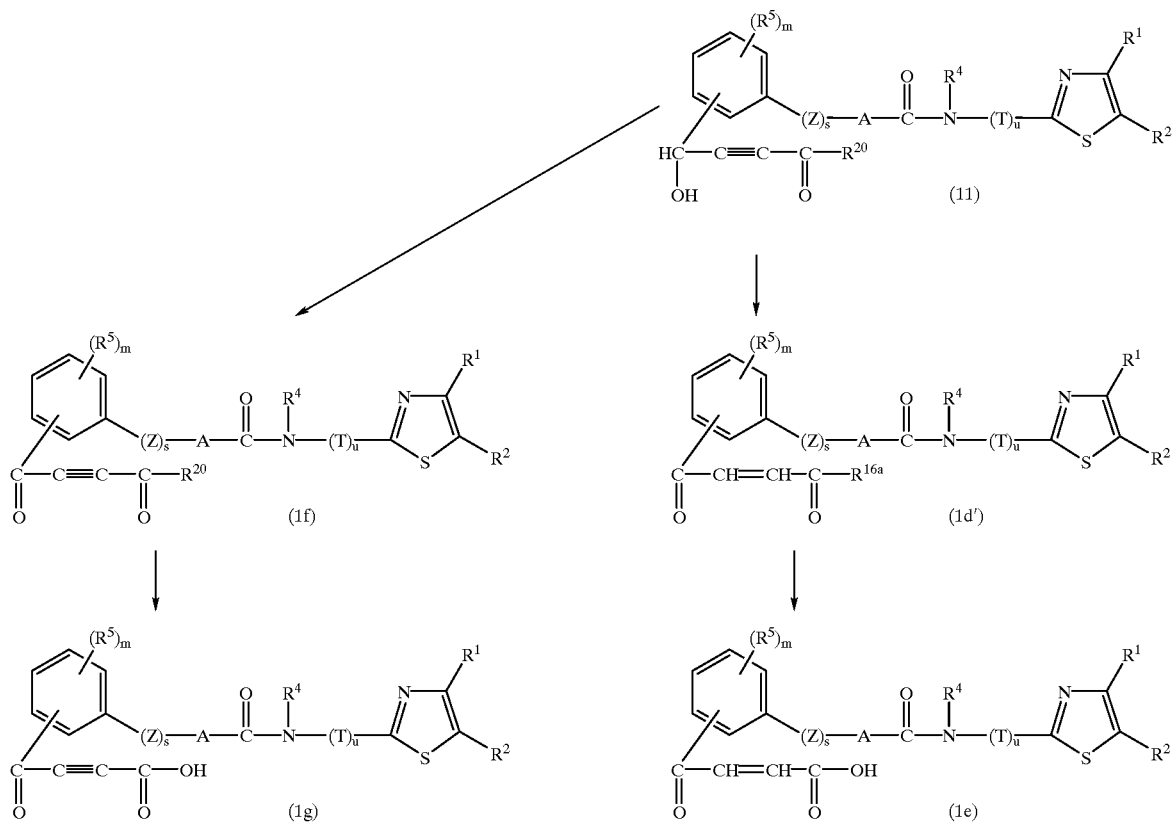

wherein $R^1$, $R^2$, $R^4$, $R^5$, Z, m, s, T, u and A are the same as defined above, $R^{20}$ is a lower alkoxy group, M is an alkali metal such as lithium, sodium, potassium, etc., and $R^{16a}$ is a lower alkoxy group.

The reaction of the compound (6) and the compound (13) is carried out in the presence of a basic compound in a suitable solvent, at −80° C. to room temperature, for 5 minutes to 6 hours. The solvent may be, for example, ethers (e.g., diethyl ether, dioxane, tetrahydrofuran, etc.), aromatic hydrocarbons (e.g., benzene, toluene, etc.), saturated hydrocarbons (e.g., hexane, heptane, pentane, cyclohexane, etc.), ureas (e.g., N,N'-dimethylpropyleneurea (DMPU), etc.). The basic compounds are the same ones which are used in the reaction of the compound (6) and the compound (7) in the above Reaction Scheme-3. The compound (13) is usually used at least in equimolar amount, preferably in an amount of 1 to 5 moles, to 1 mole of the compound (6).

The reaction of converting the compound (11) into the compound (1d') is carried out in the presence of a basic compound in a suitable solvent. The basic compound may be organic basic compound such as triethylamine, trimethylamine, diisopropylamine, tri-n-butylamine, ethylamine, pyridine, dimethylaniline, N-methylmorpholine, 4-dimethylaminopyridine, DBN, DBU, DABCO, etc. The solvent includes, for example, water, alcohols (e.g., ethanol, methanol, isopropanol, etc.), dimethylformamide, diemthylsulfoxide, hexamethylphosphoric triamide, or a mixture of these solvents. The reaction is usually carried out at room temperature to 150° C., preferably at room temperature to 100° C., for about 1 to 5 hours.

The reaction of converting the compound (11) into the compound (1f) is carried out under the same conditions as those in the reaction of converting the compound (8) into the compound (10) in the above Reaction Scheme-3.

The reaction of converting the compound (1d') into the compound (1e) is carried out in the presence of an acid or a basic compound in a suitable solvent, or without a solvent. The solvent includes, for example, water, lower alcohols (e.g., ethanol, methanol, isopropanol, etc.), ketones (e.g., acetone, methyl ethyl ketone, etc.), halogenated hydrocarbons (e.g., dichloromethane, chloroform, carbon tetrachloride, etc.), ethers (e.g., dioxane, tetrahydrofuran, ethylene glycol dimethyl ether, etc.), fatty acids (e.g., acetic acid, formic acid, etc.), or a mixture of these solvents. The acid includes, for example, mineral acids (e.g., hydrochloric acid, sulfuric acid; hydrobromic acid, etc.), organic acids (e.g., formic acid, acetic acid, trifluoric acid, aromatic sulfuric acids, etc.). The basic compound includes, for example, an alkali metal carbonate (e.g., sodium carbonate, potassium carbonate, etc.), an alkali metal hydroxide (e.g., sodium hydroxide, potassium hydroxide, calcium hydroxide, lithium hydroxide, etc.), etc. The reaction is usually carried out at room temperature to about 200° C., preferably at room temperature to 150° C., for about 10 minutes to 25 hours.

The reaction of converting the compound (1f) into the compound (1g) is carried out under the same conditions as those in the reaction of converting the compound (1d') into the compound (1e) as mentioned above.

Reaction Scheme-5

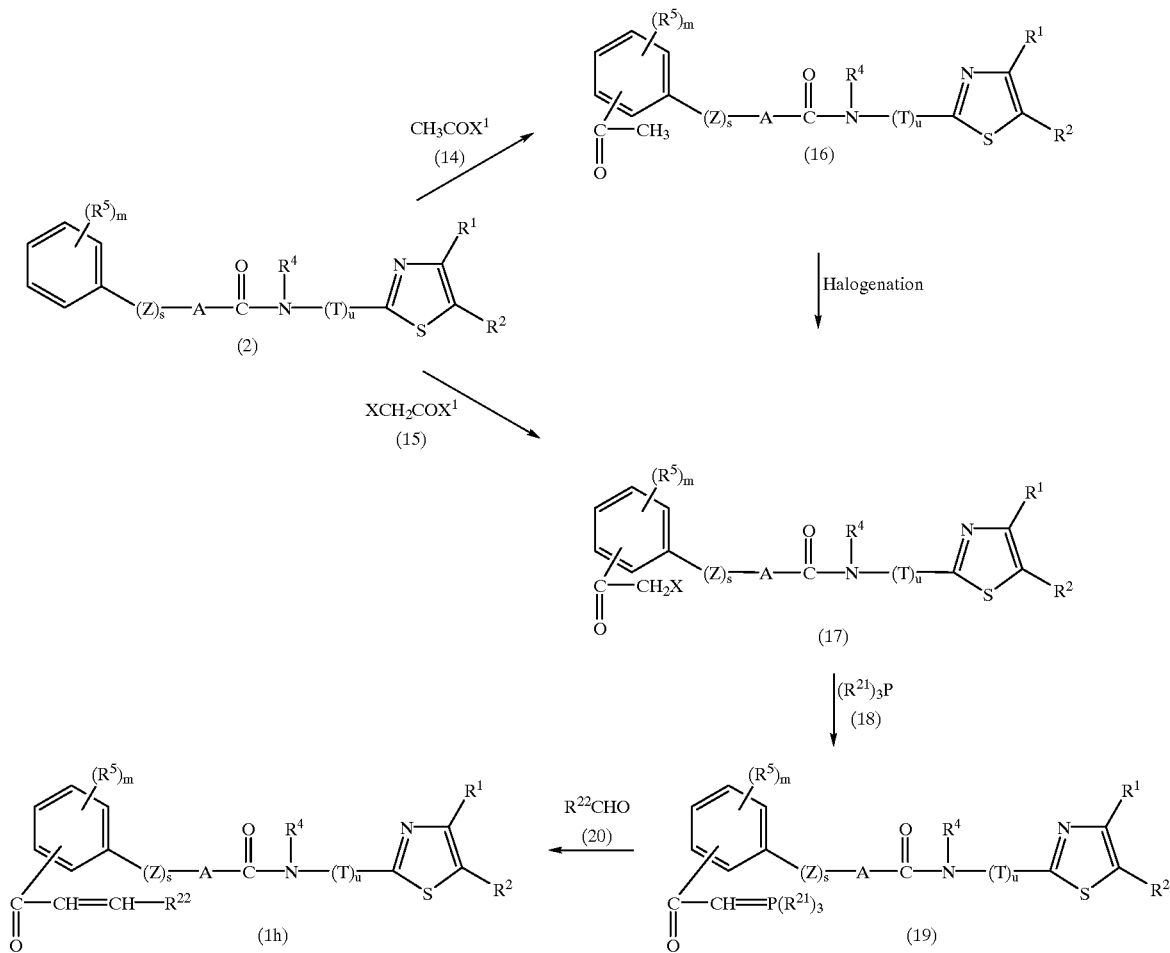

wherein $R^1$, $R^2$, $R^4$, $R^5$, Z, m, s, T, u and A are the same as defined above, $X^1$ is a halogen atom, $R^{21}$ is a phenyl group, $R^{22}$ is a 5- to 10-membered, saturated or unsaturated heteromonocyclic, heterobicyclic residue (said heterocyclic residue optionally having 1 to 3 substituents selected from (i) a lower alkyl group; (ii) a group: —(B)$_l$—NR$^{12}$R$^{13}$ (l is the same as defined above, B is a group: —CO—A— (A is the same as defined above), a carbonyl group or a lower alkylene group, $R^{12}$ and $R^{13}$ are the same or different, and each are a hydrogen atom, a lower alkyl group, an amino-substituted lower alkyl group having optionally a lower alkyl substituent, or combine together with the adjacent nitrogen atom to which they bond to form a 5- to 12-membered saturated heteromonocyclic, heterobicyclic or hetero-sprio ring with or without being intervened with another nitrogen atom or an oxygen atom, said heterocyclic group may optionally have a substituent selected from a lower alkyl group, a lower alkoxycarbonyl group, a lower alkoxy-substituted lower alkyl group, an amino group having optionally a lower alkyl substituent and a hydroxy-substituted lower alkyl group); (iii) a lower alkoxycarbonyl group; (iv) a hydroxy-substituted lower alkyl group; (v) a pyridyl group being optionally substituted by a lower alkyl group having optionally a halogen substituent on the pyridine ring; (vi) a halogen-substituted lower alkyl group; (vii) a lower alkoxy group; (viii) a cycloalkyl group; (ix) a hydroxy group; (x) a tetrahydropyranyloxy-substituted lower alkyl group; (xi) a pyrimidyl group; (xii) a lower alkoxy-substituted lower alkyl group; (xiii) a carboxyl group; (xiv) a phenyl-lower alkoxy group; (xv) a phenyl-lower alkyl group having optionally a lower alkylenedioxy substituent on the phenyl ring; (xvi) a lower alkanoyloxy group; and (xvii) a piperidinyl group having optionally a lower alkyl substituent on the piperidine ring.

The reaction of the compound (2) and the compound (14), and the reaction of the compound (2) and the compound (15) are carried out under the same conditions as those in the reaction of the compound (2) and the compound (3) or the compound (4) in the above Reaction Scheme-1.

The halogenating reaction of the compound (16) is carried out in the presence of a halogenating agent in a suitable solvent. The halogenating agent may be, for example, halogen molecules (e.g., bromine, chlorine, etc.), iodine chloride, sulfuryl chloride, copper compounds (e.g., copper (II) bromide, etc.), N-halogenated succinimides (e.g., N-bromosuccinimide, N-chlorosuccinimide, etc.). The solvent may be, for example, halogenated hydrocarbons (e.g., dichloromethane, dichloroethane, chloroform, carbon tetrachloride, etc.), fatty acids (e.g., acetic acid, propionic acid, etc.), carbon disulfide, etc. The halogenating agent is usually used in an amount of 1 to 10 moles, preferably in an amount of 1 to 5 moles, to 1 mole of the compound (16). The reaction is usually carried out at 0° C. to a boiling point of the solvent to be used, preferably at 0° C. to 100° C., for about 5 minutes to 20 hours.

The reaction of the compound (17) and the compound (18) is carried out in a suitable solvent at room temperature to 150° C., preferably at room temperature to about 100° C., for about 1 hour to 10 hours. The solvent may be the same solvents used in the reaction of the carboxylic halide and the amine compound (5) among the reactions between the compound (1b) and the compound (5) in the above Reaction Scheme-2. The compound (18) is used at least in equimolar amount, preferably in an amount of 1 to 1.5 moles, to 1 mole of the compound (17).

In the above process, there is obtained a compound of the formula (21):

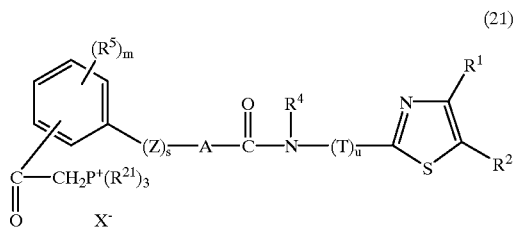

wherein $R^1$, $R^2$, $R^4$, $R^5$, Z, m, A, $R^{21}$, s, T, u and X are the same as defined above, which is further treated in the presence of a basic compound in a suitable solvent to give the compound (19). The solvent and the basic compound are the same ones which are used in the reaction of the carboxylic halide and the amine compound (5) in the reaction of the compound (1b) and the compound (5) in the Reaction Scheme-2. The reaction is usually carried out at 0° C. to 100° C., preferably at 0° C. to about 70° C., for about 1 hour to 5 hours.

The reaction of the compound (19) and the compound (20) is carried out under the same conditions as those in the reaction of the compound (6) and the compound (7) in the above Reaction Scheme-3.

Alternatively, the reaction of the compound (19) and the compound (20) is usually carried out in a suitable solvent at 0° C. to 150° C., preferably at room temperature to about 100° C., for about 0.5 hour to 8 hours. The solvent may be any one which does not disturb the reaction, for example, water, alcohols (e.g., methanol, ethanol, isopropanol, etc.), aromatic hydrocarbons (e.g., benzene, toluene, xylene, etc.), ethers (e.g., diethyl ether, tetrahydrofuran, dioxane, diglyme, monoglyme, etc.), halogenated hydrocarbons (e.g., dichloromethane, chloroform, carbon tetrachloride, etc.), aprotic polar solvents (e.g., N,N-dimethylformamide, dimethylsulfoxide, hexamethylphosphoric triamide, etc.), etc. The compound (20) is usually used at least in equimolar amount, preferably in an amount of 1 to 5 moles, to 1 mole of the compound (19). The reaction is promoted when a para-aldehyde is added into the reaction system.

Reaction Scheme-6

Reaction Scheme-7

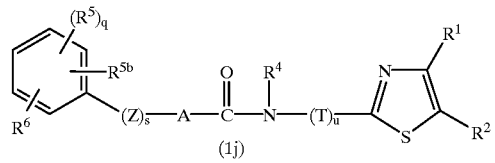

wherein $R^1$, $R^2$, $R^4$, $R^5$, $R^6$, Z, s, T, u and A are the same as defined above, q is 1, $R^{5a}$ is a halogen-substituted lower alkyl group, $R^{5b}$ is a group: —A—$NR^7R^8$ (A, $R^7$, $R^8$ are the same as defined above) or a lower alkanoyloxy-lower alkyl group, $R^{23}$ is a group: —$NR^7R^8$ ($R^7$ and $R^8$ are the same as defined above), or a lower alkanoyloxy group.

The reaction of the compound (1f) and the compound (22) is carried out in the presence or absence of a basic compound in a suitable inert solvent, or without a solvent. The inert solvent includes, for example, aromatic hydrocarbons (e.g., benzene, toluene, xylene, etc.), ethers (e.g., tetrahydrofuran, dioxane, diethylene glycol dimethyl ether, etc.), halogenated hydrocarbons (e.g., dichloromethane, chloroform, carbon tetrachloride, etc.), lower alcohols (e.g., methanol, ethanol, isopropanol, butanol, tert-butanol, etc.), water, acetic acid, ethyl acetate, acetone, acetonitrile, pyridine, dimethylsulfoxide, dimethylformamide, hexamethylphosphoric triamide, or a mixture of these solvents. The basic compound includes, for example, an alkali metal carbonate (e.g., sodium carbonate, potassium carbonate, etc.), an alkali metal hydrogen carbonate (e.g., sodium hydrogen carbonate, potassium hydrogen carbonate, etc.), an alkali metal hydroxide (e.g., sodium hydroxide, potassium hydroxide, etc.), sodium hydride, potassium, sodium, sodium amide, an alkali metal alkoxide (e.g., sodium methoxide, etc.), organic basic compounds (e.g., pyridine, N-ethyldiisopropylamine, dimethylaminopyridine, triethylamine, 1,5-diazabicyclo[4.3.0]nonen-5-(DBN), 1,8-diazabicyclo[5.4.0]undecen-7 (DBU), 1,4-diazabicyclo[2.2.2]octane (DABCO), etc. The amount of the compound (1i) and the compound (22) is not critical, but the compound (22) is usually used at least in equimolar amount, preferably in an amount of 1 to 10 moles, to 1 mole of the compound (1i). The reaction is usually carried out at 0° C. to 200° C., preferably at 0° C. to 170° C., for about 30 minutes to 75 hours. Into the reaction system, an alkali metal halide such as sodium iodide, potassium iodide or a copper powder may be added.

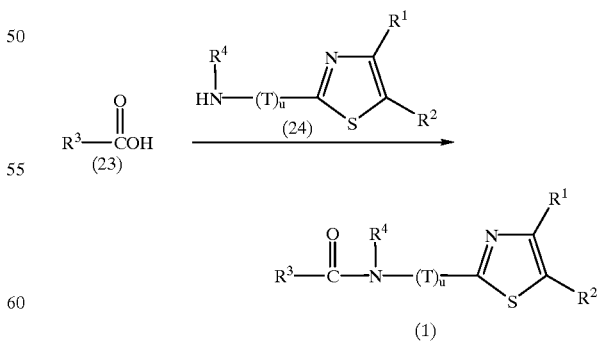

wherein $R^1$, $R^2$, $R^3$, $R^4$, T and u are the same as defined above.

The reaction of the compound (23) and the compound (24) is carried out under the same conditions as those in the reaction of the compound (1b) and the compound (5) in the above Reaction Scheme-2.

Reaction Scheme-8

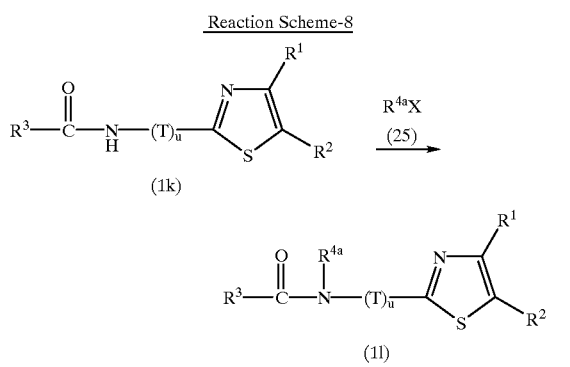

wherein $R^1$, $R^2$, $R^3$, T, X and u are the same as defined above, and $R^{4a}$ is a lower alkanoyloxy-lower alkyl group.

The reaction of the compound (1k) and the compound (25) is carried out under the same conditions as those in the reaction of the compound (1i) and the compound (22) in the above Reaction Scheme-6.

Reaction Scheme-9

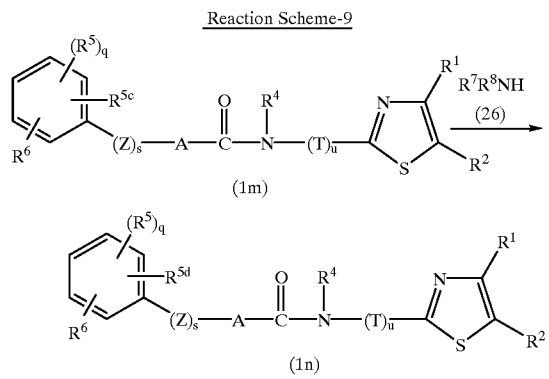

wherein $R^1$, $R^2$, $R^4$, $R^5$, $R^6$, $R^7$, $R^8$, Z, s, T, u and q are the same as defined above, and $R^{5c}$ is a carboxy-substituted lower alkyl group, $R^{5d}$ is a group: —A—CO—NR$^7$R$^8$ ($R^7$ and $R^8$ are the same as defined above).

The reaction of the compound (1m) and the compound (26) is carried out under the same conditions as those in the reaction of the compound (1b) and the compound (5) in the above Reaction Scheme-2.

The starting compounds (2), (6) and (23) in the above Reaction Schemes are prepared by the following processes.

Reaction Scheme-10

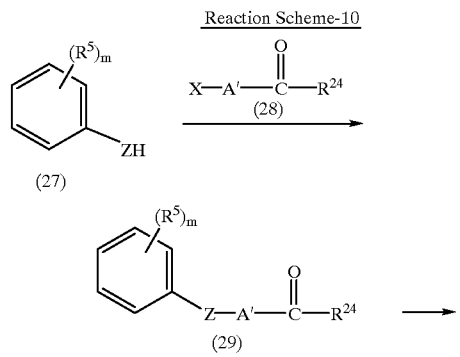

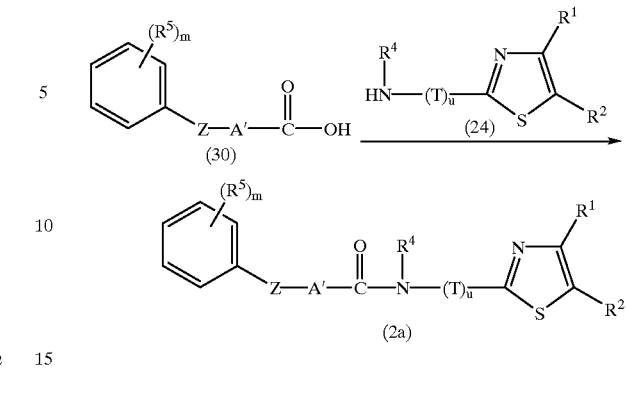

wherein $R^1$, $R^2$, $R^4$, $R^5$, X, Z, T, u and m are the same as defined above, and $R^{24}$ is a hydroxy group, a lower alkoxy group or a phenyl-lower alkoxy group, and A' is a lower alkylene group.

The reaction of the compound (27) and the compound (28) is carried out under the same conditions as those in the reaction of the compound (1i) and the compound (22) in the above Reaction Scheme-6.

The reaction of converting the compound (29) wherein $R^{24}$ is a lower alkoxy group into the compound (30) is carried out under the same conditions as those in the reaction of converting the compound (1d) into the compound (1e) in the above Reaction Scheme-4.

The reaction of converting the compound (29) wherein $R^{24}$ is a phenyl-lower alkoxy group into the compound (30) is carried out under the same conditions as those in the reaction of converting the compound (5b) into the compound (5c) in Reaction Scheme-13, which is described hereinbelow.

The reaction of the compound (30) and the compound (24) is carried out under the same conditions as those in the reaction of the compound (1b) and the compound (5) in the above Reaction Scheme-2.

Reaction Scheme-11

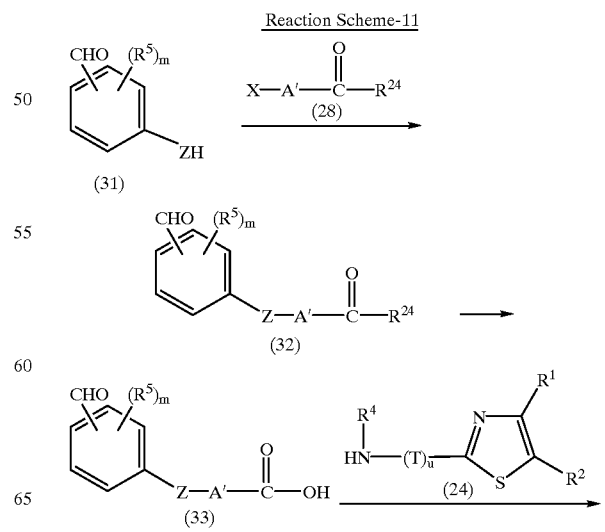

-continued

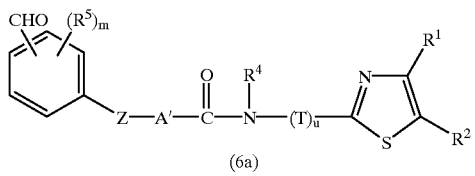

(6a)

wherein $R^1$, $R^2$, $R^4$, $R^5$, A', Z, $R^{24}$, T, u and m are the same as defined above.

The reaction of the compound (31) and the compound (28) is carried out under the same conditions as those in the reaction of the compound (27) and the compound (28) in the above Reaction Scheme-10.

The reaction of converting the compound (32) wherein $R^{24}$ is a lower alkoxy group into the compound (33) is carried out under the same conditions as those in the reaction of converting the compound (29) wherein $R^{24}$ is a lower alkoxy group into the compound (30) in the above Reaction Scheme-10.

The reaction of converting the compound (32) wherein $R^{24}$ is a phenyl-lower alkoxy group into the compound (33) is carried out under the same conditions as those in the reaction of converting the compound (5b) into the compound (5c) in Reaction Scheme-13, which is described hereinbelow.

The reaction of the compound (33) and the compound (24) is carried out under the same conditions as those in the reaction of the compound (30) and the compound (24) in the above Reaction Scheme-10.

Reaction Scheme-12

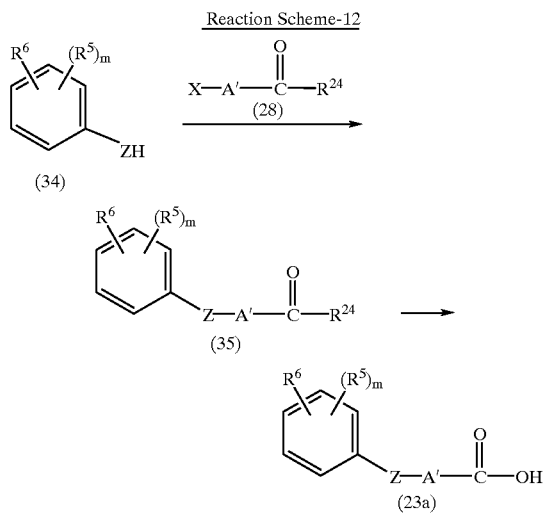

wherein $R^5$, $R^6$, m, A', X, Z and $R^{24}$ are the same as defined above.

The reaction of the compound (34) and the compound (28) is carried out under the same conditions as those in the reaction of the compound (27) and the compound (28) in the above Reaction Scheme-10.

The reaction of converting the compound (35) wherein $R^{24}$ is a lower alkoxy group into the compound (23a) is carried out under the same conditions as those in the reaction of converting the compound (29) wherein $R^{24}$ is a lower alkoxy group into the compound (30) in the above Reaction Scheme-10.

The reaction of converting the compound (35) wherein $R^{24}$ is a phenyl-lower alkoxy group into the compound (23a) is carried out under the same conditions as those in the reaction of converting the compound (5b) into the compound (5c) in Reaction Scheme-13, which is described hereinbelow.

The starting compound (5) is prepared by the following processes.

Reaction Scheme-13

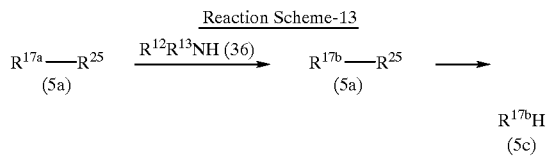

wherein $R^{12}$, $R^{13}$ are the same as defined above, $R^{17a}$ is the same groups for $R^{17}$ having at least one oxo group on the heterocyclic group, $R^{17b}$ is the same groups for $R^{17}$ having at least one group: —N—$R^{12}R^{13}$ ($R^{12}$ and $R^{13}$ are the same as defined above) on the heterocyclic group, and $R^{25}$ is a phenyl-lower alkyl group.

The reaction of the compound (5a) and the compound (36) is carried out in the presence of a reducing agent in a suitable solvent or without a solvent. The solvent may be, for example, water, alcohols (e.g., methanol, ethanol, isopropanol, etc.), acetonitrile, formic acid, acetic acid, ethers (e.g., dioxane, diethyl ether, diglyme, tetrahydrorfuran, etc.), aromatic hydrocarbons (e.g., benzene, toluene, xylene, etc.), or a mixture of these solvents. The reducing agent may be, for example, formic acid, an alkali metal salt of fatty acid (e.g., sodium formate, etc.), hydrogenating agent (e.g., sodium borohydride, sodium cyanoborohydride, lithium aluminum hydride, etc.), catalysts (e.g., palladium-black, palladium-carbon, platinum oxide, platinum black, Raney-nickel, etc.).

When formic acid is used as a reducing agent, the reaction is usually carried out at room temperature to about 200° C., preferably at 50 to 150° C., for one to about 10 hours. The formic acid is used in an excess amount to the amount of the compound (5a).

When a hydrogenating agent is used as a reducing agent, the reaction is usually carried out at –30° C. to about 100° C., preferably at 0° C. to 70° C., for 30 minutes to about 12 hours. The hydrogenating agent is used in an amount of 1 to 20 moles, preferably in an amount of 1 to 6 moles, to 1 mole of the compound (5a). Especially, when lithium aluminum hydride is used as a hydrogenating agent, the solvent may be ethers (e.g., diethyl ether, dioxane, tetrahydrofuran, diglyme, etc.), or aromatic hydrogen carbonates (e.g., benzene, toluene, xylene, etc.).

When a catalyst is used as a reducing agent, the reaction is usually carried out under a pressure of atmospheric pressure to 20 aims, preferably under atmospheric pressure to 10 atom of hydrogen gas, in the presence of a hydrogen donor such as formic acid, ammonium formate, cyclohexene, hydrazine hydrate, etc. at a temperature of –30° C. to about 100° C., preferably at a temperature of 0° C. to 60° C., for about one to 12 hours. The catalyst is used in an amount of 0.1 to 40% by weight, preferably in an amount of 0.1 to 20% by weight, to the weight of the compound (5a).

The compound (36) is usually used at least in an equimolar amount, preferably in an amount of 1 to 3 moles, to 1 mole of the compound (5a).

The reaction of converting the compound (5b) into the compound (5c) is carried out by hydrogenation in the presence of a catalyst in a suitable solvent. The solvent may be, for example, water, acetic acid, alcohols (e.g., methanol, ethanol, isopropanol, etc.), hydrocarbons (e.g., hexane, cyclohexane, etc.), ethers (e.g., dioxane, tetrahydrorfuran, diethyl ether, ethylene glycol dimethyl ether, etc.), esters (e.g., ethyl acetate, methyl acetate, etc.), aprotic polar solvents (e.g., dimethylformamide, etc.), or a mixture of these solvents. The catalyst may be, for example, palladium. palladium black, palladium hydroxide, palladium hydroxide-carbon, palladium-carbon, platinum, platinum oxide, copper cromite, Raney nickel, etc. The catalyst is used usually in an amount of 0.02 to 1 time of the amount of the compound (5b). The reaction is usually carried out at a temperature of −20° C. to about 100° C., preferably at a temperature of 0° C. to about 70° C., under 1 to 10 atms of hydrogen gas, for about 0.5 to about 20 hours.

Reaction Scheme-14

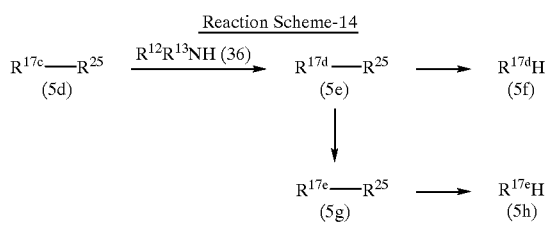

wherein $R^{12}$, $R^{13}$ and $R^{25}$ are the same as defined above, $R^{17c}$ is the same groups for $R^{17}$ but having at least one carboxyl group on the heterocyclic group, $R^{17d}$ is the same groups for $R^{17}$ but having at least one —CONR$^{12}$R$^{13}$ (R$^{12}$ and R$^{13}$ are the same as defined above) on the heterocyclic group, and $R^{17e}$ is the same groups for $R^{17}$ but having at least one —CH$_2$NR$^{12}$R$^{13}$ (R$^{12}$ and R$^{13}$ are the same as defined above) on the heterocyclic group.

The reaction of the compound (5d) and the compound (36) is carried out under the same conditions as those in the reaction of the compound (1b) and the compound (5) in the above Reaction Scheme-2.

The reactions of converting the compound (5e) into the compound (5f), and converting the compound (5g) into the compound (5h), are carried out under the same conditions as those in the reaction of converting the compound (5b) into the compound (5c) in the above Reaction Scheme-13.

The reaction of converting the compound (5e) into the compound (5g) is carried out by reduction with using a hydrogenation agent. The hydrogenation agent may be, for example, lithium aluminum hydride, sodium borohydride, diboran, etc., and is used at least in an equimolar amount, preferably in an amount of 1 to 15 moles, to 1 mole of the starting compound. The reduction is carried out in a suitable solvent such as water, a lower alcohol (e.g., methanol, ethanol, isopropanol, etc.), ethers (e.g., tetrahydrofuran, diethyl ether, diisopropyl ether, diglyme, etc.), or a mixture of these solvents. The reaction is usually carried out at a temperature of −60° C. top 150° C., preferably at a temperature of −30° C. to 100° C., for about 10 minutes to 5 hours. When lithium aluminum hydride or diboran is used as a hydrogenating agent, an anhydrous solvent such as tetrahydrofuran, diethyl ether, diisopropyl ether, diglyme, etc. may be preferably used.

Reaction Scheme-15

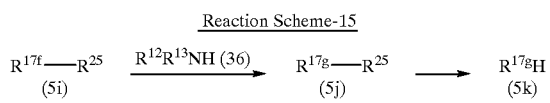

wherein $R^{12}$, $R^{13}$ and $R^{25}$ are the same as defined above, $R^{17f}$ is the same groups for $R^{17}$ but having at least one halogen-substituted lower alkyl group on the heterocyclic group, and $R^{17g}$ is the same groups for $R^{17}$ but having at least one —B'—NR$^{12}$R$^{13}$ (B' is a lower alkylene group, $R^{12}$, $R^{13}$ are the same as defined above) on the heterocyclic group.

The reaction of the compound (5i) and the compound (36) is carried out under the same conditions as those in the reaction of the compound (1i) and the compound (22) in the above Reaction Scheme-6.

The reaction of converting the compound (5j) into the compound (5k) is carried out under the same conditions as those in the reaction of converting the compound (5b) into the compound (5c) in the above Reaction Scheme-13.

The compound of the formula (1) wherein $R^6$ is a group of the formula:

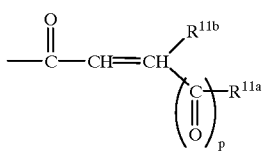

wherein $R^{11b}$, p and $R^{11a}$ are the same as defined above, and showing a trans-configuration at the double bond of the above formula may be isomerized into a cis-compound at the corresponding double bond by being exposed to sunlight, a suitable solvent. The solvent may be the same solvents used in the reaction of the carboxylic halide and the amine compound (5) in the reactions of the compound (1b) and the compound (5) in the above Reaction Scheme-2. The reaction is carried out at a temperature of 0° C. to 70° C., preferably at 0° C. to room temperature, for about 1 to 10 hours.

Among the starting compounds (32) used in the Reaction Scheme-11, some compounds (32) are prepared by the following process.

Reaction Scheme-16

wherein $R^5$, m, A', M and $R^{24}$ are the same as defined above, and $R^{26}$ and $R^{27}$ are the same or different and each are a lower alkyl group.

The compound of converting the compound (37) into the compound (38) is carried out in the presence of a basic compound in a suitable solvent. The solvent may be, for example, water, lower alcohols (e.g., methanol, ethanol, isopropanol, etc.), ketones (e.g., acetone, methyl ethyl ketone, etc.), halogenated hydrocarbons (e.g., dichloromethane, chloroform, carbon tetrachloride, etc.), ethers (e.g., dioxane, tetrahydrofuran, ethylene glycol dimethyl ether, etc.), or a mixture of these solvents. The basic compound may be, for example, an alkali metal carbonate (e.g., sodium carbonate, potassium carbonate, etc.), or an alkali metal hydroxide (e.g., sodium hydroxide, potassium hydroxide, calcium hydroxide, lithium hydroxide, etc.), etc. The reaction is usually carried out at room temperature to about 200° C., preferably at room temperature to about 150° C., for about 10 minutes to about 25 hours.

The reaction of the compound (38) and the compound (28) is carried out under the same conditions as those in the reaction of the compound (27) and the compound (28) in the above Reaction Scheme-10.

The each step of the above Reaction Scheme-16 can be carried out in one-pot system without isolating the compound (38) from the reaction system.

Reaction Scheme-17

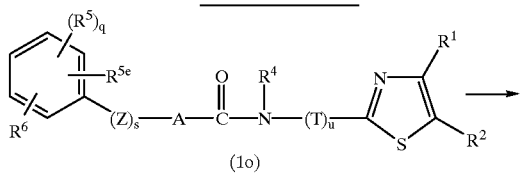

(1o)

-continued

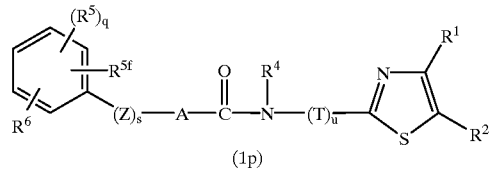

(1p)

wherein $R^1$, $R^2$, $R^4$, $R^5$, $R^6$, s, T, u, q, Z and A are the same as defined above, $R^{5e}$ is a lower alkenyloxy group, and $R^{5f}$ is a hydroxy group.

The reaction of converting the compound (1o) into the compound (1p) is carried out in the presence of a catalyst and an acid in a suitable solvent. The solvent may be, for example, water, acetic acid, alcohols (e.g., methanol, ethanol, isopropanol, etc.), hydrocarbons (e.g., hexane, cyclohexane, etc.), ethers (e.g., dioxane, tetrahydrorfuran, diethyl ether, ethylene glycol dimethyl ether, etc.), esters (e.g., ethyl acetate, methyl acetate, etc.), aprotic polar solvents (e.g., dimethylformamide, etc.), or a mixture of these solvents. The catalyst may be, for example, palladium, palladium black, palladium hydroxide, palladium hydroxide-carbon, palladium-carbon, platinum, platinum oxide, copper cromite, Raney nickel, etc. The acid includes, for example, organic acids such as p-toluene-sulfonic acid, etc. The catalyst is used in an amount of 0.02 to 1 time of the amount of the compound (1o). The acid is usually used in a catalytic amount. The reaction is usually carried out at a temperature of −20° C. to about 150° C., preferably at a temperature of 0° C. to about 120° C., for about 0.5 to about 20 hours.

Reaction Scheme-18

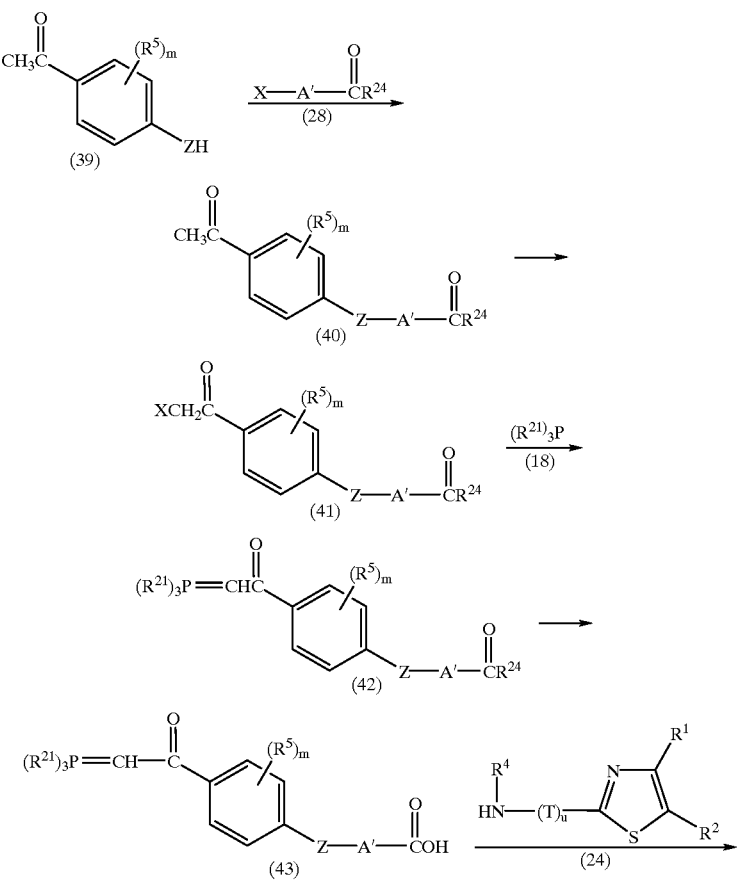

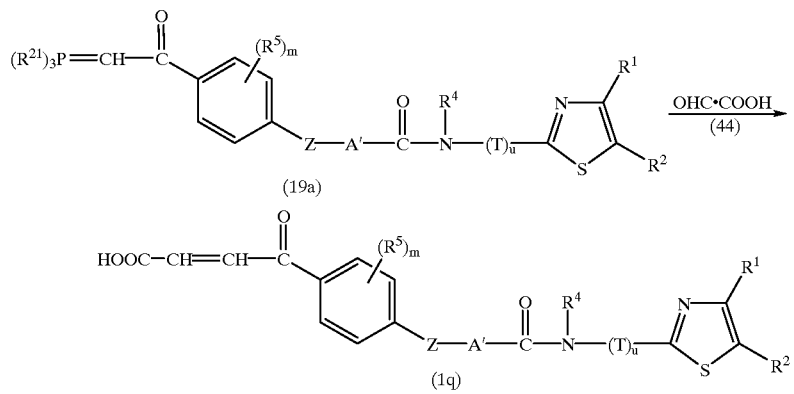

wherein T, u, $R^1$, $R^2$, $R^4$, A', Z, $R^5$, m, $R^{21}$, $R^{24}$ and X are the same as defined above.

The reaction of the compound (39) and the compound (28) is carried out under the same conditions as those in the reaction of the compound (1i) and the compound (22) in the above Reaction Scheme-6.

The reaction of converting the compound (40) into the compound (41) is carried out under the same conditions as those in the reaction of converting the compound (16) into the compound (17) in the above Reaction Scheme-5.

The reaction of the compound (41) and the compound (18) is carried out under the same conditions as those in the reaction of the compound (17) and the compound (18) in the above Reaction Scheme-5.

The reaction of converting the compound (42) wherein $R^{24}$ is a lower alkoxy group into the compound (43) is carried out under the same conditions as those in the reaction of converting the compound (1d) into the compound (1e) in the above Reaction Scheme-4.

The reaction of converting the compound (42) wherein $R^{24}$ is a phenyl-lower alkoxy group into the compound (43) is carried out under the same conditions as those in the reaction of converting the compound (5b) into the compound (5c) in the above Reaction Scheme-13.

The reaction of the compound (43) and the compound (24) is carried out under the same conditions as those in the reaction of the compound (1b) and the compound (5) in the above Reaction Scheme-2.

The reaction of the compound (19a) and the compound (44) is carried out in a suitable solvent in the presence of a basic compound, at 0° C. to 150° C., preferably at room temperature to about 100° C., for about 0.5 to 8 hours. The solvent may be any solvent which does not disturb the reaction, and may be water, alcohols (e.g., methanol, ethanol, isopropanol, etc.), aromatic hydrocarbons (e.g., benzene, toluene, xylene, etc.), ethers (e.g., diethyl ether, tetrahydrofuran, dioxane, diglyme, monoglyme, etc.), halogenated hydrocarbons (e.g., dichloromethane, chloroform, carbon tetrachloride, etc.), polar solvents (e.g., dimethylformamide, dimethylsulfoxide, hexamethylphosphoric triamide, etc.), or a mixture of these solvents. The compound (44) is usually used at least in an equimolar amount, preferably in an amount of 1 to 5 moles, to 1 mole of the compound (19a). The basic compound may be the same basic compounds which are used in the reaction of the compound (6) and the compound (7) in the above Reaction Scheme-3. The starting compound (9) can be prepared, for example, by the process in Reaction Scheme-19 or -20, as explained below.

Reaction Scheme-19

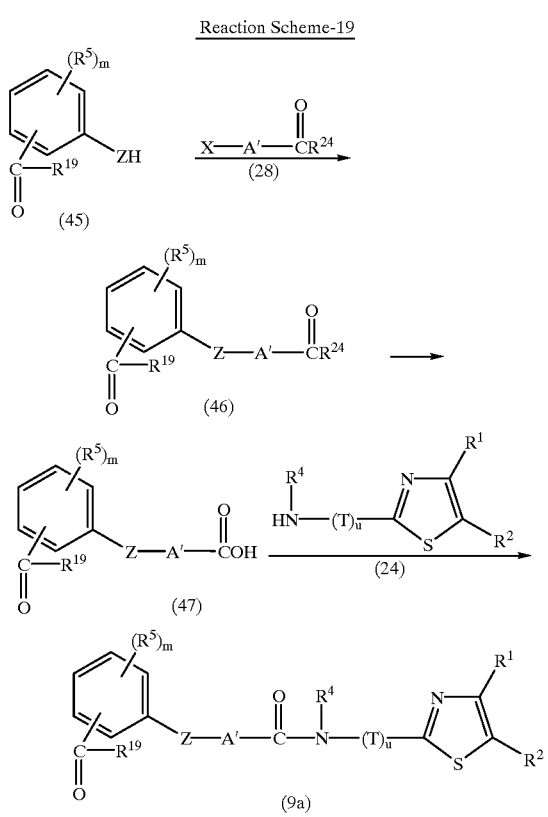

wherein T, u, $R^1$, $R^2$, $R^4$, A', Z, $R^5$, m, X, $R^{24}$ and $R^{19}$ are the same as defined above.

The reaction of the compound (45) and the compound (28) is carried out under the same conditions as those in the reaction of the compound (1i) and the compound (22) in the above Reaction Scheme-6.

The reaction of converting the compound (46) wherein $R^{24}$ is a lower alkoxy group into the compound (47) is carried out under the same conditions as those in the reaction of converting the compound (1d) into the compound (1e) in the above Reaction Scheme-4.

The reaction of converting the compound (46) wherein $R^{24}$ is a phenyl-lower alkoxy group into the compound (47) is carried out under the same conditions as those in the reaction of converting the compound (5b) into the compound (5c) in the above Reaction Scheme-13.

The reaction of the compound (47) and the compound (24) is carried out under the same conditions as those in the reaction of the compound (1b) and the compound (5) in the above Reaction Scheme-2.

The reaction of converting the compound (53) into the compound (50) is carried out under the same conditions as those in the reaction of converting the compound (1d) into the compound (1e) in the above Reaction Scheme-4.

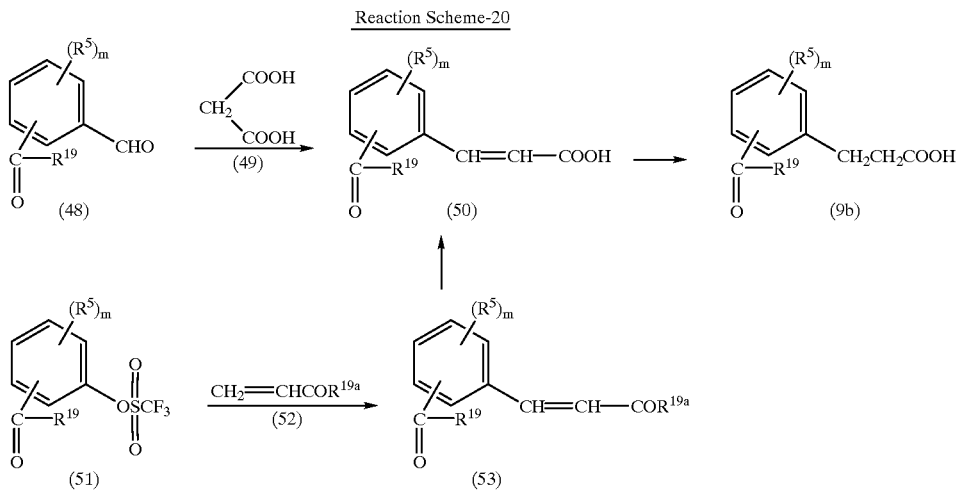

Reaction Scheme-20 wherein $R^{19}$, $R^5$ and m are the same as defined above, $R^{19a}$ is a lower alkoxy group.

The reaction of the compound (48) and the compound (49) is carried out in a suitable solvent in the presence of a basic compound. The solvents and the basic compounds are the same ones which are used in the reaction of the compound (6) and the compound (7) in the above Reaction Scheme-3. The compound (49) is usually used at least in an equimolar amount, preferably in an amount of 1 to 3 moles, to 1 mole of the compound (48). The reaction is usually carried out at room temperature to 200° C., preferably at room temperature to about 150° C., for about 1 to about 60 hours.

The reaction of converting the compound (50) into the compound (9b) is carried out under the same conditions as those in the reaction of converting the compound (5b) into the compound (5c) in the above Reaction Scheme-13.

The reaction of the compound (51) and the compound (52) is carried out in a suitable solvent in the presence of a basic compound and a catalyst. The solvent includes, for example, ethers (e.g., diethyl ether, tetrahydrofuran, dioxane, monoglyme, diglyme, etc.), aromatic hydrocarbons (e.g., benzene, toluene, xylene, etc.), aliphatic hydrocarbons (e.g., n-hexane, heptane, cyclo-hexane, etc.), dimethylformamide, dimethylsulfoxide, hexamethylphosphoric triamide, or a mixture of these solvents. The basic compound may be the same ones which are used in the reaction of the compound (1b) and the compound (5) using a carboxylic halide in the above Reaction Scheme-2. The catalyst includes, for example, palladium chloride, tetrakis (triphenylphosphine)palladium, palladium acetate, 1,3-bis (diphenylphosphino)propane, or a mixture of these solvents. The reaction is usually carried out at 0° C. to 200° C., preferably at room temperature to about 150° C., for about 1 to about 20 hours. The compound (52) is usually used at least in an equimolar amount, preferably in an amount of 1 to 10 moles, to 1 mole of the compound (51), The basic compound is usually used at least in an equimolar amount, preferably in an amount of 1 to 3 moles, to 1 mole of the compound (51). The catalyst is used at least in an excess amount of the compound (51).

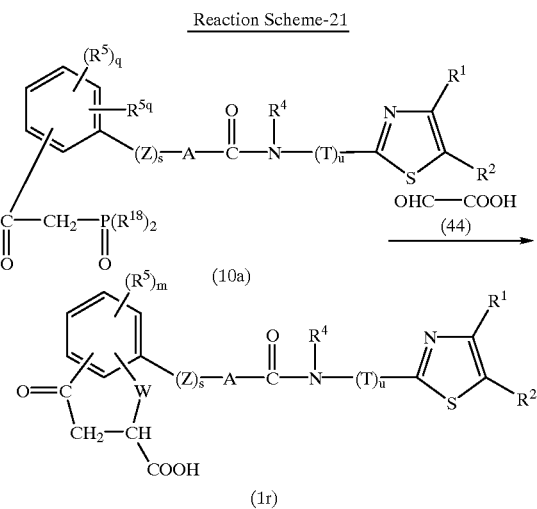

Reaction Scheme-21 wherein T, u, $R^5$, q, $R^{18}$, $R^1$, $R^2$, $R^4$, A, Z, s and W are the same as defined above, $R^{5q}$ is an amino group having optionally a lower alkyl substituent, and a group: —C(O)CH$_2$—P(O)(R$^{18}$)$_2$ and a group: —R$^{5q}$ are positioned each other at ortho-position.

The reaction of the compound (10a) and the compound (44) is carried out under the same conditions as those in the reaction of the compound (10) and the compound (12) in the above Reaction Scheme-3.

The compound (1r) wherein W is a group of the formula:

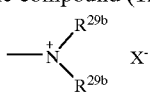

wherein $R^{29b}$ and $X^-$ are the same as defined above) can be obtained by treating with a hydrohalogenic acid such as hydrochloric acid, hydrobromic acid, etc., after the reaction is complete.

Reaction Scheme-22

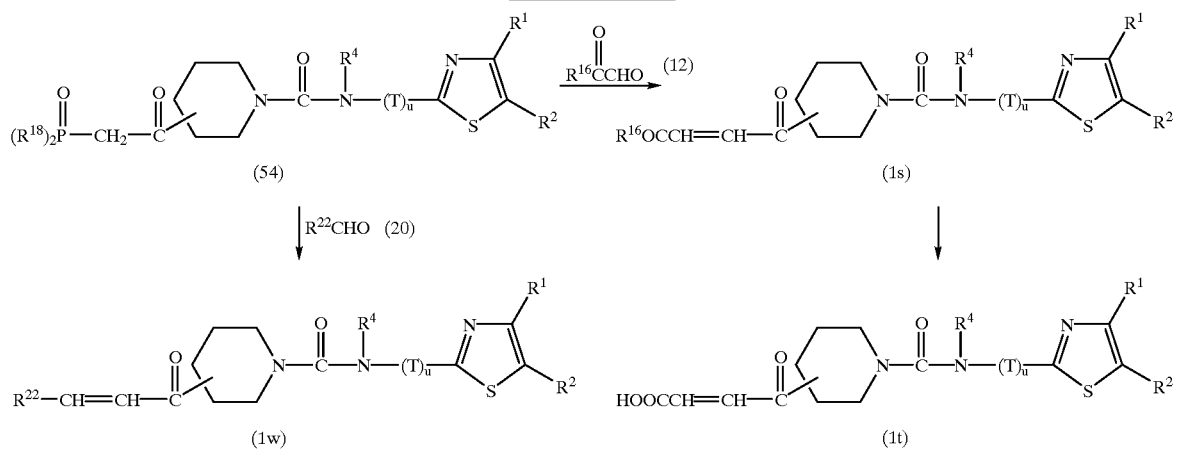

wherein $R^1$, $R^2$, T, u, $R^4$ $R^{16}$, $R^{18}$ and $R^{22}$ are the same as defined above.

The reaction of the compound (54) and the compound (12) is carried out under the same conditions as those in the reaction of the compound (10) and the compound (12) in the above Reaction Scheme-3.

The reaction of converting the compound (1s) wherein $R^{16}$ is a lower alkoxy group into the compound (1t) is carried out under the same conditions as those in the reaction of converting the compound (1d) into the compound (1e) in the above Reaction Scheme-4.

The reaction of the compound (54) and the compound (20) is carried out under the same conditions as those in the reaction of the compound (10) and the compound (20) in the above Reaction Scheme-3.

The starting compound (54) is prepared, for example, by the following process.

Reaction Scheme-23

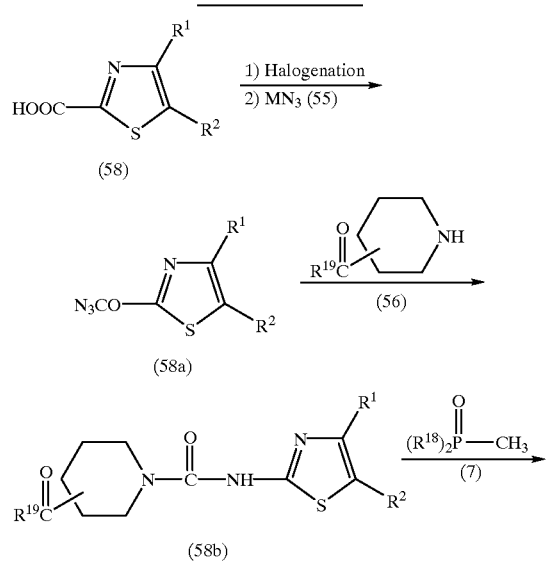

-continued

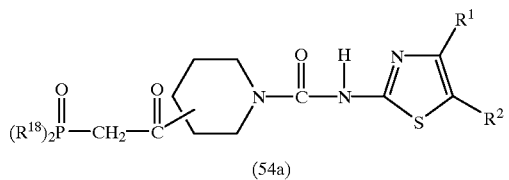

wherein $R^1$, $R^2$, M, $R^{19}$ and $R^{18}$ are the same as defined above.

The halogenation reaction of the compound (58) is carried out under conventional halogenation conditions which are employed in the halogenation reaction of a carboxylic acid. The reaction of the carboxylic acid halide compound of the compound (58) and the compound (55) is carried out in the presence or absence of a basic compound in a suitable solvent. The solvent includes, for example, halogenated hydrocarbons (e.g., methylene chloride, chloroform, etc.), aromatic hydrocarbons (e.g., benzene, toluene, xylene, etc.), ethers (e.g., diethyl ether, tetrahydrofuran, dimethoxyethane, etc.), esters (e.g., methyl acetate, ethyl acetate, etc.), aprotic polar solvents (e.g., N,N-dimethylformamide, dimethylsulfoxide, hexamethylphosphoric triamide, etc.), alcohols (e.g., methanol, ethanol, propanol, butanol, 3-methoxy-1-butanol, ethylcellosolve, methylcellosolve, et.), pyridine, acetone, acetonitrile, water, or a mixture of these solvents. The basic compound includes, for example, organic basic compounds such as triethylamine, trimethylamine, pyridine, dimethylaniline, N-methylmorpholine, DBN, DBU, DABCO, etc., or inorganic basic compounds such as potassium carbonate, sodium carbonate, potassium hydride, sodium hydride, potassium hydroxide, sodium hydroxide, silver carbonate, sodium methoxide, sodium ethoxide, etc. The compound (55) is used at least in an equimolar amount, preferably in an amount of 1 to 3 moles, to 1 mole of the carboxylic acid halide compound of the compound (58). The reaction is usually carried out at −30° C. to about 180° C., preferably at 0° C. to about 150° C., for about 5 minutes to about 30 hours.

The reaction of the compound (58a) and the compound (56) is carried out in a suitable solvent, or without a solvent, at 0° C. to about 200° C., preferably at room temperature to about 150° C. The solvent may be the same solvents used in the above reaction of the carboxylic halide of the compound (58) and the compound (55). The compound (56) is used at least in an equimolar amount, preferably in an amount of 1 to 1.5 mole, to 1 mole of the compound (58a). The reaction is carried out for about 1 hour to about 5 hours.

The reaction of the compound (58b) and the compound (7) is carried out under the same conditions as those in the reaction of the compound (9) and the compound (7) in the above Reaction Scheme-3.

Reaction Scheme-24

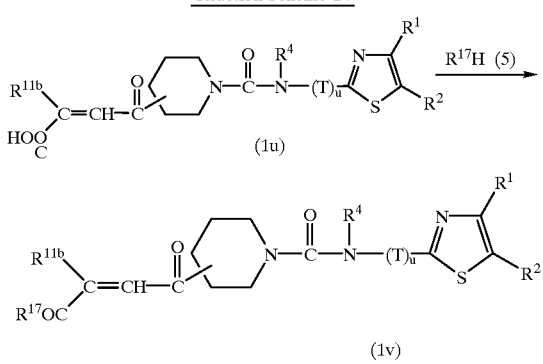

wherein $R^1$, $R^2$, $R^4$, $R^{11b}$, T, u and $R^{17}$ are the same as defined above.

The reaction of the compound (1u) and the compound (5) is carried out under the same conditions as those in the reaction of the compound (1b) and the compound (5) in the above Reaction Scheme-2. The starting compound (24) can be prepared, for example, by the method of Reaction Scheme-25, as explained below.

Reaction Scheme-25

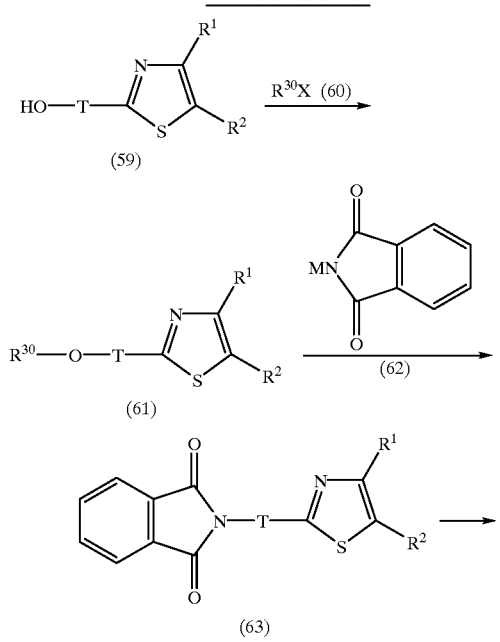

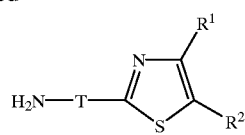

(24a)

wherein $R^1$, $R^2$, M, X and T are the same as defined above, and $R^{30}$ is a lower alkylsulfonyl group.

The reaction of the compound (59) and the compound (60) is carried out under the same conditions as those in the reaction of the compound (1i) and the compound (22) in the above Reaction Scheme-6. The reaction of the compound (61) and the compound (62) is carried out under the same conditions as those in the reaction of the compound (1i) and the compound (22) in the above Reaction Scheme-6.

The reaction of converting the compound (63) into the compound (24a) is carried out by treating the compound (63) with hydrazine in a suitable solvent, or hydrolyzing the compound (63). The solvent used in the reaction with hydrazine may be, in addition to water, the same solvents used in the reaction using a carboxylic acid halide in the reaction of the compound (1b) and the compound (5) in Reaction Scheme-2. The reaction is usually carried out at room temperature to about 120° C., preferably at 0° C. to about 100° C., for about 0.5 hour to about 5 hours. The hydrazine is usually used at least in an equimolar amount, preferably in an amount of 1 to 6 moles, to 1 mole of the compound (63).

The hydrolysis is carried out in a suitable solvent or without a solvent in the presence of an acid or a basic compound. The solvent includes, for example, water, lower alcohols (e.g., methanol, ethanol, isopropanol, etc.), ketones (e.g., acetone, methyl ethyl ketone, etc.), ethers (e.g., diethyl ether, dioxane, tetra-hydrofuran, ethylene glycol dimethyl ether, etc.), fatty acids (e.g., acetic acid, formic acid, etc.), or a mixture of these solvents. The acid includes, for example, mineral acids (e.g., hydrochloric acid, hydrobromic acid, etc.), organic acids (e.g., formic acid, acetic acid, aromatic sulfonic acids, etc.). The basic compound includes, for example, an alkali metal carbonate (e.g., sodium carbonate, potassium carbonate, etc.), an alkali metal or alkaline earth metal hydroxide (e.g., sodium hydroxide, potassium hydroxide, calcium hydroxide, etc.). The reaction is usually carried out at room temperature to about 200° C., preferably at room temperature to about 150° C., for about 10 minutes to about 25 hours.

Among the desired compounds (1) of the present invention, the compounds having an acidic group can easily be converted into salts by treating them with a pharmaceutically acceptable basic compound. The basic compound includes, for example, an alkali metal hydroxide such as sodium hydroxide, potassium hydroxide, lithium hydroxide, calcium hydroxide, etc., an alkali metal carbonate such as sodium carbonate, etc., an alkali metal hydrogen carbonate such as potassium hydrogen carbonate, an alkali metal alkoxide such as sodium methylate, potassium ethylate, and the like.

Besides, among the desired compounds (1) of the present invention, the compounds having a basic group can easily be converted into acid addition salts thereof by treating them with a pharmaceutically acceptable acid. The acid includes, for example, inorganic acids (e.g. sulfuric acid, nitric acid, hydrochloric acid, hydrobromic acid, etc.), and organic acids (e.g. acetic acid, p-toluenesulfonic acid, ethanesulfonic acid, oxalic acid, maleic acid, fumaric acid, citric acid, succinic acid, benzoic acid, etc.). These salts can be also used as an active ingredient of the pharmaceutical composition of the present invention as well as the compound (1) in a free form. In addition, the compounds of the present invention also include stereoisomers and optical isomers, and these isomers are also used as an active ingredient.

The desired compound obtained in the above Reaction Schemes can easily be isolated and purified by conventional isolation methods from the reaction system. The isolation methods are, for example, distillation method, recrystallization method, column chromatography, ion exchange chromatography, gel chromatography, affinity chromatography, preparative thin layer chromatography, extraction with solvent, dilution method, and the like.

The compounds (1) of the present invention are useful as a protein kinase inhibitor, and can be used in the form of a conventional pharmaceutical preparation. The preparation is prepared by using conventional diluents or carriers such as fillers, thickening agents, binders, wetting agent, disintegrators, surfactants, lubricants, and the like. The pharmaceutical preparations can be selected from various forms in accordance with the desired utilities, and the representative forms are tablets, pills, powders, solutions, suspensions, emulsions, granules, capsules, suppositories, injections (solutions, suspensions, etc.), and the like. In order to form in tablets, there are used carriers such as vehicles (e.g. lactose, white sugar, sodium chloride, glucose, urea, starch, calcium carbonate, kaolin, crystalline cellulose, silicic acid, etc.), binders (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium alginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium base, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), and the like. Moreover, the tablets may also be in the form of a conventional coated tablet, such as sugar-coated tablets, gelatin-coated tablets, enteric coated tablets, film coating tablets, or double or multiple layer tablets. In the preparation of pills, the carriers may be conventional ones, and include, for example, vehicles (e.g. glucose, lactose, starches, cacao butter, hydrogenated vegetable oils, kaolin, talc, etc.), binders (e.g. gum arabic powder, tragacanth powder, gelatin, ethanol, etc.), disintegrators (e.g. laminaran, agar, etc.), and the like. In the preparation of suppositories, the carriers may be conventional ones, and include, for example, polyethylene glycol, cacao butter, higher alcohols, higher alcohol esters, gelatin, semi-synthetic glycerides, and the like. The capsules are prepared by mixing the active compound with a conventional carrier, and fulfilling the mixture into hard gelatin capsules or soft capsules. In the preparation of injections, the solutions and suspensions are sterilized and are preferably made isotonic with the blood. In the preparation of these solutions, emulsions and suspensions, there are used conventional diluents, such as water, ethyl alcohol, macrogol, propylene glycol, ethoxylated isostearyl alcohol, polyoxylated isostearyl alcohol, polyoxyethylene sorbitan fatty acid esters, and the like. In this case, the pharmaceutical preparations may also be incorporated with sodium chloride, glucose, or glycerin in an amount sufficient to make them isotonic, and may also be incorporated with conventional solubilizers, buffers, anesthetizing agents. Besides, the pharmaceutical preparations may optionally be incorporated with coloring agents, preservatives, perfumes, flavors, sweetening agents, and other medicaments, if required.

The amount of the desired compound (1) of the present invention or a salt thereof to be incorporated into the pharmaceutical preparation is not specified but may be selected from a broad range, but usually, it is preferably in the range of about 1 to 70% by weight, preferably in the range of about 5 to 50% by weight.

The pharmaceutical preparation of the present invention may be administered in any method, and the suitable method for administration may be determined in accordance with various forms of preparations, ages, sexes and other conditions of the patients, the degree of severity of diseases, and the like. For example, tablets, pills, solutions, suspensions, emulsions, granules and capsules are administered orally. Injections are intravenously administered alone or together with a conventional auxiliary liquid (e.g. glucose, amino acid solutions), and further are optionally administered alone in intramuscular, intracutaneous, subcutaneous, or intraperitoneal route, if required. Suppositories are administered in intrarectal route.

The dosage of the pharmaceutical preparation of the present invention may be selected in accordance with the usage, ages, sexes and other conditions of the patients, the degree of severity of the diseases, and the like, but it is usually in the range of about 0.6 to 50 mg of the compound (1) or a salt thereof per 1 kg of body weight of the patient per day. The active compound is contained in an amount of about 10 to 1000 mg per one unit of the dosage form.

BEST MODE FOR CARRYING OUT THE INVENTION

The present invention is illustrated in more detail by the following Preparations of pharmaceutical composition, Reference Examples of processes for preparing the starting compounds to be used for preparing the desired compounds of the present invention, and Examples of processes for preparing the desired compounds, and Experiment of the activities of the desired compounds of the present invention.

Preparation 1

Film coated tablets are prepared from the following components.

| Components | Amount |
| --- | --- |
| 2-[2-Methoxy-4-{3-[4-(4-methyl-1-piperazinyl)-1-piperidinylcarbonyl]acryloyl}phenoxymethyl-carbonylamino]benzothiazole | 150 g |
| Avicel (trade mark of microcrystalline cellulose manufactured by Asahi Chemical Industry, Co., Ltd.) | 40 g |
| Corn starch | 30 g |
| Magnesium stearate | 2 g |
| Hydroxypropyl methylcellulose | 10 g |
| Polyethylene glycol-6000 | 3 g |
| Castor oil | 40 g |
| Ethanol | 40 g |

The active compound of the present invention, Avicel, corn starch and magnesium stearate are mixed and kneaded, and the mixture is tabletted by using a conventional pounder (R 10 mm) for sugar coating. The tablets thus obtained are coated with a film coating agent consisting of hydroxypropyl methylcellulose, polyethylene glycol-6000, castor oil and ethanol to give film coated tablets.

Preparation 2

Tablets are prepared from the following components.

| Components | Amount |
|---|---|
| 2-[3-Methoxy-4-{3-[4-(3,4-dimethyl-1-piperazinyl)-1-piperidinylcarbonyl]acryloyl}phenoxymethyl-carbonylamino]benzimidazole | 150 g |
| Citric acid | 1.0 g |
| Lactose | 33.5 g |
| Dicalcium phosphate | 70.0 g |
| Pullonic F-68 | 30.0 g |
| Sodium laurylsulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium stearate | 3.0 g |
| Dry magnesium stearate | 3.0 g |
| Ethanol | q.s. |

The active compound of the present invention, citric acid, lactose, dicalcium phosphate, Pullonic F-68 and sodium laurylsulfate are mixed.

The mixture is screened with No. 60 screen and is granulated with an alcohol solution containing polyvinylpyrrolidone, Carbowax 1500 and 6000. If required, an alcohol is added thereto so that the powder mixture is made a paste-like mass. Corn starch is added to the mixture and the mixture is continuously mixed to form uniform particles. The resulting particles are passed through No. 10 screen and entered into a tray and then dried in an oven at 100° C. for 12 to 14 hours. The dried particles are screened with No. 16 screen and thereto are added dry sodium laurylsulfate and dry magnesium stearate, and the mixture is tabletted to form the desired shape.

The core tablets thus prepared are vanished and dusted with talc in order to guard from wetting. Undercoating is applied to the core tablets. In order to administer the tablets orally, the core tablets are vanished several times. In order to give round shape and smooth surface to the tablets, further undercoating and coating with lubricant are applied thereto. The tablets are further coated with a coloring coating material until the desired colored tablets are obtained. After drying, the coated tablets are polished to obtain the desired tablets having uniform gloss.

Preparation 3

An injection preparation is prepared from the following components.

| Components | Amount |
|---|---|
| 2-{2-(3-Morpholinopropyl)-4-[3-(4-pyridyl)acryloyl]-phenoxymethylcarbonylamino}benzothiazole | 5 g |
| Polyethylene glycol (molecular weight: 4000) | 0.3 g |
| Sodium chloride | 0.9 g |
| Polyoxyethylene sorbitan monooleate | 0.4 g |
| Sodium metabisulfite | 0.1 g |
| Methyl-paraben | 0.18 g |

| Components | Amount |
|---|---|
| Propyl-paraben | 0.02 g |
| Distilled water for injection | 10.0 ml |

The above parabens, sodium metabisulfite and sodium chloride are dissolved with stirring in distilled water of half volume of the above at 80° C. The solution thus obtained is cooled to 40° C., and the active compound of the present invention and further polyethylene glycol and polyoxyethylene sorbitan monooleate are dissolved in the above solution. To the solution is added distilled water for injection to adjust to the desired volume, and the solution is sterilized by filtering with an appropriate filter paper to give an injection preparation.

Reference Example 1

A solution of o-isopropylphenol (39.5 g), potassium carbonate (40 g) and ethyl α-bromoacetate (40 ml) in dimethylformamide (300 ml) is heated with stirring at 80° C. for 8 hours. To the mixture is added water, and the mixture is extracted with ethyl acetate. The extract is washed with water, dried, and concentrated under reduced pressure to remove the solvent. The residue thus obtained is dissolved in a solution of sodium hydroxide (20 g) in water (300 ml) and ethanol (200 ml), and the mixture is refluxed for 1.5 hour. After cooling, the mixture is acidified with conc. hydrochloric acid, and the precipitated crystals are collected by filtration to give α-(2-isopropylphenoxy)acetic acid (37 g).

White powder; $^1$H-NMR (CDCl$_3$) δppm: 1.24 (6H, d, J=7 Hz), 3.39 (1H, sept, J=7 Hz), 4.69 (2H, s), 6.75 (1H, dd, J=1 Hz, J=8 Hz), 6.95–7.3 (3H, m).

Reference Example 2

A solution of α-(2-isopropylphenoxy)acetic acid (13.1 g) in thionyl chloride (30 ml) is refluxed for 30 minutes. The mixture is concentrated under reduce pressure to remove the excess thionyl chloride, and the resultant is dissolved in dichloromethane (50 ml). The mixture is added dropwise into a solution of 2-aminobenzothiazole (9.1 g) and pyridine (7.2 ml) in dichloromethane (100 ml) under ice-cooling. The mixture is stirred at the same temperature for five hours, and then washed with water, dried, and concentrated under reduced pressure. To the residue is added ethanol to give 2-(2-isopropylphenoxymethylcarbonylamino)benzothiazole (16.66 g).

Yellow powder; $^1$H-NMR (CDCl$_3$) δppm: 1.32 (6H, d, J=7 Hz) 3.43 (1H, sept, J=7 Hz), 4.78 (2H, s), 6.85 (1H, dd, J=1 Hz, J=8 Hz), 7.0–7.55 (5H, m), 7.8–7.9 (2H, m), 9.74 (1H, br).

Reference Example 3

To a solution of dimethyl methylphosphonate (19.5 ml) in anhydrous tetrahydrofuran (300 ml) is added a 1.72 M solution of n-butyl lithium in n-hexane (107 ml) at −50° C. Thirty minutes later, to the mixture is added in portions 2-(2-methoxy-4-formylphenoxymethylcarbonylamino) benzothiazole (20.5 g) under nitrogen atmosphere. The mixture is stirred at −50° C. for one hour, and thereto is added water. The mixture is acidified with conc. hydrochloric acid, and extracted with ethyl acetate. The extract is washed with water, dried and concentrated under reduced pressure. The residue is purified by silica gel column chromatography (solvent; dichloromethane:methanol=200:1→30:1) to give dimethyl {2-[3-methoxy-4-(2-benzothiazolylaminocarbonylmethoxy)phenyl]-2-hydroxyethyl}phosphonate (19.0 g).

$^1$H-NMR (CDCl$_3$) δppm: 2.05–2.35 (2H, m), 3.73, 3.76, 3.78 and 3.81 (6H, each s), 3.98 (2H, d, J=2.5 Hz), 4.01 (3H, s), 4.77 (2H, s), 5.0–5.15 (1H, m), 6.90 (1H, dd, J=2 Hz, J=8 Hz), 6.98 (1H, d, J=8 Hz), 7.07 (1H, d, J=2 Hz), 7.25–7.5 (2H, m), 7.8–7.9 (2H, m), 10.66 (1H, br).

To a solution of dimethyl {2-[3-methoxy-4-(2-benzothiazolylaminocarbonylmethoxy)phenyl]-2-hydroxyethyl}phosphonate (19.0 g) in chloroform (300 ml) is added active manganese dioxide (17.7 g), and the mixture is refluxed for three hours. To the mixture is additionally added active manganese dioxide (18 g), and the mixture is refluxed for three hours. To the mixture is further added active manganese dioxide (20 g), and the mixture is refluxed for three hours. The manganese dioxide is collected by filtration, and washed with chloroform. The filtrate and the washings are combined and concentrated under reduced pressure to remove the chloroform. The residue is purified by silica gel column chromatography (solvent; dichloromethane:methanol=200:1→50:1) to give dimethyl {[3-methoxy-4-(2-benzothiazolylaminocarbonylmethoxy)benzoyl]methyl}phosphonate (7.76 g).

White powder; $^1$H-NMR (CDCl$_3$) δppm: 3.62 (2H, d, J=22.5 Hz), 3.79 (6H, d, J=11.2 Hz), 4.04 (3H, s), 4.85 (2H, s), 7.02 (1H, d, J=8.5 Hz), 7.3–7.55 (2H, m), 7.6–7.7 (2H, m), 7.8–7.9 (2H, m), 10.31 (1H, br).

Reference Example 4

To a solution of chloroacetyl chloride (10.0 ml) in anhydrous 1,2-dichloroethane (250 ml) is added aluminum chloride (12 g) at room temperature, and the mixture is stirred for 20 minutes. To the mixture is added at once 2-(2-isopropylphenoxymethylcarbonylamino)benzothiazole (20 g), and the mixture is stirred at room temperature for one hour. The reaction mixture is poured into water, and thereto is added n-hexane. The precipitates are collected by filtration, washed with water, and dried to give 2-[2-isopropyl-4-(2-chloroacetyl)phenoxymethylcarbonylamino]benzothiazole (25.9 g).

White powder; $^1$H-NMR (DMSO-d$_6$) δppm: 1.24 (6H, d, J=7 Hz), 3.38 (1H, m), 5.12 (4H, s), 7.01 (1H, d, J=9 Hz), 7.25–7.55 (2H, m), 7.7–7.95 (3H, m), 7.97 (1H, d, J=8 Hz), 13.00 (1H, br).

Reference Example 5

A suspension of 2-[2-isopropyl-4-(2-chloroacetyl)phenoxymethylcarbonylamino]benzimidazole (4.0 g) and triphenylphosphine (2.8 g) in chloroform (100 ml) is refluxed for 7 hours. The reaction mixture is concentrated under reduced pressure, and the residue is crystallized from dichloromethane-diethyl ether to give [3-isopropyl-4-(2-benzothiazolylaminocarbonylmethoxy)benzoyl]methyltriphenylphosphonium chloride (3.8 g).

$^1$H-NMR (DMSO-d$_6$) δppm: 1.23 (6H, d, J=7 Hz), 3.40 (1H, m), 5.18 (2H, s), 6.19 (2H, d, J=13.5 Hz), 7.09 (1H, d, J=9 Hz), 7.25–7.5 (2H, m), 7.6–8.05 (19H, m), 12.77 (1H, s).

To a solution of [3-isopropyl-4-(2-benzothiazolylaminocarbonylmethoxy)benzoyl]methyltriphenylphosphonium chloride (3.3 g) in methanol (50 ml) is added DBU (1 ml), and the mixture is stirred at room temperature for two hours. The precipitated crystals are collected by filtration, washed with methanol, and dried to give [3-isopropyl-4-(2-benzothiazolylaminocarbonylmethoxy)benzoyl]methylenetriphenylphosphorane (2.27 g).

White powder; $^1$H-NMR (CDCl$_3$) δppm: 1.32 (6H, d, J=7 Hz), 3.42 (1H, sept, J=7 Hz), 4.2–4.6 (1H, m), 4.73 (2H, s), 6.75 (1H, d, =8.5 Hz), 7.25–8.0 (21H, m), 10.01 (1H, br).

Using the suitable starting compounds, the following compound is obtained in the same manner as in Reference Example 5. [3-(3-chloropropyl)-4-(2-benzothiazolylaminocarbonylmethoxy)benzoyl]methylenetriphenylphosphonium chloride:

White powder; $^1$H-NMR (CDCl$_3$) δppm: 2.11 (2H, tt, J=6.6 Hz, J=8.0 Hz), 2.86 (2H, t, J=8.0 Hz), 3.71 (2H, t, J=6.6 Hz), 5.20 (2H, s), 6.17 (2H, d, J=12.8 Hz), 7.13 (1H, d, J=8.7 Hz), 7.34 (1H, t, J=7.5 Hz), 7.48 (1H, t, J=7.0 Hz), 7.76–8.02 (19H, m), 12.75 (1H, br).

Reference Example 6

To dimethylformamide (200 ml) are added 2-methoxy-4-acetylphenol (20 g), ethyl α-bromoacetate (15 ml) and potassium carbonate (18.3 g), and the mixture is stirred at room temperature overnight. After the reaction is complete, water is added to the mixture, and the mixture is extracted with ethyl acetate. The extract is washed with aqueous sodium hydrogen carbonate solution, and dried over magnesium sulfate, and concentrated under reduced pressure to remove the solvent. The resulting crystals are collected, and washed with n-hexane-diethyl ether to give ethyl α-(2-methoxy-4-acetylphenoxy)acetate (23.86 g).

To chloroform (230 ml) are added ethyl α-(2-methoxy-4-acetylphenoxy)acetate (23 g) and copper (II) bromide (55 g), and the mixture is refluxed for 3.5 hours. After the reaction is complete, the mixture is filtered through a cerite pad to remove the precipitates, and washed with sodium hypochlorite. The filtrate is dried over magnesium sulfate, and concentrated under reduced pressure to remove the solvent, and then crystallized to give ethyl α-[2-methoxy-4-(2-bromoacetyl)phenoxy]acetate (21.28 g).

To chloroform (200 ml) are added ethyl α-[2-methoxy-4-(2-bromoacetyl)phenoxy]acetate (20 g) and triphenylphosphine (20.6 g) in an ice-bath, and the mixture is stirred for one hour. After confirming that the starting compounds are well consumed, the mixture is washed with an aqueous potassium carbonate solution. The mixture is dried over magnesium sulfate, and concentrated under reduced pressure to remove the solvent. To the residue is added methanol (200 ml), and thereto is added dropwise sodium hydroxide in an ice-bath. After confirming that the starting compounds are well consumed, to the mixture is added conc hydrochloric acid. The precipitated crystals are washed with water and diethyl ether, and dried to give (3-methoxy-4-carboxymethoxybenzoyl)methylenetriphenylphosphorane (25 g).

To dichloromethane (50 ml) are added (3-methoxy-4-carboxymethoxybenzoyl)methylenetriphenylphosphorane (5 g), 2-aminobenzothiazole (1.9 g), bis(2-oxo-3-oxazolidinyl)phosphinic chloride (2.93 g) and triethylamine (3.3 ml), and the mixture is stirred overnight. After the reaction is complete, the mixture is washed with an aqueous sodium hydrogen carbonate solution, and dried over magnesium sulfate to remove the solvent, and further recrystallized from toluene to give [3-methoxy-4-(2-benzothiazolylaminocarbonylmethoxy)benzoyl]methylenetriphenylphosphorane (5.17 g).

Pale yellow powder; $^1$H-NMR (CDCl$_3$) δppm: 4.03 (3H, s), 4.12–4.62 (1H, m), 4.79 (2H, s), 6.96 (1H, d, J=8.3 Hz), 7.25–7.90 (22H, m).

Reference Example 7

To a solution of N-benzyl-4-piperidone (8.0 g) and 3,4-dimethylpiperazine (9.5 g) in ethanol (100 ml) are added 5% platinum-carbon (2 g) and acetic acid (14.4 ml), and the mixture is subjected to catalytic hydrogenation at room temperature under atmospheric pressure. The catalyst is removed by filtration, and the filtrate is concentrated under reduced pressure. Water is added to the resultant, and the mixture is basified with a 5% aqueous sodium hydroxide solution, and the mixture is extracted with diethyl ether. The extract is washed with water, dried and concentrated under reduced pressure to remove the solvent. The residue is dissolved in ethanol, and thereto is added to conc. hydrochloric acid to give a hydrochloride. The resulting white powder is collected by filtration, dissolved in water, and basified with a 5% aqueous sodium hydroxide solution. The mixture is extracted with diethyl ether, washed with water, dried, and concentrated under reduced pressure to give 4-(3,4-dimethyl-1-piperazinyl)-1-benzylpiperidine (4.2 g).

$^1$H-NMR (CDCl$_3$) δppm: 1.04 (3H, d, J=6 Hz), 1.45–2.5 (12H, m), 2.27 (3H, s), 2.7–3.05 (4H, m), 3.48 (2H, s), 7.31 (5H, m).

To a solution of 4-(3,4-dimethyl-1-piperazinyl)-1-benzylpiperidine (4.2 g) in ethanol (50 ml) is added 20% palladium hydroxide-carbon (0.4 g), and the mixture is subjected to catalytic hydrogenation at 50° C. under atmospheric pressure. The catalyst is removed by filtration, and the filtrate is concentrated under reduced pressure. The residue is evaporated to give 4-(3,4-dimethyl-1-piperazinyl) piperidine (1.65 g).

Colorless oil; b.p. 145° C. (0.3 mmHg); $^1$H-NMR (CDCl$_3$) δppm: 1.05 (3H, d, J=6 Hz), 1.25–1.55 (2H, m), 1.75–3.3 (14H, m), 2.31 (3H, s).

Reference Example 8

A solution of 1-benzyl-L-proline (50 g) in dichloromethane (300 ml) is cooled with ice. To the solution is added N-methylmorpholine (22.5 g), and then further thereto is added dropwise isobutyl chloroformate (30 g). The mixture is stirred at the same temperature for about one hour, and thereto is added dropwise pyrrolidine (18.8 ml) at the same temperature. The mixture is warmed to room temperature, and stirred for two days. The mixture is washed twice with water (250 ml), and dried over magnesium sulfate. The mixture is concentrated under reduced pressure, and the residue is recrystallized from ethyl acetate-n-hexane to give 2-(1-pyrrolidinyl)carbonyl-1-benzylpyrrolidine (31 g), as white powder.

In ethanol (300 ml) is suspended 5% palladium-carbon (3 g), and thereto is added 2-(1-pyrrolidinyl)carbonyl-1-benzylpyrrolidine (30 g), and the mixture is subjected to catalytic hydrogenation at room temperature under atmospheric pressure. The mixture is filtered, and the filtrate is concentrated under reduced pressure to remove the solvent to give 2-(1-pyrrolidinyl)carbonylpyrrolidine (about 18 g) as an oily product.

Lithium aluminum hydride (9 g) is suspended in dry tetrahydrofuran (100 ml) under ice-cooling, and thereto is added dropwise a solution of 2-(1-pyrrolidinyl)carbonylpyrrolidine (33 g) in dry tetrahydrofuran (80 ml). The mixture is refluxed under nitrogen atmosphere for four hours. The mixture is cooled with ice, and thereto is added a saturated aqueous sodium sulfate solution (about 15 ml), and then mixture is further stirred at room temperature for three hours. The precipitated sodium sulfate is removed by filtration, washed well with chloroform. The filtrate and the washings are combined, concentrated under reduced pressure, and evaporated to give 2-(1-pyrrolidinyl)methylpyrrolidine (22 g).

Colorless oil; B.p. 99–101° C. (20 mmHg).

Reference Example 9

4-Benzyl-2-chloromethylmorpholine (15 g) and 4-(2-hydroxyethyl)piperazine (25 ml) are mixed, and the mixture is heated with stirring at 130° C. for five hours. After the reaction is complete, the mixture is extracted with chloroform, and the extract is dried over magnesium sulfate. The residue thus obtained is concentrated under reduced pressure to give 4-benzyl-2-[4-(2-hydroxyethyl)-1-piperazinyl]methylmorpholine (16 g).

$^1$H-NMR (CDCl$_3$) δppm: 1.86 (1H, t, J=10.6 Hz), 2.07–2.27 (2H, m), 2.37–3.05 (14H, m), 3.49 (2H, d, J=2.3 Hz), 3.57–3.89 (5H, m), 7.24–7.33 (5H, m).

4-Benzyl-2-[4-(2-hydroxyethyl)-1-piperazinyl]methylmorpholine (16 g) is dissolved in ethanol (160 ml), and thereto is added palladium hydroxide (1.6 g). The mixture is subjected to de-benzylation at 50° C. under hydrogen atmosphere. Five hours later, the mixture is filtered through a cerite pad, and the filtrate is concentrated under reduced pressure. The resulting crystals are washed with diethyl ether-n-hexane to give 2-[4-(2-hydroxyethyl)-1-piperazinyl]methylmorpholine (9.09 g).

M.p. 73–75.5° C.; White powder; $^1$H-NMR (CDCl$_3$) δppm: 2.25 (1H, dd, J=4.2 Hz, J=13.0 Hz), 2.37–2.74 (11H, m), 2.74–3.02 (6H, m), 3.49–3.77 (4H, m), 3.85–3.93 (1H, m).

Using the suitable starting compounds, the compounds as listed in Tables 1 to 4 are obtained in the same manner as in Reference Example 1.

TABLE 1

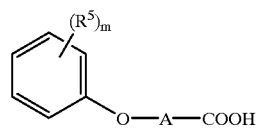

Reference Example 10

| | | |
|---|---|---|
| R$^5$: CH$_3$ (2-position) | m: 1 | A: —CH$_2$— |
| Crystalline form: white powder | Form: Free | NMR (1) |

TABLE 1-continued

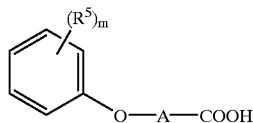

Reference Example 11

| | | |
|---|---|---|
| R⁵: C₂H₅ (2-position) | m: 1 | A: —CH₂— |
| Crystalline form: White powder | Form: Free | NMR (2) |

Reference Example 12

| | | |
|---|---|---|
| R⁵: —(CH₂)₂CH₃ (2-position) | m: 1 | A —CH₂— |
| Crystalline form: White powder | Form: Free | NMR (3) |

Reference Example 13

| | | |
|---|---|---|
| R⁵: —(CH₂)₃CH₃ (2-position) | m: 1 | A: —CH₂— |
| M.p. 102–104° C. | Solvent for recrystallization: Ethanol-water | |
| Crystalline form: White powder | Form: Free | |

TABLE 2

Reference Example 14

R⁵: —(CH₂)₄CH₃ (2-position)
m: 1
A: —CH₂—
M.p. 71.4–74.4° C.
Solvent for recrystallization: Ethanol-water
Crystalline form: White powder
Form: Free Reference Example 15

R⁵: F (2-position)
m: 1
A: —CH₂—
Crystalline form: White powder
Form: Free
NMR (4)

Reference Example 16

R⁵: Cl (2-position)
m: 1
A: —CH₂—
Crystalline form: White powder
Form: Free
NMR (5)

Reference Example 17

R⁵: —(CH₂)₄— (combined at 2- and 3-positions)
m: 2
A: —CH₂—
Crystalline form: white powder
Form: Free
NMR (6)

Reference Example 18

R⁵: CH₃ (2- and 3-positions)
m: 2
A: —CH₂—
Crystalline form: White powder
Form: Free
NMR (7)

TABLE 3

Reference Example 19

R⁵: CH₃ (2- and 6-positions)
m: 2
A: —CH₂—
Crystalline form: Yellow powder

TABLE 3-continued

Form: Free
NMR (8)

Reference Example 20

R⁵: CH₃ (3- and 5-positions)
m: 2
A: —CH₂—
Crystalline form: White powder
Form: Free
NMR (9)

Reference Example 21

R⁵: CH₃ (3-position)
m: 1
A: —CH₂—
Crystalline form: White powder
Form: Free
NMR (10)

Reference Example 22

R⁵: C₂H₅ (3-position)
m: 1
A: —CH₂—
M.p. 102–104° C.
Solvent for recrystallization: Ethanol-water
Crystalline form: White powder
Form: Free Reference Example 23

R⁵: —(CH₂)₂CH₃ (3-position)
m: 1
A: —CH₂—
M.p. 63.5–66.0° C.
Solvent for recrystallization: Ethanol-water
Crystalline form: White powder
Form: Free

TABLE 4

Reference Example 24

R⁵: —(CH₂)₃CH₃ (3-position)  m: 1  A: —CH₂—
M.p. 69.0–72.5° C.  Solvent for recrystallization: Ethanol-water
Crystalline form: Colorless prisms  Form: Free  NMR (11)
Reference Example 25

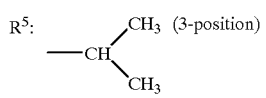
R⁵:  —CH(CH₃)CH₃ (3-position)  m: 1  A: —CH₂—

Crystalline form: white solid  Form: Free  NMR (12)
Reference Example 26

R⁵: Cl (3-position)  m: 1  A: —CH₂—
Crystalline form: White powder  Form: Free  NMR (13)
Reference Example 27

R⁵: F (3-position)  m: 1  A: —CH₂—
Crystalline form: White powder  Form: Free  NMR (14)
Reference Example 28

R⁵: CH₃O (3-position)  m: 1  A —CH₂—
Crystalline form: Beige powder  Form: Free  NMR (15)
Reference Example 29

R⁵: C₂H₅O (3-position)  m: 1  A: —CH₂—
Crystalline form: Beige powder  Form: Free  NMR (16)

¹H-NMR spectrum (NMR (1) to NMR (17)) as described in Tables 1 to 4 are as follows:

NMR (1) (DMSO-d₆) δppm: 2.19 (3H, s), 4.68 (2H, s), 6.83 (2H, dd, J=7.8 Hz, J=13.2 Hz), 7.12 (2H, t, J=7.8 Hz), 12.96 (1H, s); NMR (2) (DMSO-d₆) δppm: 1.14 (3H, t, J=7.5 Hz), 2.61 (2H, q, J=7.5 Hz), 4.69 (2H, s), 6.78–6.95 (2H, m), 7.05–7.20 (2H, m), 12.97 (1H, s); NMR (3) (CDCl₃) δppm: 0.95 (3H, t, J=7.4 Hz), 1.5–1.8 (2H, m), 2.65 (2H, t, J=7.4 Hz), 4.65 (2H, s), 6.73 (1H, d, J=8.3 Hz), 6.9–7.05 (1H, m), 7.15 (2H, t, J=7.2 Hz), 9.4–10.1 (1H, m); NMR (4) (DMSO-d₆) δppm: 4.77 (2H, s), 6.88–7.30 (4H, m), 13.09 (1H, s); NMR (5) (CDCl₃) δppm: 4.76 (2H, s), 6.89 (1H, dd, J=1.5 Hz, J=8.0 Hz), 6.99 (1H, dt, J=1.5 Hz, J=7.6 Hz), 7.23 (1H, dt, J=1.5 Hz, J=7.6 Hz), 7.41 (1H, dd, J=1.5 Hz, J=8.0 Hz), 8.16 (1H, br); NMR (6) (DMSO-d₆) δppm: 1.6–1.85 (4H, m), 2.55–2.75 (4H, m), 4.63 (2H, s), 6.57 (1H, d, J=8 Hz), 6.65 (1H, d, J=7.5 Hz), 6.9–7.05 (1H, m), 12.94 (1H, br); NMR (7) (DMSO-d₆) δppm: 2.10 (3H, s), 2.20 (3H, s), 4.63 (2H, s), 6.64 (1H, d, J=8 Hz), 6.75 (1H, d, J=7.5 Hz), 6.95–7.1 (1H, m), 12.9 (1H, br); NMR (8) (DMSO-d₆) δppm: 2.22 (6H, s), 4.35 (2H, s), 6.87–7.06 (3H, m), 12.87 (1H, s); NMR (9) (DMSO-d₆) δppm: 2.22 (6H, s), 4.48 (2H, s), 6.48 (2H, s), 6.60 (1H, s); NMR (10) (DMSO-d₆) δppm: 2.26 (3H, s), 4.62 (2H, s), 6.60–6.80 (3H, m), 7.11–7.18 (1H, m); NMR (11) (DMSO-d₆) δppm: 0.85 (3H, t, J=7.2 Hz), 1.17–1.38 (2H, m), 1.45–1.60 (2H, m), 2.49–2.57 (2H, m), 4.63 (2H, s), 6.66–6.79 (3H, m), 7.13–7.21 (1H, m), 13.00 (1H, br); NMR (12) (CDCl₃) δppm: 1.22 (6H, d, J=6.9 Hz), 2.77–3.00 (1H, m), 4.68 (2H, s), 6.66–6.76 (1H, m), 6.81–6.95 (2H, m), 7.17–7.29 (1H, m), 8.65 (1H, brs); NMR (13) (CDCl₃) δppm: 4.69 (2H, s), 6.79–6.85 (1H, m), 6.85–7.04 (2H, m), 7.19–7.28 (1H, m), 8.00 (1H, br); NMR (14) (CDCl₃) δppm: 4.69 (2H, s), 6.62–6.79 (3H, m), 7.20–7.32 (1H, m), 9.07 (1H, br); NMR (15) (CDCl₃) δppm: 3.79 (3H, s), 4.67 (2H, s), 6.47–6.61 (3H, m), 7.16–7.26 (1H, m), 9.12 (1H, br); NMR (16) (CDCl₃) δppm: 1.40 (3H, t, J=7.0 Hz), 4.01 (2H, q, J=7.0 Hz), 4.66 (2H, s), 6.45–6.62 (3H, m), 7.13–7.25 (1H, m), 8.34 (1H, br).

Using the suitable starting compounds, the compounds as listed in Tables 5–9 are obtained in the same manner as Reference Example 2.

TABLE 5

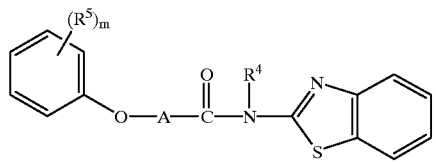

Reference Example 30

R⁵: CH₃ (2-position)  m: 1  A: —CH₂—  R⁴: H
Crystalline form: Yellow powder  Form: Free  NMR (1)
Reference Example 31

R⁵: C₂H₅ (2-position)  m: 1  A: —CH₂—  R⁴: H
Crystalline form: Pale yellow powder  Form: Free  NMR (2)
Reference Example 32

R⁵: —(CH₂)₂CH₃ (2-position)  m: 1  A: —CH₂—  R⁴: H
Crystalline form: Yellow powder  Form: Free  NMR (3)
Reference Example 33

R⁵: —(CH₂)₃CH₃ (2-position)  m: 1  A: —CH₂—  R⁴: H
Crystalline form: Yellow solid  Form: Free  NMR (4)

TABLE 6

Reference Example 34

R⁵: H (2-position)
m: 1
A: —CH₂—
R⁴: H
Crystalline form: Pale yellow powder
Form: Free

TABLE 6-continued

NMR (5)
Reference Example 35

$R^5$: —$(CH_2)_4CH_3$ (2-position)
m: 1
A: —$CH_2$—
$R^4$: H
Crystalline form: Yellow powder
Form: Free
NMR (6)
Solvent for recrystallization: Ethyl acetate-n-hexane
Reference Example 36

$R^5$: F (2-position)
m: 1
A: —$CH_2$—
$R^4$: H
Crystalline form: Pale yellow powder
Form: Free
NMR (7)
Reference Example 37

$R^5$: Cl (2-position)
m: 1
A: —$CH_2$—
$R^4$: H
Crystalline form: Yellow powder
Form: Free
NMR (8)
Reference Example 38

$R^5$: —$(CH_2)_4$— (combined at 2- and 3-positions)
m: 2
A: —$CH_2$—
$R^4$: H
Crystalline form: White powder
Form: Free
NMR (9)

TABLE 7

Reference Example 39

$R^5$: $CH_3$ (2- and 3-positions)
m: 2
A: —$CH_2$—
$R^4$: H

TABLE 7-continued

Crystalline form: Yellow powder
Form: Free
NMR (10)
Reference Example 40

$R^5$: $CH_3$ (2- and 6-positions)
m: 2
A: —$CH_2$—
$R^4$: H
Crystalline form: Yellow powder
Form: Free
NMR (11)
Reference Example 41

$R^5$: $CH_3$ (3- and 5-positions)
m: 2
A: —$CH_2$—
$R^4$: H
Crystalline form: White powder
Form: Free
NMR (12)
Reference Example 42

$R^5$: —$(CH_2)_3Cl$ (2-position)
m: 1
A: —$CH_2$—
$R^4$: H
Crystalline form: Yellow powder
Form: Free
NMR (13)
Reference Example 43

$R^5$: —$(CH_2)_2Cl$ (2-position)
m: 1
A: —$CH_2$—
$R^4$: H
Crystalline form: White powder
Form: Free
NMR (14)

TABLE 8

Reference Example 44

$R^5$: $CH_3$ (3-position)　　　m: 1　　A: —$CH_2$—　　$R^4$: H
Solvent for recrystailization: Ethyl acetate-n-hexane
Crystalline form: Pale brown powder　　Form: Free　　NMR (15)
Reference Example 45

$R^5$: $C_2H_5$ (3-position)　　m: 1　　A: —$CH_2$—　　$R^4$: H
Crystalline form: Beige needles　　Form: Free　　NMR (16)
Reference Example 46

$R^5$: —$(CH_2)_2CH_3$ (3-position)　m: 1　A: —$CH_2$—　$R^4$: H
M.p. 110.0—111.0° C.　　Solvent for recrystallization: Ethyl acetate-n-hexane
Crystalline form: Pale yellow needles　　Form: Free
Reference Example 47

$R^5$: —$(CH_2)_3CH_3$ (3-position)　m: 1　A: —$CH_2$—　$R^4$: H
M.p. 110.5–111.0° C.　　Solvent for recrystallization: Ethyl acetate-n-hexane
Crystalline form: Pale yellow needles　　Form: Free

TABLE 8-continued

Reference Example 48

R⁵: —CH(CH₃)₂ (3-position)    m: 1    A: —CH₂—    R⁴: H

M.p. 93.7–94.0° C.  Solvent for recrystallization: Ethyl acetate-n-hexane
Crystalline form: Pink powder  Form: Free

TABLE 9

Reference Example 49

R⁵: Cl (3-position)
m: 1
A: —CH₂—
R⁴: H
Crystalline form: Pale yellow powder
Form: Free
NMR (17)

Reference Example 50

R⁵: F (3-position)
m: 1
A: —CH₂—
R⁴: H
Crystalline form: Pale yellow powder
Form: Free
NMR (18)

Reference Example 51

R⁵: CH₃O (3-position)
m: 1
A: —CH₂—
R⁴: H
Crystalline form: Beige powder
Form: Free
NMR (19)

Reference Example 52

R⁵: C₂H₅O (3-position)
m: 1
A: —CH₂—
R⁴: H
Crystalline form: Brown powder
Form: Free
NMR (20)

$^1$H-NMR spectrum (NMR (1) to NMR (20)) as described in Tables 5 to 9 are as follows:

NMR (1) (DMSO-$d_6$) δppm: 2.45 (3H, s), 4.95 (2H, s), 6.81–6.95 (2H, m), 7.10–7.22 (2H, m), 7.32 (1H, t, J=6.1 Hz), 7.45 (1H, t, J=6.4 Hz), 7.77 (1H, d), J=6.4 Hz), 7.99 (1H, d, J=6.3 Hz), 12.60 (1H, s); NMR (2) (DMSO-$d_6$) δppm: 1.18 (3H, t, J=7.5 Hz), 2.67 (2H, q, J=7.5 Hz), 4.96 (2H, s), 6.89 (2H, dd, J=8.0 Hz, J=12.5 Hz), 7.09–7.23 (2H, m), 7.28–7.38 (1H, m), 7.40–7.52 (1H, m), 7.77 (1H, d, J=8.0 Hz), 7.98 (1H, d, J=7.8 Hz), 12.58 (1H, s); NMR (3) (CDCl₃) δppm: 1.03 (3H, t, J=7.4 Hz), 1.6–1.8 (2H, m), 2.73 (2H, t, J=7.4 Hz), 4.76 (2H, s), 6.84 (1H, d, J=8.0 Hz), 7.01–7.50 (5H, m), 7.79–7.86 (2H, m), 9.6–9.8 (1H, s); NMR (4) (CDCl₃) δppm: 0.95 (3H, t J=7.2 Hz), 1.37–1.55 (2H, m), 1.59–1.74 (2H, m), 2.71 (2H, d, J=7.2 Hz), 4.77 (2H, s), 6.82 (1H, d, J=8.1 Hz), 6.98–7.06 (1H, m), 7.16–7.26 (2H, m), 7.30–7.38 (1H, m), 7.41–7.50 (1H, m), 7.79–7.86 (2H, m), 9.78 (1H, brs); NMR (5) (CDCl₃) δppm: 4.76 (2H, s), 6.95–7.11 (3H, m), 7.26–7.47 (4H, m), 7.79–7.87 (2H, m), 9.92 (1H, br); NMR (6) (CDCl₃) δppm: 0.92 (3H, t, J=6.8 Hz), 1.30–1.55 (4H, m), 1.55–1.90 (2H, m), 2.71 (2H, t, J=7.6 Hz), 4.77 (2H, s), 6.82 (1H, d, J=8.0 Hz), 6.98–7.05 (1H, m), 7.17–7.26 (2H, m), 7.31–7.38 (1H, m), 7.42–7.50 (1H, m), 7.79–7.87 (2H, m), 9.73 (1H, brs); NMR (7) (DMSO-$d_6$) δppm: 5.03 (2H, s), 6.90–7.07 (1H, m), 7.07–7.20 (2H, m), 7.20–7.50 (2H, m), 7.45 (1H, dt, J=1.3 Hz, J=7.3 Hz), 7.77 (1H, d, J=7.8 Hz), 7.99 (1H, dd, J=0.7 Hz, J=7.7 Hz), 12.63 (1H, s); NMR (8) (CDCl₃) δppm: 4.80 (2H, s), 6.95–7.10 (2H, m), 7.23–7.49 (4H, m), 7.85 (2H, dd, J=2.0 Hz, J=6.6 Hz), 9.97 (1H, br); NMR (9) (CDCl₃) δppm: 1.75–2.0 (4H, m), 2.75–2.9 (4H, m), 4.74 (2H, s), 6.63 (1H, d, J=8 Hz), 6.82 (1H, d, J=8 Hz), 7.05–7.15 (1H, m), 7.3–7.5 (2H, m), 7.75–7.9 (2H, m), 9.73 (1H, br); NMR (10) (CDCl₃) δppm: 2.29 (3H, s), 2.32(3H, s), 4.75 (2H, s), 6.70 (1H, d, J=8 Hz), 6.90 (1H, d, J=7.5 Hz), 7.05–7.15 (1H, m), 7.3–7.5 (2H, m), 7.75–7.9 (2H, m), 9.76 (1H, br); NMR (11) (DMSO-$d_6$) δppm: 2.27 (6H, s), 4.63 (2H, s), 6.90–7.12 (3H, s), 7.29–7.40 (1H, m), 7.42–7.52 (1H, s), 7.76 (1H, d, J=7.8 Hz), 8.02 (1H, d, J=7.4 Hz), 12.49 (1H, s); NMR (12) (CDCl₃) δppm: 2.32 (6H, s), 4.73 (2H, s), 6.61 (2H, s), 6.72 (1H, s), 7.3–7.55 (2H, m), 7.8–7.95 (2H, m), 9.86 (1H, br); NMR (13) (CDCl₃) δppm: 2.18 (2H, tt, J=7.0 Hz, J=8.0 Hz), 2.96 (2H, t, J=7.0 Hz), 3.63 (2H, t, J=8.0 Hz), 4.80 (2H, s), 6.87 (1H, d, J=8.5 Hz), 7.04 (1H, t, J=7.2 Hz), 7.15–7.29 (2H, m), 7.34 (1H, t, J=8.9 Hz), 7.43 (1H, t, J=8.0 Hz), 7.79–7.87 (2H, m), 9.73 (1H, br); NMR (14) (CDCl₃) δppm: 3.22 (2H, t, J=7.0 Hz), 3.82 (2H, t, J=7.0 Hz), 4.81 (2H, s), 6.86 (1H, d, J=8.2 Hz), 7.05 (1H, t, J=7.2 Hz), 7.15–7.52 (4H, m), 7.81 (2H, t, J=8.4 Hz), 9.78 (1H, br); NMR (15) (CDCl₃) δppm: 2.37 (3H, s), 4.74 (2H, s), 6.74–6.85 (2H, m 6.85 (1H, d, J=7.3 Hz), 7.17–7.30 (1H, m), 7.30–7.40 (1H, m), 7.40–7.54 (1H, m), 7.77–7.90 (2H, m), 9.88 (1H, brs); NMR (16) (CDCl₃) δppm: 1.25 (3H, t, J=7.6 Hz), 2.65 (2H, q, J=7.6 Hz), 4.74 (2H, s), 6.74–6.84 (2H, m), 6.88–6.95 (1H, m), 7.21–7.50 (3H, m), 7.79–7.86 (2H, m), 9.94 (1H, br); NMR (17) (CDCl₃) δppm: 4.73 (2H, s), 6.75–6.84 (1H, m), 6.84–6.98 (1H, m), 7.01–7.08 (1H, m), 7.21–7.46 (3H, m), 7.82 (2H, t, J=8.4 Hz), 10.09 (1H, br); NMR (18) (DMSO-$d_6$) δppm: 4.94 (2H, s), 6.75–6.92 (3H, m), 7.27–7.47 (3H, m), 7.75 (1H, d, J=8.0 Hz), 7.97 (1H, d, J=8.0 Hz); NMR (19) (CDCl₃) δppm: 3.81 (3H, s), 4.73 (2H, s), 6.53–6.65 (3H, m), 7.20–7.51 (3H, m), 7.79–7.86 (2H, m), 9.89 (1H, br); NMR (20) (CDCl₃) δppm: 1.43 (3H, t, J=7.0 Hz), 4.04 (2H, q, J=7.0 Hz), 4.73 (2H, s), 6.50–6.66 (3H, m), 7.18–7.51 (3H, m), 7.78–7.90 (2H, m), 9.87 (1H, br).

Using the suitable starting compounds, the compounds as listed in Table 10 are obtained in the same manner as in Reference Example 3.

TABLE 10

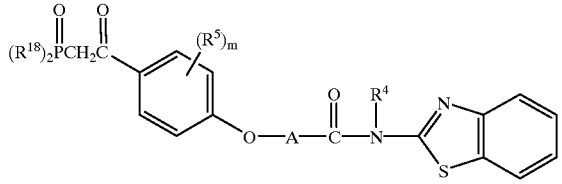

Reference Example 53

| | | | | |
|---|---|---|---|---|
| R⁵: C₂H₅O (2-position) | m: 1 | A: —CH₂— | R⁴: H | R¹⁸: CH₃O |
| Crystalline form: Pale yellow powder | | Form: Free | | NMR (1) |

Reference Example 54

R⁵: —OCH(CH₃)(CH₃) (3-position)   m: 1   A: —CH₂—   R⁴: H   R¹⁸: CH₃O

| | | | |
|---|---|---|---|
| Crystalline form: White powder | Form: Free | | NMR (2) |

Reference Example 55

| | | | | |
|---|---|---|---|---|
| R⁵: CF₃CH₂O (3-position) | m: 1 | A: —CH₂— | R⁴: H | R¹⁸: CH₃O |
| Crystalline form: White powder | | Form: Free | | NMR (3) |

Reference Example 56

| | | | | |
|---|---|---|---|---|
| R⁵: CF₃ (2-position) | m: 1 | A: —CH₂— | R⁴: H | R¹⁸: CH₃O |
| Crystalline form: White powder | | Form: Free | | NMR (4) |

Reference Example 57

| | | | | |
|---|---|---|---|---|
| R⁵: CH₃O (3-position) | m: 1 | A: —CH₂— | R⁴: H | R¹⁸: CH₃O |
| Crystalline form: White powder | | Form: Free | | NMR (5) |

¹H-NMR spectrum (NMR (1) to NMR (5)) as described in Table 10 are as follows:

NMR (1) (CDCl₃) δppm: 1.58 (3H, t, J=7.0 Hz), 3.61 (2H, d, J=22.8 Hz), 3.76 (3H, s), 3.82 (3H, s), 4.25 (2H, q, J=7.0 Hz), 4.85 (2H, s), 7.04 (1H, d, J=8.6 Hz), 7.33 (1H, t, J=7.5 Hz), 7.46 (1H, t, J=7.5 Hz), 7.60–7.65 (2H, m), 7.79–7.86 (2H, m), 10.28 (1H, br); NMR (2) (CDCl₃) δppm: 1.47 (6H, d, J=6.0 Hz), 3.74 (3H, s), 3.79 (3H, s), 3.85 (2H, d, J=20.2 Hz), 4.69 (1H, sept, J=6.0 Hz), 4.79 (2H, s), 6.51–6.56 (2H, m), 7.36 (1H, t, J=7.0 Hz), 7.49 (1H, t, J=7.0 Hz), 7.79–7.88 (3H, m), 9.98 (1H, br; NMR (3) (CDCl₃) δppm: 3.76 (2H, d, J=21.3 Hz), 3.75 (3H, s), 3.80 (3H, s), 4.40 (2H, q, J=7.9 Hz), 4.79 (2H, s), 6.44 (1H, d, J=2.2 Hz), 6.60 (1H, dd, J=2.2 Hz, J=8.8 Hz), 7.34 (1H, dt, J=1.3 Hz, J=7.3 Hz), 7.45 (1H, dt, J=1.3 Hz, J=7.3 Hz), 7.75–7.86 (3H, m); NMR (4) (DMSO-d₆) δppm: 3.62 (3H, s), 3.68 (3H, s), 3.93 (2H, d, J=22.5 Hz), 5.27 (2H, s), 7.3–7.55 (3H, m), 7.78 (1H, d, J=8 Hz), 7.98 (1H, d, J=8 Hz), 8.2–8.35 (2H, m), 12.68 (1H, br); NMR (5) (CDCl₃) δppm: 3.74 (3H, s), 3.80 (3H, s), 3.81 (2H, d, J=21 Hz), 3.95 (3H, s), 4.81 (2H, s), 6.5–6.65 (2H, m), 7.25–7.55 (2H, m), 7.75–7.95 (3H, m), 10.01 (1H, s).

Using the suitable starting compounds, the compounds as listed in Tables 11–13 are obtained in the same manner as in Reference Example 4.

TABLE 11

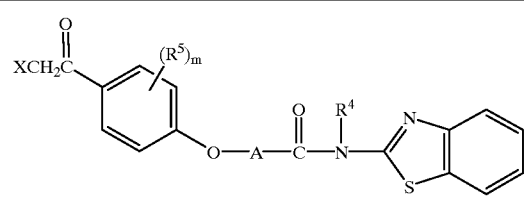

Reference Example 58

| | | | | |
|---|---|---|---|---|
| R⁵: H | m:1 | A: —CH₂— | R⁴: H | X: Br |
| Crystalline form: Pale yellow powder | | Form: Free | | NMR (1) |

Reference Example 59

| | | | | |
|---|---|---|---|---|
| R⁵: CH₃ (2-position) | m: 1 | A: —CH₂— | R⁴: H | X: Cl |
| Crystalline form: Beige powder | | Form: Free | | NMR (2) |

Reference Example 60

| | | | | |
|---|---|---|---|---|
| R⁵: C₂H₅ (2-position) | m: 1 | A: —CH₂— | R⁴: H | X: Cl |

TABLE 11-continued

[Structure: XCH₂C(O)-phenyl(R⁵)ₘ-O-A-C(O)-N(R⁴)-benzothiazole]

| | | |
|---|---|---|
| Crystalline form: Beige powder | Form: Free | NMR (3) |
| Reference Example 61 | | |
| R⁵: —(CH₂)₃CH₃ (2-position)  m: 1  A: —CH₂—  R⁴: H  X: Cl | | |
| Crystalline form: White powder | Form: Free | NMR (4) |

TABLE 12

Reference Example 62

R⁵: Cl (2-position)
m: 1
A: —CH₂—
R⁴: H
X: Cl
M.p. 199–201° C.
Solvent for recrystallization: 1,2-Dichloroethane-n-hexane
Crystalline form: White powder
Form: Free Reference Example 63

R⁵: —(CH₂)₂Cl (2-position)
m: 1
A: —CH₂—
R⁴: H
X: Br
Crystalline form: Pale yellow powder
Form: Free
NMR (5)

TABLE 12-continued

Reference Example 64

R⁵: —(CH₂)₃Cl (2-position)
m: 1
A: —CH₂—
R⁴: H
X: Br
Crystalline form: Pale yellow powder
Form: Free
NMR (6)

Reference Example 65

R⁵: —(CH₂)₄Cl (2-position)
m: 1
A: —CH₂—
R⁴: H
X: Cl
M.p. 146.5–149° C.
Solvent for recrystallization: Ethyl acetate-n-hexane
Crystalline form: White powder
Form: Free

TABLE 13

Reference Example 66

R⁵: —(CH₂)₂CO₂C₂H₅ (2-position)  m: 1  A: —CH₂—  R⁴: H  X: Cl
M.p. 131.0–133.0° C.
Solvent for recrystallization: Ethyl acetate-n-hexane
Crystalline form: White powder    Form: Free Reference Example 67

R⁵: —(CH₂)₂CO₂CH₃ (2-position)  m: 1  A: —CH₂—  R⁴: H  X: Cl
Crystalline form: White powder    Form: Free  NMR (7)

Reference Example 68

R⁵: 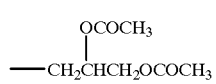  (2-position)  m: 1  A: —CH₂—  R⁴: H  X: Cl

Crystalline form: White powder    Form: Free  NMR (8)

TABLE 13-continued

Reference Example 69

R⁵ and A combine to form: 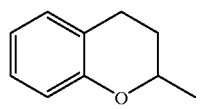   m: 1   R⁴: H   X: Cl

M.p. 206–208° C.
Solvent for recrystallization: Dimethylformamide-ethanol
Crystalline form: White powder    Form: Free $^1$H-NMR spectrum (NMR (1) to NMR (8)) as described in Tables 11–13 are as follows:

NMR (1) (CDCl$_3$) δppm: 4.41 (2H, s), 4.84 (2H, s), 7.07 (2H, d, J=9.0 Hz), 7.36 (1H, t, J=7.3 Hz), 7.45 (1H, t, J=7.3 Hz), 7.88 (2H, t, J=8.5 Hz), 8.03 (2H, d, J=9.0 Hz); NMR (2) (DMSO-d$_6$) δppm: 2.30 (3H, s), 5.11 (4H, s), 7.00–7.10 (1H, m), 7.28–7.40 (1H, m), 7.40–7.55 (1H, m), 7.70–7.93 (3H, m), 7.98 (1H, d, J=7.1 Hz), 12.68 (1H, s); NMR (3) (DMSO-d$_6$) δppm: 1.21 (3H, t, J=7.4 Hz), 2.72 (2H, q, J=7.4 Hz), 5.12, 5.13 (4H, each s), 7.02 (1H, d, J=8.6 Hz), 7.31 (1H, dt, J=1.2 Hz, J=7.3 Hz), 7.45 (1H, dt, J=1.3 Hz, J=7.3 Hz), 7.75–7.92 (3H, m), 7.95–8.00 (1H, m), 12.68 (1H, brs); NMR (4) (CDCl$_3$) δppm: 0.97 (3H, t, J=7.2 Hz), 1.39–1.59 (2H, m), 1.59–1.86 (2H, m), 2.77 (2H, t, J=7.6 Hz), 4.67 (2H, s), 4.86 (2H, s), 6.89 (1H, d, J=8.6 Hz), 7.32–7.39 (1H, m), 7.43–7.51 (1H, m), 7.79–7.87 (4H, m), 9.10–10.01 (1H, brs); NMR (5) (CDCl$_3$) δppm: 3.16 (2H, t, J=6.9 Hz), 3.92 (2H, t, J=6.9 Hz), 4.83 (2H, s), 5.13 (2H, s), 7.07 (1H, d, J=9.4 Hz), 7.31 (1H, t, J=6.9 Hz), 7.45 (1H, t, J=8.3 Hz), 7.76 (1H, d, J=7.9 Hz), 7.82–8.06 (3H, m); NMR (6) (CDCl$_3$) δppm: 2.17 (2H, tt, J=6.1 Hz, J=7.5 Hz), 3.03 (2H, t, J=7.5 Hz), 3.64 (2H, t, J=6.1 Hz), 4.40 (2H, s), 4.88 (2H, s), 6.95 (1H, d, J=9.3 Hz), 7.35 (1H, t, J=6.8 Hz), 7.47 (1H, t, J=9.4 Hz), 7.80–7.94 (4H, m), 9.68 (1H, br); NMR (7) (CDCl$_3$) δppm: 2.75 (2H, t, J=7.0 Hz), 3.13 (2H, t, J=7.0 Hz), 3.74 (3H, s), 4.65 (2H, s), 4.89 (2H, s), 6.89 (1H, d, J=8.4 Hz), 7.30–7.37 (1H, m), 7.41–7.48 (1H, m), 7.78–7.89 (4H, m), 9.00–11.30 (1H, brs); NMR (8) (CDCl$_3$) δppm: 2.00 (3H, s), 2.09 (3H, s), 3.08 (1H, dd, J=8 Hz, J=14 Hz), 3.23 (1H, dd, J=6 Hz, J=14 Hz), 4.14 (1H, dd, J=5.5 Hz, J=12 Hz), 4.33 (1H, dd, J=3 Hz, J=12 Hz), 4.64 (2H, s), 4.5 (2H, s), 5.49 (1H, m), 6.90 (1H, d, J=9 Hz), 7.3–8.0 (6H, m), 8.79 (1H, br).

Using the suitable starting compounds, the compounds as listed in Tables 14–22 are obtained in the same manner as in Reference Example 5 or 6.

TABLE 14

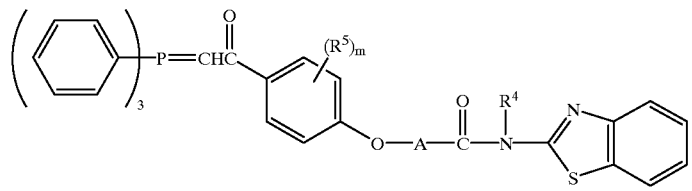

Reference Example 70

| R⁵: H | m: 1 | A: —CH$_2$— | R⁴: H |
|---|---|---|---|
| Crystalline form: Pale yellow amorphous | | Form: Free | NMR (1) |

Reference Example 71

| R⁵: CH$_3$ (2-position) | m: 1 | A: —CH$_2$— | R⁴: H |
|---|---|---|---|
| Crystalline fomi: Pale yellow amorphous | | Form: Free | NMR (2) |

Reference Example 72

| R⁵: C$_2$H$_5$ (2-position) | m: 1 | A: —CH$_2$— | R⁴: H |
|---|---|---|---|
| Crystalline form: White powder | | Form: Free | NMR (3) |

Reference Example 73

| R⁵: 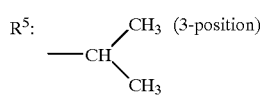 (3-position) | m: 1 | A: —CH$_2$— | R⁴: H |
|---|---|---|---|
| Crystalline form: White powder | | Form: Free | NMR (4) |

TABLE 15

Reference Example 74

$R^5$: —(CH$_2$)$_3$CH$_3$ (2-position)
m: 1
A: —CH$_2$—
$R^4$: H
Crystalline form: Pale yellow powder
Form: Free
NMR (5)

Reference Example 75

$R^5$: Cl (2-position)
m: 1
A: —CH$_2$—
$R^4$: H
Crystalline form: Pale yellow amorphous
Form: Free
NMR (6)

Reference Example 76

$R^5$: F (2-position)
m: 1

TABLE 15-continued

A: —CH$_2$—
$R^4$: H
Crystalline form: White powder
Form: Free
NMR (7)

Reference Example 77

$R^5$: —(CH$_2$)$_2$Cl (2-position)
m: 1
A: —CH$_2$—
$R^4$: H
Crystalline form: White powder
Form: Free
NMR (8)

Reference Example 78

$R^5$: —(CH$_2$)$_4$Cl (2-position)
m: 1
A: —CH$_2$—
$R^4$: H
Crystalline form: White needles
Form: Free
NMR (9)

TABLE 16

Reference Example 79

$R^5$: —(CH$_2$)$_2$CO$_2$C$_2$H$_5$ (2-position)    m: 1    A: —CH$_2$—    $R^4$: H
Crystalline form: White powder                       Form: Free    NMR (10)

Reference Example 80

$R^5$: —CH$_2$CH(OCOCH$_3$)CH$_2$OCOCH$_3$ (2-position)    m: 1    A: —CH$_2$—    $R^4$: H Crystalline form: White powder                       Form: Free    NMR (11)

Reference Example 81

$R^5$: —(CH$_2$)$_2$—N(morpholino) (2-position)    m: 1    A: —CH$_2$—    $R^4$: H Crystalline form: White powder                       Form: Free    NMR (12)

Reference Example 82

$R^5$: —(CH$_2$)$_2$—N(4-methylpiperazin-1-yl) (2-position)    m: 1    A: —CH$_2$—    $R^4$: H Crystalline form: Pale yellow amorphous              Form: Free    NMR (13)

TABLE 17

Reference Example 83

R⁵: —(CH₂)₃N(C₂H₅)₂ (2-position)     m: 1     A: —CH₂—     R⁴: H
Crystalline form: White powder     Form: Free     NMR (14)
Reference Example 84

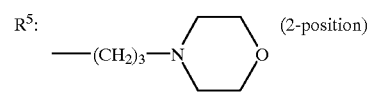 (2-position)     m: 1     A: —CH₂—     R⁴: H

Crystalline form: White powder     Form: Free     NMR (15)
Reference Example 85

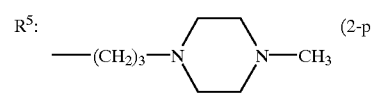 (2-position)     m: 1     A: —CH₂—     R⁴: H

Crystalline form: White powder     Form: Free     NMR (16)
Reference Example 86

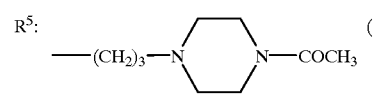 (2-position)     m: 1     A: —CH₂—     R⁴: H

M.p. 153–155 °C.     Solvent for recrystallization: Ethyl acetate
Crystalline form: White powder     Form: Free

TABLE 18

Reference Example 87

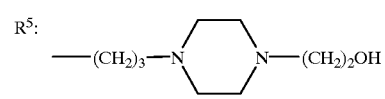 (2-position)     m: 1     A: —CH₂—     R⁴: H

Crystalline form: White amorphous     Form: Free     NMR (17)
Reference Example 88

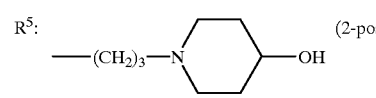 (2-position)     m: 1     A: —CH₂—     R⁴: H

Crystalline form: White amorphous     Form Free     NMR (18)
Reference Example 89

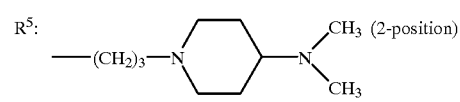 (2-position)     m: 1     A: —CH₂—     R⁴: H

Crystalline form: Colorless amorphous     Form Free     NMR (19)
Reference Example 90

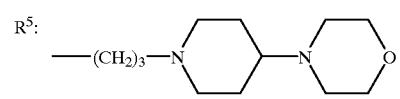 (2-position)     m: 1     A: —CH₂—     R⁴: H

Crystalline form: Colorless amorphous     Form: Free     NMR (20)

TABLE 19

Reference Example 91

R⁵: 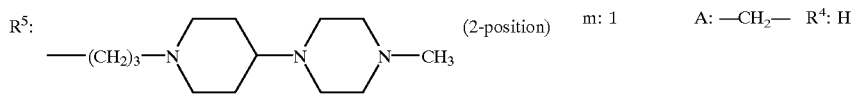 (2-position)  m: 1  A: —CH₂—  R⁴: H

Crystalline form: Yellow amorphous  Form: Free  NMR (21)

Reference Example 92

R⁵: 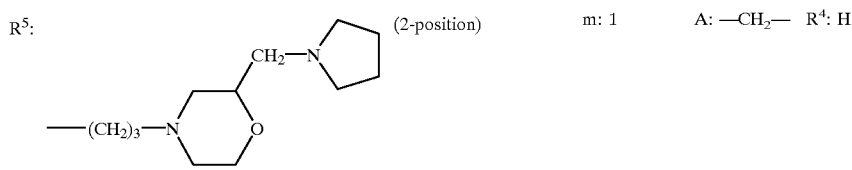 (2-position)  m: 1  A: —CH₂—  R⁴: H

Crystalline form: Colorless amorphous  Form: Free  NMR (22)

Reference Example 93

R⁵: 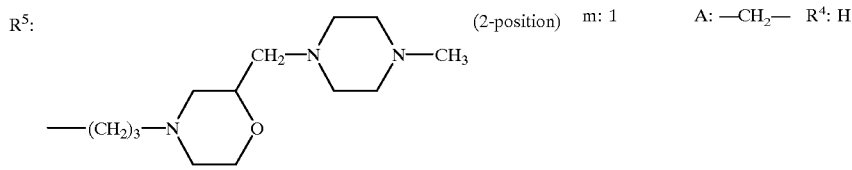 (2-position)  m: 1  A: —CH₂—  R⁴: H

Crystalline form: Yellow amorphous  Form: Free  NMR (23)

Reference Example 94

R⁵: 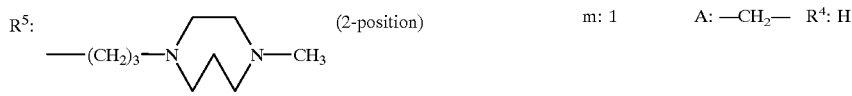 (2-position)  m: 1  A: —CH₂—  R⁴: H

Crystalline form: Yellow amorphous  Form: Free  NMR (24)

TABLE 20

Reference Example 95

R⁵: 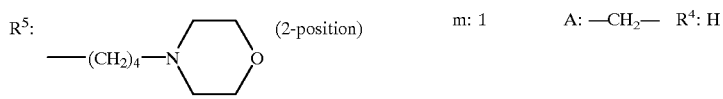 (2-position)  m: 1  A: —CH₂—  R⁴: H

Crystalline form: White powder  Form: Free  NMR (25)

Reference Example 96

R⁵: 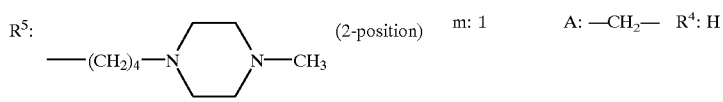 (2-position)  m: 1  A: —CH₂—  R⁴: H

Crystalline form: Pale yellow powder  Form: Free  NMR (26)

TABLE 20-continued

Reference Example 97

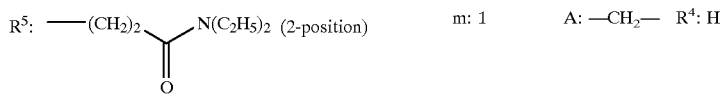

R⁵: —(CH₂)₂—C(=O)—N(C₂H₅)₂ (2-position)  m: 1    A: —CH₂—   R⁴: H

Crystalline form: White amorphous                 Form: Free   NMR (27)

Reference Example 98

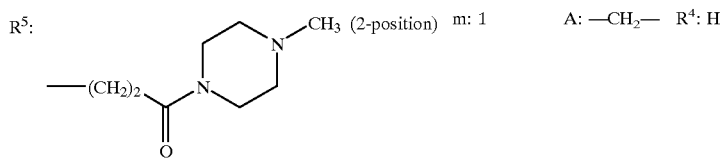

R⁵: —(CH₂)₂—C(=O)—N(piperazine)—CH₃ (2-position)   m: 1    A: —CH₂—   R⁴: H

Crystalline form: White amorphous                 Form: Free   NMR (28)

TABLE 21

Reference Example 99

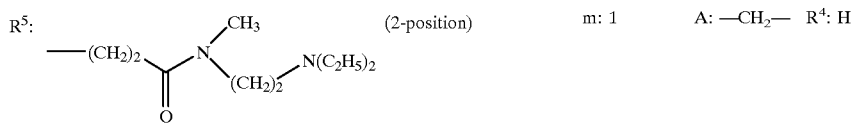

R⁵: —(CH₂)₂—C(=O)—N(CH₃)—(CH₂)₂—N(C₂H₅)₂  (2-position)   m: 1    A: —CH₂—   R⁴: H Crystalline form: White amorphous                 Form: Free   NMR (29)

Reference Example 100

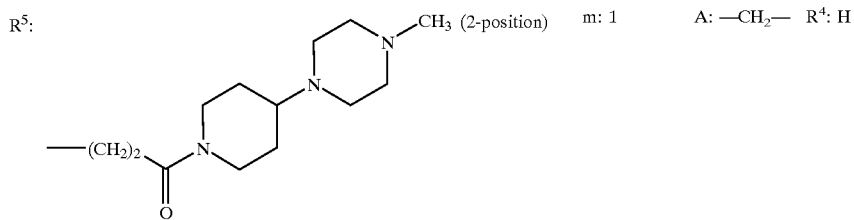

R⁵: —(CH₂)₂—C(=O)—N(piperidine)—N(piperazine)—CH₃ (2-position)   m: 1    A: —CH₂—   R⁴: H Crystalline form: White amorphous                 Form Free    NMR (30)

Reference Example 101

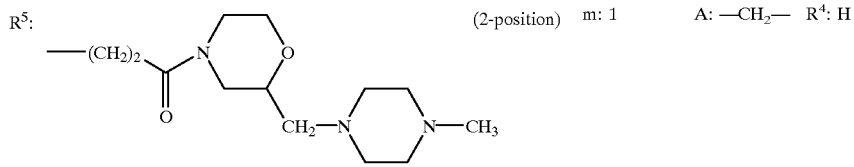

R⁵: —(CH₂)₂—C(=O)—N(morpholine)—CH₂—N(piperazine)—CH₃ (2-position)   m: 1    A: —CH₂—   R⁴: H Crystalline form: Yellow amorphous                Form: Free   NMR (31)

Reference Example 102

R⁵: —COOCH₃ (2-position)                          m: 1         A: —CH₂—   R⁴: H
Crystalline form: Pale yellow amorphous           Form: Free   NMR (32)

TABLE 22

Reference Example 103

R⁵: —(CH₂)₂CONH— (combined at 2- and 3-positions)  m: 2  A: —CH₂—  R⁴: H
Crystalline form: Yellow amorphous  Form: Free  NMR (33)

Reference Example 104

R⁵ and A combine to form:

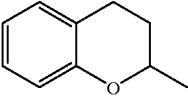

m: 1  R⁴: H

Crystalline form: White powder  Form: Free  NMR (35)

¹H-NMR spectrum (NMR (1) to NMR (35)) as described in Tables 14–22 are as follows:

NMR (1) (CDCl₃) δppm: 4.37 (1H, d, J=24 Hz), 4.77 (2H, s), 6.91 (2H, d, J=8.8 Hz), 7.16 (1H, t, J=7.3 Hz), 7.32 (1H, t, J=7.3 Hz), 7.38–7.82 (17H, m), 7.89 (2H, d, J=8.8 Hz); NMR (2) (CDCl₃) δppm: 2.35 (3H, s), 4.41 (1H, brs), 4.70 (2H, s), 6.70 (1H, d, J=8.2 Hz), 7.20–8.00 (21H, m); NMR (3) (DMSO-d₆) δppm: 1.19 (3H, t, J=7.4 Hz), 2.69 (2H, q, J=7.4 Hz), 4.43 (1H, d, J=2.5 Hz), 5.00 (2H, s), 6.83 (1H, d, J=8.9 Hz), 7.25–7.38 (1H, m), 7.38–7.85 (19H, m), 7.98 (1H, d, J=7.1 Hz), 12.65 (1H, brs); NMR (4) (CDCl₃) δppm: 1.32 (6H, d, J=7 Hz), 3.42 (1H, sept, J=7 Hz), 4.2–4.6 (1H, m), 4.73 (2H, s), 7.25–8.0 (21H, m), 10.01 (1H, br); NMR (5) (CDCl₃) δppm: 0.86 (3H, t, J=7.2 Hz), 1.31–1.51 (2H, m), 1.51–1.72 (2H, m), 2.65–2.72 (2H, m), 3.76 (3H, s), 4.34 (1H, br-d, J=24.7 Hz), 4.66 (2H, s), 5.98 (1H, br-s), 6.66 (1H, d, J=8.3 Hz), 6.99–7.10 (1H, m), 7.19–7.31 (1H, m), 7.38–7.60 (11H, m), 7.60–7.87 (8H, m); NMR (6) (DMSO-d₆) δppm: 4.52 (1H, d, J=23 Hz), 5.12 (2H, s), 7.07 (1H, d, J=8.4 Hz), 7.31 (1H, td, J=7.6 Hz, J=1.0 Hz), 7.45 (1H, td, J=7.6 Hz, J=1.4 Hz), 7.45–8.15 (19H, m), 12.68 (1H, s); NMR (7) (CDCl₃) δppm: 4.34 (1H, d, J=22 Hz), 4.79 (2H, s), 6.97 (1H, t, J=8.4 Hz), 7.30–7.38 (2H, m), 7.38–7.92 (19H, m), 9.97 (1H, br); NMR (8) (DMSO-d₆) δppm: 3.16 (2H, t, J=7.0 Hz), 3.92 (2H, t, J=7.0 Hz), 4.23 (2H, s), 5.13 (2H, s), 7.07 (1H, d, J=9.4 Hz), 7.34 (1H, t, J=6.5 Hz), 7.44 (1H, t, J=6.5 Hz), 7.60–8.12 (19H, m), 12.70 (1H, br); NMR (9) (CDCl₃) δppm: 1.67–1.90 (4H, m), 2.64–2.82 (2H, m), 3.68 (1H, bt, J=6.0 Hz), 5.19 (2H, s), 6.12 (2H, d, J=14.0 Hz), 7.10 (1H, d, J=10.0 Hz), 7.29–7.41 (1H, m), 7.41–7.52 (1H, m), 7.69–7.95 (17H, m), 7.95–8.06 (2H, m), 12.74 (1H, br-s); NMR (10) (DMSO-d₆) δppm: 1.10 (3H, t, J=7.1 Hz), 2.62 (2H, t, J=8.0 Hz), 2.90 (2H, t, J=8.0 Hz), 4.00 (2H, q, J=7.1 Hz), 4.33 (1H, d, J=30.0 Hz), 5.01 (2H, s), 6.82 (1H, d, J=14.0 Hz), 7.29–7.38 (1H, m), 7.40–7.50 (1H, m), 7.50–7.80 (18H, m), 8.00–8.02 (1H, d, J=4.0 Hz), 12.61 (1H, brs); NMR (11) (CDCl₃) δppm: 2.00 (3H, s), 2.05 (3H,s), 3.0–3.15 (2H, m), 4.0–4.35 (2H, m), 4.93, 5.05 (2H, ABq, J=16 Hz), 5.40 (1H, m), 6.1–6.6 (2H, br), 6.98 (1H, d, J=8 Hz), 7.2–8.5 (2H, m); NMR (12) (CDCl₃) δppm: 2.54–2.78 (6H, m), 2.87–3.12 (2H, m), 3.69–3.90 (4H, m), 4.36 (1H, d, J=24.0 Hz), 4.78 (2H, s), 6.77 (1H, d, J=8.5 Hz), 7.27–7.88 (21H, m); NMR (13) (CDCl₃) δppm: 2.27 (3H, s), 2.32–2.76 (10H, m), 2.76–3.05 (2H, m), 4.36 (1H, d, J=26.0 Hz), 4.71 (2H, s), 6.77 (1H, d, J=8.3 Hz), 7.27–8.02 (21H, m); NMR (14) (CDCl₃) δppm: 1.00 (6H, t, J=7.1 Hz), 1.80–2.00 (2H, m), 2.48–2.62 (6H, m), 2.78 (2H, t, J=6.2 Hz), 4.37 (1H, d, J=24.4 Hz), 4.76 (2H, s), 6.80 (1H, d, J=6.8 Hz), 7.32 (1H, t, J=7.3 Hz), 7.39–7.93 (20H, m); NMR (15) (CDCl₃) δppm: 1.72–2.05 (2H, m), 2.30–2.57 (4H, m), 2.70–2.89 (2H, m), 3.54–3.83 (4H, m), 4.37 (1H, d, J=28.0Hz), 4.74 (2H, s), 6.77 (1H, d, J=8.3 Hz), 7.33 (1H, t, J=7.3 Hz), 7.40–7.96 (20H, m); NMR (16) (CDCl₃) δppm: 1.81–2.01 (2H, m), 2.22 (3H, s), 2.28–2.68 (10H, m), 2.79 (2H, t, J=6.9 Hz), 4.37 (1H, d, J=24.0 Hz), 4.76 (2H, s), 6.79 (1H, d, J=8.4 Hz), 7.33 (1H, t, J=8.8 Hz), 7.40–7.64 (10H, m), 7.64–7.95 (10H, m); NMR (17) (CDCl₃) δppm: 1.7–3.3 (16H, m), 3.59 (2H, m), 4.81 (2H, s), 6.82 (1H, d, J=8.5 Hz), 7.2–8.0 (21H, m); NMR (18) (CDCl₃) δppm: 1.4–1.7 (2H, m), 1.75–2.0 (4H, m), 2.2–2.4 (2H, m), 2.4–2.6 (2H, m), 2.65–2.9 (4H, m), 3.65 (1H, m), 4.1–4.8 (2H, br), 4.68 (2H, s), 6.70 (1H, d, J=8.5 Hz), 7.2–7.9 (21H, m); NMR (19) (CDCl₃) δppm: 1.41–2.31 (9H, m), 2.24 (6H, s), 2.46 (2H, t, J=7.5 Hz), 2.77 (2H, t, J=7.5 Hz), 2.93–3.12 (2H, m), 4.23–4.60 (1H, br), 4.73 (2H, s), 6.75 (1H, d, J=8.5 Hz), 7.23–7.92 (21H, m); NMR (20) (CDCl₃) δppm: 1.48–2.28 (9H, m), 2.36–2.61 (6H, m), 2.77 (2H, t, J=7.5 Hz), 2.92–3.13 (2H, m), 3.65 (4H, t, J=4.5 Hz), 4.19–4.58 (1H, m), 4.70 (2H, s), 6.71 (1H, d, J=8.5 Hz), 7.02–7.94 (21H, m); NMR (21) (CDCl₃) δppm: 1.41–2.03 (8H, m), 2.05–2.80 (13H, m), 2.77 (2H, t, J=7.6 Hz), 2.88–3.07 (2H, m), 4.73 (2H, s), 6.75 (1H, d, J=8.5 Hz), 7.32 (1H, t, J=6.4 Hz), 7.40–7.90 (20H, m); NMR (22) (CDCl₃) δppm: 1.62–2.23 (8H, m), 2.29–2.97 (12H, m), 3.48–3.93 (3H, m), 4.22–4.57 (1H, br), 4.69 (2H, s), 6.70 (1H, d, J=8.5 Hz), 7.22–8.04 (21H, m); NMR (23) (CDCl₃) δppm: 1.69–2.00 (3H, m), 2.00–2.62 (16H, m), 2.62–2.87 (4H, m), 3.50–3.92 (3H, m), 4.37 (1H, d, J=26.8 Hz), 4.75 (2H, s), 6.77 (1H, d, J=8.4 Hz), 7.28–7.92 (21H, m); NMR (24) (CDCl₃) δppm: 1.82–2.22 (4H, m), 2.50 (3H, s), 2.54–3.12 (12H, m), 4.73 (2H, s), 6.71 (1H, d, J=8.6 Hz), 7.29–7.88 (21H, m); NMR (25) (CDCl₃) δppm: 1.55–1.85 (4H, m), 2.3–2.5 (6H, m), 2.7–2.9 (2H, m), 3.67 (4H, t, J=4.5 Hz), 4.25–4.55 (2H, m), 4.76 (2H, s), 6.78 (1H, d, J=8.5 Hz), 7.25–7.95 (21H, m); NMR (26) (DMSO-d₆) δppm: 1.37–1.70 (4H, m), 2.08 (3H, s), 2.14–2.43 (10H, m), 2.60–2.77 (2H, m), 4.33 (1H, d, J=26.0 Hz), 4.96 (2H, s), 6.80 (1H, d, J=10.0 Hz), 7.27–7.38 (1H, m), 7.38–7.80 (19H, m), 7.90–8.03 (1H, m); NMR (27) (CDCl₃) δppm: 1.00 (3H, t, J=7.0 Hz), 1.01 (3H, t, J=7.0 Hz), 2.68 (2H, t, J=6.9 Hz), 3.12–3.27 (4H, m), 3.35–3.46 (2H, m), 4.25–4.60 (1H, m), 4.96 (2H, s), 6.67 (1H, d, J=8.5 Hz), 7.23–7.27 (1H, m), 7.29–7.57 (10H, m), 7.68–7.81 (9H, m), 7.92 (1H, brs), 11.97 (1H, brs); NMR (28) (CDCl₃) δppm: 2.14–2.39 (4H, m), 2.22 (3H, s), 2.74 (2H, t, J=6.3 Hz), 2.98–3.20 (2H, m), 3.29–3.48 (2H, m), 3.63–3.80 (2H, m), 4.17–4.54 (1H, m), 4.73 (2H, s), 6.67 (1H, d, J=8.6 Hz), 7.26–7.33 (1H, m), 7.33–7.62 (10H, m), 7.62–7.85 (9H, m), 7.90 (1H, brs); NMR (29) (CDCl₃) δppm: 0.89 (3H, t, J=7.1 Hz), 1.00 (3H, t, J=7.1 Hz), 2.35–4.47 (15H, m), 4.73 (2H, s), 6.67–6.74 (1H, m), 7.20–7.61 (11H, m), 7.61–7.85 (9H, m), 7.85–7.93 (1H, m); NMR (30) (CDCl₃) δppm: 1.01–1.47 (2H, m), 1.65–1.90 (2H, m), 2.29 (3H, s), 2.35–2.65 (11H, m), 2.65–2.91 (2H, m), 3.03–3.22 (2H, m), 3.73–3.91 (1H, m), 4.22–4.54 (1H, m), 4.73 (2H, s), 4.75–4.92 (1H, m), 6.69 (1H, d, J=8.6 Hz), 7.22–7.63 (11H, m), 7.63–7.88 (9H, m), 7.88–8.00 (1H, m); NMR (31) (CDCl$_3$) δppm: 2.18–3.50 (20H, m), 3.50–3.71 (1H, m), 3.71–3.95 (1H, m), 4.20–4.82 (4H, m), 6.65–6.74 (1H, m), 7.20–7.63 (12H, m), 7.63–7.86 (9H, m), 7.86–7.98 (1H, m); NMR (32) (CDCl$_3$) δppm: 4.09 (3H, s), 4.42 (1H, d, J=22.9 Hz), 4.85 (2H, s), 6.93 (1H, d, J=8.7 Hz), 7.00–7.18 (1H, m), 7.18–7.98 (18H, m), 8.19 (1H, dd, J=2.2 Hz, J=8.7 Hz), 8.60 (1H, d, J=2.2 Hz), 11.55 (1H, br); NMR (33) (CDCl$_3$) δppm: 2.73 (2H, t, J=7.4 Hz), 3.37 (2H, t, J=7.4 Hz), 4.06 (1H, d, J=20.6 Hz), 4.84 (2H, s), 6.77 (1H, d, J=8.6 Hz), 7.28–7.77 (20H, m), 10.85 (1H, br), 12.16 (1H, br); NMR (35) (DMSO-d$_6$) δppm: 2.03–2.46 (2H, m), 2.67–3.06 (2H, m), 4.28–4.52 (1H, m), 4.94–5.24 (1H, m), 6.83–8.11 (22H, m), 12.61 (1H, brs).

Using the suitable starting compounds, the compounds as listed in Tables, 23–31 are obtained in the same manner as in Reference Example 2.

$^1$H-NMR spectrum (NMR (1)) as described in Table 23 are as follows:

NMR (1) (CDCl$_3$) δppm: 4.81 (2H, s), 7.05 (1H, d, J=3.5 Hz), 7.25–7.35 (2H, m), 7.45–7.65 (2H, m), 7.50 (1H, d, J=3.5 Hz), 10.00 (1H, s), 10.06 (1H, brs).

TABLE 23

[Structure: CHO-substituted phenyl with (R$^5$)$_m$, connected via O—A—C(=O)—N(R$^4$)—thiazole with R$^1$, R$^2$ substituents]

Reference Example 105

| | | |
|---|---|---|
| R$^1$: H | R$^2$: H | R$^4$: H |
| R$^5$: H | m: 1 | A: —CH$_2$— |
| Crystalline form: White powder | Form: Free | NMR (1) |

TABLE 24

[Structure: CHO-substituted phenyl with (R$^5$)$_m$, connected via O—A—C(=O)—N(R$^4$)—thiazole with R$^1$, R$^2$ substituents]

Reference Example 106

| | | |
|---|---|---|
| R$^1$: H | R$^2$: H | R$^4$: H |
| R$^5$: H | m: 1 | A: —(CH$_2$)$_3$— |
| Crystalline form: Pale yellow particles | Form: Free | NMR (1) |

Reference Example 107

R$^1$, R$^2$: [benzene ring structure]

| | | |
|---|---|---|
| | R$^5$: H | R$^4$: H |
| | m: 1 | A: —CH$_2$— |
| Crystalline form: Pale yellow particles | Form: Free | NMR (2) |

Reference Example 108

| | | |
|---|---|---|
| R$^1$: H | R$^2$: H | R$^4$: H |
| R$^5$: CH$_3$ (2- and 6-positions) | m: 2 | A: —CH$_2$— |
| Crystalline form: Yellow powder | Form: Free | NMR (3) |

TABLE 25

Reference Example 109

R$^1$, R$^2$: [benzene ring structure]    R$^5$: —CH$_2$N(C$_2$H$_5$)$_2$ (2-position)

| | | |
|---|---|---|
| R$^4$: H | m: 1 | A: —CH$_2$— |
| Crystalline form: White powder | Form: Free | NMR (4) |

Reference Example 110

R$^1$, R$^2$: [benzene ring structure]    R$^5$: —CH$_2$—N(piperazine)N—CH$_3$ (2-position)

| | | |
|---|---|---|
| R$^4$: H | m: 1 | A: —CH$_2$— |
| Crystalline form: Yellow powder | Form: Free | NMR (5) |

Reference Example 111

R$^1$, R$^2$: [benzene ring structure]    R$^5$: —(CH$_2$)$_2$N(C$_2$H$_5$)$_2$ (2-position)

| | | |
|---|---|---|
| R$^4$: H | m: 1 | A: —CH$_2$— |
| Crystalline form: Brown powder | Form: HCl | NMR (6) |

TABLE 25-continued

Reference Example 112

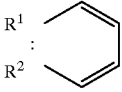

R[1], R[2]: benzene ring

R[5]: —(CH$_2$)$_2$—N(piperazine)N—CH$_3$ (2-position)

Crystalline form: White powder  Form: 2HCl  R[4]: H  m: 1  A: —CH$_2$—  NMR (7)

TABLE 26

Reference Example 113

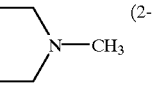

R[5]: —(CH$_2$)$_3$OH (2-position)

Crystalline form: White powder  Form: Free  R[4]: H  m: 1  A: —CH$_2$—  NMR (8)

Reference Example 114

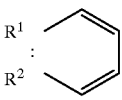

R[5]: —(CH$_2$)$_3$—N(piperazine)N—CH$_3$ (2-position)

Crystallline form: Pale yellow powder  Form: Free  R[4]: H  m: 1  A: —CH$_2$—  NMR (9)

Reference Example 115

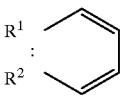

R[5]: —CH$_2$N(C$_2$H$_5$)$_2$ (2-position)

Crystalline form: Yellow oil  Form: Free  R[4]: H  m: 1  A: —(CH$_2$)$_5$—  NMR (10)

Reference Example 116

R[5]: —CH$_2$N(C$_2$H$_5$)$_2$ (2-position)

Crystalline form: Yellow amorphous  Form: Free  R[4]: H  m: 1  A: —(CH$_2$)$_3$—  NMR (11)

TABLE 27

Reference Example 117

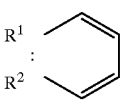

R[5]: —(CH$_2$)$_3$—N(piperidine)—N(piperazine)—CH$_3$ (2-position)

TABLE 27-continued

| | | | |
|---|---|---|---|
| Crystalline form: Pale yellow powder<br>Reference Example 118 | $R^4$: H | m: 1<br>Form: Free | A: —$CH_2$—<br>NMR (12) |

$R^1, R^2$: (benzene ring)
$R^5$: —$(CH_2)_3$—N(piperidine)—N(morpholine)—O (2-position)

| | | | |
|---|---|---|---|
| Crystalline form: Yellow powder<br>Reference Example 119 | $R^4$: H | m: 1<br>Form: 2HCl | A: —$CH_2$—<br>NMR (13) |

$R^1, R^2$: (benzene ring)
$R^5$: —$(CH_2)_3$—N(piperidine)—$N(C_2H_5)_2$ (2-position)

| | | | |
|---|---|---|---|
| Crystalline form: Pale yellow powder<br>Reference Example 120 | $R^4$: H | m: 1<br>Form: 2HCl | A: —$CH_2$—<br>NMR (14) |

$R^1, R^2$: (benzene ring with $CH_3$)

| | | | |
|---|---|---|---|
| | $R^5$: H | | $R^4$: H |
| Crystalline form: Yellow powder | m: 1<br>Form: Free | | A: —$CH_2$—<br>NMR (15) |

TABLE 28

Reference Example 121

| | | |
|---|---|---|
| $R^1$: $CH_3$ | $R^2$: H | $R^4$: H |
| $R^5$: H | m: 1 | A: —$CH_2$— |
| Crystalline form: Pale brown powder | Form: Free | NMR (16) |

Reference Example 122

| | | |
|---|---|---|
| $R^1$: $(CH_3)_3C$— | $R^2$: H | $R^4$: H |
| $R^5$: H | m: 1 | A: —$CH_2$— |
| Crystalline form: White powder | Form: Free | NMR (17) |

Reference Example 123

| | | |
|---|---|---|
| $R^1$: (phenyl) | $R^2$: H | $R^4$: H |
| $R^5$: H | m: 1 | A: —$CH_2$— |
| Crystalline form: Pale yellow powder | Form: Free | NMR (18) |

Reference Example 124

$R^1, R^2$: (benzene ring)
$R^5$: —$(CH_2)_3$—N(pyrrolidine with $CH_2$N-pyrrolidine) (2-position)

| | | |
|---|---|---|
| $R^4$: H | m: 1 | A: —$CH_2$— |
| Crystalline form: Pale yellow oil | Form: Free | NMR (19) |

TABLE 29

Reference Example 125

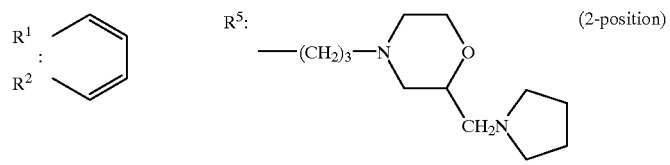

R⁴: H    m: 1    A: —CH₂—
Crystalline form: Yellow amorphous    Form: Free    NMR (20)

Reference Example 126

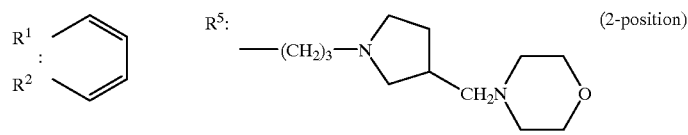

R⁴: H    m: 1    A: —CH₂—
Crystalline form: Yellow amorphous    Form: Free    NMR (21)

Reference Example 127

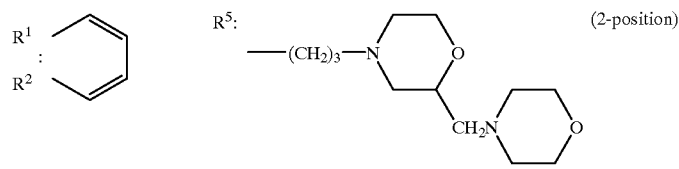

R⁴: H    m: 1    A: —CH₂—
Crystalline form: Yellow amorphous    Form: Free    NMR (22)

Reference Example 128

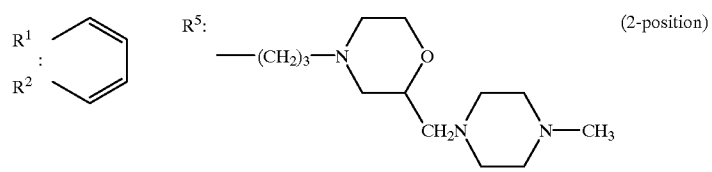

R⁴: H    m: 1    A: —CH₂—
Crystalline form: Yellow amorphous    Form: Free    NMR (23)

TABLE 30

Reference Example 129

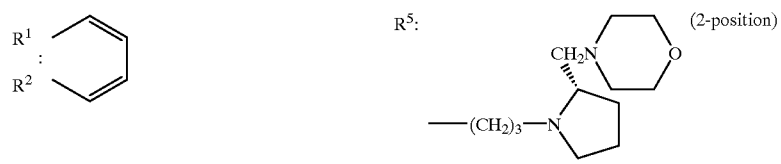

R⁴: H    m: 1    A: —CH₂—
Crystalline form: Pale yellow amorphous    Form: Free    NMR (24)

TABLE 30-continued

Reference Example 130

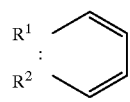 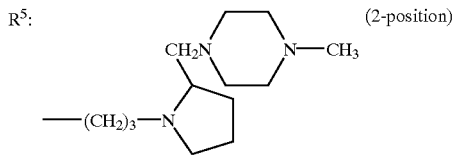

R⁴: H    m: 1    A: —CH₂—
Crystalline form: Pale yellow amorphous    Form: Free    NMR (25)

Reference Example 131

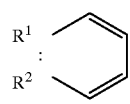 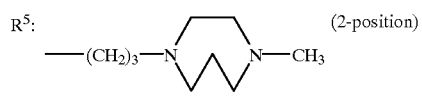

R⁴: H    m: 1    A: —CH₂—
Crystalline form: Pale yellow amorphous    Form: Free    NMR (26)

Reference Example 132

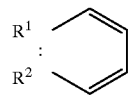 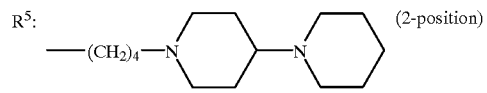

R⁴: H    m: 1    A: —CH₂—
Crystalline form: Yellow amorphous    Form: Free    NMR (27)

TABLE 31

Reference Example 133

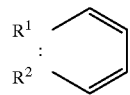 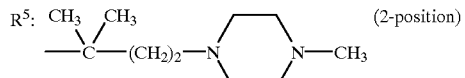

R⁴: H    m: 1    A: —CH₂—
Crystalline form: Yellow amorphous    Form: Free    NMR (28)

Reference Example 134

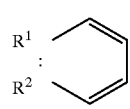 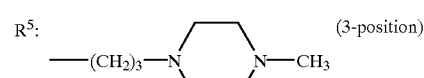

R⁴: H    m: 1    A: —CH₂—
Crystalline form: Colorless amorphous    Form: Free    NMR (29)

Reference Example 135

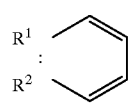    R⁵ and A combine to form: 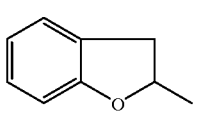

R⁴: H    m: 1
Crystalline form: White oil    Form: Free    NMR (30)

¹H-NMR spectrum (NMR (1) to NMR (30)) as described in Tables 24–31 are as follows:

NMR (1) (DMSO-d₆) δppm: 2.08 (2H, q, J=6.6 Hz), 2.62 (2H, t, J=7.2 Hz), 4.13 (2H, t, J=4.1 Hz), 7.10 (2H, d, J=8.6 Hz), 7.19 (1H, d, J=3.6 Hz), 7.45 (1H, d, J=3.6 Hz), 7.85 (2H, d, J=8.6 Hz), 9.86 (1H, s), 12.13 (1H, s); NMR (2) (DMSO-d₆) δppm: 5.07 (2H, s), 7.19 (2H, d, J=8.7 Hz), 7.27–7.40 (1H, m), 7.40–7.56 (1H, m), 7.77 (1H, d, J=7.5 Hz), 7.90 (2H, d, J=8.8 Hz), 7.98 (1H, d, J=7.1 Hz), 9.89 (1H, s), 12.1–13.0 (1H, br); NMR (3) (CDCl₃) δppm: 2.38 (6H, s), 4.57 (2H, s), 7.06 (1H, d, J=3.6 Hz), 7.51 (1H, d, J=3.6 Hz), 7.61 (2H, s), 9.92 (1H, s), 10.10 (1H, brs); NMR (4) (CDCl₃) δppm: 1.13 (6H, t, J=7.1 Hz), 2.93 (4H, q, J=7.1 Hz), 3.79 (2H, s), 5.01 (2H, s), 7.08 (1H, d, J=8.2 Hz), 7.23–7.35 (1H, m), 7.35–7.45 (1H, m), 7.74–7.87 (4H, m), 9.92 (1H, s), 10.71 (1H, s); NMR (5) (CDCl₃) δppm: 2.33 (3H, s), 2.42–2.88 (8H, m), 3.71 (2H, s), 4.92 (2H, s), 7.02 (1H, d, J=8.2 Hz), 7.27–7.40 (1H, m), 7.40–7.59 (1H, m), 7.67–7.93 (1H, m), 9.93 (1H, s); NMR (6) (CDCl₃) δppm: 1.29 (6H, t, J=7.1 Hz), 2.98–3.48 (8H, m), 5.20 (2H, s), 7.22 (1H, d, J=9.0 Hz), 7.35 (1H, d, J=7.6 Hz), 7.49 (1H, d, J=7.6 Hz), 7.80 (1H, d, J=7.8 Hz), 7.85–7.98 (2H, m), 8.01 (1H, d, J=7.4 Hz), 9.91 (1H, s), 10.36 (1H, br), 12.84 (1H, br); NMR (7) (CDCl₃) δppm: 2.86 (3H, s), 3.14–4.00 (12H, m), 5.21 (2H, s), 7.22 (1H, d, J=7.8 Hz), 7.35 (1H, t, J=7.6 Hz), 7.49 (1H, t, J=7.6 Hz), 7.78–7.87 (3H, m), 8.01 (1H, d, J=8.1 Hz), 9.90 (1H, s), 11.60 (2H, br), 12.75 (1H, br); NMR (8) (CDCl₃) δppm: 1.83–2.11 (2H, m), 3.06 (2H, t, J=7.3 Hz), 3.85 (2H, t, J=5.2 Hz), 4.22 (1H, br), 4.85 (2H, s), 6.98 (1H, d, J=8.2 Hz), 7.28–7.41 (1H, m), 7.41–7.49 (1H, m), 7.74–7.86 (4H, m), 9.92 (1H, s), 11.84 (1H, br); NMR (9) (CDCl₃) δppm: 1.83–2.06 (2H, m), 2.25 (3H, s), 2.32–2.76 (10H, m), 2.88 (2H, t, J=7.7 Hz), 4.87 (2H, s), 6.97 (1H, d, J=8.3 Hz), 7.30–7.42 (1H, m), 7.42–7.51 (1H, m), 7.72–7.87 (4H, m), 9.94 (1H, s); NMR (10) (CDCl₃) δppm: 0.99 (6H, t, J=7.1 Hz), 1.40–1.61 (2H, m), 1.70–1.92 (4H, m), 2.43–2.63 (6H, m), 3.56 (2H, s), 3.95 (2H, t, J=6.3 Hz), 6.86 (1H, d, J=8.5 Hz), 7.28–7.40 (1H, m), 7.40–7.51 (1H, m), 7.70–7.91 (3H, m), 7.95 (1H, d, J=2.1 Hz), 9.89 (1H, s). 10.39–13.00 (1H, brs); NMR (11) (CDCl₃) δppm: 0.97 (6H, t, J=7.1 Hz), 2.10–2.40 (2H, m), 2.40–2.68 (6H, m), 3.54 (2H, s), 3.95–4.23 (2H, m), 6.84 (1H, t, J=8.5 Hz), 7.20–7.40 (2H, m), 7.58–7.88 (3H, m), 7.90 (1H, d, J=2.1 Hz), 9.87 (1H, s); NMR (12) (CDCl₃) δppm: 1.38–1.76 (2H, m), 1.76–2.13 (6H, m), 2.13–2.70 (14H, m), 2.88 (2H, t, J=7.6 Hz), 2.95–3.18 (2H, m), 4.86 (2H, s), 6.97 (1H, d, J=8.2 Hz), 7.31–7.42 (1H, m), 7.42–7.57 (1H, m), 7.73–7.87 (4H, m), 9.91 (1H, s); NMR (13) DMSO-d₆) δppm: 1.92–2.45 (6H, m), 2.60–3.21 (9H, m), 3.21–3.76 (4H, m), 3.76–4.16 (4H, m), 5.17 (2H, s), 7.15 (1H, d, J=8.8 Hz), 7.31 (1H, t, J=6.9 Hz), 7.45 (1H, t, J=6.9 Hz), 7.68–7.92 (3H, m), 7.99 (1H, d, J=7.0 Hz), 9.87 (1H, s), 10.73 (1H, br), 11.78 (1H, br), 12.80 (1H, s); NMR (14) (DMSO-d₆) δppm: 1.28 (6H, t, J=7.1 Hz), 2.00–2.38 (6H, m), 2.68–2.90 (2H, m), 2.90–3.25 (8H, m), 3.47–3.83 (3H, m), 5.18 (2H, s), 7.18 (1H, d, J=8.7 Hz), 7.34 (1H, t, J=7.7 Hz), 7.45 (1H, t, J=7.7 Hz), 7.78–7.86 (3H, m), 8.00 (1H, d, J=7.0 Hz), 9.90 (1H, s), 10.78 (2H, br), 12.80 (1H, br); NMR (15) (DMSO-d₆) δppm: 2.40 (3H, s), 5.06 (2H, s), 7.15–7.40 (3H, m), 7.65 (1H, d, J=8.4 Hz), 7.77 (1H, s), 7.89 (2H, d, J=8.6 Hz), 9.88 (1H, s), 12.61 (1H, s); NMR (16) (DMSO-₆) δppm: 2.27 (3H, d, J=0.9 Hz), 4.98 (2H, s), 6.79 (1H, d, J=1.0 Hz), 7.12–7.25 (2H, m), 7.82–7.96 (2H, m), 9.88 (1H, s), 12.0–12.7 (1H, br); NMR (17) (DMSO-d₆) δppm: 1.26 (9H, s), 4.98 (2H, s), 6.78 (1H, s), 7.15 (2H, d, J=8.8 Hz), 7.90 (2H, d, J=8.8 Hz), 9.88 (1H, s), 12.42 (1H, s); NMR (18) (DMSO-d₆) δppm: 5.05 (2H, s), 7.19 (2H, d, J=8.8 Hz), 7.25–7.55 (3H, m), 7.69 (1H, s), 7.80–8.02 (4H, m), 9.89 (1H, s), 12.60 (1H, s); NMR (19) DMSO-d₆) δppm: 1.57–1.84 (7H, m), 1.84–2.05 (3H, m), 2.20 (1H, q, J=8.5 Hz), 2.30–2.72 (8H, m), 2.74–3.12 (3H, m), 3.16–3.30 (1H, m), 4.87 (2H, s), 6.97 (1H, d, J=8.3 Hz), 7.27–7.41 (1H, m), 7.41–7.53 (1H, m), 7.70–7.93 (4H, m), 9.91 (1H, s); NMR (20) (CDCl₃) δppm: 1.67–2.95 (20H, m), 3.55–3.95 (3H, m), 4.90 (2H, s), 6.96 (1H, d, J=8.3 Hz), 7.25–7.53 (2H, m), 7.55–7.95 (4H, m), 9.90 (1H, s); NMR (21) (CDCl₃) δppm: 1.55–3.80 (23H, m), 4.91 (2H, s). 6.96 (1H, d, J=8.4 Hz), 7.25–7.52 (2H, m), 7.65–7.78 (4H, m), 9.88 (1H, s); NMR (22) (CDCl₃) δppm: 1.75–2.95 (16H, m), 3.55–3.95 (7H, m), 4.88 (2H, s), 6.95 (1H, d, J=8.3 Hz) 7.28–7.55 (2H, m), 7.65–7.95 (4H, m), 9.90 (1H, s); NMR (23) (CDCl₃) δppm: 1.75–3.00 (20H, m), 2.27 (3H, s), 3.58–3.98 (3H, m), 4.88 (2H, s), 6.95 (1H, d, J=8.3 Hz), 7.30–7.52 (2H, m), 7.65–7.90 (4H, m), 9.89(1H, s); NMR (24) (CDCl₃) δppm: 1.5–3.4 (15H, m),2.40 (4H, t, J=4.5 Hz), 3.61 (4H, t, J=4.5 Hz), 4.88 (2H, s), 6.99 (1H, d, J=8.5 Hz), 7.3–7.55 (2H, m), 7.7–7.9 (4H, m), 9.92 (1H, s); NMR (25) (CDCl₃) δppm: 1.5–3.1 (23H, m), 2.24 (3H, s), 4.91 (2H, s), 7.00 (1H, d, J=8 Hz), 7.3–7.5 (2H, m), 7.7–7.9 (4H, m), 9.91 (1H, s); NMR (26) (CDCl₃) δppm: 1.7–2.0 (4H, m), 2.33 (3H, s), 2.5–3.0 (12H, m), 4.87 (2H, s), 6.97 (1H, d, J=8 Hz), 7.3–7.9 (6H, m), 9.91 (1H, s); NMR (27) (DMSO-d₆) δppm: 1.30–3.51 (25H, m), 3.51–3.75 (2H, m), 5.16 (2H, s), 7.09 (1H, d, J=8.9 Hz), 7.27–7.39 (1H, m), 7.39–7.52 (1H, m), 7.70–7.84 (3H, m), 7.98–8.09 (1H, m), 9.86 (1H, s), 10.58–11.17 (3H, m); NMR (28) (DMSO-d₆) δppm: 1.45 (6H, s), 2.68–3.01 (2H, m), 2.77 (3H, s), 3.21–3.85 (10H, m), 5.24 (2H, s), 7.10 (1H, d, J=8.3 Hz), 7.29–7.40 (1H, m), 7.40–7.52 (1H, m), 7.74–7.89 (3H, m), 7.93–8.05 (1H, m), 9.89 (1H, s), 11.10–13.00 (3H, m); NMR (29) (CDCl₃) δppm: 1.86 (2H, quint, J=7.5 Hz), 2.18–2.63 (10H, m), 2.30 (3H, s), 3.05 (2H, t, J=7.5 Hz), 4.82 (2H, s), 6.24–7.01 (2H, m), 7.10–7.59 (3H, m), 7.73–7.93 (3H, m), 10.17 (1H, s); NMR (30) (CDCl₃) δppm: 3.46 (1H, dd, J=6.5 Hz, J=16.5 Hz), 3.68 (1H, dd, J=10.5 Hz, J=16.5 Hz), 5.67 (1H, dd, J=6.5 Hz, J=10.5 Hz), 7.08 (1H, d, J=8.5 Hz), 7.25–7.55 (2H, m), 7.75–7.85 (3H, m), 7.99 (2H, d, J=8.5 Hz), 9.84 (1H, s).

Using the suitable starting compounds, the compounds as listed in Tables 32–37 are obtained in the same manner as in Reference Examples 7, 8 or 9.

TABLE 32

Reference Example 136

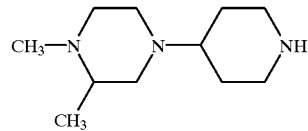

B.p.: 145° C. (0.3 mmHg)
Crystalline form: Colorless oil
Form: Free
NMR (1)

Reference Example 137

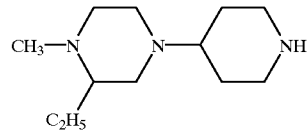

TABLE 32-continued

Crystalline form: Pale yellow oil
Form: Free
NMR (2)
Reference Example 138

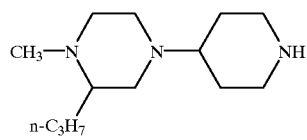

Crystalline form: Colorless oil
Form: Free
NMR (3)
Reference Example 139

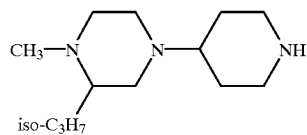

Crystalline form: Brown oil
Form: Free
NMR (4)
Reference Example 140

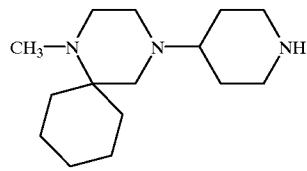

Crystalline form: Brown oil
Form: Free
NMR (5)
Reference Example 141

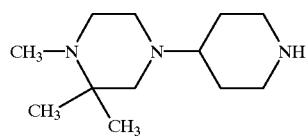

B.p.: 90–95° C. (0.15 mmHg)
Crystalline form: Colorless oil
Form: Free
Reference Example 142

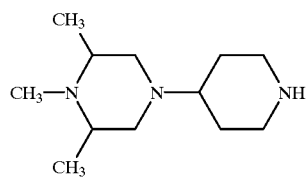

B.p.: 90–95° C. (0.2 mmHg)
Crystalline form: Colorless oil
Form: Free

TABLE 32-continued

Reference Example 143

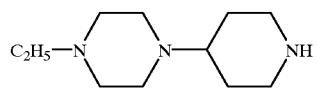

B.p.: 107° C. (0.35 mmHg)
Crystalline form: Colorless oil
Form: Free

TABLE 33

Reference Example 144

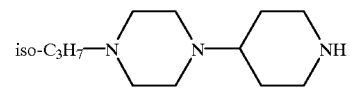

Crystalline form: White solid
Form: Free
NMR (6)
Reference Example 145

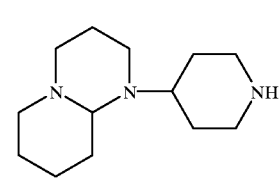

B.p.: 160–154° C. (0.25–0.3 mmHg)
Crystalline form: Colorless oil
Form: Free
Reference Example 146

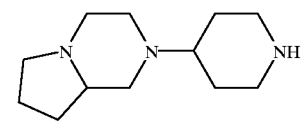

B.p.: 135–140° C. (0.25–0.3 mmHg)
Crystalline form: Colorless oil
Form: Free
NMR (7)
Reference Example 145

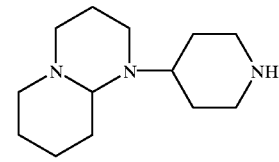

B.p.: 160–154° C. (0.25–0.3 mmHg)
Crystalline form: Colorless oil
Form: Free

TABLE 33-continued

Reference Example 147

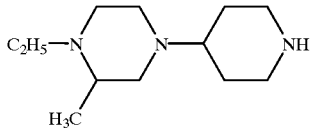

Crystalline form: Colorless oil
Form: Free
NMR (8)

Reference Example 148

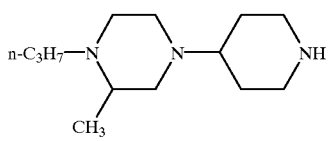

Crystalline form: Colorless oil
Form: Free
NMR (9)

Reference Example 149

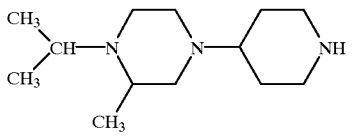

Crystalline form: White amorphous
Form: Free
NMR (10)

Reference Example 150

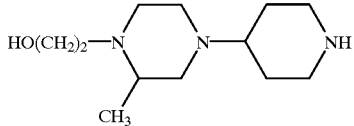

Crystalline form: Colorless oil
Form: Free
NMR (11)

Reference Example 151

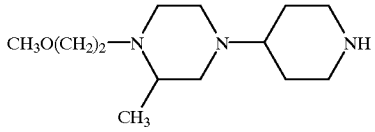

Crystalline form: Brown oil
Form: Free
NMR (12)

TABLE 34

Reference Example 152

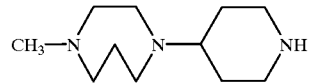

B.p.: 110–115° C. (0.22 mmHg)
Crystalline form: Colorless oil
Form: Free

Reference Example 153

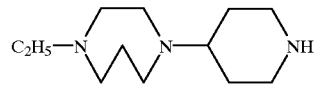

Crystalline form: Pale yellow oil
Form: Free
NMR (13)

Reference Example 154

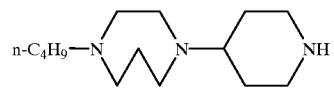

Crystalline form: Yellow powder
Form: Free
NMR (14)

Reference Example 155

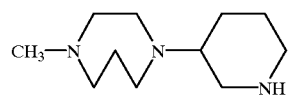

B.p.: 110° C. (0.35 mmHg)
Crystalline form: Colorless oil
Form: Free

Reference Example 156

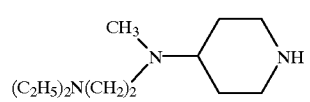

B.p.: 110–115° C. (0.28 mmHg)
Crystalline form: Colorless oil
Form: Free

Reference Example 157

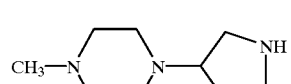

B.p.: 120–127° C. (12 mmHg)
Crystalline form: Colorless oil
Form: Free

TABLE 34-continued

Reference Example 158

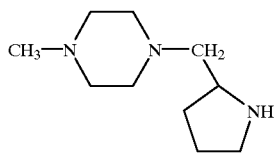

B.p.: 113–130° C. (18 mmHg)
Crystalline form: Colorless oil
Form: Free
Reference Example 159

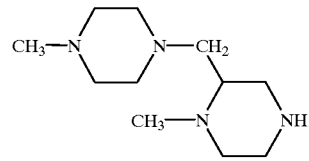

B.p.: 165–170° C. (15 mmHg)
Crystalline form: Colorless oil
Form: Free
NMR (15)

TABLE 35

Reference Example 160

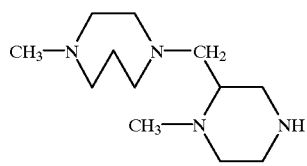

B.p.: 180–185° C. (15 mmHg)
Crystalline form: Colorless oil
Free: Form
NMR (16)
Reference Example 161

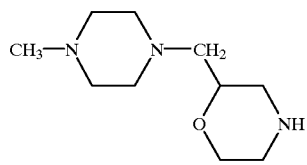

B.p.: 138–143° C. (12 mmHg)
Crystalline form: Colorless oil
Free: Form
Reference Example 162

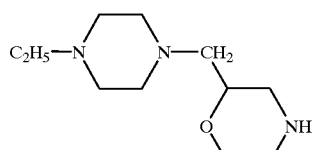

TABLE 35-continued

B.p.: 112–116° C. (0.23 mmHg)
M.p. 39–41° C.
Crystalline form: Colorless oil
Free: Form
Reference Example 163

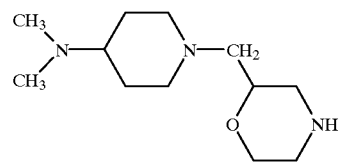

B.p.: 116° C. (0.23 mmHg)
Crystalline form: Colorless oil
Free: Form
Reference Example 164

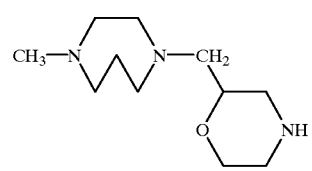

B.p.: 108° C. (0.3 mmHg)
Crystalline form: Colorless oil
Free: Form
Reference Example 165

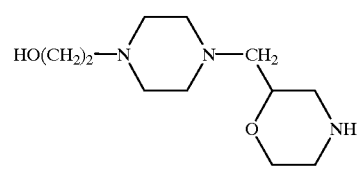

M.p. 73–75.5° C.
Crystalline form: White powder
Free: Form
Reference Example 166

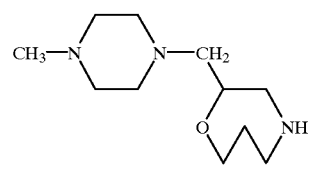

B.p.: 134–137° C. (2.5 mmHg)
Crystalline form: Colorless oil
Free: Form
Reference Example 167

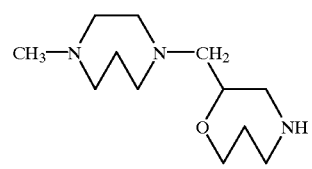

B.p.: 124–130° C. (0.7 mmHg)
Crystalline form: Colorless oil
Free: Form

TABLE 36

Reference Example 168

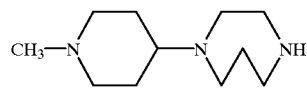

Crystalline form: White powder
Form: 3HCl
NMR (17)

Reference Example 169

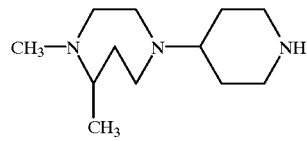

Form: Free
NMR (18)

Reference Example 170

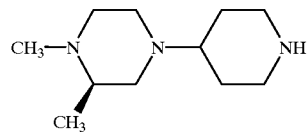

Crystalline form: Colorless oil
Form: Free
NMR (19)

Reference Example 171

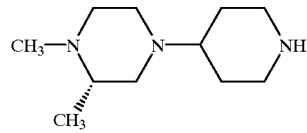

Crystalline form: Colorless oil
Form: Free
NMR (20)

Reference Example 172

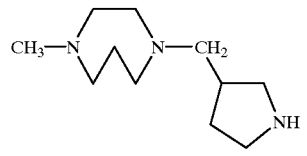

B.p.: 110–128° C. (20 mmHg)
Crystalline form: Colorless oil
Form: Free

Reference Example 173

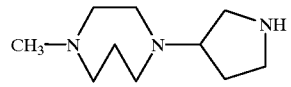

B.p.: 115–136° C. (20 mmHg)
Crystalline form: Colorless oil
Form: Free

TABLE 36-continued

Reference Example 174

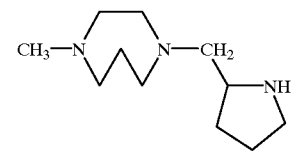

B.p.: 115–133° C. (20 mmHg)
Crystalline form: Colorless oil
Form: Free

Reference Example 175

Crystalline form: White powder
Form: 3HCl
NMR (21)

TABLE 37

Reference Example 176

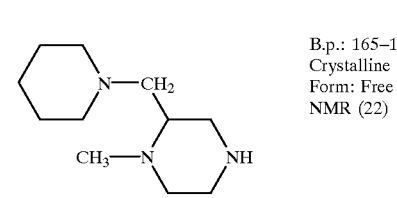

B.p.: 165–170° C. (18 mmHg)
Crystalline form: Yellow oil
Form: Free
NMR (22)

$^1$H-NMR spectrum (NMR (1) to NMR (22)) as described in Tables 32–37 are as follows:

NMR (1) (CDCl$_3$) δppm: 1.05 (3H, d, J=6 Hz), 1.25–1.55 (2H, m), 1.75–3.3 (14H, m), 2.31 (3H, s); NMR (2) (CDCl$_3$) δppm: 0.89 (3H, t, J=7.5 Hz), 1.17–1.54 (3H, m), 1.54–1.78 (1H, m), 1.78–1.94 (2H, m), 1.94–2.18 (3H, m), 2.18–2.49 (6H, m), 2.49–2.72 (2H, m), 2.72–2.95 (3H, m), 3.03–3.27 (2H, m); NMR (3) (CDCl$_3$) δppm: 0.91 (3H, t, J=7 Hz), 1.15–1.7 (5H, m), 1.75–2.15 (6H, m), 2.28 (3H, s), 2.15–2.45 (3H, m), 2.45–2.65 (2H, m), 2.7–2.95 (3H, m), 3.05–3.25 (2H, m); NMR (4) (CDCl$_3$) δppm: 0.85–0.94 (6H, m), 1.23–1.54 (2H, m), 1.62 (1H, br), 1.80–1.96 (3H, m), 1.96–2.18 (2H, m), 2.18–2.45 (6H, m), 2.45–2.68 (2H, m), 2.68–2.92 (3H, m), 3.00–3.24 (2H, m); NMR (5) (CDCl$_3$) δppm: 1.06–1.98 (15H, m), 2.20–2.47 (5H, m), 2.47–2.61 (1H, m), 2.61–2.90 (6H, m), 3.09–3.33 (2H, m); NMR (6) (CDCl$_3$) δppm: 1.06 (6H, d, J=6.5 Hz), 1.25–1.55 (2H, m), 1.75–1.95 (2H, m), 2.2–2.4 (1H, m), 2.45–2.75 (11H, m), 3.05–3.2 (2H, m); NMR (7) (CDCl$_3$) δppm: 1.25–1.6 (3H, m), 1.6–2.75 (14H, m), 2.85 (1H, dd, J=2 Hz, J=11.5 Hz), 2.9–3.3 (5H, m); NMR (8) (CDCl$_3$) δppm: 1.00 (3H, t, J=7.3 Hz), 1.04 (3H, d, J=6.3 Hz), 1.24–1.51 (2H, m), 1.70–1.92 (3H, m), 2.03 (1H, t, J=10.7 Hz), 2.20–2.50 (5H, m), 2.50–2.69 (2H, m), 2.69–3.00 (4H, m), 3.07–3.22 (2H, m); NMR (9) (CDCl$_3$) δppm: 0.84 (3H, t, J=7.3 Hz), 1.03 (3H, d, J=6.2 Hz), 1.25–1.65 (4H, m), 1.65–1.93 (3H, m), 2.02 (1H, q, J=10.7 Hz), 2.19–2.48 (5H, m), 2.48–2.95 (6H, m), 3.05–3.21 (2H, m); NMR (10) (CDCl$_3$) δppm: 0.89 (3H, d, J=6.5 Hz), 1.03 (6H, dd, J=6.5 Hz, J=15.1 Hz), 1.44–1.69

(2H, m), 1.80–2.00 (2H, m), 2.05–2.24 (2H, m), 2.24–2.50 (2H, m), 2.50–2.95 (6H, m), 3.13–3.40 (3H, m), 4.85 (1H, br); NMR (11) (CDCl$_3$) δppm: 1.03 (3H, d, J=6.2 Hz), 1.33–1.52 (2H, m), 1.72–3.08 (16H, m), 3.08–3.23 (2H, m), 3.45–3.80 (2H, m); NMR (12) (CDCl$_3$) δppm: 1.04 (3H, d, J=6.2 Hz), 1.49–1.68 (2H, m), 1.80–1.99 (2H, m), 2.06 (1H, t, J=10.1 Hz), 2.24–2.55 (5H, m), 2.57–2.88 (4H, m), 2.90–3.10 (2H, m), 3.15–3.31 (3H, m), 3.34 (3H, s), 3.44–3.62 (2H, m); NMR (13) (CDCl$_3$) δppm: 1.07 (3H, t, J=7.1 Hz), 1.40 (2H, dq, J=3.8 Hz, J=12.0 Hz), 1.65–1.98 (5H, m), 2.39–2.72 (9H, m), 2.72–2.84 (4H, m), 3.05–3.22 (2H, m); NMR (14) (CDCl$_3$) δppm: 0.91 (3H, t, J=7.1 Hz), 1.14–1.58 (5H, m), 1.58–2.13 (5H, m), 2.22–2.87 (13H, m), 3.01–3.24 (2H, m); NMR (15) (CDCl$_3$) δppm: 2.0–3.2 (17H, m), 2.26 (3H, s), 2.32 (3H, s); NMR (16) (CDCl$_3$) δppm: 1.8–1.9 (2H, m), 2.0–3.2 (17H, m), 2.33 (3H, s), 2.34 (3H, s); NMR (17) (DMSO-d$_6$) δppm: 1.94–2.46 (6H, m), 2.69 (3H, d, J=3.7 Hz), 2.84–3.16 (2H, m), 3.16–4.30 (11H, m), 9.56 (1H, br), 9.99 (1H, br), 11.04 (1H, br), 12.06 (1H, br); NMR (18) (CDCl$_3$) δppm: 1.08 (3H, d, J=6.2 Hz), 1.28–1.55 (2H, m), 1.55–1.95 (5H, m), 2.38 (3H, s), 2.40–2.99 (10H, m), 3.02–3.22 (2H, m); NMR (19) (CDCl$_3$) δppm: 1.05 (3H, d, J=6 Hz), 1.25–1.55 (2H, m), 1.75–3.3 (14H, m), 2.31 (3H, s); NMR (20) (CDCl$_3$) δppm: 1.05 (3H, d, J=6 Hz), 1.25–1.55 (2H, m), 1.75–3.3 (14H, m), 2.31 (3H, s); NMR (21) (DMSO-d$_6$) δppm: 1.78–2.47 (6H, m), 2.68–3.06 (2H, m), 3.14–4.32 (16H, m), 5.20–5.78 (2H, m), 9.1–9.82 (2H, m), 10.54–11.36 (1H, m), 11.82–12.38 (1H, m); NMR (22) (CDCl$_3$) δppm: 1.3–1.7 (6H, m), 2.0–3.2 (13H, m), 2.32 (3H, s).

Reference Example 182

To a solution of t-butyl propiolate (9.7 g) in tetrahydrofuran (300 ml) is added dropwise a 1.6M solution of n-butyl lithium in n-hexane (48 ml) at −70° C., and the mixture is reacted for 10 minutes. To the mixture is added dropwise a solution of 2-{(2-methoxy-4-formylphenoxy)methylcarbonylamino}benzothiazole (10 g) in tetrahydrofuran (200 ml) and N,N-dimethylpropylene urea (20 ml) at the same temperature over a period of 20 minutes. The reaction mixture is further reacted for 20 minutes, and then the reaction vessel is taken out from the iced bath, and the mixture is further stirred for 20 minutes. To the mixture is added acetic acid (5 ml), and the mixture is diluted with ethyl acetate. The organic layer is washed with a saturated aqueous sodium hydrogen carbonate solution, dried over sodium sulfate, concentrated, and the residue thus obtained is recrystallized from ethyl acetate-n-hexane. The crystals are collected by filtration to give 2-[2-methoxy-4-(3-t-butoxycarbonyl-1-hydroxypropargyl)phenoxymethylcarbonylamino]benzothiazole (13 g) as white power.

Reference Example 183

A solution of sodium hydroxide (4.92 g) in water (5 ml) is diluted with ethanol (80 ml), and the mixture is subjected to deaeration, and then put under nitrogen atmosphere. To the mixture is added 3-methoxy-4-dimethylaminocarbonylthiobenzaldehyde (20 g), and the mixture is refluxed for 14 hours. After cooling, to the mixture is added dropwise ethyl bromoacetate (9.74 ml), and the mixture is stirred at room temperature for three hours. To the mixture are added ethanol, 1.5N hydrochloric acid and water, and the mixture is extracted with chloroform. The extract is dried over sodium sulfate and concentrated, and the residue is purified by silica gel column chromatography (solvent; n-hexane:ethyl acetate=9:1→5.6:1→4:1) to give 3-methoxy-4-ethoxycarbonylmethylthiobenzaldehyde (11.8 g) as white solid.

$^1$H-NMR (CDCl$_3$) δppm: 1.21 (3H, t, J=7.1 Hz), 3.74 (2H, s), 3.99 (3H, s), 4.14 (2H, q, J=7.1 Hz), 7.32–7.48 (3H, m), 9.92 (1H, s).

Reference Example 184

Using the suitable starting compounds, the following compound is obtained in the same manner as in Reference Example 1.

α-(2-Methoxy-4-formylphenoxymethyl)acetic acid: Yellow powder; $^1$H-NMR (DMSO-d$_6$) δppm: 3.84 (3H, s), 4.82 (2H, s), 7.05 (1H, d, J=8 Hz), 7.41 (1H, d, J=2 Hz), 7.51 (1H, dd, J=2 Hz, J=8 Hz), 9.83 (1H, s), 13.14 (1H, br).

Reference Example 185

Using the suitable starting compounds, the following compounds are obtained in the same manner as in Reference Example 2.

2-(2-Methoxy-4-formylphenoxymethylcarbonylamino)benzimidazole: Yellow powder; $^1$H-NMR (CDCl$_3$) δppm: 4.06 (3H, s), 4.86 (2H, s), 7.09 (1H, d, J=8.5 Hz), 7.3–7.55 (4H, m), 7.8–7.9 (2H, m), 9.91 (1H, s), 10.25 (1H, br).

2-(2-Ethoxy-4-formylphenoxymethylcarbonylamino)benzimidazole: White powder; $^1$H-NMR (CDCl$_3$) δppm: 1.60 (3H, t, J=7.0 Hz), 4.26 (2H, q, J=7.0 Hz), 4.87 (2H, s), 7.11 (1H, d, J=8.3 Hz), 7.30–7.49 (4H, m), 7.79–7.88 (2H, m), 9.90 (1H, s), 10.34 (1H, br).

2-[2-(Diethylaminocarbonylmethoxy)-4-formylphenoxymethylcarbonylamino]benzimidazole: White powder; $^1$H-NMR (CDCl$_3$) δppm: 1.16 (3H, t, J=7 Hz), 1.30 (3H, t, J=7 Hz), 3.35 (2H, q, J=7 Hz), 3.49 (2H, q, J=7 Hz), 4.92 (2H, s), 5.00 (2H, s), 7.09 (1H, d, J=8 Hz), 7.25–7.55 (4H, m), 7.7–7.85 (2H, m), 9.86 (1H, s).

Reference Example 186

Using the suitable starting compounds, the following compounds are obtained in the same manner in Reference Example 5.

[3-(2-Chloroethyl)-4-(2-benzothiazolylaminocarbonylmethoxy)benzoyl]methyltriphenylphosphonium bromide: $^1$H-NMR (DMSO-d$_6$) δppm: 3.16 (2H, t, J=7.0 Hz), 3.92 (2H, t, J=7.0 Hz), 5.18 (2H, s), 6.12 (2H, d, J=13.1 Hz), 7.14 (1H, d, J=9.4 Hz), 7.31 (1H, t, J=6.5 Hz), 7.44 (1H, t, J=6.5 Hz), 7.60–8.12 (19H, m), 12.70 (1H, br).

[3-(2,3-Diacetyloxypropyl)-4-(2-benzothiazolylaminocarbonylmethoxy)benzoyl]methyltriphenylphosphonium chloride: $^1$H-NMR (CDCl$_3$) δppm: 2.00 (3H, s), 2.05 (3H, s), 3.0–3.15 (2H, m), 4.0–4.35 (2H, m), 4.93, 5.05 (2H, AB-q, J=16 Hz), 5.40 (1H, m), 6.1–6.6 (2H, br), 6.98 (1H, d, J=8 Hz), 7.2–8.5 (21H, m).

Reference Example 187

To a solution of methyl 2,4-dihydroxybenzoate (25.1 g) in acetone (250 ml) are added methyl bromoacetate (14.9 ml) and potassium carbonate (21.7 g), and the mixture is refluxed for 3 hours. The mixture is filtered, and the filtrate is concentrated, and the residue is purified by silica gel column chromatography (solvent; n-hexane:ethyl acetate=3:1) to give ethyl 2-(3-hydroxy-4-methoxycarbonylphenoxy)acetate (31.5 g).

White solid; $^1$H-NMR (CDCl$_3$) δppm: 3.81 (3H, s), 3.91 (3H, s), 4.65 (2H, s), 6.39 (1H, d, J=2.6 Hz), 6.45 (1H, dd, J=2.6 Hz, J=8.8 Hz), 7.73 (1H, d, J=8.8 Hz), 10.97 (1H, s).

Reference Example 188

To ethanol (50 ml) are added 2-(2-phthalimide) methylbenzothiazole (3.37 g) and hydrazine monohydrate (3 ml), and the mixture is refluxed for 30 minutes. After confirming that the starting compounds are consumed, the precipitated solid is removed by filtration, and the filtrate is concentrated. To the residue is added aqueous potassium carbonate solution, and the mixture is extracted with dichloromethane. The extract is dried over magnesium sulfate, and concentrated under reduced pressure to remove the solvent to give 2-aminomethylbenzothiazole (1.42 g).

Yellow powder; $^1$H-NMR (CDCl$_3$) δppm: 1.83 (2H, br), 4.30 (2H, s), 7.33–7.51 (2H, m), 7.85–7.99 (2H, m).

Reference Example 189

To dichloromethane (50 ml) are added 2-hydroxymethylbenzothiazole (2 g) and triethylamine (2.5 ml), and further thereto is added methanesulfonyl chloride (1.03 ml) under ice-cooling, and the mixture is stirred at the same temperature for one hour. After the reaction is complete, the mixture is washed with hydrochloric acid, dried over magnesium sulfate, and concentrated under reduced pressure to the remove the solvent. The resulting crude product is dissolved in dimethylformamide (50 ml), and thereto is added potassium phthalimide (5.6 g). The mixture is heated with stirring at 70° C. for one hour. After the reaction is complete, the reaction mixture is poured into water, and the precipitated crystals are collected by filtration. Separately, the filtrate is extracted with ethyl acetate, and the extract is concentrated under reduced pressure. The residue and the crystals obtained before are combined, and washed with n-hexane-diethyl ether to give 2-(2-phthalimide) methylbenzothiazole (3.37 g).

Yellow powder; $^1$H-NMR (CDCl$_3$) δppm: 5.30 (2H, s), 7.35–7.47 (2H, m), 7.74–8.02 (6H, m).

Reference Example 190

A solution of methyl p-formylbenzoate (12.33 g), malonic acid (16 g) and piperidine (1 ml) in pyridine (100 ml) is refluxed for two hours. The reaction mixture is poured into ice-water, and the precipitated white powder is collected by filtration, and washed with water, and dried to give 4-methoxycarbonyl cinnamic acid (14.7 g).

White powder; $^1$H-NMR (DMSO-d$_6$) δppm: 3.85 (3H, s), 6.65 (1H, d, J=16 Hz), 7.63 (1H, d, J=16 Hz), 7.82 (2H, d, J=8 Hz), 8.01 (2H, d, J=8 Hz), 12.57 (1H, br).

Reference Example 191

To a solution of 4-methoxycarbonylcinnamic acid (4.64 g) in acetic acid (300 ml) is added 10% palladium-carbon (0.5 g), and the mixture is subjected to hydrogenation at 70° C. under atmospheric pressure for two hours. The catalyst is removed by filtration, and the filtrate is concentrated under reduced pressure. To the residue is added water, and the precipitated white powder is collected by filtration to give 3-(4-methoxycarbonylphenyl)propionic acid (3.87 g).

White powder; $^1$H-NMR (CDCl$_3$) δppm: 2.71 (2H, t, J=7.5 Hz), 3.02 (2H, t, J=7.5 Hz), 3.91 (3H, s), 7.29 (2H, d, J=8.5 Hz), 7.97 (2H, d, J=8.5 Hz).

Reference Example 192

To a suspension of 2-carboxybenzothiazole (6.5 g) in anhydrous dichloromethane (100 ml) are added oxalyl chloride (3.2 ml) and a drop of dimethylformamide, and the mixture is stirred at room temperature for three hours. The mixture is evaporated to remove the dichloromethane, and the residue is dissolved in acetone (100 ml), and added dropwise into an aqueous solution of sodium azide (5 g) in water (20 ml) under ice-cooling. The mixture is stirred at the same temperature for three hours, and thereto is added water. The precipitated crystals are collected by filtration, dissolved in dichloromethane (50 ml), dried, and concentrated under reduced pressure to remove the solvent. To the residue is added benzene (50 ml), and the mixture is refluxed for four hours. To the mixture is added ethyl 4-piperidinecarboxylate (5.7 g), and the mixture is refluxed for 6 hours. To the reaction solution is added water, and the mixture is extracted with ethyl acetate. The extract is washed with water, dried, and concentrated under reduced pressure to remove the solvent. The residue is purified by silica gel column chromatography (solvent; dichloromethane:methanol=200:1→100:1) to give 2-(4-ethoxycarbonyl-1-piperidinyl)carbonylaminobenzothiazole (4.0 g).

White powder; $^1$H-NMR (CDCl$_3$) δppm: 1.25 (3H, t, J=7 Hz), 1.65–2.05 (4H, m), 2.4–2.6 (1H, m), 2.95–3.2 (2H, m), 4.0–4.2 (2H, m), 4.14 (2H, q, J=7 Hz), 7.15–7.45 (2H, m), 7.58 (1H, d, J=8 Hz), 7.75 (1H, d, J=8 Hz), 10.11 (1H, br).

Reference Example 193

To a solution of methyl 2-methoxy-4-trifluoromethanesulfonyloxybenzoate (26.8 g), t-butyl acrylate (62.5 ml), triethylamine (25 ml) in anhydrous dimethylformamide (100 ml) are added palladium acetate (0.4 g) and 1,3-bis(diphenylphosphino)propane (0.74 g) under argon atmosphere, and the mixture is heated with stirring at 75° C. for 16 hours. The reaction solution is concentrated under reduced pressure to remove the solvent, and thereto is added water. The mixture is extracted with ethyl acetate, and the extract is washed with water, dried, and concentrated under reduced pressure. The residue is purified by silica gel column chromatography (solvent; ethyl acetate:n-hexane= 1:5) to give t-butyl 3-methoxy-4-methoxycarbonylcinnamate (23.5 g).

Yellow powder; $^1$H-NMR (CDCl$_3$) δppm: 1.54 (9H, s), 3.90 (3H, s), 3.94 (3H, s), 6.42 (1H, d, J=16 Hz), 7.07 (1H, d, J=1.5 Hz), 7.13 (1H, dd, J=1.5, 8 Hz), 7.55 (1H, d, J=16 Hz), 7.80 (1H, d, J=8 Hz).

Reference Example 194

To a solution of t-butyl 3-methoxy-4-methoxycarbonylcinnamate (23.5 g) in anhydrous dichloromethane (100 ml) is added trifluoroacetic acid (50 ml) under ice-cooling, and the mixture is stirred at room temperature overnight. The reaction solution is concentrated under reduced pressure to remove the solvent, and the residue is crystallized from ethanol to give 3-methoxy-4-methoxycarbonylcinnamic acid (8.35 g).

White powder; $^1$H-NMR (CDCl$_3$+DMSO-d$_6$) δppm: 3.88 (3H, s), 3.94 (3H, s), 6.50 (1H, d, J=16 Hz), 7.13 (1H, s), 7.15 (1H, d, J=8 Hz), 7.62 (1H, d, J=16 Hz), 7.78 (1H, d, J=8 Hz).

Reference Example 195

To a suspension of 3-methoxy-4-methoxycarbonylcinnamic acid (8.35 g) in acetic acid (200 ml) is added 10% palladium-carbon (1.0 g), and the mixture is subjected to hydrogenation at room temperature. The catalyst is removed by filtration, and the filtrate is concentrated under reduced pressure. The residue is crystallized from diethyl ether-n-hexane to give 3-(3-methoxy-4-methoxycarbonylphenyl)propionic acid (7.5 g).

White powder; $^1$H-NMR (CDCl$_3$) δppm: 2.70 (2H, t, J=7.5 Hz), 2.98 (2H, t, J=7.5 Hz), 3.88 (3H, s), 3.89 (3H, s), 5.71 (1H, br), 6.75–6.9 (2H, m), 7.75 (1H, d, J=8 Hz).

Reference Example 196

To a solution of dimethyl methylphosphonate (7.7 ml) in anhydrous tetrahydrofuran (100 ml) is added dropwise a 1.66M solution of n-butyl lithium in n-hexane (43 ml) at −50° C. to −60° C. Subsequently, a solution of 2-[2-(3-methoxy-4-methoxycarbonylphenyl)ethyl]carbonylaminobenzothiazole (8.72 g) in anhydrous tetrahydrofuran (50 ml) is added dropwise to the reaction solution. A yellow gummy material generates in the reaction mixture, and thereto is further added 1,3-dimethyl-3,4,5,6-tetrahydro-2(1H)pyrimidinone (10 ml), and the mixture is stirred at the same temperature for two hours. To the reaction mixture is added a saturated aqueous ammonium chloride solution, and the mixture is acidified with diluted hydrochloric acid. The mixture is extracted with ethyl acetate, and the extract is washed with water, dried, and concentrated under reduced pressure. The residue is purified by silica gel column chromatography (solvent; dichloromethane:methanol= 100:1→10:1) to give dimethyl [{3-methoxy-4-[2-(2-benzothiazolyl)aminocarbonyl)ethyl]benzoyl}methyl]phosphonate (6.4 g), whereby the starting compound (3.1 g) is also recovered.

Yellow powder; $^1$H-NMR (CDCl$_3$) δppm: 2.80 (2H, t, J=7.5 Hz), 3.05 (2H, t, J=7.5 Hz), 3.73 (3H, s), 3.78 (3H, s), 3.79 (3H, s), 3.82 (2H, d, J=21.5 Hz), 6.65–6.8 (2H, m), 7.25–7.45 (2H, m), 7.60 (1H, d, J=8.5 Hz), 7.64 (1H, d, J=7.5 Hz), 7.82 (1H, dd, J=1 Hz, J=7.5 Hz), 11.49 (1H, br).

Reference Example 197

Dimethyl methylphosphonate (3.9 ml), 1.65M n-butyl lithium (22 ml) and 2-(4-ethoxycarbonyl-1-piperidinyl)carbonylaminobenzothiazole (4.0 g) are treated in the same manner as in Reference Example 196 to give dimethyl [1-(2-benzothiazolyl)aminocarbonyl)-4-piperidinylcarbonylmethyl]phosphonate (2.5 g).

Pale yellow oil; $^1$H-NMR (CDCl$_3$) δppm: 1.5–2.05 (4H, m), 2.75–3.1 (3H, m), 3.16 (2H, d, J=28 Hz), 3.76 (3H, s), 3.82 (3H, s), 4.1–4.35 (2H, m), 7.15–7.45 (2H, m), 7.57 (1H, d, J=7.5 Hz), 7.74 (1H, d, J=8 Hz), 10.04 (1H, br).

Using the suitable starting compounds, the compounds as listed in Table 36-1 are obtained in the same manner as in Reference Example 1.

TABLE 36-1

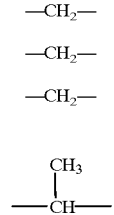

| Ref. Ex. No. | $R^5$ (substitution position) | m | A | M.p. (° C.) or NMR (Salt) | Crystalline form (Solvent for recrystallization) |
|---|---|---|---|---|---|
| 198 | —(CH$_2$)$_3$CH$_3$ (2) —OCH$_3$ (5) | 2 | —CH$_2$— | NMR (11) (Free) | White powder |
| 199 | —CH$_2$CH$_3$ (2) —OCH$_3$ (5) | 2 | —CH$_2$— | 111.8–112.5 (Free) | White powder (Ethyl acetate) |
| 200 | —CH$_3$ (2) —OCH$_3$ (3) | 2 | —CH$_2$— | NMR (17) (Free) | Yellow powder |
| 201 | —(CH$_2$)$_3$CH$_3$ (2) —OCH$_3$ (3) | 2 | —CH$_2$— | NMR (18) (Free) | White powder |
| 202 | —OCH$_3$ (3) | 1 | 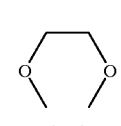 | 93–95 (Free) | White powder (Diethyl ether-n-hexane) |
| 203 |  (2, 3) | 2 | —CH$_2$— | 152–154 (Free) | Colorless needles |
| 204 | (2, 3) | 2 | —CH$_2$— | 122–123 (Free) | White powder |
| 205 | —(CH$_2$)$_2$CH$_3$ (2) —OCH$_3$ (5) | 2 | —CH$_2$— | 95–98 (Free) | White powder |
| 206 | —CH(CH$_3$)$_2$ (2) —OCH$_3$ (5) | 2 | —CH$_2$— | NMR (50) (Free) | White powder |
| 207 | —(CH$_2$)$_5$CH$_3$ (2) —OCH$_3$ (5) | 2 | —CH$_2$— | NMR (51) (Free) | White powder |
| 208 | —CH$_3$ (2) —OCH$_3$ (5) | 2 | —CH$_2$— | NMR (55) (Free) | White powder |

TABLE 36-1-continued

| Ref. Ex. No. | R⁵ (substitution position) | m | A | M.p. (° C.) or NMR (Salt) | Crystalline form (Solvent for recrystallization) |
|---|---|---|---|---|---|
| 209 | —OCH₃ (2, 5) | 2 | —CH₂— | NMR (60) (Free) | White powder |
| 210 | —OC₂H₅ (2) —OCH₃ (5) | 2 | —CH₂— | NMR (62) (Free) | White powder |

Using the suitable starting compounds, the compounds as listed in Tables 36-2 to 36-9 are obtained in the same manner as Reference Example 2.

TABLE 36-2

| Ref. Ex. No. | R⁵ (substitution position) | m | A | R⁴ | R¹ and R² | M.p. (° C.) or NMR (salt) | Crystalline form (solvent for recrystal.) |
|---|---|---|---|---|---|---|---|
| 211 | —(CH₂)₃CH₃ (2) —OCH₃ (5) | 2 | —CH₂— | H |  | 130.0–130.3 (Free) | Yellow powder (Ethyl acetate-n-hexane) |
| 212 | —CH₂CH₃ (2) —OCH₃ (5) | 2 | —CH₂— | H |  | 193–196 (Free) | Pale yellow needles (Ethyl acetate-n-hexane) |
| 213 | —(CH₂)₃CH₃ (2) —OCH₃ (3) | 2 | —CH₂— | H | 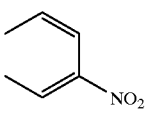 | NMR (19) (Free) | Yellow powder |
| 214 | —CH₃ (2) —OCH₃ (3) | 2 | —CH₂— | H | 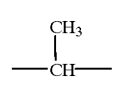 | NMR (39) (Free) | Yellow powder |
| 215 | —OCH₃ (3) | 1 | —CH₂— | H |  | 190–191 (Free) | Pale yellow powder |
| 216 | —OCH₃ (3) | 1 | CH₃ \| —CH— | H |  | NMR (42) (Free) | Orange oil |

TABLE 36-2-continued

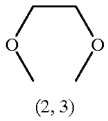

| Ref. Ex. No. | R⁵ (substitution position) | m | A | R⁴ | R¹ and R² | M.p. (° C.) or NMR (salt) | Crystalline form (solvent for recrystal.) |
|---|---|---|---|---|---|---|---|
| 217 |  (2, 3) | 2 | —CH₂— | H | 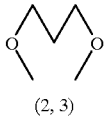 | 148–149 (Free) | Pale yellow powder (Ethanol-n-hexane) |

TABLE 36-3

| Ref. Ex. No. | R⁵ (substitution position) | m | A | R⁴ | R¹ and R² | M.p. (° C.) or NMR (salt) | Crystalline form (solvent for recrystal.) |
|---|---|---|---|---|---|---|---|
| 218 |  (2, 3) | 2 | —CH₂— | H |  | 126–128 (Free) | Pale yellow powder (Ethanol-n-hexane) |
| 219 | —(CH₂)₂CH₃ (2) —OCH₃ (5) | 2 | —CH₂— | H |  | 140–142 (Free) | Pale orange powder (Ethanol) |
| 220 | —CH₃ (2) —OCH₃ (5) | 2 | —CH₂— | H |  | NMR (52) (Free) | Yellow powder |
| 221 | —CH(CH₃)₂ (2) —OCH₃ (5) | 2 | —CH₂— | H |  | NMR (53) | Pale red powder |
| 222 | —(CH₂)₅CH₃ (2) —OCH₃ (5) | 2 | —CH₂— | H |  | NMR (54) | White powder |
| 223 | —OCH₃ (2 & 5) | 2 | —CH₂— | H |  | NMR (61) (Free) | Pale brown powder |

TABLE 36-4

[Structure: R¹⁹OC—⟨phenyl with (R⁵)ₘ⟩—O—A—C(=O)—N(R⁴)—⟨thiazole with R¹, R², S⟩]

Reference Example 224

R¹ ⟨benzene⟩ R²   R⁴: H   A: —CH$_2$—   m: 1

R¹⁹: —OCH$_3$ (4-position)   R⁵: —OCH$_2$—⟨phenyl⟩ (3-position)

M.p. 197.0–197.5° C.   Crystalline form: Yellow powder
Solvent for recrystalization: Ethyl acetate-dimethylform-   Form: Free Reference Example 225

R¹ ⟨benzene⟩ R²   R⁴: H   A: —CH$_2$—   m: 1

R¹⁹: —OCH$_3$ (4-position)   R⁵: —OCH$_2$CH=CH$_2$ (3-position)
M.p. 130–132° C.   Crystalline form: Pale yellow powder
Solvent for recrystallization: Ethyl acetate-n-hexane   Form: Free Reference Example 226

R¹ ⟨benzene⟩ R²   R⁴: H   A: —CH$_2$—   m: 1

R¹⁹: —OCH$_3$ (4-position   R⁵: —O—⟨cyclopentyl⟩ (3-position)

M.p. 131.5–132.5° C.   Crystalline form: White powder
Solvent for recrystallization: n-Hexane-ethyl acetate-dichloromethane
Form: Free Reference Example 227

R¹ ⟨benzene⟩ R²   R⁴: H   A: —CH$_2$—   m: 1

R¹⁹: —OCH$_3$ (4-position)   R⁴: —⟨phenyl⟩ (3-position)

M.p. 169.9–170.3° C.   Crystalline form: Pale yellow powder
Solvent for recrystallization: Ethyl acetate-n-hexane   Form: Free

TABLE 36-5

Reference Example 228

R¹ ⟨benzene⟩ R²   R⁴: H   A: —CH$_2$—   m: 2

R¹⁹: —OCH$_3$ (4-position)
R⁵: —(CH$_2$)$_2$CH$_3$ (2-position) & —OCH$_3$ (3-position)
M.p. 147.0–147.5° C.   Crystalline form: Pale yellow powder
Solvent for recrystalization: Ethyl acetate n-hexane   Form: Free Reference Example 229

R¹ ⟨benzene⟩ R²   R⁴: H   A: —CH$_2$—   m: 1

R¹⁹: —OCH$_3$ (4-position)   R⁵: —O—⟨phenyl⟩ (3-position)

M.p. 142.0–143.0° C.   Crystalline form: White powder
Solvent for recrystallization: Ethyl acetate-n-hexane   Form: Free Reference Example 230

R¹ ⟨benzene⟩ R²   R⁴: H   A: —CH$_2$—   m: 1

R¹⁹: —OCH$_3$ (4-position)   R⁵: —SCH$_3$ (3-position)
NMR 922)   Crystalline form: Pale yellow powder
Form: Free Reference Example 231

R¹ ⟨benzene⟩ R²   R⁴: H   A: —CH$_2$—   m: 2

R¹⁹: —OCH$_3$ (4-position)
R⁵: —(CH$_2$)$_3$CH$_3$ (2-position) & —OCH$_3$ (3-position)
NMR (27)   Crystalline form: Pale yellow powder
Form: Free

TABLE 36-6

Reference Example 232

R¹ ⟨benzene⟩ R²   R⁴: H   A: —CH$_2$—   m: 2

R¹⁹: —OCH$_3$ (4-position)
R⁵: —CH$_3$ (2-position) & —OCH$_3$ (3-position)
NMR (35)   Crystalline form: Orange powder
Form: Free Reference Example 233

R¹ ⟨benzene⟩ R²   R⁴: H   A: —CH$_2$—   m: 2

TABLE 36-6-continued

R[19]: —OCH₃ (4-position)
R⁵: —CH₃ (2-position) & —OCH₃ (3-position)
NMR (36)   Crystalline form: Orange powder Reference Example 234

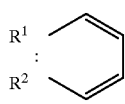

R⁴: H    A: —(CH₂)₃—    m: 2

R[19]: —OCH₃ (4-position)    R⁵: —OCH₃ (3-position)
M.p. 186–188° C.   Crystalline form: White powder
Form: Free Reference Example 235

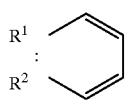

R⁴: H    A: —CH₂—    m: 2

R[19]: —OCH₃ (4-position)
R⁵: —CH₂CH=CH₂ (2-position) & —OCH₃ (5-position)
M.p. 187–189° C.   Crystalline form: Pale yellow powder
Form: Free

TABLE 36-7

Reference Example 236

R¹
:
R²    R⁴: H    A: —CH₂—    m: 2

R[19]: —OCH₃ (4-position)
R⁵: —OCH₃ (2-position) & —N(CH₃)₂ (3-position)
NMR (46)   Crystalline form: White powder
Form: Free Reference Example 237

R¹
:
R²    R⁴: H    A: —CH₂—    m: 1

R[19]: —OCH₃ (4-position)
R⁵: —N(CH₃)₂ (2-position)
NMR (65)   Crystalline form: White powder
Form: Free

TABLE 36-8

Reference Example 238

R¹
:
R²    R⁴: H    A: —CH₂—    m: 1

R[19]: —OCH₃ (4-position)    R⁵: —OCH₃ (3-position)
T: —CH₂—    u: 1
NMR (48)   Crystalline form: White powder
Form: Free

TABLE 36-9

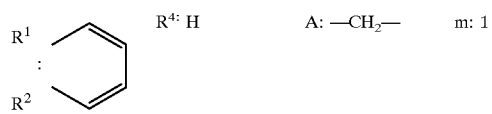

Reference Example 239

R¹
:
R²    R⁴: H    A: —(CH₂)₂—    m: 1

R[19]: —OCH₃ (4-position)    R⁵: H
NMR (73)   Crystalline form: Yellow powder
Form: Free Reference Example 240

R¹
:
R²    R⁴: H    A: —(CH₂)₂—    m: 1

R[19]: —OCH₃ (4-position)
R⁵: —OCH₃ (3-position)
NMR (75)   Crystalline form: Yellow powder
Form: Free Using the suitable starting compounds, the compounds as listed in Table 36-10 to 36-16 are obtained in the same manner as in Reference Example 3.

TABLE 36-10

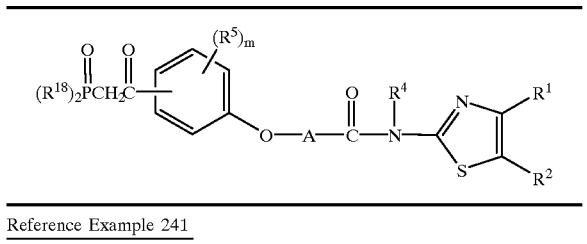

Reference Example 241

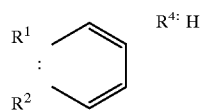
R⁴: H   A: —CH₂—   m: 1

—COCH₂PO(R¹⁸)₂: —COCH₂PO(OCH₃)₂ (4-position)
R⁵: —OCH₂CH=CH₂ (3-position)
M.p. 134–135° C.   Crystalline form: White powder
Solvent for recrystallization: Ethyl acetate-n-hexane   Form: Free
Reference Example 242

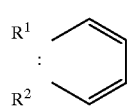
R⁴: H   A: —CH₂—   m: 1

—COCH₂PO(R¹⁸)₂: —COCH₂PO(OCH₃)₂ (4-position)

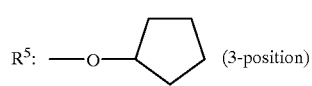
R⁵: —O—⟨cyclopentyl⟩   (3-position)

NMR (8)   Crystalline form: Yellow oil
Form: Free
Reference Example 243

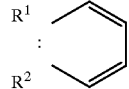
R⁴: H   A: —CH₂—   m: 1

—COCH₂PO(R¹⁸)₂: —COCH₂PO(OCH₃)₂ (4-position)

R⁵:   (3-position)

NMR (10)   Crystalline form: Yellow oil
Form: Free

TABLE 36-11

Reference Example 244

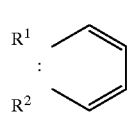
R⁴: H   A: —CH₂—   m: 2

—COCH₂PO(R¹⁸)₂: —COCH₂PO(OCH₃)₂ (4-position)
R⁵: —(CH₂)₂CH₃ (2-position) & —OCH₃ (3-position)

TABLE 36-11-continued

M.p. 156.5–157.4° C.   Crystalline form: White needles
Solvent for recrystallization: Ethyl acetate-n-hexane   Form: Free
Reference Example 245

R¹ : R²   R⁴: H   A: —CH₂—   m: 1

—COCH₂PO(R¹⁸)₂: —COCH₂PO(OCH₃)₂ (4-position)

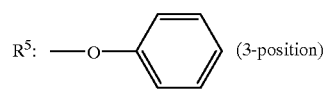
R⁵: —O—⟨phenyl⟩   (3-position)

NMR (16)   Crystalline form: Yellow amorphous   Form: Free
Reference Example 246

R¹ : R²   R⁴: H   A: —CH₂—   m: 1

—COCH₂PO(R¹⁸)₂: —COCH₂PO(OCH₃)₂ (4-position)
R⁵: —SCH₃ (3-position)
NMR (23)   Crystalline form: Pale brown powder   Form: Free
Reference Example 247

R¹ : R²   R⁴: H   A: —CH₂—   m: 2

—COCH₂PO(R¹⁸)₂: —COCH₂PO(OCH₃)₂ (4-position)
R⁵: —(CH₂)₃CH₃ (2-position) & —OCH₃ (3-position)
NMR (28)   Crystalline form: White powder   Form: Free

TABLE 36-12

Reference Example 248

R¹ : R²   R⁴: H   A: —CH₂—   m: 2

—COCH₂PO(R¹⁸)₂: —COCH₂PO(OCH₃)₂ (4-position)
R⁵: —CH₃ (2-position) & —COCH₃ (3-position)
NMR (37)   Crystalline form: Pale red powder   Form: Free
Reference Example 249

R¹ : R²   R⁴: H   A: —CH₂—   m: 2

—COCH₂PO(R¹⁸)₂: —COCH₂PO(OCH₃)₂ (4-position)
R⁵: —CH₂CH₃ (2-position) & —OCH₃ (3-position)
NMR (38)   Crystalline form: Pale red powder   Form: Free

TABLE 36-12-continued

Reference Example 250

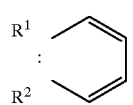 R⁴: H    A: —(CH₂)₃—    m: 1

—COCH₂PO(R¹⁸)₂: —OCH₂PO(OCH₃)₂ (4-position)
R⁵: —OCH₃ (3-position)
M.p. 140–142° C.    Crystalline form: Colorless prisms
Solvent for recrystallization: Ethanol    Form: Free Reference Example 251

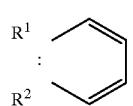 R⁴: H    A: —CH₂—    m: 2

—COCH₂PO(R¹⁸)₂: —COCH₂PO(OCH₃)₂ (4-position)
R⁵: —CH₂CH=CH₂ (2-position) & —OCH₃ (5-position)
M.p. 125–128° C.    Crystalline form: Pale brown prisms
Solvent for recrystallization: Ethanol-n-hexane    Form: Free

TABLE 36-13

Reference Example 252

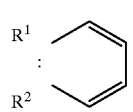 R⁴: H    A: —CH₂—    m: 2

—COCH₂PO(R¹⁸)₂: -COCH₂PO(OCH₃)₂ (4-position)
R⁵: —OCH₃ (2-position) & —N(CH₃)₂ (3-position)
NMR (47)    Crystalline form: Pale yellow powder    Form: Free

TABLE 36-13-continued

Reference Example 253

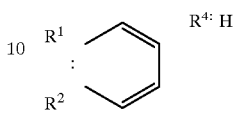 R⁴: H    A: —CH₂—    m: 2

—COCH₂PO(R¹⁸)₂: —COCH₂PO(OCH₃)₂ (4-position)
R⁵: —Br (2-position) & —OCH₃ (5-position)
M.p. 196–199° C.    Crystalline form: White powder
Solvent for recrystallization: Ethanol    Form: Free Reference Example 254

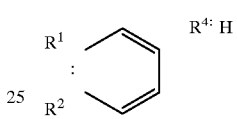 R⁴: H    A: —CH₂—    m: 1

—COCH₂PO(R¹⁸)₂: —COCH₂PO(OCH₃)₂ (4-position)
R⁵: —N(CH₃)₂ (2-position)
NMR (66)    Crystalline form: Yellow oil    Form: Free Reference Example 254A

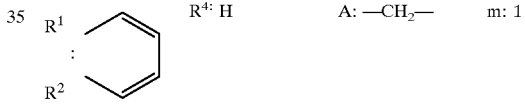 R⁴: H    A: —CH₂—    m: 1

—COCH₂PO(R¹⁸)₂: —COCH₂PO(OCH₃)₂ (4-position)
R⁵: —OCH₃ (2-position)
NMR (77)    Crystalline form: White powder    Form: Free

TABLE 36-14

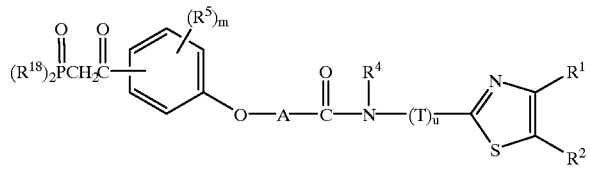

Reference Example 255

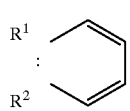 R⁴: H    A: —CH₂—    m: 1

—COCH₂PO(R¹⁸)₂: —OCH₂PO(OCH₃)₂ (4-position)
R⁵: —OCH₃ (3-position)    T: —CH₂—    u: 1
NMR (49)    Crystalline form: Brown oil    Form: Free

TABLE 36-15

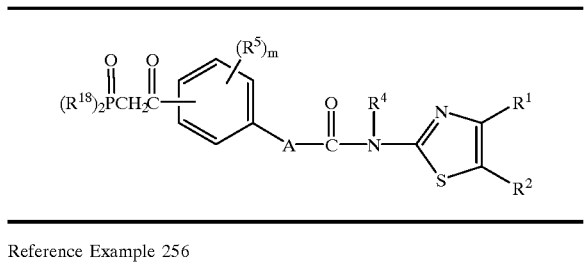

Reference Example 256

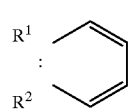

—COCH$_2$PO(R$^{18}$)$_2$: —COCH$_2$PO(OCH$_3$)$_2$ (4-position)
R$^5$: H
NMR (74) Crystalline form: Pale brown oil      Form: Free

TABLE 36-15-continued

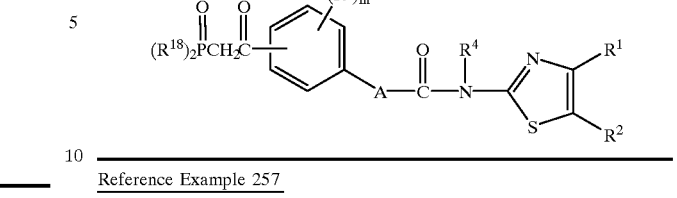

Reference Example 257

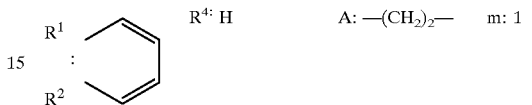
R$^4$: H     A: —(CH$_2$)$_2$—     m: 1

—COCH$_2$PO(R$^{18}$)$_2$: —COCH$_2$PO(OCH$_3$)$_2$ (4-position)
R$^5$: —OCH$_3$ (3-position)
NMR (76) Crystalline form: Yellow powder      Form: Free Using the suitable starting compounds, the compounds as listed in Table 36-16 are obtained in the same manner as in Reference Example 5 or 6.

TABLE 36-16

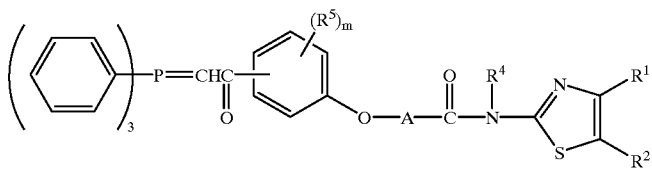

Reference Example 258

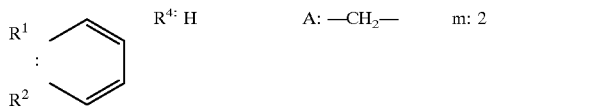
R$^4$: H     A: —CH$_2$—     m: 2

R$^5$: —OCH$_3$ (2 & 3-positions)
NMR (67) Crystalline form: Pale yellow amorphous      Form: Free Reference Example 259

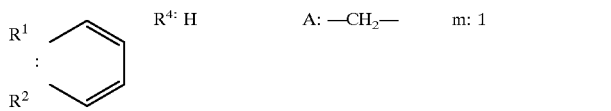
R$^4$: H     A: —CH$_2$—     m: 1

R$^5$: —O(CH$_2$)$_3$Cl (3-position)
NMR (68) Crystalline form: Colorless amorphous      Form: Free Reference Example 260

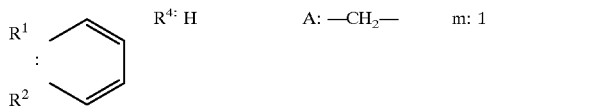
R$^4$: H     A: —CH$_2$—     m: 1

R$^5$: 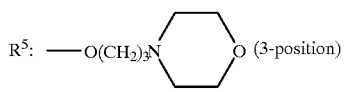 (3-position)

NMR (69) Crystalline form: Pale yellow amorphous      Form: Free

TABLE 36-16-continued

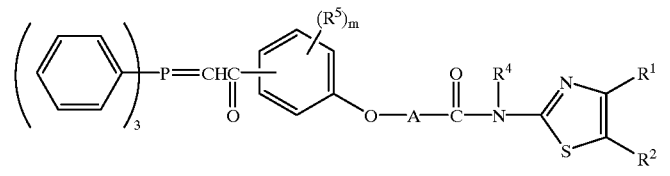

Reference Example 261

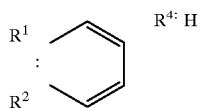

R⁴: H    A: —CH₂—    m: 1

R⁵: —OCH₃ (3-position)
NMR (70)    Crystalline form: Dark brown amorphous    Form: Free Using the suitable starting compounds, the compounds as listed in Table 36-17 are obtained in the same manner as in Reference Example 7, 8 or 9.

TABLE 36-17

Reference Example 262

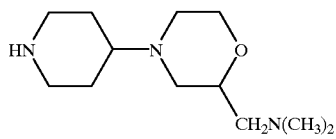

Colorless oil
Form: Free
NMR (71)
Reference Example 263

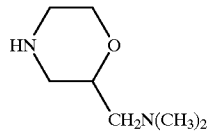

Pale yellow oil
Form: Free
NMR (72)

Using the suitable starting compounds, the compounds as listed in Tables 36-18 to 36-21 are obtained in the same manner as in Reference Example 187.

TABLE 36-18

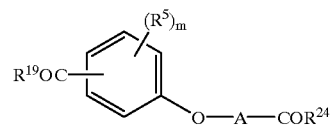

Reference Example 264

R⁵: —OH (3-position)    A: —CH₂—    m: 1
—COR¹⁹: —COOCH₃ (4-position)    R²⁴: —OCH₃
NMR (1)    Crystalline form: White solid    Form: Free TABLE 36-18-continued

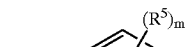

Reference Example 265

A: —CH₂—    m: 1
R⁵: —OCH₂— 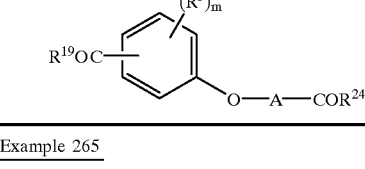 (3-position)

—COR¹⁹: —COOCH₃ (4-position)    R²⁴: —OCH₃
NMR (2)    Crystalline form: White solid    Form: Free
Reference Example 266

R⁵: —OCH₂CH=CH₂ (3-position)    A: —CH₂—    m: 1
—COR¹⁹: —COOCH₃ (4-position)    R²⁴: —OCH₃
NMR (4)    Crystalline form: Colorless oil    Form: Free
Reference Example 267

A: —CH₂—    m: 1
R⁵: —O— 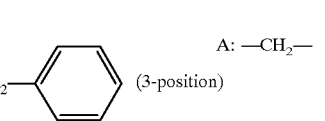 (3-position)

—COR¹⁹: —COOCH₃ (4-position)    R²⁴: —OCH₃
NMR (6)    Crystalline form: Yellow oil    Form: Free
Reference Example 268

A: —CH₂—    m: 1
R⁵: — (3-position)

—COR¹⁹: —COOCH₃ (4-position)    R²⁴: —OCH₃
NMR (9)    Crystalline form: Colorless oil    Form: Free
Reference Example 269

R⁵: —CH₂CH=CH₂ (2-position) & —OH (3-position)
A: —CH₂—    m: 2
—COR¹⁹: —COOCH₃ (4-position)    R²⁴: —OCH₃
M.p. 93.1–93.8° C    Crystalline form: Colorless needles
Solvent for recrystallization: n-Hexane-ethyl acetate    Form: Free

TABLE 36-18-continued

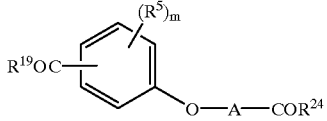

Reference Example 270

R⁵: —(CH₂)₂CH₃ (2-position) & —OH (3-position)
A: —CH₂—  m: 2
—COR¹⁹: —COOCH₃(4-position)  R²⁴: —OCH₃
NMR (12)  Crystalline form: White solid  Form: Free

TABLE 36-19

Reference Example 271

R⁵: —(CH₂)₂CH₃ (2-position) & —OCH₃ (3-position)
A: —CH₂—  m: 2
—COR¹⁹: —COOCH₃ (4-position)  R²⁴: —OCH₃
NMR (13)  Crystalline form: Colorless oil  Form: Free
Reference Example 272

A: —CH₂—  m: 1
R⁵: —O—⟨ ⟩ (3-position)

—COR¹⁹: —COOCH₃ (4-position)  R²⁴: —OCH₃
NMR (15)  Crystalline form: Colorless oil  Form: Free
Reference Example 273

R⁵: —SCH₃ (3-position)  A: —CH₂—  m: 1
—COR¹⁹: —COOCH₃ (4-position)  R²⁴: —OCH₃
NMR (20)  Crystalline form: Pale yellow powder  Form: Free
Reference Example 274

R⁵: —(CH₂)₃CH₃ (2-position) & —OH (3-position)
A: —CH₂—  m: 2
—COR¹⁹: —COOCH₃ (4-position)  R²⁴: —OCH₃
NMR (24)  Crystalline form: Pale brown powder  Form: Free
Reference Example 275

R⁵: —(CH₂)₃CH₃ (2-position) & —OCH₃ (3-position)
A: —CH₂—  m: 2
—COR¹⁹: —COOCH₃ (4-position)  R²⁴: —OCH₃
NMR (25)  Crystalline form: White powder  Form: Free
Reference Example 276

R⁵: —CH₂CH₃ (2-position) & —OH (3-position)
A: —CH₂—  m: 2
—COR¹⁹: —COOCH₃ (4-position)  R²⁴: —OCH₃
NMR (29)  Crystalline form: White powder  Form: Free
Reference Example 277

R⁵: —CH₃ (2-position) & —OH (3-position)
A: —CH₂—  m: 2
—COR¹⁹: —COOCH₃ (4-position)  R²⁴: —OCH₃
NMR (30)  Crystalline form: White powder  Form: Free

TABLE 36-20

Reference Example 278

R⁵: —CH₃ (2-position) & —OCH₃ (3-position)
A: —CH₂—  m: 2
—COR¹⁹: —COOCH₃ (4-position)  R²⁴: —OCH₃
NMR (31)  Crystalline form: Colorless needles  Form: Free
Reference Example 279

R⁵: —CH₂CH₃ (2-position) & —OCH₃ (3-position)
A: —CH₂—  m: 2
—COR¹⁹: —COOCH₃ (4-position)  R²⁴: —OCH₃
NMR (32)  Crystalline form: Colorless oil  Form: Free
Reference Example 280

R⁵: —OH (3-position)
A: —CH₂—  m: 1
—COR¹⁹: —COOCH₃ (4-position)  R²⁴: —OC₂H₅
NMR (40)  Crystalline form: Colorless oil  Form: Free
Reference Example 281

R⁵: —OCH₃ (3-position)
A: —CH₂—  m: 1
—COR¹⁹: —COOCH₃ (4-position)  R²⁴: —OC₂H₅
NMR (41)  Crystalline form: Pale brown powder  Form: Free
Reference Example 282

R⁵: —OCH₃ (3-position)
A: —(CH₂)₃—  m: 1
—COR¹⁹: —COOCH₃ (4-position)  R²⁴: —OCH₃
M.p. 48–50° C.  Crystalline form: White powder
Solvent for recrystallizafion: Ethyl acetate-n-hexane  Form: Free
Reference Example 283

R⁵: —OCH₃ (2-position) & —NH₂ (3-position)
A: —CH₂—  m: 2
—COR¹⁹: —COOCH₃ (4-position)  R²⁴: —OCH₃
NMR (44)  Crystalline form: Yellow oil  Form: Free
Reference Example 284

R⁵: —OCH₃ (2-position) & —N(CH₃)₂ (3-position)
A: —CH₂—  m: 2
—COR¹⁹: —COOCH₃ (4-position)  R²⁴: —OCH₃
NMR (45)  Crystalline form: Brown oil  Form: Free

TABLE 36-21

Reference Example 285

R⁵: —Br (2-position) & —OH (5-position)
A: —CH₂—  m: 2
—COR¹⁹: —COOCH₃ (4-position)  R²⁴: —OCH₃
NMR (56)  Crystalline form: White powder  Form: Free

TABLE 36-21-continued

Reference Example 286

$R^5$: —Br (2-position) & —$OCH_3$ (5-position)
A: —$CH_2$—  m: 2
—$COR^{19}$: —$COOCH_3$ (4-position)  $R^{24}$: —$OCH_3$
NMR (57)  Crystalline form: White powder  Form: Free Reference Example 287

$R^5$: —$NH_2$ (2-position) & —$OCH_3$ (5-position)
A: —$CH_2$—  m: 2
—$COR^{19}$: —$COOCH_3$ (4-position)  $R^{24}$: —$OC_2H_5$
NMR (59)  Crystalline form: White powder  Form: Free Reference Example 288

$R^5$: —$N(CH_3)_2$ (2-position)
A: —$CH_2$—  m: 1

—$COR^{19}$: —$COOCH_3$ (4-position)

$R^{24}$: 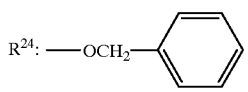

NMR (63)  Crystalline form: Yellow oil  Form: Free

Using the suitable starting compounds, the compounds as listed in Tables 36-22 to 36-23 are obtained in the same manner as in Reference Example 1 or 194.

TABLE 36-22

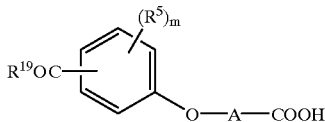

Reference Example 289

$R^5$: 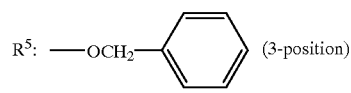 (3-position)

A —$CH_2$—  m: 1  —$COR^{19}$: —$COOCH_3$ (4-position)
NMR (3)  Crystalline form: White solid  Form: Free Reference Example 290

$R^5$: —$OCH_2CH=CH_2$ (3-position)
A: —$CH_2$—  m: 1  —$COR^{19}$: —$COOCH_3$ (4-position)
NMR (5)  Crystalline form: White solid  Form: Free Reference Example 291

$R^5$: 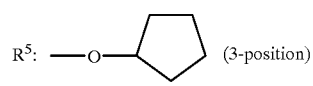 (3-position)

A: —$CH_2$—  m: 1  —$COR^{19}$: —$COOCH_3$ (4-position)
NMR (7)  Crystalline form: Pale yellow oil  Form: Free Reference Example 292

$R^5$:  (3-position)

A: —$CH_2$—  m: 1  —$COR^{19}$: —$COOCH_3$ (4-position)
M.p. 124.5–126.0° C.  Crystalline form: White powder
Solvent for recrystallization: Ethyl acetate  Form: Free

TABLE 36-22-continued

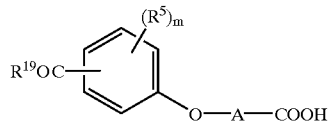

Reference Example 293

$R^5$: —$(CH_2)_2CH_3$ (2-position) & —$OCH_3$ (3-position)
A: —$CH_2$—  m: 2  —$COR^{19}$: —$COOCH_3$ (4-position)
NMR (14)  Crystalline form: White solid  Form: Free Reference Example 294

$R^5$: 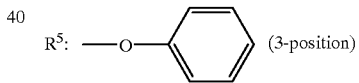 (3-position)

A: —$CH_2$—  m: 1  —$COR^{19}$: —$COOCH_3$ (4-position)
M.p. 131.5–132.0° C.  Crystalline form: Pale yellow powder
Solvent for recrystallization: Ethyl acetate  Form: Free Reference Example 295

$R^5$: —$SCH_3$ (3-position)  A: —$CH_2$—  m: 1
—$COR^{19}$: —$COOCH_3$ (4-position)  NMR (21)
Crystalline form: White powder  Form: Free

TABLE 36-23

Reference Example 296

$R^5$: —$(CH_2)_3CH_3$ (2-position) & —$OCH_3$ (3-position)
A: —$CH_2$—
m: 2
—$COR^{19}$: —$COOCH_3$ (4-position)
NMR (26)
Crystalline form: White powder
Form: Free Reference Example 297

$R^5$: —$CH_3$ (2-position) & —$OCH_3$ (3-position)
A: —$CH_2$—
m: 2
—$COR^{19}$: —$COOCH_3$ (4-position)

TABLE 36-23-continued

NMR (33)
Crystalline form: White powder
Reference Example 298

$R^5$: —CH$_2$CH$_3$ (2-position) & —OCH$_3$ (3-position)
A: —CH$_2$—
m: 2
—COR$^{19}$: —COOCH$_3$ (4-position)
NMR (34)
Crystalline form: White powder
Reference Example 299

$R^5$: —OCH$_3$ (3-position)
A: —(CH$_2$)$_3$—
m: 1
—COR$^{19}$: —COOCH$_3$ (4-position)
M.p. 89–90° C.
Crystalline form: Colorless needles
Solvent for recrystallization: Water-ethanol
Form: Free
Reference Example 300

$R^5$: —CH$_2$CH=CH$_2$ (2-position) & —OCH$_3$ (5-position)
A: —CH$_2$—
m: 2
—COR$^{19}$: —COOCH$_3$ (4-position)
NMR (43)
Crystalline form: White powder
Form: Free
Reference Example 301

$R^5$: —Br (2-position) & —OCH$_3$ (5-position)
A: —CH$_2$—
m: 2
—COR$^{19}$: —COOCH$_3$ (4-position)
NMR (58)
Crystalline form: White powder
Form: Free
Reference Example 302

$R^5$: —N(CH$_3$)$_2$ (2-position)
A: —CH$_2$—
m: 1
—COR$^{19}$: —COOCH$_3$ (4-position)
NMR (64)
Crystalline form: White amorphous
Form: Free

Reference Example 303

Using the suitable starting compounds, the following compounds are obtained in the same manner as in Reference Example 6.

Methyl α-(2,3-dihydroxy-4-acetylphenoxy)acetate: White powder; $^1$H-NMR (DMSO-d$_6$) δppm: 2.56 (3H, s), 3.69 (3H, s), 4.91 (2H, s), 6.49 (1H, d, J=9.1 Hz), 7.35 (1H, d, J=9.1 Hz), 8.79 (1H, s), 12.31 (1H, s).

Methyl α-(2,3-dimethoxy-4-acetylphenoxy)acetate: White solid; $^1$H-NMR (CDCl$_3$) δppm: 2.60 (3H, s), 3.81 (3H, s), 3.93 (3H, s), 3.99 (3H, s), 4.75 (2H, s), 6.57 (1H, d, J=8.9 Hz), 7.48 (1H, d, J=8.9 Hz).

Methyl α-[2,3-dimethoxy-4-(2-bromoacetyl)phenoxy]acetate: Colorless oil; $^1$H-NMR (CDCl$_3$) δppm: 3.81 (3H, s), 3.93 (3H, s), 4.07 (3H, s), 4.57 (2H, s), 4.76 (2H, s), 6.58 (1H, d, J=8.9 Hz), 7.54 (1H, d, J=8.9 Hz).

(2,3-Dimethoxy-4-methoxycarbonylmethoxybenzoyl)methylenetriphenylphosphorane: Colorless amorphous; $^1$H-NMR (CDCl$_3$) δppm: 3.77 (3H, s), 3.94 (6H, s), 4.61 (1H, brd, J=27.8 Hz), 4.70 (2H, s), 6.56 (1H, d, J=8.8 Hz), 7.38–7.80 (16H, m).

Ethyl α-[3-(3-chloropropoxy)-4-acetylphenoxy)acetate: Yellow oil; $^1$H-NMR (CDCl$_3$) δppm: 1.31 (3H, t, J=7 Hz), 2.2–2.5 (2H, m), 2.57 (3H, s), 3.77 (2H, t, J=6.5 Hz). 4.30 (2H, t, J=7 Hz), 4.66 (2H, s), 6.47 (1H, dd, J=2H, J=8.5 Hz), 6.57 (1H, d, J=2 Hz), 7.81 (1H, d, J=8.5 Hz).

Ethyl α-[3-(3-chloropropoxy)-4-(2-bromoacetyl)phenoxy]acetate: Colorless oil; $^1$H-NMR (CDCl$_3$) δppm: 1.31 (3H, t, J=7 Hz), 2.25–2.55 (2H, m), 3.55–3.85 (2H, m), 4.15–4.4 (4H, m), 4.50 (2H, s), 4.68 (2H, s), 6.51 (1H, dd, J=2 Hz, J=9 Hz), 6.59 (1H, d, J=2 Hz), 7.89 (1H, d, J=9 Hz).

[2-(3-Chloropropoxy)-4-ethoxycarbonylmethoxybenzoyl]methylenetriphenylphosphorane: Pale brown amorphous; $^1$H-NMR (CDCl$_3$) δppm: 1.31 (3H, t, J=7 Hz), 2.2–2.7 (2H, m), 3.67 (2H, d, J=5.5 Hz), 4.27 (2H, q, J=7 Hz), 4.2–4.4 (2H, m), 4.66 (2H, s), 6.20 (1H, br), 6.47 (1H, dd, J=2 Hz, J=9 Hz), 6.57 (1H, d, J=2 Hz), 7.4–8.0 (16H, m).

(2,3-Dimethoxy-4-carboxymethoxybenzoyl)methyltriphenylphosphonium chloride: Colorless prisms (recrystallized from diluted hydrochloric acid); M.p. 137–151° C. (decomposed); $^1$H-NMR (DMSO-d$_6$) δppm: 3.78 (3H, s), 3.81 (3H, s), 4.69 (2H, s), 6.63 (1H, d, J=8.9 Hz), 7.28 (1H, d, J=8.9 Hz), 7.50–7.80 (15H, m).

[2-(3-Chloropropoxy)-4-carboxymethoxybenzoyl]methyltriphenylphosphonium chloride: Pale yellow amorphous; $^1$H-NMR (CDCl$_3$) δppm: 2.1–2.45 (2H, m), 3.63 (2H, t, J=6.5 Hz), 4.04 (2H, t, J=5 Hz), 4.49 (2H, s), 6.35 (1H, dd, J=2 Hz, J=7 Hz), 6.48 (1H, d, J=2 Hz), 7.35–7.9 (16H, m).

$^1$H-NMR spectrum (NMR (1) to NMR (77)) as described in Tables 36-1 to 36-23 are as follows:

NMR (1) (CDCl$_3$) δppm: 3.81 (3H, s), 3.91 (3H, s), 4.65 (2H, s), 6.39 (1H, d, J=2.6 Hz), 6.45 (1H, dd, J=2.6 Hz, J=8.8 Hz), 7.73 (1H, d, J=8.8 Hz), 10.97 (1H, s); NMR (2) (CDCl$_3$) δppm: 3.80 (3H, s), 3.87 (3H, s), 4.64 (2H, s), 5.16 (2H, s), 6.42 (1H, dd, J=2.4 Hz, J=8.7 Hz), 6.60 (1H, d, J=2.4 Hz), 7.30–7.43 (3H, m), 7.49–7.52 (2H, m), 7.85 (1H, d, J=8.7 Hz); NMR (3) (DMSO-d$_6$) δppm: 3.76 (3H, s), 4.76 (2H, s), 5.19 (2H, s), 6.54 (1H, dd, J=2.3 Hz, J=8.7 Hz), 6.76 (1H, d, J=2.3 Hz), 7.27–7.44 (3H, m), 7.49–7.53 (2H, m), 7.69 (1H, d, J=8.7 Hz), 13.07 (1H, brs); NMR (4) (CDCl$_3$) δppm: 3.82 (3H, s), 3.86 (3H, s), 4.58–4.62 (2H, m), 4.66 (2H, s), 5.28–5.58 (2H, m), 5.98–6.19 (1H, m), 6.41 (1H, dd, J=2.4 Hz, J=8.7 Hz), 6.54 (1H, d, J=2.4 Hz), 7.83 (1H, d, J=8.7 Hz); NMR (5) (DMSO-d$_6$) δppm: 3.74 (3H, s), 4.59–4.63 (2H, m), 4.75 (2H, s), 5.21–5.29 (2H, m), 5.93–6.09 (1H, m), 6.52 (1H, dd, J=2.3 Hz, J=8.7 Hz), 6.64 (1H, d, J=2.3 Hz), 7.67 (1H, d, J=8.7 Hz), 13.05 (1H, brs); NMR (6) (CDCl$_3$) δppm: 1.52–2.00 (8H, m), 3.82 (3H, s), 3.84 (3H, s), 4.66 (2H, s), 4.73–4.84 (1H, m), 6.37 (1H, dd, J=2.4 Hz, J=8.7 Hz), 6.53 (1H, d, J=2.4 Hz), 7.79 (1H, d, J=8.7 Hz); NMR (7) (CDCl$_3$) δppm: 1.52–2.03 (8H, m), 3.84 (3H, s), 4.71 (2H, s), 4.30–5.20 (2H, m), 6.40 (1H, dd, J=2.4 Hz, J=8.7 Hz), 6.54 (1H, d, J=2.4 Hz), 7.80 (1H, d, J=8.7 Hz); NMR (8) (CDCl$_3$) δppm: 1.65–2.12 (8H, m), 3.74 (3H, s), 3.78 (3H, s), 3.70–3.88 (2H, m), 4.79 (2H, s), 4.83–4.94 (1H, m), 6.40–6.62 (2H, m), 7.32–7.4 (1H, m), 7.44–7.52 (1H, m), 7.79–7.90 (3H, m), 8.31–10.20 (1H, brs); NMR (9) (CDCl$_3$) δppm: 3.61 (3H, s), 3.81 (3H, s), 4.70 (2H, s), 6.83–6.97 (2H, m), 7.22–7.33 (2H, m), 7.33–7.45 (3H, m), 7.85 (1H, d, J=8.8 Hz); NMR (10) (CDCl$_3$) δppm: 3.50–3.70 (8H, m), 4.79 (2H, s), 6.77–6.97 (2H, m), 7.09–7.49 (8H, m), 7.58–7.89 (2H, m), 9.97–10.81 (1H, brs); NMR (11) (CDCl$_3$) δppm: 0.88 (3H, t, J=7.2 Hz), 1.26–1.47 (2H, m), 1.47–1.66 (2H, m), 2.56 (2H, t, J=7.5 Hz), 3.78 (3H, s), 4.66 (2H, s), 6.33 (1H, d, J=2.4 Hz), 6.46 (1H, dd, J=2.4 Hz, J=8.3 Hz), 7.05 (1H, d, J=8.3 Hz); NMR (12) (CDCl$_3$) δppm: 0.92 (3H, t, J=7.4 Hz), 1.48–1.70 (2H, m), 2.65–2.78 (2H, m), 3.79 (3H, s), 3.90 (3H, s), 4.70 (2H, s), 6.25 (1H, d, J=8.9 Hz), 7.65 (1H, d, J=8.9 Hz), 11.08 (1H, s); NMR (13) (CDCl$_3$) δppm: 0.94 (3H, t, J=7.3 Hz), 1.49–1.71 (2H, m), 2.63–2.77 (2H, m), 3.80 (3H, s), 3.83 (3H, s), 3.89 (3H, s), 4.70 (2H, s), 6.48 (1H, d, J=8.8 Hz), 7.70 (1H, d, J=8.8 Hz); NMR (14) (CDCl$_3$) δppm: 0.93 (3H, t, J=7.3 Hz), 1.47–1.70 (2H, m), 2.62–2.76 (2H, m), 3.83 (3H, s), 3.90 (3H, s), 4.74 (2H, s), 6.51 (1H, d, J=8.8 Hz), 7.20 (1H, brs), 7.72 (1H, d, J=8.8 Hz); NMR (15) (CDCl$_3$) δppm: 3.77 (3H, s), 3.79 (3H, s), 4.59 (2H, s), 6.45 (1H, d, J=2.5 Hz), 6.65 (1H, dd, J=2.5 Hz, J=8.8 Hz), 6.92–7.03 (2H, m), 7.03–7.17 (1H, m), 7.26–7.40 (2H, m), 7.91 (1H, d, J=8.8 Hz); NMR (16) (CDCl$_3$) δppm: 3.72 (3H, s), 3.77 (3H, s), 3.81 (2H, d, J=21.6 Hz), 4.68 (2H, s), 6.34 (1H, d, J=2.4 Hz), 6.62 (1H, dd, J=2.4 Hz, J=8.8 Hz), 7.04–7.15 (2H, m), 7.15–7.47 (5H, m), 7.68–7.83 (2H, m), 7.86 (1H, d, J=8.8 Hz), 10.65 (1H, brs); NMR (17) (DMSO-d$_6$) δppm: 2.02 (3H, s), 3.75 (3H, s), 4.64 (2H, s), 6.47 (1H, d, J=8.3 Hz), 6.60 (1H, d, J=8.3 Hz), 7.07 (1H, t, J=8.3 Hz), 12.93 (1H, brs); NMR (18) (DMSO-d$_6$) δppm: 0.86 (3H, t, J=7.2 Hz), 1.13–1.51 (4H, m), 2.59 (2H, t, J=7.6 Hz), 3.74 (3H, s), 4.63 (2H, s), 6.46 (1H, d, J=8.3 Hz), 6.59 (1H, d, J=8.3 Hz), 7.06 (1H, t, J=8.3 Hz), 12.89 (1H, brs); NMR (19) (CDCl$_3$) δppm: 0.97 (3H, t, J=7.1 Hz), 1.31–1.68 (4H, m), 2.77 (2H, t, J=7.0 Hz), 3.84 (3H, s), 4.75 (2H, s), 6.51 (1H, d, J=8.2 Hz), 6.64 (1H, d, J=8.2 Hz), 7.14 (1H, t, J=8.2 Hz), 7.26–7.39 (1H, m), 7.39–7.52 (1H, m), 7.73–7.90 (2H, m), 9.70 (1H, brs); NMR (20) (CDCl$_3$) δppm: 2.43 (3H, s), 3.82 (3H, s), 3.88 (3H, s), 4.70 (2H, s), 6.59 (1H, dd, J=8.8 Hz, J=2.4 Hz), 6.81 (1H, d, J=2.4 Hz), 8.00 (1H, d, J=8.8 Hz); NMR (21) (DMSO-d$_6$) δppm: 2.39 (3H, s), 3.77 (3H, s), 4.81 (2H, s), 6.62–6.83 (2H, m), 7.89 (1H, d, J=9.1 Hz), 13.14 (1H, brs); NMR (22) (CDCl$_3$) δppm: 2.48 (3H, s), 3.90 (3H, s), 4.82 (2H, s), 6.69 (1H, dd, J=8.7 Hz, J=2.4 Hz), 6.86 (1H, d, J=2.4 Hz), 7.36 (1H, dt, J=1.2 Hz, J=7.7 Hz), 7.48 (1H, dt, J=1.2 Hz, J=7.7 Hz), 7.84 (2H, t, J=7.7 Hz), 8.05 (1H, d, J=8.7 Hz), 9.91 (1H, brs); NMR (23) (CDCl$_3$) δppm: 2.41 (3H, s), 3.63 (2H, d, J=22.6 Hz), 3.80 (6H, d, J=11.2 Hz), 4.82 (2H, s), 6.71 (1H, dd, J=8.8 Hz, J=2.4 Hz), 6.85 (1H, d, J=2.4 Hz), 7.34 (1H, dt, J=1.3 Hz, J=9.2 Hz), 7.47 (1H, dt, J=1.3 H, J=9.2 Hz), 7.82 (2H, t, J=9.2 Hz), 8.01 (1H, d, J=8.8 Hz); NMR (24) (CDCl$_3$) δppm: 0.93 (3H, t, J=7.0 Hz), 1.19–1.62 (4H, m), 2.73 (2H, t, J=7.0 Hz), 3.79 (3H, s), 3.91 (3H, s), 4.70 (2H, s), 6.27 (1H, d, J=9.0 Hz), 7.67 (1H, d, J=9.0 Hz), 11.07 (1H, s); NMR (25) (CDCl$_3$) δppm: 0.94 (3H, t, J=7.2 Hz), 1.29–1.63 (4H, m), 2.72 2H, t, J=7.1 Hz), 3.80 (3H, s), 3.83 (3H, s), 3.89 (3H, s), 4.70 (2H, s), 6.50 (1H, d, J=8.8 Hz), 7.72 (1H, d, J=8.8 Hz); NMR (26) (DMSO-d$_6$) δppm: 0.88 (3H, t, J=7.1 Hz), 1.19–1.61 (4H, m), 2.60 (2H, t, J=6.7 Hz), 3.70 (3H, s), 3.78 (3H, s), 4.77 (2H, s), 6.71 (1H, d, J=8.8 Hz), 7.60 (1H, d, J=8.8 Hz), 13.05 (1H, brs); NMR (27) (CDCl$_3$) δppm: 0.99 (3H, t, J=7.1 Hz), 1.37–1.71 (4H, m), 2.80 (2H, t, J=6.9 Hz), 3.87 (3H, s), 3.91 (3H, s), 4.82 (2H, s), 6.66 (1H, d, J=8.8 Hz), 7.34 (1H, dt, J=1.3 Hz, J=7.7 Hz), 7.46 (1H, dt, J=1.3 Hz, J=7.7 Hz), 7.69–7.90 (3H, m), 9.62 (1H, brs); NMR (28) (CDCl$_3$) δppm: 1.00 (3H, t, J=7.0 Hz), 1.39–1.73 (4H, m), 2.78 (2H, t, J=8.0 Hz), 3.76 (6H, d, J=11.4 Hz), 3.79 (3H, s), 3.81 (2H, d, J=22.1 Hz), 4.82 (2H, s), 6.69 (1H, d, J=8.8 Hz), 7.34 (1H, t, J=8.6 Hz), 7.46 (1H, t, J=8.6 Hz), 7.57 (1H, d, J=8.8 Hz), 7.82 (2H, t, J=8.6 Hz), 9.87 (1H, brs); NMR (29) (CDCl$_3$) δppm: 1.14 (3H, t, J=7.5 Hz), 2.75 (2H, q, J=7.5 Hz), 3.80 (3H, s), 3.91 (3H, s), 4.71 (2H, s), 6.28 (1H, J=9.0 Hz), 7.67 (1H, d, J=9.0 Hz), 11.08 (1H, s); NMR (30) (CDCl$_3$) δppm: 2.18 (3H, s), 3.80 (3H, s), 3.91 (3H, s), 4.71 (2H, s), 6.28 (1H, d, J=9.0 Hz), 7.67 (1H, d, J=9.0 Hz), 11.11 (1H, s); NMR (31) (CDCl$_3$) δppm: 2.34 (3H, s), 3.81 (3H, s), 3.82 (3H, s), 3.89 (3H, s), 4.70 (2H, s), 6.51 (1H, d, J=8.8 Hz), 7.71 (1H, d, J=8.8 Hz); NMR (32) (CDCl$_3$) δppm: 1.18 (3H, t, J=7.5 Hz), 2.76 (2H, q, J=7.5 Hz), 3.80 (3H, s), 3.84 (3H, s), 3.89 (3H, s), 4.71 (2H, s), 6.51 (1H, d, J=8.8 Hz), 7.73 (1H, d, J=8.8 Hz); NMR (33) (DMSO-d$_6$) δppm: 2.10 (3H, s), 3.70 (3H, s), 3.78 (3H, s), 4.78 (2H, s), 6.72 (1H, d, J=8.9 Hz), 7.59 (1H, d, J=8.9 Hz), 13.11 (1H, brs); NMR (34) (DMSO-d$_6$) δppm: 1.08 (3H, t, J=7.4 Hz), 2.62 (2H, q, J=7.4 Hz), 3.72 (3H, s), 3.78 (3H, s), 4.79 (2H, s), 6.72 (1H, d, J=8.9 Hz), 7.60 (1H, d, J=8.9 Hz), 13.09 (1H, brs); NMR (35) (CDCl$_3$) δppm: 2.31 (3H, s), 3.85 (3H, s), 3.90 (3H, s), 4.82 (2s), 6.65 (1H, d, J=8.8 Hz), 7.34 (1H, dt, J=1.2 Hz, J=7.6 Hz), 7.46 (1H, dt, J=1.2 Hz, J=7.6 Hz), 7.69–7.89 (3H, m), 9.79 (1H, brs); NMR (36) (CDCl$_3$) δppm: 1.27 (3H, t, J=7.6 Hz), 2.83 (2H, q, J=7.6 Hz), 3.87 (3H, s), 3.91 (3H, s), 4.83 (2H, s), 6.66 (1H, d, J=8.8 Hz), 7.30 (1H, dt, J=1.3 Hz, J=7.3 Hz), 7.46 (1H, dt, J=1.3 Hz, J=7.3 Hz), 7.70–7.90 (3H, m), 9.72 (1H, brs); NMR (37) (CDCl$_3$) δppm: 2.33 (3H, s), 3.77 (6H, d, J=11.1 Hz), 3.80 (3H, s), 3.81 (2H, d, J=22.0 Hz), 4.82 (2H, s), 6.69 (1H, d, J=8.8 Hz), 7.35 (1H, dt, J=1.3 Hz, J=7.9 Hz), 7.47 (1H, dt, J=1.3 Hz, J=7.9 Hz), 7.61 (1H, d, J=8.8 Hz), 7.82 (2H, t, J=7.9 Hz), 9.87 (1H, brs); NMR (38) (CDCl$_3$) δppm: 1.29 (3H, t, J=7.5 Hz), 2.83 (2H, q, J=7.5 Hz), 3.76 (6H, d, J=11.2 Hz), 3.80 (2H, d, J=22.1 Hz), 3.81 (3H, s), 4.83 (2H, s), 6.70 (1H, d, J=8.8 Hz), 7.38 (1H, dt, J=1.4 Hz, J=8.6 Hz), 7.47 (1H, dt, J=1.4 Hz, 8.6 Hz), 7.59 (1H, d, J=8.8 Hz), 7.83 (2H, t, J=8.6 Hz), 9.73 (1H, brs); NMR (39) (CDCl$_3$) δppm: 2.24 (3H, s), 3.85 (3H, s), 4.75 (2H, s), 6.51 (1H, d, J=8.3 Hz), 6.63 (1H, d, J=8.3 Hz), 7.14 (1H, t, J=8.3 Hz), 7.29–7.40 (1H, m), 7.40–7.52 (1H, m), 7.74–7.91 (2H, m); NMR (40) (CDCl$_3$) δppm: 1.30 (3H, t, J=7 Hz), 3.91 (3H, s), 4.27 (2H, q, J=7 Hz), 4.63 (2H, s), 6.41 (1H, d, J=2.5 Hz), 6.48 (1H, dd, J=2.5 Hz, J=9 Hz), 7.75 (1H, d, J=9 Hz), 10.96 (1H, s); NMR (41) (CDCl$_3$) δppm: 1.30 (3H, t, J=7 Hz), 3.86 (3H, s), 3.89 (3H, s), 4.28 (2H, q, J=7 Hz), 6.43 (1H, dd, J=2.5 Hz, J=8.5 Hz), 6.58 (1H, d, J=2.5 Hz), 7.84 (1H, d, J=8.5 Hz); NMR (42) (CDCl$_3$) δppm: 1.69 (3H, d, J=7 Hz), 3.80 (3H, s), 4.95 (1H, q, J=7 Hz), 6.45–6.7 (3H, m), 7.15–7.5 (3H, m), 7.7–7.9 (2H, m), 9.77 (1H, br); NMR (43) (CDCl$_3$) δppm: 3.38 (2H, d, J=6.5 Hz), 3.84 (3H, s), 3.86 (3H, s), 4.74 (2H, s), 4.95–5.15 (2H, m), 5.85–6.1 (1H, m), 6.34 (1H, s), 7.69 (1H, s), 9.28 (1H, br); NMR (44) (CDCl$_3$) δppm: 3.80 (3H, s), 3.84 (3H, s), 3.88 (3H, s), 4.73 (2H, s), 5.98 (2H, br), 6.12 (1H, d, J=9 Hz), 7.59 (1H, d, J=9.1 Hz); NMR (45) (CDCl$_3$) δppm: 2.88 (6H, s), 3.80 (3H, s), 3.83 (3H, s), 3.87 (3H, s), 4.71 (2H, s), 6.48 (1H, d, J=8.7 Hz), 7.29 (1H, d, J=8.7 Hz); NMR (46) (CDCl$_3$) δppm: 2.91 (6H, s), 3.88 (3H, s), 3.89 (3H, s), 4.80 (2H, s), 6.64 (1H, d, J=8.7 Hz), 7.30–7.38 (2H, m), 7.42–7.51 (1H, m), 7.80–7.89 (2H, m), 10.24 (1H, br); NMR (47) (CDCl$_3$) δppm: 2.90 (6H, s), 3.69 (3H, s), 3.74 (2H, d, J=21.7 Hz), 3.75 (3H, s), 3.90 (3H, s), 4.83 (2H, s), 6.74 (1H, d, J=8.6 Hz), 7.26 (1H, d, J=8.6 Hz), 7.34 (1H, t, J=9.1 Hz), 7.43 (1H, t, J=9.1 Hz), 7.80–7.90 (2H, m), 10.10 (1H, br); NMR (48) (CDCl$_3$) δppm: 3.86 (3H, s), 3.89 (3H, s), 4.65 (2H, s), 4.97 (1H, d, J=5.9 Hz), 6.49–6.55 (2H, m), 7.34–7.54 (3H, m), 7.84–7.89 (1H, m), 7.98 (1H, d, J=7.3 Hz); NMR (49) (CDCl$_3$) δppm: 3.72 (3H, s), 3.78 (3H, s), 3.79 (2H, d, J=21.7 Hz), 3.92 (3H, s), 4.66 (2H, s), 4.97 (2H, d, J=5.9 Hz), 6.53–6.61 (1H, m), 7.39–7.54 (3H, m), 7.82–7.90 (2H, m), 7.98 (1H, d, J=7.6 Hz); NMR (50) (DMSO-d$_6$) δppm: 1.13 (6H, d, J=7.0 Hz), 3.08–3.35 (1H, m), 3.69 (3H, s), 4.66 (2H, s), 6.38 (1H, d, J=2.4 Hz), 6.48 (1H, d, J=2.4 Hz, J=8.4 Hz), 7.07 (1H, d, J=8.4 Hz), 12.93 (1H, s); NMR (51) (DMSO-d$_6$) δppm: 0.69–1.00 (3H, m), 1.08–1.62 (8H, m), 2.32–2.63 (2H, m), 3.68 (3H, s), 4.65 (2H, s), 6.30–6.53 (2H, m), 7.00 (1H, d, J=8.2 Hz), 12.92

(1H, s); NMR (52) (CDCl$_3$) δppm: 2.31 (3H, s), 3.78 (3H, s), 4.74 (2H, s), 6.42 (1H, d, J=2.4 Hz), 6.52 (1H, dd, J=2.4 Hz, J=8.8 Hz), 7.12 (1H, d, J=8.8 Hz), 7.25–7.53 (2H, m), 7.72–7.94 (2H, m), 9.71 (1H, s); NMR (53) (CDCl$_3$) δppm: 1.30 (6H, d, J=6.9 Hz), 3.19–3.46 (1H, m), 3.79 (3H, s), 4.75 (2H, s), 6.44 (1H, d, J=2.4 Hz), 6.60 (1H, dd, J=2.4 Hz, J=8.5 Hz), 7.20 (1H, d, J=8.5 Hz), 7.24–7.53 (2H, m), 7.72–7.94 (2H, m), 9.51–9.82 (1H, brs); NMR (54) (CDCl$_3$) δppm: 0.78–0.99 (3H, m), 1.18–1.77 (8H, m), 2.67 (2H, t, J=7.9 Hz), 3.78 (3H, s), 4.74 (2H, s), 6.43 (1H, d, J=2.4 Hz), 6.55 (1H, dd, J=2.4 Hz, J=8.3 Hz), 7.12 (1H, d, J=8.3 Hz), 7.23–7.52 (2H, m), 7.75–7.92 (2H, m), 9.56–9.80 (1H, brs); NMR (55) (DMSO-d$_6$) δppm: 2.09 (3H, s), 3.68 (3H, s), 4.66 (2H, s), 6.32–6.52 (2H, m), 7.02 (1H, d, J=8.1 Hz), 12.95 (1H, s); NMR (56) (CDCl$_3$) δppm: 3.82 (3H, s), 3.93 (3H, s), 4.73 (2H, s), 6.34 (1H, s), 8.02 (1H, s), 10.93 (1H, s); NMR (57) (CDCl$_3$) δppm: 3.82, 3.86, 3.88 (each 3H, each s), 4.77 (2H, s), 6.40 (1H, s), 8.07 (1H, d, J=3.1 Hz); NMR (58) (DMSO-d$_6$) δppm: 3.74, 3.82 (each 3H, each s), 4.97 (2H, s), 6.74 (1H, s), 7.85 (1H, d, J=3.6 Hz), 12.82–13.44 (1H, br); NMR (59) (DMSO-d$_6$) δppm: 3.73, 3.74 (each 3H, each s), 4.63 (2H, s), 6.76 (1H, s), 7.30 (1H, s), 10.66 (1H, brs); NMR (60) (DMSO-d$_6$) δppm: 3.66 (3H, s), 3.70 (3H, s), 4.64, 4.73 (total 1H, each s), 6.34–6.52 (2H, m), 6.79–6.96 (1H, m), 12.88–13.03 (1H, m); NMR (61) (CDCl$_3$) δppm: 3.77 (3H, s), 3.97 (3H, s), 4.78 (2H, s), 6.51–6.72 (2H, m), 6.89 (1H, d, J=8.8 Hz), 7.21–7.56 (2H, m), 7.73–7.92 (2H, m); NMR (62) DMSO-d$_6$) δppm: 1.27 (3H, t, J=7.0 Hz), 3.65 (3H, s), 3.92 (2H, q, J=7.0 Hz), 4.65 (2H, s), 6.32–6.52 (2H, m), 6.78–6.93 (1H, m), 12.81–13.01 (1H, brs); NMR (63) (CDCl$_3$) δppm: 2.84 (6H, s), 3.89 (3H, s), 4.81 (2H, s), 5.23 (2H, s), 6.70 (1H, d, J=9.0 Hz), 7.26–7.40 (5H, m), 7.60–7.64 (2H, m); NMR (64) (CDCl$_3$) δppm: 2.91 (6H, s), 3.93 (3H, s), 4.73 (2H, s), 7.14 (1H, d, J=7.8 Hz), 7.90–7.94 (2H, m), 9.72 (1H, br); NMR (65) (CDCl$_3$) δppm: 3.03 (6H, s), 3.91 (3H, s), 4.92 (2H, s), 7.12 (1H, d, J=8.3 Hz), 7.29 (1H, dt, J=1.2 Hz, J=7.8 Hz), 7.43 (1H, dt, J=1.2 Hz, J=7.8 Hz), 7.78–7.86 (4H, m), 13.22 (1H, br); NMR (66) (CDCl$_3$) δppm: 3.03 (6H, s), 3.61 (2H, d, J=22.7 Hz), 3.77 (3H, s), 3.81 (3H, s), 4.94 (2H, s), 7.15 (1H, d, J=8.4 Hz), 7.30 (1H, t, J=7.8 Hz), 7.43 (1H, t, J=7.8 Hz), 7.76–7.86 (4H, m); NMR (67) (CDCl$_3$) δppm: 3.96 (3H, s), 4.03 (3H, s), 4.55 (1H, brd, J=27.4 Hz), 4.76 (2H, s), 6.71 (1H, d, J=8.7 Hz), 7.25–7.38 (1H, m), 7.39–7.88 (19H, m), 10.50 (1H, brs); NMR (68) (CDCl$_3$) δppm: 2.10–2.30 (2H, m), 3.58 (2H, t, J=6.6 Hz), 4.04–4.19 (2H, m), 4.38–4.72 (1H, m), 4.65 (2H, s), 6.39 (1H, dd, J=2.3 Hz, J=8.6 Hz), 6.52 (1H, d, J=2.3 Hz), 7.28–7.95 (20H, m), 10.58 (1H, brs); NMR (69) (CDCl$_3$) δppm: 1.82–2.11 (2H, m), 2.11–2.38 (4H, m), 2.3–2.62 (2H, m), 3.49–3.75 (4H, m), 4.04 (2H, t, J=5.9 Hz), 4.50–4.93 (1H, m), 4.68 (2H, s), 6.40 (1H, dd, J=2.2 Hz, J=8.6 Hz), 6.54 (1H, d, J=2.2 Hz), 7.23–7.37 (1H, m), 7.37–7.62 (10H, m), 7.62–7.96 (9H, m), 10.37 (1H, brs); NMR (70) (CDCl$_3$) δppm: 3.00 (6H, s), 3.89 (3H, s), 4.70 (2H, s), 6.49 (1H, dd, J=2.5 Hz, J=8.5 Hz), 6.57 (1H, d, J=2.5 Hz), 6.93 (1H, dd, J=2.5 Hz, J=9 Hz), 7.08 (1H, d, J=2.5 Hz), 7.20–8.05 (16H, m), 8.55–8.65 (1H, m), 9.90 (1H, br); NMR (71) (CDCl$_3$) δppm: 1.21–1.56 (2H, m), 1.67 (1H, br), 1.75–1.94 (2H, m), 2.01 (1H, t, J=10.6 Hz), 2.01–2.89 (14H, m), 3.02–3.28 (2H, m), 3.55–3.78 (2H, m), 3.85–4.02 (1H, m); NMR (72) (CDCl$_3$) δppm: 1.83 (1H, br), 2.15 (1H, dd, J=4.1 Hz, J=12.8 Hz), 2.26 (6H, s), 2.43 (1H, dd, J=7.8 Hz, J=12.8 Hz), 2.53 (1H, dd, J=10.2 Hz, J=12.1 Hz), 2.68–2.98 (3H, m), 3.50–3.72 (2H, m), 3.78–3.99 (1H, m); NMR (73) (CDCl$_3$) δppm: 2.78 (2H, t, J=7.5 Hz), 3.09 (2H, t, J=7.5 Hz), 3.90 (3H, s), 7.15 (2H, d, J=8.5 Hz), 7.25–7.45 (2H, m), 7.68 (1H, d, J=7.5 Hz), 7.8–7.95 (1H, m), 7.90 (2H, d, J=8.5 Hz); NMR (74) (CDCl$_3$) δppm: 2.77 (2H, t, J=7.5 Hz), 3.06 (2H, t, J=7.5 Hz), 3.66 (2H, d, J=22.6 Hz), 3.75 (3H, s), 3.81 (3H, s), 7.10–7.22 (2H, m), 7.26–7.49 (2H, m), 7.63–7.68 (1H, m), 7.81–7.90 (3H, m); NMR (75) (CDCl$_3$) δppm: 2.79 (2H, t, J=7.5 Hz), 3.06 (2H, t, J=7.5 Hz), 3.76 (3H, s), 3.86 (3H, s), 6.65 (1H, d, J=8 Hz), 6.72 (1H, s), 7.25–7.5 (2H, m), 7.6–7.75 (2H, m), 7.85 (1H, d, J=7.5 Hz), 11.40 (1H, br); NMR (76) (CDCl$_3$) δppm: 2.80 (2H, t, J=7.5 Hz), 3.05 (2H, t, J=7.5 Hz), 3.73 (3H, s), 3.78 (3H, s), 3.79 (3H, s), 3.82 (2H, d, J=21.5 Hz), 6.65–6.8 (2H, m), 7.25–7.45 (2H, m), 7.60 (1H, d, J=8.5 Hz), 7.64 (1H, d, J=7.5 Hz), 7.82 (1H, dd, J=1 Hz, J=7.5 Hz), 11.49 (1H, br); NMR (77) (CDCl$_3$) δppm: 3.62 (2H, d, J=22.5 Hz), 3.77, 3.82 (6H, each s), 4.04 (3H, s), 4.85 (2H, s), 7.02 (1H, d, J=8.5 Hz), 7.3–7.55 (2H, m), 7.6–7.7 (2H, m), 7.8–7.9 (2H, m), 10.31 (1H, br).

Example 1

A solution of 2-(2-isopropylphenoxymethylcarbonylamino)benzothiazole (6.5 g), anhydrous maleic acid (3.9 g) and aluminum chloride (8.0 g) in 1,2-dichloroethane (50 ml) is stirred at room temperature for 7 hours. To the mixture is added water in order to decompose the aluminum chloride, and thereto is added ethyl acetate, and the mixture is stirred. The precipitated crystals are collected by filtration, washed with ethyl acetate, and dried to give a mixture (7.3 g) of a trans-compound and a cis-compound. The mixture thus obtained is dissolved in dimethylformamide (50 ml), and thereto is added conc. hydrochloric acid (1 ml), and the mixture is stirred at 60° C. for 30 minutes. To the mixture is added water (about 100 ml), and the precipitated crystals are collected by filtration, washed with methanol, and dried to give 2-[2-isopropyl-4-(trans-3-carboxyacryloyl)phenoxymethylcarbonylamino]benzothiazole (6.2 g).

$^1$H-NMR (DMSO-d$_6$) δppm: 1.25 (6H, d, J=7 Hz), 3.40 (1H, sept, J=7 Hz), 5.12 (2H, s), 6.64 (1H, d, J=15.5 Hz), 7.03 (1H, d, J=8.5 Hz), 7.25–7.5 (2H, m), 7.77 (1H, d, J=7.5 Hz), 7.85–8.05 (4H, m), 12.70 (1H, br), 13.10 (1H, br).

Example 2

To a solution of 2-[2-isopropyl-4-(3-carboxyacryloyl)phenoxymethylcarbonylamino]benzothiazole (1.0 g) and triethylamine (0.4 ml) in dichloromethane (20 ml) is added dropwise isobutyl chloroformate (0.32 ml) under ice-cooling. To the mixture is added N-methylpiperazine (0.27 ml) at the same temperature, and the mixture is stirred for 2.5 hours. The reaction solution is washed with water, dried and concentrated under reduced pressure. The residue is purified by silica gel column chromatography (solvent; dichloromethane→dichloromethane:methanol=30:1), and recrystallized from ethanol to give 2-{2-isopropyl-4-[3-(4-methyl-1-piperazinylcarbonyl)acryloyl]phenoxymethylcarbonylamino}benzothiazole (0.80 g).

Pale brown powder; M.p. 190–192° C.

Example 3

A solution of 2-[4-(3-carboxyacryloyl)phenoxymethylcarbonyamino]benzothiazole (1.0 g), thionyl chloride (0.23 ml) and a drop of dimethylformamide (20 ml) in dichloromethane (20 ml) is stirred at room temperature for 10 hours. The solution is added dropwise into a solution of 4-(4-methyl-1-piperazinyl)piperidine (0.5 g) and pyridine (1 ml) in dichloromethane (20 ml) under ice-cooling. To the reaction solution is added water, and the mixture is basified with 5% aqueous sodium hydroxide solution. The mixture is extracted with dichloromethane, and the extract is washed, dried, and concentrated under reduced pressure. The residue is purified by silica gel column chromatography (solvent; dichloromethane:methanol=50:1→10:1). The compound thus obtained is converted into a hydrochloride thereof by a conventional method and crystallized from ethanol-diethyl ether to give 2-[4-{3-[4-(4-methyl-1-piperazinyl)-1-piperidinylcarbonyl)acryloyl}phenoxymethylcarbonylamino]benzothiazole dihydrochloride (0.14 g).

White powder; M.p. 202.5–225° C. (decomposed); $^1$H-NMR (DMSO-d$_6$) δppm: 1.35–1.8 (2H, m), 2.0–2.3 (2H, m), 2.6–3.9 (11H, m), 2.81 (3H, s), 4.1–4.3 (1H, m), 4.5–4.7 (1H, m), 5.08 (2H, s), 7.15 (2H, d, J=9 Hz), 7.3–7.55 (3H, m), 7.76 (1H, d, J=14 Hz), 7.77 (1H, d, J=8.5 Hz), 7.98 (1H, d, J=8 Hz), 8.05 (2H, d, J=9 Hz), 12.67 (1H, br).

Example 4

To a solution of 2-[2-isopropyl-4-(3-carboxyacryloyl)phenoxymethylcarbonylamino]benzothiazole (0.97 g) in dimethylformamide (10 ml) are added dropwise 4-(4-methyl-1-piperazinyl)piperidine (0.65 g) and diethyl cyanophosphate (0.6 ml) at room temperature. To the mixture is added triethylamine (0.5 ml), and the mixture is stirred at room temperature for 10 minutes. To the mixture is added water, and the mixture is extracted with ethyl acetate. The extract is washed with water, dried, and concentrated under reduced pressure. The residue is purified by silica gel column chromatography (solvent; dichloromethane:methanol=100:1→10:1). The compound thus obtained is converted into a hydrochloride thereof in ethanol by a conventional method, and recrystallized from ethanol-diethyl ether to give 2-{2-isopropyl-4-[3-[4-(4-methyl-1-piperazinyl)-1-piperidinylcarbonyl]acryloyl]phenoxymethylcarbonylamino}benzothiazole dihydrochloride (0.45 g).

Yellow powder; M.p. 186–190° C. (decomposed).

Example 5

To a solution of dibutyl tartrate (4.0 g) in methanol (100 ml) is added a solution of sodium periodate (3.0 g) in water (30 ml), and the mixture is stirred for 10 minutes, and extracted with ethyl acetate. Separately, to a suspension of dimethyl {[3-methoxy-4-(2-benzothiazolylaminocarbonylmethoxy)benzoyl]methyl}phosphonate (5.7 g) in tetrahydrofuran (100 ml) is added a 5% aqueous sodium hydroxide solution under ice-cooling until the reaction solution becomes uniform, and then thereto is added dropwise a solution of glyoxalate, which is previously prepared from dibutyl tartrate, in tetrahydrofuran (30 ml) under ice-cooling. The mixture is stirred for 30 minutes, and acidified with 5% hydrochloric acid, and concentrated under reduced pressure to remove the tetrahydrofuran. The precipitated crystals are collected by filtration, and washed with dichloromethane. The dichloromethane layer is concentrated under reduced pressure, and the residue is purified by silica gel column chromatography (solvent; dichloromethane:methanol=200:1) to give 2-[2-methoxy-4-(3-butoxycarbonylacryloyl)phenoxymethylcarbonylamino]benzothiazole (2.85 g), which is further stirred in tetrahydrofuran-5% aqueous sodium hydroxide solution at room temperature for 30 minutes to give 2-[2-methoxy-4-(3-carboxyacryloyl)phenoxymethylcarbonylamino]benzothiazole (2.9 g).

$^1$H-NMR (DMSO-d$_6$) δppm: 3.89 (3H, s), 5.09 (2H, s), 6.67 (1H, d, J=15.5 Hz), 7.08 (1H, d, J=8.5 Hz), 7.25–7.55 (2H, m), 7.57 (1H, m), 7.7–8.1 (4H, m), 11.68 (1H, br).

Example 6

To a solution of ethyl propiolate (17.7 ml) in tetrahydrofuran (450 ml) is added dropwise a 1.71M solution of n-butyl lithium in n-hexane (102 ml) at −78° C., and the mixture is stirred for 10 minutes. To the solution is added dropwise a solution of 2-(2-methoxy-4-formylphenoxymethylcarbonylamino)benzothiazole (20 g) in tetrahydrofuran (400 ml) and N,N-dimethylpropylene urea (40 ml) at the same temperature over a period of 15 minutes. The mixture is further stirred for 10 minutes, and the reaction vessel is taken out from an iced bath, and further stirred for 20 minutes. To the mixture is added acetic acid (11 ml), and the mixture is diluted with ethyl acetate. The ethyl acetate layer is washed with a saturated aqueous sodium carbonate solution, dried over sodium sulfate, and concentrated. The residue is purified by silica gel column chromatography (solvent; dichloromethane:methanol=100:1→50:1) to give 2-[2-methoxy-4-(3-methoxycarbonyl-1-hydroxypropargyl)phenoxymethylcarbonylamino]benzothiazole (33.7 g) as a dark brown oil.

To a solution of 2-[2-methoxy-4-(3-methoxycarbonyl-1-hydroxypropargyl)phenoxymethylcarbonylamino]benzothiazole (33.7 g) in dimethylformamide (150 ml) is added tri-n-butylamine (14.3 ml), and the mixture is stirred at room temperature for 1.5 hour. The mixture is diluted with ethyl acetate, and washed with 0.15N hydrochloric acid, and dried over sodium sulfate. The mixture is concentrated under reduced pressure to remove the solvent, and the precipitated crystals are collected by filtration to give 2-[2-methoxy-4-(trans-3-methoxycarbonylacryloyl)phenoxymethylcarbonylamino]benzothiazole (Compound A, 5.5 g) as pale yellow powder. On the other hand, the filtrate is concentrated under reduced pressure, and crystallized from ethanol-diethyl ether give 2-[2-methoxy-4-(cis-3-methoxycarbonylacryloyl)phenoxymethylcarbonylamino]benzothiazole (Compound B, 6.0 g) as pale yellow powder.

Compound A:
$^1$H-NMR (DMSO-d$_6$) δppm: 1.26 (3H, t, J=7.1 Hz), 3.92 (3H, s), 4.21 (2H, q, J=7.1 Hz), 5.11 (2H, s), 6.71 (1H, d, J=15.5 Hz), 7.08 (1H, d, J=8.6 Hz), 7.31–7.37 (1H, m), 7.44–7.50 (1H, m), 7.59 (1H, d, J=2.0 Hz), 7.75–7.81 (2H, m), 7.98 (1H, d, J=15.5 Hz), 8.00–8.02 (1H, m), 12.67 (1H, brs).

Compound B:
$^1$H-NMR (DMSO-d$_6$) δppm: 1.05 (3H, t, J=7.1 Hz), 3.89 (3H, s), 3.97 (2H, q, J=7.1 Hz), 5.11 (2H, s), 6.35 (1H, d, J=12.3 Hz), 7.05 (1H, d, J=8.8 Hz), 7.21 (1H, d, J=12.3 Hz), 7.31–7.37 (1H, m), 7.44–7.50 (3H, m), 7.78–7.81 (1H, m), 7.99–8.02 (1H, m), 12.62 (1H, brs).

Example 7

A solution of 2-{2-isopropyl-4-[trans-3-(4-methyl-1-piperazinyl)carbonylacryloyl]phenoxymethylcarbonylamino}benzothiazole (100 mg) in dimethylformamide (10 ml) is allowed to stand for 6.5 hours by a window in order to be exposed to direct sunlight. To the mixture is added water, the precipitated crystals are collected by filtration, and recrystallized from ethanol to give 2-{2-isopropyl-4-[cis-3-(4-methyl-1-piperazinyl)carbonylacryloyl]phenoxymethylcarbonylamino}benzothiazole (45 mg).

Pale yellow powder; M.p. 114–115° C.

Example 8

To a solution of dimethyl {[3-methoxy-4-(2-benzothiazolylaminocarbonylmethoxy)benzoyl]methyl}phosphonate (1.7 g) and pyridine-4-aldehyde (0.5 g) in tetrahydrofuran (30 ml) is added a 5% aqueous sodium hydroxide solution (6 ml) under ice-cooling, and the mixture is stirred for 5 hours. The mixture is neutralized with acetic acid, and the precipitated crystals are collected by filtration, and then recrystallized from dichloromethane-ethanol-diethyl ether to give 2-{2-methoxy-4-[3-(4-pyridyl)acryloyl]phenoxymethylcarbonylamino}benzothiazole (1.3 g).

Pale yellow powder; M.p. 206–207° C.

Example 9

To a solution of 2-[2-methoxy-4-(3-t-butoxycarbonyl-1-hydoxypropargyl)phenoxymethylcarbonylamino]benzothiazole (1 g) in chloroform (50 ml) is added active manganese dioxide (1 g), and the mixture is refluxed for two hours. To the mixture is further added active manganese dioxide (1 g), and the mixture is refluxed for 1.5 hour. The mixture is filtered through a cerite pad, and the filtrate is concentrated. The residue is recrystallized from ethanol to give 2-[2-methoxy-4-(3-t-butoxycarbonylpropiolyl)phenoxymethylcarbonylamino]benzothiazole (0.5 g).

Example 10

To a solution of 2-[2-methoxy-4-(3-t-butoxycarbonylpropioloyl)phenoxymethylcarbonylamino]benzothiazole (0.5 g) in methylene chloride (30 ml) is added trifluoroacetic acid (10 ml), and the mixture is stirred at room temperature for 4 hours. The mixture is concentrated, and to the residue is added methylene chloride. The mixture is stirred, and the precipitated crystals are collected by filtration, and recrystallized from dichloromethane-trifluoroacetic acid to give 2-[2-methoxy-4-(3-carboxypropioloyl)phenoxymethylcarbonylamino]-benzothiazole (0.26 g) as brown powder.

M.p. 174–176° C.

Using the suitable starting compounds, the following compounds are obtained in the same manner as in Example 1 or 5.

TABLE 38

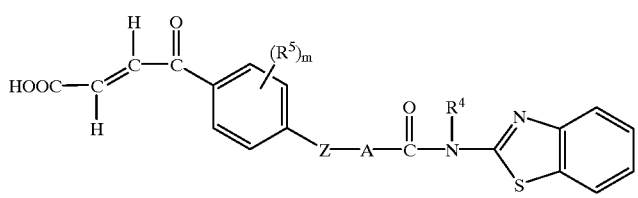

Example 11

R⁴: H        A: —CH₂—        Z: O
R⁵: CH₃ (2-position)              m: 1
M.p. 261–262°0 C.        Crystalline form: Beige powder
Solvent for recrystallization: Dimethylformamide-methanol
Form: Free Example 12

R⁴: H        A: —CH₂—        Z: O
R⁵: C₂H₅ (2-position)              m: 1
M.p. 245–246°C.        Crystalline form: Beige powder
Solvent for recrystallization: Dimethylformamide-methanol
Form: Free Example 13

R⁴: H        A: —CH₂—        Z: O
R⁵: n-Propyl (2-position)              m: 1
Crystalline form: Yellow powder        Form: Free
NMR(1)

TABLE 39

Example 14

R⁴: H
A: —CH₂—
Z: O
R⁵: Isopropyl (2-position)
m: 1
M.p. 225–240° C. (decomp.)
Crystalline form: Yellow powder
NMR (2)
Solvent for recrystallization: Dimethylformamide-methanol
Form: Free Example 15

R⁴: H
A: —CH₂—
Z: O
R⁵: n-Butyl (2-position)
m: 1
M.p. 187.5–190° C.
Crystalline form: Pale yellow powder
Solvent for recrystallization: Chloroform-dimethylformamide
Form: Free Example 16

R⁴: H
A: —CH₂—
Z: O
R⁵: H
m: 1
M.p. 250–275° C. (decomp.)
Crystalline form: White powder
NMR (3)
Solvent for recrystallization: Dimethylformamide-methanol
Form: Free Example 17

R⁴: H
A: —CH₂—

TABLE 39-continued

Z: O
$R^5$: n-Pentyl (2-position)
m: 1
M.p. 139–163° C.
Crystalline form: Pale yellow powder
NMR (4)
Solvent for recrystallization: Dimethylformamide-dichloromethane
Form: Free

TABLE 40

Example 18

$R^4$: H
A: —$CH_2$—
Z: O
$R^5$: F (2-position)
m: 1
M.p. 233–234° C.
Crystalline form: Pale brown powder
Solvent for recrystallization: Dimethylformamide-methanol
Form: Free
Example 19

$R^4$: H
A: —$CH_2$—
Z: O
$R^5$: Cl (2-position)
m: 1
Crystalline form: Yellow powder
Form: Free
NMR (5)
Example 20

$R^4$: H
A: —$CH_2$—
Z: O
$R^5$: —$(CH_2)_4$ (combined at 2- and 3-positions)
m: 2
Crystalline form: Yellow powder
NMR (6)
Form: Free
Example 21

$R^4$: H
A: —$CH_2$—
Z: O
$R^5$: $CH_3$ (2- and 3-positions)
m: 2
Crystalline form: Yellow powder
NMR (7)
Form: Free

TABLE 41

Example 22

$R^4$: H
A: —$CH_2$—
Z: O
$R^5$: $CH_3$ (2- and 6-positions)
m: 2
Crystalline form: Beige powder
NMR (8)
Solvent for recrystallization: Dimethylformamide-methanol
Form: Free
Example 23

$R^4$: H
A: —$CH_2$—
Z: O
$R^5$: $CH_3$ (3- and 5-positions)
m: 2
Crystalline form: Yellow powder

TABLE 41-continued

Form: Free
NMR (9)
Example 24

$R^4$: H
A: —$CH_2$—
Z: O
$R^5$: —$(CH_2)_2CO_2C_2H_5$ (2-position)
m: 1
M.p. 199.6–203.8° C.
Crystalline form: Pale yellow powder
Solvent for recrystallization: Chloroform-dimethylformamide
Form: Free
Example 25

$R^4$: H
A: —$CH_2$—
Z: O
$R^5$: —$(CH_2)_4OCOCH_3$ (2-position)
m: 1
M.p. 176–177.5° C.
Crystalline form: Pale yellow powder
Solvent for recrystallization: Chloroform
Form: Free

TABLE 42

Example 26

$R^4$: H
A: —$CH_2$—
Z: O
$R^5$: $C_2H_5O$ (2-position)
m: 1
Crystalline form: Yellow powder
NMR (10)
Form: Free
Example 27

$R^4$: H
A: —$CH_2$—
Z: O
$R^5$: $CH_3$ (3-position)
m: 1
M.p. 290° C. (decomp.)
Crystalline form: White needles
NMR (11)
Solvent for recrystallization: Dimethylformamide
Form: Free
Example 28

$R^4$: H
A: —$CH_2$—
Z: O
$R^5$: $C_2H_5$ (3-position)
m: 1
Crystalline form: Yellow powder
NMR (12)
Form: Free
Example 29

$R^4$: H
A: —$CH_2$—
Z: O
$R^5$: n-Propyl (3-position)
m: 1
M.p. 282° C. (decomp.)
Crystalline form: Pale brown needles
Solvent for recrystallization: Dimethylformamide-dichloromethane
Form: Free

TABLE 43

Example 31

$R^4$: H
A: —$CH_2$—
Z: O
$R^5$: n-Butyl (3-position)
m: 1
M.p. 267–279° C. (decomp.)
Crystalline form: Pink powder
Form: Free
NMR (14)

Example 32

$R^4$: H
A: —$CH_2$—
Z: O
$R^5$: Isopropyl (3-position)
m: 1
M.p. 262.5–265.5° C.
Crystalline form: Yellow powder
Solvent for recrystallization: Dimethylformamide-dichloromethane
Form: Free Example 33

$R^4$: H
A: —$CH_2$—
Z: O
$R^5$: Cl (3-position)
m: 1
Crystalline form: Pale yellow powder
NMR (15)
Form: Free

TABLE 44

Example 34

$R^4$: H  A: —$CH_2$—  Z: O
$R^5$: F (3-position)  m: 1
Crystalline form: Pale yellow powder  NMR (16)
Form: Free Example 35

$R^4$: H  A: —$CH_2$—  Z: O
$R^5$: $CH_3O$ (3-position)  m: 1
Crystalline form: Yellow powder  NMR (17)
Form: Free Example 36

$R^4$: H  A: —$CH_2$—  Z: O
$R^5$: $C_2H_5O$ (3-position)  m: 1
Crystalline form: Yellow powder  NMR (18)
Form: Free Example 37

$R^4$: H  m: 1  Z: O $R^5$ and A combine to form:

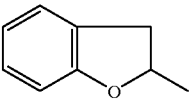

M.p. 294–295° C. (decomp.)  Crystalline form: White powder
Solvent for recrystallization: Dimethylformamide  Form: Free

TABLE 45

Example 38

$R^4$: H
A: —$CH_2$—
Z: O
$R^5$: $CH_3O$ (2-position)

TABLE 45-continued m: 1
Crystalline form: Yellow powder
NMR (19)
Form: Free

Example 39

$R^4$: H
A: —$CH_2$—
Z: O
$R^5$: $(CH_3)_2CHO$— (3-position)
m: 1
Crystaliine form: Pale yellow powder
NMR (20)
Form: Free Example 40

$R^4$: H
A: —$CH_2$—
Z: O
$R^5$: $CF_3CH_2O$— (3-position)
m: 1
Crystalline form: Pale yellow powder
NMR (21)
Form: Free Example 41

$R^4$: H
A: —$CH_2$—
Z: O
$R^5$: $CF_3$ (2-position)
m: 1
Crystalline form: Colorless powder
NMR (22)
Form: Free

TABLE 46

Example 42

$R^4$: H
A: —$CH_2$—
Z: O
$R^5$: —$OCH_2CON(C_2H_5)_2$ (2-position)
m: 1
Crystalline form: Yellow powder
NMR (23)
Form: Free Example 43

$R^4$: H
A: —$CH_2$—
Z: O
$R^55$; —$COOCH_3$ (2-position)
m: 1
Crystalline form: Pale yellow powder
NMR (24)
Form: Free Example 44

$R^4$: H
A: —$CH_2$—
Z: O
$R^5$: —$(CH_2)_2$—CONH— (combined at 2- and 3-positions)
m: 2
Crystalline form: Yellow powder
NMR (25)
Form: Free Example 45

$R^4$: H
A: —$CH_2$—
Z: O
$R^5$: $(CH_3)_3C$— (2-position)
m: 1
M.p. 263–266° C. (decomp.)
Crystalline form: Yellow powder

TABLE 46-continued

Solvent for recrystallization: Dimethylformamide-dichloromethane
Form: Free

TABLE 47

Example 46

$R^4$: H
A: —$CH_2$—
Z: O
$R^5$: —$(CH_2)_2COOCH_3$ (2-position)
m: 1
Crystalline form: Yellow powder
NMR (26)
Form: Free
Example 47

$R^4$: H
A: —$CH_2$—
Z: O
$R^5$: —$(CH_2)_2CON(CH_3)_2$ (2-position)
m: 1
Crystalline form: Pale yellow powder
NMR (27)
Form: Free
Example 48

$R^4$: H
A: —$CH_2$—
Z: O
$R^5$: —$(CH_2)_2CON(C_2H_5)_2$ (2-position)
m: 1
Crystalline form: Yellow amorphous
NMR (28)
Form: Free
Example 49

$R^4$: H
A: —$CH_2$—
Z: O
$R^5$: Cl (2-position)
m: 1
M.p. 235.5–237° C.
Crystalline form: Yellow powder
Solvent for recrystallization: Dimethylformamide-water
Form: Free

TABLE 48

Example 50

$R^4$: H
A: —$CH_2$—
Z: O
$R^5$: —$(CH_2)_2COOC_2H_5$ (2-position)
m: 1
M.p. 199.6–203.8° C.
Crystalline form: Pale yellow powder
Solvent for recrystallization: Chloroform-dimethylformamide
Form: Free
NMR (29)
Example 51

$R^4$: H
A: —$CH_2$—
Z: O
$R^5$: n-Butyl (2-position)
m: 1
M.p. 187.5–190° C.
Crystalline form: Pale yellow powder
Solvent for recrystallization: Chloroform-dimethylformamide
Form: Free

TABLE 48-continued

Example 52

$R^4$: H
A: —$CH_2$—
Z: O
$R^5$: —$(CH_2)_4OCOCH_3$ (2-position)
m: 1
M.p. 176–177.5° C.
Crystalline form: Pale yellow powder
Solvent for recrystallization: Chloroform
Form: Free

TABLE 49

Example 53

$R^4$: H   m: 1   Z: O $R^5$ and A combine to form:

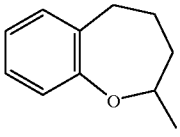

M.p. 285–287° C. (decomp.)   Crystalline form: White powder
Solvent for recrystallization: Dimethylformamide-water
Form: Free
Example 54

$R^4$: H      A: —$CH_2$—      Z: O
$R^5$: n-Heptyl (2-position)          m: 1
M.p. 187–188.5° C.   Crystalline form: Pale yellow powder
Solvent for recrystallization: Dichloromethane-dimethylformamide
Form: Free
Example 55

$R^4$: H      A: —$CH_2$—      Z: S
$R^5$: $CH_3O$ (2-position)          m: 1
M.p. 241–244° C.   Crystalline form: Yellow powder
Form: Free $^1$H-NMR spectrum (NMR (1) to NMR (29)) as described in Tables 38–49 are as follows:

NMR (1) (DMSO-$d_6$) δppm: 0.92 (3H, t, J=7.4 Hz), 1.58–1.69 (2H, m), 2.69 (2H, t, J=7.4 Hz), 5.12 (2H, s), 6.65 (1H, d, J=15.4 Hz), 7.03 (1H, d, J=8.6 Hz), 7.31 (1H, t, J=7.6 Hz), 7.44 (1H, t, J=7.7 Hz), 7.76 (1H, d, J=7.7 Hz), 7.87–7.99 (4H, m); NMR (2) (DMSO-$d_6$) δppm: 1.25 (6H, d, J=7 Hz), 3.40 (1H, sept, J=7 Hz), 5.12 (2H, s), 6.64 (1H, d, J=15.5 Hz), 7.03 (1H, d, J=8.5 Hz), 7.25–7.5 (2H, m), 7.77 (1H, d, J=7.5 Hz), 7.85–8.05 (4H, m), 12.70 (1H, br), 13.10 (1H, br); NMR (3) DMSO-$d_6$) δppm: 5.07 (2H, s), 6.65 (1H, d, J=15.5 Hz), 7.15 (2H, d, J=9 Hz), 7.1–7.5 (2H, m), 7.76 (1H, d, J=7 Hz), 7.89 (1H, d, J=15.5 Hz), 7.99 (1H, d, J=7 Hz), 8.05 (2H, d, J=9 Hz), 12.70 (1H, br), 13.04 (1H, br); NMR (4) DMSO-$d_6$) δppm: 0.89 (3H, t, J=6.4 Hz), 1.21–1.50 (4H,), 1.53–1.79 (2H, m), 2.69 (2H, t, J=8.0 Hz), 5.14 (2H, s), 6.64 (1H, d, J=15.5 Hz), 7.04 (1H, d, J=8.5 Hz), 7.30–7.38 (1H, m), 7.43–7.51 (1H, m), 7.78–7.82 (1H, d, J=7.9 Hz), 7.85–8.10 (4H, m); NMR (5) (DMSO-$d_6$) δppm: 5.22 (2H, s), 6.67 (1H, d, J=15.5 Hz), 7.24–7.49 (3H, m), 7.77 (1H, d, J=7.6 Hz), 7.89 (1H, d, J=15.5 Hz), 7.96–8.12 (3H, m), 12.83 (1H, br); NMR (6) DMSO-$d_6$) δppm: 1.6–1.9 (4H, m), 2.65–3.0 (4H, m), 5.06 (2H, s), 6.45 (1H, d, J=16 Hz), 6.82 (1H, d, J=8.5 Hz), 7.25–7.65 (4H, m), 7.75 (1H, d, J=8 Hz), 7.97 (1H, d, J=8 Hz), 12.85 (1H, br); NMR (7) (DMSO-$d_6$) δppm: 2.22 (3H, s), 2.31 (3H, s), 5.05 (2H, s), 6.44 (1H, d, J=15.5 Hz), 6.85 (1H, d, J=8.5 Hz), 7.25–7.6 (4H, m), 7.76 (1H, d, J=8 Hz), 7.98 (1H, d, J=8 Hz), 12.83

(1H, br); NMR (8) (DMSO-d$_6$) δppm: 2.36 (6H, s), 4.75 (2H, s), 6.67 (1H, d, J=15.5 Hz), 7.30–7.53 (2H, m), 7.77 (1H, d, J=8.9 Hz), 7.79 (2H, s), 7.91 (1H, d, J=15.5 Hz), 8.00 (1H, d, J=7.00 Hz), 12.09–13.2 (2H, br); NMR (9) (DMSO-d$_6$) δppm: 2.10 (6H, s), 4.95 (2H, s), 6.22 (1H, d, J=16 Hz), 6.78 (2H, s), 7.02 (1H, d, J=16 Hz), 7.25–7.5 (2H, m), 7.76 (1H, d, J=8 Hz), 7.98 (1H, d, J=7.5 Hz), 12.9 (2H, br); NMR (10) (CDCl$_3$) δppm: 1.37 (3H, d, J=7.0 Hz), 4.14 (2H, q, J=7.0 Hz), 5.09 (2H, s), 6.65 (1H, d, J=15.5 Hz), 7.06 (1H, d, J=8.6 Hz), 7.31 (1H, d, J=7.4 Hz), 7.44 (1H, t, J=7.4 Hz), 7.55 (1H, s), 7.67–7.78 (2H, m), 7.90 (1H, d, J=15.5 Hz), 7.98 (1H, d, J=7.4 Hz), 12.74 (2H, br); NMR (11) (DMSO-d$_6$) δppm: 2.45 (3H, s), 5.03 (2H, s), 6.45 (1H, d, J=15.6 Hz), 6.90–7.06 (2H, m), 7.28–7.35 (1H, m), 7.41–7.48 (1H, m), 7.56 (1H, d, J=15.6 Hz), 7.75 (2H, t, J=7.4 Hz), 7.97–8.00 (1H, m), 12.80 (2H, brs); NMR (12) DMSO-d$_6$ δppm: 1.13 (3H, t, J=7.4 Hz). 2.80 (2H, q, J=7.4 Hz), 5.03 (2H, s), 6.47 (1H, d, J=15.6 Hz), 6.94 (1H, dd, J=2.5 Hz, J=8.6 Hz), 7.01 (1H, d, J=2.5 Hz), 7.27–7.50 (2H, m), 7.53 (1H, t, J=15.6 Hz), 7.68–7.81 (2H, m), 7.92–8.03 (1H, m), 12.86 (2H, br); NMR (14) DMSO-d$_6$ δppm: 0.82 (3H, t, J=7.2 Hz), 1.17–1.40 (2H, m), 1.40–1.61 (2H, m), 2.72–2.90 (2H, m), 5.06 (2H, s), 6.46 (1H, d, J=15.7 Hz). 6.91–7.07 (2H, m), 7.30–7.41 (1H, m), 7.41–7.54 (1H, m), 7.51 (1H, d, J=15.7 Hz), 7.74–7.82 (2H, m), 8.00–8.04 (1H, m); NMR (15) (DMSO-d$_6$) δppm: 5.08 (2H, s), 6.50 (1H, d, =15.7 Hz), 7.13 (1H, dd, J=2.5 Hz, J=8.7 Hz), 7.27–7.49 (4H, m), 7.71 (1H, d, J=8.7 Hz), 7.76 (1H, d, J=7.0 Hz), 7.99 (1H, d, J=7.0 Hz), 12.85 (1H, br); NMR (16) (DMSO-d$_6$) δppm: 5.09 (2H, s), 6.61 (1H, d, J=15.6 Hz), 6.98–7.13 (2H, m), 7.30 (1H, t, J=7.1 Hz), 7.44 (1H, t, J=7.1 Hz), 7.63 (1H, dd, J=3.4 Hz, J=15.6 Hz), 7.74–7.90 (2H, m), 7.97 (1H, d, J=7.1 Hz), 12.88 (1H, br); NMR (17) (DMSO-d$_6$) δppm: 3.89 (3H, s), 5.06 (2H, s), 6.51 (1H, d, J=15.5 Hz), 6.71 (1H, d, J=2.2 Hz, J=8.7 Hz), 6.82 (1H, d, J=2.2 Hz), 7.25–7.50 (2H, m), 7.66 (1H, d, J=8.7 Hz), 7.70 (1H, d, J=15.5 Hz), 7.74–7.81 (1H, m), 7.94–8.03 (1H, m), 12.80 (2H, br); NMR (18) (DMSO-d$_6$) δppm: 1.34 (3H, t, J=6.9 Hz), 4.15 (2H, q, J=6.9 Hz), 5.05 (2H, s), 6.45 (1H, d, J=15.5 Hz), 6.68 (1H, dd, J=2.0 Hz, J=8.7 Hz), 6.77 (1H, d, J=2.0 Hz), 7.26–7.50 (2H, m), 7.66 (1H, d, J=8.7 Hz), 7.72–7.81 (1H, m), 7.79 (1H, d, J=15.5 Hz), 7.91–8.05 (1H, m), 12.77 (2H, br); NMR (19) DMSO-d$_6$) δppm: 3.89 (3H, s), 5.09 (2H, s), 6.67 (1H, d, J=15.5 Hz), 7.08 (1H, d, J=8.5 Hz), 7.25–7.55 (2H, m), 7.57 (1H, m), 7.7–8.1 (4H, m), 11.68 (1H, br); NMR (20) (DMSO-d$_6$) δppm: 1.29 (6H, d, J=6.0 Hz), 4.82 (1H, sept, J=6.0 Hz), 5.05 (2H, s), 6.43 (1H, d, J=15.5 Hz), 6.89 (1H, dd, J=2.3 Hz, J=8.7 Hz), 6.78 (1H, d, J=2.3 Hz), 7.31 (1H, t, J=7.0 Hz), 7.45 (1H, t, J=7.0 Hz), 7.66 (1H, d, J=8.7 Hz), 7.78 (1H, d, J=15.5 Hz), 7.80 (1H, d, J=7.0 Hz), 7.99 (1H, d, J=7.0 Hz), 12.76 (1H, br); NMR (21) (DMSO-d$_6$) δppm: 4.92 (2H, q, J=8.7 Hz), 5.07 (2H, s), 6.48 (1H, d, J=15.5 Hz), 6.81 (1H, dd, J=2.3 Hz, J=8.8 Hz), 6.93 (1H, d, J=2.3 Hz), 7.32 (1H, t, J=7.0 Hz), 7.45 (1H, t, J=7.0 Hz), 7.62–7.79 (3H, m), 7.99 (1H, d, J=7.0 Hz), 12.78 (1H, br); NMR (22) DMSO-d$_6$) δppm: 5.28 (2H, s), 6.69 (1H, d, J=15.5 Hz), 7.25–7.55 (3H, m), 7.77 (1H, d, J=8 Hz), 7.92 (1H, d, J=15.5 Hz), 7.98 (1H, d, J=7.5 Hz), 8.15–8.45 (2H, m), 12.88 (1H, br); NMR (23) (DMSO-d$_6$) δppm: 1.03 (3H, t, J=7 Hz), 1.18 (3H, t, J=7 Hz), 3.1–3.5 (4H, m), 4.96 (2H, s), 5.10 (2H, s), 6.63 (1H, d, J=15.5 Hz), 7.10 (1H, d, J=8.5 Hz), 7.25–7.55 (3H, m), 7.7–7.85 (2H, m), 7.86 (1H, d, J=15.5 Hz), 7.98 (1H, d, J=7.5 Hz), 12.66 (1H, br); NMR (24) (DMSO-d$_6$) δppm: 3.90 (3H, s), 5.18 (2H, s), 6.67 (1H, d, J=15.5 Hz), 7.28–7.36 (2H, m), 7.46 (1H, t, J=7.6 Hz), 7.78 (1H, d, J=7.6 Hz), 7.89 (1H, d, J=15.5 Hz), 7.99 (1H, t, J=7.6 Hz), 8.25 (1H, dd, J=2.3 Hz, J=8.9 Hz) 8.38 (1H, d, J=2.3 Hz); NMR (25) DMSO-d$_6$) δppm: 2.48 (2H, t, J=7.5 Hz), 3.12 (2H, t, J=7.5 Hz), 5.04 (2H, s), 6.52 (1H, d, J=15.7 Hz), 7.13 (1H, d, J=8.7 Hz), 7.34 (1H, t, J=7.2 Hz), 7.42–7.63 (3H, m), 7.80 (1H, d, J=7.6 Hz), 8.02 (1H, d, J=7.2 Hz), 10.33 (1H, br), 12.98 (1H, br); NMR (26) (DMSO-d$_6$) δppm: 2.71 (2H, t, J=7.6 Hz), 2.98 (2H, t, J=7.6 Hz), 3.59 (3H, s), 5.13 (2H, s), 6.60–6.75 (1H, m), 7.04–7.08 (1H, m), 7.27–7.38 (1H, m), 7.38–7.51 (1H, m), 7.55–7.78 (1H, m), 7.84–7.99 (4H, m), 9.40 (2H, brs); NMR (27) (DMSO-d$_6$+CDCl$_3$) δppm: 2.66 (2H, t, J=8.8 Hz), 2.84 (3H, s), 2.89–3.06 (5H, m), 5.01 (2H, s), 6.57–6.75 (1H, m), 6.90–7.10 (1H, m), 7.18–7.30 (1H, m), 7.30–7.41 (1H, m), 7.63–7.72 (1H, m), 7.72–7.90 (3H, m), 7.96 (1H, s), 11.50–13.00 (2H, brs); NMR (28) (DMSO-d$_6$) δppm: 1.00 (3H, t, J=7.0 Hz), 1.07 (3H, t, J=7.0 Hz), 2.68 (2H, t, J=7.4 Hz), 3.01 (2H, t, J=7.4 Hz), 3.15–3.46 (4H, m), 5.06 (2H, s), 6.78 (2H, d, J=15.4 Hz), 6.95–6.99 (1H, m), 7.25–7.30 (1H, m), 7.38–7.43 (1H, m), 7.72–7.85 (5H, m); NMR (29) (DMSO-d$_6$) δppm: 1.12 (3H, t, J=7.1 Hz), 2.69 (2H, t, J=7.8 Hz), 2.98 (2H, t, J=7.8 Hz), 4.00 (2H, q, J=7.1 Hz), 5.13 (2H, s), 6.61 (1H, d, J=15.4 Hz), 7.04 (1H, d, J=8.8 Hz), 7.30–7.40 (1H, m), 7.55 (1H, m), 7.75 (1H, d, J=7.3 Hz), 7.86 (1H, d, J=15.4 Hz), 7.91–8.10 (3H, m), 12.40–13.30 (2H, m).

Using the suitable starting compounds, the compounds as listed in Tables 50–125 are obtained in the same manner as in Example 3 or 4.

TABLE 50

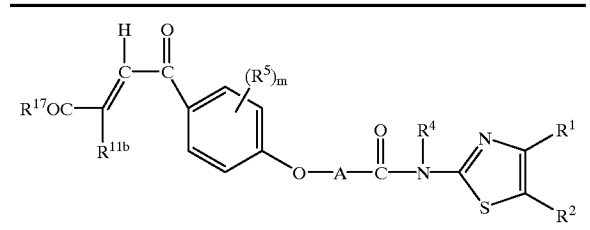

Example 56

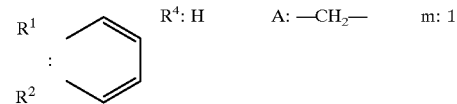

R$^4$: H    A: —CH$_2$—    m: 1

R$^{11b}$: H    R$^5$: H

M.p. 175–185° C.    Crystalline form: White powder
Solvent for recrystallization: Ethanol    Form: Free    NMR (1)

Example 57

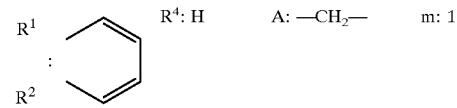

R$^4$: H    A: —CH$_2$—    m: 1

R$^{11b}$: H    R$^5$: Isopropyl (2-position)

M.p. 190–192° C.    Crystalline form: Pale brown powder
Solvent for recrystallization: Ethanol    Form: Free    Trans-form

TABLE 51

Example 58

R¹ :
R² :  R⁴: H    A: —CH₂—    m: 1

R¹¹ᵇ: H    R⁵: H
R¹⁷: 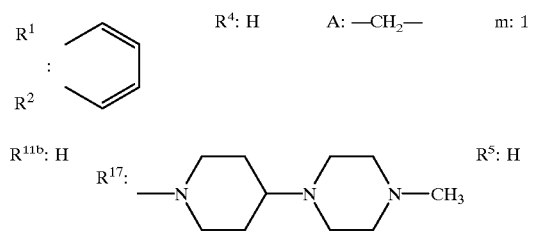

M.p. 202.5–225° C. (decomp.) Crystalline form: White powder NMR (2)
Solvent for recrystallization: Ethanol-diethyl ether    Form: 2HCl Example 59

R¹ :
R² :  R⁴: H    A: —CH₂—    m: 1

R¹¹ᵇ: H    R⁵: Isopropyl (2-position)
R¹⁷: 

M.p. 186–190° C. (decomp.)    Crystalline form: Yellow powder
Solvent for recrystallization: Ethanol-diethyl ether    Form: 2HCl Example 60

R¹ :
R² :  R⁴: H    A: —CH₂—    m: 1

R¹¹ᵇ: H    R⁵: H
R¹⁷: 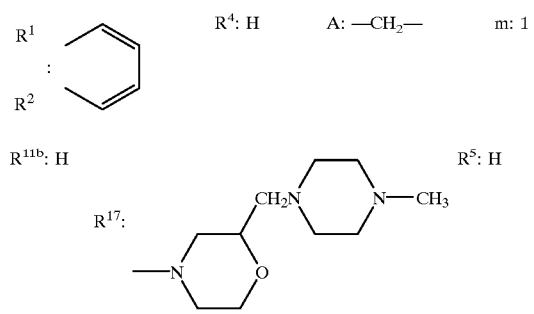

M.p. 202–206° C.(decomp.) Crystalline form: Yellow powder Form: 2HCl
Solvent for recrystallization: Ethanol-diethyl ether

TABLE 52

Example 61

R¹ :
R² :  R⁴: H    A: —CH₂—    m: 1

R¹¹ᵇ: H    R⁵: Isopropyl (2-position)
R¹⁷: 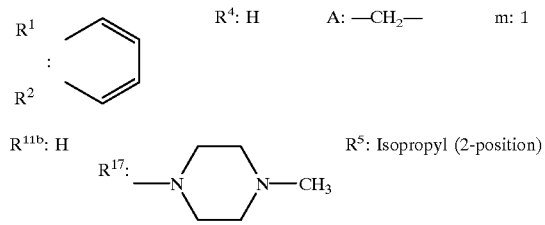

M.p. 114–115° C. Crystalline form: Pale yellow powder Cis-form
Solvent for recrystallization: Ethanol-water    Form: Free

TABLE 52-continued

Example 62

R¹ :
R² :  R⁴: H    A: —CH₂—    m: 1

R¹¹ᵇ: H    R⁵: Cl (2-position)
R¹⁷: 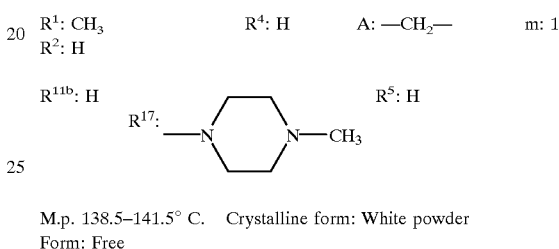

M.p. 206.5–209° C.    Crystalline form: White powder
Solvent for recrystallization: Ethanol-water    Form: Free Example 63

R¹: CH₃    R⁴: H    A: —CH₂—    m: 1
R²: H

R¹¹ᵇ: H    R⁵: H
R¹⁷: 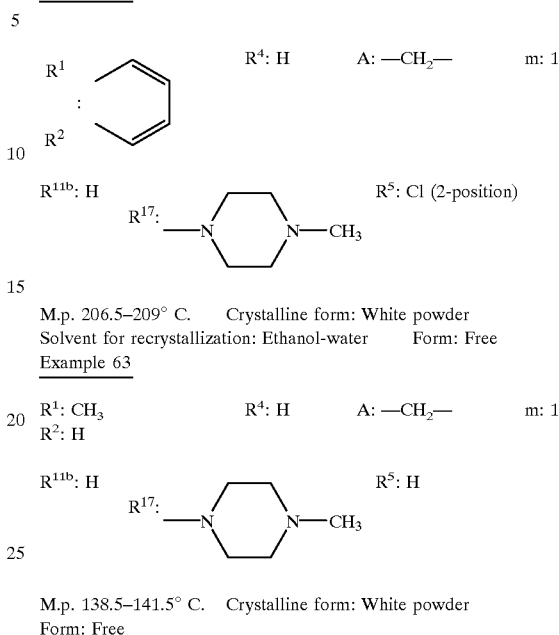

M.p. 138.5–141.5° C.    Crystalline form: White powder
Form: Free

TABLE 53

Example 64

R¹ :
R² :  R⁴: H    A: —CH₂—    m: 1
     F

R¹¹ᵇ: H    R⁵: H
R¹⁷: 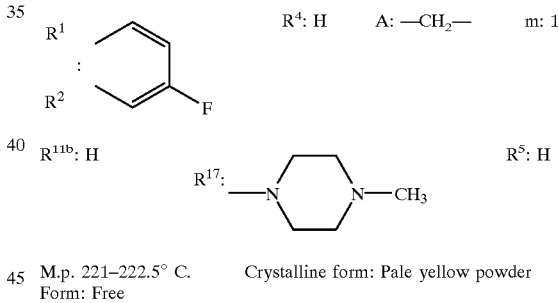

M.p. 221–222.5° C.    Crystalline form: Pale yellow powder
Form: Free

Example 65

R¹ :
R² :  R⁴: H    A: —CH₂—    m: 1

R¹¹ᵇ: H    R⁵: Cl (2-position)
R¹⁷: 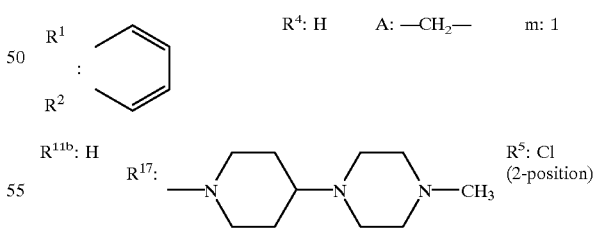

M.p. 181–183° C.    Crystalline form: White powder
Solvent for recrystallization: Ethanol-diethyl ether    Form: Free Example 66

R¹ :
R² :  R⁴: H    A: —CH₂—    m: 1

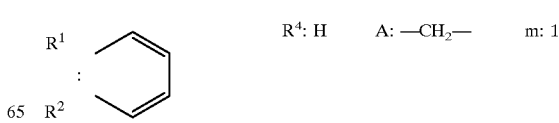

TABLE 53-continued

R^{11b}: H  R^{17}: [piperidine-piperazine-CH₃]  R^5: CH₃ (2-position)

M.p. 261–262° C.    Crystalline form: Yellow powder
Solvent for recrystallization: Ethanol    Form: 2HCl

TABLE 54

Example 67

R^1 / R^2: [phenyl]    R^4: H    A: —CH₂—    m: 1

R^{11b}: H    R^{17}: [piperidine-piperazine-CH₃]    R^5: C₂H₅ (2-position)

M.p. 227–229° C.    Crystalline form: Pale yellow powder
Solvent for recrystallization: Ethanol    Form: 2HCl Example 68

R^1 / R^2: [phenyl]    R^4: H    A: —CH₂—    m: 1

R^{11b}: H    R^{17}: [piperidine-piperazine-CH₃]    R^5: F (2-position)

M.p. 226–227° C.    Crystalline form: Brown powder
Solvent for recrystallization: Ethanol    Form: 2HCl Example 69

R^1 / R^2: [phenyl]    R^4: H    A: —CH₂—    m: 1

R^{11b}: H    R^{17}: [morpholine-CH₂-piperazine-CH₃]    R^5: CH₃ (2-position)

Solvent for recrystallization: Ethanol    Crystalline form: Pale yellow powder
Form: 3HCl    NMR (3)

TABLE 55

Example 70

R^1 / R^2: [phenyl]    R^4: H    A: —CH₂—    m: 1

R^{11b}: H    R^{17}: [morpholine-CH₂-piperazine-CH₃]    R^5: C₂H₅ (2-position)

M.p. 157–160° C.    Crystalline form: Pale yellow powder
Solvent for recrystallization: Ethanol    Form: 3HCl Example 71

R^1 / R^2: [phenyl]    R^4: H    A: —CH₂—    m: 1

R^{11b}: H    R^{17}: [morpholine-CH₂-piperazine-CH₃]    R^5: F (2-position)

Solvent for recrystallization: Ethanol    Crystalline form: Brown powder
Form: 3HCl    NMR (4)

Example 72

R^1 / R^2: [phenyl]    R^4: H    A: —CH₂—    m: 1

R^{11b}: H    R^{17}: [piperidine-piperazine-CH₃]    R^5: n-Propyl (2-position)

Crystalline form: Yellow powder    Form: 3HCl    NMR (5)

TABLE 56

Example 73

R^1 / R^2: [phenyl]    R^4: H    A: —CH₂—    m: 1

R^{11b}: H    R^{17}: [morpholine-CH₂-piperazine-CH₃]    R^5: Cl (2-position)

TABLE 56-continued

M.p. 200° C.  Crystalline form: Yellow powder
Solvent for recrystallization: Ethanol-water  Form: 2HCl Example 74

$R^1$, $R^2$: benzene ring    $R^4$: H   A: —$CH_2$—   m: 1

$R^{11b}$: H $R^{17}$: (1-methylpyrrolidin-2-ylmethyl)-(4-methylpiperazine)

$R^5$: $C_2H_5$ (2-position)

M.p. 115–118° C.  Crystalline form: Pale beige powder
Solvent for recrystallization: Ethanol  Form: 2HCl Example 75

$R^1$, $R^2$: benzene ring    $R^4$: H   A: —$CH_2$—   m: 1

$R^{11b}$: H $R^{17}$: (4-methylmorpholin-2-ylmethyl)-(4-methylpiperazine)

$R^5$: Isopropyl (2-position)

M.p. 188–191° C.  Crystalline form: White powder  Form: 2HCl
Solvent for recrystallization: Ethanol-water-diethyl ether

TABLE 57

Example 76

$R^1$, $R^2$: benzene ring    $R^4$: H   A: —$CH_2$—   m: 1

$R^{11b}$: H $R^{17}$: (4-methylmorpholin-2-ylmethyl)-(4-methylpiperazine)

$R^5$: n-Propyl (2-position)

Crystalline form: Pale yellow powder  Form: 3HCl  NMR (6)

Example 77

$R^1$, $R^2$: benzene ring    $R^4$: H   A: —$CH_2$—   m: 1

$R^{11b}$: H $R^{17}$: (1-methylpyrrolidin-2-ylmethyl)-(4-methylpiperazine)

$R^5$: $C_2H_5$ (2-position)

M.p. 228–230° C.  Crystalline form: Pale yellow powder
Solvent for recrystallization: Ethanol  Form: 2HCl Example 78

$R^1$, $R^2$: benzene ring    $R^4$: H   m: 1

$R^5$ and A combine to form: 2-methyl-2,3-dihydrobenzofuran $R^{11b}$: H $R^{17}$: 1-methyl-4-(4-methylpiperazin-1-yl)piperidine M.p. 203–205° C.  Crystalline form White powder  Form: 3HCl
Solvent for recrystallization: Methanol-diethyl ether

TABLE 58

Example 79

$R^1$, $R^2$: benzene ring    $R^4$: H   A: —$CH_2$—   m: 1

$R^{11b}$: H $R^{17}$: (1-methylpyrrolidin-3-yl)-(4-methylpiperazine)

$R^5$: n-Propyl (2-position)

M.p. 202–204° C.  Crystalline form: White powder
Solvent for recrystallization: Ethyl acetate-n-hexane  Form: 3HCl Example 80

$R^1$, $R^2$: benzene ring    $R^4$: H   A: —$CH_2$—   m: 1

$R^{11b}$: H $R^{17}$: (1-methylpyrrolidin-2-ylmethyl)-(4-methylpiperazine)

$R^5$: n-Propyl (2-position)

Crystalline form: Yellow powder  Form: 2HCl  NMR (9)

TABLE 58-continued

Example 81

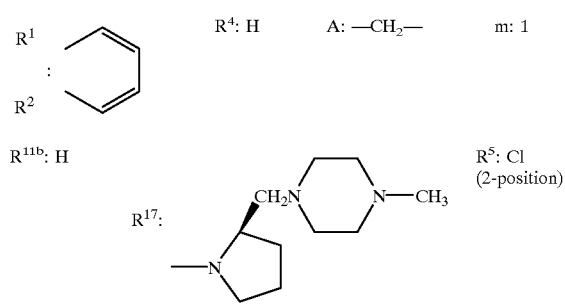

R⁴: H   A: —CH₂—   m: 1
R¹¹ᵇ: H
R⁵: Cl (2-position)

M.p. 171° C.   Crystalline form: Pale yellow powder   Form: 2HCl
Solvent for recrystallization: Ethanol-water

TABLE 59

Example 82

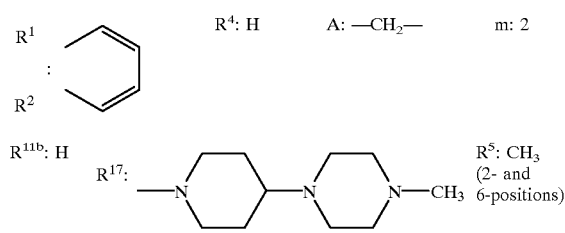

R⁴: H   A: —CH₂—   m: 2
R¹¹ᵇ: H
R⁵: CH₃ (2- and 6-positions)

M.p. 233–235° C.   Crystalline form: Pale yellow powder
Solvent for recrystallization: Ethanol   Form: Free Example 83

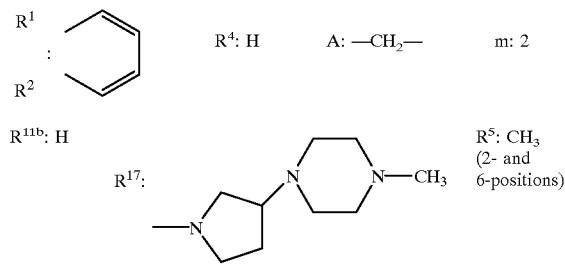

R⁴: H   A: —CH₂—   m: 2
R¹¹ᵇ: H
R⁵: CH₃ (2- and 6-positions)

M.p. 206–210° C.   Crystalline form: Pale yellow powder
Solvent for recrystallization: Ethanol   Form: Free Example 84

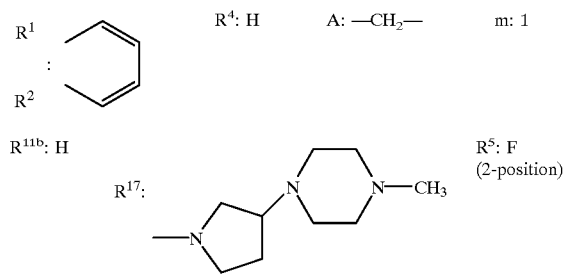

R⁴: H   A: —CH₂—   m: 1
R¹¹ᵇ: H
R⁵: F (2-position)

M.p. 205–208° C.   Crystalline form: White powder
Solvent for recrystallization: Ethanol-water   Form: 2HCl

TABLE 60

Example 85

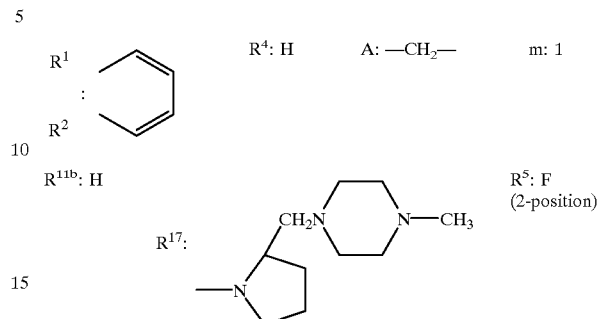

R⁴: H   A: —CH₂—   m: 1
R¹¹ᵇ: H
R⁵: F (2-position)

M.p. 173–175° C.   Crystalline form: Pale yellow powder
Solvent for recrystallization: Ethanol-water-diethyl ether   Form: 2HCl Example 86

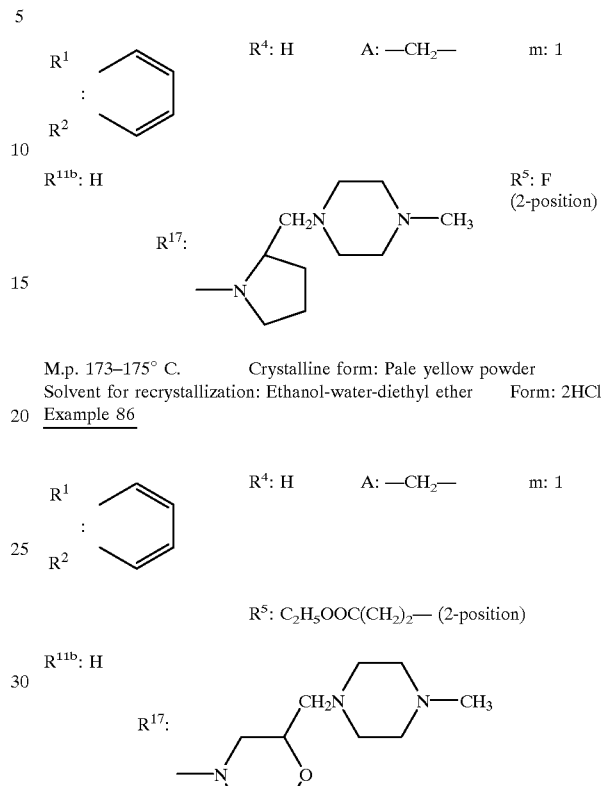

R⁴: H   A: —CH₂—   m: 1
R⁵: C₂H₅OOC(CH₂)₂— (2-position)
R¹¹ᵇ: H

M.p. 152.4–156.3° C.   Crystalline form: White powder
Solvent for recrystallization: Ethanol-water-diethyl ether   Form: 3HCl Example 87

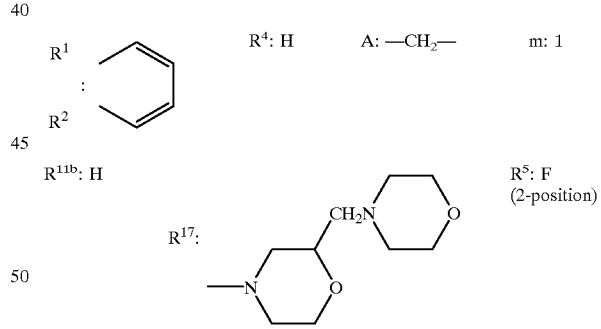

R⁴: H   A: —CH₂—   m: 1
R¹¹ᵇ: H
R⁵: F (2-position)

M.p. 150–153° C.   Crystalline form: Pale yellow powder
Solvent for recrystallization: Dichloromethane-diethyl ether   Form: Free

TABLE 61

Example 88

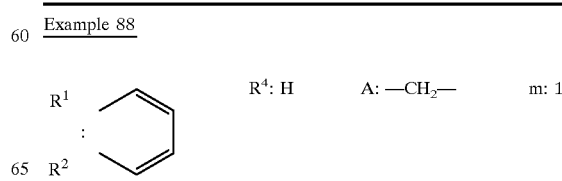

R⁴: H   A: —CH₂—   m: 1

TABLE 61-continued

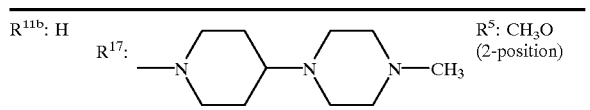

R[11b]: H  R[17]: (piperidine-piperazine-CH3)  R[5]: CH3O (2-position)

Crystalline form: Pale yellow powder  Form: 2HCl
Solvent for recrystallization: Ethanol-water  NMR (11)
Example 89

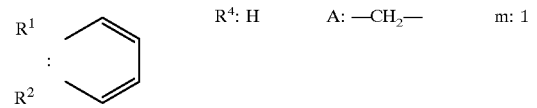

R[1]/R[2]: phenyl  R[4]: H  A: —CH2—  m: 1

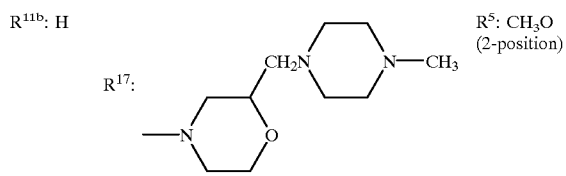

R[11b]: H  R[17]: (morpholine-CH2-piperazine-CH3)  R[5]: CH3O (2-position)

M.p. 203–206° C.  Crystalline form: Pale yellow powder
Solvent for recrystallization: Ethanol-water-diethyl ether  Form: 2HCl
Example 90

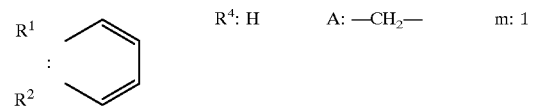

R[1]/R[2]: phenyl  R[4]: H  A: —CH2—  m: 1

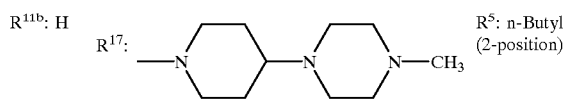

R[11b]: H  R[17]: (piperidine-piperazine-CH3)  R[5]: n-Butyl (2-position)

M.p. 161.7–165° C.  Crystalline form: Pale yellow powder
Solvent for recrystallization: Ethanol-water-diethyl ether  Form: 3HCl

TABLE 62

Example 91

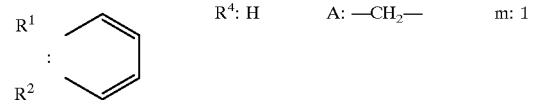

R[1]/R[2]: phenyl  R[4]: H  A: —CH2—  m: 1

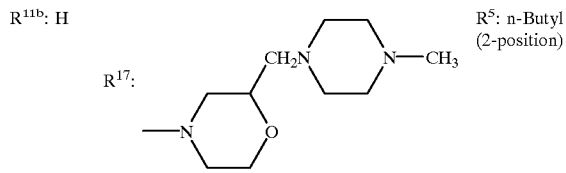

R[11b]: H  R[17]: (morpholine-CH2-piperazine-CH3)  R[5]: n-Butyl (2-position)

M.p. 153–155.5° C.  Crystalline form: Pale yellow powder
Solvent for recrystallization: Ethanol-water-diethyl ether  Form: 3HCl
Example 92

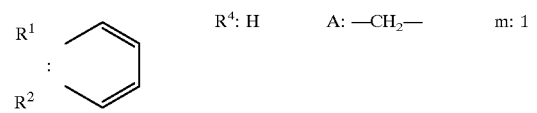

R[1]/R[2]: phenyl  R[4]: H  A: —CH2—  m: 1

TABLE 62-continued

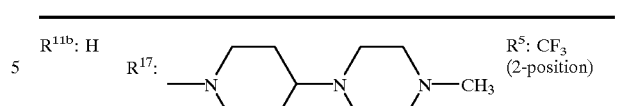

R[11b]: H  R[17]: (piperidine-piperazine-CH3)  R[5]: CF3 (2-position)

M.p. 185–187° C.  Crystalline form: Pale yellow powder
Solvent for recrystallization: Isopropyl alcohol-water  Form: 2HCl
Example 93

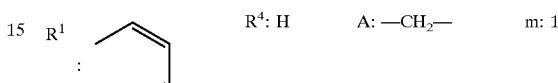

R[1]/R[2]: phenyl  R[4]: H  A: —CH2—  m: 1

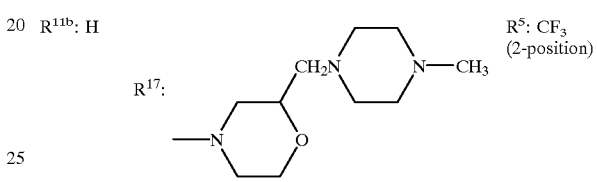

R[11b]: H  R[17]: (morpholine-CH2-piperazine-CH3)  R[5]: CF3 (2-position)

M.p. 175–178° C.  Crystalline form: Pale yellow powder
Solvent for recrystallization: Ethanol-water  Form: 2HCl

TABLE 63

Example 94

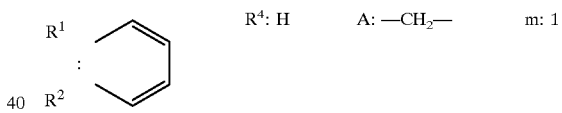

R[1]/R[2]: phenyl  R[4]: H  A: —CH2—  m: 1

R[5]: CH3COO(CH2)4— (2-position)
R[11b]: H

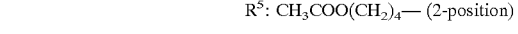

R[17]: (morpholine-CH2-piperazine-CH3)

M.p. 151–154° C.  Crystalline form: White powder
Solvent for recrystallization: Ethanol-water-diethyl ether  Form: 3HCl
Example 95

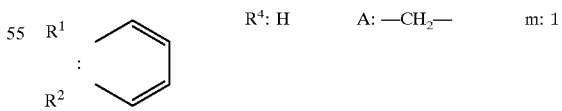

R[1]/R[2]: phenyl  R[4]: H  A: —CH2—  m: 1

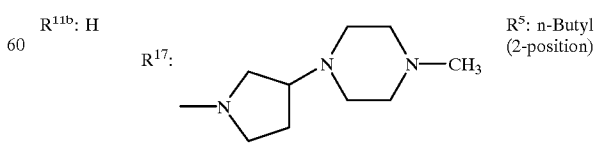

R[11b]: H  R[17]: (pyrrolidine-piperazine-CH3)  R[5]: n-Butyl (2-position)

M.p. 167–168° C.  Crystalline form: White powder
Solvent for recrystallization: Ethanol-water  Form: 3HCl

TABLE 63-continued

Example 96

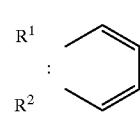

R⁴: H   A: —CH₂—   m: 1

R¹¹ᵇ: H

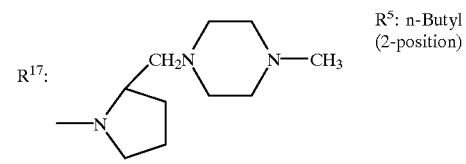

R⁵: n-Butyl (2-position)

M.p. 135–137° C.   Crystalline form: Pale yellow powder
Solvent for recrystallization: Ethanol-water-diethyl ether   Form: 3HCl

TABLE 64

Example 97

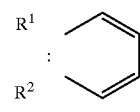

R⁴: H   A: —CH₂—   m: 1

R¹¹ᵇ: H

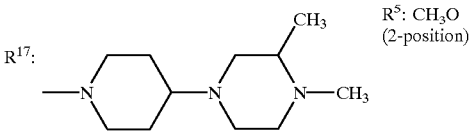

R⁵: CH₃O (2-position)

M.p. 183.5–186° C.   Crystalline form: Yellow powder
Solvent for recrystallization: Ethanol-water   Form: 2HCl Example 98

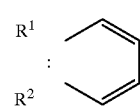

R⁴: H   A: —CH₂—   m: 1

R¹¹ᵇ: H

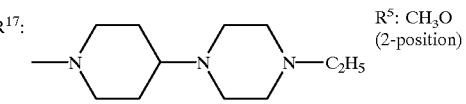

R⁵: CH₃O (2-position)

M.p. 174–176° C.   Crystalline form: Pale yellow powder
Solvent for recrystallization: Ethanol-water   Form: 2HCl Example 99

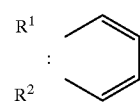

R⁴: H   A: —CH₂—   m: 1

R¹¹ᵇ: H

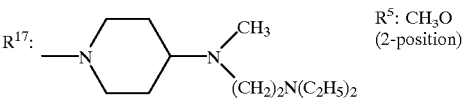

R⁵: CH₃O (2-position)

M.p. 153–154° C.   Crystalline form: Yellow powder
Solvent for recrystallization: Ethanol-water   Form: 2HCl

TABLE 65

Example 100

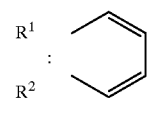

R⁴: H   A: —CH₂—   m: 1

R¹¹ᵇ: H

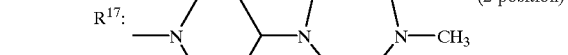

R⁵: CH₃O (2-position)

M.p. 177.5–179.5° C.   Crystalline form: Pale yellow powder
Solvent for recrystallization: Ethanol-water   Form: 3HCl Example 101

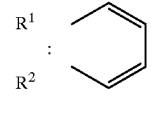

R⁴: H   A: —CH₂—   m: 1

R¹¹ᵇ: H

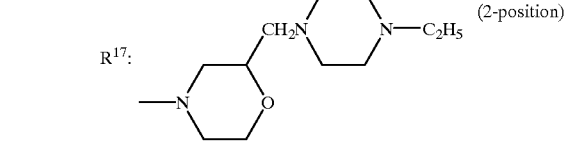

R⁵: CH₃O (2-position)

M.p. 165–168° C.   Crystalline form: Pale yellow powder
Solvent for recrystallization: Ethanol-water-diethyl ether   Form: 3HCl Example 102

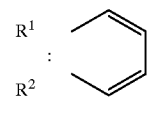

R⁴: H   A: —CH₂—   m: 1

R¹¹ᵇ: H

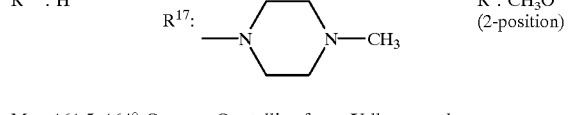

R⁵: CH₃O (2-position)

M.p. 161.5–164° C.   Crystalline form: Yellow powder
Solvent for recrystallization: Ethanol-water   Form: HCl

TABLE 66

Example 103

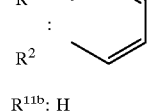

R⁴: H   A: —CH₂—   m: 1

R¹¹ᵇ: H

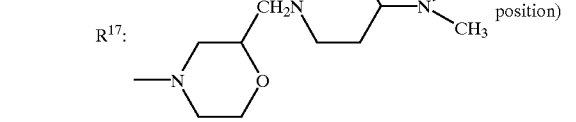

R⁵: CH₃O (2-position)

M.p. 181–183° C.   Crystalline form: White powder
Solvent for recrystallization: Ethanol-water   Form: 2HCl

TABLE 66-continued

Example 104

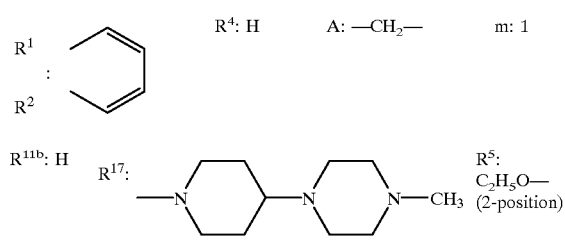

R⁴: H   A: —CH₂—   m: 1

R¹¹ᵇ: H   R⁵: C₂H₅O— (2-position)

M.p. 174–177° C.   Crystalline form: Pale yellow powder   Form: 2HCl
Solvent for recrystallization: Ethanol-water-isopropyl alcohol-diethyl ether

Example 105

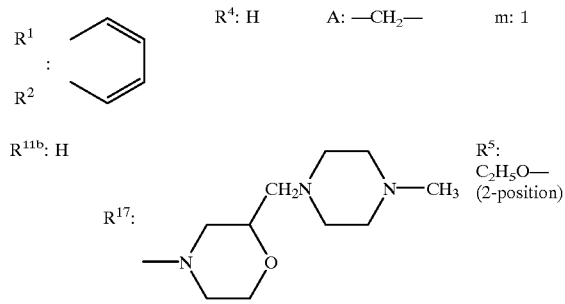

R⁴: H   A: —CH₂—   m: 1

R¹¹ᵇ: H   R⁵: C₂H₅O— (2-position)

M.p. 194–196° C.   Crystalline form: Yellow powder   Form: 2HCl
Solvent for recrystallization: Ethanol-water-isopropyl alcohol-diethyl ether

TABLE 67

Example 106

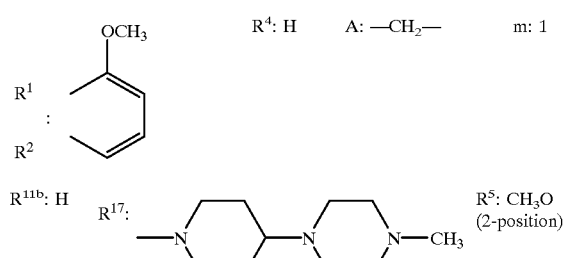

R⁴: H   A: —CH₂—   m: 1

R¹¹ᵇ: H   R⁵: CH₃O (2-position)

M.p. 200–203° C.   Crystalline form: Pale yellow powder
Solvent for recrystallization: Ethanol-water   Form: 2HCl

Example 107

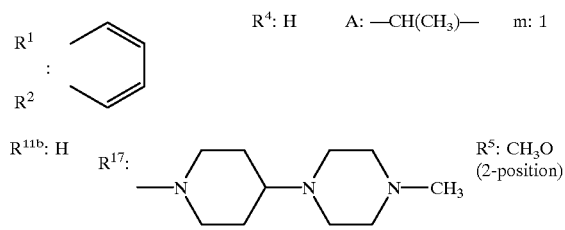

R⁴: H   A: —CH(CH₃)—   m: 1

R¹¹ᵇ: H   R⁵: CH₃O (2-position)

M.p. 169–170° C.   Crystalline form: Pale yellow powder
Solvent for recrystallization: Ethanol   Form: 2HCl

TABLE 67-continued

Example 108

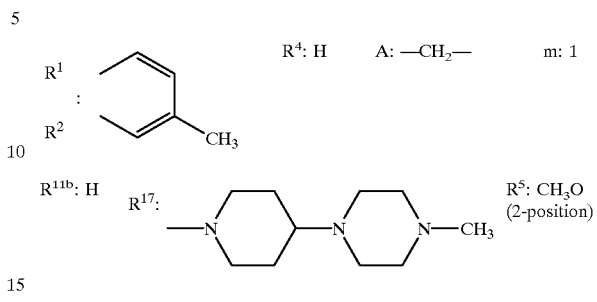

R⁴: H   A: —CH₂—   m: 1

R¹¹ᵇ: H   R⁵: CH₃O (2-position)

M.p. 181–189° C.   Crystalline form: Pale yellow powder
Solvent for recrystallization: Ethanol-water   Form: 3HCl   NMR (12)

TABLE 68

Example 109

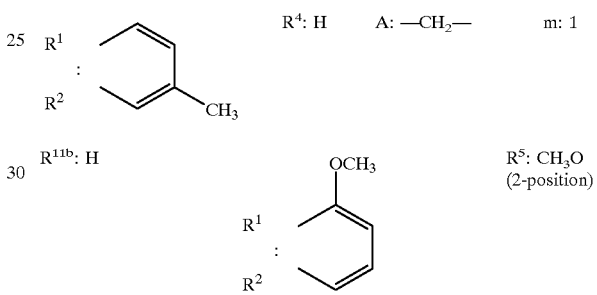

R⁴: H   A: —CH₂—   m: 1

R¹¹ᵇ: H   R⁵: CH₃O (2-position)

M.p. 158–160° C.   Crystalline form: Pale yellow powder
Solvent for recrystallization: Ethanol-water   Form: 3HCl

Example 110

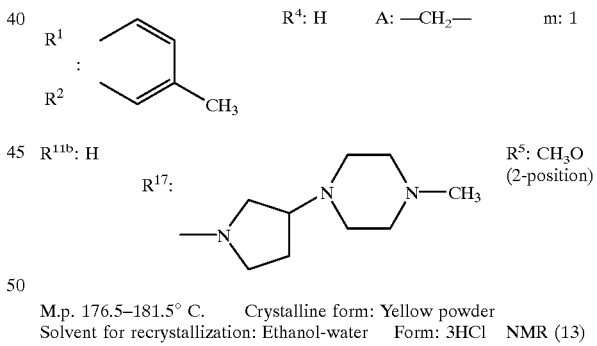

R⁴: H   A: —CH₂—   m: 1

R¹¹ᵇ: H   R⁵: CH₃O (2-position)

M.p. 176.5–181.5° C.   Crystalline form: Yellow powder
Solvent for recrystallization: Ethanol-water   Form: 3HCl   NMR (13)

Example 111

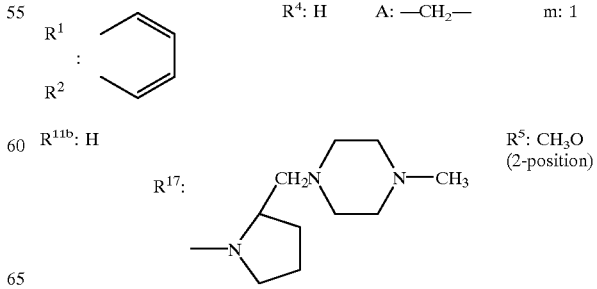

R⁴: H   A: —CH₂—   m: 1

R¹¹ᵇ: H   R⁵: CH₃O (2-position)

TABLE 68-continued

M.p. 141–142° C.  Crystalline form: White powder
Solvent for recrystallization: Ethanol-dichloromethane  Form: Free

TABLE 69

Example 112

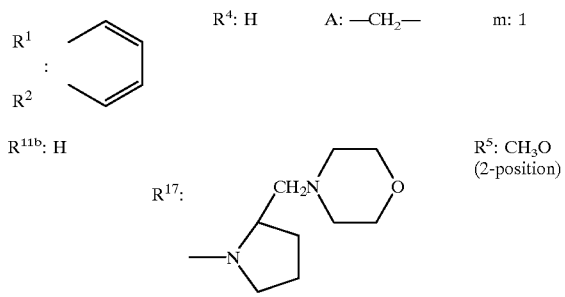

R⁴: H  A: —CH₂—  m: 1
R¹¹ᵇ: H
R⁵: CH₃O (2-position)

M.p. 131.5–133° C.  Crystalline form: Pale yellow powder
Solvent for recrystallization: Ethanol-dichloromethane  Form: Free Example 113

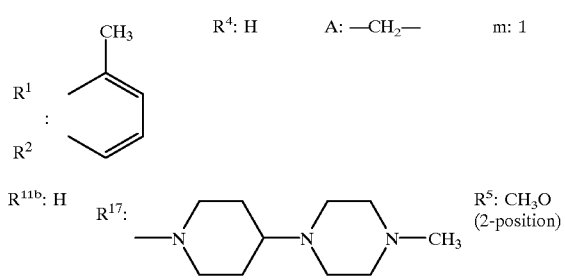

R⁴: H  A: —CH₂—  m: 1
R¹¹ᵇ: H
R⁵: CH₃O (2-position)

Crystalline form: Pale yellow amorphous  Form: Free  NMR (14)

Example 114

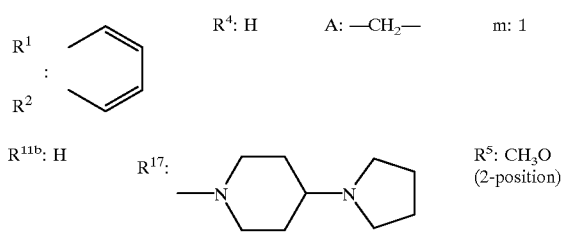

R⁴: H  A: —CH₂—  m: 1
R¹¹ᵇ: H
R⁵: CH₃O (2-position)

M.p. 140–142° C.  Form: Methanesulfonate
Solvent for recrystallization: Ethanol-diisopropyl ether
Crystalline form: Pale yellow powder

TABLE 70

Example 115

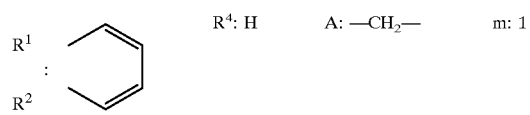

TABLE 70-continued

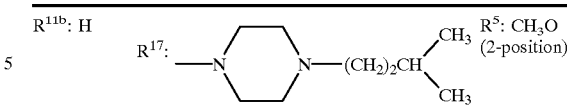

R¹¹ᵇ: H
R⁵: CH₃O (2-position)

M.p. 168.5–169° C.  Crystalline form: White powder
Solvent for recrystallization: Ethanol-dichloromethane  Form: Free Example 116

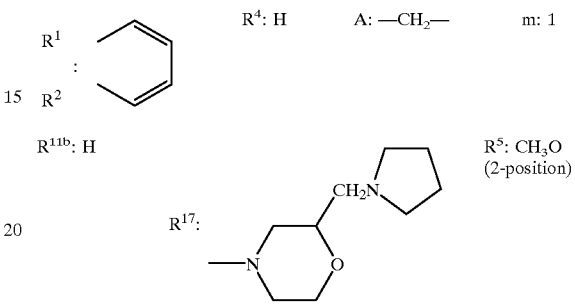

R⁴: H  A: —CH₂—  m: 1
R¹¹ᵇ: H
R⁵: CH₃O (2-position)

M.p. 128.2–131.5° C.  Crystalline form: Yellow powder  Form: Free
Solvent for recrystallization: Ethanol-diethyl ether-dichloromethane Example 117

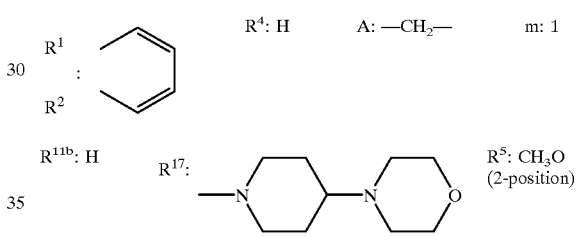

R⁴: H  A: —CH₂—  m: 1
R¹¹ᵇ: H
R⁵: CH₃O (2-position)

M.p. 144–146° C.  Crystalline form: Pale yellow powder
Solvent for recrystallization: Ethanol  Form: Methanesulfonate

TABLE 71

Example 118

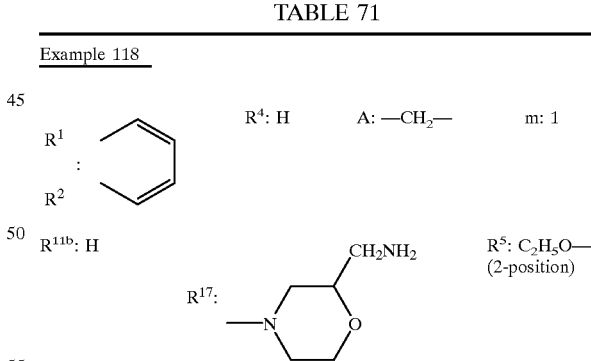

R⁴: H  A: —CH₂—  m: 1
R¹¹ᵇ: H
R⁵: C₂H₅O— (2-position)

M.p. 190–192° C.  Crystalline form: Yellow powder
Form: Methanesulfonate
Solvent for recrystallization: Ethanol-isopropyl alcohol-diethyl ether-water Example 119

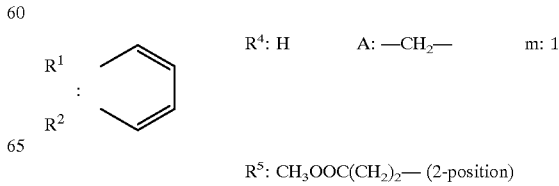

R⁴: H  A: —CH₂—  m: 1

R⁵: CH₃OOC(CH₂)₂— (2-position)

TABLE 71-continued

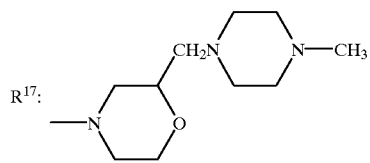

$R^{11b}$: H $R^{17}$:

M.p. 110–111° C.  Crystalline form: Pale yellow powder
Solvent for recrystallization: Ethanol    Form: Free Example 120

$R^1$ / $R^2$ : (cyclohexene)  $R^4$: H   A: —CH$_2$—   m: 1

$R^5$: (CH$_3$)$_2$NOC(CH$_2$)$_2$— (2-position)

$R^{11b}$: H $R^{17}$:

M.p. 162.5–164° C.  Crystalline form: Yellow powder
Solvent for recrystallization: Ethanol-water   Form: HCl

TABLE 72

Example 121

$R^1$ / $R^2$ : (cyclohexane)  $R^4$: H   A: —CH$_2$—   m: 1

$R^{11b}$: H $R^{17}$:

$R^5$: CH$_3$O— (2-position)

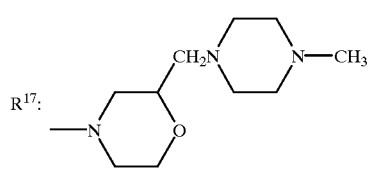

M.p. 205–207.5° C.  Crystalline form: Pale yellow powder
Solvent for recrystallization: Ethanol-water   Form: 2HCl Example 122

$R^1$ / $R^2$ : (cyclohexene)  $R^4$: H   A: —CH$_2$—   m: 1

$R^5$: (C$_2$H$_5$)$_2$NOCCH$_2$O— (2-position)

$R^{11b}$: H $R^{17}$:

M.p. 167–169° C.  Crystalline form: White powder
Solvent for recrystallization: Ethanol-water   Form: 2HCl Example 123

$R^1$ / $R^2$ : (cyclohexene)  $R^4$: H   A: —CH$_2$—   m: 1

$R^{11b}$: H $R^{17}$:

$R^5$: CH$_3$O— (2-position)

M.p. 190.5–192.5° C.  Crystalline form: Yellow powder  Form: Free
Solvent for recrystallization: Ethanol-dichloromethane-diethyl ether

TABLE 73

Example 124

$R^1$ / $R^2$ : (cyclohexene)  $R^4$: H   A: —CH$_2$—   m: 1

$R^{11b}$: H $R^{17}$:

$R^5$: CH$_3$O— (2-position)

M.p. 148.2–149° C.  Crystalline form: Pale yellow powder   Form: Free
Solvent for recrystallization: Ethanol-dichloromethane-diethyl ether

TABLE 73-continued

Example 125

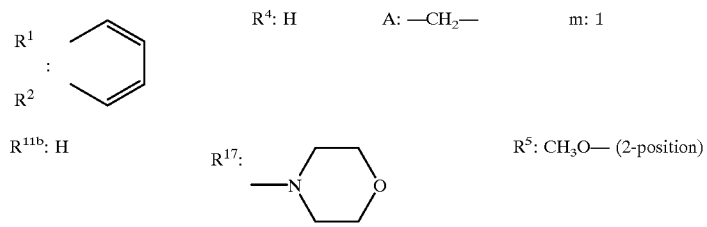

R$^1$ :
R$^2$

R$^{11b}$: H    R$^{17}$:    R$^4$: H    A: —CH$_2$—    m: 1
R$^5$: CH$_3$O— (2-position)

M.p. 211–211.5° C.    Crystalline form: Pale yellow powder
Solvent for recrystallization: Ethanol-dichloromethane    Form: Free Example 126

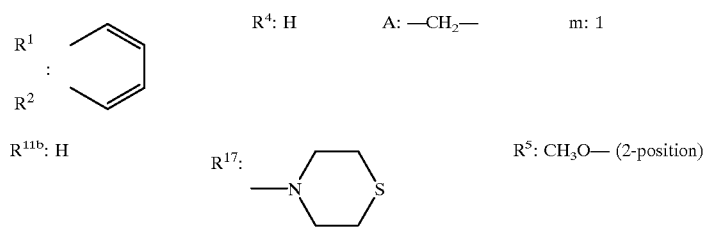

R$^1$ :
R$^2$

R$^{11b}$: H    R$^{17}$:    R$^4$: H    A: —CH$_2$—    m: 1
R$^5$: CH$_3$O— (2-position)

M.p. 204–206° C.    Crystalline form: White needles
Solvent for recrystallization: Ethanol-dichloromethane    Form: Free

TABLE 74

Example 127

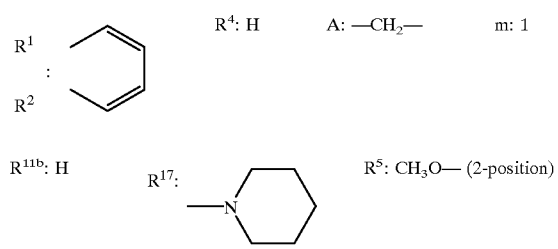

R$^1$ :
R$^2$

R$^{11b}$: H    R$^{17}$:    R$^4$: H    A: —CH$_2$—    m: 1
R$^5$: CH$_3$O— (2-position)

M.p. 168–170.4° C.    Crystalline form: White needles    Form: Free
Solvent for recrystallization: Ethanol-dichloromethane-diethyl ether Example 128

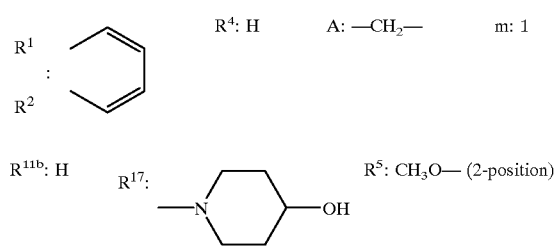

R$^1$ :
R$^2$

R$^{11b}$: H    R$^{17}$:    R$^4$: H    A: —CH$_2$—    m: 1
R$^5$: CH$_3$O— (2-position)

M.p. 175.8–177.2° C.    Crystalline form: White powder
Solvent for recrystallization: Ethanol-dichloromethane    Form: Free

TABLE 74-continued

Example 129

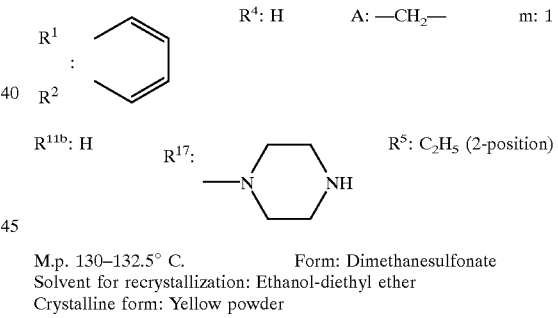

R$^1$ :
R$^2$

R$^{11b}$: H    R$^{17}$:    R$^4$: H    A: —CH$_2$—    m: 1
R$^5$: C$_2$H$_5$ (2-position)

M.p. 130–132.5° C.    Form: Dimethanesulfonate
Solvent for recrystallization: Ethanol-diethyl ether
Crystalline form: Yellow powder

TABLE 75

Example 130

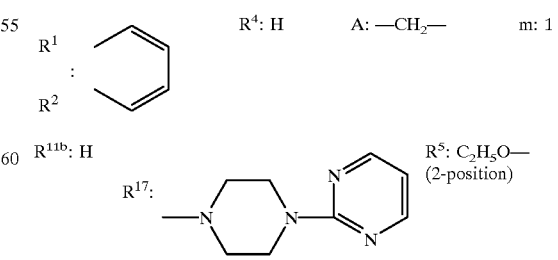

R$^1$ :
R$^2$

R$^{11b}$: H    R$^{17}$:    R$^4$: H    A: —CH$_2$—    m: 1
R$^5$: C$_2$H$_5$O— (2-position)

M.p. 225–226° C.    Crystalline form: Pale yellow powder
Solvent for recrystallization: Dichloromethane-ethanol    Form: Free

TABLE 75-continued

Example 131

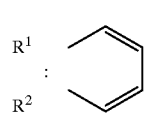
R⁴: H  A: —CH₂—  m: 1

R¹¹ᵇ: H  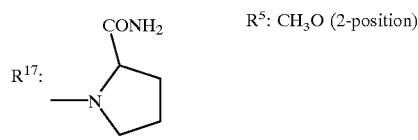  R⁵: CH₃O (2-position)

M.p. 222–223° C.  Crystalline form: White powder
Solvent for recrystallization: Methanol-dichloromethane  Form: Free

Example 132

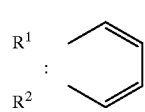
R⁴: H  A: —CH₂—  m: 1

R¹¹ᵇ: H  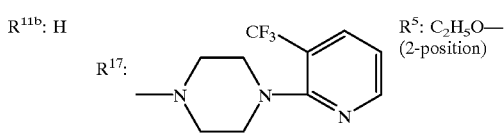  R⁵: C₂H₅O— (2-position)

M.p. 122.5–125° C.  Crystalline form: Pale yellow powder
Solvent for recrystallization: Ethanol-dichloromethane  Form: Free

TABLE 76

Example 133

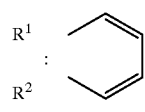
R⁴: H  A: —CH₂—  m: 1

R¹¹ᵇ: H  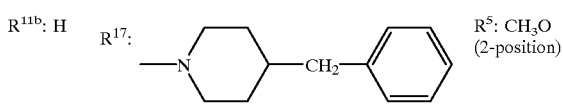  R⁵: CH₃O (2-position)

M.p. 162–163° C.  Crystalline form: White powder
Solvent for recrystallization: Ethanol-dichloromethane  Form: Free

Example 134

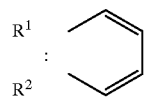
R⁴: H  A: —CH₂—  m: 1

R¹¹ᵇ: H  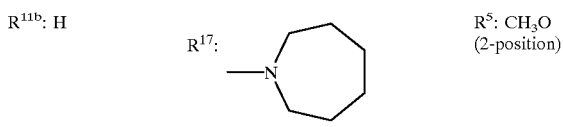  R⁵: CH₃O (2-position)

M.p. 177.2–178° C.  Crystalline form: Pale yellow powder
Solvent for recrystallization: Ethanol-dichloromethane  Form: Free

TABLE 76-continued

Example 135

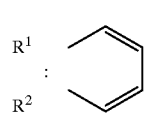
R⁴: H  A: —CH₂—  m: 1

R¹¹ᵇ: H  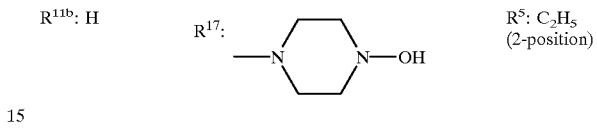  R⁵: C₂H₅ (2-position)

M.p. 140–155° C. (decomp.)  Crystalline form: White powder  NMR (27)
Solvent for recrystallization: Ethanol-dichloromethane-diethyl ether
Form: Free

TABLE 77

Example 136

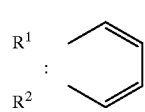
R⁴: H  A: —CH₂—  m: 1

R¹¹ᵇ: H  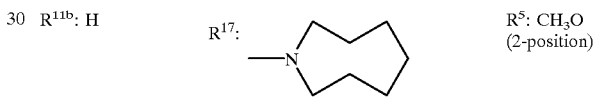  R⁵: CH₃O (2-position)

M.p. 171–172.2° C.  Crystalline form: White needles  Form: Free
Solvent for recrystallization: Ethanol-dichloromethane-diethyl ether

Example 137

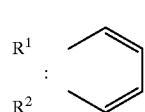
R⁴: H  A: —CH₂—  m: 1

R¹¹ᵇ: H  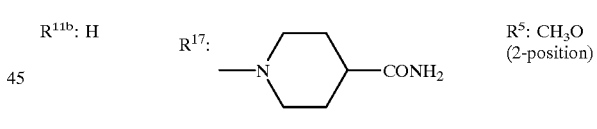  R⁵: CH₃O (2-position)

M.p. 232.5–233° C.  Crystalline form: Yellow powder
Solvent for recrystallization: Dichloromethane-ethanol  Form: Free

Example 138

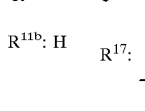
R⁴: H  A: —CH₂—  m: 1

R¹¹ᵇ: H  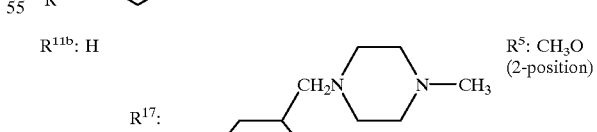  R⁵: CH₃O (2-position)

Crystalline form: Pale yellow amorphous  NMR (28)
Form: 3HCl

TABLE 78

Example 139

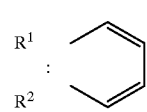  R⁴: H   A: —CH₂—   m: 1

R¹¹ᵇ: H   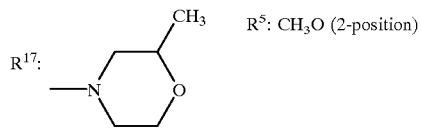   R⁵: CH₃O (2-position)

M.p. 192–194° C.   Crystalline form: Yellow powder
Solvent for recrystallization: Ethanol-dichloromethane   Form: Free Example 140

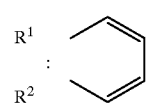  R⁴: H   A: —CH₂—   m: 1

R¹¹ᵇ: H   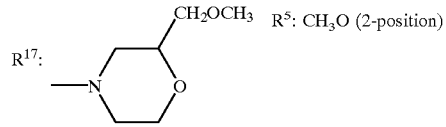   R⁵: CH₃O (2-position)

M.p. 201–204° C.   Crystalline form: Yellow powder
Solvent for recrystallization: Ethanol-dichloromethane   Form: Free Example 141

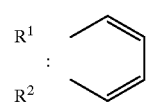  R⁴: H   A: —CH₂—   m: 1

R¹¹ᵇ: H   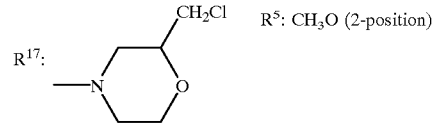   R⁵: CH₃O (2-position)

M.p. 172–175° C.   Crystalline form: Yellow powder
Solvent for recrystallization: Ethanol-dichloromethane   Form: Free

TABLE 79

Example 142

R¹ : R²   R⁴: H   A: —CH₂—   m: 1

R¹¹ᵇ: H   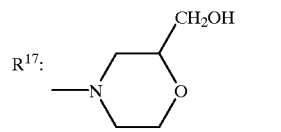   R⁵: CH₃O (2-position)

TABLE 79-continued

M.p. 146.5–148° C.   Crystalline form: Yellow powder
Solvent for recrystallization: Ethanol-dichloromethane   Form: Free Example 143

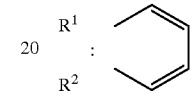   R⁴: H   A: —CH₂—   m: 1

R¹¹ᵇ: H   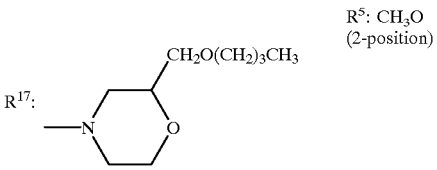   R⁵: CH₃O (2-position)

M.p. 114–117° C.   Crystalline form: Pale yellow powder
Solvent for recrystallization: Ethanol-dichloromethane   Form: Free Example 144

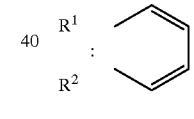   R⁴: H   A: —CH₂—   m: 1

R¹¹ᵇ: H   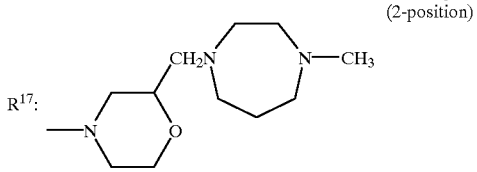   R⁵: CH₃O (2-position)

M.p. 176–181° C.   Crystalline form: Pale yellow powder   Form: 2HCl
Solvent for recrystallization: Ethanol-water-diethyl ether   NMR (29)

TABLE 80

Example 145

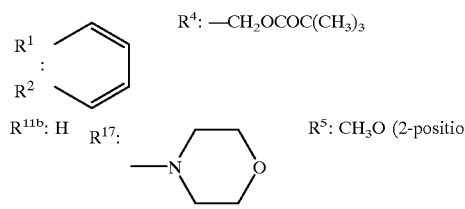

R⁴: —CH₂OCOC(CH₃)₃   A: —CH₂—   m: 1

R¹¹ᵇ: H   R¹⁷: [morpholine]   R⁵: CH₃O (2-position)

M.p. 106.5–108.2° C.    Crystalline form: Pale yellow powder
Solvent for recrystallization: Ethanol-diethyl ether-n-hexane    Form: Free Example 146

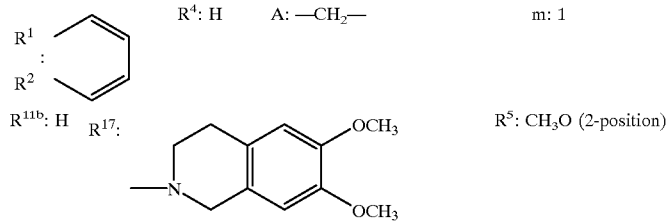

R⁴: H   A: —CH₂—   m: 1

R¹¹ᵇ: H   R¹⁷: [6,7-dimethoxy-tetrahydroisoquinoline]   R⁵: CH₃O (2-position)

M.p. 189–190° C.    Crystalline form: White powder
Solvent for recrystallization: Ethanol-dichloromethane    Form: Free Example 147

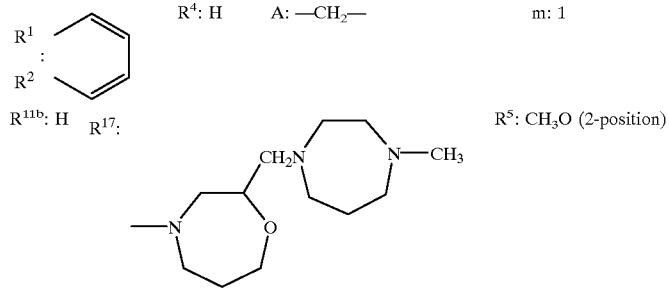

R⁴: H   A: —CH₂—   m: 1

R¹¹ᵇ: H   R¹⁷:    R⁵: CH₃O (2-position)

M.p. 151–153° C.    Crystalline form: White powder
Solvent for recrystallization: Ethyl acetate-diethyl ether    Form: Free

TABLE 81

Example 148

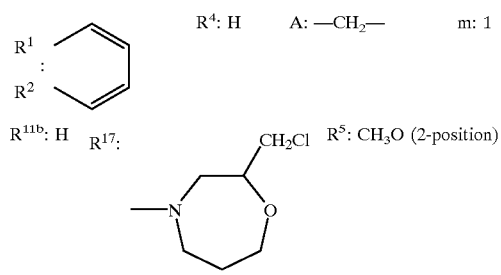

R⁴: H   A: —CH₂—   m: 1

R¹¹ᵇ: H   R¹⁷: [CH₂Cl oxazepane]   R⁵: CH₃O (2-position)

M.p. 145–147° C.    Crystalline form: White powder   Form: Free
Solvent for recrystallization: Ethyl acetate-chloroform

TABLE 81-continued

Example 149

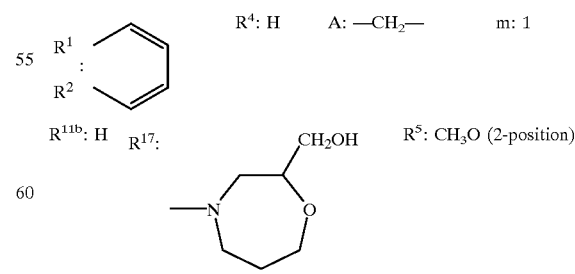

R⁴: H   A: —CH₂—   m: 1

R¹¹ᵇ: H   R¹⁷: [CH₂OH oxazepane]   R⁵: CH₃O (2-position)

M.p. 189–190.5° C.    Crystalline form: Pale yellow powder
Solvent for recrystallization: Ethyl acetate-chloroform    Form: Free

TABLE 81-continued

Example 150

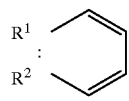

R⁴: H    A: —CH₂—    m: 1

R¹¹ᵇ: H    R¹⁷: 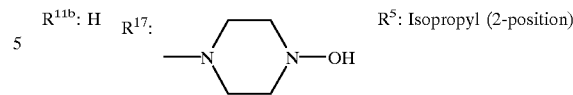    R⁵: Isopropyl (2-position)

M.p. 196–199° C. (decomp.)    Crystalline form: Pale yellow powder
Solvent for recrystallization: Ethanol-dichloromethane    Form: Free

TABLE 82

Example 151

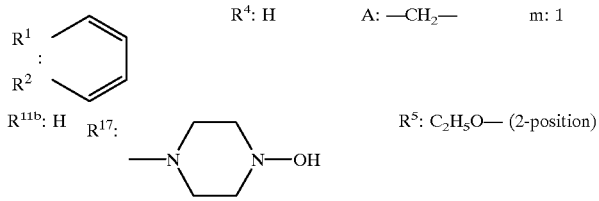

R⁴: H    A: —CH₂—    m: 1

R¹¹ᵇ: H    R¹⁷: (piperazine-N-OH)    R⁵: C₂H₅O— (2-position)

M.p. 155–158° C. (decomp.)    Crystalline form: Yellow powder    Form: Free
Solvent for recrystallization: Ethanol-dichloromethane-diethyl ether Example 152

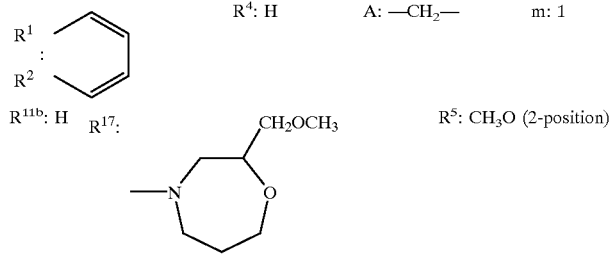

R⁴: H    A: —CH₂—    m: 1

R¹¹ᵇ: H    R¹⁷: (CH₂OCH₃-substituted morpholine)    R⁵: CH₃O (2-position)

M.p. 162–164° C.    Crystalline form: White powder
Solvent for recrystallization: Ethyl acetate-diethyl ether    Form: Free Example 153

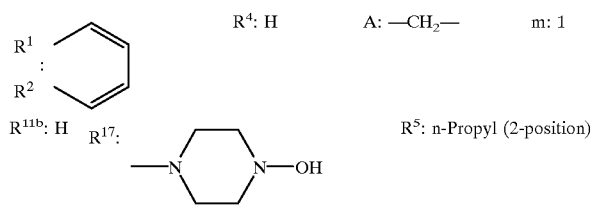

R⁴: H    A: —CH₂—    m: 1

R¹¹ᵇ: H    R¹⁷: (piperazine-N-OH)    R⁵: n-Propyl (2-position)

M.p. 137–139° C. (decomp.)    Crystalline form: Pale yellow powder
Solvent for recrystallization: Ethanol-dichloromethane    Form: Free

TABLE 83

Example 154

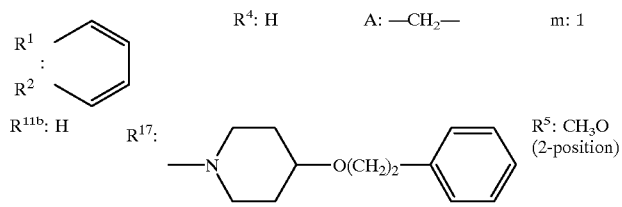

R⁴: H  A: —CH₂—  m: 1
R¹¹ᵇ: H  R⁵: $CH_3O$ (2-position)
R¹⁷: (1-methylpiperidin-4-yl)-O(CH₂)₂-phenyl M.p. 158–159° C.  Crystalline form: White powder  Form: Free
Solvent for recrystallization: Ethanol-dichloromethane-diethyl ether Example 155

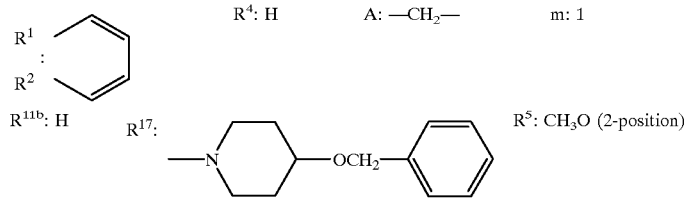

R⁴: H  A: —CH₂—  m: 1
R¹¹ᵇ: H  R⁵: $CH_3O$ (2-position)
R¹⁷: (1-methylpiperidin-4-yl)-OCH₂-phenyl M.p. 154–154.5 C.  Crystalline form: White powder  Form: Free
Solvent for recrystallization: Ethanol-dichloromethane-diethyl ether Example 156

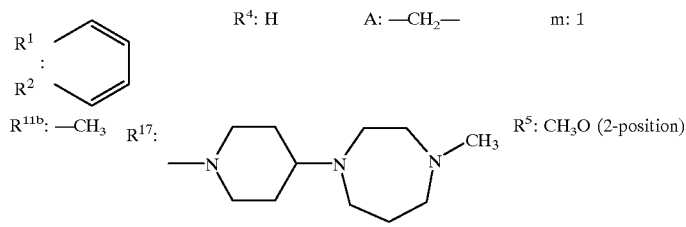

R⁴: H  A: —CH₂—  m: 1
R¹¹ᵇ: —CH₃  R⁵: $CH_3O$ (2-position)
R¹⁷:

M.p. 180–181.5° C.  Crystalline form: Dark yellow powder  Form: HCl
Solvent for recrystallization: Ethanol-dichloromethane-diethyl ether

TABLE 84

Example 157

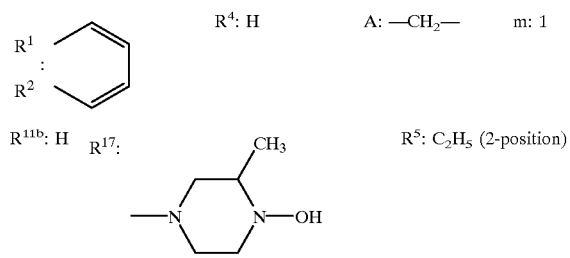

R⁴: H  A: —CH₂—  m: 1
R¹¹ᵇ: H  R⁵: $C_2H_5$ (2-position)
R¹⁷:

M.p. 165–175° C. (decomp.)  Crystalline form: Yellow powder  NMR (30)
Solvent for recrystallization: Dichloromethane-ethanol-diethyl ether  Form: Free

TABLE 84-continued

Example 158

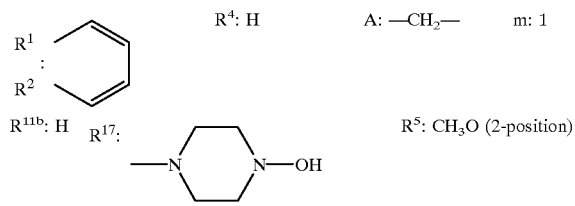

R⁴: H        A: —CH₂—        m: 1

R¹¹ᵇ: H   R¹⁷:                R⁵: CH₃O (2-position)

M.p. 125–128° C.      Crystalline form: Yellow powder      Form: Free
Solvent for recrystallization: Ethanol-dichloromethane Example 159

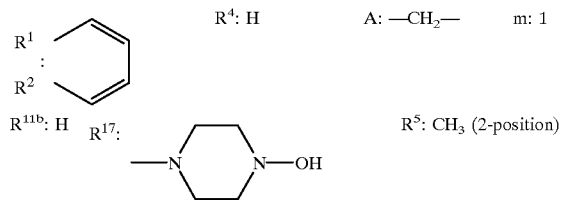

R⁴: H        A: —CH₂—        m: 1

R¹¹ᵇ: H   R¹⁷:                R⁵: CH₃ (2-position)

M.p. 195–195.5° C.      Crystalline form: Pale yellow powder      Form: Free
Solvent for recrystallization: Ethanol-dichloromethane

TABLE 85

Example 160

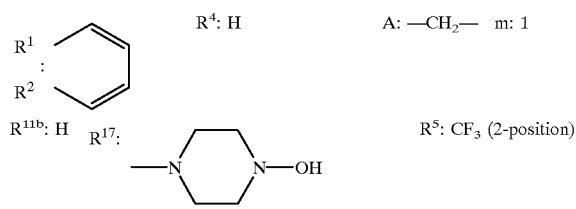

R⁴: H        A: —CH₂—   m: 1

R¹¹ᵇ: H   R¹⁷:                R⁵: CF₃ (2-position)

M.p. 188–189° C.      Crystalline form: Pale yellow powder      Form: Free
Solvent for recrystallization: Ethanol-dichloromethane Example 161

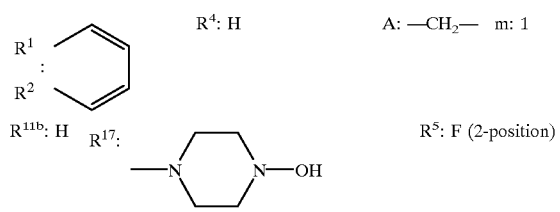

R⁴: H        A: —CH₂—   m: 1

R¹¹ᵇ: H   R¹⁷:                R⁵: F (2-position)

M.p. 197–200 ° C.      Crystalline form: Pale yellow powder      Form: Free
Solvent for recrystallization: Ethanol-dichloromethane Example 162

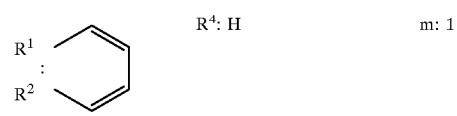

R⁴: H                m: 1

TABLE 85-continued

R⁵ and A combine to form: 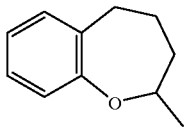  R¹¹ᵇ: H

R¹⁷: 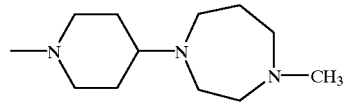

M.p. 138–141° C.    Crystalline form: White powder    Form: Free

TABLE 86

Example 163

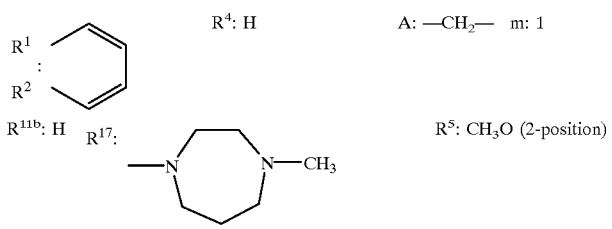

R⁴: H    A: —CH₂—    m: 1

R⁵: CH₃O (2-position)

M.p. 155.5–158° C.    Crystalline form: Pale brown powder    Form: Free
Solvent for recrystallization: Ethanol-dichloromethane Example 164

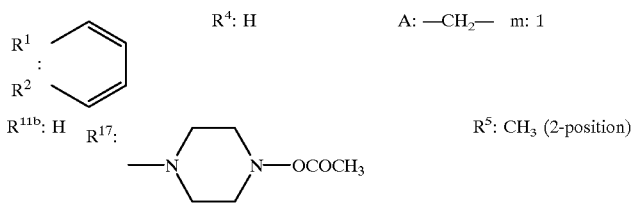

R⁴: H    A: —CH₂—    m: 1

R⁵: CH₃ (2-position)

M.p. 163–166° C.    Crystalline form: Brown powder    Form: Free
Solvent for recrystallization: Dichloromethane-ethanol-diethyl ether Example 165

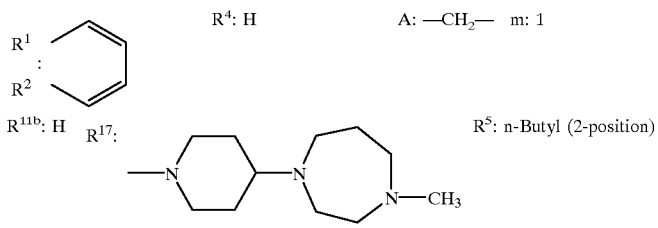

R⁴: H    A: —CH₂—    m: 1

R⁵: n-Butyl (2-position)

M.p. 161–163.4° C.    Crystalline form: Yellow powder    Form: 2HCl
Solvent for recrystallization: Ethanol-dichloromethane-water

TABLE 87

Example 166

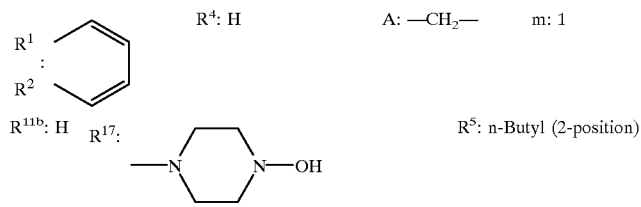

R⁴: H      A: —CH₂—      m: 1

R¹¹ᵇ: H   R¹⁷:           R⁵: n-Butyl (2-position)

M.p. 137–139° C.      Crystalline form: Pale brown powder      Form: Free
Solvent for recrystallization: Ethanol-dichloromethane-water Example 167

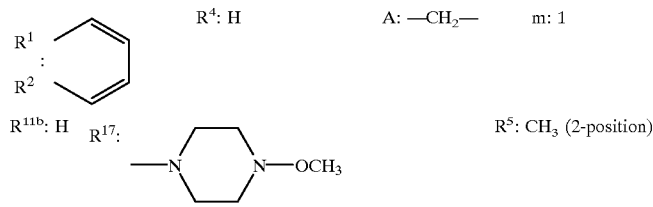

R⁴: H      A: —CH₂—      m: 1

R¹¹ᵇ: H   R¹⁷:           R⁵: CH₃ (2-position)

M.p. 215–217° C.      Crystalline form: Pale yellow powder      Form: Free
Solvent for recrystallization: Ethanol-dichloromethane Example 168

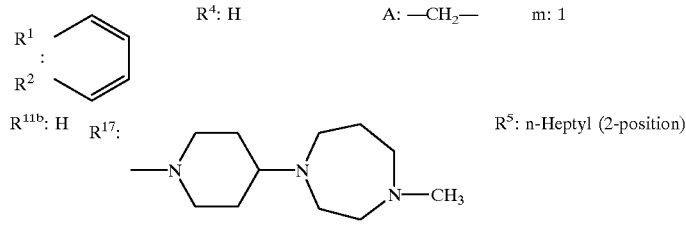

R⁴: H      A: —CH₂—      m: 1

R¹¹ᵇ: H   R¹⁷:           R⁵: n-Heptyl (2-position)

M.p. 146.5–149° C.      Crystalline form: Pale yellow powder
Solvent for recrystallization: Ethanol-dichloromethane-water      Form: 2HCl

TABLE 88

Example 169

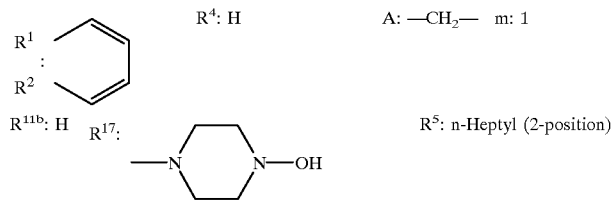

R⁴: H      A: —CH₂—   m: 1

R¹¹ᵇ: H   R¹⁷:           R⁵: n-Heptyl (2-position)

M.p. 152–153.5° C.      Crystalline form: White powder
Solvent for recrystallization: Ethanol-dichloromethane-water      Form: Free Example 170

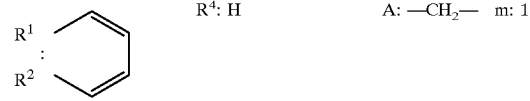

R⁴: H      A: —CH₂—   m: 1

TABLE 88-continued

R$^{11b}$: H  R$^{17}$: 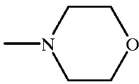  R$^5$: n-Heptyl (2-position)

M.p. 166.5–169.3° C.  Crystalline form: Yellow powder
Solvent for recrystallization: Ethanol-dichloromethane  Form: Free Example 171

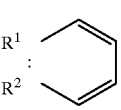  R$^4$: H  A: —CH$_2$—  m: 1

R$^{11b}$: H  R$^{17}$: 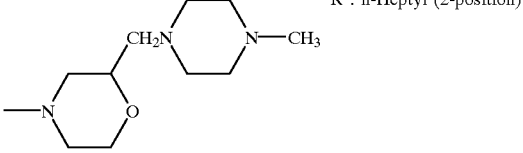  R$^5$: n-Heptyl (2-position)

M.p. 155–165° C.  Crystalline form: Pale yellow powder  Form: 2HCl
Solvent for recrystallization: Ethanol-dichloromethane-water  NMR (31)

TABLE 89

Example 172

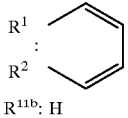  R$^4$: H  A: —(CH$_2$)$_3$—  m: 1

R$^{11b}$: H  R$^{17}$: 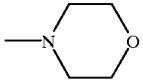  R$^5$: CH$_3$O (2-position)

M.p. 219–220° C.  Crystalline form: Dark yellow powder  Form: Free
Solvent for recrystallization: Ethanol-dichloromethane Example 173

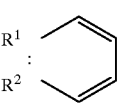  R$^4$: H  A: —(CH$_2$)$_3$—  m: 1

R$^{11b}$: H  R$^{17}$: 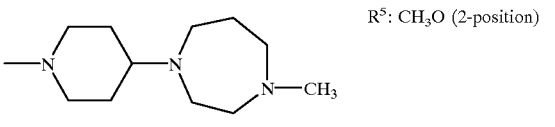  R$^5$: CH$_3$O (2-position)

M.p. 177–185° C.  Crystalline form: Dark yellow powder  Form: 3HCl
Solvent for recrystallization: Ethanol-dichloromethane-water  NMR (32)

TABLE 90

Example 175

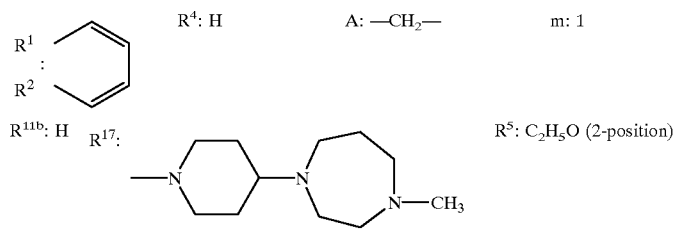

R¹, R²: (phenyl ring)  R⁴: H    A: —CH₂—    m: 1
R¹¹ᵇ: H   R¹⁷: (piperidine-homopiperazine-N-CH₃)    R⁵: $C_2H_5O$ (2-position)

M.p. 182–184° C.   Crystalline form: Pale yellow powder    Form: 2HCl
Solvent for recrystallization: Ethanol-water-diethyl ether Example 176

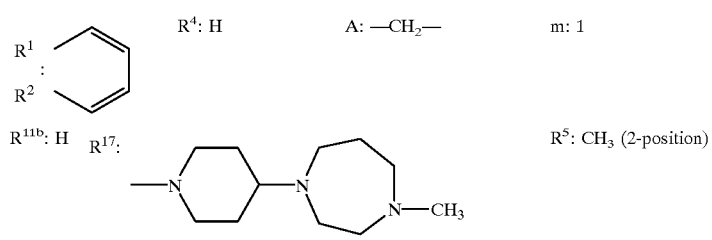

R¹, R²: (phenyl ring)  R⁴: H    A: —CH₂—    m: 1
R¹¹ᵇ: H   R¹⁷: (piperidine-homopiperazine-N-CH₃)    R⁵: $CH_3$ (2-position)

M.p. 265–270° C.   Crystalline form: Pale yellow powder    Form: 2HCl
Solvent for recrystallization: Ethanol-water-diethyl ether                NMR (33)

Example 177

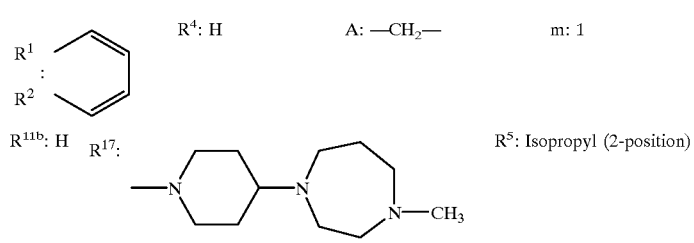

R¹, R²: (phenyl ring)  R⁴: H    A: —CH₂—    m: 1
R¹¹ᵇ: H   R¹⁷: (piperidine-homopiperazine-N-CH₃)    R⁵: Isopropyl (2-position)

M.p. 203–207° C.   Crystalline form: Pale yellow powder    Form: 2HCl
Solvent for recrystallization: Ethanol-water-diethyl ether

TABLE 91

Example 178

R¹, R²: (phenyl ring)   R⁴: H    A: —CH₂—    m: 2

R¹¹ᵇ: H   R¹⁷:

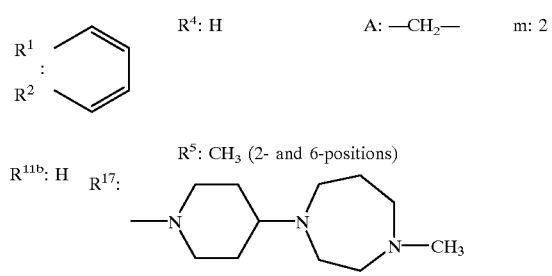

R⁵: $CH_3$ (2- and 6-positions)

M.p. 234–238° C.   Crystalline form: Pale yellow powder    Form: 2HCl
Solvent for recrystallization: Ethanol-water-diethyl ether

TABLE 91-continued

Example 179

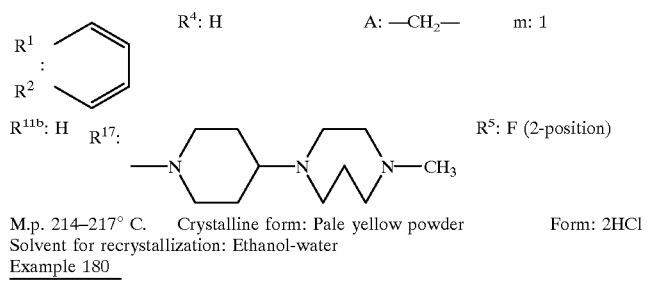

R⁴: H  A: —CH₂—  m: 1

R¹¹ᵇ: H  R¹⁷:  R⁵: F (2-position)

M.p. 214–217° C.  Crystalline form: Pale yellow powder  Form: 2HCl
Solvent for recrystallization: Ethanol-water Example 180

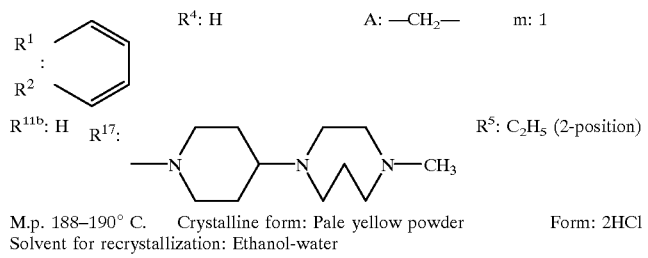

R⁴: H  A: —CH₂—  m: 1

R¹¹ᵇ: H  R¹⁷:  R⁵: C₂H₅ (2-position)

M.p. 188–190° C.  Crystalline form: Pale yellow powder  Form: 2HCl
Solvent for recrystallization: Ethanol-water

TABLE 92

Example 181

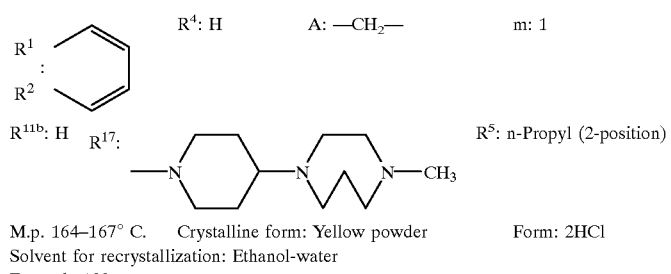

R⁴: H  A: —CH₂—  m: 1

R¹¹ᵇ: H  R¹⁷:  R⁵: n-Propyl (2-position)

M.p. 164–167° C.  Crystalline form: Yellow powder  Form: 2HCl
Solvent for recrystallization: Ethanol-water Example 182

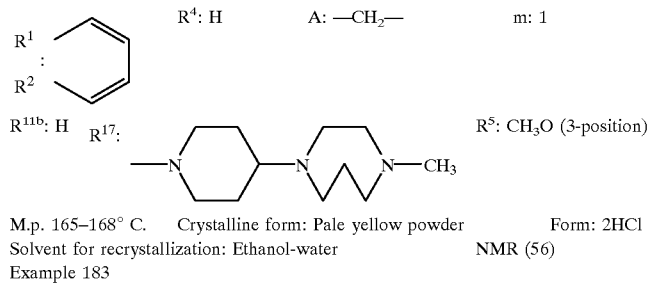

R⁴: H  A: —CH₂—  m: 1

R¹¹ᵇ: H  R¹⁷:  R⁵: CH₃O (3-position)

M.p. 165–168° C.  Crystalline form: Pale yellow powder  Form: 2HCl
Solvent for recrystallization: Ethanol-water  NMR (56)

Example 183

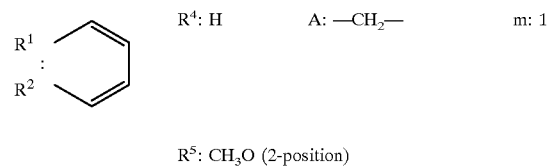

R⁴: H  A: —CH₂—  m: 1

R⁵: CH₃O (2-position)

TABLE 92-continued

R[11b]: H    R[17]: —N(piperidine)—N(piperazine)—COOC(CH$_3$)$_3$

M.p. 143–145° C.    Crystalline form: Pale yellow powder    Form: Free
Solvent for recrystallization: Ethanol-dichloromethane

TABLE 93

Example 184

R$^1$, R$^2$ (phenyl)    R$^4$: H    A: —CH$_2$—    m: 1

R[11b]: H    R[17]: —N(piperidine)—N(piperazine)—CH$_3$    R$^5$: H

M.p. 215–218.5° C. (decomp.)    Crystalline form: White powder
Solvent for recrystallization: Ethanol-water-diethyl ether    Form: 2HCl Example 185

R$^1$, R$^2$ (phenyl)    R$^4$: H    A: —CH$_2$—    m: 1

R[11b]: H    R[17]: —N(piperidine)—N(piperazine)—CH$_3$    R$^5$: CF$_3$ (2-position)

M.p. 101–106° C.    Crystalline form: White powder    Form: 2HCl
Solvent for recrystallization: Diethyl ether-ethanol-water    NMR (34)

Example 186

R$^1$, R$^2$ (phenyl)    R$^4$: H    A: —CH$_2$—    m: 1

R$^5$: CH$_3$O (2-position)

R[11b]: H    R[17]: —N(piperidine)—N(piperazine)—(CH$_2$)$_3$CH$_3$

M.p. 179–183° C.    Crystalline form: White powder    Form: 2HCl
Solvent for recrystallization: Ethanol-water-diethyl ether

TABLE 94

Example 187

R$^1$, R$^2$ (phenyl)    R$^4$: H    A: —CH$_2$—    m: 1

R$^5$: C$_2$H$_5$CH(CH$_3$)— (2-position)

R[11b]: H    R[17]: —N(piperidine)—N(piperazine)—CH$_3$

M.p. 129–131° C.    Crystalline form: Pale yellow powder
Solvent for recrystallization: Isopropyl alcohol-water    Form: Dioxalate Example 188

R$^1$, R$^2$ (phenyl)    R$^4$: H    A: —CH$_2$—    m: 1

TABLE 94-continued $R^{11b}$: H  $R^{17}$: 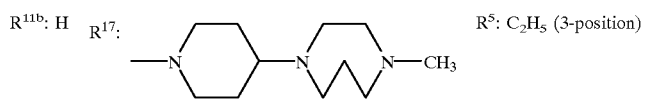  $R^5$: $C_2H_5$ (3-position)

M.p. 163–165° C.   Crystalline form: Pale yellow powder   Form: 2HCl
Solvent for recrystallization: Water-ethanol-dichloromethane

Example 189

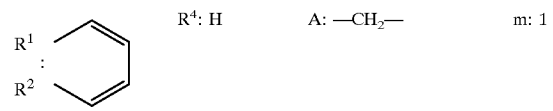  $R^4$: H   A: —$CH_2$—   m: 1

$R^{11b}$: H  $R^{17}$: 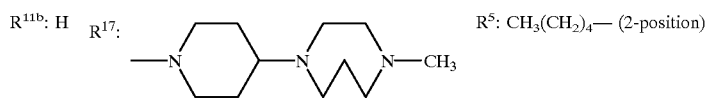  $R^5$: $CH_3(CH_2)_4$— (2-position)

M.p. 161–162° C.   Crystalline form: White powder   Form: 2HCl
Solvent for recrystallization: Isopropyl alcohol-water

TABLE 95

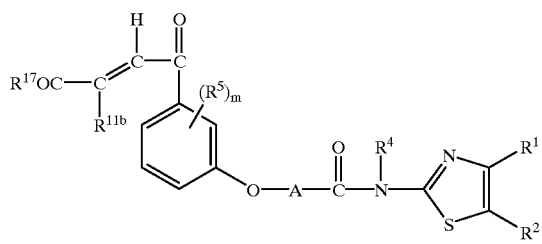

Example 190

  $R^4$: H   A: —$CH_2$—   m: 1

$R^{11b}$: H  $R^{17}$: 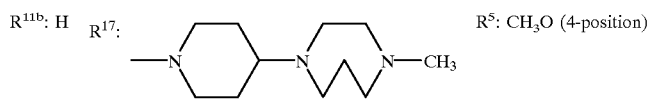  $R^5$: $CH_3O$ (4-position)

M.p. 166–168° C.   Crystalline form: Yellow powder   Form: 2HCl
Solvent for recrystallization: Water-ethanol-dichloromethane

TABLE 96

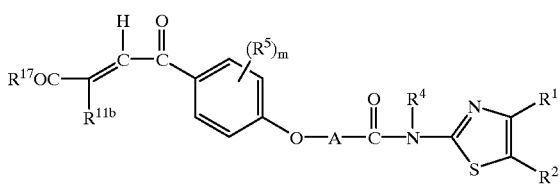

Example 191

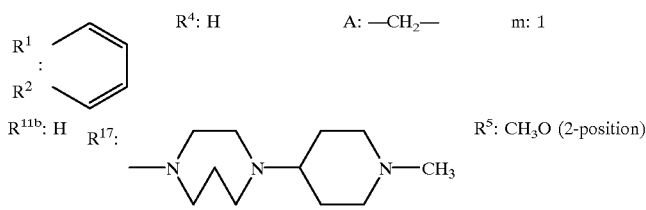

R⁴: H   A: —CH₂—   m: 1

R⁵: CH₃O (2-position)

R¹¹ᵇ: H   R¹⁷: [piperidine-piperazine-CH₃ structure]

M.p. 175–177° C.   Crystalline form: White powder   Form: 2HCl
Solvent for recrystallization: Ethanol-water-diethyl ether Example 192

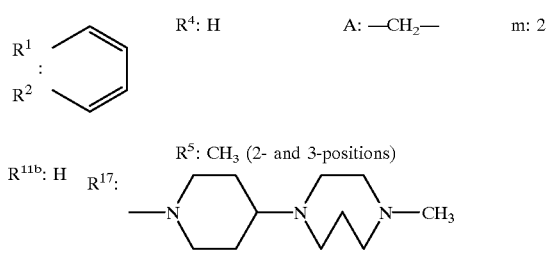

R⁴: H   A: —CH₂—   m: 2

R⁵: CH₃ (2- and 3-positions)

R¹¹ᵇ: H   R¹⁷: [piperidine-piperazine-CH₃ structure]

M.p. 158–162° C.   Crystalline form: Pale yellow powder   Form: Succinate
Solvent for recrystallization: Ethanol-diisopropyl ether Example 193

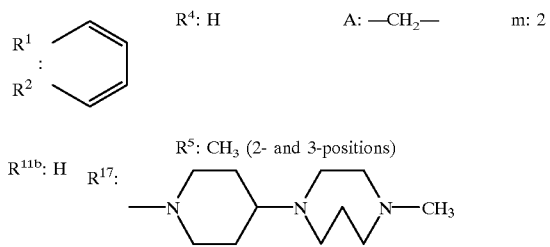

R⁴: H   A: —CH₂—   m: 2

R⁵: CH₃ (2- and 3-positions)

R¹¹ᵇ: H   R¹⁷: [piperidine-piperazine-CH₃ structure]

M.p. 126–128.5° C.   Crystalline form: Yellow powder   Form: Succinate
Solvent for recrystallization: Ethanol-diethyl ether

TABLE 97

Example 194

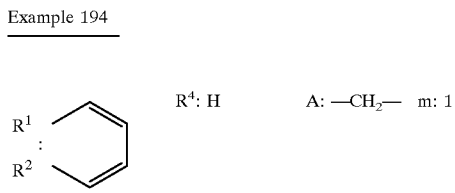

R⁴: H   A: —CH₂—   m: 1

R¹¹ᵇ: H   R¹⁷: 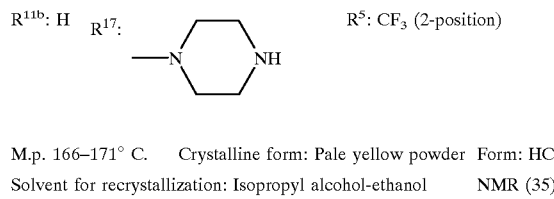   R⁵: CF₃ (2-position)

M.p. 166–171° C.   Crystalline form: Pale yellow powder   Form: HCl
Solvent for recrystallization: Isopropyl alcohol-ethanol   NMR (35)

TABLE 97-continued

Example 195

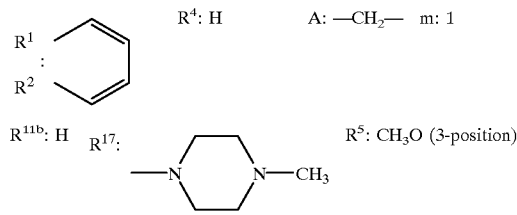

R⁴: H     A: —CH₂—     m: 1

R¹¹ᵇ: H     R¹⁷:     R⁵: CH₃O (3-position)

M.p. 175–178° C.     Crystalline form: Yellow powder     Form: Free
Solvent for recrystallization: Methanol

TABLE 97-continued

Example 196

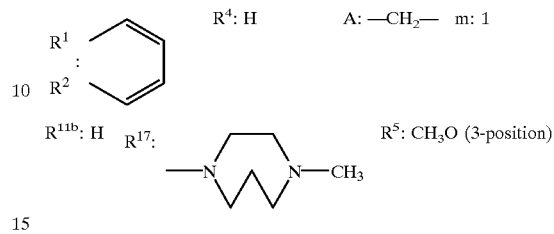

R⁴: H     A: —CH₂—     m: 1

R¹¹ᵇ: H     R¹⁷:     R⁵: CH₃O (3-position)

M.p. 240–245° C.     Crystalline form: Pale yellow powder     Form: HCl
Solvent for recrystallization: Ethanol-water

TABLE 98

Example 197

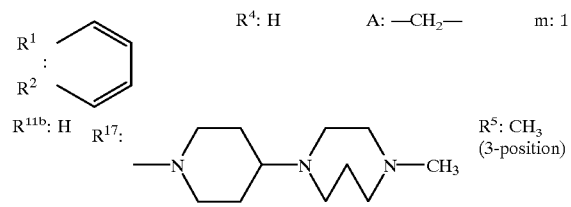

R⁴: H     A: —CH₂—     m: 1

R¹¹ᵇ: H     R¹⁷:     R⁵: CH₃ (3-position)

M.p. 212—215° C.     Crystalline form: White powder     Form: 2HCl
Solvent for recrystallization: Ethanol-water

Example 198

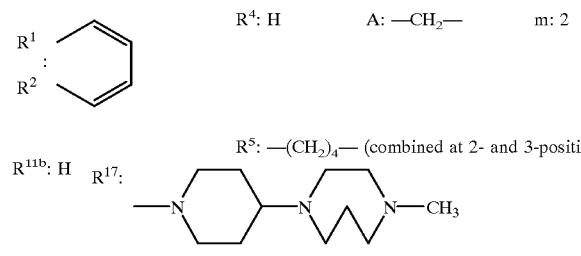

R⁴: H     A: —CH₂—     m: 2

R¹¹ᵇ: H     R¹⁷:     R⁵: —(CH₂)₄— (combined at 2- and 3-positions)

M.p. 180–190° C.     Crystalline form: Yellow powder     Form: 2HCl
Solvent for recrystallization: Ethanol-diethyl ether     NMR (36)

Example 199

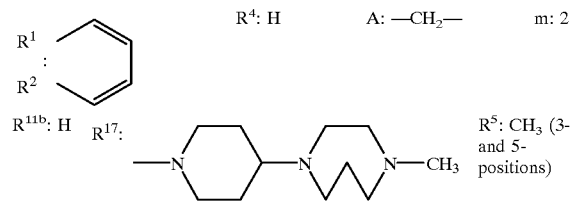

R⁴: H     A: —CH₂—     m: 2

R¹¹ᵇ: H     R¹⁷:     R⁵: CH₃ (3- and 5-positions)

M.p. 210–216° C.     Crystalline form: White powder     Form: 2HCl
Solvent for recrystallization: Ethanol-water-diethyl ether     NMR (37)

TABLE 99

Example 200

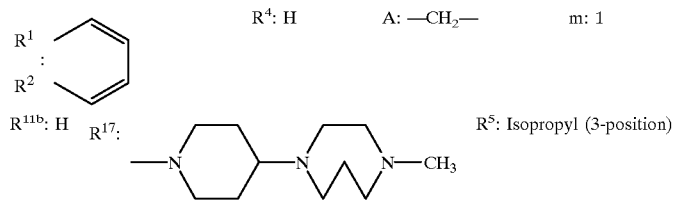

R⁴: H    A: —CH₂—    m: 1

R¹¹ᵇ: H    R¹⁷:    R⁵: Isopropyl (3-position)

M.p. 177.5–180.5° C.    Crystalline form: Pale yellow powder.
Solvent for recrystallization: Ethanol-water    Form: 2HCl Example 201

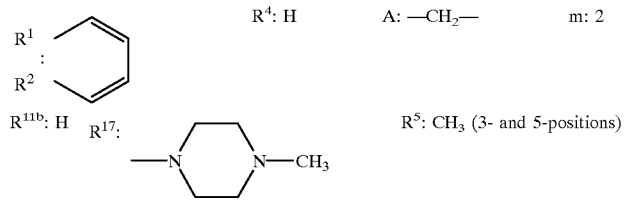

R⁴: H    A: —CH₂—    m: 2

R¹¹ᵇ: H    R¹⁷:    R⁵: CH₃ (3- and 5-positions)

M.p. 119–122.5° C.    Crystalline form: White powder
Solvent for recrystallization: Ethanol-diisopropyl ether    Form: Methanesulfonate Example 202

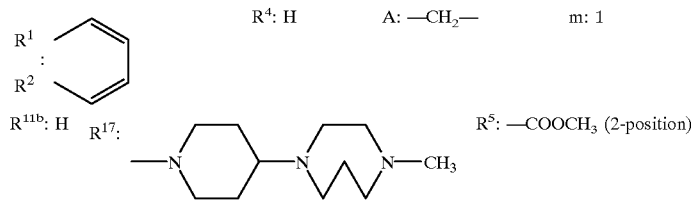

R⁴: H    A: —CH₂—    m: 1

R¹¹ᵇ: H    R¹⁷:    R⁵: —COOCH₃ (2-position)

M.p. 169–172° C.    Crystalline form: white powder
Solvent for recrystallization: Ethanol-water    Form: Dimethanesulfonate

TABLE 100

Example 203

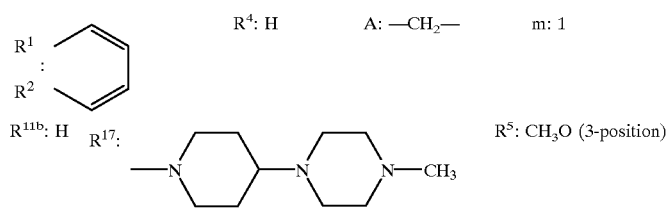

R⁴: H    A: —CH₂—    m: 1

R¹¹ᵇ: H    R¹⁷:    R⁵: CH₃O (3-position)

M.p. 214–220° C.    Crystalline form: Pale yellow powder    Form: Free
Solvent for recrystallization: Methanol Example 204

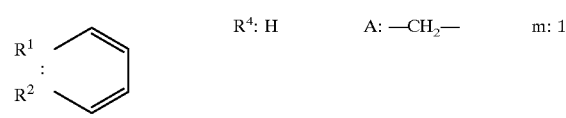

R⁴: H    A: —CH₂—    m: 1

TABLE 100-continued $R^{11b}$: H    $R^{17}$: 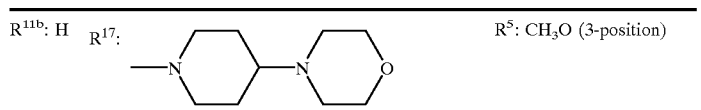    $R^5$: $CH_3O$ (3-position)

M.p. 195–197° C.   Crystalline form: Yellow powder   Form: Free
Solvent for recrystallization: Dichloromethane-methanol Example 205

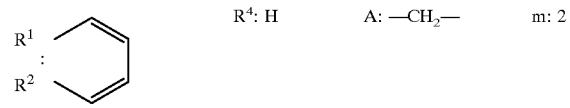   $R^4$: H   A: —$CH_2$—   m: 2

$R^{11b}$: H   $R^{17}$: 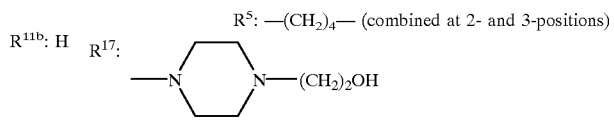   $R^5$: —$(CH_2)_4$— (combined at 2- and 3-positions)

M.p. 151–153° C.   Crystalline form: Pale yellow powder
Solvent for recrystallization: Water   Form: Free

TABLE 101

Example 206

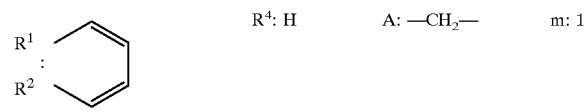   $R^4$: H   A: —$CH_2$—   m: 1

$R^{11b}$: H   $R^{17}$: 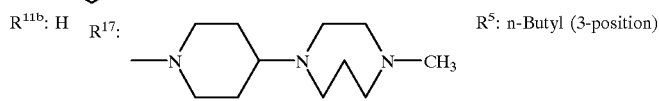   $R^5$: n-Butyl (3-position)

M.p. 148–150.4° C.   Crystalline form: Pale yellow powder   Form: 2HCl
Solvent for recrystallization: Isopropyl alcohol-water-diethyl ether Example 207

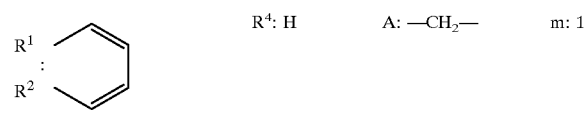   $R^4$: H   A: —$CH_2$—   m: 1

$R^{11b}$: H   $R^{17}$: 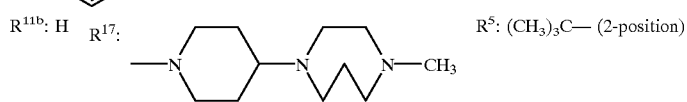   $R^5$: $(CH_3)_3C$— (2-position)

M.p. 142–144.5° C.   Crystalline form: Pale yellow powder   Form: Oxalate
Solvent for recrystallization: Isopropyl alcohol-water Example 208

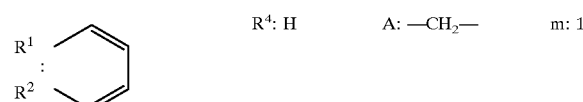   $R^4$: H   A: —$CH_2$—   m: 1

$R^{11b}$: H   $R^{17}$: 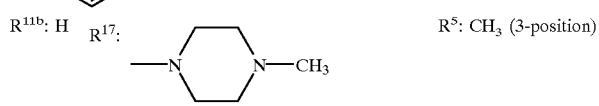   $R^5$: $CH_3$ (3-position)

M.p. 139.2–140.8° C.   Crystalline form: Pale yellow powder
Solvent for recrystallization: Ethanol-water   Form: Methanesulfonate

TABLE 102

Example 209

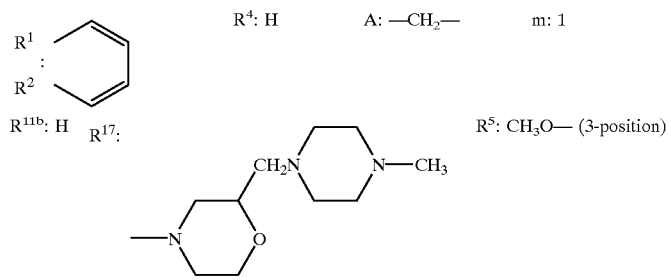

$R^4$: H  A: —$CH_2$—  m: 1

$R^{11b}$: H  $R^{17}$:  $R^5$: $CH_3O$— (3-position)

M.p. 158–163° C.  Crystalline form: Pale yellow powder  Form: 2HCl
Solvent for recrystallization: Ethanol-water-diethyl ether  NMR (38)

Example 210

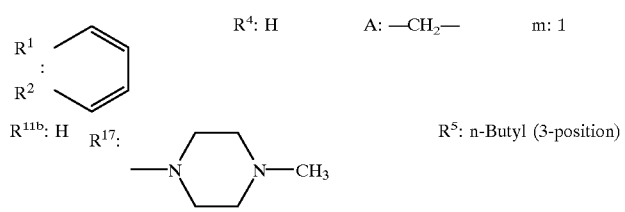

$R^4$: H  A: —$CH_2$—  m: 1

$R^{11b}$: H  $R^{17}$:  $R^5$: n-Butyl (3-position)

M.p. 84–86° C.  Crystalline form: Yellow amorphous  Form: Free

Example 211

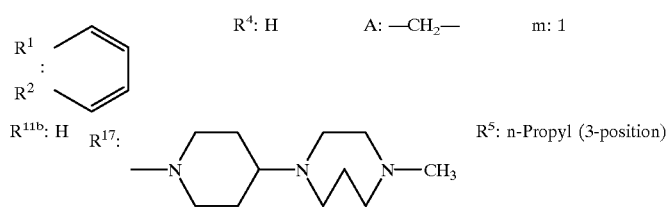

$R^4$: H  A: —$CH_2$—  m: 1

$R^{11b}$: H  $R^{17}$:  $R^5$: n-Propyl (3-position)

M.p. 121–124° C.  Crystalline form: Pale yellow powder  Form: Dioxalate
Solvent for recrystallization: Isopropyl alcohol-water

TABLE 103

Example 212

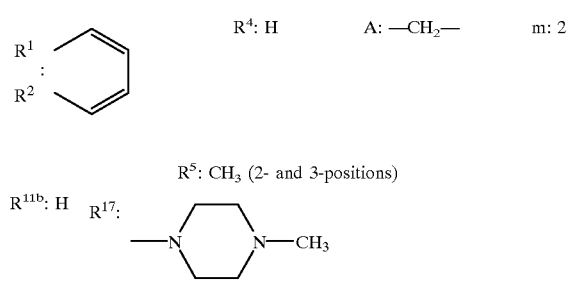

$R^4$: H  A: —$CH_2$—  m: 2

$R^5$: $CH_3$ (2- and 3-positions)

$R^{11b}$: H  $R^{17}$:

M.p. 140–150° C.  Crystalline form: Yellow powder  NMR (39)
Solvent for recrystallization: Acetone-water  Form: Methanesulfonate

TABLE 103-continued

Example 213

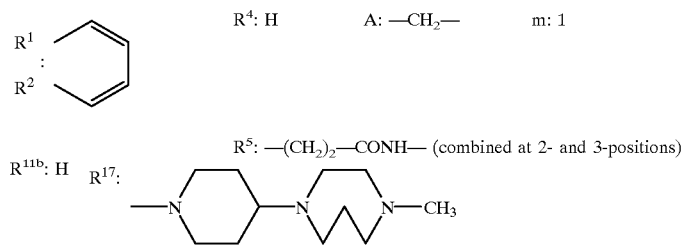

R⁴: H   A: —CH₂—   m: 1

R¹¹ᵇ: H   R¹⁷:   R⁵: —(CH₂)₂—CONH— (combined at 2- and 3-positions)

M.p. 173–175° C.    Form: Dimethanesulfonate
Solvent for recrystallization: Diethyl ether-ethanol-water
Crystalline form: Yellow powder Example 214

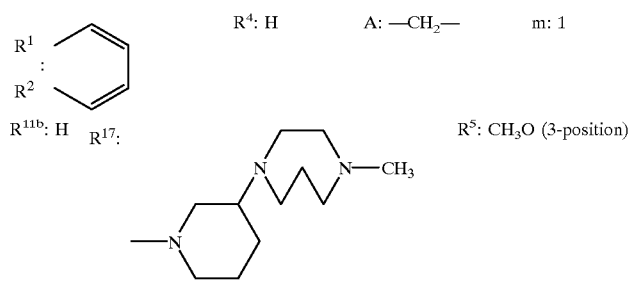

R⁴: H   A: —CH₂—   m: 1

R¹¹ᵇ: H   R¹⁷:   R⁵: CH₃O (3-position)

M.p. 168–172° C.    Crystalline form: Yellow powder
Solvent for recrystallization: Ethanol-diethyl ether    Form: 2HCl

TABLE 104

Example 215

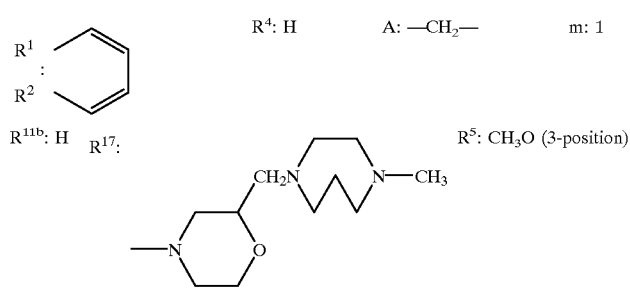

R⁴: H   A: —CH₂—   m: 1

R¹¹ᵇ: H   R¹⁷:   R⁵: CH₃O (3-position)

M.p. 155–160° C.    NMR (40)
Crystalline form: Pale yellow powder    Form: 2HCl
Solvent for recrystallization: Ethanol-water-isopropyl alcohol-diethyl ether Example 216

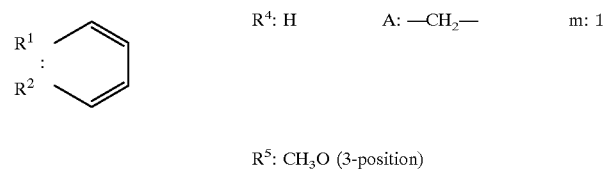

R⁴: H   A: —CH₂—   m: 1

R⁵: CH₃O (3-position)

TABLE 104-continued

R¹¹ᵇ: H    R¹⁷: —N(piperidine)—N(piperazine)N—C₂H₅

M.p. 163–165° C.    Crystalline form: Pale yellow powder
Solvent for recrystallization: Ethanol-water    Form: 2HCl Example 217

R¹: CH₃    R⁴: H    A: —CH₂—    m: 1
R²: CH₃    R⁵: CH₃O (3-position)
R¹¹ᵇ: H    R¹⁷: —N(piperidine)—N(piperazine)N—CH₃

M.p. 190–193° C. (decomp.)    Crystalline form: Yellow powder
Solvent for recrystallization: Ethanol-water    Form: 2HCl

TABLE 105

$$R^{17}OC-C(R^{11b})=C(H)-C(O)-[C_6H_3(R^5)_m]-S-A-C(O)-N(R^4)-[thiazole\ R^1, R^2]$$

Example 218

R¹ ⟩ : R² ⟩    R⁴: H    A: —CH₂—    m: 1

R¹¹ᵇ: H    R¹⁷: —N(piperidine)—N(piperazine)N—CH₃    R⁵: CH₃O (2-position)

M.p. 174.4–176.5° C.    Crystalline form: Yellow powder
Solvent for recrystallization: Ethanol-water-diethyl ether    Form: 2HCl

TABLE 106

$$R^{17}OC-C(R^{11b})=C(H)-C(O)-[C_6H_3(R^5)_m]-O-A-C(O)-N(R_4)-[thiazole\ R^1, R^2]$$

Example 219

R¹ ⟩ : R² ⟩    R⁴: H    A: —CH₂—    m: 1

TABLE 106-continued

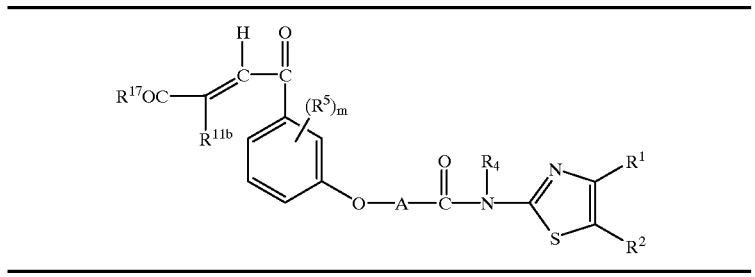

| | | |
|---|---|---|
| $R^{11b}$: H    $R^{17}$: 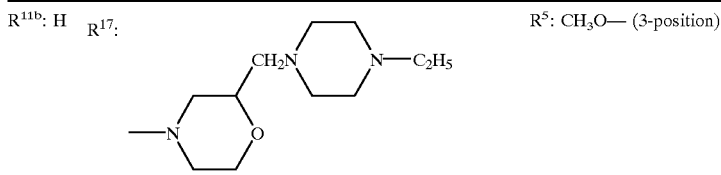 | | $R^5$: $CH_3O$— (3-position) |

M.p. 162–165° C.      Crystalline form: Pale yellow powder
Solvent for recrystallization: Diethyl ether-water-ethanol      Form: 2HCl
Example 220

| $R^1$ $R^2$ | R4: H | A: —$CH_2$— | m: 1 |
|---|---|---|---|
| $R^{11b}$: H   $R^{17}$: 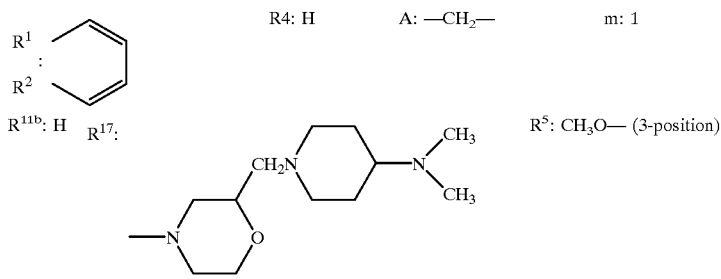 | | | $R^5$: $CH_3O$— (3-position) |

M.p. 206–211° C.      Crystalline form: Pale yellow powder      Form: 2HCl
Solvent for recrystallization: Ethanol-water-diethyl ether-isopropyl alcohol
NMR (41)
Example 221

| $R^1$ $R^2$ | $R^4$: H | A: —$CH_2$— | m: 1 |
|---|---|---|---|
| $R^{11b}$: H   $R^{17}$: 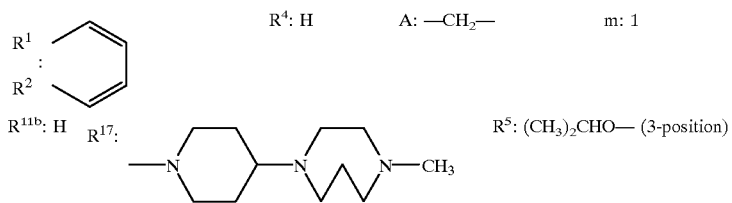 | | | $R^5$: $(CH_3)_2CHO$— (3-position) |

M.p. 168–172° C.      Crystalline form: Yellow powder      Form: 2HCl
Solvent for recrystallization: Ethanol-water-isopropyl alcohol-diethyl ether

TABLE 107

Example 222

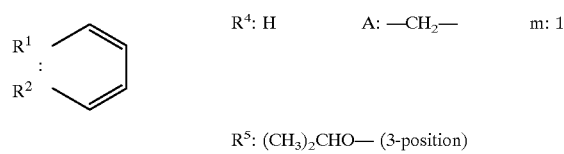      $R^4$: H      A: —$CH_2$—      m: 1

$R^5$: $(CH_3)_2CHO$— (3-position)

TABLE 107-continued

R$^{11b}$: H  R$^{17}$:

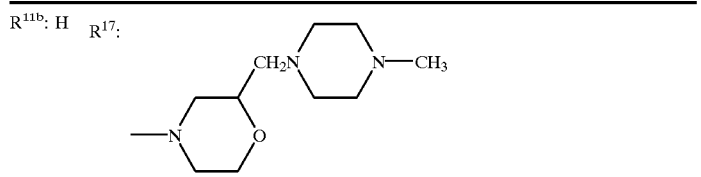

M.p. 203–208° C.   Crystalline form: Pale yellow powder   Form: 2HCl
Solvent for recrystallization: Ethanol-water-isopropyl alcohol-diethyl ether
NMR (42)
Example 223

R$^1$  
R$^2$    R$^4$: H    A: —CH$_2$—    m: 1

R$^{11b}$: H  R$^{17}$:

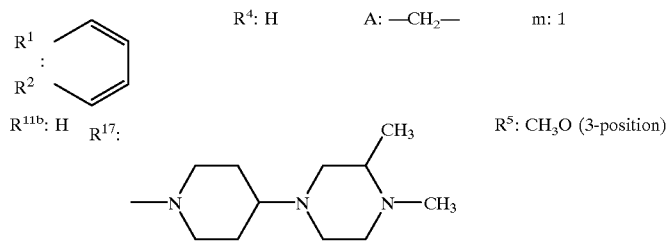

R$^5$: CH$_3$O (3-position)

M.p. 180–185° C.   Crystalline form: White powder   Form: 2HCl
Solvent for recrystallization: Ethanol-water   NMR (43)
Example 224

R$^1$  
R$^2$    R$^4$: H    A: —CH$_2$—    m: 1

R$^{11b}$: H  R$^{17}$:

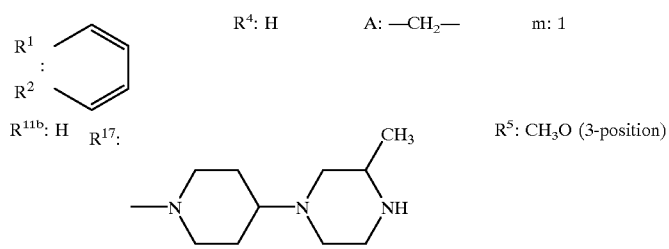

R$^5$: CH$_3$O (3-position)

M.p. 180–190° C.   Crystalline form: Yellow powder   Form: 2HCl
Solvent for recrystallization: Ethanol   NMR (44)

TABLE 108

Example 225

R$^1$  
R$^2$    R$^4$: H    A: —CH$_2$—    m: 1

R$^{11b}$: H  R$^{17}$:

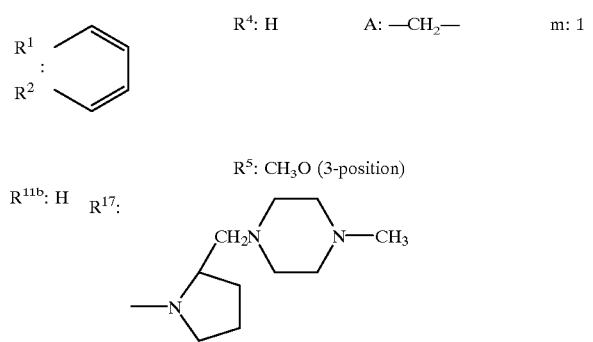

R$^5$: CH$_3$O (3-position)

M.p. 157–160° C.   Crystalline form: Pale yellow powder   Form: 2HCl
Solvent for recrystallization: Ethanol-water

TABLE 108-continued

Example 226

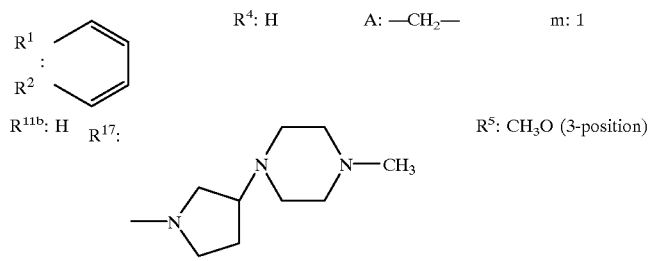

R⁴: H  A: —CH₂—  m: 1

R⁵: CH₃O (3-position)

M.p. 171–174° C.  Crystalline form: Pale yellow powder  Form: 2HCl
Solvent for recrystallization: Ethanol-water Example 227

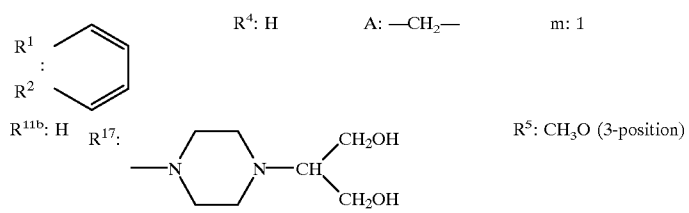

R⁴: H  A: —CH₂—  m: 1

R⁵: CH₃O (3-position)

M.p. 236–238° C.  Crystalline form: Pale yellow powder  Form: HCl
Solvent for recrystallization: Ethanol-water

TABLE 109

Example 228

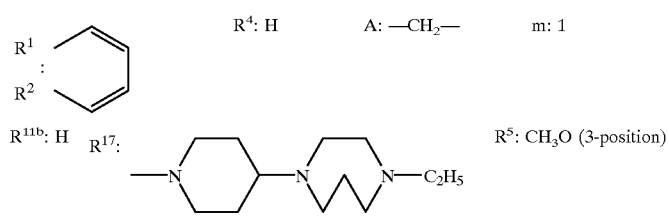

R⁴: H  A: —CH₂—  m: 1

R⁵: CH₃O (3-position)

M.p. 161–165° C.  Crystalline form: Pale yellow powder  Form: 2HCl
Solvent for recrystallization: Ethanol-water-diethyl ether-isopropyl alcohol Example 229

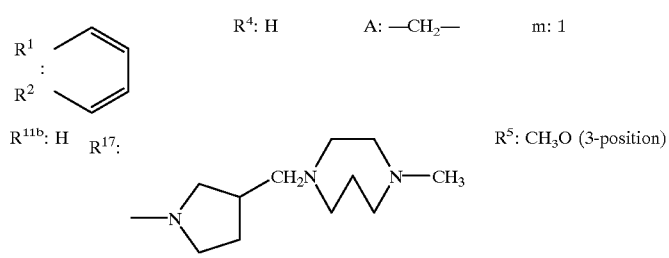

R⁴: H  A: —CH₂—  m: 1

R⁵: CH₃O (3-position)

M.p. 191–194° C.  Crystalline form: Pale yellow powder  Form: 2HCl
Solvent for recrystallization: Ethanol-water

TABLE 109-continued

Example 230

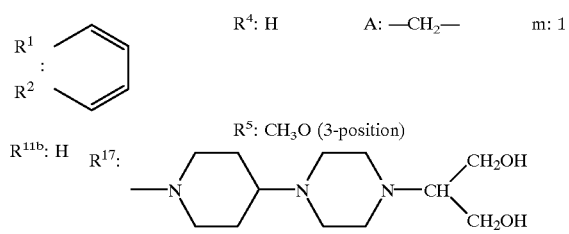

R⁴: H    A: —CH₂—    m: 1

R⁵: CH₃O (3-position)

R¹¹ᵇ: H    R¹⁷:

M.p. 200–210° C. (decomp.)    Crystalline form: Yellow powder    NMR (45)
Solvent for recrystallization: Ethanol-water-diethyl ether    Form: 2HCl

TABLE 110

Example 231

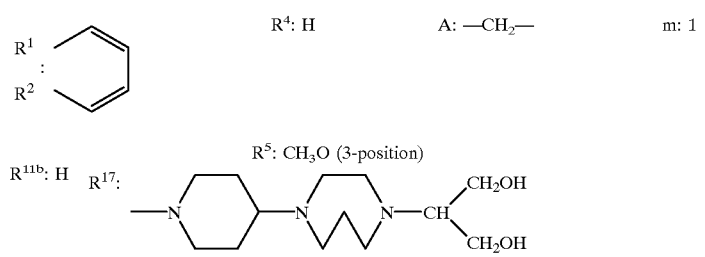

R⁴: H    A: —CH₂—    m: 1

R⁵: CH₃O (3-position)

R¹¹ᵇ: H    R¹⁷:

M.p. 165–170° C.    Crystalline form: Yellow powder    Form: 2HCl
Solvent for recrystallization: Diethyl ether-ethanol-isopropyl alcohol-water
NMR (46)

Example 232

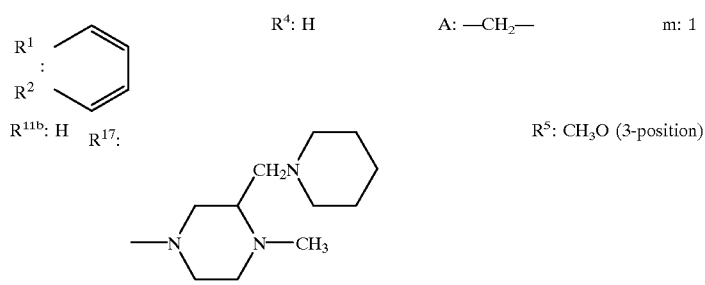

R⁴: H    A: —CH₂—    m: 1

R¹¹ᵇ: H    R¹⁷:    R⁵: CH₃O (3-position)

M.p. 150–170° C.    Crystalline form: Yellow powder    NMR (47)
Solvent for recrystallization: Isopropyl alcohol    Form: Dimethanesulfonate Example 233

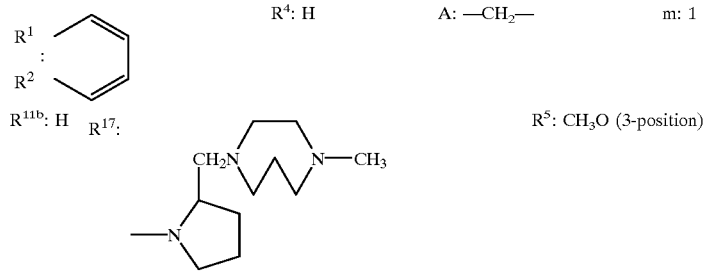

R⁴: H    A: —CH₂—    m: 1

R¹¹ᵇ: H    R¹⁷:    R⁵: CH₃O (3-position)

M.p. 166–169° C.    Crystalline form: Pale yellow powder
Solvent for recrystallization: Ethanol-water    Form: 2HCl

TABLE 111

Example 234

R¹ ⌬ R²

R⁴: H　　A: —CH₂—　　m: 1

R¹¹ᵇ: H　R¹⁷:

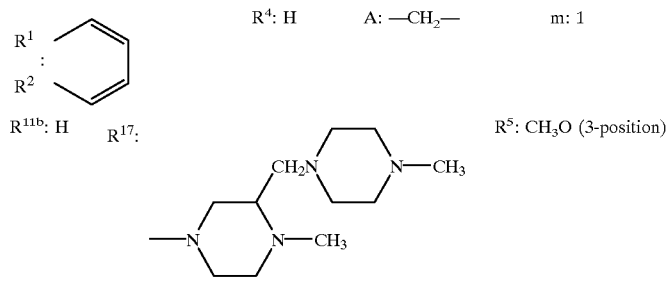

R⁵: CH₃O (3-position)

M.p. 186–200° C. (decomp.)　　Crystalline form: Yellow powder　　Form: 3HCl
Solvent for recrystallization: Isopropyl alcohol　　　　NMR (48)

Example 235

R¹: CH₃　　　　R⁴: H　　A: —CH₂—　　m: 1
R²: CH₃　　　　R⁵: CH₃O (3-position)
R¹¹ᵇ: H　R¹⁷:

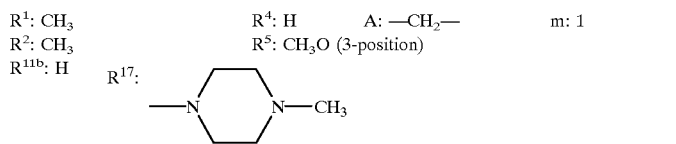

M.p. 204–210° C. (decomp.)　　Crystalline form: Yellow powder　　Form: HCl
Solvent for recrystallization: Ethanol-water-diethyl ether　　　　NMR (49)

Example 236

R¹: H　　　　R⁴: H　　A: —CH₂—　　m: 1
R²: H　　　　R⁵: CH₃O (3-position)
R¹¹ᵇ: H　R¹⁷:

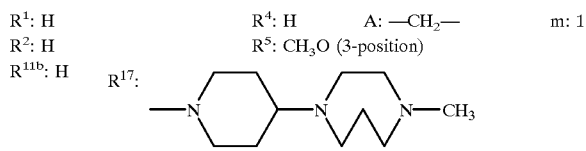

M.p. 157–160° C.　　Crystalline form: Yellow powder
Solvent for recrystallization: Ethanol-water　　　　Form: 2HCl

TABLE 112

Example 237

R¹: H　　　　R⁴: H　　A: —CH₂—　　m: 1
R²: H　　　　R⁵: CH₃O (3-position)
R¹¹ᵇ: H　R¹⁷:

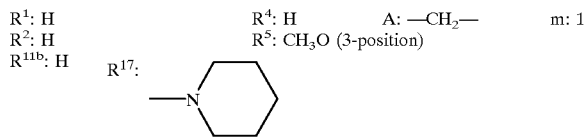

M.p. 83.1–85.5° C.　　Crystalline form: Yellow powder　　Form: Free
Solvent for recrystallization: Ethanol-diethyl ether-n-hexane Example 238

R¹ ⌬ R²

R⁴: H　　A: —CH₂—　　m: 1

R¹¹ᵇ: H　R¹⁷:

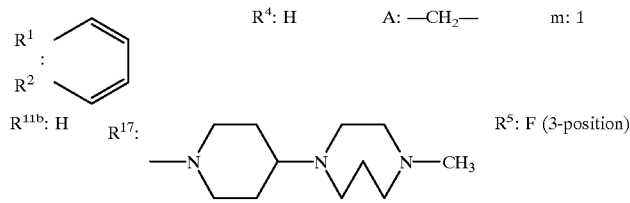

R⁵: F (3-position)

M.p. 215–220° C.　　Crystalline form: White powder　　Form: 2HCl
Solvent for recrystallization: Ethanol-isopropyl alcohol-diethyl ether-water
NMR (50)

TABLE 112-continued

Example 239

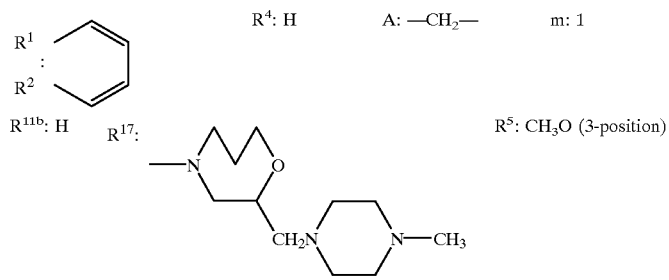

R⁴: H  A: —CH₂—  m: 1
R⁵: CH₃O (3-position)

M.p. 149–154° C.  Crystalline form: Pale yellow powder  Form: 2HCl
Solvent for recrystallization: Ethanol-water-isopropyl alcohol-diethyl ether
NMR (51)

TABLE 113

Example 240

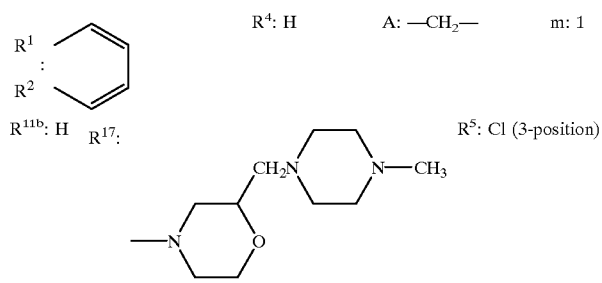

R⁴: H  A: —CH₂—  m: 1
R⁵: Cl (3-position)

M.p. 126–129° C.  Crystalline form: Pale yellow powder  Form: Free
Solvent for recrystallization: Ethanol-isopropyl alcohol

Example 241

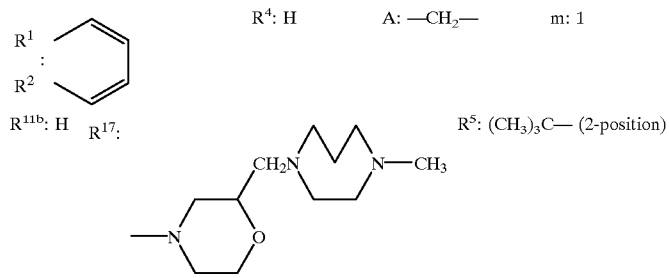

R⁴: H  A: —CH₂—  m: 1
R⁵: (CH₃)₃C— (2-position)

M.p. 181–183.8° C.  Crystalline form: Pale yellow powder  Form: 2HCl
Solvent for recrystallization: Ethanol-water-diethyl ether

Example 242

R¹: CH₃  R⁴: H  A: —CH₂—  m: 1
R²: CH₃  R⁵: CH₃O (3-position)
R¹¹ᵇ: H  R¹⁷:

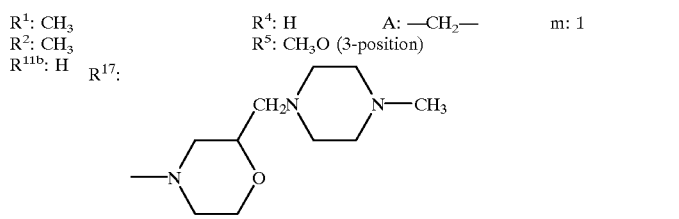

M.p. 192–197° C. (decomp.)  Crystalline form: Yellow powder  Form: 2HCl
Solvent for recrystallization: Ethanol-water  NMR (52)

TABLE 114

Example 243

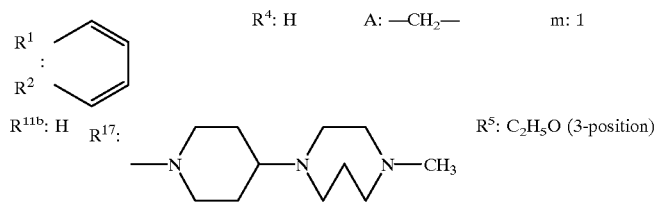

R⁴: H    A: —CH₂—    m: 1
R¹¹ᵇ: H    R¹⁷:    R⁵: C₂H₅O (3-position)

M.p. 166–170° C.    Crystalline form: Pale yellow powder    Form: 2HCl
Solvent for recrystallization: Ethanol-water Example 244

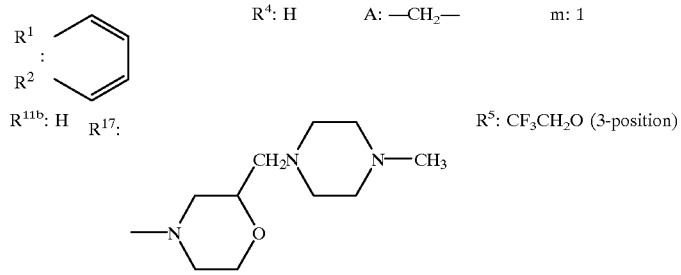

R⁴: H    A: —CH₂—    m: 1
R¹¹ᵇ: H    R¹⁷:    R⁵: CF₃CH₂O (3-position)

Crystalline form: Pale yellow powder    Form: Dimethanesulfonate    NMR (53)
Solvent for recrystallization: Ethanol-water-diethyl ether-isopropyl alcohol Example 245

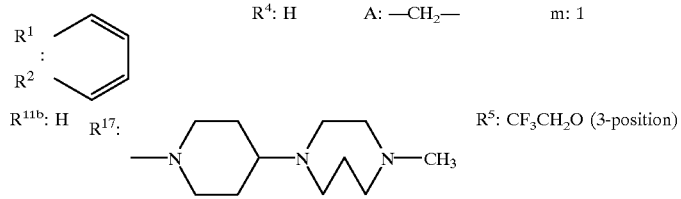

R⁴: H    A: —CH₂—    m: 1
R¹¹ᵇ: H    R¹⁷:    R⁵: CF₃CH₂O (3-position)

M.p. 179–183° C.    Crystalline form: Pale yellow powder    Form: 2HCl
Solvent for recrystallization: Isopropyl alcohol-ethanol-water-diethyl ether

TABLE 115

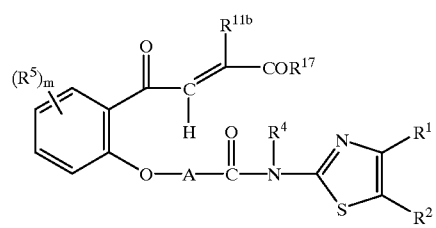

Example 246

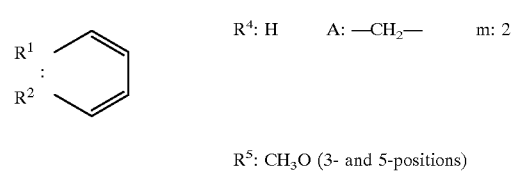

R⁴: H    A: —CH₂—    m: 2

R⁵: CH₃O (3- and 5-positions)

TABLE 115-continued

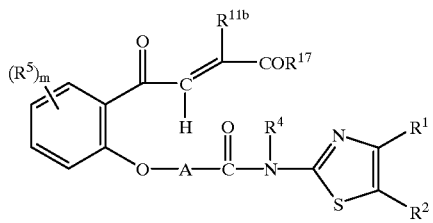

R¹¹ᵇ: H    R¹⁷:

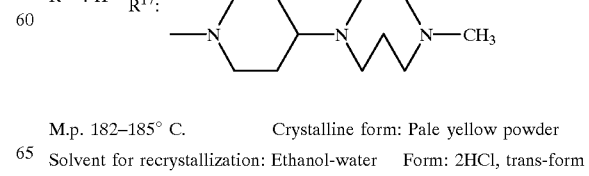

M.p. 182–185° C.    Crystalline form: Pale yellow powder
Solvent for recrystallization: Ethanol-water    Form: 2HCl, trans-form

TABLE 115-continued

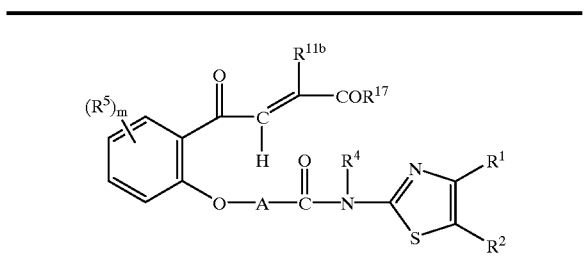

Example 247

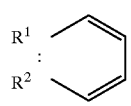    R$^4$: H    A: —CH$_2$—    m: 2

TABLE 115-continued

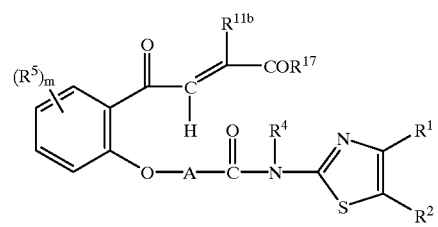

R$^{11b}$: H    R$^{17}$: 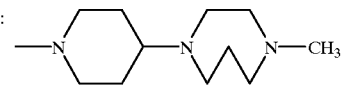    R$^5$: CH$_3$O (3- and 5-positions)

M.p. 177–183° C.    Crystalline form: Pale yellow powder
Solvent for recrystallization Ethanol-water    Form: 2HCl, cis-form

TABLE 116

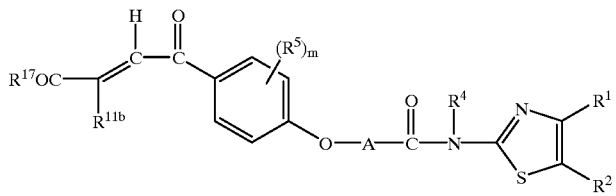

Example 248

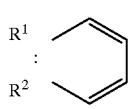    R$^4$: H    A: —CH$_2$—    m: 1

R$^{11b}$: H    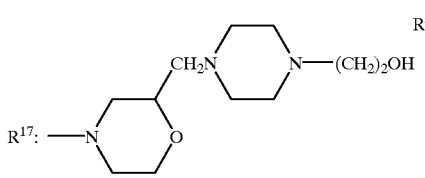    R$^5$: CH$_3$O (3-position)

M.p. 158–162° C.    Crystalline form: Pale yellow powder    Form: 2HCl
Solvent for recrystallization: Ethanol-water-diethyl ether Example 249

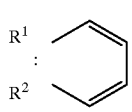    R$^4$: H    A: —CH$_2$—    m: 1

TABLE 116-continued

[Structure: R^17OC(=O)-C(R^11b)=C(H)-C(=O)-phenyl(R^5)_m-O-A-C(=O)-N(R^4)-thiazole(R^1, R^2)]

R^11b: H  R^5: CH₃O (3-position)

R^17: —N(piperazine)—CH₂N(piperazine)N—CH₃, with N—CH₃

M.p. 167–171° C. (decomp.)  Crystalline form: Yellow powder
Solvent for recrystallization: Ethanol-water  Form: 3HCl

Example 250

R^1: CH₃  R^4: H  A: —CH₂—  m: 1
R^2: CH₃  R^5: CH₃O (3-position)

R^11b: H

R^17: —N(piperazine)N—(CH₂)₂OH

M.p. 137–140° C.  Crystalline form: Yellow powder
Solvent for recrystallization: Ethanol-water  Form: Methanesulfonate

TABLE 117

Example 251

R^1: (CH₃)₃C— (3-position)  R^4: H  A: —CH₂—  m: 1
R^2: H  R^5: CH₃O (3-position)

R^11b: H

R^17: —N(piperazine)N—CH₃

M.p. 129–131° C.  Crystalline form: Pale yellow powder
Solvent for recrystallization: Ethanol-water-diethyl ether-isopropyl alcohol
Form: Dimethanesulfonate

Example 252

R^1, R^2: cyclohexyl  R^4: H  A: —CH₂—  m: 1

R^11b: H  R^5: CH₃O (3-position)

R^17: —N(piperazine)N—CH₃

M.p. 230–231° C.  Crystalline form: Pale yellow powder
Solvent for recrystallization: Ethanol-water  Form: Dimethanesulfonate

TABLE 117-continued

Example 253

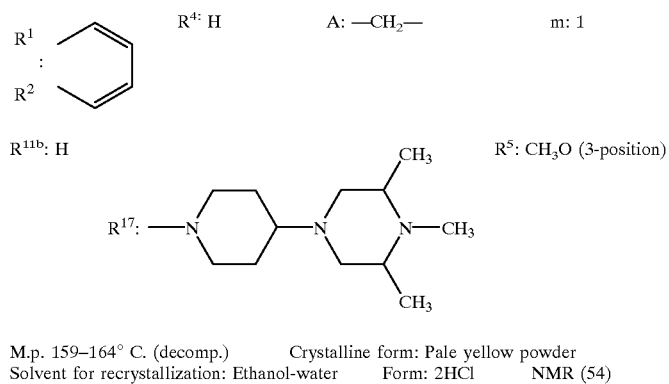

M.p. 159–164° C. (decomp.)  Crystalline form: Pale yellow powder
Solvent for recrystallization: Ethanol-water  Form: 2HCl  NMR (54)

TABLE 118

Example 254

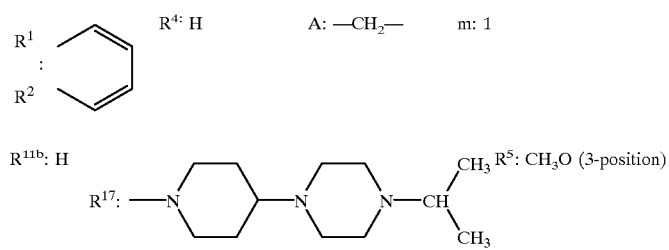

M.p. 202–205° C. (decomp.)  Crystalline form: White powder
Solvent for recrystallization: Ethanol-water  Form: 2HCl Example 255

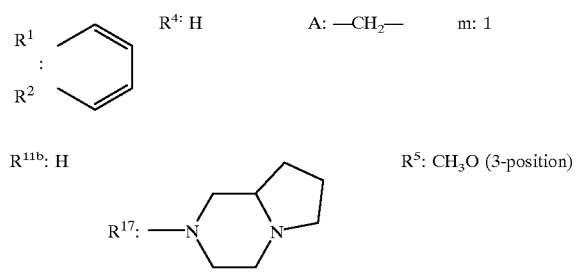

M.p. 115–120° C.  Crystalline form: Pale brown powder  NMR (55)
Solvent for recrystallization: Ethanol-water-isopropyl alcohol-diethyl ether
Form: Methanesulfonate Example 256

TABLE 118-continued $R^{11b}$: H $R^{17}$: —[piperidine]—[octahydropyrrolo[1,2-a]pyrazine]

$R^5$: $CH_3O$ (3-position)

M.p. 168.5–171.5° C.   Crystalline form: White powder
Solvent for recrystallization: Ethanol-water   Form: 2HCl

TABLE 119

Example 257

$R^1$ / $R^2$ : [benzene ring]   $R^4$: H   A: —$CH_2$—   m: 1

$R^{11b}$: H $R^{17}$: —[piperidine]—[N-(3,3-dimethyl-4-methylpiperazine)]

$R^5$: $CH_3O$ (3-position)

M.p. 163–166° C.   Crystalline form: White powder
Solvent for recrystallization: Ethanol-water   Form: 2HCl

Example 258

$R^1$ / $R^2$ : [benzene ring]   $R^4$: H   A: —$CH_2$—   m: 1

$R^{11b}$: H $R^{17}$: —[piperidine]—[decahydroquinolizine]

$R^5$: $CH_3O$ (3-position)

M.p. 177.5–179° C.   Crystalline form: White powder
Solvent for recrystallization: Ethanol-water   Form: 2HCl

Example 259

$R^1$ / $R^2$ : [cyclohexane ring]   $R^4$: H   A: —$CH_2$—   m: 1

$R^{11b}$: H $R^{17}$: —[piperidine]—[N-methylpiperazine]

$R^5$: $CH_3O$ (3-position)

M.p. 165–168.5° C.   Crystalline form: Pale yellow powder   Form: 2HCl
Solvent for recrystallization: Ethanol-water-diethyl ether

TABLE 120

Example 260

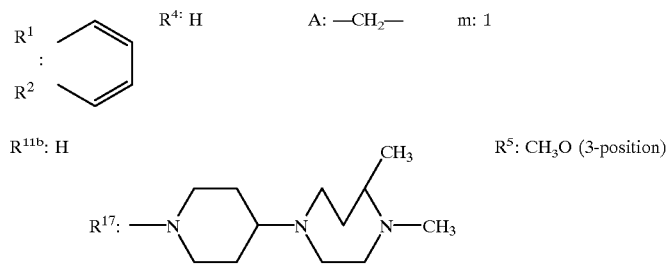

R⁴: H     A: —CH₂—     m: 1

R¹¹ᵇ: H     R⁵: CH₃O (3-position)

M.p. 159–160° C.     Crystalline form: Pale yellow powder
Solvent for recrystallization: Ethanol-water     Form: 2HCl Example 261

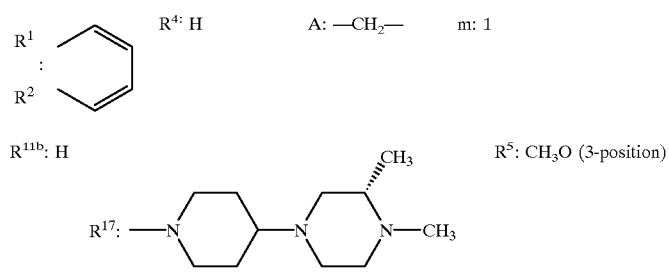

R⁴: H     A: —CH₂—     m: 1

R¹¹ᵇ: H     R⁵: CH₃O (3-position)

M.p. 177–178.2° C.     Crystalline form: Pale yellow powder
Solvent for recrystallization: Ethanol-water     Form: 2HCl
S-(−)-compound: $[\alpha]_D^{22}$: −5.75°(c = 2, water)

Example 262

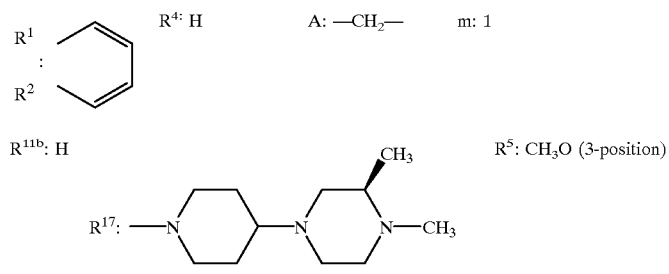

R⁴: H     A: —CH₂—     m: 1

R¹¹ᵇ: H     R⁵: CH₃O (3-position)

M.p. 173–175° C.     Crystalline form: Pale yellow powder
Solvent for recrystallization: Ethanol-water     Form: 2HCl
R-(+)-compound: $[\alpha]_D^{22}$: +4.35°(c = 2, water)

TABLE 121

Example 263

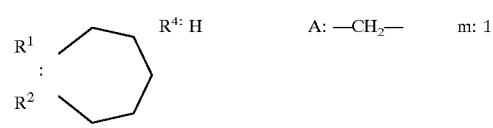

R⁴: H     A: —CH₂—     m: 1

TABLE 121-continued

R[11b]: H 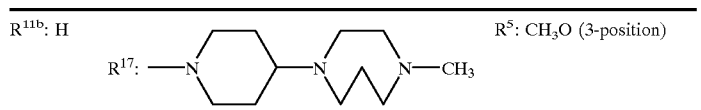 R[5]: CH$_3$O (3-position)

M.p. 168–170.5° C.　　Crystalline form: White powder
Solvent for recrystallization: Ethanol-water　　　　Form: 2HCl
Example 264

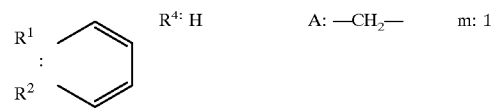 R[4]: H　　A: —CH$_2$—　　m: 1

R[11b]: H 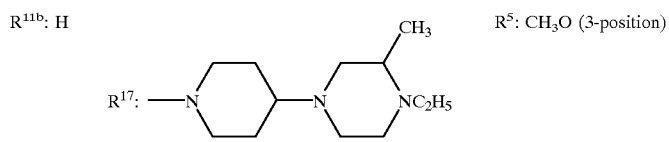 R[5]: CH$_3$O (3-position)

M.p. 156–159° C.　　Crystalline form: Pale yellow powder
Solvent for recrystallization: Ethanol-water　　　　Form: 2HCl
Example 265

 R[4]: H　　A: —CH$_2$—　　m: 1

R[5]: CH$_3$O (3-position)

R[11b]: H 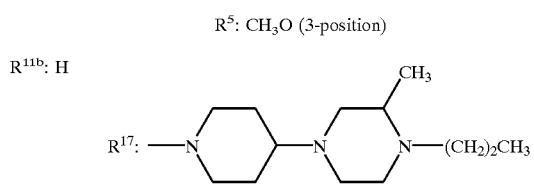

M.p. 176–179° C.　　Crystalline form: Pale yellow powder
Solvent for recrystallization: Ethanol-water　　　　Form: 2HCl

TABLE 122

Example 266

 R[4]: H　　A: —CH$_2$—　　m: 1

R[5]: C$_2$H$_5$O (3-position)

R[11b]: H 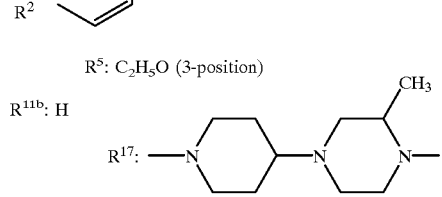

M.p. 159–161° C.　　Crystalline form: Yellow powder　　Form: 2HCl
Solvent for recrystallization: Ethanol-water-isopropyl alcohol-diethyl ether
Example 267

R[1]:  R[4]: H　　A: —CH$_2$—　　m: 1

R[2]: CH$_3$　　R[5]: CH$_3$O (3-position)

TABLE 122-continued

R[11b]: H 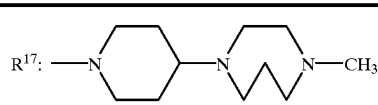

M.p. 166–169° C.　　Crystalline form: Yellow powder　　Form: 2HCl
Solvent for recrystallization: Ethanol-water-diethyl ether-isopropyl alcohol
Example 268

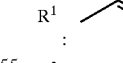  R[4]: H　　A: —CH$_2$—　　m: 1

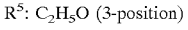

R[5]: C$_2$H$_5$O (3-position)

R[11b]: H 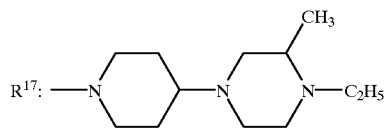

M.p. 215–217°C.　　Crystalline form: White powder
Solvent for recrystallization: Ethanol-water　　　　Form: 2HCl

TABLE 123

Example 269

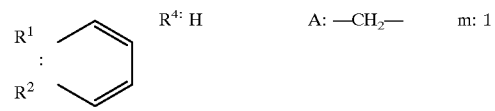

R⁴: H  A: —CH₂—  m: 1

R¹¹ᵇ: H

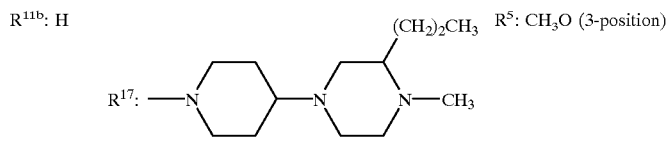

R⁵: CH₃O (3-position)

M.p. 174–177° C.  Crystalline form: Yellow powder  Form: Free
Solvent for recrystallization: Ethanol-water Example 270

R⁴: H  A: —CH₂—  m: 1

R⁵: CH₃O (3-position)

R¹¹ᵇ: H

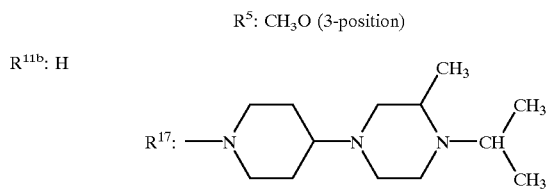

M.p. 202.5–205° C.  Crystalline form: White powder  Form: 2HCl
Solvent for recrystallization: Ethanol-water Example 271

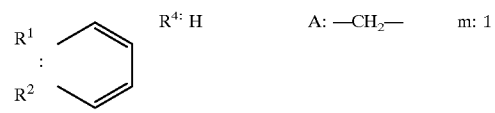

R⁴: H  A: —CH₂—  m: 1

R⁵: CH₃O (3-position)

R¹¹ᵇ: H

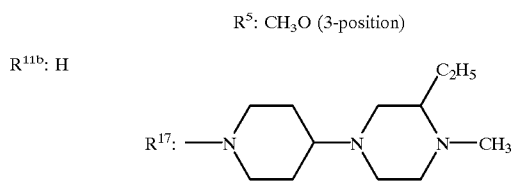

M.p. 155–158° C.  Crystalline form: Yellow powder  Form: 2HCl
Solvent for recrystallization: Ethanol-water-diisopropyl alcohol-diethyl ether

TABLE 124

Example 272

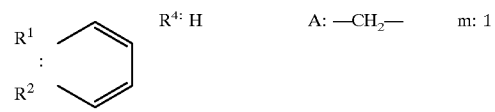

R⁴: H  A: —CH₂—  m: 1

TABLE 124-continued

R¹¹ᵇ: H 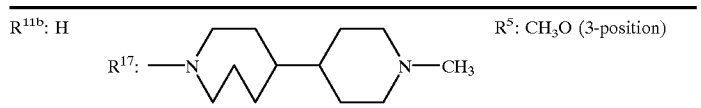 R⁵: CH₃O (3-position)

M.p. 202–204° C.  Crystalline form: Pale yellow powder  Form: 2HCl
Solvent for recrystallization: Ethanol-water

Example 273

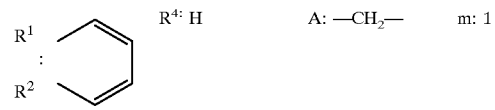 R⁴: H    A: —CH₂—    m: 1

R⁵: CH₃O (3-position)

R¹¹ᵇ: H 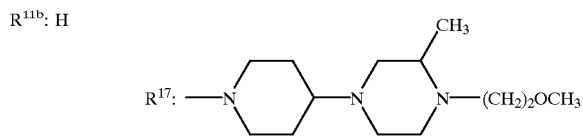

M.p. 163–165° C.  Crystalline form: Pale brown powder  Form: 2HCl
Solvent for recrystallization: Ethanol-water

Example 274

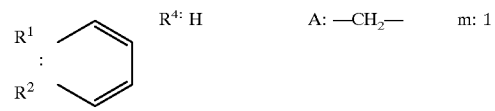 R⁴: H    A: —CH₂—    m: 1

R¹¹ᵇ: H 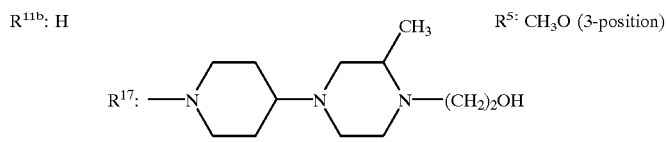 R⁵: CH₃O (3-position)

M.p. 160–162° C.  Crystalline form: Pale yellow powder
Solvent for recrystallization: Ethanol-water            Form: 2HCl

TABLE 125

Example 275

 R⁴: H    A: —CH₂—    m: 1

R¹¹ᵇ: H                                   R⁵: CH₃O (3-position)

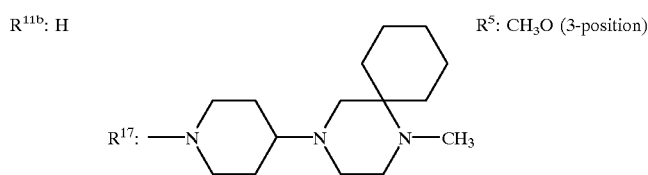

M.p. 158–160° C.     Crystalline form: Pale yellow powder     Form: 2HCl
Solvent for recrystallization: Ethanol-diethyl ether-water TABLE 125-continued Example 276

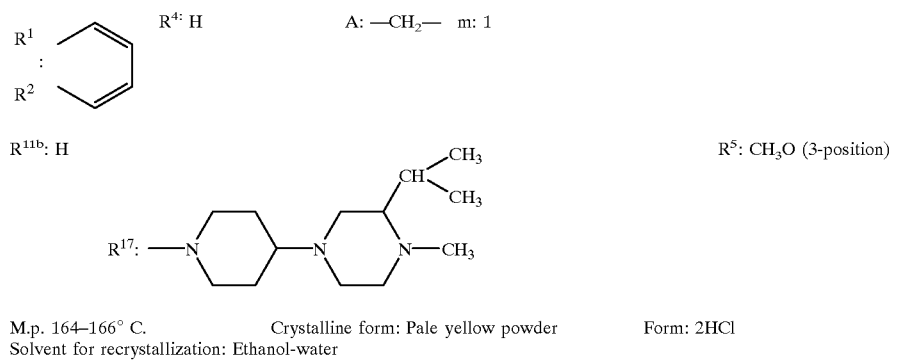

M.p. 164–166° C.   Crystalline form: Pale yellow powder   Form: 2HCl
Solvent for recrystallization: Ethanol-water Using the suitable starting compounds, the compounds as listed in Tables 126–128 are obtained in the same manner as in Example 5.

TABLE 126

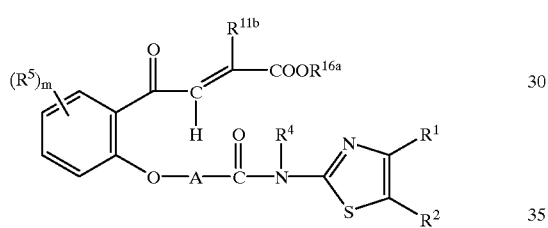

Example 277

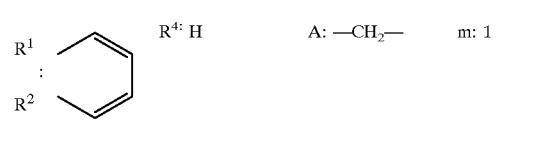

$R^{16a}$: $C_2H_5$   $R^{11b}$: H   $R^5$: H
M.p. 130.5–132° C.   Crystalline form: Pale orange powder   Form: Free
Solvent for recrystallization: Dimethylformamide-methanol

TABLE 127

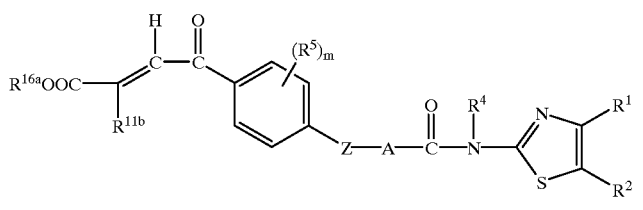

Example 278

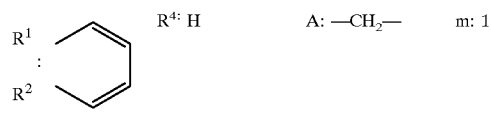

R⁴: H    A: —CH₂—    m: 1

R¹⁶ᵃ: C₂H₅    Z: O
R¹¹ᵇ: H    R⁵: H
M.p. 183.5–184° C.    Crystalline form: White powder
Solvent for recrystallization: Dichloromethane-ethanol    Form: Free Example 279

R⁴: H    A: —CH₂—    m: 1

R¹⁶ᵃ: C₂H₅    Z: O
R¹¹ᵇ: H

R⁵: —(CH₂)₃N(piperazine)N—CH₃  (2-position)

M.p. 221° C. (decomp.)    Crystalline form: Pale yellow powder
Solvent for recrystallization: Diethyl ether-ethanol    Form: 2HCl

TABLE 128

Example 280

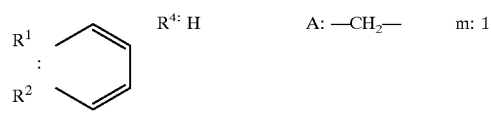

R⁴: H    A: —CH₂—    m: 1

R¹⁶ᵃ: CH₃    Z: O
R¹¹ᵇ: CH₃    R⁵: CH₃O (2-position)
M.p. 124–126.5° C.    Crystalline form: Pale yellow powder
Solvent for recrystallization: Ethyl acetate-n-hexane    Form: Free Example 281

R⁴: H    A: —CH₂—    m: 1

R¹⁶ᵃ: C₂H₅    Z: S
R¹¹ᵇ: H    R⁵: CH₃O (2-position)
M.p. 156–159° C.    Crystalline form: Yellow powder
Solvent for recrystallization: Ethanol-dichloromethane    Form: Free Using the suitable starting compounds, the compounds as listed in Tables 129–149 are obtained in the same manner as in Example 8.

TABLE 129

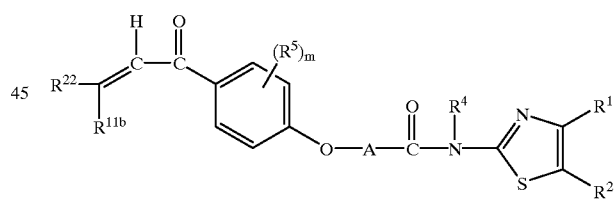

Example 282

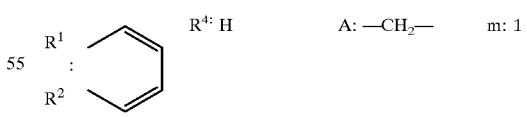

R⁴: H    A: —CH₂—    m: 1

R⁵: Isopropyl (2-position)

R¹¹ᵇ: H

R²²: 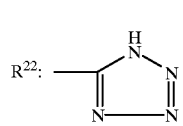

M.p. 137–138° C.    Crystalline form: Pale yellow powder    Form: Free

TABLE 129-continued

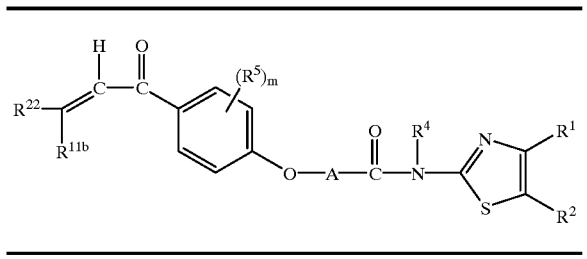

Example 283

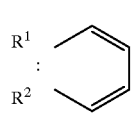  R⁴: H   A: —CH₂—   m: 1

R⁵: Isopropyl (2-position)

TABLE 129-continued

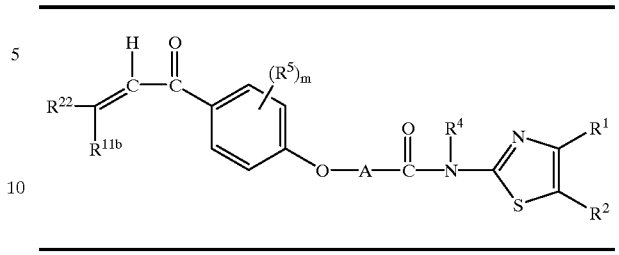

R¹¹ᵇ: H

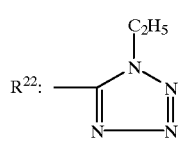

M.p. 197–198° C.   Crystalline form: White powder   Form: Free
Solvent for recrystallization: Dichloromethane-ethanol

TABLE 130

Example 284

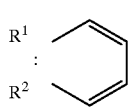  R⁴: H   A: —CH₂—   m: 1

R¹¹ᵇ: H

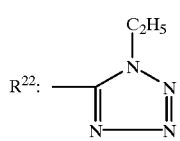   R⁵: 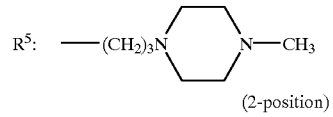
(2-position)

M.p. 240° C. (decomp.)   Crystalline form: Pale yellow powder   Form: 2HCl
Solvent for recrystallization: Ethanol-water Example 285

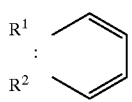  R⁴: H   A: —CH₂—   m: 1

R¹¹ᵇ: H   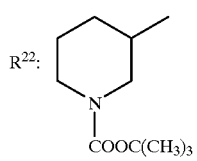   R⁵: Isopropyl (2-position)

M.p. 169.5–170° C.   Crystalline form: White powder   Form: Free
Solvent for recrystallization: Ethanol Example 286

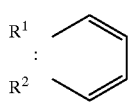  R⁴: H   A: —CH₂—   m: 1

TABLE 130-continued

R$^{11b}$: H

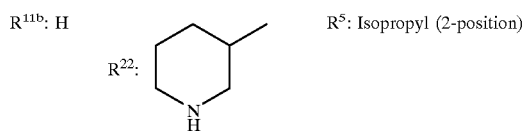

R$^{22}$:

R$^5$: Isopropyl (2-position)

Crystalline form: Pale brown powder   Form: HCl   NMR (7)

TABLE 131

Example 287

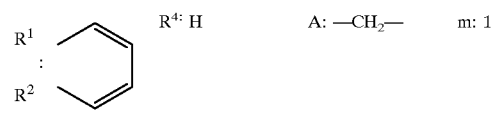

R$^1$
:
R$^2$

R$^4$: H   A: —CH$_2$—   m: 1

R$^{11b}$: H

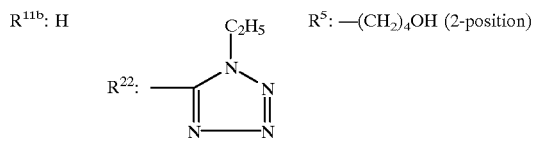

R$^{22}$:

R$^5$: —(CH$_2$)$_4$OH (2-position)

M.p. 170.5–175.5° C.   Crystalline form: Pale yellow powder   Form: Free
Solvent for recrystallization: Ethyl acetate-n-hexane   NMR (8)

Example 288

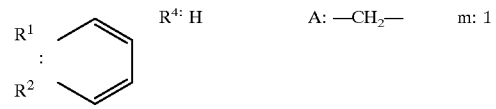

R$^1$
:
R$^2$

R$^4$: H   A: —CH$_2$—   m: 1

R$^{11b}$: H

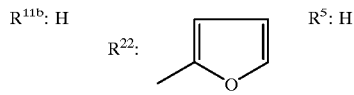

R$^{22}$:

R$^5$: H

M.p. 201.5–202.5° C. (decomp.)   Crystalline form: Pale yellow powder
Solvent for recrystallization: Ethanol-dichloromethane   Form: Free Example 289

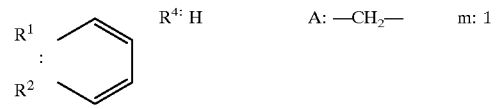

R$^1$
:
R$^2$

R$^4$: H   A: —CH$_2$—   m: 1

R$^{11b}$: H

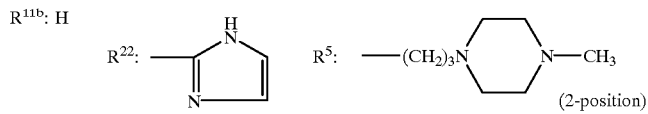

R$^{22}$:   R$^5$: —(CH$_2$)$_3$N⟨⟩N—CH$_3$ (2-position)

M.p. 195–198° C.   Crystalline form: Yellow powder
Solvent for recrystallization: Ethanol-water   Form: 3HCl

TABLE 132

Example 290

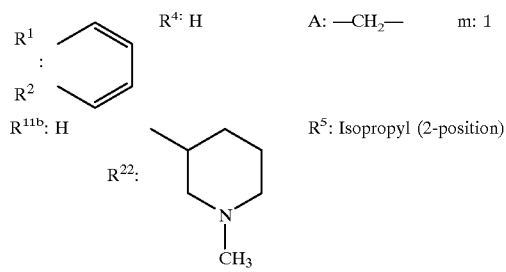

R⁴: H   A: —CH₂—   m: 1

R¹¹ᵇ: H

R⁵: Isopropyl (2-position)

M.p. 101–103.5° C.   Crystalline form: Yellow amorphous   Form: Free

Example 291

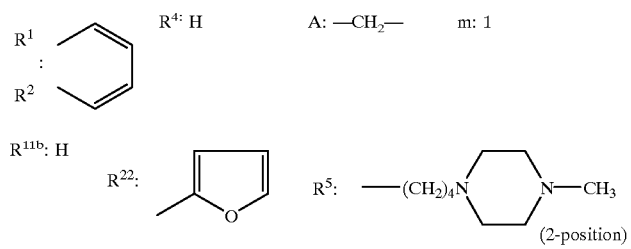

R⁴: H   A: —CH₂—   m: 1

R¹¹ᵇ: H

R⁵: —(CH₂)₄N⟨piperazine⟩—CH₃ (2-position)

M.p. 148.2–153° C.   Crystalline form: Pale brown powder   Form: 3HCl
Solvent for recrystallization: Ethanol-diethyl ether   NMR (10)

Example 292

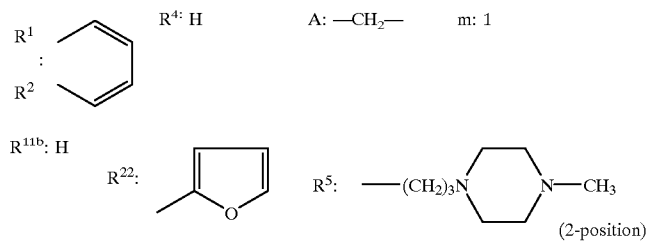

R⁴: H   A: —CH₂—   m: 1

R¹¹ᵇ: H

R⁵: —(CH₂)₃N⟨piperazine⟩—CH₃ (2-position)

M.p. 184–187° C.   Crystalline form: Pale yellow powder
Solvent for recrystallization: Ethanol-water-diethyl ether   Form: 2HCl

TABLE 133

Example 293

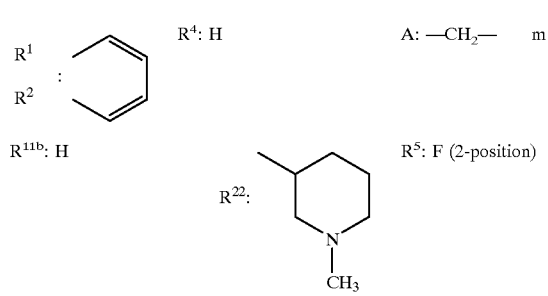

R⁴: H   A: —CH₂—   m: 1

R¹¹ᵇ: H

R⁵: F (2-position)

M.p. 151–154° C.   Crystalline form: White powder   Form: HCl
Solvent for recrystallization: Ethanol-water-diethyl ether-isopropyl alcohol

TABLE 133-continued

Example 294

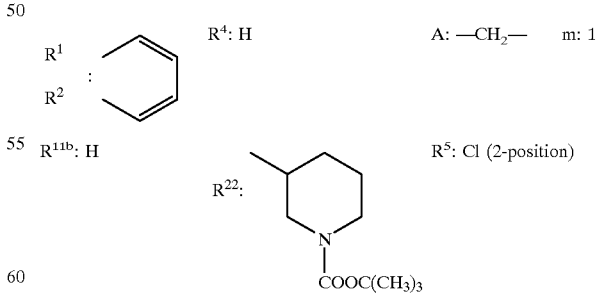

R⁴: H   A: —CH₂—   m: 1

R¹¹ᵇ: H

R⁵: Cl (2-position)

M.p. 207–209° C.   Crystalline form: White powder   Form: Free
Solvent for recrystallization: Ethyl acetate-n-hexane

TABLE 133-continued

Example 295

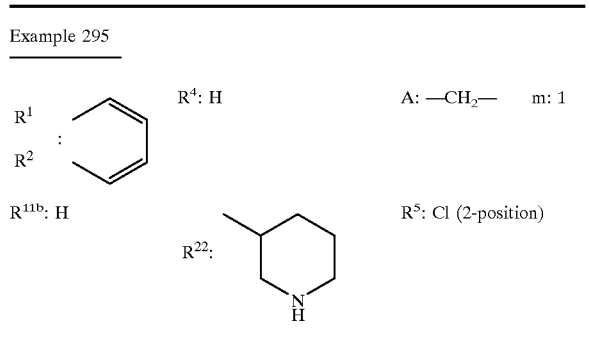

M.p. 164–166° C.   Crystalline form: Pale yellow powder
Solvent for recrystallization: Methanol-diethyl ether   Form: HCl

TABLE 134

Example 296

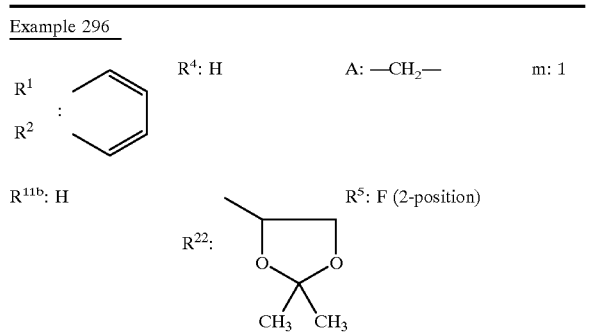

M.p. 141–141.5° C.   Crystalline form: White powder   Form: Free
Solvent for recrystallization: Dichloromethane-diethyl ether

TABLE 134-continued

Example 297

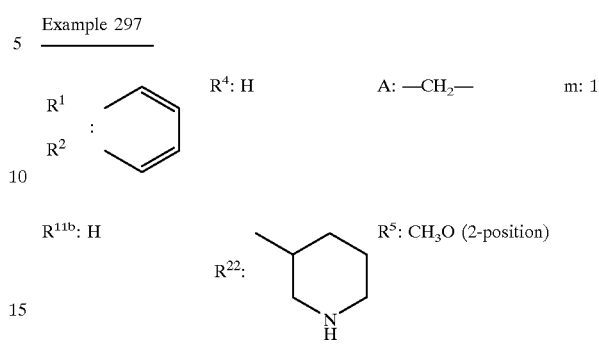

M.p. 186.5–191° C. (decomp.)   Crystalline form: Pale yellow powder
Solvent for recrystallization: Ethanol-diethyl ether
Form: Methanesulfonate Example 298

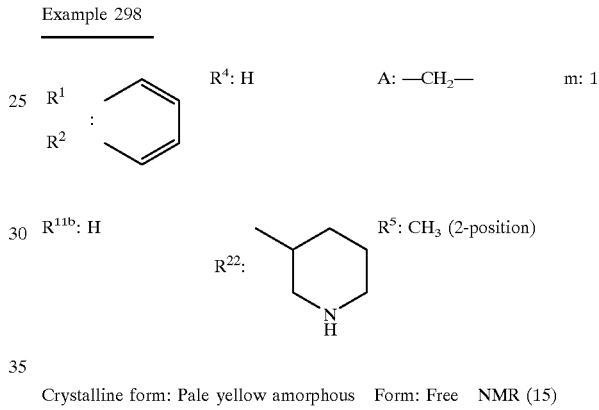

Crystalline form: Pale yellow amorphous   Form: Free   NMR (15)

TABLE 135

Example 299

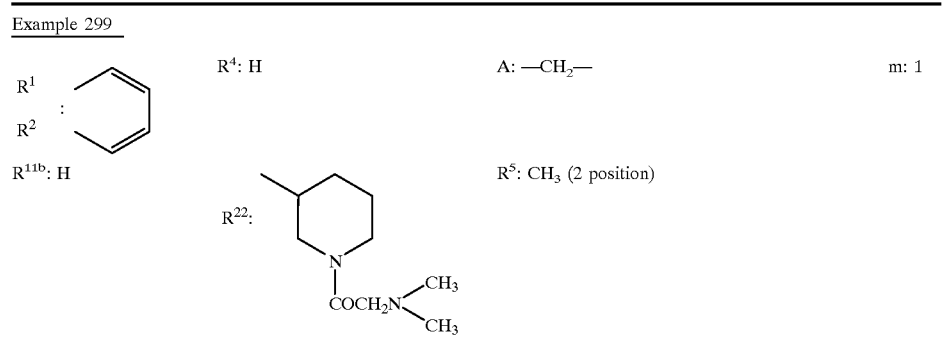

Crystalline form: Pale yellow amorphous   Form: Free   NMR (16)

Example 300

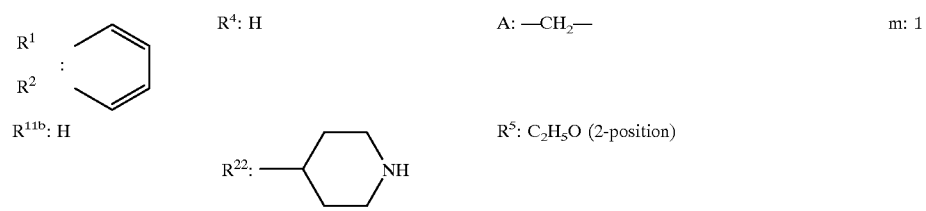

TABLE 135-continued

M.p. 202.5–203° C.  Crystalline form: Pale powder
Solvent for recrystallization: Ethanol-isopropyl alcohol-water-diethyl ether
Form: Methanesulfonate Example 301

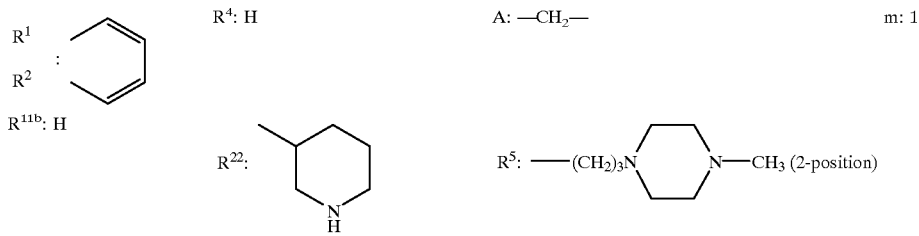

R$^1$ ⟨⟩ R$^2$  R$^4$: H   A: —CH$_2$—   m: 1

R$^{11b}$: H

R$^{22}$: (3-methylpiperidine)   R$^5$: —(CH$_2$)$_3$N⟨⟩N—CH$_3$ (2-position)

M.p. 186–189° C.  Crystalline form: Pale yellow powder
Solvent for recrystallization: Water-ethanol-diethyl ether   Form: 3HCl

TABLE 136

Example 302

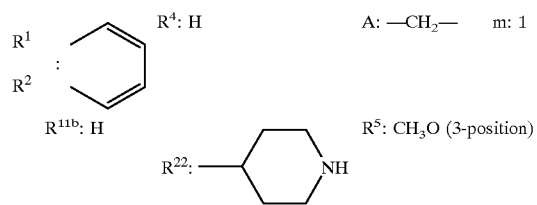

R$^1$ ⟨⟩ R$^2$   R$^4$: H   A: —CH$_2$—   m: 1

R$^{11b}$: H   R$^{22}$: (4-piperidinyl)   R$^5$: CH$_3$O (3-position)

M.p. 135–145° C.  Crystalline form: White powder  Form: Free
Solvent for recrystallization: Ethanol-dichloromethane  NMR (17)

Example 303

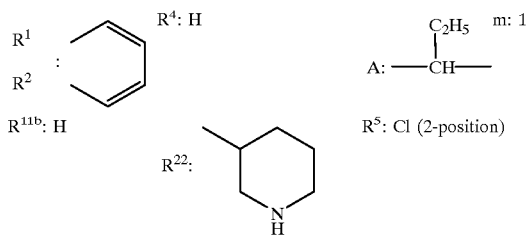

R$^1$ ⟨⟩ R$^2$   R$^4$: H   A: —CH(C$_2$H$_5$)—   m: 1

R$^{11b}$: H   R$^{22}$: (3-methylpiperidine)   R$^5$: Cl (2-position)

Crystalline form: Pale yellow amorphous  Form: Free  NMR (18)

Example 304

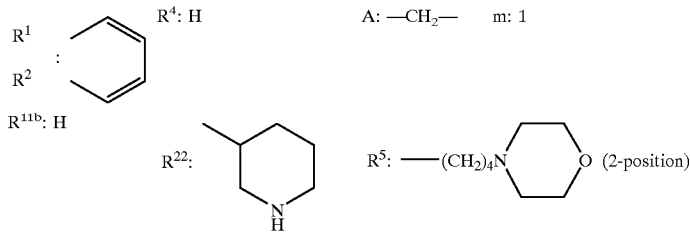

R$^1$ ⟨⟩ R$^2$   R$^4$: H   A: —CH$_2$—   m: 1

R$^{11b}$: H   R$^{22}$: (3-methylpiperidine)   R$^5$: —(CH$_2$)$_4$N⟨⟩O (2-position)

M.p. 146.5–150° C.  Crystalline form: White powder
Solvent for recrystallization: Ethanol-water  Form: 2HCl

TABLE 137

Example 305

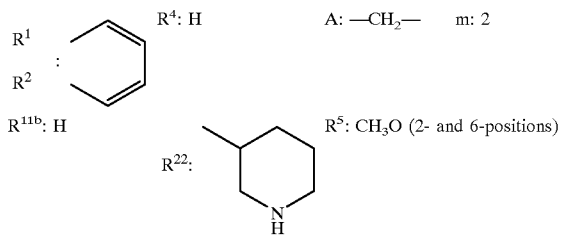

R⁴: H    A: —CH₂—    m: 2

R¹¹ᵇ: H    R⁵: CH₃O (2- and 6-positions)

M.p. 115–120° C.  Crystalline form: Pale yellow powder  NMR (19)
Solvent for recrystallization: Ethanol-diethyl ether  Form: Methanesulfonate Example 306

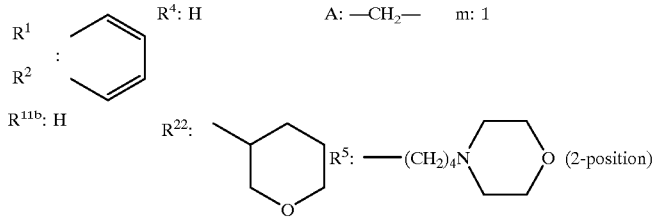

R⁴: H    A: —CH₂—    m: 1

R¹¹ᵇ: H    R⁵: —(CH₂)₄N(morpholine)O (2-position)

M.p. 207–208.5° C.  Crystalline form: White powder
Solvent for recrystallization: Diethyl ether-ethanol  Form: Methanesulfonate Example 307

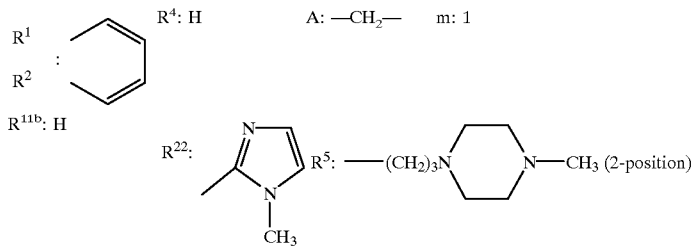

R⁴: H    A: —CH₂—    m: 1

R¹¹ᵇ: H    R⁵: —(CH₂)₃N(piperazine)N—CH₃ (2-position)

Crystalline form: Pale yellow amorphous  Form: Free  NMR (20)

TABLE 138

Example 308

R⁴: H    A: —CH₂—    m: 1

R¹¹ᵇ: H

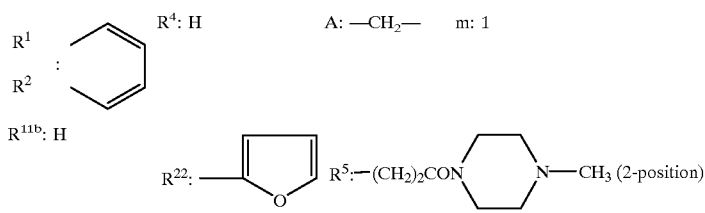

R⁵: —(CH₂)₂CON(piperazine)N—CH₃ (2-position)

M.p. 139–141° C.  Crystalline form: Yellow powder
Solvent for recrystallization: Ethanol  Form: Methanesulfonate Example 309

R⁴: H    A: —CH₂—    m: 1

TABLE 138-continued

R$^{11b}$: H  R$^{22}$: 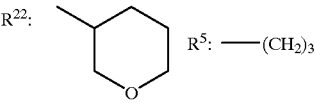  R$^5$: —(CH$_2$)$_3$N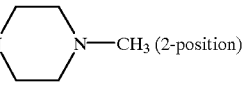N—CH$_3$ (2-position)

M.p. 194–197° C.   Crystalline form: White powder
Solvent for recrystallization: Ethanol-water   Form: Dimethanesulfonate Example 310

R$^1$ 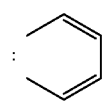  R$^4$: H   A: —CH$_2$—   m: 1
R$^2$

R$^{11b}$: H  R$^{22}$: 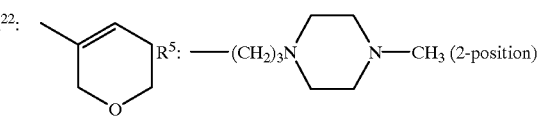  R$^5$: —(CH$_2$)$_3$N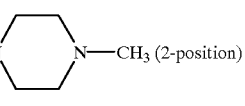N—CH$_3$ (2-position)

M.p. 218–220° C.   Crystalline form: Pale yellow powder
Solvent for recrystallization: Ethanol-water   Form: Dimethanesulfonate

TABLE 139

Example 311

R$^1$ 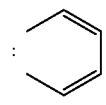  R$^4$: H   A: —CH$_2$—   m: 1
R$^2$

R$^{11b}$: H

R$^{22}$: 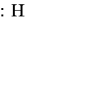  R$^5$: 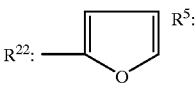

M.p. 182.5–186° C.   Crystalline form: Yellow powder
Solvent for recrystallization: Ethanol-diethyl ether   Form: 2HCl Example 312

R$^1$: CH$_3$   R$^4$: H   A: —CH$_2$—   m: 1
R$^2$: CH$_3$
R$^{11b}$: H
         R$^{22}$: 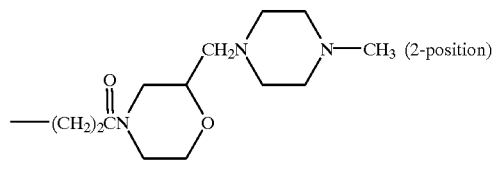  R$^5$: —(CH$_2$)$_3$N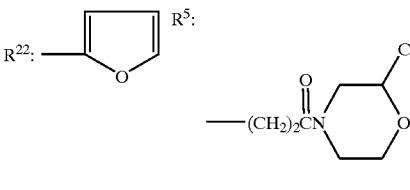O (2-position)

Crystalline form: White powder   Form: Methanesulfonate
Solvent for recrystallization: Ethanol-diethyl ether   NMR (21)

Example 313

R$^1$ 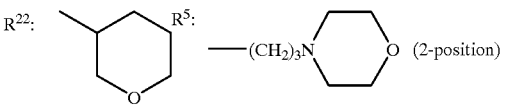  R$^4$: H   A: —CH$_2$—   m: 1
R$^2$

R$^{11b}$: H  R$^{22}$: 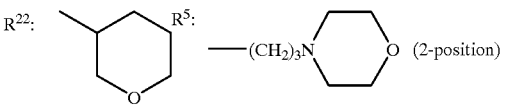  R$^5$: —(CH$_2$)$_3$N(C$_2$H$_5$)(C$_2$H$_5$) (2-position)

M.p. 140–141° C.   Crystalline form: White powder   Form: Methanesulfonate
Solvent for recrystallization: Ethanol-isopropyl alcohol-diethyl ether

TABLE 140

Example 314

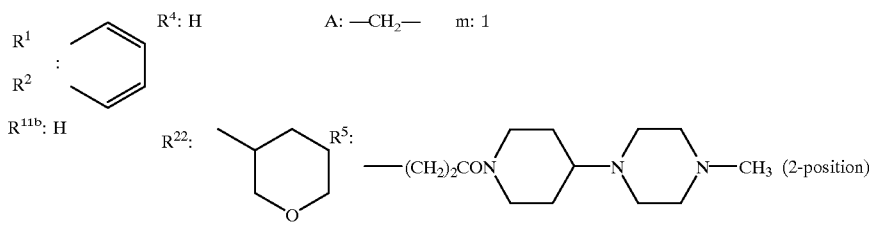

M.p. 166–177° C.   Crystalline form: White powder   NMR (22)
Solvent for recrystallization: Ethanol-diethyl ether   Form: 2HCl Example 315

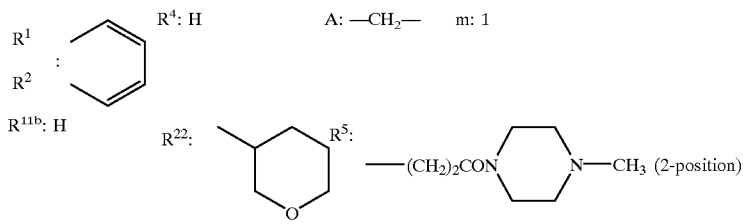

M.p. 156–157° C.   Crystalline form: White powder
Solvent for recrystallization: Ethanol   Form: Free Example 316

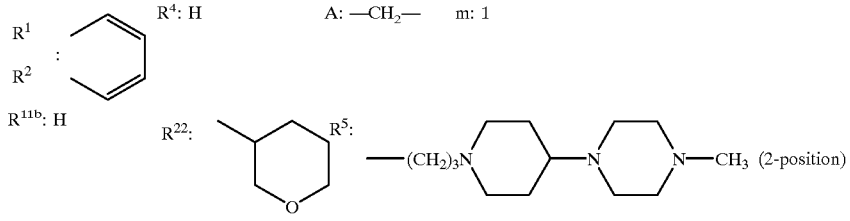

M.p. 191–192° C.   Crystalline form: White powder   Form: 3HCl
Solvent for recrystallization: Ethanol-water-isopropyl alcohol

TABLE 141

Example 317

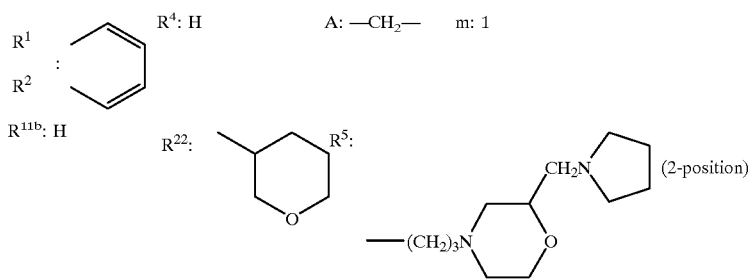

Crystalline form: Pale yellow amorphous   Form: Free   NMR (23)

Example 318

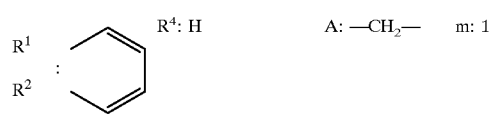

TABLE 141-continued

Example 319

R¹, R²: (benzene ring)
R⁴: H
R¹¹ᵇ: H
R²²: 3-methyltetrahydropyran
R⁵: —(CH₂)₃N(piperidine-4-yl)N(morpholine)O (2-position)
A: —CH₂—  m: 1

Crystalline form: Colorless amorphous  Form: Free  NMR (24)

Example 320 (should be 319 continued data below — actually next entry)

R¹, R²: (benzene ring)
R⁴: H
R¹¹ᵇ: H
R²²: 3-methyltetrahydropyran
R⁵: —(CH₂)₃N(morpholin-2-yl)CH₂N(piperazine)N—CH₃ (2-position)
A: —CH₂—  m: 1

M.p. 178–180° C.  Crystalline form: White powder  Form: 3HCl
Solvent for recrystallization: Ethanol-isopropanol-diethyl ether-water

TABLE 142

Example 320

R¹, R²: (benzene ring)
R⁴: H
R¹¹ᵇ: H
R²²: 1-ethyl-5-methyl-tetrazole
R⁵: —(CH₂)₃N(piperidine-4-yl)N(morpholine)O (2-position)
A: —CH₂—  m: 1

Crystalline form: Pale yellow amorphous  Form: Free  NMR (25)

Example 321

R¹, R²: (benzene ring)
R⁴: H
R¹¹ᵇ: H
R⁵: —(CH₂)₃N(piperazine)N—CH₃ (2-position)
R²²: 5-methyl-1H-tetrazole
A: —CH₂—  m: 1

M.p. 198–201° C.  Crystalline form: Pale yellow powder  Form: 2HCl
Solvent for recrystallization: Ethanol-water Example 322

R¹, R²: (benzene ring)
R⁴: H
R¹¹ᵇ: H
R²²: 4-pyridyl
R⁵: —(CH₂)₃N(morpholine)O (2-position)
A: —CH₂—  m: 1

M.p. 177–178° C.  Crystalline form: White powder  Form: Free
Solvent for recrystallization: Diethyl ether-ethanol-dichloromethane

TABLE 143

Example 323

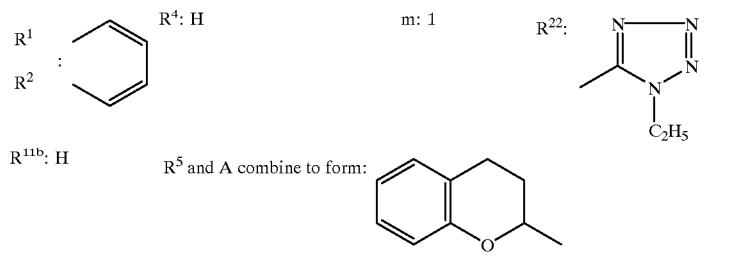

R$^1$ ⋮ R$^2$ : (phenyl ring)  R$^4$: H   m: 1   R$^{22}$: (1-ethyl-5-methyltetrazol-yl)

R$^{11b}$: H   R$^5$ and A combine to form: (2-methylchroman)

M.p. 234–235° C.   Crystalline form: White powder   Form: Free
Solvent for recrystallization: Ethyl acetate-n-hexane Example 324

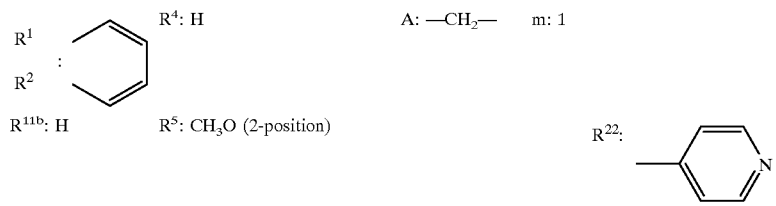

R$^1$ ⋮ R$^2$ : (phenyl ring)   R$^4$: H   A: —CH$_2$—   m: 1

R$^{11b}$: H   R$^5$: CH$_3$O (2-position)   R$^{22}$: (4-pyridyl)

M.p. 206–207° C.   Crystalline form: Pale yellow powder   Form: Free
Solvent for recrystallization: Dichloromethane-ethanol-diethyl ether Example 325

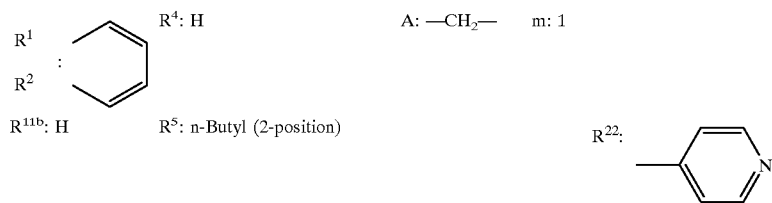

R$^1$ ⋮ R$^2$ : (phenyl ring)   R$^4$: H   A: —CH$_2$—   m: 1

R$^{11b}$: H   R$^5$: n-Butyl (2-position)   R$^{22}$: (4-pyridyl)

M.p. 195.5–196.5° C.   Crystalline form: Pale yellow needles
Solvent for recrystallization: Ethanol-dichloromethane   Form: Free

TABLE 144

Example 326

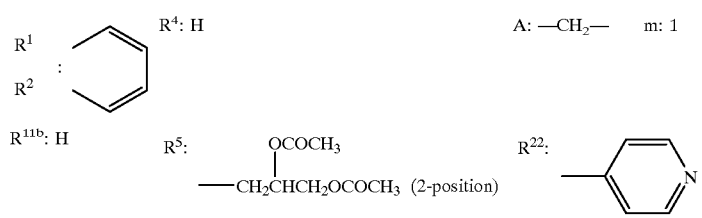

R$^1$ ⋮ R$^2$ : (phenyl ring)   R$^4$: H   A: —CH$_2$—   m: 1

R$^{11b}$: H   R$^5$: —CH$_2$CHCH$_2$OCOCH$_3$ (with OCOCH$_3$) (2-position)   R$^{22}$: (4-pyridyl)

M.p. 134–136° C. (decomp.) Crystalline form: Yellow powder   Form: Free
Solvent for recrystallization: Dichloromethane-diisopropyl ether Example 327

R$^1$ ⋮ R$^2$ : (phenyl ring)   R$^4$: H   A: —CH$_2$—   m: 1

TABLE 144-continued

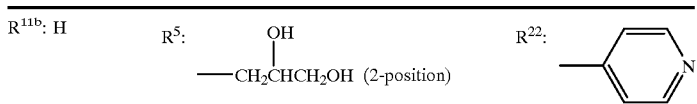

M.p. 207.6–214° C. (decomp.)  Crystalline form: White powder
Solvent for recrystallization: Dichloromethane  NMR (26)  Form: Free Example 328

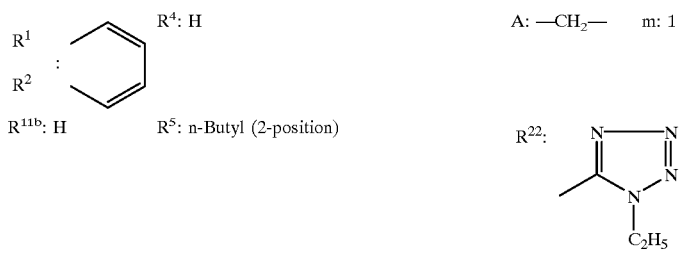

M.p. 191–193° C.  Crystalline form: Pale yellow powder
Solvent for recrystallization: Ethanol-dichloromethane  Form: Free

TABLE 145

Example 329

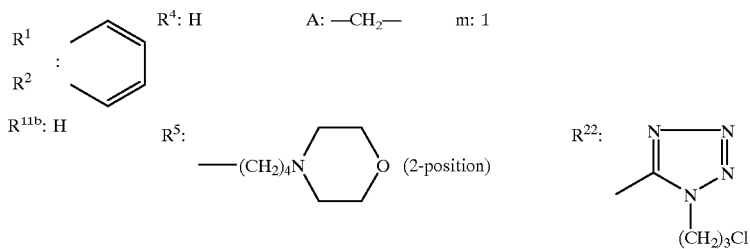

M.p. 112–114° C.  Crystalline form: Pale yellow powder  Form: Free
Solvent for recrystallization: Ethyl acetate-diethyl ether Example 330

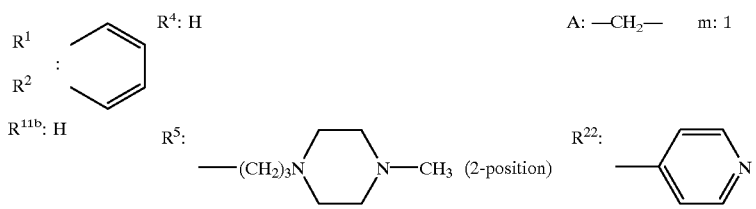

M.p. 209–211° C.  Crystalline form: Yellow powder
Solvent for recrystallization: Ethanol-water  Form: 3HCl Example 331

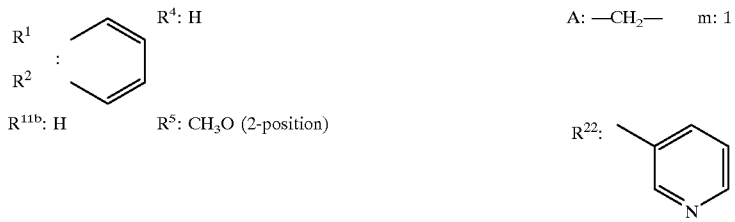

M.p. 208–210° C.  Crystalline form: Pale yellow powder
Solvent for recrystallization: Ethanol-dichloromethane  Form: Free

TABLE 146

Example 332

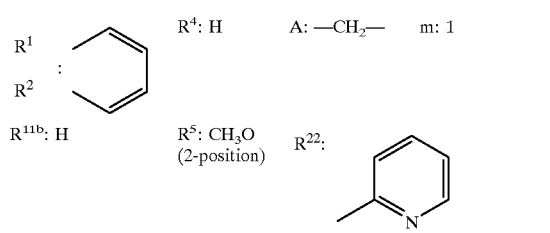

R$^1$ :
R$^2$

R$^{11b}$: H    R$^5$: CH$_3$O (2-position)    R$^{22}$:    R$^4$: H    A: —CH$_2$—    m: 1

M.p. 200–203° C.   Crystalline form: Yellow powder   Form: Free
Solvent for recrystallization: Ethanol-isopropyl alcohol-dichloromethane Example 333

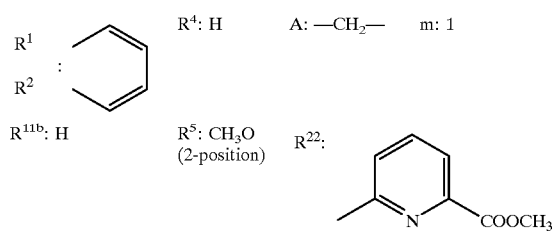

R$^1$ :
R$^2$

R$^{11b}$: H    R$^5$: CH$_3$O (2-position)    R$^{22}$:    R$^4$: H    A: —CH$_2$—    m: 1

M.p. 196–197° C.   Crystalline form: White powder   Form: Free
Solvent for recrystallization: Ethanol-dichloromethane Example 334

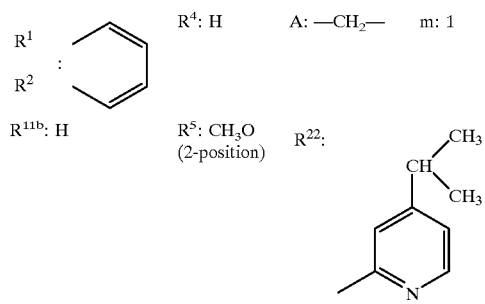

R$^1$ :
R$^2$

R$^{11b}$: H    R$^5$: CH$_3$O (2-position)    R$^{22}$:    R$^4$: H    A: —CH$_2$—    m: 1

M.p. 203–204° C.   Crystalline form: White powder   Form: Free
Solvent for recrystallization: Dichloromethane-ethanol-isopropyl alcohol

TABLE 147

Example 335

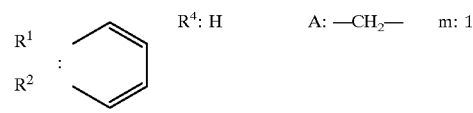

R$^1$ :
R$^2$

R$^4$: H    A: —CH$_2$—    m: 1

TABLE 147-continued

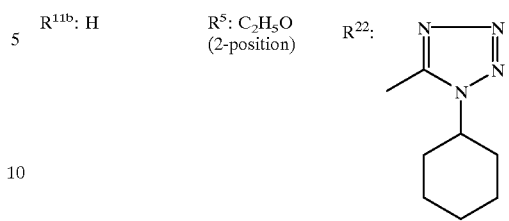

R$^{11b}$: H    R$^5$: C$_2$H$_5$O (2-position)    R$^{22}$:

M.p. 206–208° C.   Crystalline form: Pale yellow powder   Form: Free
Solvent for recrystallization: Dichloromethane-n-hexane Example 336

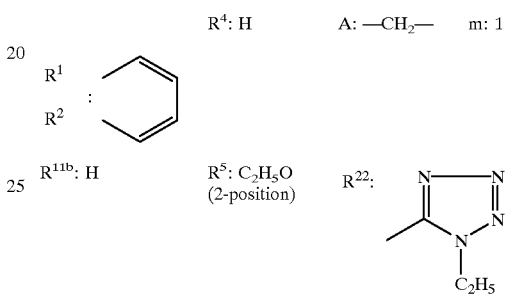

R$^1$ :
R$^2$

R$^{11b}$: H    R$^5$: C$_2$H$_5$O (2-position)    R$^{22}$:    R$^4$: H    A: —CH$_2$—    m: 1

M.p. 190–192° C.   Crystalline form: Pale yellow needles   Form: Free
Solvent for recrystallization: Chloroform-ethyl acetate Example 337

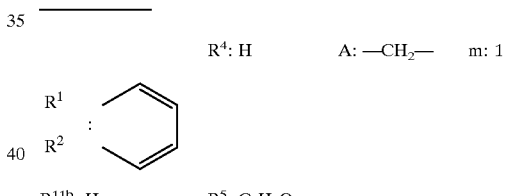

R$^1$ :
R$^2$

R$^{11b}$: H    R$^5$: C$_2$H$_5$O (2-position)    R$^{22}$:    R$^4$: H    A: —CH$_2$—    m: 1

M.p. 207–209° C.   Crystalline form: Pale yellow powder   Form: Free
Solvent for recrystallization: Ethyl acetate-diisoropyl ether

TABLE 148

Example 338

R$^1$ :
R$^2$

R$^4$: H    A: —CH$_2$—    m: 1

TABLE 148-continued

R11b: H    R5: Isopropyl (2-position)    R22:

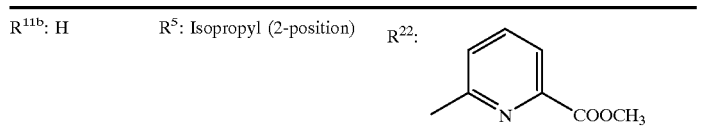

M.p. 199–200.5° C.    Crystalline form: White powder
Solvent for recrystallization: Methanol-dimethylformamide    Form: Free
Example 339

R1
  :    R4: H    A: —CH2—    m: 1
R2

R11b: H    R5: C2H5O (2-position)    R22:

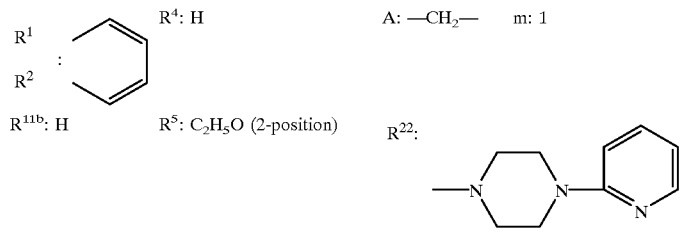

M.p. 204–206° C.    Crystalline form: Pale yellow powder    Form: Free
Solvent for recrystallization: Ethanol-dichloromethane
Example 340

R1
  :    R4: H    A: —CH2—    m: 1
R2

R11b: H    R5: C2H5O (2-position)    R22:

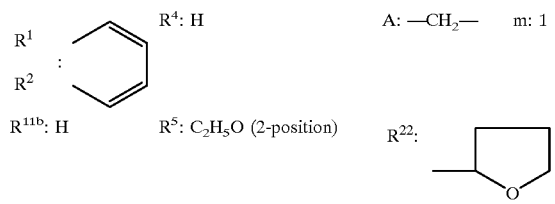

M.p. 115–117° C.    Crystalline form: Pale yellow powder    Form: Free
Solvent for recrystallization: Ethyl acetate-diisopropyl ether

TABLE 149

Example 341

R1
  :    R4: H    A: —CH2—    m: 1
R2

R11b: H    R5: C2H5O
         (2-position)    R22:

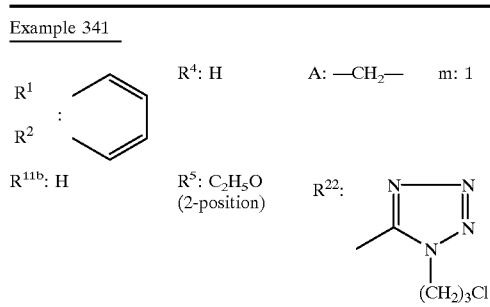

M.p. 225–227° C.    Crystalline form: Pale yellow powder    Form: Free
Solvent for recrystallization: Ethyl acetate-diisopropyl ether
Example 342

R1
  :    R4: H    A: —CH2—    m: 1
R2

R11b: H    R5: C2H5O
         (2-position)    R22:

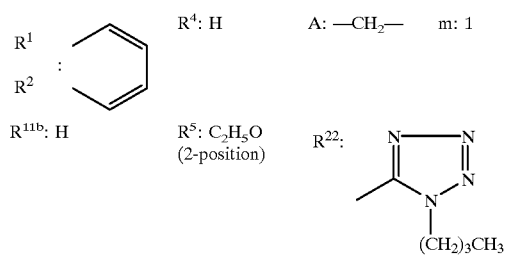

M.p. 196.5–198° C.    Crystalline form: Pale yellow powder
Solvent for recrystallization: Chloroform-ethyl acetate    Form: Free

TABLE 149-continued

Example 343

R1
  :    R4: H    A: —CH2—    m: 1
R2

R11b: H    R5: CH3O
         (2-position)    R22:

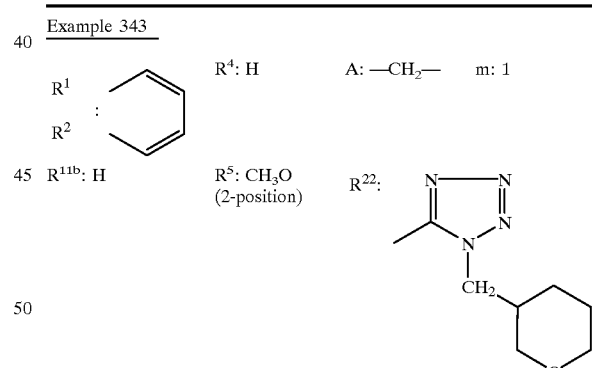

M.p. 192–194° C.    Crystalline form: Pale yellow powder
Solvent for recrystallization: Ethyl acetate-diisopropyl ether    Form: Free $^1$H-NMR spectrum (NMR (1) to NMR (55)) as described in Tables 50–149 are as follows:

NMR (1) (CDCl$_3$) δppm: 2.33 (3H, s), 2.45 (4H, t, J=5 Hz), 3.6–3.8 (4H, m), 4.85 (2H, s), 7.09 (2H, d, J=9 Hz), 7.3–7.55 (2H, m), 7.50 (1H, d, J=15 Hz), 7.8–7.95 (2H, m), 7.93 (1H, d, J=15 Hz), 8.10 (2H, d, J=9 Hz), 9.88 (1H, br); NMR (2) (DMSO-d$_6$) δppm: 1.35–1.8 (2H, m), 2.0–2.3 (2H, m), 2.6–3.9 (11H, m), 2.81 (3H, s), 4.1–4.3 (1H, m), 4.5–4.7 (1H, m), 5.08 (2H, s), 7.15 (2H, d, J=9 Hz), 7.3–7.55 (3H, m), 7.76 (1H, d, J=14 Hz), 7.77 (1H, d, J=8.5 Hz), 7.98 (1H, d, J=8 Hz), 8.05 (2H, d, J=9 Hz), 12.67 (1H, br); NMR (3)

(DMSO-d$_6$) δppm: 2.32 (3H, s), 2.45–4.50 (20H, m, 2.50 (s)), 5.14 (2H, s), 7.04 (1H, d, J=9.3 Hz), 7.26–7.52 (3H, m), 7.70–8.10 (5H, m), 11.30–12.35, 12.35–13.20 (all 3H, br); NMR (4) (DMSO-d$_6$) δppm: 2.60–4.50 (20H, m), 5.23 (2H, s), 7.20–7.55 (4H, m), 7.70–8.10 (5H, m), 11.30–13.20 (3H, br); NMR (5) (DMSO-d$_6$) δppm: 0.926 (3H, t, J=7.4 Hz), 1.5–1.9 (4H, m), 2.05–2.3 (2H, m), 2.6–2.8 (3H, m), 2.81 (3H, s), 3.0–3.3 (1H, m), 3.3–3.9 (9H, m), 4.15–4.35 (1H, m), 4.5–4.8 (1H, m), 5.12 (2H, s), 7.02 (1H, d, J=8.6 Hz), 7.27–7.47 (3H, m), 7.74–7.99 (4H, m), 7.91 (1H, d, J=15 Hz), 11.5–13.0 (3H, br); NMR (6) (DMSO-d$_6$) δppm: 0.93 (3H, t, J=7.4 Hz), 1.55–1.75 (2H, m), 2.6–2.8 (4H, m), 2.79 (3H, s), 3.0–4.15 (14H, m), 4.2–4.4 (1H, m), 5.12 (2H, s), 7.03 (1H, d, J=8.5 Hz), 7.25–7.55 (2H, m), 7.45 (1H, s), 7.75–7.9 (4H, m), 7.79 (1H, d, J=8.5 Hz); NMR (7) (DMSO-d$_6$) δppm: 1.25 (6H, d, J=7 Hz), 1.3–2.0 (4H, m), 2.6–3.5 (6H, m), 5.12 (2H, s), 6.77 (1H, dd, J=6 Hz, J=15.5 Hz), 7.00 (1H, d, J=8.5 Hz), 7.17 (1H, d, J=15.5 Hz), 7.25–7.5 (2H, m), 7.7–8.05 (4H, m), 9.14 (2H, br), 12.73 (1H, br); NMR (8) (CDCl$_3$) δppm: 1.62 (3H, t, J=7.3 Hz), 1.76–2.03 (4H, m), 2.85–3.09 (2H, m), 3.95–4.11 (2H, m), 4.52 (2H, q, J=7.3 Hz), 4.88 (2H, s), 5.28 (1H, brs), 6.98 (1H, d, J=7.5 Hz), 7.32–7.43 (1H, m), 7.43–7.55 (1H, m), 7.56 (1H, d, J=15.2 Hz), 7.77–7.93 (2H, m), 8.00–8.12 (2H, m), 8.35 (1H, d, J=15.2 Hz), 10.85 (1H, brs); NMR (9) DMSO-d$_6$) δppm: 0.93 (3H, t, J=7.4 Hz), 1.5–1.8 (2H, m), 1.8–2.2 (4H, m), 2.69 (2H, t, J=7.4 Hz), 2.8 (3H, s), 3.0–4.3 (12H, m), 4.3–4.6 (1H, m), 5.13 (2H, s), 7.03 (1H, d, J=8.6 Hz), 7.17 (1H, d, J=15.1 Hz), 7.30 (1H, t, J=7 Hz), 7.74–7.99 (5H, m), 11.5–12.3 (1H, br), 12.3–13.3 (1H, br); NMR (10) DMSO-d$_6$) δppm: 1.56–1.91 (4H, m), 2.70–2.90 (7H, m), 3.10–3.52 (8H, m), 5.14 (2H, s), 6.65–6.75 (1H, m), 6.99–7.15 (2H, m), 7.28–7.40 (1H, m), 7.40–7.52 (1H, m), 7.52–7.60 (2H, m), 7.72–7.85 (1H, m), 7.90–8.08 (4H, m), 10.90–13.18 (3H, m); NMR (11) (DMSO-d$_6$) δppm: 1.40–1.89 (2H, m), 1.96–2.32 (2H, m), 2.58–2.96 (4H, m), 2.96–3.83 (10H, m), 3.89 (3H, s), 4.06–4.34 (1H, m), 4.42–4.71 (1H, m), 5.08 (2H, s), 7.07 (1H, d, J=8.5 Hz), 7.31 (11H, t, J=7.0 Hz), 7.38–7.69 (3H, m), 7.69–7.92 (3H, m), 7.98 (1H, d, J=8.5 Hz), 11.76 (2H, br), 12.71 (1H, br), NMR (12) (DMSO-d$_6$) δppm: 1.40–1.85 (2H, m), 2.00–2.23 (2H, m), 2.40 (3H, s), 2.60–2.88 (1H, m), 2.81 (3H, s), 3.00–3.80 (10H, m), 3.89 (3H, s), 4.10–4.30 (1H, m), 4.48–4.78 (1H, m), 5.06 (2H, s), 7.04 (1H, d, J=8.5 Hz), 7.21–7.31 (1H, m), 7.40 (1H, d, J=15.2 Hz), 7.52–7.60 (1H, m), 7.60–7.88 (4H, m), 11.02–12.33 (2H, m), 12.33–12.80 (1H, m); NMR (13) (DMSO-d$_6$) δppm: 2.40 (3H, s), 2.81 (3H, s), 2.90–4.35 (15H, m), 3.89 (3H, s), 5.07 (2H, s), 6.99–7.12 (1H, m), 7.12–7.35 (2H, m), 7.52–7.60 (1H, m), 7.60–7.91 (4H, m), 11.00–13.28 (3H, m); NMR (14) (CDCl$_3$) δppm: 1.31–1.64 (2H, m), 1.77–2.07 (2H, m), 2.21–2.87 (10H, m), 2.29 (3H, s), 2.67 (3H, s), 3.06–3.26 (1H, m), 3.96–4.28 (1H, m), 4.10 (3H, s), 4.62–4.78 (1H, m), 4.87 (2H, s), 7.07 (1H, d, J=8.1 Hz), 7.14–7.32 (2H, m), 7.52 (1H, d, J=14.9 Hz), 7.61–7.77 (3H, m), 7.91 (1H, d, J=14.9 Hz); NMR (15) (CDCl$_3$) δppm: 1.20–2.16 (4H, m), 2.31–2.72 (3H, m), 2.44 (3H, s), 2.72–3.34 (2H, m), 4.85 (2H, s), 6.76–7.06 (3H, m), 7.21–7.58 (2H, m), 7.72–8.00 (4H, m); NMR (16) (CDCl$_3$) δppm: 1.43–2.13 (4H, m), 2.28 (6H, s), 2.45 (3H, s), 2.53–3.28 (5H, m), 3.56–4.56 (2H, m), 4.86 (2H, s), 6.80–7.11 (3H, m), 7.28–7.53 (2H, m), 7.74–7.93 (4H, m); NMR (17) (CDCl$_3$) δppm: 1.3–1.5 (2H, m), 1.7–1.9 (2H, m), 2.6–2.8 (2H, m), 2.8–3.3 (2H, m), 3.90 (3H, s), 4.80 (2H, s), 6.5–6.65 (2H, m), 6.73 (1H, d, J=15.5 Hz), 6.87 (1H, dd, J=15.5 Hz, J=6 Hz), 7.3–7.55 (2H, m), 7.6–7.95 (4H, m); NMR (18) (CDCl$_3$) δppm: 1.12 (3H, t, J=5.9 Hz), 1.28–3.78 (11H, m), 4.97 (1H, t, J=5.3 Hz), 6.68–7.53 (5H, m), 7.70–8.14 (4H, m); NMR (19) (DMSO-d$_6$) δppm: 1.29–2.11 (4H, m), 2.32 (3H, m), 2.60–3.08 (2H, m), 3.08–3.56 (3H, m), 3.91 (6H, s), 4.85 (2H, s), 6.73–6.93 (1H, m), 7.19–7.54 (5H, m), 7.71–7.83 (1H, m), 7.93–8.05 (1H, m), 8.29–8.80 (1H, m), 12.14 (1H, brs); NMR (20) (CDCl$_3$) δppm: 1.86–2.13 (2H, m), 2.39 (3H, m), 2.48–3.06 (12H, m), 3.82 (3H, s), 4.87 (2H, s), 6.82–8.09 (9H, m), 7.04 (1H, s), 7.21 (1H, s); NMR (21) (DMSO-d$_6$) δppm: 1.4–2.2 (6H, m), 2.35 (3H, s), 2.65–2.85 (2H, m), 2.95–4.05 (14H, m), 5.07 (2H, s), 6.78 (1H, dd, J=7 Hz, J=15.5 Hz), 7.02 (1H, d, J=8.5 Hz), 7.16 (1H, d, J=15.5 Hz), 7.26 (1H, d, J=3.5 Hz), 7.50 (1H, d, J=3.5 Hz), 7.8–8.0 (2H, m), 9.58 (1H, br), 12.45 (1H, br); NMR (22) (DMSO-d$_6$) δppm: 1.33–1.71 (5H, m), 1.80–2.00 (1H, m), 2.00–2.21 (2H, m), 2.65–2.77 (2H, m), 2.80 (3H, s), 2.88–3.10 (4H, m), 3.10–4.00 (14H, m), 4.00–4.23 (1H, m), 4.47–4.66 (1H, m), 5.13 (2H, s), 6.71–6.87 (1H, m), 6.98–7.09 (1H, m), 7.09–7.22 (1H, m), 7.26–7.40 (1H, m), 7.40–7.52 (1H, m), 7.72–7.83 (1H, m), 7.83–7.97 (2H, m), 7.97–8.08 (1H, m), 11.32–12.55 (2H, m), 12.70 (1H, brs); NMR (23) (CDCl$_3$) δppm: 1.43–2.28 (12H, m), 2.28–3.01 (13H, m), 3.23–3.56 (2H, m), 3.56–4.09 (5H, m), 4.87 (2H, s), 6.74–7.02 (3H, m), 7.22–7.53 (2H, m), 7.70–7.97 (4H, m); NMR (24) (CDCl$_3$) δppm: 1.43–2.18 (12H, m), 2.37–2.68 (8H, m), 2.86 (2H, t, J=7.7 Hz), 2.97–3.16 (2H, m), 3.25–3.53 (2H, m), 3.56–3.80 (4H, m), 3.82–4.03 (2H, m), 4.85 (2H, s), 6.79–7.00 (3H, m), 7.22–7.53 (2H, m), 7.68–7.93 (4H, m); NMR (25) (CDCl$_3$) δppm: 1.48–3.22 (19H, m), 1.62 (3H, t, J=7.4 Hz), 3.57–3.78 (4H, m), 4.54 (2H, q, J=7.4 Hz), 4.89 (2H, s), 6.99 (1H, d, J=8.5 Hz), 7.22–7.53 (3H, m), 7.59 (1H, d, J=15.2 Hz), 7.76–7.90 (2H, m), 7.92–8.09 (1H, m), 8.36 (1H, d, J=15.2 Hz); NMR (26) (DMSO-d$_6$) δppm: 2.65–2.8 (1H, m), 2.9–3.05 (1H, m), 3.3–3.45 (2H, m), 3.8 (1H, m), 4.65 (2H, br), 5.11 (2H, s), 7.06 (1H, d, J=8.5 Hz), 7.25–7.5 (2H, m), 7.64 (1H, d, J=15.5 Hz), 7.75–7.9 (3H, m), 7.95–8.2 (4H, m), 8.66 (2H, br), 12.58 (1H, br); NMR (27) (CDCl$_3$) δppm: 1.36 (3H, t, J=7.5 Hz), 2.6–3.6 (6H, m), 2.86 (2H, q, J=7.5 Hz), 4.05 (1H, m), 4.50 (1H, m), 4.87 (2H, s), 6.93 (1H, d, J=8 Hz), 7.35–7.55 (3H, m), 7.8–8.0 (1H, m), 9.66 (1H, br); NMR (28) (DMSO-d$_6$) δppm: 1.67–1.97 (2H, m), 2.80 (3H, s), 2.88–4.35 (17H, m), 3.90 (3H, s), 5.10 (2H, s), 7.08 (1H, d, J=8.6 Hz), 7.20–7.66 (4H, m), 7.66–7.95 (3H, m), 7.99 (1H, d, J=7.1 Hz), 12.70 (1H, s); NMR (29) (DMSO-d$_6$) δppm: 2.05–2.35 (2H, m), 2.55–4.18 (22H, m), 4.18–4.42 (1H, m), 5.09 (2H, s), 7.07 (1H, d, J=8.6 Hz), 7.27–7.57 (4H, m), 7.74–7.77 (3H, m), 7.98 (1H, d, J=7.1 Hz), 11.52 (2H, br), 12.55 (1H, br); NMR (30) (CDCl$_3$) δppm: 1.1–1.4 (3H, m), 1.37 (3H, t, J=7.5 Hz), 2.5–2.8 (2H, m), 2.86 (2H, q, J=7.5 Hz), 2.9–3.1 (3H, m), 3.2–3.6 (2H, m), 3.8–4.1 (1H, m), 4.5–4.8 (1H, m), 4.87 (2H, s), 5.35 (1H, br), 6.93 (1H, d, J=9 Hz), 7.25–7.6 (3H, m), 7.75–8.05 (5H, m), 9.60 (1H, br); NMR (31) (DMSO-d$_6$) δppm: 0.74–0.91 (3H, m), 1.12–1.44 (6H, m), 1.50–1.71 (2H, m), 2.55–2.90 (3H, m), 2.79 (3H, s), 2.90–3.80 (13H, m), 3.80–4.12 (4H, m), 4.19–4.42 (1H, m), 5.11 (2H, s), 7.01 (1H, d, J=8.7 Hz), 7.27–7.51 (3H, m), 7.71–8.02 (5H, m), 11.00–13.00 (3H, m); NMR (32) (DMSO-d$_6$) δppm: 1.45–1.89 (2H, m), 2.00–2.38 (6H, m), 2.55–2.86 (6H, m), 3.01–3.22 (1H, m), 3.22–3.94 (9H, m), 3.77 (3H, s), 3.99–4.50 (3H, m), 4.50–4.70 (1H, m), 7.07–7.20 (1H, m), 7.20–7.37 (1H, m), 7.37–7.54 (3H, m), 7.67–7.89 (3H, m), 7.89–8.03 (1H, m), 11.06–12.62 (3H, m); NMR (33) (DMSO-d$_6$) δppm: 1.40–1.92 (2H, m), 1.92–2.30 (4H, m), 2.31 (3H, m), 2.55–2.90 (4H, m), 2.90–4.03 (10H, m), 4.03–4.34 (1H, m), 4.44–4.73 (1H, m), 5.11 (2H, s), 7.23 (1H, d, J=9.3H), 7.31 (1H, t, J=6.9 Hz), 7.32–7.48 (2H, m), 7.74–7.86 (2H, m), 7.86–8.05 (3H, m), 10.88–12.00 (2H, m), 12.70 (1H, br); NMR (34) (DMSO-d$_6$) δppm: 1.48–1.94 (2H, m), 2.00–2.39 (4H, m), 2.57–2.85 (4H, m), 2.85–4.03 (10H, m), 4.10–4.39 (1H, m), 4.48–4.71 (1H, m), 5.29 (2H, s), 7.21–7.57 (4H, m), 7.75–7.83 (2H, m), 7.98 (1H, d, J=7.4 Hz), 8.23 (1H, s), 8.32 (1H, d, J=8.7 Hz), 10.89–12.06 (2H, m), 12.76 (1H, br); NMR (35) (DMSO-d$_6$) δppm: 2.88–3.28 (4H, m), 3.73–4.31 (5H, m), 5.30 (2H, s), 7.31 (1H, t, J=6.9 Hz), 7.35–7.48 (3H, m), 7.75–7.85 (2H, m), 7.97 (1H, d, J=7.1 Hz), 8.23 (1H, s), 8.33

(1H, d, J=8.7 Hz), 9.37 (2H, br), 12.78 (1H, br); NMR (36) (DMSO-d₆) δppm: 1.2–1.5 (2H, m), 1.6–1.85 (8H, m), 2.31 (3H, s), 2.5–3.15 (15H, m), 3.9–4.0 (1H,), 4.4–4.5 (1H, m), 5.04 (2H, s), 6.81 (1H, d, J=8.5 Hz), 7.20 (1H, d, J=15.5 Hz), 7.25–7.5 (3H, m), 7.55 (1H, d, J=8.5 Hz), 7.75 (1H, d, J=7.5 Hz), 7.97 (1H, d, J=7 Hz); NMR (37) (DMSO-d₆) δppm: 1.4–1.9 (2H, m), 2.12 (6H, s), 2.0–4.0 (19H, m), 4.45–4.6 (1H, m), 4.95 (2H, s), 6.77 (2H, s), 6.88 (1H, d, J=16 Hz), 7.03 (1H, d, J=16 Hz), 7.35–7.5 (2H, m), 7.76 (1H, d, J=7.5 Hz), 7.99 (1H, d, J=8 Hz), 11.24, 12.04 (all 1H, br), 11.74 (1H, br), 12.64 (1H, br); NMR (38) (DMSO-d₆) δppm: 2.54–2.93 (5H, m), 2.93–3.78 (10H, m), 3.78–4.17 (7H, m), 4.17–4.44 (1H, m), 5.07 (2H, s), 6.65–6.78 (1H, m), 6.78–6.90 (1H, m), 7.18–7.71 (5H, m), 7.76 (1H, d, J=7.5 Hz), 7.98 (1H, d, J=7.1 Hz), 11.28 (2H, br), 12.68 (1H, br); NMR (39) (DMSO-d₆) δppm: 2.22 (3H, s), 2.33 (3H, s), 2.36 (3H, s), 2.80 (3H, d, J=4 Hz), 2.9–3.6 (6H, m), 4.15–4.3 (1H, m), 4.4–4.55 (1H, m), 5.06 (2H, s), 6.85 (1H, d, J=9 Hz), 7.24 (1H, d, J=15.5 Hz), 7.37 (1H, d, J=15.5 Hz), 7.25–7.55 (3H, m), 7.76 (1H, d, J=7 Hz), 7.98 (1H, d, J=7 Hz), 9.76 (1H, br), 12.60 (1H, br); NMR (40) (DMSO-d₆) δppm: 2.05–2.35 (2H, m), 2.54–2.98 (5H, m), 2.98–3.85 (10H, m), 3.85–4.19 (7H, m), 4.19–4.47 (1H, m),5.07 (2H, s), 6.65–6.79 (1H, m), 6.79–6.90 (1H, m), 7.18–7.71 (5H, m), 7.77 (1H, d, J=7.7 Hz), 8.00 (1H, d, J=7.8 Hz), 11.22 (2H, br), 12.68 (1H, br); NMR (41) (DMSO-d₆) δppm: 1.89–2.44 (4H, m), 2.53–3.78 (16H, m), 3.78–4.13 (6H, m), 4.13–4.42 (1H, m), 5.07 (2H, s), 6.70 (1H, dd, J=2.2 Hz, J=8.7 Hz). 6.81 (1H, d, J=2.2 Hz), 7.19–7.73 (5H, m), 7.76 (1H, d, J=7.8 Hz), 7.98 (1H, d, J=7.0 Hz), 10.61 (1H, br), 11.27 (1H,br), 12.71 (1H,br); NMR (42) (DMSO-d₆) δppm: 1.30 (6H, d, J=5.9 Hz), 2.55–4.19 (19H, m), 4.19–4.41 (1H, m), 4.82 (1H, sept, J=5.9 Hz), 5.07 (2H, s), 6.60–6.71 (1H, m), 6.76–6.79 (1H, m), 7.22–7.49 (3H, m), 7.64 (1H, d, J=8.7 Hz), 7.71–7.90 (2H, m), 7.98 (1H, d, J=7.1 Hz), 11.81 (2H, br), 12.58 (1H, br); NMR (43) DMSO-d₆) δppm: 1.35 (3H, d, J=6 Hz), 1.5–2.2 (4H, m),2.5–3.8 (13H, m), 3.88 (3H, s), 4.1–4.3 (1H, m), 4.45–4.65 (1H, m), 5.06 (2H, s), 6.70 (1H, d, J=9 Hz), 6.81 (1H, s), 7.27 (1H, d, J=15.5 Hz), 7.25–7.5 (2H, m), 7.56 (1H, d, J=15.5 Hz), 7.64 (1H, d, J=8.5 Hz), 7.77 (1H, d, J=8 Hz), 7.99 (1H, d, J=8 Hz), 12.5–13 (3H, br); NMR (44) (DMSO-d₆) δppm: 1.30 (3H, d, J=6.5 Hz), 1.5–2.3 (4H, m), 2.55–2.8 (1H, m), 3.0–4.7 (13H, m), 3.88 (3H, s), 5.07 (2H, s), 6.70 (1H, d, J=9 Hz), 6.81 (1H, m), 7.27 (1H, d, J=15.5 Hz), 7.25–7.5 (2H, m), 7.56 (1H, d, J=15.5 Hz), 7.64 (1H, d, J=8.5 Hz), 7.77 (1H, d, J=8 Hz), 7.98 (1H, d, J=7.5 Hz), 9.85 (1H, br), 10.01 (1H, br), 12.25 (1H, br); NMR (45) (DMSO-d₆) δppm: 2.05–2.20 (2H, m), 2.5–4.0 (18H, m), 3.88 (3H, s), 4.1–4.25 (1H, m), 4.5–4.65 (1H, m), 5.06 (2H, s), 6.70 (1H, d, J=8.5 Hz), 6.81 (1H, m), 7.28 (1H, d, J=15 Hz), 7.25–7.5 (2H, m), 7.56 (1H, d, J=15 Hz), 7.64 (1H, d, J=8.5 Hz), 7.77 (1H, d, J=8 Hz), 7.99 (1H, d, J=7.5 Hz), 10.78 (1H, br), 11.94 (1H, br), 12.66 (1H, br); NMR (46) (DMSO-d₆) δppm: 1.43–1.85 (2H, m), 1.97–2.42(4H, m), 2.58–2.82 (1H, m), 2.82–4.08 (18H, m), 4.08–4.30 (1H, m), 4.42–4.72 (1H, m), 5.06 (2H, s), 5.22–5.68 (2H, m), 6.62–6.78 (1H, m), 6.78–6.95(1H, m), 7.24–7.70 (5H, m), 7.77 (1H, d, J=6.2 Hz), 7.99 (1H, d, J=5.8 Hz), 10.35 (2H, br), 11.48 (1H, br); NMR (47) DMSO-d₆) δppm: 1.3–2.0 (6H, m), 2.37 (6H, s), 2.8–4.2 (16H, m), 3.88 (3H, s), 5.07 (2H, s), 6.71 (1H, dd, J=7H, J=2 Hz), 6.81 (1H, d, J=2 Hz), 7.25 (1H, d, J=15 Hz), 7.25–7.5 (3H, m), 7.65–7.75 (2H, m), 7.77 (1H, d, J=7 Hz), 7.98 (1H, d, J=6 Hz), 9.40 (1H, br); NMR (48) DMSO-d₆) δppm: 2.4–4.5(23H, m), 3.88 (3H, s), 5.09 (2H, s), 6.71 (1H, d, J=9 Hz), 6.82 (1H, s), 7.2–7.75 (5H, m), 7.77 (1H, d, J=8 Hz), 7.98 (1H, d, J=7 Hz), 10.98 (1H, br), 11.58 (1H, br), 12.71 (1H, br); NMR (49) DMSO-d₆) δppm: 2.16 (3H, s), 2.23 (3H, s), 2.74 (3H, d, J=4 Hz), 2.85–3.7 (6H, m), 3.86 (3H, s), 4.15–4.6 (2H, m), 4.95 (2H, s), 6.66 (1H, d J=8.5 Hz), 6.79 (1H, m), 7.27 (1H, d, J=15 Hz), 7.61 (1H, d, J=15 Hz), 7.63 (1H, d, J=8.5 Hz), 11.42 (1H, br); NMR (50) DMSO-d₆) δppm: 1.39–1.90 (2H, m), 1.98–2.37 (4H, m), 2.58–2.90 (4H, m), 2.98–3.99 (10H, m), 4.11–4.32 (1H, m), 4.48–4.70 (1H, m), 5.09 (2H, s), 6.93–7.15 (2H, m), 7.20–7.62 (4H, m), 7.80–7.92 (2H, m), 7.99 (1H, d, J=7.3 Hz), 10.80–11.95 (2H, m), 12.68 (1H, br); NMR (51) (DMSO-d₆) δppm: 1.67–2.03 (2H, m), 2.80 (3H, s), 2.99–4.35 (20H, m), 5.07 (2H, s), 6.70 (1H, dd, J=2.2 Hz, J=8.7 Hz), 6.82 (1H, d, J=2.2 Hz), 7.19–7.74 (5H, m), 7.77 (1H, d, J=7.5 Hz), 7.99 (1H, d, J=7.9 Hz), 10.80–12.32 (2H, m), 12.69 (1H, br); NMR (52) (DMSO-d₆) δppm: 2.15 (3H, s), 2.22 (3H, s), 2.83 (3H, s), 2.5–4.4 (17H, m), 3.86 (3H, s), 4.94 (2H, s), 6.65 (1H, d, J=8.5 Hz), 6.78 (1H, s), 7.2–7.7 (3H, m), 12.05 (1H, br); NMR (53) (DMSO-d₆) δppm: 2.36 (6H, s), 2.55–4.45 (20H, m), 4.92 (2H, q, J=8.9 Hz), 5.08 (2H, s), 6.80 (1H, dd, J=2.3 Hz, J=8.9 Hz), 6.94 (1H, d, J=2.3 Hz), 7.21–7.75 (5H, m), 7.77 (1H, d, J=8.1 Hz), 7.98 (1H, d, J=7.1 Hz), 9.95 (2H, br), 12.63 (1H, br); NMR (54) (DMSO-d₆) δppm: 1.40 (6H, d, J=6.0 Hz), 1.51–1.86 (2H, m), 2.05–2.30 (2H, m), 2.57–2.73 (1H, m), 2.79 (3H, s), 2.98–3.87 (8H, m), 3.88 (3H, s), 4.14–4.25 (1H, m), 4.40–4.70 (1H, m), 5.06 (2H, s), 6.70 (1H, dd, J=2.2 Hz, J=8.8 Hz), 6.81 (1H, d, J=2.2 Hz), 7.23–7.66 (5H, m), 7.77 (1H, d, J=7.6 Hz), 8.00 (1H, d, J=7.0 Hz), 11.40–13.10 (3H, m); NMR (55) (DMSO-d₆) δppm: 1.4–2.4 (4H, m), 2.34 (3H, s), 2.7–5.0 (9H, m), 3.88 (3H, s), 5.06 (2H, s), 6.71 (1H, dd, J=2 Hz, J=9 Hz), 6.82 (1H, d, J=2 Hz), 7.2–7.5 (3H, m), 7.55–7.8 (3H, m), 7.99 (1H, d, J=7 Hz), 9.6–10.2 (1H, m), 12.60 (1H, br); NMR (56) (DMSO-d₆) δppm: 1.40–1.84 (2H, m), 2.00–2.42 (4H, m), 2.67 (1H, t, J=12.5 Hz), 2.77 (3H, s), 3.12 (1H, t, J=12.5 Hz), 3.24–4.05 (12H, m), 4.10–4.31 (1H, m), 4.48–4.71 (1H, m), 5.07 (2H, s), 6.70 (1H, dd, J=2.1 Hz, J=8.7 Hz), 6.82 (1H, d, J=2.1 Hz), 7.19–7.62 (4H, m), 7.64 (1H, d, J=8.6 Hz), 7.77 (1H, d, J=8.1 Hz), 7.99 (1H, d, J=7.9 Hz), 11.05–12.10 (2H, m), 12.68 (1H, br).

Example 344

2-{3-Allyloxy-4-[3-(1-piperidinyl)carbonylacryloyl] phenoxymethylcarbonylamino}benzothiazole (0.55 g) is dissolved in methanol (70 ml) and dioxane (40 ml), and thereto are added 10% palladium-carbon (0.15 g), p-toluenesulfonic acid monohydrate (70 mg) and water (3 ml). The mixture is subjected to deaeration, and the mixture is refluxed under nitrogen atmosphere overnight. The mixture is filtered through a cerite pad, and to the filtrate is added water-methylene chloride, and the mixture is separated, and dried over sodium sulfate. The residue is crystallized from ethanol-methylene chloride, and recrystallized from dimethylformamide-ethanol to give 2-{3-hydroxy-4-[3-(1-piperidinyl)carbonylacryloyl] phenoxymethylcarbonylamino}benzothiazole (120 mg).

Yellow powder; M.p. 207.3–210° C.

Example 345

To a solution of dimethyl [{2-methoxy-4-[2-(2-benzothiazolylaminocarbonyl)ethyl]benzoyl}methyl] phosphonate (6.4 g) in tetrahydrofuran (100 ml) is added 40% glyoxylic acid (7.7 ml), and further thereto is added dropwise a 5% aqueous sodium hydroxide solution (70 ml) under ice-cooling. The mixture is stirred for 30 minutes, and the mixture is acidified with 5% hydrochloric acid. The precipitated yellow powder is collected by filtration, washed with ethanol, dried, and then recrystallized from dimethylformamide-ethanol to give 2-{2-[3-methoxy-4-(trans-3-carboxyacryloyl)phenyl]ethylcarbonyl amino}benzothiazole (4.0 g).

Yellow powder; M.p. 260–261° C.

Example 346

To tetrahydrofuran (50 ml) is added dimethyl[{2-dimethylamino-4-[(2-benzothiazolyl)aminocarbonylmethoxy]benzoyl}methyl]phosphonate (4.70 g), and thereto are added 5% aqueous sodium hydroxide solution (40 ml) and glyoxylic acid (3.5 ml) under ice-cooling, and the mixture is stirred at the same temperature for 10 minutes. After confirming that the starting compounds are consumed, the mixture is acidified with hydrochloric acid, and concentrated under reduced pressure to remove the solvent. The precipitated crystals are collected by filtration, dissolved in dimethylformamide (100 ml), and the mixture is heated with stirring at 100° C. for 30 minutes. After cooling, to the reaction solution is added isopropyl alcohol, and the precipitated crystals are collected by filtration. The crystals are recrystallized from dimethylformamide-isopropyl alcohol to give 1,1-dimethyl-2-carboxy-4-oxo-7-[(2-benzothiazolyl)aminocarbonylmethoxy]-1,2,3,4-tetrahydroquinolinium chloride (2.46 g).

Pale green powder; M.p. 184.5–186.5° C.

Using the suitable starting compounds, the compounds as listed in Table 150–160 are obtained in the same manner as in Example 1 or 5.

TABLE 151

Example 350

$R^5$: —OCH$_3$ (3-position)   A: —CH$_2$—   m: 1   s: 1
Z: O   $R^A$: —N(CH$_3$)$_2$ (6-position)   $R^4$: H
Position of —COCH=CHCOOH: 4-position
M.p. 263–264° C. (decomp.)   Crystalline form: Pale brown powder
Solvent for recrystallization: Dimethylformamide-ethanol-water
Form: Hydrate Example 351

$R^5$: —OCH$_2$—phenyl (3-position)   A: —CH$_2$—   m: 1   s: 1
Z: O   $R^A$: H   $R^4$: H
Position of —COCH=CHCOOH: 4-position
M.p. 294–297° C.   Crystalline form: Yellow powder
Solvent for recrystallization: Dimethylformamide
Form: Free

TABLE 150

[Structure: general formula with HOOC—CH=CH—C(=O)— attached to phenyl ring bearing ($R^5$)$_m$ substituent and (Z)$_s$—A—C(=O)—N($R^4$)— linker to benzothiazole ring bearing $R^A$]

Example 347

$R^5$: H   A: —CH$_2$CH$_2$—   m: 1   s: 0
Z: —   $R^A$: H   $R^4$: H
Position of —COCH=CHCOOH: 4-position
M.p. 253.5–255° C.   Crystalline form: White powder
Solvent for recrystallization: Dimethylformamide-ethanol
Form: Free Example 348

$R^5$: —OCH$_3$ (3-position)   A: —CH$_2$CH$_2$—   m: 1   s: 0
Z: —   $R^A$: H   $R^4$: H
Position of —COCH=CHCOOH: 4-position
M.p. 260–261° C.   Crystalline form: Yellow powder
Solvent for recrystallization: Dimethylformamide-ethanol
Form: Free Example 349

$R^5$: —O(CH$_2$)$_3$N(morpholino) (5-position)   A: —CH$_2$—   m: 1   s: 1
Z: O   $R^A$: H   $R^4$: H
Position of —COCH=CHCOOH: 4-position
M.p. 184–186° C.   Crystalline form: Pale yellow powder
Solvent for recrystallization: Dimethylformamide-ethanol-water
Form: HCl

TABLE 151-continued

Example 352

R⁵: —OCH₂CH=CH₂ (3-position)  A: —CH₂—  m: 1  s: 1
Z: O  Rᴬ: H  R⁴: H
Position of —COCH=CHCOOH: 4-position
M.p. 248–254° C.  Crystalline form: Pale yellow powder
Solvent for recrystallization: Diluted hydrochloric acid
NMR (36)  Form: Free

TABLE 152

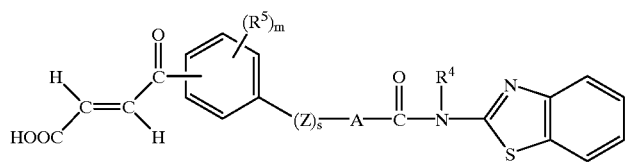

Example 353

R⁵: —O-cyclopentyl  (3-position)  A: —CH₂—  m: 1  s: 1

Z: O  R⁴: H
Position of —COCH=CHCOOH: 4-position
M.p. 270.0–271.5° C.  Crystalline form: Pale yellow powder
Solvent for recrystallization: Dimethylformamide-dichloromethane
Form: Free Example 354

R⁵: phenyl  (3-position)  A: —CH₂—  m: 1  s: 1

Z: O  R⁴: H
Position of —COCH=CHCOOH: 4-position
M.p. 270.5–273.3° C.  Crystalline form: Yellow powder
Solvent for recrystallization: Dimethylformamide-dichloromethane
Form: Free Example 355

R⁵: —(CH₂)₃CH₃ (2-position) & —OCH₃ (5-position)
A: —CH₂—  m: 2  s: 1  Z: O  R⁴: H
Position of —COCH=CHCOOH: 4-position
M.p. 203–206° C.  Crystalline form: Yellow powder
Solvent for recrystallization: Dimethylformamide-dichloromethane
Form: Free

TABLE 153

Example 356

R⁵: —(CH₂)₂CH₃ (2-position) & —OCH₃ (3-position)
A: —CH₂—  m: 2  s: 1  Z: O  R⁴: H
Position of —OCH=CHCOOH: 4-position
M.p. 232–234° C.  Crystalline form: Yellow powder
Solvent for recrystallization: Tetrahydrofuran-water
Form: Free

TABLE 153-continued

Example 357

R⁵: —O-phenyl  (3-position)  A: —CH₂—  m: 1  s: 1

Z: O  R⁴: H
Position of —COCH=CHCOOH: 4-position
M.p. 237–245° C. (decomp.)  Crystalline form: White powder
Solvent for recrystallization: Tetrahydrofuran-water
NMR (37)  Form: Free Example 358

R⁵: —CH₂CH₃ (2-position) & —OCH₃ (5-position)
A: —CH₂—  m: 2  s: 1  Z: O  R⁴: H
Position of —COCH=CHCOOH: 4-position
M.p. 127–138° C. (decomp.)  Crystalline form: Yellow powder
Solvent for recrystallization: Dimethylformamide-acetonitrile
NMR (38)  Form: Free

TABLE 154

Example 359

R$^5$: —OCH$_3$ (2- & 6-positions)
A: —CH$_2$—
m: 2
s: 1
Z: O
R$^4$: H
Position of —COCH═CHCOOH: 4-position
M.p. 137–138° C.
Crystalline form: Yellow powder
Solvent for recrystallization: Dimethylformamide-ethanol-diethyl ether-n-hexane
Form: Free Example 360

R$^5$: —OCH$_3$ (2- & 3-positions)
A: —CH$_2$—
m: 2
s: 1
Z: O
R$^4$: H
Position of —COCH═CHCOOH: 4-position
M.p. 235–237° C.
Crystalline form: Yellow powder
Solvent for recrystallization: Dichloromethane-dimethylformamide
Form: Free Example 361

R$^5$: —CH$_3$ (2-position) & —OCH$_3$ (3-position)
A: —CH$_2$—
m: 2
s: 1
Z: O
R$^4$: H
Position of —COCH═CHCOOH: 4-position
Crystalline form: Pale yellow powder
NMR (39)
Form: Free Example 362

R$^5$: —CH$_3$ (2-position) & —OCH$_3$ (3-position)
A: —CH$_2$—
m: 2
s: 1
Z: O
R$^4$: H
Position of —COCH═CHCOOH: 6-position
Crystalline form: Pale brown powder
NMR (40)
Form: Free

TABLE 155

Example 363

R$^5$: —(CH$_2$)$_3$CH$_3$ (2-position) & —OCH$_3$ (3-position)
A: —CH$_2$—
m: 2
s: 1
Z: O
R$^4$: H
Position of —COCH═CHCOOH: 4-position
Crystalline form: Yellow powder
NMR (41)
Form: Free Example 364

R$^5$: —SCH$_3$ (3-position)
A: —CH$_2$—
m: 1
s: 1
Z: O
R$^4$: H
Position of —COCH═CHCOOH: 4-position
Crystalline form: Yellow powder

TABLE 155-continued

NMR (42)
Form: Free

Example 365

R$^5$: —CH$_2$CH$_3$ (2-position) & —OCH$_3$ (3-position)
A: —CH$_2$—
m: 2
s: 1
Z: O
R$^4$: H
Position of —COCH═CHCOOH: 4-position
Crystalline form: Pale brown powder
NMR (43)
Form: Free Example 366

R$^5$: —OCH$_3$ (3-position)
A: —CH(CH$_3$)—
m: 1
s: 1
Z: O
R$^4$: H
Position of —COCH═CHCOOH: 4-position
M.p. 225–228° C. (decomp.)
Crystalline form: Pale brown powder
Solvent for recrystallization: Dimethylformamide-ethanol-diethyl ether-water
Form: Free

TABLE 156

Example 367

R$^5$: 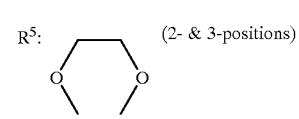 (2- & 3-positions)

A: —CH$_2$— m: 2 s: 1 Z: O R$^4$: H
Position of —COCH═CHCOOH: 4-position
M.p. 255–256° C. (decomp.)  Crystalline form: Yellow powder
Solvent for recrystallization: Dimethylformamide-acetonitrile  Form: Free Example 368

R$^5$: —OCH$_3$ (3-position)
A: —(CH$_2$)$_3$— m: 1 s: 1 Z: O R$^4$: H
Position of —COCH═CHCOOH: 4-position
M.p. 239–241° C. (decomp.)  Crystalline form: Pale yellow powder
Solvent for recrystallization: Dimethylformamide-acetonitrile  Form: Free Example 369

R$^5$: —(CH$_2$)$_2$CH$_3$ (2-position) & —OCH$_3$ (5-position)
A: —CH$_2$— m: 2 s: 1 Z: 0 R$^4$: H
Position of —COCH═CHCOOH: 4-position
M.p. 222–224° C. (decomp.)  Crystalline form: Pale yellow powder
Solvent for recrystallization: Dimethylformamide-acetonitrile  Form: Free Example 370

R$^5$: —CH$_2$CH═CH$_2$ (2-position) & —OCH$_3$ (5-position)
A: —CH$_2$— m: 2 s: 1 Z: O R$^4$: H
Position of —COCH═CHCOOH: 4-position
M.p. 224–225° C. (decomp.)  Crystalline form: Yellow powder
Solvent for recrystallization: Dimethylformamide-acetonitrile  Form: Free

TABLE 157

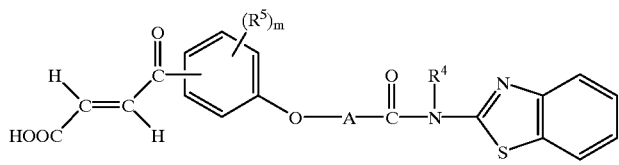

Example 371

R⁵: —OCH₃ (2- & 5-positions)
A: —CH₂—   m: 2   R⁴: H
Position of —COCH=CHCOOH: 4-position
NMR (44)   Crystalline form: Yellow powder   Form: Free Example 372

R⁵: —CH₃ (2-position) & —OCH₃ (5-position)
A: —CH₂—   m: 2   R⁴: H
Position of —COCH=CHCOOH: 4-position
NMR (45)   Crystalline form: Yellow powder Example 373

R⁵: —OC₂H₅ (2-position) & —OCH₃ (5-position)
A: —CH₂—   m: 2   R⁴: H
Position of —COCH=CHCOOH: 4-position
M.p. 202–204° C. (decomp.)   Crystalline form: Yellow powder
Solvent for recrystallization: Dimethylformamide-acetonitrile   Form: Free

TABLE 158

Example 374

R⁵: —Br (2-position) & —OCH₃ (5-position)
A: —CH₂—
m: 2
R⁴: H
Position of —COCH=CHCOOH: 4-position
M.p. 238–239° C. (decomp.)
Crystalline form: Yellow powder
Solvent for recrystallization: Dimethylformamide-acetonitrile
Form: Free Example 375

R⁵: —CH(CH₃)₂ (2-position) & —OCH₃ (5-position)
A: —CH₂—
m: 2
R⁴: H
Position of —COCH=CHCOOH: 4-position
NMR (46)
Crystalline form: Yellow powder
Form: Free

TABLE 158-continued

Example 376

R⁵: —(CH₂)₅CH₃ (2-position) & —OCH₃ (5-position)
A: —CH₂—
m: 2
R⁴: H
Position of —COCH=CHCOOH: 4-position
NMR (47)
Crystalline form: Yellow powder
Form: Free Example 377

R⁵: —N(CH₃)₂ (2-position)
A: —CH₂—
m: 1
R⁴: H
Position of —COCH=CHCOOH: 4-position
NMR (48)
Crystalline form: Pale yellow powder
Form: Free

TABLE 159

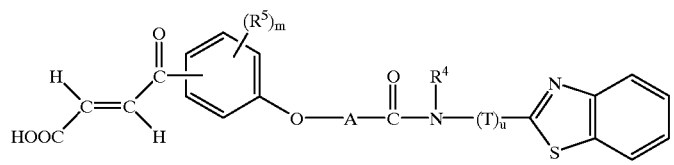

Example 378

R⁵: —OCH₃ (3-position)
A: —CH₂—   m: 1   R⁴: H   T: —CH₂—   u: 1
Position of —COCH=CHCOOH: 4-position
NMR (49)   Crystalline form: Yellow powder   Form: Free

TABLE 160

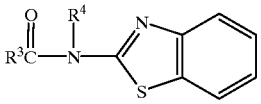

Example 379

R⁴: H

R³: 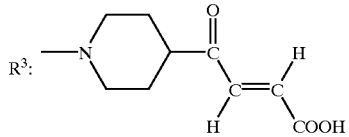

M.p. 211.5–213° C.   Crystalline form: White powder   Form: Free
Solvent for recrystallization: Dimethylformamide-methanol Using the suitable starting compounds, the compounds as listed in Tables 161–193 are obtained in the same manner as in Example 3 or 4.

TABLE 161

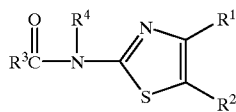

Example 380

R¹ 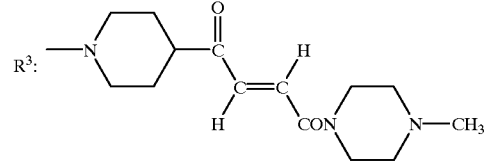 R⁴: H
:
R²

R³: 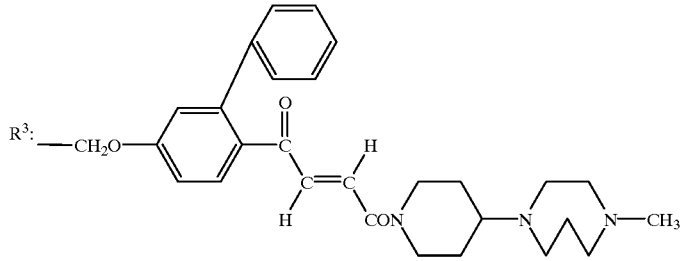

M.p. 187.5–188.5° C.   Crystalline form: White powder
Solvent for recrystallization: Ethanol-diethyl ether   Form: Free Example 381

R¹ 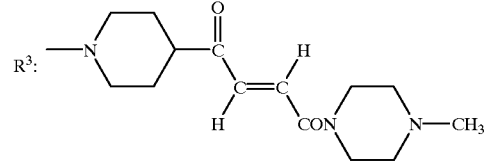 R⁴: H
:
R²

R³: —CH₂O— [structure]

M.p. 164–166° C.   Crystalline form: white powder
Solvent for recrystallization: Ethanol-diethyl ether   Form: 2HCl

TABLE 162

Example 382

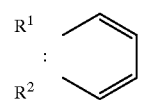
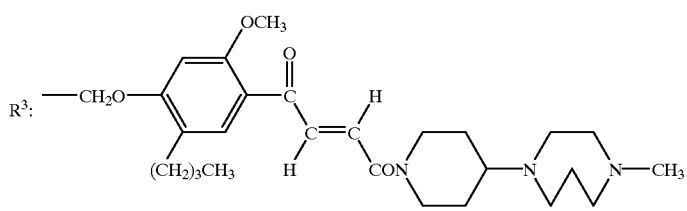

R⁴: H  M.p. 148.4–151.2° C.  Crystalline form: Yellow powder
Solvent for recrystallization: Ethanol-diethyl ether  Form: 2HCl Example 383

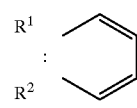
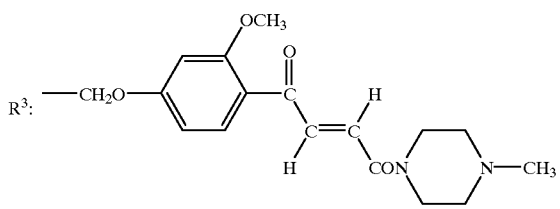

R⁴: H  M.p. 200–210° C. (decomp.)  Crystalline form: Pale brown powder
Solvent for recrystallization: Ethanol-water-diethyl ether  Form: 2HCl—H₂O
NMR (1)

Example 384

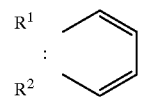
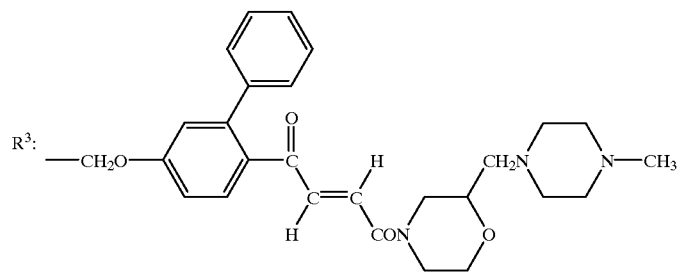

R⁴: H  M.p. 160.2–162.3° C.  Crystalline form: Pale yellow powder
Solvent for recrystallization: Ethanol-diethyl ether  Form: 2HCl

TABLE 163

Example 385

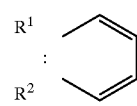
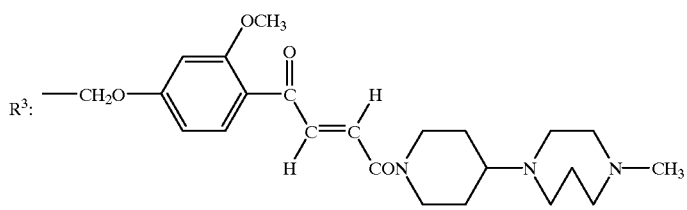

R⁴: H  M.p. 156–166° C. (decomp.)  Crystalline form: Pale brown powder
Solvent for recrystallization: Ethanol-water-diethyl ether  Form: 3HCl—3H₂O
NMR (2)

TABLE 163-continued

Example 386

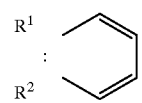 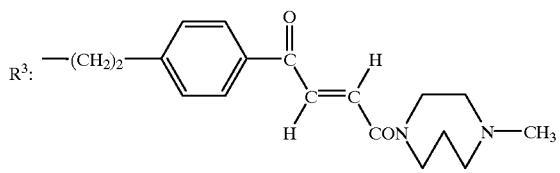

R⁴: H   M.p. 178–179° C.   Crystalline form: Pale yellow powder
Solvent for recrystallization: Ethanol   Form: Free Example 387

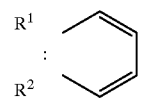 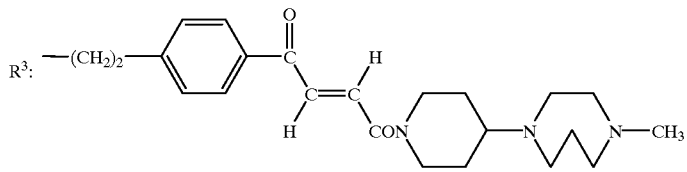

R⁴: H   M.p. 252–253.5° C.   Crystalline form: White powder
Solvent for recrystallization: Ethanol-water-diethyl ether   Form: Free

TABLE 164

Example 388

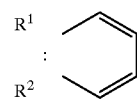 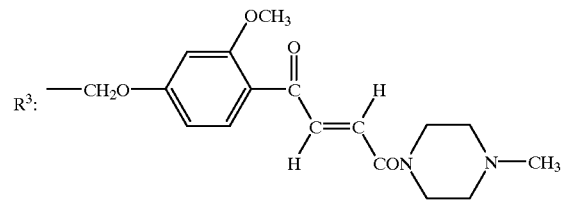

R⁴: H   M.p. 244–246° C. (decomp.)   Crystalline form: Pale brown powder
Solvent for recrystallization: Ethanol-chloroform   Form: Free Example 389

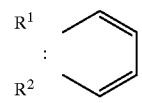 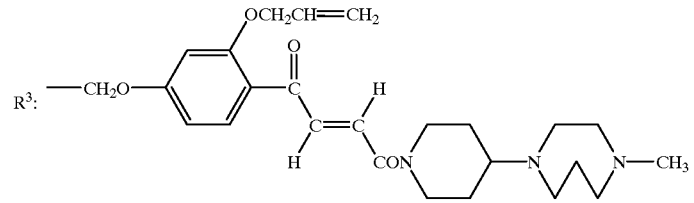

R⁴: H   M.p. 173–176° C.   Crystalline form: Pale yellow powder
Solvent for recrystallization: Ethanol-water-diethyl ether   Form: 2HCl TABLE 164-continued Example 390

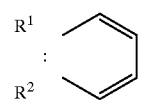
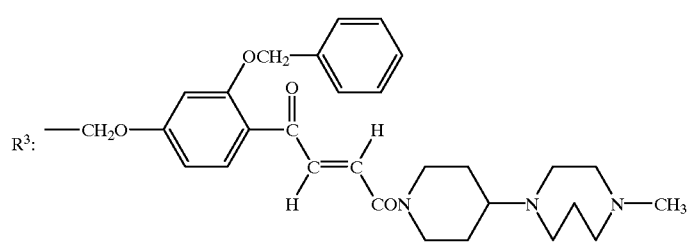

R⁴: H  M.p. 161.2–163.0° C.  Crystalline form: Pale yellow powder
Solvent for recrystallization: Ethanol-water-diethyl ether  Form: 2HCl

TABLE 165

Example 391

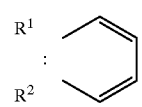
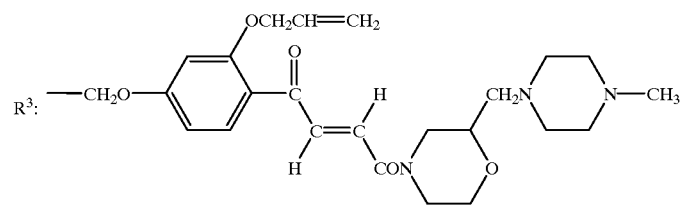

R⁴: H  M.p. 172–176° C.  Crystalline form: White powder
Solvent for recrystallization: Ethanol-water-diethyl ether  Form: Free Example 392

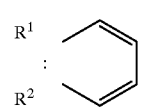
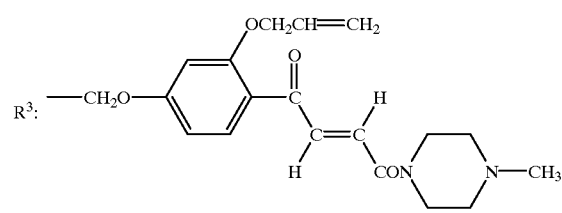

R⁴: H  M.p. 234.5–236.5° C.  Crystalline form: Yellow powder
Solvent for recrystallization: Ethanol-water  Form: Methanesulfonate Example 393

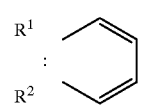
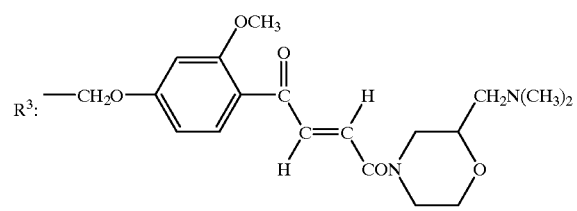

R⁴: H  M.p. 114–117° C.  Crystalline form: Pale yellow powder
Solvent for recrystallization: Ethanol-diethyl ether  Form: Dimethanesulfonate

TABLE 166

Example 394

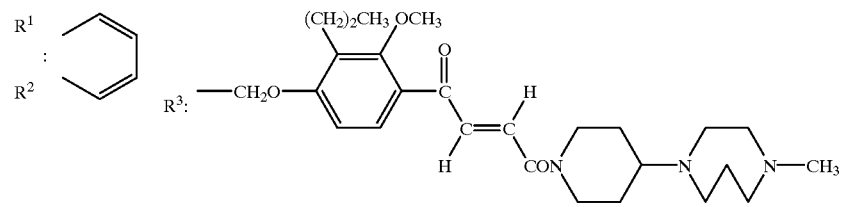

R⁴: H  M.p. 167.0–168.5° C.  Crystalline form: Pale yellow powder
Solvent for recrystallization: Ethanol-water  Form: 2HCl Example 395

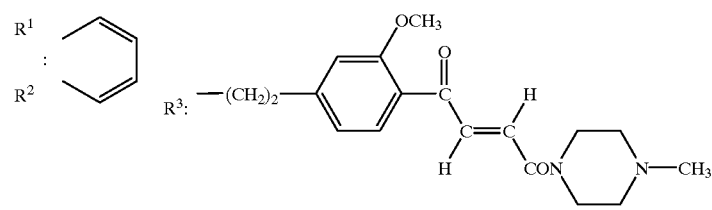

R⁴: H  M.p. 183–183.5° C.  Crystalline form: Pale brown powder
Solvent for recrystallization: Ethanol  Form: Free Example 396

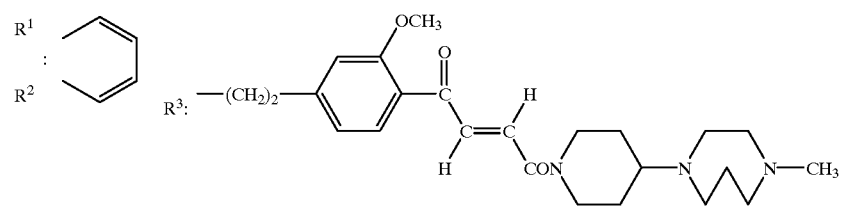

R⁴: H  M.p. 237.5–238.5° C.  Crystalline form: Yellow powder
Solvent for recrystallization: Ethanol-water  Form: 2HCl

TABLE 167

Example 397

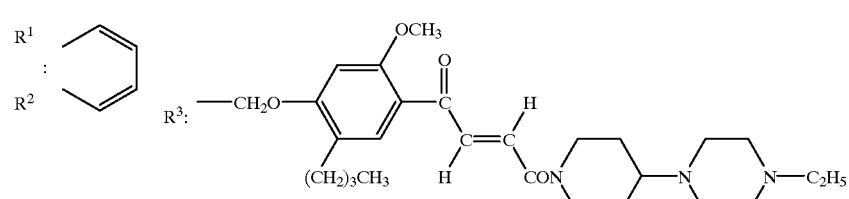

R⁴: H  M.p. 158.0–161.0° C.  Crystalline form: Yellow powder
Solvent for recrystallization: Ethanol-water  Form: 2HCl

TABLE 167-continued

Example 398

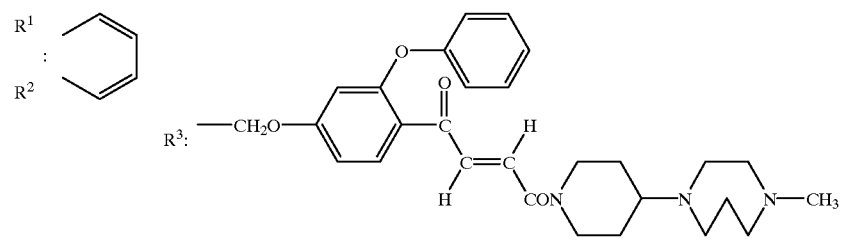

R[4]: H  M.p. 162.0–164.3° C.  Crystalline form: Pale yellow powder
Solvent for recrystallization: Ethanol-water  Form: 2HCl Example 399

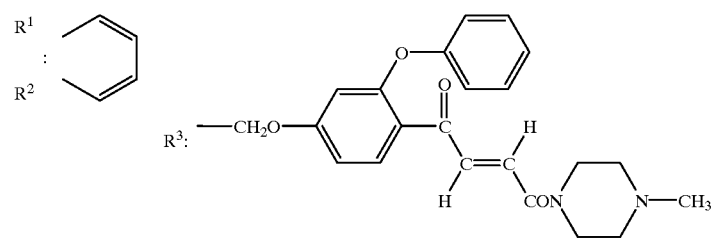

R[4]: H  M.p. 133–136° C.  Crystalline form: Yellow powder
Solvent for recrystallization: Ethanol-water  Form: Methanesulfonate

TABLE 168

Example 400

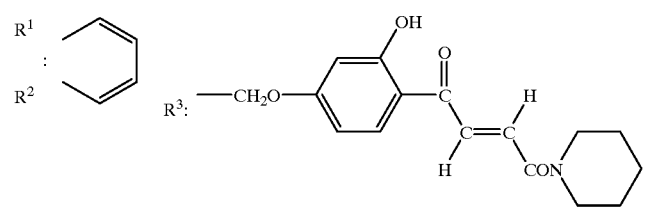

R[4]: H  M.p. 207.3–210.0° C.  Crystalline form: Yellow powder
Solvent for recrystallization: Dimethylformamide-ethanol  Form: Free Example 401

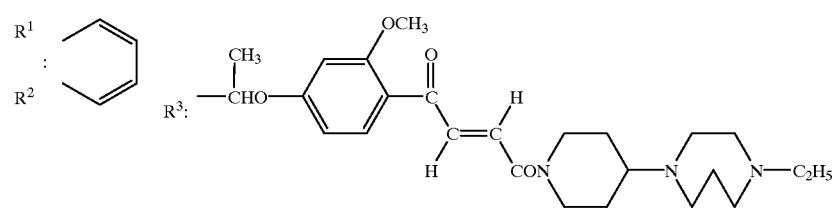

R[4]: H  M.p. 220–240° C. (decomp.)  Crystalline form: Pale yellow powder
Solvent for recrystallization: Ethanol-diethyl ether  Form: 2HCl
NMR (3)

TABLE 168-continued

Example 402

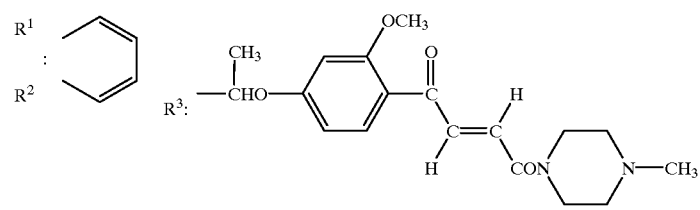

$R^4$: H    M.p. 170–180° C. (decomp.)    Crystalline form: Pale yellow powder
Solvent for recrystallization: Ethanol-diethyl ether    Form: HCl
NMR (4)

TABLE 169

Example 403

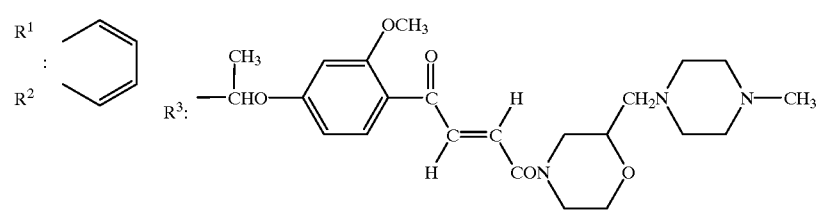

$R^4$: H    M.p. 190–220° C. (decomp.)    Crystalline form: Pale orange powder
Solvent for recrystallization: Ethanol-diethyl ether    Form: 2HCl
NMR (5)
Example 404

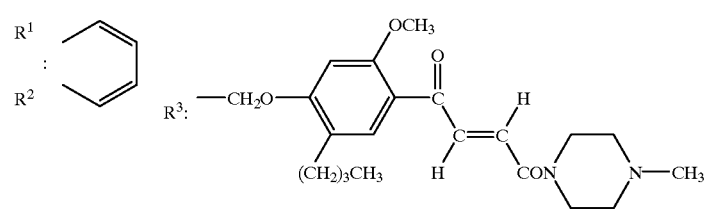

$R^4$: H    M.p. 138.5–140.3° C.    Crystalline form: Yellow powder
Solvent for recrystallization: Ethanol-water-diethyl ether
Form: Methanesulfonate
Example 405

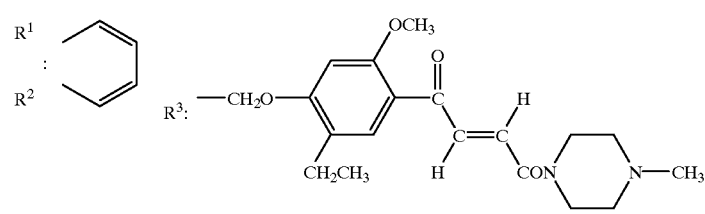

$R^4$: H    M.p. 217.4–219.0° C.    Crystalline form: Yellow powder
Solvent for recrystallization: Ethanol-diethyl ether-dichloromethane
Form: Methanesulfonate

TABLE 170

Example 406

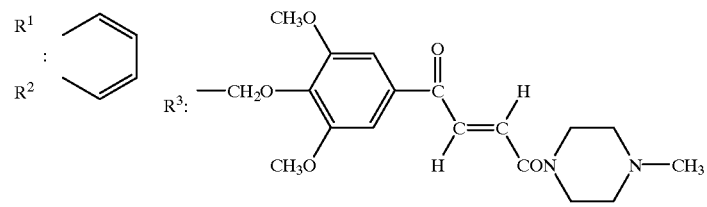

R⁴: H  M.p. 138.2–139.5° C.  Crystalline form: Pale yellow powder
Solvent for recrystallization: Ethanol-water-diethyl ether
Form: Methanesulfonate Example 407

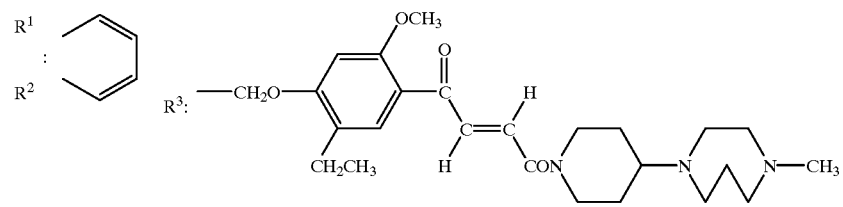

R⁴: H  M.p. 168.5–171.0° C.  Crystalline form: Yellow powder
Solvent for recrystallization: Ethanol-water-diethyl ether  Form: 2HCl Example 408

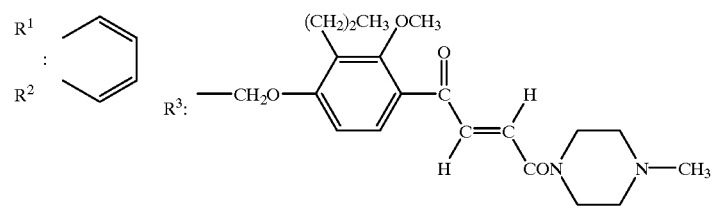

R⁴: H  M.p. 132–134° C.  Crystalline form: White powder
Solvent for recrystallization: Ethanol-diethyl ether
Form: Methanesulfonate

TABLE 171

Example 409

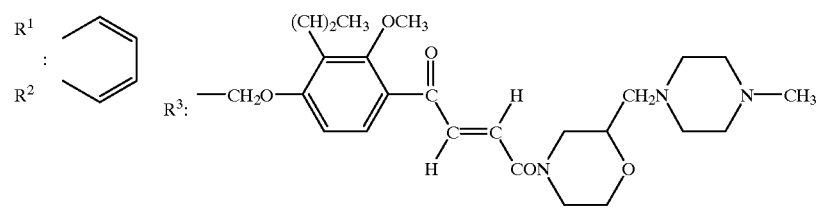

R⁴: H  M.p. 190–193° C.  Crystalline form: Yellow powder
Solvent for recrystallization: Ethanol-acetone-diethyl ether
Form: 2HCl

TABLE 171-continued

Example 410

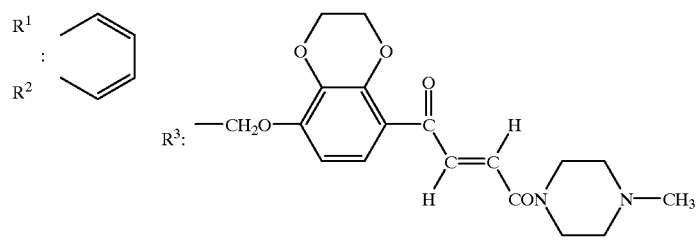

R⁴: H  M.p. 110–150° C. (decomp.)  Crystalline form: Pale yellow powder
Solvent for recrystallization: Ethanol-dichloromethane-diethyl ether
Form: Dimethanesulfonate  NMR (6)

Example 411

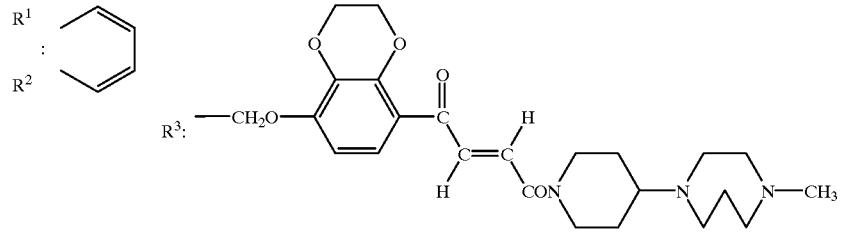

R⁴: H  M.p. 190–240° C. (decomp.)  Crystalline form: Pale yellow powder
Solvent for recrystallization: Ethanol-diethyl ether
Form: 2HCl  NMR (7)

TABLE 172

Example 412

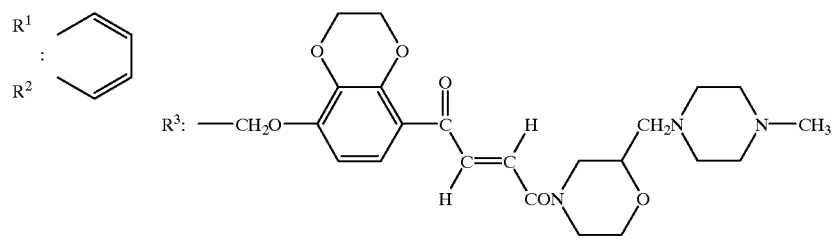

R⁴: H  M.p. 190–210° C. (decomp.)  Crystalline form: Pale yellow powder
Solvent for recrystallization: Ethanol-diethyl ether
Form: 2HCl  NMR (8)

Example 413

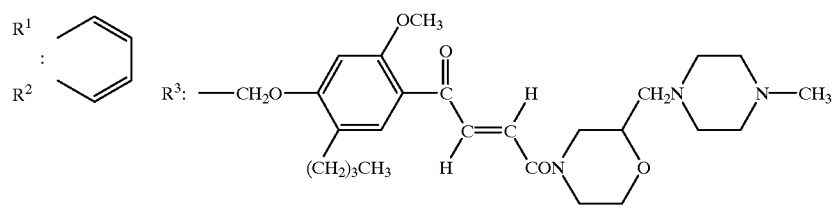

R⁴: H  M.p. 167.0–169.0° C.  Crystalline form: Yellow powder
Solvent for recrystallization: Ethanol  Form: 2HCl

TABLE 172-continued

Example 414

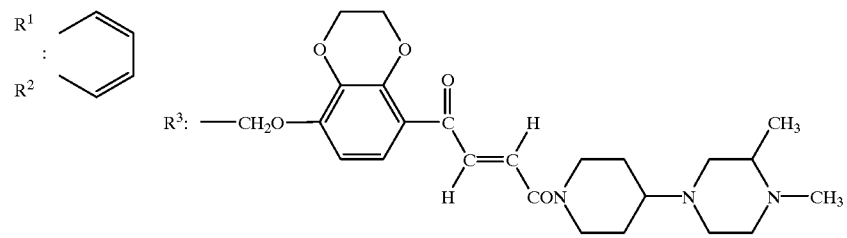

R⁴: H   M.p. 200–220° C. (decomp.)   Crystalline form: Pale yellow powder
Solvent for recrystallization: Ethanol-water-diethyl ether
Form: 2HCl   NMR (9)

TABLE 173

Example 415

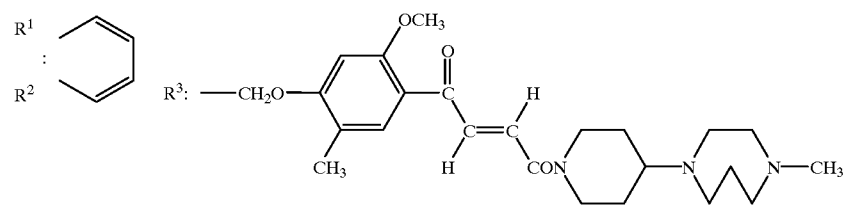

R⁴: H   M.p. 177–180° C.   Crystalline form: Yellow powder
Solvent for recrystallization: Dichloromethane-diisopropyl ether
Form: 2HCl Example 416

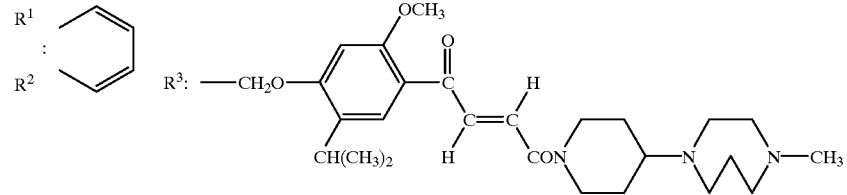

R⁴: H   M.p. 179–182° C.   Crystalline form: Yellow powder
Solvent for recrystallization: Dichloromethane-diisopropyl ether
Form: 2HCl Example 417

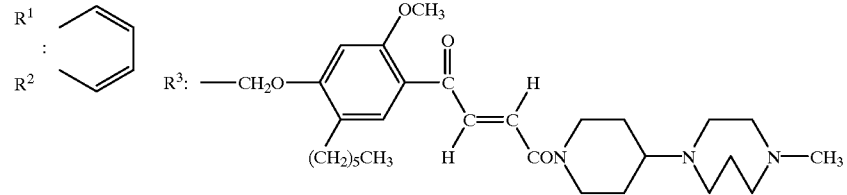

R⁴: H   M.p. 158–159° C.   Crystalline form: Yellow powder
Solvent for recrystallization: Dichloromethane-diisopropyl ether
Form: 2HCl

TABLE 174

Example 418

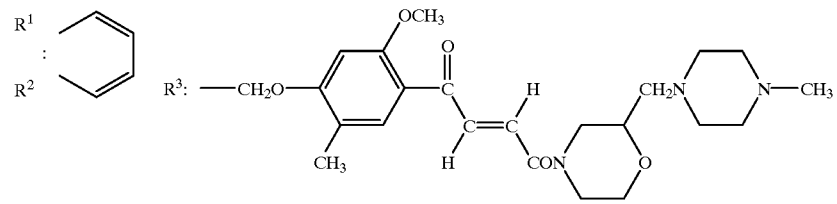

R⁴: H  M.p. 230–232° C.  Crystalline form: Yellow powder
Solvent for recrystallization: Methanol-diethyl ether
Form: 2HCl Example 419

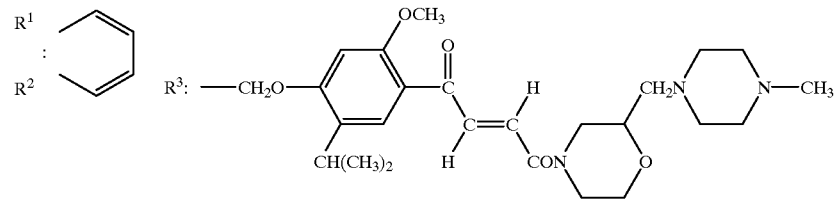

R⁴: M.p. 221–224° C.  Crystalline form: Yellow powder
Solvent for recrystallization: Methanol-diethyl ether
Form: 2HCl Example 420

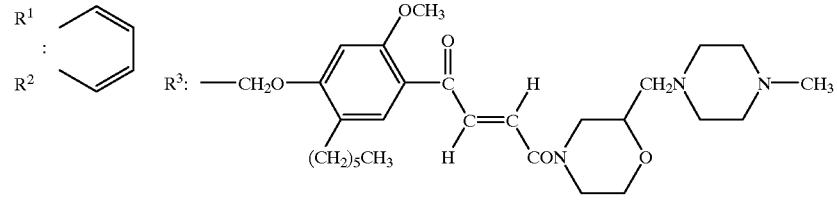

R⁴: H  M.p. 179–182° C.  Crystalline form: Yellow powder
Solvent for recrystallization: Methanol-diethyl ether
Form: 2HCl

TABLE 175

Example 421

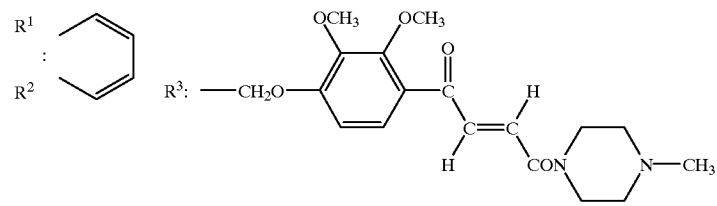

R⁴: H  M.p. 146.2–148.5° C.  Crystalline form: Gray powder
Solvent for recrystallization: Ethanol
Form: HCl

TABLE 175-continued

Example 422

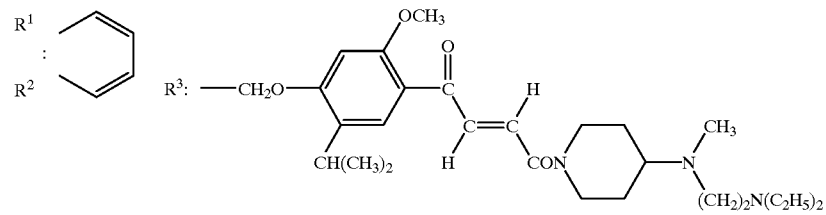

R⁴: H  M.p. 153–155° C.  Crystalline form: Yellow powder
Solvent for recrystallization: Dichloromethane  Form: 2HCl Example 423

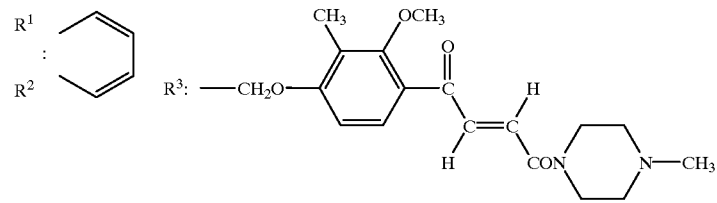

R⁴: H  M.p. 225–228° C.  Crystalline form: Pale yellow powder
Solvent for recrystallization: Ethanol  Form: Methanesulfonate

TABLE 176

Example 424

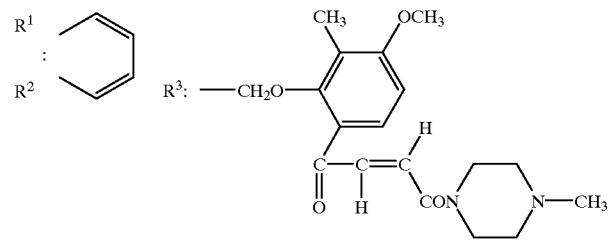

R⁴: H  NMR (10)  Crystalline form: Pale yellow amorphous
Form: Methanesulfonate

Example 425

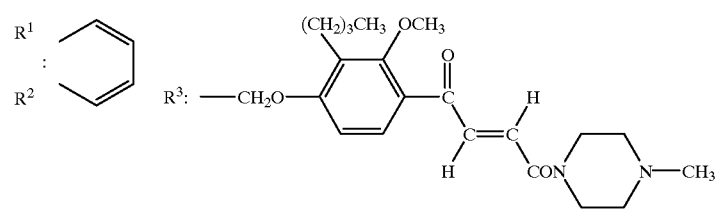

R⁴: H  M.p. 140–143° C.  Crystalline form: Pale yellow powder
Solvent for recrystallization: Ethanol  Form: Methanesulfonate

TABLE 176-continued

Example 426

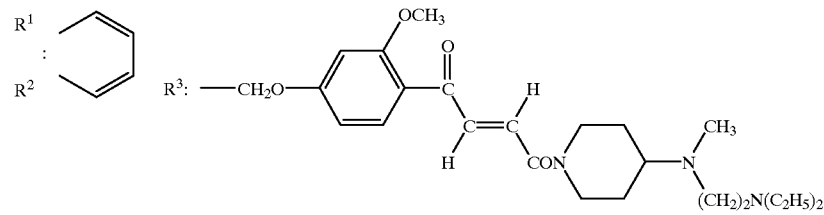

R[4]: H   M.p. 152.4–154.8° C.   Crystalline form: Pale yellow powder
Solvent for recrystallization: Acetone-dichloromethane-water
Form: 2HCl

TABLE 177

Example 427

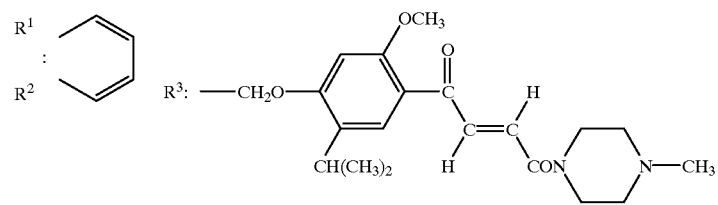

R[4]: H   M.p. 154–155° C.   Crystalline form: Yellow powder
Solvent for recrystallization: Ethanol-diethyl ether   Form: Methanesulfonate Example 428

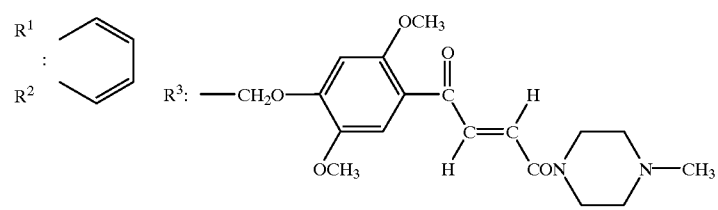

R[4]: H   M.p. 165–168° C.   Crystalline form: Yellow powder
Solvent for recrystallization: Dichloromethane-diethyl ether
Form: Methanesulfonate Example 429

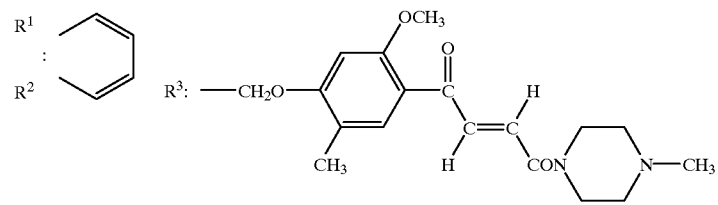

R[4]: H   M.p. 234–235° C.   Crystalline form: Yellow powder
Solvent for recrystallization: Dichloromethane-diethyl ether
Form: Methanesulfonate

TABLE 178

Example 430

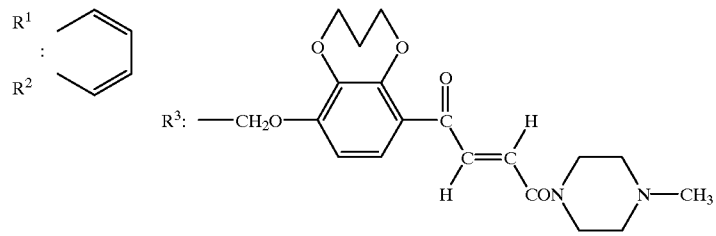

R⁴: H  M.p. 195–200° C. (decomp.)  Crystalline form: Pale yellow powder
Solvent for recrystallization: Acetone-water-diethyl ether
NMR (11)  Form: Methanesulfonate Example 431

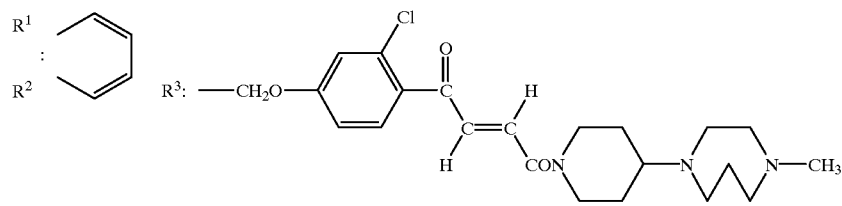

R⁴: H  M.p. 183–220° C. (decomp.)  Crystalline form: White powder
Solvent for recrystallization: Acetone-ethanol-diethyl ether
NMR (12)  Form: 2HCl Example 432

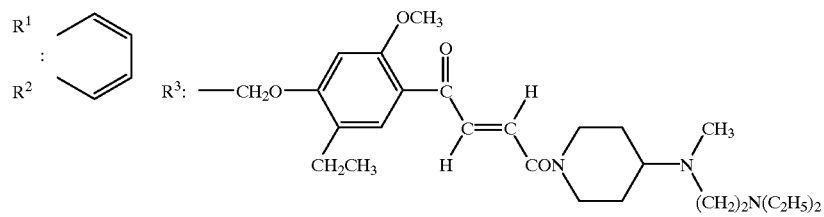

R⁴: H  M.p. 159–161° C.  Crystalline form: Yellow powder
Solvent for recrystallization: Ethanol-acetone-diethyl ether
Form: 2HCl

TABLE 179

Example 433

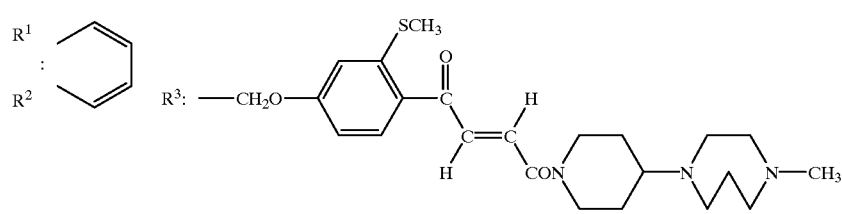

R⁴: H  M.p. 177–180° C.  Crystalline form: Yellow amorphous
Solvent for recrystallization: Ethanol-water-diethyl ether  Form: 2HCl

TABLE 179-continued

Example 434

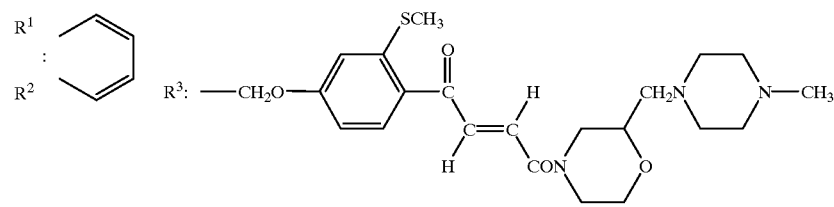

R⁴: H   M.p. 178–181° C.   Crystalline form: Yellow powder
Solvent for recrystallization: Ethanol-water   Form: 2HCl Example 435

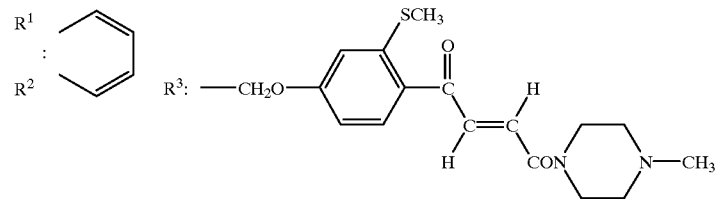

R⁴: H   M.p. 199–202° C.   Crystalline form: Pale orange powder
Solvent for recrystallization: Ethanol-water   Form: Methanesulfonate

TABLE 180

Example 436

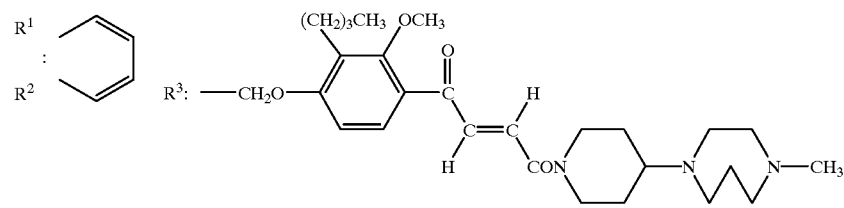

R⁴: H   NMR (13)   Crystalline form: Yellow amorphous   Form: 2HCl

Example 437

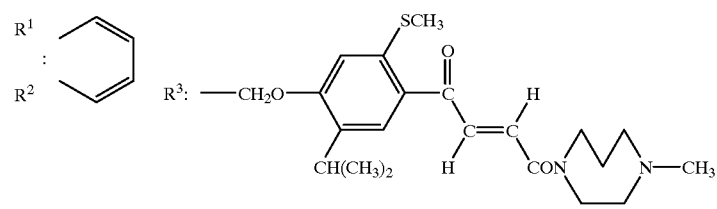

R⁴: H   M.p. 151–154° C.   Crystalline form: Yellow powder
Solvent for recrystallizaiton: Ethanol-diethyl ether   Form: Methanesulfonate Example 438

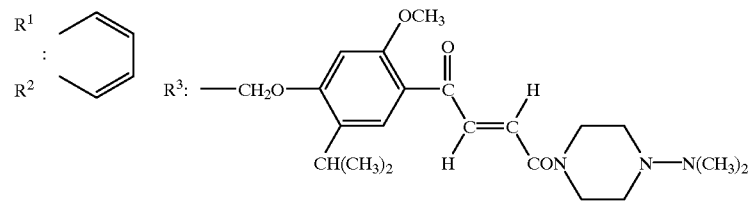

R⁴: H   M.p. 114–116° C.   Crystalline form: Yellow powder
Solvent for recrystallization: Acetone-water   Form: Methanesulfonate

TABLE 181

Example 439

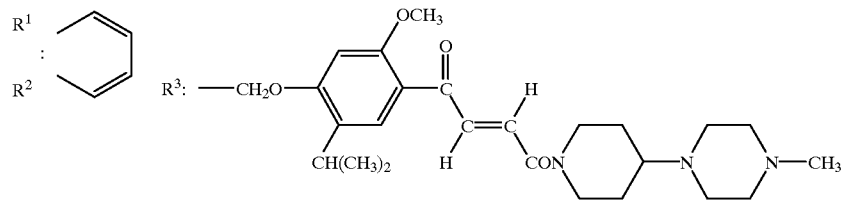

R⁴: H  M.p. 205–208° C.  Crystalline form: Yellow powder
Solvent for recrystallization: Acetone-water  Form: 2HCl Example 440

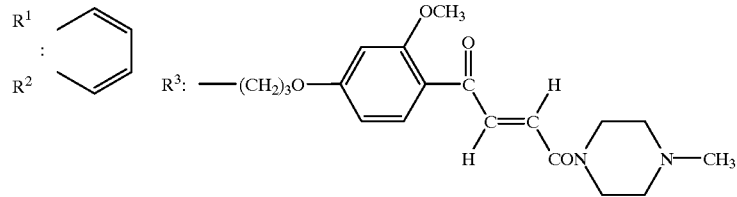

R⁴: H  M.p. 185–190° C. (decomp.)  Crystalline form: Pale yellow powder
Solvent for recrystallization: Ethanol-dichloromethane-diethyl ether
NMR (14)  Form: Methanesulfonate Example 441

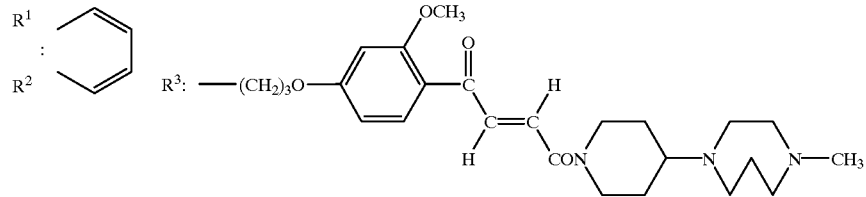

R⁴: H  M.p. 160–180° C. (decomp.)  Crystalline form: Pale yellow powder
Solvent for recrystallization: Ethanol-dichloromethane-diethyl ether
NMR (15)  Form: 2HCl

TABLE 182

Example 442

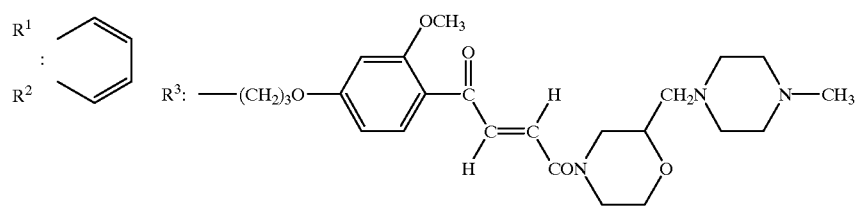

R⁴: H  M.p. 170–190° C.  Crystalline form: Pale yellow powder
Solvent for recrystallization: Ethanol-dichloromethane-diethyl ether
NMR (16)  Form: 2HCl TABLE 182-continued Example 443

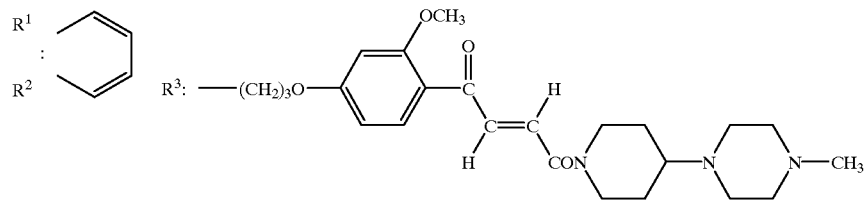

R⁴: H  M.p. 178–183° C. (decomp.)  Crystalline form: Pale yellow powder
Solvent for recrystallization: Ethanol-dichloromethane-diethyl ether
NMR (17)  Form: 2HCl Example 445

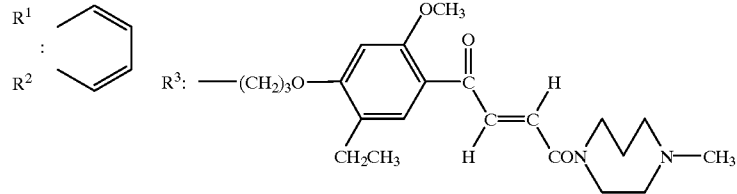

R⁴: H  M.p. 138–150° C. (decomp.)  Crystalline form: Pale brown powder
Solvent for recrystallization: Ethanol-dichloromethane-diethyl ether
NMR (18)  Form: Methanesulfonate

30

TABLE 183

Example 446

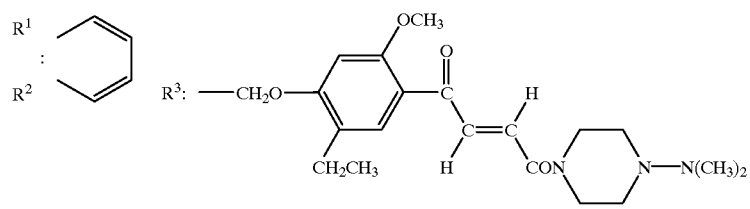

R⁴: H  M.p. 120–160° C. (decomp.)  Crystalline form: Pale brown powder
Solvent for recrystallization: Ethanol-dichloromethane-diethyl ether-acetone
NMR (19)  Form: Methanesulfonate Example 447

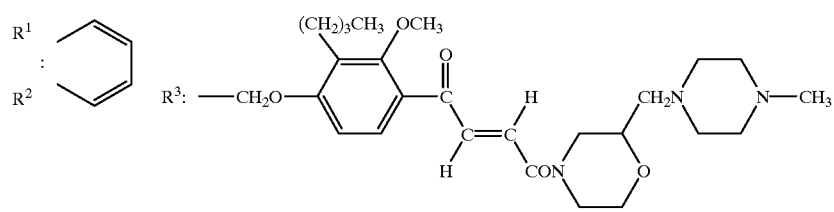

R⁴: H  M.p. 169–171° C.  Crystalline form: Pale yellow powder
Solvent for recrystallization: Ethanol-water  Form: 2HCl TABLE 183-continued Example 448

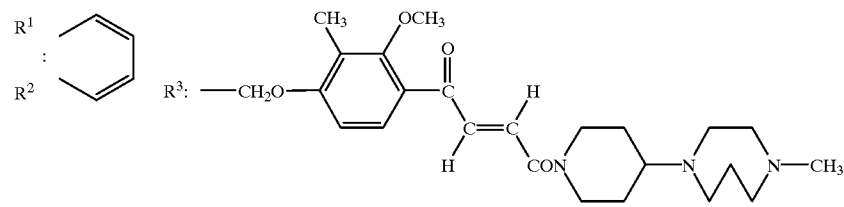

R⁴: H   M.p. 178–180° C.   Crystalline form: Pale yellow powder
Solvent for recrystallization: Ethanol-water-diethyl ether   Form: 2HCl

TABLE 184

Example 449

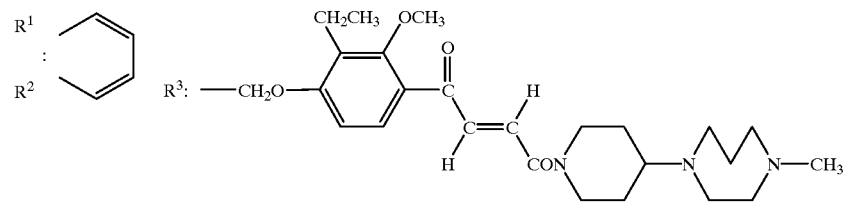

R⁴: H   M.p. 162–164° C.   Crystalline form: Pale yellow powder
Solvent for recrystallization: Ethanol-water-diethyl ether
Form: 2HCl Example 450

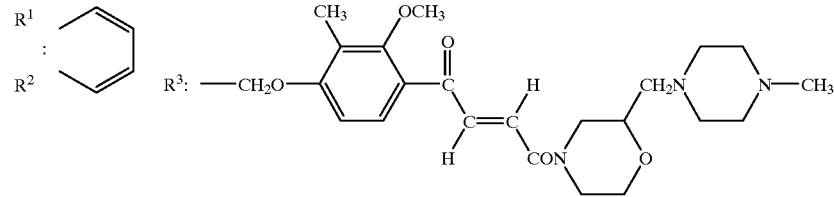

R⁴: H   M.p. 172–175° C.   Crystalline form: Pale yellow powder
Solvent for recrystallization: Ethanol-water   Form: 2HCl Example 451

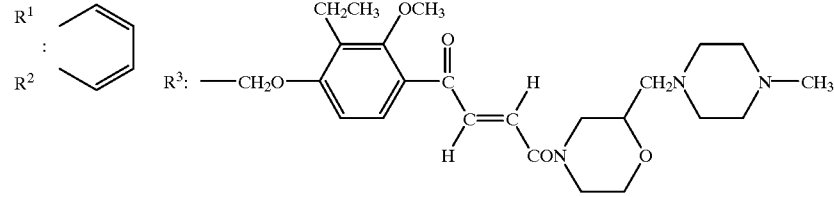

R⁴: H   M.p. 167–170° C.   Crystalline form: Pale yellow powder
Solvent for recrystallization: Ethanol-water   Form: 2HCl

TABLE 185

Example 452

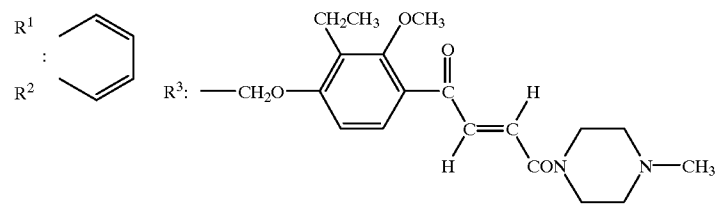

R⁴: H  M.p. 208–209° C.  Crystalline form: Pale yellow powder
Solvent for recrystallization: Ethanol-water
Form: Methanesulfonate Example 453

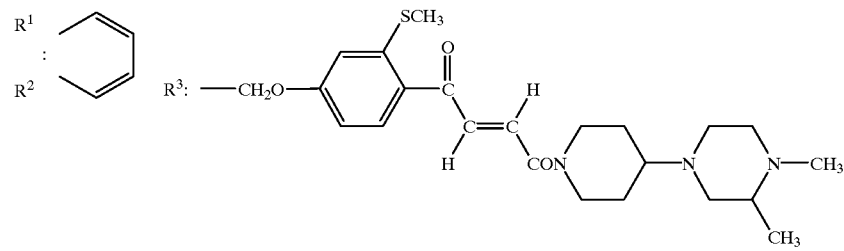

R⁴: H  M.p. 246–249° C.  Crystalline form: Yellow powder
Solvent for recrystallization: Ethanol-water  Form: 2HCl Example 454

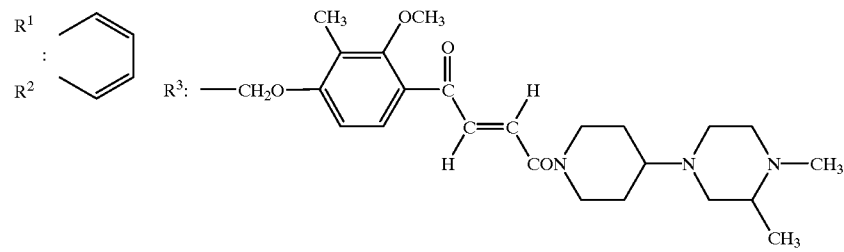

R⁴: H  M.p. 188–190° C.  Crystalline form: Pale yellow powder
Solvent for recrystallization: Ethanol-water  Form: 2HCl

TABLE 186

Example 455

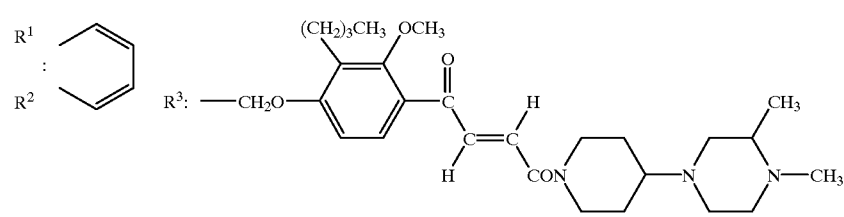

R⁴: H  M.p. 167–169° C.  Crystalline form: Pale yellow powder
Solvent for recrystallization: Ethanol-water  Form: 2HCl TABLE 186-continued Example 456

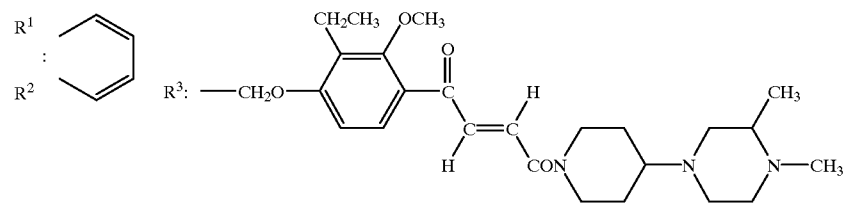

R⁴: H   M.p. 170–173° C.   Crystalline form: Pale yellow powder
Solvent for recrystallization: Ethanol-water   Form: 2HCl Example 457

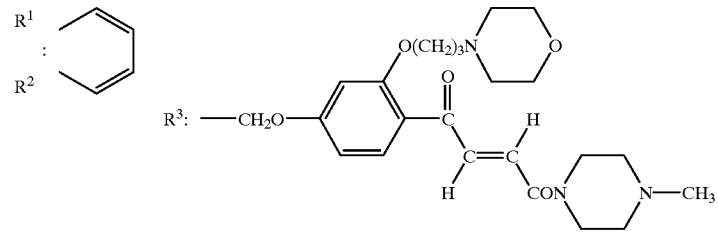

R⁴: H   M.p. 225–228° C.   Crystalline form: Pale yellow powder
Solvent for recrystallization: Ethanol-dichloromethane   Form: 2HCl

TABLE 187

Example 458

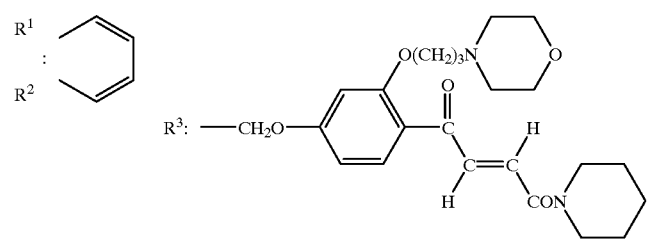

R⁴: H   M.p. 162.0–163.5° C.   Crystalline form: Yellow powder
Solvent for recrystallization: Ethanol-water   Form: Methanesulfonate Example 459

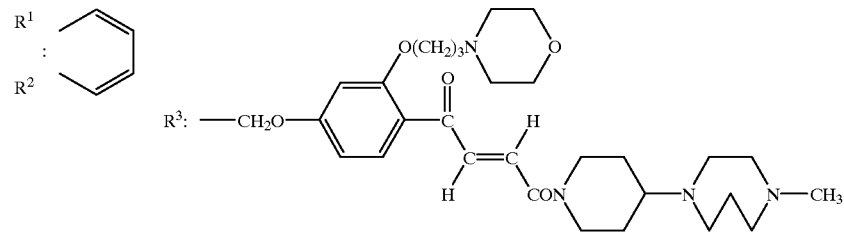

R⁴: H   M.p. 209.5–212.5° C.   Crystalline form: White powder
Solvent for recrystallization: Ethanol-water   Form: 3HCl

TABLE 187-continued

Example 460

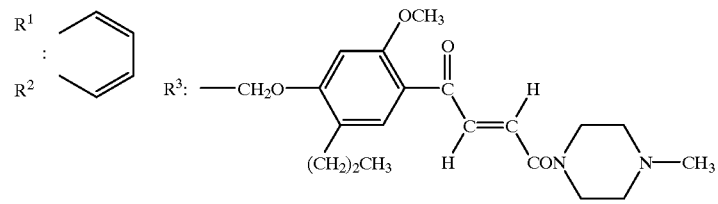

R[4]: H   M.p. 155–185° C. (decomp.)   Crystalline form: Pale yellow powder
Solvent for recrystallization: Ethanol-dichloromethane-diethyl ether
NMR (20)   Form: Methanesulfonate

TABLE 188

Example 461

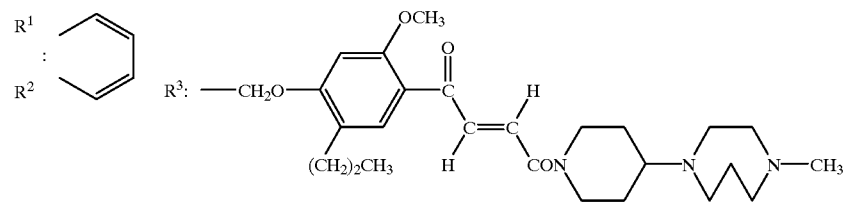

R[4]: H   M.p. 180–215° C. (decomp.)   Crystalline form: Pale yellow powder
Solvent for recrystallization: Ethanol-dichloromethane-diethyl ether
NMR (21)   Form: 2HCl Example 462

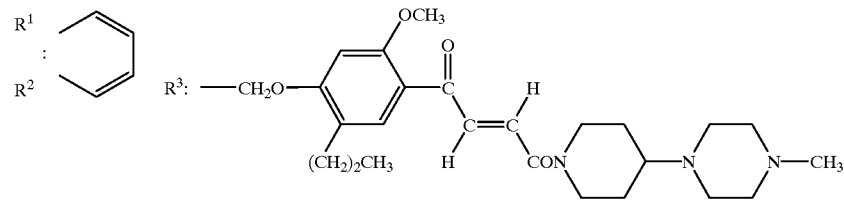

R[4]: H   M.p. 220–225° C. (decomp.)   Crystalline form: Pale yellow powder
Solvent for recrystallization: Ethanol-dichloromethane-diethyl ether
NMR (22)   Form: 2HCl Example 463

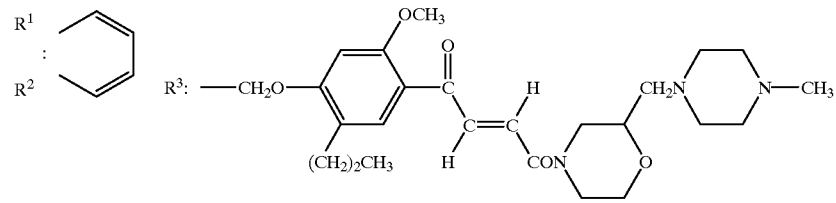

R[4]: H   M.p. 180–215° C. (decomp.)   Crystalline form: Pale yellow powder
Solvent for recrystallization: Ethanol-dichloromethane-diethyl ether
NMR (23)   Form: 2HCl

TABLE 189

Example 464

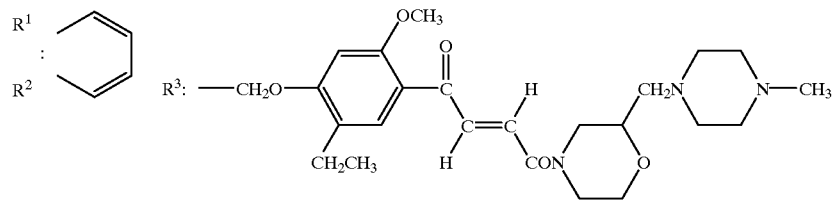

$R^4$: H  M.p. 185.5–192° C.  Crystalline form: Yellow powder
Solvent for recrystallization: Ethanol-water
NMR (24)  Form: 2HCl Example 465

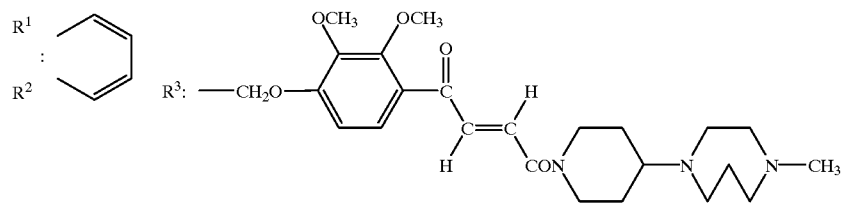

$R^4$: H  M.p. 159.5–161.2° C.  Crystalline form: Pale yellow powder
Solvent for recrystallization: Ethanol-diethyl ether-water  Form: 2HCl Example 466

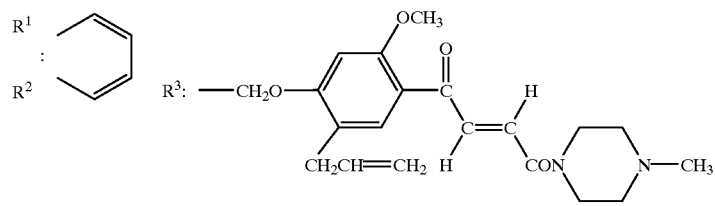

$R^4$: H  M.p. 150–158° C. (decomp.)  Crystalline form: Pale yellow powder
Solvent for recrystallization: Ethanol-dichloromethane-diethyl ether
NMR (25)  Form: Methanesulfonate

TABLE 190

Example 467

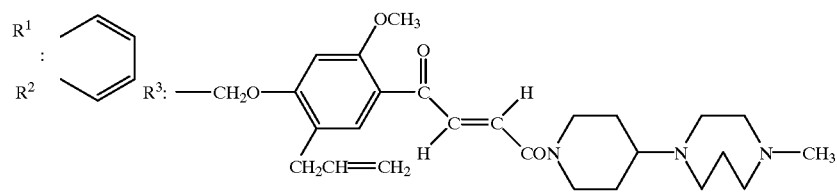

$R^4$: H   M.p. 193–204° C. (decomp.)

Crystalline form: Pale yellow powder

Solvent for recrystallization: Ethanol-dichloromethane-diethyl ether

NMR (26)     Form: 2HCl

TABLE 190-continued

Example 468

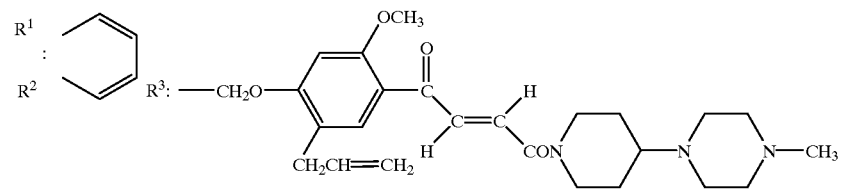

R[4]: H  M.p. 205–213° C. (decomp.)
Crystalline form: Pale yellow powder
Solvent for recrystallization: Ethanol-dichloromethane-diethyl ether
NMR (27)  Form: 2HCl Example 469

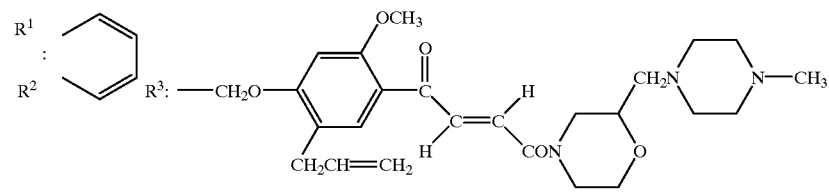

R[4]: H  M.p. 205–213° C. (decomp.) Crystalline form: Pale yellow powder
Solvent for recrystallization: Ethanol-dichloromethane-diethyl ether
NMR (28)   Form: 2HCl

TABLE 191

Example 470

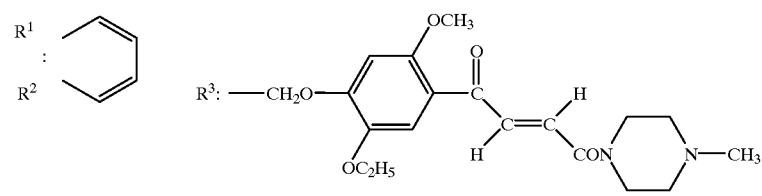

R[4]: H  M.p. 131–160° C. (decomp.)
Crystalline form: Pale yellow powder
Solvent for recrystallization: Dichloromethane-ethanol-diethyl ether
NMR (29)   Form: Methanesulfonate Example 471

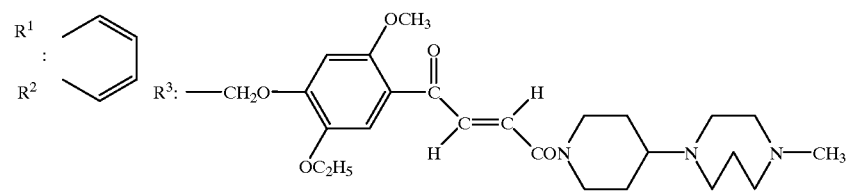

R[4]: H M.p. 180–210° C. (decomp.)    Crystalline form: Pale brown powder
Solvent for recrystallization: Dichloromethane-ethanol-diethyl ether
NMR (30)   Form: 2HCl

TABLE 191-continued

Example 472

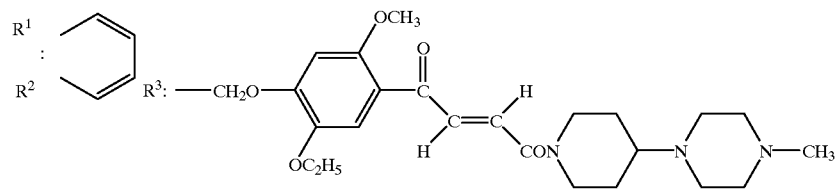

R[4]: H  M.p. 231–235° C. (decomp.)     Crystalline form: Pale yellow powder
Solvent for recrystallization: Dichloromethane-ethanol-diethyl ether
Form: 2HCl

TABLE 192

Example 473

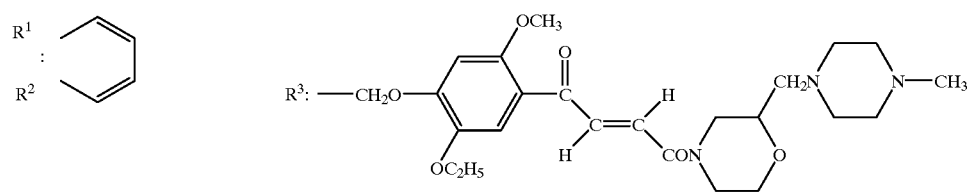

R[4]: H     M.p. 216–221° C. (decomp.)
Crystalline form: Pale yellow powder
Solvent for recrystallization: Dichloromethane-ethanol-diethyl ether
NMR (31)          Form: 2HCl Example 474

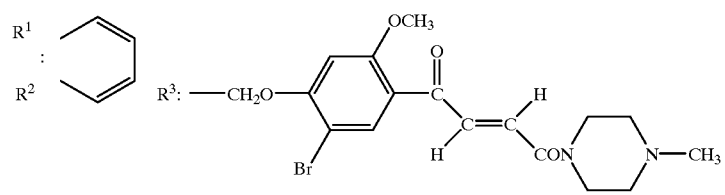

R[4]: H  M.p. 175–205° C. (decomp.)     Crystalline form: Pale yellow powder
Solvent for recrystallization: Dichloromethane-ethanol-diethyl ether
NMR (32)          Form: Methanesulfonate Example 475

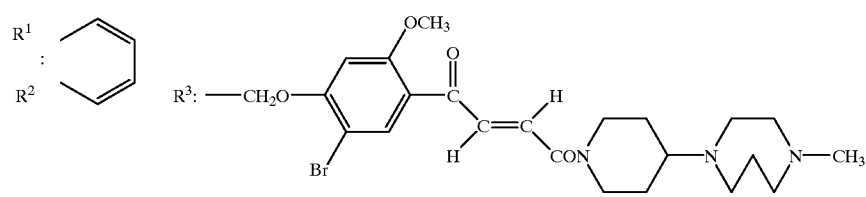

R[4]: H  M.p. 185–230° C. (decomp.)     Crystalline form: Pale yellow powder
Solvent for recrystallization: Dichloromethane-ethanol-diethyl ether
NMR (33)          Form: 2HCl

TABLE 193

Example 476

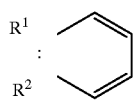 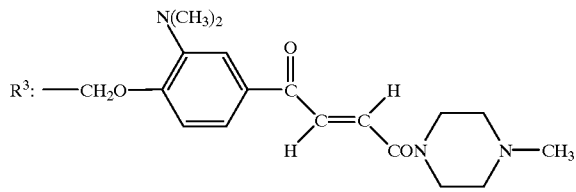

R⁴: H  M.p. 160–170° C.
Crystalline form: Pale yellow powder
Solvent for recrystallization: Ethanol-water
NMR (34)          Form: Dimethanesulfonate Example 477

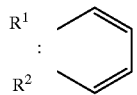 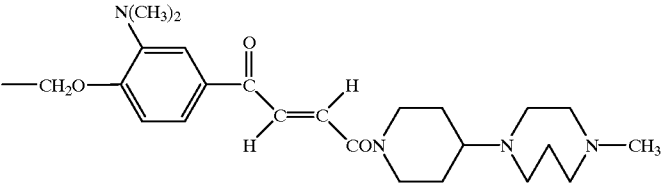

R⁴: H  M.p. 172–178° C.           Crystalline form: Pale yellow powder
Solvent for recrystallization: Ethanol-water   NMR (35)   Form: 3HCl Example 478

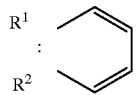 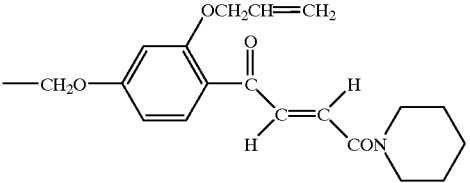

R⁴: H  M.p. 185.2–186.0° C.      Crystalline form: White powder
Solvent for recrystallization: Ethanol           Form: Free Using the suitable starting compounds, the compounds as listed in Table 194 are obtained in the same manner as in Example 8.

TABLE 194

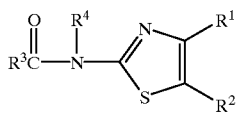

Example 479

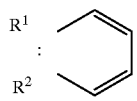

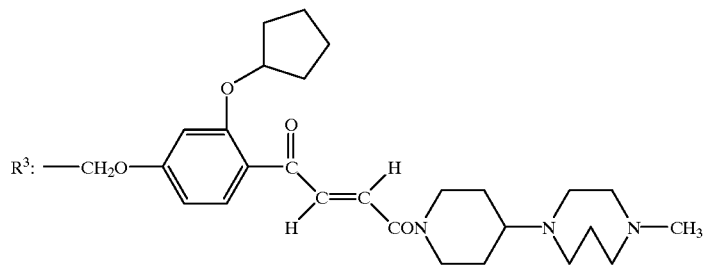

R⁴: H    M.p. 171.5–173.0° C.
Crystalline form: Pale yellow powder
Solvent for recrystallization: Ethanol-diethyl ether-dichloromethane
Form: 2HCl Example 480

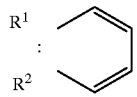

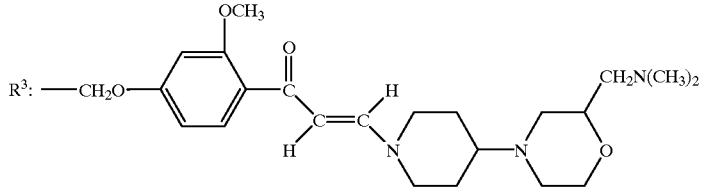

R⁴: H  M.p. 111.5–114.5° C.        Crystalline form: Pale yellow powder
Solvent for recrystallization: Ethanol-water-isopropyl alcohol      Form: 2HCl Using the suitable starting compounds, the compound as listed in Table 195 are obtained in the same manner as in Example 3 or 4.

TABLE 195

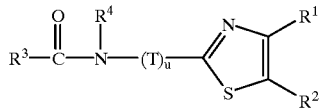

Example 481

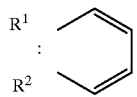

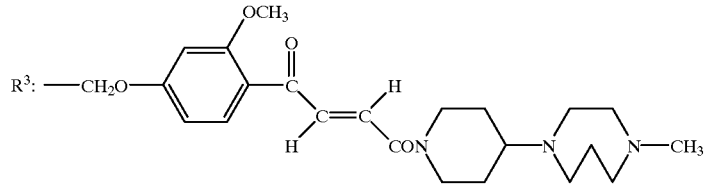

R⁴: H        T: —CH₂—  u:1
M.p. 147–150° C.    Crystalline form: Pale yellow powder
Solvent for recrystallization: Ethanol-water-diethyl ether-isopropyl alcohol
Form: 2HCl $^1$H-NMR spectrum (NMR (1) to NMR (49)) as described in Tables 150–195 are as follows:

NMR (1) (DMSO-d$_6$) δppm: 2.65–2.8 (4H, m), 3.06 (9H, s), 3.87 (3H, s), 4.15–4.65 (4H, m), 5.07 (2H, s), 6.70 (1H, dd, J=2 Hz, J=8.5 Hz), 6.81 (1H, d, J=2 Hz), 7.29 (1H, d, J=15 Hz), 7.48 (1H, br), 7.62 (1H, d, J=15 Hz), 7.65 (1H, d, J=8.5 Hz), 7.77 (1H, d, J=9 Hz), 7.93 (1H, br), 11.0 (1H, br), 12.7 (1H, br); NMR (2) (DMSO-d$_6$) δppm: 1.65 (2H, br), 2.05–2.40 (4H, m), 2.55–2.9 (4H, m), 3.13 (6H, s), 3.25–4.8 (15H, m), 5.10 (2H, s), 6.70 (1H, dd, J=2 Hz, J=9 Hz), 6.81 (1H, d, J=2 Hz), 7.26 (1H, d, J=15 Hz), 7.55 (1H, d, J=15 Hz), 7.64 (1H, d, J=8.5 Hz), 7.7–7.8 (1H, m), 7.88 (1H, d, J=9 Hz), 8.31 (1H, br), 11.2–12.2 (2H, m); NMR (3) (DMSO-d$_6$) δppm: 1.61 (3H, d, J=6.5 Hz), 1.6 (2H, br), 2.12 (4H, br), 2.5–2.85 (4H, m), 2.95–4.05 (13H, m), 4.1–4.3 (1H, m), 4.4–4.7 (1H, m) 5.35 (1H, q, J=6.5 Hz), 6.63 (1H, dd, J=2 Hz, 9 Hz), 6.77 (1H, d, J=2 Hz), 7.15–7.7 (4H, m), 7.69 (1H, d, J=9 Hz), 7.76 (1H, d, J=7.5 Hz), 7.98 (1H, d, J=7.5 Hz), 11.1–13.1 (3H, m); NMR (4) (DMSO-d$_6$) δppm: 1.61 (3H, d, J=6.5 Hz), 2.73 (3H, d, J=4 Hz), 2.8–4.1 (6H, m), 3.85 (3H, s), 4.1–4.35 (1H, m), 4.35–4.6 (1H, m), 5.38 (1H, q, J=6.5 Hz), 6.63 (1H, dd, J=2 Hz, 9 Hz), 6.78 (1H, d, J=2 Hz), 7.26 (1H, d, J=15 Hz), 7.25–7.5 (2H, m), 7.59 (1H, d, J=15 Hz), 7.63(1H, d, J=9 Hz), 7.76 (1H, d, J=7.5 Hz), 7.97 (1H, d, J=7 Hz), 11.40 (1H, br), 12.9 (1H, br); NMR (5) (DMSO-d$_6$) δppm: 1.61 (3H, d, J=6.5 Hz), 2.35–4.4 (23H, m), 5.37 (1H, q, J=6.5 Hz), 6.63 (1H, dd, J=2 Hz, J=8.5 Hz), 6.78 (1H, d, J=2 Hz), 7.1–7.7 (5H, m), 7.76 (1H, d, J=7.5 Hz), 7.98 (1H, d, J=7 Hz), 11.85 (2H, br) 12.90 (1H, br); NMR (6) (DMSO-d$_6$) δppm: 2.42 (6H, s), 2.82 (3H, d, J=4 Hz), 2.9–3.25 (3H, m), 3.3–3.6 (3H, m), 4.15–4.6 (6H, m), 5.03 (2H, s), 6.68 (1H, d, J=9 Hz), 7.23 (1H, d, J=9 Hz), 7.31 (1H, d, J=15 Hz), 7.15–7.5 (2H, m), 7.61 (1H, d, J=15 Hz), 7.76 (1H, d, J=7.5 Hz), 7.98 (1H, d, J=7 Hz), 9.85 (1H, br); NMR (7) DMSO-d$_6$) δppm: 1.64 (2H, br), 2.17 (4H, br), 2.55–2.7 (4H, m), 2.95–4.0 (10H, m), 4.05–4.7 (6H, m), 5.03 (2H, s), 6.68 (1H, d, J=9 Hz), 7.22 (1H, d, J=9 Hz), 7.25–7.6 (4H, m), 7.76 (1H, d, J=7.5 Hz), 7.98 (1H, d, J=7.5 Hz), 11.1–12.2 (2H, m), 12.65 (1H, br); NMR (8) (DMSO-d$_6$) δppm: 2.55–2.7 (1H, m), 2.79 (3H, s), 2.85–4.5 (20H, m), 5.04 (2H, s), 6.68 (1H, d, J=8.5 Hz), 7.15–7.7 (5H, m), 7.76 (1H, d, J=7.5 Hz), 7.98 (1H, d, J=7 Hz), 11.4–13.1 (2H, m); NMR (9) (DMSO-d$_6$) δppm: 1.35 (3H, d, J=5.5 Hz), 1.64 (2H, br), 2.14 (2H, br), 2.55–2.95 (4H, m), 2.95–4.0 (9H, m), 6.0 (1H, d, J=9 Hz), 7.22 (1H, d, J=9 Hz), 7.29 (1H, d, J=15.5 Hz), 4.05–4.7 (6H, m), 5.03 (2H, s), 7.4–7.5 (1H, m), 7.53 (1H, d, J=15.5 Hz), 7.76 (1H, d, J=7.5 Hz), 7.98 (1H, d, J=7 Hz), 11.5–13.0 (2H, m); NMR (10) (DMSO-d$_6$) δppm; 2.16 (3H, s), 2.37 (3H, s), 2.77 (3H, d, J=4.2 Hz), 2.83–3.19 (3H, m), 3.29–3.58 (3H, m), 3.88 (3H, s), 4.12–4.57 (2H, m), 4.65 (2H,s), 6.95 (1H, d, J=8.8 Hz), 7.19–7.37 (2H, m), 7.37–7.50 (1H, m), 7.50–7.66 (2H, m), 7.75 (1H, d, J=7.9 Hz), 7.99 (1H, d, J=7.9 Hz), 9.82 (1H, brs), 11.95–12.71 (1H, m); NMR (11) (DMSO-d$_6$) δppm; 2.17 (2H, br), 2.34 (3H, s), 2.82 (3H, s), 3.05 (4H, br), 3.4 (2H, br), 4.05–4.4 (5H, m), 4.49 (1H, br), 5.05 (2H, s), 6.83 (1H, d, J=9 Hz), 7.28 (1H, d, J=15 Hz), 7.29 (1H, d, J=9 Hz), 7.25–7.35 (1H, m), 7.35–7.5 (1H, m), 7.52 (1H, d, J=15 Hz), 7.76 (1H, d, J=7.5 Hz), 7.98 (1H, d, J=7 Hz), 9.81 (1H, br), 12.6 (1H, br); NMR (12) DMSO-d$_6$) δppm: 1.61 (2H, br), 2.15 (4H, br), 2.55–2.9 (4H, m), 3.0–4.3 (11H, m), 4.4–4.7 (1H, m), 5.09 (2H, s), 7.12 (1H, dd, J=2.5 Hz, J=8.5 Hz), 7.25–7.41 (4H, m), 7.4–7.5 (1H, m), 7.69 (1H, d, J=8.5 Hz), 7.77 (1H, d, J=7.5 Hz), 7.99 (1H, d, J=7 Hz), 11.0–12.2 (2H, m); NMR (13) (DMSO-d$_6$) δppm; 0.91 (3H, t, J=7.2 Hz), 1.20–1.86 (6H, m), 1.93–2.39 (4H, m), 2.58–2.89 (4H, m), 2.76 (3H, s), 2.95–3.98 (9H, m), 3.64 (3H, s), 4.07–4.31 (1H, m), 4.41–4.69 (1H, m), 5.09 (2H, s), 6.83 (1H, d, J=8.9 Hz), 7.20–7.64 (5H, m), 7.76 (1H, d, J=7.9 Hz), 7.97 (1H, d, J=7.9 Hz), 11.11–12.29 (2H, m), 12.72 (1H, brs); NMR (14) (DMSO-d$_6$) δppm; 2.0–2.2 (2H, m), 2.34 (3H,s), 2.68 (2H, t, J=7 Hz), 2.81 (3H, d, J=3 Hz), 2.9–3.2 (2H, m), 3.3–3.65 (4H, m), 3.79 (3H, s), 4.15 (2H, t, J=6 Hz), 4.2–4.4 (1H, m), 4.4–4.6 (1H, m), 6.55–6.7 (2H, m), 7.2–7.35 (1H, m), 7.27 (1H, d, J=15 Hz), 7.35–7.5 (1H, m), 7.63 (1H, d, J=9.5 Hz), 7.63 (1H, d, J=15 Hz), 7.72 (1H, d, J=7.5 Hz), 7.9–8.0 (1H, m), 9.79 (1H, br), 12.38 (1H, br); NMR (15) (DMSO-d$_6$) δppm; 1.64 (2H, br), 2.0–2.4(6H, m), 2.55–2.9 (6H,m), 2.95–4.0 (3H, m), 4.0–4.35 (3H, m), 4.4–4.7 (1H, m), 6.55–6.75 (2H, m), 7.0 (1H, br), 7.2–7.35 (2H, m), 7.35–7.45 (1H, m), 7.5–7.65 (2H, m), 7.65–7.75 (1H, m), 7.9–8.0 (1H, m), 11.2–12.6 (2H, m); NMR (16) DMSO-d$_6$) δppm; 2.0–2.2 (2H, m), 2.69 (2H, t, J=7 Hz), 2.80 (3H, s), 2.9–4.4 (22H, m), 6.4–6.75 (2H, m), 7.15–7.5 (3H, m), 7.5–7.8 (3H, m), 7.96 (1H, d, J=7 Hz), 11.95 (1H, br), 12.41 (1H, br); NMR (17) (DMSO-d$_6$) δppm; 1.45–1.9 (2H, m), 2.0–2.35 (4H, m), 2.55–2.95 (6H, m), 2.95–3.25 (1H, m), 3.3–3.95 (12H, m), 4.0–4.35 (3H, m), 4.4–4.65 (1H, m), 6.4–6.75 (2H, m), 7.25 (1H, d, J=15 Hz), 7.2–7.5 (2H, m), 7.55 (1H, d, J=15 Hz), 7.61 (1H, d, J=9.5 Hz), 7.71 (1H, d, J=7.5 Hz), 7.96 (1H, d, J=7 Hz), 11.9–12.8 (2H,m); NMR (18) (DMSO-d$_6$) δppm; 1.16 (3H, t, J=7.5 Hz), 1.9–2.2 (2H, m), 2.48 (3H, s), 2.62 (2H, q, J=7.5 Hz), 2.82 (3H, d, J=4.5 Hz), 3.0–3.8 (5H, m), 3.84 (3H, s), 3.9–4.3 (3H, m), 5.16 (2H, s), 6.71 (1H, s), 7.22 (1H, d, J=15 Hz), 7.25–7.35 (1H, m), 7.4–7.5 (1H, m), 7.51 (1H, s), 7.66 (1H, dd, J=5.5 Hz, J=15 Hz), 7.77 (1H, d, J=7.5 Hz), 7.98 (1H, d, J=7 Hz), 9.55 (1H, br), 11.7 (1H,br); NMR (19) (DMSO-d$_6$) δppm; 1.15 (3H, t, J=7.5 Hz), 1.35–1.7 (2H, m), 1.9–2.1 (2H, m), 2.36 (3H, s), 2.5–2.7 (3H, m), 2.73 (3H, s), 2.75 (3H, s), 3.0–3.2 (1H, m), 3.3–3.55 (1H, m), 3.84 (3H, s), 4.05–4.25 (1H, m), 4.45–4.65 (1H, m), 5.16 (2H, s), 6.71 (1H, s), 7.26 (1H, d, J=15 Hz), 7.25–7.35 (1H, m), 7.4–7.5 (1H, m), 7.50 (1H, s), 7.58 (1H, d, J=15 Hz), 7.77 (1H, d, J=7.5 Hz), 7.98 (1H, d, J=7 Hz), 9.58 (1H, br); NMR (20) (DMSO-d$_6$) δppm; 0.90 (3H, t, J=7.5 Hz), 1.57 (2H, tq, J=7.5 Hz, J=8 Hz), 2.35 (3H, s), 2.57 (2H, t, J=8 Hz), 2.81 (3H, d, J=3.5 Hz), 2.9–3.25 (3H, m), 3.3–3.7 (3H, m), 3.83 (3H, s), 4.15–4.4 (1H, m), 4.4–4.65 (1H, m), 5.16 (2H, s), 6.70 (1H, s), 7.28 (1H, d, J=15 Hz), 7.25–7.4 (1H, m), 7.4–7.5 (1H, m), 7.49 (1H, s), 7.66 (1H, d, J=15 Hz), 7.77 (1H, d, J=8 Hz), 7.98 (1H, d, J=7.5 Hz), 9.85 (1H, br) 12.6 (1H, br); NMR (21) (DMSO-d$_6$) δppm; 0.89 (3H, t, 7.5 Hz), 1.4–1.9 (4H, m), 2.0–2.4 (4H, m), 2.5–2.85 (6H, m), 3.0–4.05 (10H, m), 3.84 (3H, s), 4.05–4.3 (1H, m), 4.45–4.7 (1H, m), 5.17 (2H, s), 6.71 (1H, s), 7.15–7.35 (2H, m), 7.35–7.5 (1H, m), 7.48 (1H, s), 7.58 (1H, d, J=15 Hz), 7.77 (1H, d, J=7.5 Hz), 7.98 (1H, d, J=7 Hz), 11.1–13.2 (2H, m); NMR (22) (DMSO-d$_6$) δppm; 0.90 (3H, t, J=7.5 Hz), 1.4–1.8 (4H, m), 1.95–2.25 (2H, m), 2.57 (2H, t, J=8 Hz), 2.6–2.9 (1H, m), 2.81 (3H, s), 2.95–4.0 (10H, m), 3.84 (3H, s), 4.05–4.3 (1H, m), 4.4–4.65 (1H, m), 5.16 (2H, s), 6.70 (1H, s), 7.26 (1H, d, J=15 Hz), 7.25–7.35 (1H, m), 7.35–7.5 (1H, m), 7.48 (1H, s), 7.58 (1H, d, J=15 Hz), 7.77 (1H, d, J=7.5 Hz), 7.98 (1H, d, J=7 Hz), 11.4–13.0 (3H, m); NMR (23) (DMSO-d$_6$) δppm: 0.90 (3H, t, J=7.5 Hz), 1.57 (2H, tq, J=7.5 Hz, J=8 Hz), 2.57 (2H, t, J=8 Hz), 2.65–4.4 (17H, m), 2.79 (3H, s), 3.84 (3H, s), 5.18 (2H, s), 6.71 (1H, s), 7.15–7.5 (3H, m), 7.48 (1H, s), 7.5–7.8 (2H, m), 7.98 (1H, d, J=7 Hz), 11.0–13.0 (3H, m); NMR (24) (DMSO-d$_6$) δppm; 1.11 (3H, t, J=7.4 Hz), 2.53–4.17 (16H, m), 2.59 (2H, q, J=7.4 Hz), 2.79 (3H, s), 3.84 (3H, s), 4.17–4.40 (1H, m), 5.20 (2H, s), 6.73 (1H, s), 7.18–7.38 (2H, m), 7.38–7.54 (2H, m), 7.54–7.74 (1H, m), 7.74–7.81 (1H, m), 7.92–8.05 (1H, m), 11.32–13.11 (3H, m); NMR

(25) (DMSO-d$_6$) δppm; 2.35 (3H, s), 2.80 (3H, d, J=3.5 Hz), 2.85–3.6 (6H, m), 3.85 (3H, s), 4.04 (2H, br), 4.2–4.6 (2H, m), 5.0–5.25 (4H, m), 5.81–6.1 (1H, m), 6.74 (1H, s), 7.28 (1H, d, J=15 Hz), 7.25–7.55 (2H, m), 7.48(1H, s), 7.65 (1H, d, J=15 Hz), 7.77 (1H, d, J=7.5 Hz), 7.98 (1H, d, J=7 Hz), 9.99 (1H, br), 12.6 (1H, br); NMR (26) (DMSO-d$_6$) δppm; 1.65 (2H, br), 2.0–2.4 (4H, m), 2.55–2.95 (4H, m), 3.0–3.25 (1H, m), 3.25–4.05 (14H, m), 4.05–4.3 (1H, m), 4.45–4.7 (1H, m), 4.95–5.3 (4H, m), 5.85–6.1 (1H, m), 6.75 (1H, s), 7.15–7.7 (5H, m), 7.77 (1H, d, J=8 Hz), 7.98 (1H, d, J=7.5 Hz), 11.1–13.0 (3H, m); NMR (27) (DMSO-d$_6$) δppm; 1.4–1.85 (2H, m), 1.95–2.3 (2H, m), 2.55–2.95 (4H, m), 2.95–3.2 (1H, m), 3.2–3.95 (11H, m), 5.86 (3H, s), 4.1–4.3 (1H, m), 4.45–4.7 (1H, m), 4.95–5.25 (4H, m), 5.86–6.1 (1H, m), 6.74 (1H, s), 7.26 (1H, d, J=15 Hz), 7.25–7.55 (3H, m), 7.56 (1H, d, J=15 Hz), 7.77 (1H, d, J=7.5 Hz), 7.98 (1H, d, J=7 Hz), 11.3–13.2 (3H, m); NMR (28) (DMSO-d$_6$) δppm; 2.55–4.45 (25H, m), 4.9–5.3 (4H, m), 5.85–6.1 (1H, m), 6.75 (1H, s), 7.15–7.85 (6H, m), 7.98 (1H, d, J=7 Hz), 11.0–13.3 (3H, m); NMR (29) (DMSO-d$_6$) δppm; 1.32 (3H, t, J=7 Hz), 2.33 (3H, s), 2.80 (3 H,s), 2.9–3.2 (3H, m), 3.3–3.5 (3H, m), 3.81 (3H, s), 4.03 (2H, q, J=7 Hz), 4.2–4.65 (2H, m), 5.15 (2H, s), 6.83 (1H, s), 7.2–7.4 (3H, m), 7.44 (1H, t, J=8 Hz), 7.69 (1H, d, J=15 Hz), 7.77 (1H, d, J=8 Hz), 7.98 (1H, d, J=8 Hz), 9.83 (1H, br), 12.60 (1H, br); NMR (30) (DMSO-d$_6$) δppm; 1.32 (3H, t, J=7 Hz), 1.4–1.9 (2H, m), 2.05–2.4 (4H, m), 2.6–3.9 (4H, m), 3.05–3.95 (13H, m), 4.03 (2H, q, J=7 Hz), 4.1–4.3 (1H, m), 4.5–4.7 (1H, m), 5.17 (2H, s), 6.83 (1H, s), 7.2–7.4 (3H, m), 7.44 (1H, t, J=8 Hz), 7.60 (1H, d, J=15.5 Hz), 7.76 (1H, d, J=8 Hz), 7.98 (1H, d, J=8 Hz), 11.25–12.2 (2H, m); NMR (31) (DMSO-d$_6$) δppm; 1.32 (3H, t, J=7 Hz), 2.55–4.5 (19H, m), 2.80 (3H, s), 3.82 (3H, s), 5.17 (2H, s), 6.84 (1H, s), 7.2–7.4 (3H, m), 7.44 (1H, t, J=8 Hz), 7.64 (1H, d, J=15.5 Hz), 7.76 (1H, d, J=8 Hz), 7.98 (1H, d, J=8 Hz), 11.5–12.5 (2H, m); NMR (32) DMSO-d$_6$) δppm; 2.32 (3H, s), 2.81 (3H, s), 3.4–3.7 (4H, m), 3.25–3.6 (2H, m), 3.86 (3H, s), 4.15–4.65 (2H, m), 5.26 (2H, s), 6.89 (1H, s), 7.32 (1H, d, J=15 Hz), 7.32 (1H, t, J=7.5 Hz), 7.45 (1H, t, J=8 Hz), 7.61 (1H, d, J=15 Hz), 7.77 (1H, d, J=8 Hz), 7.83 (1H,s), 7.98 (1H, d, J=7.5 Hz), 9.78 (1H, br), 12.65 (1H, br); NMR (33) DMSO-d$_6$) δppm; 1.4–1.85 (2H, m), 2.1–2.4 (4H, m), 2.6–3.9 (4H, m), 3.05–4.5 (14H, m), 4.5–4.65 (1H, m), 5.27 (2H, s), 6.89 (1H, s), 7.2–7.4 (2H, m), 7.4–7.6 (2H, m), 7.77 (1H, d, J=8 Hz), 7.81 (1H, s), 7.98 (1H, d, J=8 Hz), 11.1–12.1 (2H, m); NMR (34) (DMSO-d$_6$) δppm; 2.35(s, 6H), 2.82 (s, 3H), 2.92–3.27 (m, 9H), 3.30–3.59 (m, 3H), 4.18 (br, 1H), 4.19–4.34 (m, 1H), 4.47–4.65 (m, 1H), 5.24 (s, 2H), 7.33 (t, J=7.6 Hz, 2H), 7.44 (d, J=7.3 Hz, 1H), 7.46 (d, J=15.1 Hz, 1H), 7.78 (d, J=8.0 Hz, 1H), 7.84 (d, J=15.1 Hz, 1H), 7.96–8.15 (m, 3H), 9.82 (br, 1H), 12.66 (br, 1H); NMR (35) (DMSO-d$_6$) δppm; 1.42–1.88 (m, 2H), 1.93–2.39(m, 4H), 2.59–2.85 (m, 4H), 3.13 (s, 6H), 3.26–3.96 (m, 10H), 4.05–4.28 (m, 1H), 4.51–4.68 (m, 1H), 5.26 (s, 2H), 7.29–7.35 (m, 2H), 7.42–7.48 (m, 2H), 7.74–7.80 (m, 2H, 7.96–8.04 (m, 2H), 8.19 (br, 1H), 11.35–12.13 (m, 2H); NMR (36) (DMSO-d$_6$) δppm; 4.61–4.78 (2H, m), 5.05 (2H, s), 5.18–5.50 (2H, m), 5.91–6.17 (1H, m), 6.46 (1H, d, J=15.5 Hz), 6.62–6.78 (1H, m), 6.78–6.88 (1H, m), 7.28–7.39 (1H, m), 7.39–7.52 (1H, m), 7.54–7.81 (8H, m), 7.71 (1H, d, J=15.5 Hz), 7.92–8.05 (1H, m), 12.72 (2H, brs); NMR (37) DMSO-d$_6$) δppm; 4.97 (2H, s), 6.40–6.58 (2H, m), 6.91 (1H, dd, J=2.4 Hz, J=8.8 Hz), 7.00–7.22 (3H, m), 7.22–7.51 (4H, m), 7.61–7.89 (3H, m), 7.89–8.04 (1H, m), 12.75 (2H, brs); NMR (38) DMSO-d$_6$) δppm; 1.12 (3H, t, J=7.4 Hz), 2.60 (2H, q, J=7.4 Hz), 3.85 (3H, s), 5.15 (2H, s), 6.46 (1H, d, J=15.5 Hz), 6.71 (1H, s), 7.26–7.39 (1H, m), 7.39–7.50 (1H, m), 7.51 (1H, s), 7.68 (1H, d, J=15.5 Hz), 7.72–7.81 (1H, m) 7.91–8.03 (1H, m), 12.75 (2H, brs); NMR (39) DMSO-d$_6$) δppm; 2.19 (3H, s), 3.64 (3H, s), 5.07 (2H, s), 6.54 (1H, d, J=15.6 Hz), 6.85 (1H, d, J=8.7 Hz), 7.25–7.40 (1H, m), 7.40–7.51 (1H, m), 7.54 (1H, d, J=8.8 Hz), 7.68 (1H, d, J=15.6 Hz), 7.76 (1H, d, J=7.5 Hz), 7.98 (1H, d, J=7.5 Hz), 12.41–13.16 (2H, m); NMR (40) (DMSO-d$_6$) δppm; 2.16 (3H, s), 3.88 (3H, s), 4.64 (2H, s), 6.52 (1H, d, J=15.6 Hz), 6.95 (1H, d, J=8.8 Hz), 7.21–7.38 (1H, m), 7.38–7.51 (1H, m), 7.55–7.80 (3H, m), 7.98 (1H, d, J=7.1 Hz); NMR (41) (DMSO-d$_6$) δppm; 0.91 (3H, t, J=7.3 Hz), 1.20–1.65 (4H, m), 2.54–2.78 (2H, m), 3.63 (3H, s), 5.07 (2H, s), 6.58 (1H, d, J=15.6 Hz), 6.84 (1H, d, J=8.7 Hz), 7.21–7.39 (1H, m), 7.39–7.51 (1H, m), 7.55 (1H, d, J=8.7 Hz), 7.67 (1, d, J=15.6 Hz), 7.76 (1H, d, J=7.8 Hz), 7.97 (1H, d, J=7.8 Hz), 12.05–13.51 (2H, m); NMR (42) (DMSO-d$_6$) δppm; 2.41 (3H, s), 5.10 (2H, s), 6.56 (1H, d, J=15.5 Hz), 6.90 (1H, dd, J=8.8 Hz, J=2.2 Hz), 6.98 (1H, d, J=2.2 Hz), 7.32 (1H, t, J=7.2 Hz), 7.45 (1H, t, J=7.2 Hz), 7.65–7.85 (2H, m), 7.99 (1H, d, J=7.7 Hz), 8.05 (1H, d, J=8.8 Hz), 12.06–13.45 (2H, m); NMR (43) DMSO-d$_6$) δppm; 1.17 (3H, t, J=7.5 Hz), 2.70 (2H, q, J=7.5 Hz), 3.65 (3H, s), 5.09 (2H, s), 6.57 (1H, d, J=15.6 Hz), 6.85 (1H, d, J=8.9 Hz), 7.30 (1H, dt, J=1.2 Hz, J=7.1 Hz), 7.43 (1H, dt, J=1.2 Hz, J=7.1 Hz), 7.56 (1H, d, J=8.9 Hz), 7.67 (1H, d, J=15.6 Hz), 7.76 (1H, d, J=7.1 Hz), 7.97 (1H, d, J=7.1 Hz), 12.51–13.12 (2H, m); NMR (44) (DMSO-d$_6$) δppm; 3.79 (3H, s), 3.83 (3H, s), 5.12 (2H, s), 6.51 (1H, d, J=15.5 Hz), 6.84 (1H, s), 7.15–7.54 (3H, m with 1H s at 7.26), 7.61–7.86 (2H, m with 1H, d at 7.76 J=15.5 Hz), 7.99 (1H, d, J=7.1 Hz), 12.20–13.25 (2H, m); NMR (45) DMSO-d$_6$) δppm; 2.19 (3H, s), 3.85 (3H, s), 5.14 (2H, s), 6.49 (1H, d, J=15.5 Hz), 6.70 (1H, s), 7.20–7.56 (3H, m, with 1H s at 7.52), 7.60–7.82 (2H, m, with 1H d at 7.71 J=15.5 Hz), 7.98 (1H, d, J=7.0 Hz), 12.41–13.17(2H, m); NMR (46) DMSO-d$_6$) δppm; 1.19 (6H, d, J=6.9 Hz), 3.10–3.42 (1H, m), 3.86 (3H, s), 5.16 (2H, s), 6.50 (1H, d, J=15.5 Hz), 6.70 (1H, s), 7.21–7.60 (3H, m with 1H s at 7.55), 7.65–7.82 (2H, m with 1H d at 7.73 J=15.5 Hz), 7.89–8.08 (1H, m), 12.42–13.12 (2H, m); NMR (47) (DMSO-d$_6$) δppm; 0.68–0.92 (3H, m), 1.08–1.64 (8H, m), 2.38–2.68 (2H, m), 3.85 (3H, s), 5.14 (2H, s), 6.49 (1H, d, J=15.5 Hz), 6.71 (1H, s), 7.20–7.57 (3H, m), 7.62–7.85 (2H, m with 1H d at 7.72 J=15.5 Hz), 7.88–8.05 (1H, m), 12.45–13.12 (2H, m); NMR (48) (DMSO-d$_6$) δppm; 3.17 (s, 6H), 5.28 (s, 2H), 6.71 (d, J=15.5 Hz, 1H), 7.29–7.49 (m, 3H), 7.78 (d, J=8.0 Hz, 1H), 7.91–8.06 (m, 2H), 8.09 (d, J=8.4 Hz, 1H), 8.25 (s, 1H); NMR (49) (DMSO-d$_6$) δppm; 3.87 (s, 3H), 4.75 (d, J=5 Hz, 2H), 4.77 (s, 2H), 6.50 (d, J=15.5 Hz, 1H), 6.72 (dd, J=2.2 Hz J=8.6 Hz, 1H), 6.78 (d, J=2.2 Hz, 1H), 7.33–7.57 (m, 2H), 7.66 (d, J=8.6 Hz, 1H), 7.69 (d, J=15.5 Hz, 1H), 7.94 (d, J=7.4 Hz, 1H), 8.05 (d, J=6.9 Hz, 1H), 9.18 (t, J=5.1 Hz, 1H), 12.99 (br, 1H).

PHARMACOLOGICAL EXPERIMENTS (1) Protein Kinase C (PKC) Inhibitory Activity

Method for determining PKC activity:

The purification of PKC using rat's brain soluble fractions was carried out by a method of Kikkawa et al. (cf. Ushio Kikkawa, Yoshimi Takai, Ryoji Minakuchi, Sinichi Inohara and Yasutomi Nishizuka: The Journal of Biological Chemistry, vol. 257, No. 22, pp. 13341–13348 (1982)). PKC activity was determined by the transfer of radio activity from the [γ-$^{32}$P] adenosine triphosphate (ATP) to H1 histone derived from calf thymus in the presence of 20 mM Tris-HCl buffer (pH 7.5), H1 histone derived from calf thymus (200 μg/ml), 10 μM [γ-$^{32}$P]ATP, 5 mM magnesium acetate, 8 μg/ml phosphatidyl serine, 2 μg/ml diacylglycerol and 0.3 mM Ca$^{2+}$. The test compound was dissolved in dimethylformamide, and the test compound solution was added to the assay system so that the final concentration thereof was adjusted to 0.8%. The reaction mixture was incubated at 30° C. for 30 minutes, and the reaction was quenched with 25% trichloroacetic acid. The acid-insoluble protein was collected on a nitrocellulose membrane by suction filtration. The radio activity of $^{32}P$ was determined by scintillation counter. The PKC inhibitory activity of the test compounds was expressed by $IC_{50}$, which is a concentration of the test compound to be required to reduce the PKC activity by 50%. The results are shown in Table 196.

Results:

TABLE 196

| Test compound | PKC inhibitory activity ($IC_{50}$, μM) |
|---|---|
| The compound of Example 71 | 0.8 |
| The compound of Example 88 | 0.1 |
| The compound of Example 89 | 0.3 |
| Tbe compound of Example 100 | 0.3 |
| The compound of Example 160 | 0.6 |
| The compound of Example 182 | 0.08 |
| The compound of Example 192 | 0.8 |
| The compound of Example 197 | 0.3 |

(2) Mouse Collagen Arthritis

Bovine II-type collagen (provided by Collagen Gijyutsu Kensyukai) (0.1%) was emulsified with Complete Fleund's adjuvant (CFA) (50%) (manufactured by DIFCO, Ltd.), and the emulsion thus obtained was injected intracutaneously to mice at the tail (primary sensitization). Three weeks later, bovine II-type collagen (0.1%) was injected intraperitoneally again to the mice (secondary sensitization). Three weeks later, the swelling of limbs of the mice was observed, and evaluated by four-degree as 0 to 3 each limb. The degree (0 to 3) each limb was added, and the results were used a score of the arthritis. That is, the maximum degree is 12 (degree 3×4 limb). The test compound was administered orally to the mice once a day, which started after two weeks from the primary sensitization.

In the mice treated with the compound of Example 182 at a dose of 30 to 50 mg/kg, the score of arthritis was significantly reduced in comparison with the control mice.

In the mice treated with the compounds of Example 160, 192 or 197 at a dose of 50 mg/kg, the score of arthritis was significantly reduced in comparison with the control mice.

(3) Mouse cGVHD (chromic Graft-versus-host disease model)

Female mice (DBA/2NCrj) were subjected to an operation of cervical vertebra dislocation, and the spleen was taken out to give the spleen cells preparation. The preparation were adjusted to $37.5 \times 10^7$ cells/ml, and administered to the BDF1 female mice on the tail vein at a dose of 200 μl per a mouse. Two weeks later, the blood was collected in the absence of heparin, and anti-DNA antibody therein was determined by ELISA.

The compound of Example 182 was administered orally to the mice at a dose of 30 to 50 mg/kg once a day for two weeks, and the effect of the test compound on cGVHD was determined.

The amount of anti-DNA antibody in the blood was determined with $OD_{405}$. The amounts of anti-DNA antibody were 0.348±0.111 (mean±s.e.) in the control group, 0.255±0.062 (mean±s.e.) in the group treated with the compound of Example 182 at a dose of 30 mg/kg, and 0.094±0.026 (mean±s.e.) in the group treated with the compound of Example 182 at a dose of 50 mg/kg. From the results, it was proved that the compound of Example 182 reduced the anti-DNA antibody in the blood dose-dependently, compared with the control group.

Further, the compound of Example 100 was also administered orally to the mice at 30 mg/kg once a day for two weeks, and the effect of the compound on cGVHD was also determined.

The amount of anti-DNA antibody in the blood was determined with $OD_{405}$. The amounts of anti-DNA antibody were 0.258±0.084 (mean±s.e.) in the control group, and 0.177±0.061 (mean±s.e.) in the group treated with the compound of Example 100 at a dose of 30 mg/kg. From the results, it was proved that the compound of Example 100 reduced the anti-DNA antibody in the blood, compared with the control group.

(4) Rat Kidney Ischemic Re-perfusion Model

The right kidney of a SD male rat was taken out, and the left kidney artery was clumped, and then, re-perfused to give a kidney ischemic re-perfusion model. The effect of the compounds of Examples 71, 89 and 100 on the kidney ischemic re-perfusion model was estimated.

The compound of Example 71 was administered intravenously to the rat at a dose of 3 mg/kg 5 minutes before the ischemic. Twenty-four hours later, the blood was collected from the tail vein, and the amounts of creatine and urea nitrogen were determined. The amount of creatine in the blood was 2.19±0.21 (mean±s.e.) in the control group; 1.4±0.11 (mean±s.e.) in the group treated with the compound of Example 71, and the amount of urea nitrogen in the blood was 78.8±5.6 (mean s.e.) in the control group, and 54.1±5.0 (mean±s.e.) in the group treated with the compound of Example 71. That is, the compound of Example 71 significantly reduced the amounts of both of creatine and urea nitrogen, compared with the control group.

The compound of Example 89 was administered intravenously to the rat at a dose of 3 mg/kg 5 minutes before the ischemic and the re-perfusion. Forty-eight hours later, the blood was collected from the tail vein, and the amounts of creatine and urea nitrogen were determined. The amount of creatine in the blood was 4.31±0.53 (mean±s.e.) in the control group; 2.34±0.46 (mean±s.e.) in the group treated with the compound of Example 89, and the amount of urea nitrogen in the blood was 155.1±15.4 (mean±s.e.) in the control group, and 99.1±16.0 (mean±s.e.) in the group treated with the compound of Example 89. That is, the compound of Example 89 significantly reduced the amounts of both of creatine and urea nitrogen, compared with the control group.

The compound of Example 100 was administered orally to the rat at a dose of 30 mg/kg one hour before the ischemic. Forty-eight hours later, the blood was collected from the tail vein, and the amounts of creatine and urea nitrogen were determined. The amount of creatine in the blood was 2.48±0.59 (mean±s.e.) in the control group; 1.53±0.20 (mean±s.e.) in the group treated with the compound of Example 100, and the amount of urea nitrogen in the blood was 91.3±20.1 (mean±s.e.) in the control group, and 63.1±10.3 (mean±s.e.) in the group treated with the compound of Example 100. Thus, it is proved that the compound of Example 100 reduced the amounts of both of creatine and urea nitrogen, compared with the control group.

(5) Phorbol Ester (TPA)-induced Mouse Auricle Edema, Acanthosis Model

A 200 μg/ml phorbol ester (TPA) (10 μl) was applied to the one side to the ear of a female mouse (ICR). Twenty-four hours later, the thickness of the auricle of the mouse was determined with using a dialthickness gage, and the increase in the thickness of auricle was calculated. A test compound was dissolved in acetone, and the solution of a test compound was applied to the both sides of the ear 30 minutes before the application of TPA.

The compound of Example 88 was applied to the ear at a dose of 20 μl of 0.3% or 1% solution. The increase in the thickness of auricle in the control group is 215±40 μm (mean±s.e.) after 24 hours, while 87±53 μm (mean±s.e.) in the group treated with the compound of Example 88 in 0.3%, and 67±23 μm (mean±s.e.) in the group treated with the compound of Example 88 in 1%. Thus, the compound of Example 88 significantly reduced the increase in auricle thickness, compared with the control group.

(6) Mouse Atopic Dermatitis Model:

1% Trinitrobenzene (TNCB), (10 μl) was applied to each side of the ear of female mice (Balb/c), once every two days for 24 days. Twenty-four days later, the mice were grouped, and the auricle thickness of the mouse was determined by using a dial thickness gage, and the increase in the thickness of auricle was calculated. The compounds of Examples 88 and 89 were dissolved in acetone in a concentration of 1%. The compound of Example 182 was dissolved in a mixture of acetone:methanol in a concentration of 0.75%. Twenty-four days after the beginning of the experiment, the solution of a test compound was applied to each side of the ear 30 minutes before and after the application of TNCB, once a day for two weeks. The compound of Example 88 inhibited the increase in the auricle thickness by 25 to 30%, and the compounds of Examples 89 and 182 inhibited the increase in the auricle thickness by about 25%. Thus, it is proved that the compounds of the present invention is useful in the treatment of acanthosis induced by the application of TNCB.

What is claimed is:

1. A thiazole compound of the formula:

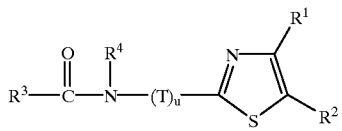

wherein T is a lower alkylene;

u is 0 or 1;

$R^1$ and $R^2$ are the same or different and are each a hydrogen atom or a lower alkyl, or both combine to form a group: —(CH$_2$)$_n$— wherein n is 4 or 5 or to form a benzene ring which may optionally be substituted by a member selected from a lower alkyl, a lower alkoxy, a nitro, an amino having optionally a lower alkyl substituent, or a halogen atom;

$R^3$ is a group of the formula:

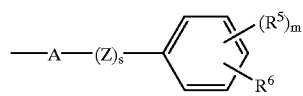

wherein A is a lower alkylene; Z is O or S; s is 0 or 1; m is 1 or 2;

$R^4$ is a hydrogen atom or a lower alkanoyloxy-lower alkyl;

$R^5$ is/are the same or different and are each a member selected from (a) a hydrogen atom, (b) an alkyl having optionally a hydroxy substituent, (c) a halogen atom, (d) a group of the formula: —(O)$_t$—A—(CO)$_l$—NR$^7$R$^8$ wherein t is 0 or 1, A is a lower alkylene, l is 0 or 1, and $R^7$ and $R^8$ are the same or different and are each a hydrogen atom or a lower alkyl, or both combine together with the nitrogen atom to which they bond to form a 5- to 7-membered saturated heterocyclic group which may be intervened with a nitrogen or oxygen atom, said heterocyclic group being optionally substituted by a member selected from a group of the formula: —(A)$_l$—NR$^9$R$^{10}$ wherein A and l are as defined above, and $R^9$ and $R^{10}$ are the same or different and are each a hydrogen atom or a lower alkyl, or both combine together with the nitrogen atom to which they bond to form a 5- to 7-membered saturated heterocyclic group which may be intervened with a nitrogen or oxygen atom, said heterocyclic group having optionally a lower alkyl substituent, a lower alkyl having optionally a hydroxy substituent, a hydroxy group, and a lower alkanoyl; (e) a lower alkoxycarbonyl-lower alkyl, (f) a lower alkanoyloxy-lower alkyl, (g) a lower alkoxy having optionally a halogen substituent, (h) a halogen-substituted lower alkyl, (i) a carboxyl-substituted lower alkyl, (j) a lower alkoxycarbonyl, (k) a lower alkenyloxy, (l) a phenyl-lower alkoxy, (m) a cycloalkyloxy, (n) a phenyl, (o) a phenyloxy, (p) a hydroxy, (q) a lower alkylthio, (r) a lower alkenyl, or (s) an amino having optionally a lower alkyl substituent;

$R^6$ is a group of the formula:

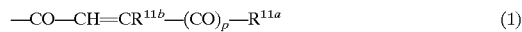

or

p is 0 or 1;

$R^{11b}$ is a hydrogen atom or a lower alkyl;

$R^{11a}$ is a hydroxy, a lower alkoxy, or a 5- to 10-membered, monocyclic or dicyclic, saturated or unsaturated heterocyclic group which contains 1 to 4 hetero atoms selected from a nitrogen, oxygen or sulfur atom as a ring member, said heterocyclic group having optionally 1 to 3 substituents selected from the group consisting of (i) a lower alkyl, (ii) a group of the formula: —(B)$_l$—NR$^{12}$R$^{13}$ wherein l is as defined above, B is —CO—A— wherein A is as defined above, a carbonyl, or a lower alkylene, and $R^{12}$ and $R^{13}$ are the same or different and are each a hydrogen atom, a lower alkyl, or a lower alkyl substituted by an amino having optionally a lower alkyl substituent, or both combine together with the nitrogen atom to which they bond to form a 5- to 12-membered saturated, monocyclic, dicyclic or spirocyclic heterocyclic group which may be intervened with a nitrogen or oxygen atom, said heterocyclic group having optionally a substituent selected from a lower alkyl, a lower alkoxycarbonyl, a lower alkoxy-substituted lower alkyl, an amino having optionally a lower alkyl substituent, and a hydroxy-substituted lower alkyl), (iii) a lower alkoxycarbonyl, (iv) a hydroxy-substituted lower alkyl, (v) a pyridyl being optionally substituted by a lower alkyl having optionally a halogen substituent on the pyridine ring, (vi) a halogen-substituted lower alkyl, (vii) a lower alkoxy, (viii) a cycloalkyl, (ix) a hydroxy, (x) a tetrahydropyranyloxy-substituted lower alkyl, (xi) a pyrimidyl, (xii) a lower alkoxy-substituted lower alkyl, (xiii) a carboxyl, (xiv) a phenyl-lower alkoxy, (xv) a phenyl-lower alkyl having optionally a lower alkylenedioxy on the phenyl ring, (xvi) a lower alkanoyloxy, and (xvii) a piperidinyl having optionally a lower alkyl substituent on the piperidine ring;

$R^{14}$ is a hydroxy or a lower alkoxy; and when m is 1, the groups A and $R^5$ may combine to form a group of the formula:

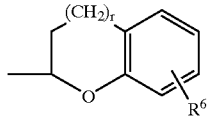

wherein $R^6$ is as defined above, and r is 0, 1 or 2, or when m is 2, two $R^5$ groups may combine to form a lower alkylenedioxy, a lower alkylene, or a group of the formula: —(CH$_2$)$_2$—CONH—, or the groups $R^5$ and $R^6$ may combine to form a group of the formula: —CO—CH(R$^{28}$)—CH(R$^{28'}$)—W— wherein $R^{28}$ and $R^{28'}$ are a hydrogen atom or a carboxyl group, provided that both $R^{28}$ and $R^{28'}$ are not simultaneously a carboxyl group, and W is —N(R$^{29a}$)— or

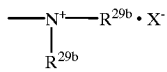

wherein $R^{29a}$ is a hydrogen atom or a lower alkyl, $R^{29b}$ is a lower alkyl, and X is as defined above, or a salt thereof.

2. The thiazole compound according to claim 1, wherein u is 0; $R^1$ and $R^2$ are the same or different and are each a hydrogen atom or a lower alkyl; and $R^3$ is a group of the formula:

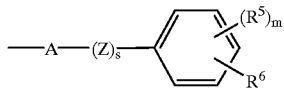

wherein A, $R^5$, $R^6$ and m are as defined in claim 1, and s is 0), or a salt thereof.

3. The thiazole compound according to claim 1, wherein u is 0; $R^1$ and $R^2$ are the same or different and are each a hydrogen atom or a lower alkyl; and $R^3$ is a group of the formula:

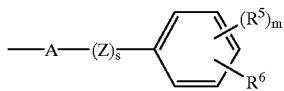

wherein A, $R^5$, $R^6$ and m are as defined in claim 1, s is 1, and Z is O, or a salt thereof.

4. The thiazole compound according to claim 1, wherein u is 0; $R^1$ and $R^2$ are the same or different and are each a hydrogen atom or a lower alkyl; and $R^3$ is a group of the formula:

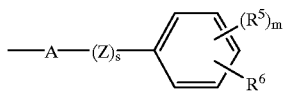

wherein A, $R^5$, $R^6$ and m are as defined in claim 1, s is 1, and Z is S, or a salt thereof.

5. The thiazole compound according to claim 1, wherein u is 0; $R^1$ and $R^2$ combine to form a group: —(CH$_2$)$_n$— wherein n is 4; and $R^3$ is a group of the formula:

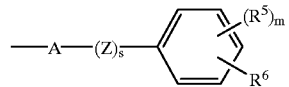

wherein A, $R^5$, $R^6$ and m are as defined in claim 1, and s is 0, or a salt thereof.

6. The thiazole compound according to claim 1, wherein u is 0; $R^1$ and $R^2$ combine to form a group: —(CH$_2$)$_n$— wherein n is 4; and $R^3$ is a group of the formula:

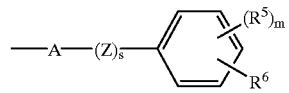

wherein A, $R^5$, $R^6$ and m are as defined in claim 1, s is 1, and Z is O; or a salt thereof.

7. The thiazole compound according to claim 1, wherein u is 0; $R^1$ and $R^2$ combine to form a group: —(CH$_2$)$_n$— (n is 4); and $R^3$ is a group of the formula:

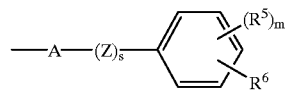

wherein A, $R^5$, $R^6$ and m are as defined in claim 1, s is 1, and Z is S, or a salt thereof.

8. The thiazole compound according to claim 1, wherein u is 0; $R^1$ and $R^2$ combine to form a group: —(CH$_2$)$_n$— wherein n is 5; and $R^3$ is a group of the formula:

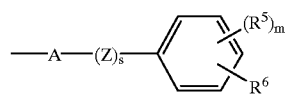

wherein A, $R^5$, $R^6$ and m are as defined in claim 1, and s is 0, or a salt thereof.

9. The thiazole compound according to claim 1, wherein u is 0; $R^1$ and $R^2$ combine to form a group: —(CH$_2$)$_n$— wherein n is 5; and $R^3$ is a group of the formula:

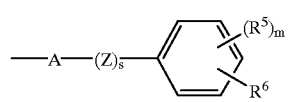

wherein A, $R^5$, $R^6$ and m are as defined in claim 1, s is 1, and Z is O, or a salt thereof.

10. The thiazole compound according to claim 1, wherein u is 0; $R^1$ and $R^2$ combine to form a group: —(CH$_2$)$_n$— (n is 5); and $R^3$ is a group of the formula:

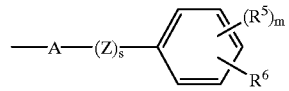

wherein A, $R^5$, $R^6$ and m are as defined in claim 1, s is 1, and Z is S, or a salt thereof.

11. The thiazole compound according to claim 1, wherein u is 0; $R^1$ and $R^2$ combine to form a benzene ring which may optionally be substituted by a member selected from a lower alkyl, a lower alkoxy, a nitro, an amino having optionally a lower alkyl substituent, or a halogen atom; and $R^3$ is a group of the formula:

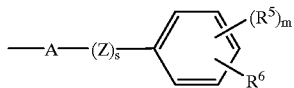

wherein A, $R^5$, $R^6$ and m are as defined in claim 1, and s is 0, or a salt thereof.

12. The thiazole compound according to claim 1, wherein u is 0; $R^1$ and $R^2$ combine to form a benzene ring which may optionally be substituted by a member selected from a lower alkyl, a lower alkoxy, a nitro, an amino having optionally a lower alkyl substituent, or a halogen atom; and $R^3$ is a group of the formula:

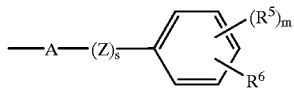

wherein A, $R^5$, $R^6$ and m are as defined in claim 1, s is 1, and Z is O, or a salt thereof.

13. The thiazole compound according to claim 1, wherein u is 0; $R^1$ and $R^2$ combine to form a benzene ring which may optionally be substituted by a member selected from a lower alkyl, a lower alkoxy, a nitro, an amino having optionally a lower alkyl substituent, or a halogen atom; and $R^3$ is a group of the formula:

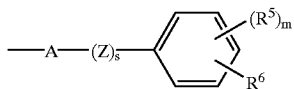

wherein A, $R^5$, $R^6$ and m are as defined in claim 1, s is 1, and Z is S, or a salt thereof.

14. The thiazole compound according to claim 3, wherein $R^6$ is a group of the formula: —CO—CH=$CR^{11b}$—$(CO)_p$—$R^{11a}$ wherein $R^{11a}$ is a hydroxy or a lower alkoxy, or a salt thereof.

15. The thiazole compound according to claim 3, wherein $R^6$ is a group of the formula: —CO—CH=$CR^{11b}$—$(CO)_p$—$R^{11a}$ wherein p is 1, and $R^{11a}$ is a 5- to 10-membered, monocyclic or dicyclic, saturated or unsaturated heterocyclic group which contains 1 to 4 hetero atoms selected from a nitrogen, oxygen or sulfur atom as a ring member, said heterocyclic group having optionally 1 to 3 substituents selected from the group consisting of (i) a lower alkyl, (ii) a group of the formula: —$(B)_l$—$NR^{12}R^{13}$ wherein B is —CO—A—, a carbonyl, or a lower alkylene, and $R^{12}$ and $R^{13}$ are the same or different and are each a hydrogen atom, a lower alkyl, or a lower alkyl substituted by an amino having optionally a lower alkyl substituent, or both combine together with the nitrogen atom to which they bond to form a 5- to 12-membered saturated, monocyclic, dicyclic or spirocyclic heterocyclic group which may be intervened with a nitrogen or oxygen atom, said heterocyclic group having optionally a substituent selected from a lower alkyl, a lower alkoxycarbonyl, a lower alkoxy-substituted lower alkyl, an amino having optionally a lower alkyl substituent, and a hydroxy-substituted lower alkyl), (iii) a lower alkoxycarbonyl, (iv) a hydroxy-substituted lower alkyl, (v) a pyridyl being optionally substituted by a lower alkyl having optionally a halogen substituent on the pyridine ring, (vi) a halogen-substituted lower alkyl, (vii) a lower alkoxy, (viii) a cycloalkyl, (ix) a hydroxy, (x) a tetrahydropyranyloxy-substituted lower alkyl, (xi) a pyrimidyl, (xii) a lower alkoxy-substituted lower alkyl, (xiii) a carboxyl, (xiv) a phenyl-lower alkoxy, (xv) a phenyl-lower alkyl having optionally a lower alkylenedioxy on the phenyl ring, (xvi) a lower alkanoyloxy, and (xvii) a piperidinyl having optionally a lower alkyl substituent on the piperidine ring, or a salt thereof.

16. The thiazole compound according to claim 3, wherein $R^6$ is a group of the formula: —CO—CH=$CR^{11b}$—$(CO)_p$—$R^{11a}$ wherein p is 0, and $R^{11a}$ is as defined in claim 15, or a salt thereof.

17. The thiazole compound according to claim 3, wherein $R^6$ is a group of the formula: —CO—C≡C—$COR^{14}$ or a salt thereof.

18. The thiazole compound according to claim 12, wherein $R^6$ is a group of the formula: —CO—CH=$CR^{11b}$—$(CO)_p$—$R^{11a}$ wherein $R^{11a}$ is a hydroxy or a lower alkoxy, or a salt thereof.

19. The thiazole compound according to claim 12, wherein $R^6$ is a group of the formula —CO—CH=$CR^{11b}$—$(CO)_p$—$R^{11a}$ wherein p is 1, and $R^{11a}$ is a 5- to 10-membered, monocyclic or dicyclic, saturated or unsaturated heterocyclic group which contains 1 to 4 hetero atoms selected from a nitrogen, oxygen or sulfur atom as a ring member, said heterocyclic group having optionally 1 to 3 substituents selected from the group consisting of (i) a lower alkyl, (ii) a group of the formula: —$(B)_l NR^{12}R^{13}$ wherein l is 0 or 1, B is —CO—A— wherein A is alkylene, a carbonyl, or a lower alkylene, and $R^{12}$ and $R^{13}$ are the same or different and are each a hydrogen atom, a lower alkyl, or a lower alkyl substituted by an amino having optionally a lower alkyl substituent, or both combine together with the nitrogen atom to which they bond to form a 5- to 12-membered saturated, monocyclic, dicyclic or spirocyclic heterocyclic group which may be intervened with a nitrogen or oxygen atom, said heterocyclic group having optionally a substituent selected from a lower alkyl, a lower alkoxycarbonyl, a lower alkoxy-substituted lower alkyl, an amino having optionally a lower alkyl substituent, and a hydroxy-substituted lower alkyl, (iii) a lower alkoxycarbonyl, (iv) a hydroxy-substituted lower alkyl, (v) a pyridyl being optionally substituted by a lower alkyl having optionally a halogen substituent on the pyridine ring, (vi) a halogen-substituted lower alkyl, (vii) a lower alkoxy, (viii) a cycloalkyl, (ix) a hydroxy, (x) a tetrahydropyranyloxy-substituted lower alkyl, (xi) a pyrimidyl, (xii) a lower alkoxy-substituted lower alkyl, (xiii) a carboxyl, (xiv) a phenyl-lower alkoxy, (xv) a phenyl-lower alkyl having optionally a lower alkylenedioxy on the phenyl ring, (xvi) a lower alkanoyloxy, and (xvii) a piperidinyl having optionally a lower alkyl substitutent on the piperidine ring, or a salt thereof.

20. The thiazole compound according to claim 12, wherein $R^6$ is a group of the formula: —CO—CH=$CR^{11b}$—$(CO)_p$—$R^{11a}$ wherein p is 0, and $R^{11a}$ is a 5- to 10-membered, monocyclic or dicyclic, saturated or unsaturated heterocyclic group which contains 1 to 4 hetero atoms selected from a nitrogen, oxygen or sulfur atom as a ring member, said heterocyclic group having optionally 1 to 3 substituents selected from the group consisting of (i) a lower alkyl, (ii) a group of the formula: —$(B)_l NR^{12}R^{13}$ wherein l is 0 or 1, B is —CO—A— wherein A is alkylene, a carbonyl, or a lower alkylene, and $R^{12}$ and $R^{13}$ are the same or different and are each a hydrogen atom, a lower alkyl, or a lower alkyl substituted by art amino having optionally a lower alkyl substituent, or both combine together with the nitrogen atom to which they bond to form a 5- to 12-membered saturated, monocyclic, dicyclic or spirocyclic heterocyclic group which may be intervened with a nitrogen or oxygen atom, said heterocyclic group having optionally a substituent selected from a lower alkyl, a lower alkoxycarbonyl, a lower alkoxy-substituted lower alkyl, an amino having optionally a lower alkyl substituent, and a hydroxy-substituted lower alkyl, (iii) a lower alkoxycarbonyl, (iv) a hydroxy-substituted lower alkyl, (v) a pyridyl being optionally substituted by a lower alkyl having optionally a halogen substituent on the pyridine ring, (vi) a halogen-substituted lower alkyl, (vii) a lower alkoxy, (viii) a cycloalkyl, (ix) a hydroxy, (x) a tetrahydropyranyloxy-substituted lower alkyl, (xi) a pyrimidyl, (xii) a lower alkoxy-substituted lower alkyl, (xiii) a carboxyl, (xiv) a phenyl-lower alkoxy, (xv) a phenyl-lower alkyl having optionally a lower alkylenedioxy on the phenyl ring, (xvi) a lower alkanoyloxy, and (xvii) a piperidinyl having optionally a lower alkyl substitutent on the piperidine ring, or a salt thereof.

21. The thiazole compound according to claim 12, wherein $R^6$ is a group of the formula: —CO—C≡C—COR$^{14}$ or a salt thereof.

22. The thiazole compound according to claim 1, wherein u is 1; $R^1$ and $R^2$ are the same or different and are each a hydrogen atom or a lower alkyl; and $R^3$ is a group of the formula:

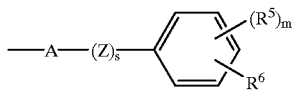

wherein A, Z, s, $R^5$, $R^6$ and m are as defined in claim 1, or a salt thereof.

23. The thiazole compound according to claim 1, wherein u is 1; $R^1$ and $R^2$ combine to form a group: —(CH$_2$)$_n$— wherein n is 4; and $R^3$ is a group of the formula:

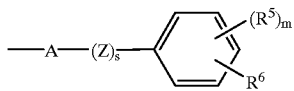

wherein A, Z, s, $R^5$, $R^6$ and m are as defined in claim 1, or a salt thereof.

24. The thiazole compound according to claim 1, wherein u is 1; $R^1$ and $R^2$ combine to form a group: —(CH$_2$)$_n$— wherein n is 5; and $R^3$ is a group of the formula:

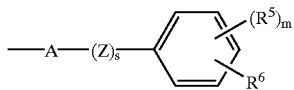

wherein A, Z, s, $R^5$, $R^6$ and m are as defined in claim 1, or a salt thereof.

25. The thiazole compound according to claim 1, wherein u is 1; $R^1$ and $R^2$ combine to form a benzene ring which may optionally be substituted by a member selected from a lower alkyl, a lower alkoxy, a nitro, an amino having optionally a lower alkyl substituent, or a halogen atom; and $R^3$ is a group of the formula:

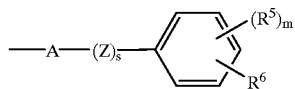

wherein A, Z, s, $R^5$, $R^6$ and m are as defined in claim 1, or a salt thereof.

26. The thiazole compound according to any one of claims 2, 5–7, 8–10, 11, 13 and 22–25, wherein the heterocyclic group for $R^{11a}$ is a member selected from the group consisting of pyrrolidinyl, piperidinyl, piperazinyl, morpholino, 1-azacyclooctyl, homopiperazinyl, homomorpholino, 1,4-diazabicyclo[4.3.0]nonyl, 1,4-diazabicyclo[4.4.0]decyl, pyridyl, 1,2,5,6-tetrahydropyridyl, thienyl, 1,2,4-triazolyl, 1,2,3,4-tetrazolyl, 1,3,4-triazolyl, quinolyl, 1,4-dihydroquinolyl, benzothiazolyl, pyrazyl, pyrimidyl, pyridazyl, pyrrolyl, pyrrolinyl, carbostyril, 1,3-dioxolanyl, thiomorpholino, 3,4-dihydrocarbostyril, 1,2,3,4-tetrahydroquinolyl, 2,3,4,5-tetrahydrofuryl, indolyl, isoindolyl, 3H-indolyl, indolinyl, indolidinyl, indazolyl, benzimidazolyl, benzoxazolyl, imidazolinyl, imidazolidinyl, isoquinolyl, naphthylidinyl, quinazolidinyl, quinoxalinyl, cinnolinyl, phthalazinyl, chromanyl, isoindolinyl, isochromanyl, pyrazolyl, 1,3,4-oxadiazolyl, 1,3,4-thiadiazolyl, thienyl, imidazolyl, pyrazolidinyl, benzofuryl, 2,3-dihydrobenzo[b]furyl, benzothienyl, tetrahydropyranyl, 4H-chromenyl, 1H-indazolyl, isoindolinyl, 2-imidazolinyl, 2-pyrrolinyl, furyl, oxazolyl, isoxazolyl, thiazolyl, thiazolinyl, isothiazolyl, pyranyl, pyrazolidinyl, 2-pyrazolinyl, quinuclidinyl, 1,4-benzoxazinyl, 3,4-dihydro-2H-1,4-benzoxazinyl, 3,4-dihydro-2H-1,4-benzothiazinyl, 1,4-benzothiazinyl, 1,2,3,4-tetrahydroisoquinolyl, 1,2,3,4-tetrahydroquinoxalinyl, 1,3-dithia-2,4-dihydronaphthalenyl, 1,4-dithianaphthalenyl, 2,5-dihydrofurano[3,4-c]pyridyl, 2,3,4,5,6,7-hexahydro-1H-azepinyl, 1,2,3,4,5,6,7,8-octahydroazocinyl, 1,2,3,4,5,6-hexahydrooxepinyl, 1,3-dioxolanyl, 3,4,5,6-tetrahydro-2H-pyranyl, and 5,6-dihydro-2H-pyranyl.

27. A thiazole compound selected from the group consisting of
(1) 2-{(3-methoxy-4-(3-(4-(4-methyl-1-homopiperazinyl)-1-piperidinylcarbonyl)acryloyl)phenoxy)methylcarbonylamino}benzothiazole,
(2) 2-{(2-isopropyl-4-(3-(4-(4-methyl-1-piperazinyl)-1-piperidinylcarbonyl)acryloyl)phenoxy)methylcarbonylamino}benzothiazole,
(3) 2-{(2-methoxy-4-(3-(2-(4-methyl-1-piperazinyl)-methyl-4-morpholinocarbonyl)acryloyl)phenoxy)methylcarbonylamino}benzothiazole,
(4) 2-{(2-ethoxy-4-(3-(4-(4-methyl-1-piperazinyl)-1-piperidinylcarbonyl)acryloyl)phenoxy)methylcarbonylamino}benzothiazole,
(5) 2-{(3-methyl-4-(3-(4-(4-methyl-1-homopiperazinyl)-1-piperidinylcarbonyl)acryloyl)phenoxy)methylcarbonylamino}benzothiazole,
(6) 2-{(3-methoxy-6-ethyl-4-(3-(4-(4-methyl-1-homopiperazinyl)-1-piperidinylcarbonyl)acryloyl)phenoxy)methylcarbonylamino}benzothiazole,
(7) 2-{(3-methoxy-6-ethyl-4-(3-(4-(4-methyl-1-piperazinyl)acryloyl)-phenoxy)methylcarbonylamino}benzothiazole,
(8) 2-{(2-trifluoromethyl-4-(3-(4-hydroxy-1-piperazinyl)acryloyl)-phenoxy)methylcarbonylamino}benzothiazole,
(9) 2-{(2-fluoro-4-(3-(2-(4-methyl-1-piperazinyl)methyl-4-morpholino-carbonyl)acryloyl)phenoxy)methylcarbonylamino}benzothiazole,

(10) 2-{(2-methoxy-4-(3-(4-(4-methyl-1-piperazinyl)-1-piperidinylcarbonyl)acryloyl)phenoxy)methylcarbonylamino}benzothiazole,

(11) 2-{(2,3-dimethyl-4-(3-(4-(4-methyl-1-homopiperazinyl)-1-piperidinylcarbonyl)acryloyl)phenoxy)methylcarbonylamino}benzothiazole,

(12) 2-{(3-methoxy-4-(3-(4-(3,4-dimethyl-1-piperazinyl)-1-piperidinylcarbonyl)acryloyl)phenoxy)methylcarbonylamino}benzothiazole,

(13) 2-{(3-methoxy-6-isopropyl-4-(3-(4-methyl-1-piperazinyl)-carbonyl)acryloyl)phenoxy)methylcarbonylamino}benzothiazole,

(14) 2-{(2-methoxy-4-(3-(4-(4-methyl-1-homopiperazinyl)-1-piperidinylcarbonyl)acryloyl)phenoxy)methylcarbonylamino}benzothiazole, and

(15) 2-{(2-n-butyl-4-(3-(4-(4-methyl-1-homopiperazinyl)-1-piperidinylcarbonyl)acryloyl)phenoxy)methylcarbonylamino}benzothiazole, or a salt thereof.

28. A protein kinase C inhibitor composition which comprises as an active ingredient a thiazole compound or a salt thereof as set forth in claim 1.

29. A process for preparing a thiazole compound as set forth in claim 1, which comprises the following steps of (a) reacting a compound of the formula (2):

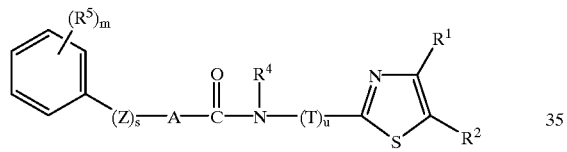

(2)

wherein $R^1$, $R^2$, $R^4$, $R^5$, Z, m, s, T, u and A are the same as defined in claim 1, with a compound of the formula (3):

(3)

wherein $R^{11b}$ is the same as defined in claim 1, or a compound of the formula (4):

(4)

wherein $R^{15}$ is a group: —CH=C($R^{11b}$)(COR$^{16}$) wherein $R^{11b}$ is the same as defined in claim 1, and $R^{16}$ is a hydroxy group or a lower alkoxy group, or a group: —C≡C—COR$^{14}$ wherein $R^{14}$ is the same as defined in claim 1, and X is a halogen atom, to give a compound of the formula (1a):

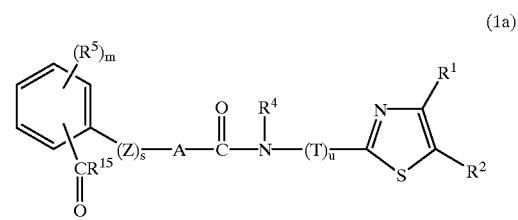

(1a)

wherein $R^1$, $R^2$, $R^4$, $R^5$, Z, m, s, T, u and A are the same as defined in claim 1, and $R^{15}$ is the same as defined above;

(b) reacting a compound of the formula (1b):

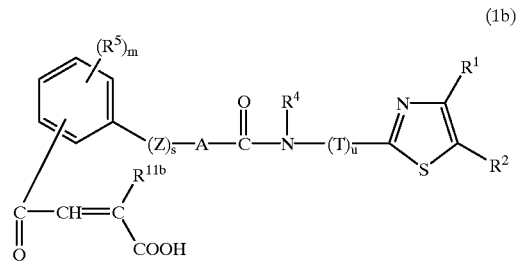

(1b)

wherein $R^1$, $R^2$, $R^4$, $R^5$, $R^{11b}$, Z, m, s, T, u and A are the same as defined in claim 1, with a compoud of the formula (5):

$R^{17}H$ (5)

wherein $R^{17}$ is the heterocyclic groups as defined for $R^{11a}$ of claim 1 but having at least one

in the heterocyclic nucleus, to give a compoud of the formula (1c):

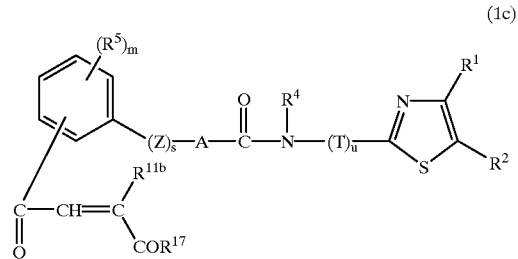

(1c)

wherein $R^1$, $R^2$, $R^4$, $R^5$, $R^{11b}$, Z, m, s, T, u and A are the same as defined in claim 1, and $R^{17}$ is the same as defined above;

(c) reacting a compound of the formula (10):

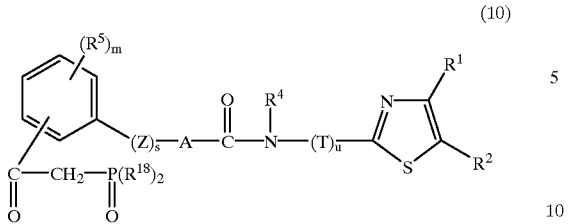
(10)

wherein $R^1$, $R^2$, $R^4$, $R^5$, Z, m, s, T, u and A are the same as defined in claim 1, $R^{18}$ is a lower alkoxy group, with a compound of the formula (12):

(12)

wherein $R^{16}$ is the same as defined above, to give a compound of the formula (1d):

(1d)

wherein $R^1$, $R^2$, $R^4$, $R^5$, Z, m, s, T, u and A are the same as defined in claim 1 and $R^{16}$ is the same as defined above;

(d) reacting a compound of the formula (10):

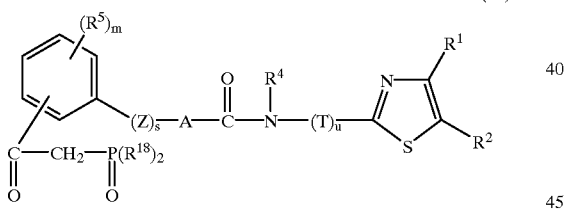
(10)

wherein $R^1$, $R^2$, $R^4$, $R^5$, Z, m, S, T, u and A are the same as defined in claim 1, and $R^{18}$ is the same as defined above, with a compound of the formula (20):

(20)

wherein $R^{22}$ is a 5- to 10-membered, saturated or unsaturated heteromonocyclic or heterobicyclic group said heteromonocyclic or heterobicyclic group optionally having 1 to 3 substituents selected from (i) a lower alkyl group; (ii) a group: $-(B)_l NR^{12}R^{13}$, wherein l is 0 or 1, B is a group: $-CO-A-$ (wherein A is alkylene), a carbonyl group or a lower alkylene group, $R^{12}$ and $R^{13}$ are the same or different, and each are a hydrogen atom, a lower alkyl group, an amino-substituted lower alkyl group having optionally a lower alkyl substituent, or both combine together with the adjacent nitrogen atom to which they bond to form a 5- to 12-membered saturated heteromonocyclic, heterobicyclic or hetero-sprio ring with or without being intervened with another nitrogen atom or an oxygen atom, said heterocyclic group may optionally have a substituent selected from a lower alkyl group, a lower alkoxycarbonyl group, a lower alkoxy-substituted lower alkyl group, an amino group having optionally a lower alkyl substituent and a hydroxy-substituted lower alkyl group); (iii) a lower alkoxycarbonyl group; (iv) a hydroxy-substituted lower alkyl group; (v) a pyridyl group being optionally substituted by a lower alkyl group having optionally a halogen substituent on the pyridine ring; (vi) a halogen-substituted lower alkyl group; (vii) a lower alkoxy group; (viii) a cycloalkyl group; (ix) a hydroxy group; (x) a tetrahydropyranyloxy-substituted lower alkyl group; (xi) a pyrimidyl group; (xii) a lower alkoxy-substituted lower alkyl group; (xiii) a carboxyl group; (xiv) a phenyl-lower alkoxy group; (xv) a phenyl-lower alkyl group having optionally a lower alkylenedioxy substituent on the phenyl ring; (xvi) a lower alkanoyloxy group; and (xvii) a piperidinyl group having optionally a lower alkyl substituent on the piperidine ring, to give a compound of the formula (1h):

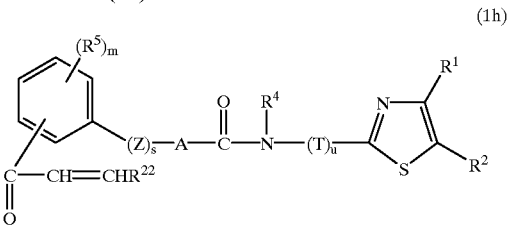
(1h)

wherein $R^1$, $R^2$, $R^4$, $R^5$, Z, m, s, T, u and A are the same as defined in claim 1, and $R^{18}$ and $R^{22}$ are the same as defined above;

(e) converting, a compound of the formula (11):

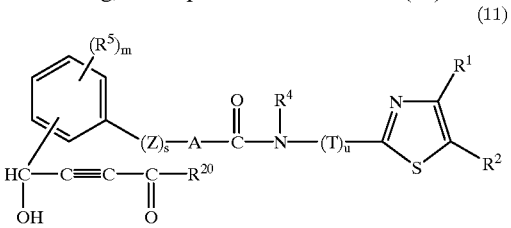
(11)

wherein $R^1$, $R^2$, $R^4$, $R^5$, Z, m, s, T, u and A are the same as defined in claim 1, and $R^{20}$ is a lower alkoxy group, into a compound of the formula (1d'):

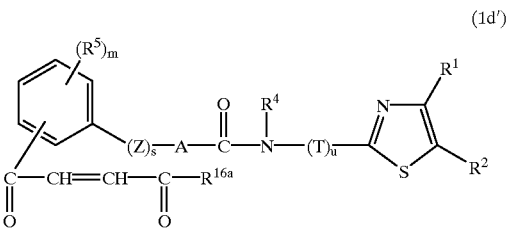
(1d')

wherein $R^1$, $R^2$, $R^4$, $R^5$, Z, m, s, T, u and A are the same as defined in claim 1, and $R^{16a}$ is a lower alkoxy group, in the presence of a basic compound, option ally followed by converting the compound (1d') into a compound of the formula (1e):

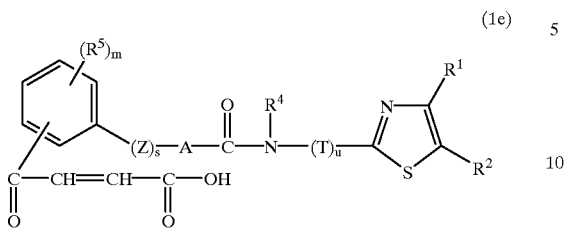

wherein $R^1$, $R^2$, $R^4$, $R^5$, Z, m, s, T, u and A are the same as defined in claim 1, in the presence of an acid or a basic compound;

(f) converting a compound of the formula (11):

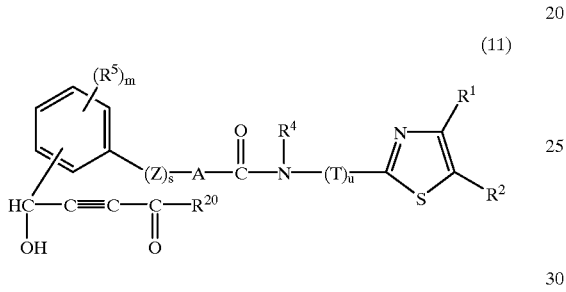

wherein $R^1$, $R^2$, $R^4$, $R^5$, Z, m, s, T, u and A are the same as defined in claim 1, and $R^{20}$ is a lower alkoxy group, into a compound of the formula (1f):

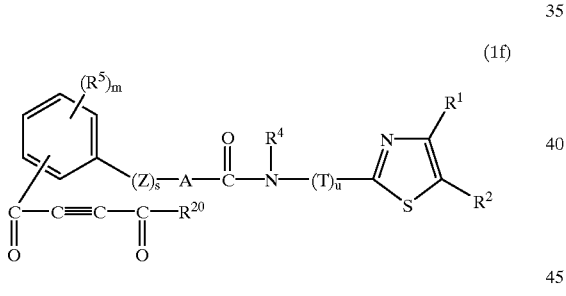

wherein $R^1$, $R^2$, $R^4$, $R^5$, Z, m, s, T, u, and A are the same as defined in claim 1, and $R^{20}$ is the same as defined above, in the presence of an oxidizing agent, optionally followed by converting, the compound (1f) into a compound of the formula (1g):

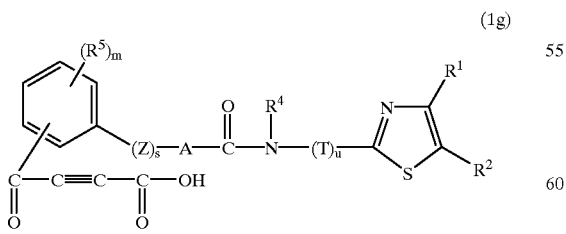

wherein $R^1$, $R^2$, $R^4$, $R^5$, Z, m, s, T, u and A are the same as defined in claim 1, in the presence of an acid or a basic compound;

(g) reacting a compound of the formula (19):

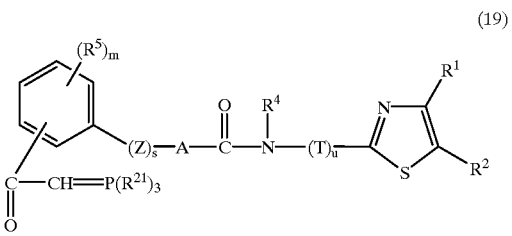

wherein $R^1$, $R^2$, $R^4$, $R^5$, Z, m, s, T, u and A are the same as defined in claim 1, and $R^{21}$ is a phenyl group, with a compound of the formula (20):

$R^{22}$CHO   (20)

wherein $R^{22}$ is the same as defined above, to give a compound of the formula (1h):

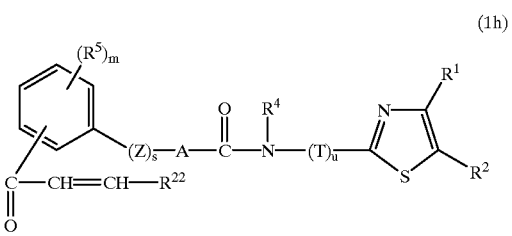

wherein $R^1$, $R^2$, $R^4$, $R^5$, Z, m, s, T, u and A are the same as defined in claim 1, and $R^{22}$ is the same as defined above;

(h) reacting a compound of the formula (23):

wherein $R^3$ is the same as defined in claim 1, with a compound of the formula (24):

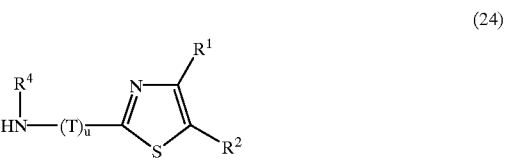

wherein $R^1$, $R^2$, $R^4$, T and u are the same as defined in claim 1, to give a compound of the formula (1):

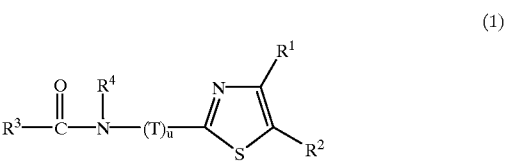

wherein $R^1$, $R^2$, $R^3$, $R^4$, T and u are the same as defined in claim 1;

(i) reacting a compound of the formula (19a):
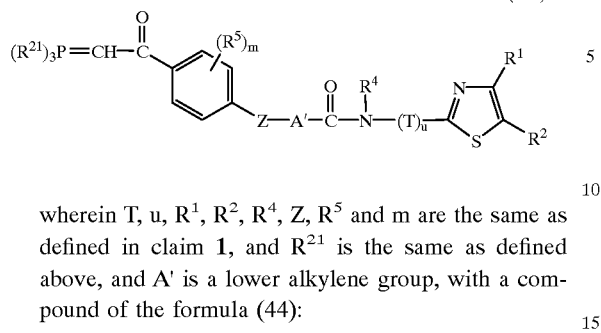
wherein T, u, $R^1$, $R^2$, $R^4$, Z, $R^5$ and m are the same as defined in claim 1, and $R^{21}$ is the same as defined above, and A' is a lower alkylene group, with a compound of the formula (44):
OHC.COOH  (44)
to give a compound of the formula (1q):
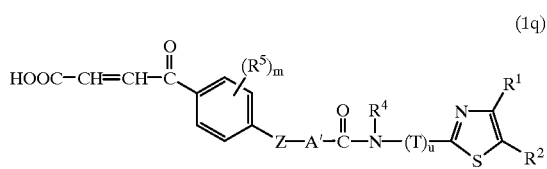
wherein T, u, $R^1$, $R^2$, $R^4$, Z, $R^5$ and m are the same as defined in claim 1 and A' is a lower alkylene group.
* * * * *